(12) United States Patent
Barnes et al.

(10) Patent No.: US 9,789,118 B2
(45) Date of Patent: Oct. 17, 2017

(54) BICYCLIC ACETYL-COA CARBOXYLASE INHIBITORS AND USES THEREOF

(71) Applicants: David Weninger Barnes, Waban, MA (US); Gregory Raymond Bebernitz, Stow, MA (US); Kevin Clairmont, Acton, MA (US); Scott Louis Cohen, Peabody, MA (US); Robert Edson Damon, II, Hopkinton, MA (US); Robert Francis Day, Watertown, MA (US); Stephanie Kay Dodd, Ayer, MA (US); Christoph Gaul, Aesch (CH); Hatice Belgin Gulgeze Efthymiou, Lynn, MA (US); Monish Jain, Belmont, MA (US); Rajeshri Ganesh Karki, Somerville, MA (US); Louise Clare Kirman, Swampscott, MA (US); Kai Lin, Waltham, MA (US); Justin Yik Ching Mao, North Reading, MA (US); Tajesh Jayprakash Patel, Medford, MA (US); Brian Kenneth Raymer, Holliston, MA (US); Su Liansheng, Quincy, MA (US)

(72) Inventors: David Weninger Barnes, Waban, MA (US); Gregory Raymond Bebernitz, Stow, MA (US); Kevin Clairmont, Acton, MA (US); Scott Louis Cohen, Peabody, MA (US); Robert Edson Damon, II, Hopkinton, MA (US); Robert Francis Day, Watertown, MA (US); Stephanie Kay Dodd, Ayer, MA (US); Christoph Gaul, Aesch (CH); Hatice Belgin Gulgeze Efthymiou, Lynn, MA (US); Monish Jain, Belmont, MA (US); Rajeshri Ganesh Karki, Somerville, MA (US); Louise Clare Kirman, Swampscott, MA (US); Kai Lin, Waltham, MA (US); Justin Yik Ching Mao, North Reading, MA (US); Tajesh Jayprakash Patel, Medford, MA (US); Brian Kenneth Raymer, Holliston, MA (US); Su Liansheng, Quincy, MA (US)

(73) Assignee: NOVARTIS AG, Basel (CH)

( * ) Notice: Subject to any disclaimer, the term of this patent is extended or adjusted under 35 U.S.C. 154(b) by 73 days.

(21) Appl. No.: 14/188,647

(22) Filed: Feb. 24, 2014

(65) Prior Publication Data
US 2014/0171363 A1   Jun. 19, 2014

Related U.S. Application Data

(63) Continuation of application No. 13/189,760, filed on Jul. 25, 2011, now Pat. No. 8,697,739.

(Continued)

(51) Int. Cl.
C07D 215/36   (2006.01)
C07D 235/18   (2006.01)
C07D 263/57   (2006.01)
C07D 401/04   (2006.01)
C07D 401/12   (2006.01)
C07D 403/04   (2006.01)
(Continued)

(52) U.S. Cl.
CPC .......... A61K 31/542 (2013.01); A61K 9/0014 (2013.01); A61K 9/0019 (2013.01); A61K 9/0095 (2013.01); A61K 9/08 (2013.01); A61K 9/1075 (2013.01); A61K 31/404 (2013.01); A61K 31/4184 (2013.01); A61K 31/423 (2013.01); A61K 31/496 (2013.01); A61K 31/5377 (2013.01); A61K 45/06 (2013.01); C07D 209/24 (2013.01); C07D 215/36 (2013.01); C07D 235/08 (2013.01); C07D 235/12 (2013.01); C07D 235/16 (2013.01); C07D 235/18 (2013.01); C07D 235/30 (2013.01); C07D 263/57 (2013.01); C07D 401/04 (2013.01); C07D 401/12 (2013.01); C07D 403/04 (2013.01); C07D 405/04 (2013.01); C07D 405/14 (2013.01); C07D 413/12 (2013.01); C07D 471/04 (2013.01); C07D 513/04 (2013.01); C12N 9/93 (2013.01); C12Y 604/01002 (2013.01)

(58) Field of Classification Search
CPC ............ A61K 31/5377; A61K 31/4396; A61K 31/496; C07D 401/12; C07D 401/14; C07D 405/04; C07D 403/04
USPC ........ 546/153, 159, 162, 171; 514/312, 313, 514/314
See application file for complete search history.

(56) References Cited

FOREIGN PATENT DOCUMENTS

WO   2009/082346 A1   7/2009
WO   2010/053829 A1   5/2010
(Continued)

Primary Examiner — Kahsay Habte
(74) Attorney, Agent, or Firm — Joshua Roth

(57) ABSTRACT

The present invention provides compounds of formula (IV);

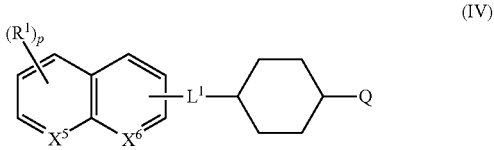

(IV)

or pharmaceutically acceptable salts thereof, wherein the variables are defined as herein. The present invention provides a method for manufacturing the compounds of formula (IV), their therapeutic uses, combinations with other of pharmacologically active agents, and a pharmaceutical compositions.

20 Claims, No Drawings

Related U.S. Application Data

(60) Provisional application No. 61/368,820, filed on Jul. 29, 2010.

(51) Int. Cl.

| | |
|---|---|
| *C07D 405/04* | (2006.01) |
| *C07D 413/12* | (2006.01) |
| *C07D 471/04* | (2006.01) |
| *C07D 513/04* | (2006.01) |
| *A61K 31/542* | (2006.01) |
| *A61K 31/4184* | (2006.01) |
| *A61K 9/00* | (2006.01) |
| *A61K 9/08* | (2006.01) |
| *A61K 9/107* | (2006.01) |
| *C12N 9/00* | (2006.01) |
| *A61K 31/404* | (2006.01) |
| *A61K 31/423* | (2006.01) |
| *A61K 31/496* | (2006.01) |
| *A61K 31/5377* | (2006.01) |
| *A61K 45/06* | (2006.01) |
| *C07D 209/24* | (2006.01) |
| *C07D 235/08* | (2006.01) |
| *C07D 235/12* | (2006.01) |
| *C07D 235/16* | (2006.01) |
| *C07D 235/30* | (2006.01) |
| *C07D 405/14* | (2006.01) |

(56) References Cited

FOREIGN PATENT DOCUMENTS

| | | |
|---|---|---|
| WO | 2010/065799 A2 | 6/2010 |
| WO | 2010/065800 A1 | 6/2010 |
| WO | 2010/065801 A1 | 6/2010 |
| WO | 2010/065802 A2 | 6/2010 |
| WO | 2010/107040 A1 | 9/2010 |
| WO | 2011/039735 A2 | 4/2011 |

BICYCLIC ACETYL-COA CARBOXYLASE INHIBITORS AND USES THEREOF

BACKGROUND OF THE INVENTION

In mammals, Acetyl-CoA carboxylase (ACC) exists as two isozymes. ACC1 is generally expressed in all tissues but its expression is higher in lipogenic tissues such as liver and adipose tissue. ACC2 is highly expressed in muscle tissue and to a lesser extent in liver tissue.

ACC has a central role in lipid metabolism. Malonyl-CoA, the product of the ACC-catalyzed reaction, inhibits mitochondrial fatty acid oxidation through direct inhibition of carnitine palmitoyltransferase 1 (CPT-1), and so controls the switch between carbohydrate and fatty acid oxidative utilization in liver and skeletal muscle. Malonyl-CoA is also a key intermediate in the de novo synthesis of lipids. When metabolic fuel is low, ACC is turned off by phosphorylation and the consequential reduction of levels of malonyl-CoA leads to generation of ATP by increasing fatty acid oxidation and decreasing consumption of ATP for fatty acid synthesis. Thus, in addition to inhibition of fatty acid synthesis, reduction in malonyl-CoA levels through ACC inhibition may provide a mechanism for increasing fatty acid utilization.

By decreasing de novo fatty acid synthesis and increasing fatty acid oxidation in liver, chronic administration of an ACC inhibitor may deplete liver triglyceride and other pathological lipid species, leading to improved liver function and hepatic insulin sensitivity. One might also expect a reduction in the secretion of triglyceride rich lipoprotein (VLDL), so reducing the risk of atherosclerosis.

High levels of triglycerides and free fatty acids lead to glucolipotoxicity of the pancreatic beta cells, contributing to beta cell dysfunction and apoptosis and further impairing glycemic control. ACC inhibitors may decrease glucolipotoxicity and protect beta cells from dysfunction and death, improving insulin secretion and beta cell health and treating diabetes.

Therefore, a well-tolerated agent that effectively and simultaneously treats the multiple risk factors associated with metabolic syndrome would have a significant impact on the prevention and treatment of the cardiovascular disease associated with obesity, hypertension, diabetes and atherosclerosis.

Metabolic syndrome (a.k.a. insulin resistance syndrome, syndrome X) is a common clinical disorder that is defined as the presence of increased insulin concentrations in association with other disorders including visceral obesity, hyperlipidemia and dyslipidemia, hyperglycemia, hypertension, and sometimes hyperuricemia and renal dysfunction.

Metabolic syndrome is considered by many as a common basic defect for type 2 diabetes, android obesity, dyslipidemia, and hypertension, leading to a clustering of these diseases. This syndrome has particular significance since it has been shown to be an antecedent of both type-2 diabetes and atherosclerosis, with cardiovascular events accounting for the majority of deaths in both populations.

It is estimated that more than 100 million people in the U.S. alone suffer from some form of metabolic syndrome.

Type 2 diabetes is a severe and prevalent disease in the Western world that affects roughly 13 million persons in the U.S., along with 5 million presumed to have undiagnosed type 2 diabetes and another 14 million with impaired glucose tolerance.

Projections indicate that the incidence of type 2 diabetes will increase to over 25 million by 2010 in the U.S., and to over 300 million worldwide by 2025. The annual direct medical cost associated with type 2 diabetes in the United States is significant, primarily due to the costs of hyperglycemia-related complications, such as retinopathy, nephropathy, peripheral neuropathy, and cardiovascular, peripheral vascular and cerebrovascular disease. Although the causes of type 2 diabetes have not yet been identified, it is well established that it is a polygenic disease characterized by multiple defects in insulin action in muscle, adipose, and liver, and defects in pancreatic insulin secretion. However, the relative importance of each of these defects to the etiology of type 2 diabetes is not clear.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatments for diabetes are currently believed to be inadequate. The use of insulin typically requires multiple daily doses. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of type 2 diabetes usually consists of a combination of diet, exercise, oral hypoglycemic agents, e.g., thiazolidenediones, and in more severe cases, insulin. However, the clinically available hypoglycemic agents can have side effects that limit their use. Moreover as few as 26% of patients with type 2 diabetes achieve target control using current therapies.

Obesity is a major health risk that leads to increased mortality and incidence of Type 2 diabetes mellitus, hypertension and dyslipidemia. It is the second leading cause of preventable death in the United States, and contributes to >300,000 deaths per year. In the U.S., more than 50% of the adult population is overweight, and almost ¼ of the population is considered to be obese (BMI greater than or equal to 30). Furthermore, the prevalence of obesity in the United States has increased by about 50% in the past 10 years. The prevalence of obesity in adults is 10%-25% in most countries of Western Europe. While the vast majority of obesity occurs in the industrialized world, particularly in US and Europe, the prevalence of obesity is also increasing in Japan. The rise in the incidence of obesity has prompted the WHO to recognize obesity as a significant disease. Two recently marketed anti-obesity agents, Xenical (Orlistat/Roche) and Meridia (Reductil/BASF) exhibit only modest efficacy (Orlistat) and have safety/side effect concerns (Orlistat-gastrointestinal and Meridia-hypertensive effects, respectively), that limit their use.

Thus, although there are a variety of anti-atherosclerosis, obesity and diabetes therapies, there is a continuing need and a continuing search in this field of art for alternative therapies.

Non-alcoholic fatty liver disease (NAFLD), and the more pathologic liver disorder, non-alcoholic steatohepatitis (NASH), develop from fat accumulation in the liver. Some degree of NAFLD affects up to one third of the general population. In particular insulin resistance, type 2 diabetes, obesity, hypertriglyceridemia, and female gender are independently associated with NAFLD. NAFLD is found in 30-100% of subjects with one or more metabolic abnormalities and is found in the majority of subject with type 2 diabetes. NAFLD is not only found in adults, but is also present in obese/diabetic children and adolescents. Patients with, or being treated for, human immunodeficiency virus are also at a much greater risk of developing NAFLD.

Recent studies indicate that the progression of NAFLD to NASH can result in the development of fibrous tissue in the liver (fibrosis) in up to 40% of patients or cirrhosis in 5-10% of patients. Current treatments are limited, relying largely on exercise and weight loss.

Moreover, in patients with NAFLD and insulin resistance, de novo lipogenesis may contribute up to 25% of total liver lipid. It has been noted that patients with NAFLD have substantially increased mRNA levels of both ACC1 and ACC2, compared to control subjects.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth muscle cells and in macrophages of the intima layer of the arteries and aorta. Further, it is postulated that most of the cholesterol found within the fatty streaks, in turn, gives rise to development of the "fibrous plaque," which consists of accumulated intimal smooth muscle cells laden with lipid and surrounded by extra-cellular lipid, collagen, elastin and proteoglycans. These cells plus matrix form a fibrous cap that covers a deeper deposit of cell debris and more extra-cellular lipid. The lipid is primarily free and esterified cholesterol. The fibrous plaque forms slowly, and is likely in time to become calcified and necrotic, advancing to a "complicated lesion," which accounts for arterial occlusion and a tendency toward mural thrombosis and arterial muscle spasm that characterize advanced atherosclerosis. Hyperlipidemia has been established as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Additional independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

More than half a century ago it was first demonstrated that fatty acid synthesis in tumor tissues occurs at a very high rates. A number of studies have demonstrated that in tumor cells almost all fatty acids derive from de novo synthesis despite adequate nutritional supply. In addition, tumors overexpressing fatty acid synthase (FAS), the enzyme responsible for de novo synthesis of fatty acids, display aggressive biologic behavior compared to those tumors with normal FAS levels, suggesting that FAS overexpression confers a selective growth advantage.

Heptatitis C virus (HCV) causes serious, life-threatening, chronic disease in infected humans. HCV is a member of the Flavivirus family, and it packages a positive RNA strand (the sense of mRNA) into its virions. Positive-strand RNA viruses, such as HCV, have been shown to replicate their genomes at cellular membrane sites within infected cells (Sagan et al., Biochem. Cell Biol. 84, 67-79, 2006 and references therein), and could be expected to be sensitive to drugs that modulate lipid biosynthesis and composition within the cell.

SUMMARY OF THE INVENTION

This invention relates to compounds which are Acetyl-Coenzyme A Carboxylase (ACC) inhibitors, pharmaceutical compositions containing such inhibitors and the use of such inhibitors to treat, for example, metabolic syndrome, diabetes, obesity, fatty liver disease, atherosclerosis, cardiovascular disease and cancer in mammals, including humans. The invention also relates to the use of ACC inhibitor for the treatment of HCV-associated disorders since ACC has a central role in lipid metabolism.

For the purposes of this invention inhibition of ACC means inhibitions exclusively of ACC2, inhibitions exclusively of ACC1 or inhibition of both ACC1 and ACC2. Inhibition of either isozyme of ACC should beneficially affect the abnormalities associated with metabolic syndrome. Preferably an ACC inhibitor should inhibit both isoforms of the enzyme.

Accordingly, in one aspect, the invention provides compounds of formula (I):

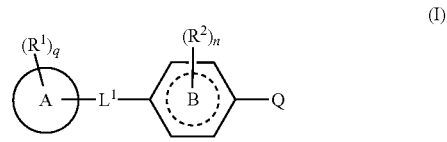

or a pharmaceutically acceptable salt thereof, wherein:
Ring A is a bicyclic ring system selected from the group consisting of:

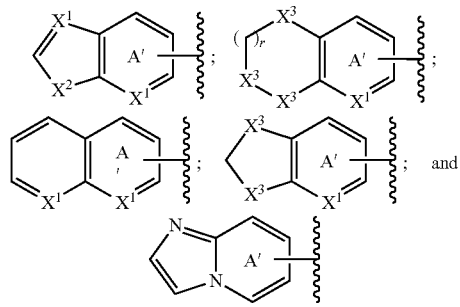

wherein the symbol

indicates the point of attachment of $L^1$ is on ring A'; and wherein $R^1$ may replace a hydrogen atom of any CH bond in ring A;
$X^1$, for each occurrence, is independently CH or N;
$X^2$ is $NR^{19}$, O, or S;
$X^3$, for each occurrence, is independently $NR^{19}$, $CH_2$, O, or S;
r is 1 or 2;

Ring B is cyclohexyl or phenyl; provided that when ring B is phenyl, ring A is

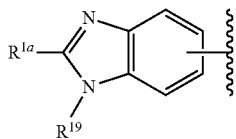

wherein $R^{1a}$ is hydrogen, phenyl, phenylamino, or a 5- to 10-membered heteroaryl, wherein $R^{1a}$ may be optionally substituted on one or more carbon atom with one or more independently selected $R^{13}$; and wherein when $R^{1a}$ is a heteroaryl comprising one or more —NH—, the hydrogen of each —NH— group may be optionally replaced with $R^{22}$;

Q is selected from the group consisting of:

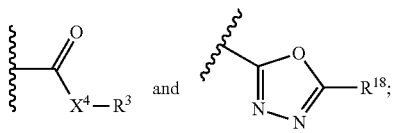

wherein the symbol

indicates the point of attachment to ring B;

$X^4$ is —$NR^4$— or —O—;

q and n are each, independently, 0, 1, 2, 3, or 4;

$L_1$ is —$NHSO_2$—, —$SO_2NH$—, —$NHSO_2NH$— or —NHC(O)NH—;

$R^1$ may replace a hydrogen atom of any CH bond in ring A and, for each occurrence, is independently deutero, hydroxy, nitro, halo, cyano, carboxy, formyl, $C_{1-7}$alkyl, $C_{3-8}$-carbocyclyl, $C_{2-7}$alkenyl, $C_{2-7}$alkynyl, $C_{1-7}$alkoxy, $C_{1-7}$alkylthio, $C_{3-8}$cycloalkoxy, $C_{6-10}$aryl, $C_{6-10}$aryl$C_{1-4}$alkyl, $C_{6-10}$aryloxy, amino, N—$C_{1-7}$alkylamino, N,N-di-($C_{1-7}$alkyl)amino, N—$C_{6-10}$arylamino, 3- to 10-membered heterocyclyl, N-(3- to 10-membered heterocyclyl)amino, (3- to 10-membered heterocyclyl)oxy, 5- to 10-membered heteroaryl, (5- to 10-membered heteroaryl)$C_{1-4}$alkyl, N-(5- to 10-membered heteroaryl)amino, (5- to 10-membered heteroaryl)oxy, $C_{1-7}$alkanoyl, $C_{1-7}$alkoxycarbonyl, $C_{1-7}$alkanoyloxy, $C_{1-7}$alkylamido, $C_{6-10}$arylamido, (3- to 10-membered heterocyclyl)amido, carbamoyl, N—$C_{1-7}$alkylcarbamoyl, N,N-di-($C_{1-7}$alkyl)carbamoyl, $C_{1-7}$alkoxyamido, $C_{1-7}$alkylureido, and $C_{6-10}$arylureido, wherein $R^1$ is optionally substituted on one or more carbon atom with one or more independently selected $R^{13}$; and wherein when $R^1$ comprises a heterocyclyl or a heteroaryl comprising one or more —NH—, the hydrogen of each —NH— group may be independently optionally replaced with $R^{22}$; or two $R^1$ on the same carbon atom together may form an oxo; or two $R^1$ on the same carbon atom together with the carbon to which they are attached form a spiro $C_{3-8}$carbocyclyl; or two $R^1$ on adjacent carbon atoms together with the carbon atoms to which they are attached may form a fused $C_{3-8}$carbocyclyl or phenyl which may be optionally substituted with one or more $R^{13}$; and $R^2$, for each occurrence, is independently selected from the group consisting of hydroxy, cyano, $C_{1-7}$alkyl, $C_{1-7}$alkoxy, $C_{2-7}$alkenyl, amino, $C_{1-7}$alkylamino, di-($C_{1-7}$alkyl)amino, $C_{1-7}$alkylamido, $C_{1-7}$alkoxyamido; wherein $R^2$, for each occurrence, may be independently optionally substituted with one or more halo; or two or more $R^2$ groups on non-adjacent carbon atoms together form a $C_{1-4}$alkylene bridge; or two or more $R^2$ groups on adjacent carbon atoms may form a fused $C_{3-8}$carbocyclyl;

$R^3$ is selected from the group consisting of a $C_{1-7}$alkyl, $C_{3-8}$carbocyclyl, $C_{3-8}$carbocyclyl$C_{1-4}$alkyl, $C_{6-10}$aryl, $C_{6-10}$aryl$C_{1-4}$alkyl, a 5- to 10-membered heteroaryl, a (5- to 10-membered heteroaryl)$C_{1-4}$alkyl, a 3- to 10-membered heterocyclyl, and a (3- to 10-membered heterocyclyl)$C_{1-4}$alkyl, wherein $R^3$ is optionally substituted on one or more carbon atom with one or more $R^{14}$; and wherein when $R^3$ comprises a heteroaryl or heterocyclyl comprising one or more —NH—, the hydrogen of each —NH— group may be independently optionally replaced with a $C_{1-7}$alkyl;

$R^4$ is hydrogen, $C_{1-7}$ alkyl, or $C_{1-4}$alkoxy$C_{1-4}$alkyl; or $R^3$ and $R^4$, together with the nitrogen atom to which they are attached form a 3- to 7-membered heterocyclyl, wherein the heterocyclyl may be optionally substituted on one or more carbon atoms with one or more $R^{15}$; and wherein when the heterocyclyl comprises one or more —NH—, the hydrogen of each —NH— group may be independently optionally replaced with $R^{16}$;

$R^{13}$, for each occurrence, is independently deutero, nitro, halo, cyano, hydroxy, carboxy, $C_{1-7}$alkyl, $C_{3-8}$cycloalkyl, $C_{1-7}$alkoxy, $C_{6-10}$aryl, $C_{6-10}$aryloxy, 3- to 10-membered heterocyclyl, 5- to 10-membered heteroaryl, amino, $C_{1-7}$alkylamino, di-($C_{1-7}$alkyl)amino, $C_{1-7}$alkanoyl, $C_{1-7}$alkoxycarbonyl, $C_{1-7}$alkanoyloxy, $C_{1-7}$alkylamido, $C_{1-7}$alkoxyamido, carbamoyl, N—$C_{1-7}$alkylcarbamoyl, N,N-di-($C_{1-7}$alkyl)carbamoyl, $C_{1-7}$alkylsulfonyl, $C_{1-7}$alkylsulfonyloxy, $C_{1-7}$alkylsulfonamido, sulfamoyl, N—$C_{1-7}$alkylsulfamoyl, or N,N-di-($C_{1-7}$alkyl)sulfamoyl, wherein $R^{13}$ is optionally substituted on one or more carbon atom with one or more independently selected $R^{17}$; and wherein when $R^{13}$ is a heterocyclyl or a heteroaryl comprising one or more —NH—, the hydrogen of each —NH— group may be independently optionally replaced with $R^{20}$; or two $R^{13}$ on the same carbon atom together may form an oxo or a spiro $C_{3-8}$carbocyclyl; or two $R^{13}$ on adjacent carbon atoms together with the carbons to which they are attached may form a 3- to 7-membered heterocyclyl which may be optionally substituted on one or more carbon atom with one or more $R^{17}$ and if the heterocyclyl comprises one or more —NH— group, the hydrogen of each —NH— group may be independently optionally replaced with $R^{20}$;

$R^{14}$, for each occurrence, is independently halo, hydroxy, carboxy, $C_{1-7}$alkoxycarbonyl, $C_{1-7}$alkyl, $C_{1-7}$alkoxy, $C_{3-8}$cycloalkyl, $C_{6-10}$aryl, or 5- to 10-membered heteroaryl, wherein $R^{14}$ may be optionally substituted on one or more carbon atoms with one or more independently selected $R^{24}$; or two $R^{14}$ on the same carbon atom together may form an oxo, a spiro $C_{3-8}$carbocyclyl or a 3- to 7-membered spiro heterocyclyl; or two $R^{14}$ on adjacent carbon atoms together with the carbon atoms to which they are attached may form a phenyl which may be optionally substituted on one or more carbon atoms with one or more $R^{24}$;

$R^{15}$, for each occurrence, is independently selected from the group consisting of hydroxy, carboxy, $C_{1-7}$alkyl, $C_{1-7}$alkoxy, $C_{3-8}$carbocyclyl, phenyl, and $C_{1-7}$alkoxycarbonyl; wherein $R^{15}$ may be optionally substituted on one or more carbon atoms with one or more substituent independently selected from halo, hydroxy, $C_{1-4}$alkoxy; or two $R^{15}$ on the same carbon atom together form an oxo or together with the carbon atom to which they are attached form a $C_{2-8}$cycloalkyl or a 3- to 10-membered heterocyclyl; or two $R^{15}$ on adjacent carbon atoms together with the carbon atoms to which they are attached may form a fused phenyl;

$R^{16}$, for each occurrence, is independently selected from the group consisting of $C_{1-7}$alkyl, $C_{3-8}$carbocyclyl, $C_{1-7}$alkanoyl, $C_{1-7}$alkoxycarbonyl, or 5- to 10-membered heteroaryl;

$R^{17}$, for each occurrence, is independently selected from cyano, halo, hydroxy, carboxy, $C_{1-7}$alkyl, $C_{1-7}$alkoxy, amino, $C_{1-7}$alkylamino, di-($C_{1-7}$alkyl)amino, $C_{6-10}$arylamino, $C_{6-10}$aryl$C_{1-4}$alkylamino, $C_{1-7}$alkoxycarbonyl, $C_{1-7}$alkanoyloxy, 3- to 10-membered heterocyclyl, wherein $R^{17}$ may be optionally substituted on one or more carbon atoms with one or more independently selected halo, amino, $C_{1-7}$alkyl, $C_{1-7}$alkoxy, $C_{1-7}$haloalkyl, carboxy, or $C_{1-7}$alkyoxycarbonyl; and wherein when $R^{17}$ is a heterocyclyl comprising one or more —NH—, the hydrogen of each —NH— group may be independently optionally replaced with $R^{23}$; or two $R^{17}$ on the same carbon atom together may form an oxo;

$R^{18}$ is a $C_{1-7}$alkyl, $C_{3-8}$cycloalkyl, phenyl or a $C_{1-7}$alkoxy$C_{1-7}$alkyl;

$R^{19}$, for each occurrence, is independently hydrogen, $C_{1-7}$alkyl, $C_{1-7}$alkanoyl, tri-($C_{1-7}$alkyl)silyl, $C_{3-8}$cycloalkyl, $C_{1-7}$alkoxycarbonyl, $C_{3-8}$cycloalkoxycabonyl, carbamoyl, N—$C_{1-7}$alkylcarbamoyl, N,N-di-($C_{1-7}$alkyl)carbamoyl, or $C_{6-10}$aryl$C_{1-4}$alkyl; wherein $R^{19}$ is optionally substituted on one or more carbon atoms with one or more $R^{21}$;

$R^{20}$, $R^{21}$, $R^{22}$, and $R^{23}$, for each occurrence, are independently deutero, halo, carboxy, $C_{1-7}$alkyl, $C_{1-7}$alkoxy, $C_{6-10}$aryloxy, $C_{6-10}$aryl$C_{1-4}$alkoxy, or $C_{1-7}$alkoxycarbonyl; and $R^{24}$, for each occurrence, is independently hydroxy, halo, carboxy, $C_{1-7}$alkyl, $C_{1-7}$haloalkyl, $C_{1-7}$alkoxy, amino, N—$C_{1-7}$alkylamino, N,N-di-($C_{1-7}$alkyl)amino, $C_{1-7}$alkoxycarbonyl, $C_{1-7}$alkanoyloxy, phosphonooxy, $C_{1-7}$alkoxy(hydroxy)phosphoryloxy or di-($C_{1-7}$alkoxy)phosphoryloxy; wherein $R^{24}$ may be optionally substituted on one or more carbon atom with a group independently selected from amino, N—$C_{1-7}$alkylamino, and phenyl; provided that the compound is not ethyl 4-(2-phenyl-1H-benzo[d]imidazole-6-sulfonamido)benzoate, N-(1-hydroxy-3-phenylpropan-2-yl)-4-(naphthalene-2-sulfonamido)cyclohexanecarboxamide, 4-(naphthalene-2-sulfonamido)-N-(1-oxo-3-phenylpropan-2-yl)cyclohexanecarboxamide, or ethyl 4-(naphthalene-2-sulfonamido)cyclohexanecarboxylate.

In another aspect, the invention relates to pharmaceutical compositions, comprising a compound according to formula (I), or a pharmaceutically acceptable salt thereof; and a pharmaceutically acceptable excipient or carrier. In another aspect, the invention relates to the use of this pharmaceutical composition as a medicament. In one embodiment, the medicament is used for the treatment of a disorder or disease in a subject mediated by the inhibition of acetyl CoA carboxylase.

In another aspect, the invention relates to pharmaceutical compositions, comprising a therapeutically effective amount of a compound according to formula (I), or a pharmaceutically acceptable salt thereof, in combination with a therapeutically effective amount of insulin, an insulin derivative or mimetic; an insulin secretagogue; an insulinotropic sulfonylurea receptor ligand; a PPAR ligand; an insulin sensitizer; a biguanide; an alpha-glucosidase inhibitors; a GLP-1, GLP-1 analog or mimetic; a DPPIV inhibitor; a HMG-CoA reductase inhibitor; a squalene synthase inhibitor; a FXR or a LXR ligand; a cholestyramine; a fibrates; a nicotinic acid; or aspirin. In another aspect, the invention relates to the use of this pharmaceutical composition as a medicament. In one embodiment, the medicament is used for the treatment of a disorder or disease in a subject mediated by the inhibition of acetyl CoA carboxylase.

In another aspect, the invention relates to a method of inhibiting Acetyl CoA carboxylase activity, comprising contacting a source of acetyl CoA carboxylase with a compound according to formula (I), or a pharmaceutically acceptable salt thereof.

In another aspect, the invention relates to a method of treating a disease or condition mediated by the inhibition of acetyl CoA carboxylase in a mammal, comprising administering to the mammal in need thereof a therapeutically effective amount of a compound according to formula (I), or a pharmaceutically acceptable salt thereof. In one embodiment, the disease or condition is metabolic syndrome, Syndrome X, diabetes, insulin resistance, decreased glucose tolerance, non-insulin-dependent diabetes mellitus, Type II diabetes, Type I diabetes, diabetic complications, body weight disorders, or leptin related diseases. In another embodiment, the disease or condition is insulin resistance, decreased glucose tolerance, non-insulin-dependent diabetes mellitus, Type II diabetes, or Type I diabetes. In another embodiment, the disease or condition is a metabolic syndrome wherein the metabolic syndrome is dyslipidemia, obesity, insulin resistance, hypertension, microalbuminemia, hyperuricaemia, or hypercoagulability. In another embodiment, the disease or condition is a bodyweight disorder and the bodyweight disorder is obesity, overweight, cachexia or anorexia.

In another aspect, the invention relates to the use of a compound of Formula (I), or a pharmaceutically acceptable salt thereof, for use as a medicament.

In another aspect, the invention relates to the use of a compound of Formula (I), or a pharmaceutically acceptable salt thereof, for the preparation of a pharmaceutical composition for the treatment of a disorder or disease in a subject mediated by the inhibition of acetyl CoA carboxylase.

Definitions

For purposes of interpreting this specification, the following definitions will apply unless specified otherwise and whenever appropriate, terms used in the singular will also include the plural and vice versa.

The requisite number of carbon atoms in a group is represented by using the prefix $C_{1-6}$, $C_{1-4}$, etc. For example, an alkyl group which may have from one to six carbons can be designated "$C_{1-6}$alkyl." Likewise, an aryl group having from six to ten carbon atom can be designated $C_{6-10}$aryl.

As used herein, the term "alkyl" refers to a fully saturated branched or unbranched hydrocarbon moiety having from 1 to 20 carbon atoms. In one embodiment, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. In one embodiment, an alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, iso-pentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "alkenyl" refers to a monovalent hydrocarbon which can be branched or unbranched and which has at least one carbon-carbon double bond. The term "$C_{2-7}$alkenyl" refers to a monovalent hydrocarbon having two to seven carbon atoms and comprising at least one carbon-carbon double bond. Non-limiting examples of alkenyl groups include ethenyl, prop-2-en-1-yl, and 1-methyl-prop-1-en-1-yl.

The term "alkynyl" refers to a monovalent hydrocarbon which may be branched or unbranched and which has at least one carbon-carbon triple bond. The term "$C_{2-7}$alkynyl" refers to a monovalent hydrocarbon having two to seven carbon atoms and comprising at least one carbon-carbon triple bond. An example of an alkyne group is acetylenyl.

The term "aryl" refers to an aromatic hydrocarbon group having 6-20 carbon atoms in the ring portion. Typically, aryl is monocyclic, bicyclic or tricyclic. In one embodiment, an aryl group is mono- or bicyclic and contains 6 to 10 carbon atoms. Examples of aryl groups include phenyl, naphthyl, and anthracenyl. An aryl group also includes an aromatic hydrocarbon which is fused to another ring which is not aromatic if the point of attachment to another moiety is on the aromatic ring, such as 1,2,3,4-tetrahydronaphth-5-yl, 1H-inden-5-yl, and 1,2,3,4-tetrahydroquinolin-7-yl.

The term "arylalkyl" refers to an aryl group, as defined above, which is attached to another moiety through an alkylene group, as defined above. For example, a $C_{6-10}$aryl$C_{1-4}$alkyl refers to an aryl group that has from 6 to 10 carbon atoms which is attached to another moiety through an alkylene group having from 1 to 4 carbon atoms. Representative $C_{6-10}$aryl$C_{1-4}$alkyl groups include benzyl, 2-phenyl-ethyl, and 2-(naphth-2-yl)-propyl.

As used herein, the term "alkoxy" refers to alkyl-O—, wherein alkyl is defined herein above. Representative examples of alkoxy groups include, but are not limited to, methoxy, ethoxy, propoxy, 2-propoxy, n-butoxy, tert-butoxy, n-pentyloxy, n-hexyloxy, 2-methyl-propoxy, and the like. Typically, alkoxy groups have about 1-7, more preferably about 1-4 carbons.

As used herein, the term "arylalkoxy" refers to an arylalkyl group which is attached to another moiety via an oxygen. Examples for arylalkoxy groups include benzyloxy, naphth-2-ylmethoxy, and 2-phenyl-ethoxy.

As used herein, the term "alkylthio" refers to alkyl-S—, wherein alkyl is defined herein above. Representative examples of alkylthio groups include, but are not limited to, methylthio, ethylthio, propylthio, 2-propylthio, n-butylthio, tert-butylthio, n-pentylthio, n-hexylthio, 2-methyl-propylthio, and the like. Typically, alkylthio groups have about 1-7, more preferably about 1-4 carbons.

As used herein, the term "alkoxyalkyl" refers to $R^i$—O—$R^{iv}$—, wherein $R^i$ is an alkyl as defined above and $R^{iv}$ is an alkylene as defined above. For example, a $C_{1-4}$alkoxy$C_{1-4}$alkyl group is an alkoxy group having from 1 to 4 carbon atoms which is attached to another moiety via an alkylene group having from 1 to 4 carbon atoms. Representative examples of alkoxyalkyl groups include, but are not limited to, methoxymethyl, ethoxymethyl, and (2-tert-butoxy)-ethyl.

As used herein, the term "heterocyclyl" or "heterocyclo" refers to a saturated or unsaturated non-aromatic ring or ring system, e.g., which is a 3-, 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. In one embodiment, a heterocyclyl has 3- to 10-ring members. The heterocyclyl group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like. A heterocyclyl also includes a non-aromatic heterocyclic ring system which is fused to another ring which is aromatic if the point of attachment to another moiety is on the non-aromatic ring, such as 1,2,3,4-tetrahydroquinoxalin-1-yl an 1,2,3,4-tetrahydropyrido[3,2-b]pyrazin-1-yl.

The term "heterocyclylalkyl" refers to a heterocyclyl group, as defined above, which is attached to another moiety through an alkylene group, as defined above. For example, a (3- to 10-membered heterocyclyl)$C_{1-4}$alkyl refers to a heterocyclyl group that has from 3 to 10 atoms which is attached to another moiety through an alkylene group having from 1 to 4 carbon atoms. Representative (3- to 10-membered heterocyclyl)$C_{1-4}$alkyl groups include aziridin-2-ylmethyl and 2-(pyrrolidin-2-yl)-ethyl.

As used herein, the term "carbocyclyl" refers to saturated or unsaturated monocyclic, bicyclic or tricyclic non-aromatic hydrocarbon groups which have 3-12 carbon atoms. In one embodiment, carbocyclyl refers to cyclic hydrocarbon groups having between 3 and 9 ring carbon atoms or between 3 and 7 ring carbon atoms. In a preferred embodiment, a carbocyclyl is a monocyclic hydrocarbon having from 3 to 7 carbon atoms. The carbocyclyl groups can include fused or bridged rings as well as spirocyclic rings. Exemplary monocyclic carbocyclyl groups include, but are not limited to, cyclopropyl, cyclobutyl, cyclopentyl, cyclopentenyl, cyclohexyl and cyclohexenyl and the like. Exemplary bicyclic carbocyclic groups include bicyclo[2.2.1]heptanyl, decahydronaphthyl, bicyclo[2.1.1]hexanyl, bicyclo[2.2.1]heptanyl, bicyclo[2.2.1]heptenyl, bicyclo[2.2.2]octyl and the like. Exemplary tricyclic carbocyclic groups include adamantyl, dodecahydros-indacene, and the like. A carbocyclyl also includes a non-aromatic hydrocarbon ring which is fused to an aromatic ring if the point of attachment to another moiety is on the non-aromatic ring, such as 1,2,3,4-tetrahydronaphth-1-yl, 1H-inden-2-yl, and 5,6,7,8-tetrahydroquinolin-5-yl.

The term "carbocyclyl" encompasses cycloalkyl groups. The term "cycloalkyl" refers to a saturated monocyclic, bicyclic or tricyclic hydrocarbon groups which have 3-12 carbon atoms. In one embodiment, cycloalkyl refers to a saturated cyclic hydrocarbon groups having between 3 and 9 ring carbon atoms or between 3 and 8 ring carbon atoms. In a preferred embodiment, a cycloalkyl is a monocyclic hydrocarbon having from 3 to 8 carbon atoms. Exemplary monocyclic cycloalkyl groups include, but are not limited to, cyclopropyl, cyclobutyl, cyclopentyl, cyclohexyl, and the like. Exemplary bicyclic cycloalkyl groups include bicyclo[2.2.1]heptanyl, decahydronaphthyl, bicyclo[2.1.1]hexanyl, bicyclo[2.2.1]heptanyl, bicyclo[2.2.2]octyl and the like. Exemplary tricyclic cycloalkyl groups include adamantyl, dodecahydros-indacene, and the like.

The term "carbocyclylalkyl" refers to a carbocyclyl group, as defined above, which is attached to another moiety through an alkylene group, as defined above. For example, a $C_{3-8}$carbocyclyl$C_{1-4}$alkyl refers to a carbocyclyl group that has from 3 to 8 carbon atoms which is attached to another moiety through an alkylene group having from 1 to 4 carbon atoms. Representative $C_{3-8}$carbocyclyC$_{1-4}$alkyl groups include cyclohex-1-en-4ylmethyl, cyclopropylmethyl, and 2-cyclopentyl-ethyl.

As used herein, the term "heteroaryl" refers to a 5-14 membered monocyclic- or bicyclic- or tricyclic-aromatic ring system, having 1 to 8 heteroatoms selected from N, O or S, where the N and S can also optionally be oxidized to various oxidation states. Typically, the heteroaryl is a 5-10 membered ring system (e.g., 5-7 membered monocycle or an 8-10 membered bicycle). Typical heteroaryl groups include 2- or 3-thienyl, furanyl, pyrrolyl, imidazolyl, pyrazolyl, thiazolyl, isothiazolyl, oxazolyl, isoxazolyl, triazolyl, tetrazolyl, 2-, 3-, or pyridyl, pyridazinyl, pyrazinyl, pyrimidinyl, quinolinyl, isoquinolinyl, purinyl, indolinyl, benzo[b]thiophene, benzofuran, and the like. A heteroaryl group also includes an aromatic heteroaryl ring which is fused to another ring which is not aromatic if the point of attachment to another moiety is on the heteroaromatic ring, such as 5,6,7,8-tetrahydroquinolin-4-yl and 1,2,3,4-tetrahydropyrido[2,3-b]pyrazin-8-yl.

The term "heteroarylalkyl" refers to a heteroaryl group, as defined above, which is attached to another moiety through an alkylene group, as defined above. For example, a (5- to 10-membered heteroaryl)$C_{1-4}$alkyl refers to a heteroaryl group that has from 5 to 10 atoms which is attached to another moiety through an alkylene group having from 1 to 4 carbon atoms. Representative (5- to 10-membered heteroaryl)$C_{1-4}$alkyl groups include pyridin-4-ylmethyl, 2-(quinolin-2-yl)-ethyl, and 3-(pyrrol-3-yl)-butyl.

As used herein, the term "halogen" or "halo" refers to fluoro, chloro, bromo, and iodo.

As used herein, the term "aryloxy" refers to aryl-O—, wherein aryl is defined herein above. An example of an aryloxy is phenoxy.

As used herein, the term "cycloalkoxy" refers to cycloalkyl-O—, wherein cycloalkyl is defined herein above. Representative examples of cycloalkoxy groups include cyclopentyloxy and cyclohexyloxy.

As used herein, the term "heterocyclyloxy" refers to heterocyclyl-O—, wherein heterocyclyl is defined herein above. Representative examples of heterocyclyoxy groups include piperadin-4-yloxy and piperazin-3-yloxy.

As used herein, the term "heteroaryloxy" refers to heteroaryl-O—, wherein heteroaryl is defined herein above. Representative examples of heteroaryoxy groups include pyridin-4-yloxy, imidazol-4-yloxy, purin-8-yloxy, and pyrimidin-5-yloxy.

An "amino" group as used herein refers to —NH$_2$. The term "N-alkylamino" refers to an amino group in which one hydrogen is replaced by an alkyl group as defined above. For example, N—$C_{1-7}$alkylamino refers to an amino group in which one of the hydrogens has been replaced with an alkyl group having from 1 to 7 carbon atoms. Representative N—$C_{1-7}$alkylamino groups include N-methylamino, N-ethylamino, N-isopropylamino and the like. The term "N,N-di-(alkyl)amino" refers to an amino group in which both hydrogens have been replaced by an alkyl group, as defined above, which may be the same or different. For example, N,N-di-($C_{1-7}$alkyl)amino refers to an amino group in which both of the hydrogens have been replaced with an alkyl group which may be the same or different having from 1 to 7 carbon atoms. Representative N,N-di-($C_{1-7}$alkyl)amino groups include N,N-dimethylamino, N-methyl-N-ethylamino, N-isopropyl-N-ethyl-amino, and the like. The term "N-arylamino" refers to an amino group in which one hydrogen is replaced by an aryl group, as defined above. For example, N—$C_{6-10}$arylamino refers to an amino group in which one of the hydrogens has been replaced with an aryl group having from 6 to 10 carbon atoms. Representative N—$C_{6-10}$arylamino groups include phenylamino and naphthylamino. The term "N-heterocyclylamino" refers to an amino group in which one hydrogen is replaced by a heterocyclyl group as defined above. For example, a N-(3- to 10-membered heterocyclyl)amino refers to an amino group in which one of the hydrogens has been replaced with a heterocycyl group having from 3 to 10 atoms. Representative N-(3- to 10-membered heterocyclyl)amino groups include piperidin-4-ylamino, piperazin-2-ylamino and morpholin-3-ylamino. The term "N-heteroarylamino" refers to an amino group in which one hydrogen is replaced by a heteroaryl group as defined above. For example, a N-(5- to 10-membered heteroaryl)amino refers to an amino group in which one of the hydrogens has been replaced with a heteroaryl group having from 5 to 10 atoms. Representative N-(5- to 10-membered heteroaryl)amino groups include pyridin-4-ylamino and indol-7-ylamino.

A "carbamoyl" group as used herein refers to —C(O)NH$_2$. The term "N-(alkyl)-carbamoyl" refers to a carbamoyl group in which one hydrogen is replaced by an alkyl group, as defined above. For example, N—($C_{1-7}$alkyl)-carbamoyl refers to a carbamoyl group in which one of the hydrogens has been replaced with an alkyl group having from 1 to 7 carbon atoms. Representative N—($C_{1-7}$alkyl)-carbamoyl include N-methylcarbamoyl, N-isopropyl-carbamoyl, and the like. The term "N,N-di-(alkyl)-carbamoyl" refers to a carbamoyl group in which both hydrogens have been replaced by an alkyl group, as defined above, which may be the same or different. For example, N,N-di-($C_{1-7}$alkyl)-carbamoyl refers to a carbamoyl group in which both of the hydrogens have been replaced with an alkyl group which may be the same or different having from 1 to 7 carbon atoms. Representative N,N-di-($C_{1-7}$alkyl)-carbamoyl include N,N-dimethylcarbamoyl, N-methyl-N-isopropyl-carbamoyl, and the like.

The term "alkylamido" refers to a group having the formula —NHC(O)—R$^i$, wherein R$^i$ is an alkyl group, as defined above. For example, $C_{1-7}$alkylamido refers to an alkylamido group which has from one to seven carbon atoms (not including the carbonyl carbon atom). An example of an alkylamido is butyramido.

The term "arylamido" refers to a group having the formula —NHC(O)—R$^{ii}$, wherein R$^{ii}$ is an aryl group, as defined above. For example, C$_{6-10}$arylamido refers to an arylamido group which has from six to ten carbon atoms in the aryl group. An example of an arylamido is benzamido.

The term "heterocyclylamido" refers to a group having the formula —NHC(O)—R$^{iii}$, wherein R$^{iii}$ is an heterocycyl group, as defined above. For example, a (3- to 10-membered heterocyclyl)amido is a heterocyclyl having from 3 to 10 atoms which is attached to another moiety through an amido group. Examples of heterocyclylamido groups include piperidine-1-carboxamido, and piperidine-3-carboxamido.

The term "alkanoyl" refers to a group having the formula —C(O)—R$^{i}$, wherein R$^{i}$ is an alkyl group, as defined above. For example, C$_{1-7}$alkanoyl refers to an alkanoyl group which has from one to seven carbon atoms (not including the carbonyl carbon atom), such as acetyl, isopropyl-carbonyl, and the like.

The term "alkanoyloxy" refers to a group having the formula —OC(O)—R$^{i}$, wherein R$^{i}$ is an alkyl group, as defined above. For example, C$_{1-7}$alkanoyl refers to an alkanoyloxy group which has from one to seven carbon atoms (not including the carbonyl carbon atom), such as ethoxycarbonyloxy, isopropoxycarbonyloxy, and the like.

The term "alkoxycarbonyl" refers to a group having the formula —C(O)—OR$^{i}$, wherein R$^{i}$ is an alkyl group, as defined above. For example, C$_{1-7}$alkoxycarbonyl refers to an alkoxycarbonyl group which has from one to seven carbon atoms (not including the carbonyl carbon atom), such as methoxycarbonyl, tert-butoxycarbonyl, and the like.

The term "cycloalkoxycarbonyl" refers to a group having the formula —C(O)—OR$^{v}$, wherein R$^{v}$ is a cycloalkyl group, as defined above. For example, C$_{3-8}$cycloalkoxycarbonyl refers to a cycloalkoxycarbonyl group which has from three to eight carbon atoms (not including the carbonyl carbon atom), such as cyclohexyloxy and cyclopentyloxy.

The term "alkoxyamido" refers to a group having the formula —NHC(O)—OR$^{i}$, wherein R$^{i}$ is an alkyl group, as defined above. For example, C$_{1-7}$alkoxamido refers to an alkoxyamido group which has from one to seven carbon atoms (not including the carbonyl carbon atom), such as methoxycarbonylamino, tert-butoxycarbonylamino, and the like.

The term "alkylureido" refers to a group having the formula —NHC(O)—NHR$^{i}$, wherein R$^{i}$ is an alkyl group, as defined above. For example, C$_{1-7}$alkylureido refers to an alkylureido group which has from one to seven carbon atoms (not including the carbonyl carbon atom), such as N'-methylureido, N'-(tert-butyl)-ureido, and the like.

The term "arylureido" refers to a group having the formula —NHC(O)—NHR$^{ii}$, wherein R$^{ii}$ is an aryl group, as defined above. For example, C$_{6-10}$arylureido refers to an arylureido group which has from six to ten carbon atoms (not including the carbonyl carbon atom), such as N'-phenylureido, N'-(naphth-3-yl)-ureido, and the like.

The term "alkylsulfonyl" refers to a group having the formula —S(O)$_2$R$^{i}$, wherein R$^{i}$ is an alkyl group, as defined above. For example, C$_{1-7}$alkylsulfonyl refers to an alkylsulfonyl group which has from one to seven carbon atoms, such as mesyl, tert-butylsulfonyl, and the like.

The term "alkylsulfonyloxy" refers to a group having the formula —OS(O)$_2$R$^{i}$, wherein R$^{i}$ is an alkyl group, as defined above. For example, C$_{1-7}$alkylsulfonyloxy refers to an alkylsulfonyloxy group which has from one to seven carbon atoms, such as methylsulfonyloxy, tert-butylsulfonyloxy, and the like.

The term "alkylsulfonamido" refers to a group having the formula —NHS(O)$_2$R$^{i}$, wherein R$^{i}$ is an alkyl group, as defined above. For example, C$_{1-7}$alkylsulfonylamido refers to an alkylsulfonylamido group which has from one to seven carbon atoms, such as methylsulfonamido.

The term "sulfamoyl" refers to a group having the formula —S(O)$_2$NH$_2$. The term "N-alkylsulfamoyl" refers to a sulfamoyl group wherein one of the hydrogens is replaced by an alkyl group, as defined above. For example, an N—C$_{1-7}$alkylsulfamoyl refers to an N-alkylsulfamoyl group which has from 1 to 7 carbon atoms, such as methylsulfamoyl, tert-butylsulfamoyl, and isopropylsulfamoyl. The term "N,N-di-alkylsulfamoyl" refers to a sulfamoyl group wherein both of the hydrogens are replaced by alkyl groups, as defined above, which may be the same or different. For example, an N,N-di-C$_{1-7}$alkylsulfamoyl refers to an N,N-di-alkylsulfamoyl group wherein the alkyl groups may be the same or different and have from 1 to 7 carbon atoms, such as N,N-dimethylsulfamoyl and N-methyl-N-ethylsulfamoyl.

The term "trialkylsilyl" refers to a group having the formula —Si(R$^{1}$)$_3$, wherein each R$^{i}$ is an alkyl group as defined above which may be the same or different. For example, a tri-(C$_{1-7}$alkyl)silyl is a trialkylsilyl group wherein each of the alkyl groups may be the same or different and has from 1 to 7 carbon atoms. An example of a trialkylsilyl group is trimethylsilyl.

The term "oxo" refers to a double bonded oxygen substituent (i.e. =O).

The term "phosphonooxy" refers to a group having the following formula:

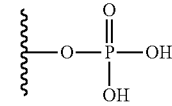

which may be neutral (as shown) or a mono- or di-anion depending on the pH of the media in which it is formed or in which it is dissolved in.

The term "alkoxy(hydroxy)phosphoryloxy" refers to a group having the following formula:

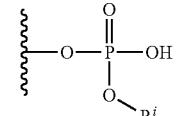

wherein R$^{i}$ is an alkyl group as defined above. An alkoxy (hydroxy)phosphoryloxy group may be neutral (as shown) or a mono-anion depending on the pH of the media in which it is formed or in which it is dissolved in.

The term "di-(alkoxy)phosphoryloxy" refers to a group having the following formula:

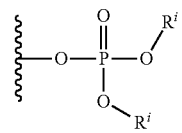

wherein each $R^i$ is an alkyl group, as defined above, which may be the same or different.

Formula (I) encompasses Formulas (II), (IIa), (IIb), (III), (IIIa), (IIIb), (IV), (Iva), (IVb), (V), (Va), and (Vb). Thus, the phrase "a compound of Formula (I)" includes compounds of Formulas (II), (IIa), (IIb), (III), (IIIa), (IIIb), (IV), (Iva), (IVb), (V), (Va), and (Vb).

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood or conversion in the gut or liver. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, Anglican Pharmaceutical Association arid Pergamon Press, 1987.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious solvent such as water or be a mixture of water plus some adventitious solvent. Compounds of the present invention, including their salts, can also be obtained in the form of their solvates (e.g., hydrates) used for their crystallization.

Compounds of the present invention are either obtained in the free form, as a salt thereof, or as prodrug derivatives thereof. When both a basic group and an acid group are present in the same molecule, the compounds of the present invention may also form internal salts, e.g., zwitterionic molecules.

A "pharmaceutical composition" refers to a formulation of a compound of the invention, or a pharmaceutically acceptable salt thereof, and a medium generally accepted in the art for the delivery of the biologically active compound to mammals, e.g., humans. Such a medium includes all pharmaceutically acceptable carriers, diluents or excipients thereof.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques. Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

When the compounds described herein contain olefinic double bonds or other centers of geometric asymmetry, and unless specified otherwise, it is intended that the compounds include both E and Z geometric isomers. Likewise, all tautomeric forms are also intended to be included.

The present invention includes all pharmaceutically acceptable isotopically-labeled compounds of Formula (I) wherein one or more atoms are labeled with an atom having the same atomic number, but an atomic mass or mass number different from the atomic mass or mass number usually found in nature.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Enrichment with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Isotopically-labeled compounds of Formula (I) can generally be prepared by conventional techniques known to those skilled in the art or by processes analogous to those described in the accompanying Examples and Preparations Sections using an appropriate isotopically-labeled reagent in place of the non-labeled reagent previously employed.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by ACC2, (ii) associated with ACC2 activity, or (iii) characterized by abnormal activity of ACC2; (2) reduce or inhibit the activity of ACC2; or (3) reduce or inhibit the expression of ACC2. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of ACC2; or at least partially reduce or inhibit the expression of ACC2.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibit," "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing, arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

EMBODIMENTS OF THE INVENTION

In one aspect, the invention provides compounds of formula (I):

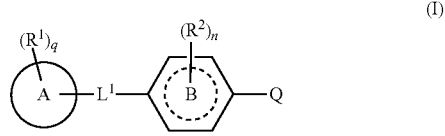

or a pharmaceutically acceptable salt thereof, wherein:
Ring A is a bicyclic ring system selected from the group consisting of:

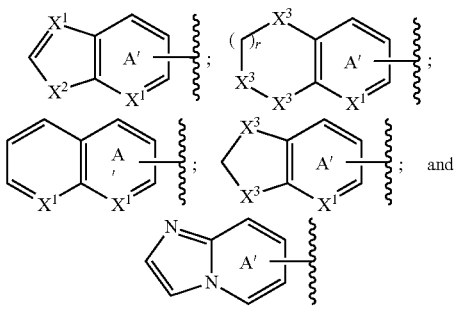

wherein the symbol

indicates the point of attachment of $L^1$ is on ring A'; and wherein $R^1$ may replace a hydrogen atom of any CH bond in ring A;

$X^1$, for each occurrence, is independently CH or N;

$X^2$ is $NR^{19}$, O, or S;

$X^3$, for each occurrence, is independently $NR^{19}$, $CH_2$, O, or S;

r is 1 or 2;

Ring B is cyclohexyl or phenyl; provided that when ring B is phenyl, ring A is

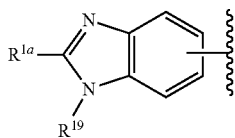

wherein $R^{1a}$ is hydrogen, phenyl, phenylamino, or a 5- to 10-membered heteroaryl, wherein $R^{1a}$ may be optionally substituted on one or more carbon atom with one or more independently selected $R^{13}$; and wherein when $R^{1a}$ is a heteroaryl comprising one or more —NH—, the hydrogen of each —NH— group may be optionally replaced with $R^{22}$;

Q is selected from the group consisting of:

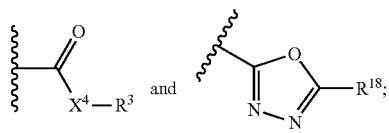

wherein the symbol

indicates the point of attachment to ring B;

$X^4$ is $-NR^4-$ or $-O-$;

q and n are each, independently, 0, 1, 2, 3, or 4;

$L_1$ is $-NHSO_2-$, $-SO_2NH-$, $-NHSO_2NH-$ or $-NHC(O)NH-$;

$R^1$ may replace a hydrogen atom of any CH bond in ring A and, for each occurrence, is independently deutero, hydroxy, nitro, halo, cyano, carboxy, formyl, $C_{1-7}$alkyl, $C_{3-8}$carbocyclyl, $C_{2-7}$alkenyl, $C_{2-7}$alkynyl, $C_{1-7}$alkoxy, $C_{1-7}$alkylthio, $C_{3-8}$cycloalkoxy, $C_{6-10}$aryl, $C_{6-10}$aryl$C_{1-4}$alkyl, $C_{6-10}$aryloxy, amino, $N-C_{1-7}$alkylamino, N,N-di-$(C_{1-7}$alkyl)amino, $N-C_{6-10}$arylamino, 3- to 10-membered heterocyclyl, N-(3- to 10-membered heterocyclyl)amino, (3- to 10-membered heterocyclyl)oxy, 5- to 10-membered heteroaryl, (5- to 10-membered heteroaryl)$C_{1-4}$alkyl, N-(5- to 10-membered heteroaryl)amino, (5- to 10-membered heteroaryl)oxy, $C_{1-7}$alkanoyl, $C_{1-7}$alkoxycarbonyl, $C_{1-7}$alkanoyloxy, $C_{1-7}$alkylamido, $C_{6-10}$arylamido, (3- to 10-membered heterocyclyl)amido, carbamoyl, $N-C_{1-7}$alkylcarbamoyl, N,N-di-$(C_{1-7}$alkyl)carbamoyl, $C_{1-7}$alkoxyamido, $C_{1-7}$alkylureido, and $C_{6-10}$arylureido, wherein $R^1$ is optionally substituted on one or more carbon atom with one or more independently selected $R^{13}$; and wherein when $R^1$ comprises a heterocyclyl or a heteroaryl comprising one or more —NH—, the hydrogen of each —NH— group may be independently optionally replaced with $R^{22}$; or two $R^1$ on the same carbon atom together may form an oxo; or two $R^1$ on the same carbon atom together with the carbon to which they are attached form a spiro $C_{3-8}$carbocyclyl; or two $R^1$ on adjacent carbon atoms together with the carbon atoms to which they are attached may form a fused $C_{3-8}$carbocyclyl or phenyl which may be optionally substituted with one or more $R^{13}$; and $R^2$, for each occurrence, is independently selected from the group consisting of hydroxy, cyano, $C_{1-7}$alkyl, $C_{1-7}$alkoxy, $C_{2-7}$alkenyl, amino, $C_{1-7}$alkylamino, di-$(C_{1-7}$alkyl)amino, $C_{1-7}$alkylamido, $C_{1-7}$alkoxyamido; wherein $R^2$, for each occurrence, may be independently optionally substituted with one or more halo; or two or more $R^2$ groups on non-adjacent carbon atoms together form a $C_{1-4}$alkylene bridge; or two or more $R^2$ groups on adjacent carbon atoms may form a fused $C_{3-8}$carbocyclyl;

$R^3$ is selected from the group consisting of a $C_{1-7}$alkyl, $C_{3-8}$carbocyclyl, $C_{3-8}$carbocyclyl$C_{1-4}$alkyl, $C_{6-10}$aryl, $C_{6-10}$aryl$C_{1-4}$alkyl, a 5- to 10-membered heteroaryl, a (5- to 10-membered heteroaryl)$C_{1-4}$alkyl, a 3- to 10-membered heterocyclyl, and a (3- to 10-membered heterocyclyl)$C_{1-4}$alkyl, wherein $R^3$ is optionally substituted on one or more carbon atom with one or more $R^{14}$; and wherein when $R^3$ comprises a heteroaryl or heterocyclyl comprising one or more —NH—, the hydrogen of each —NH— group may be independently optionally replaced with a $C_{1-7}$alkyl;

$R^4$ is hydrogen, $C_{1-7}$ alkyl, or $C_{1-4}$alkoxy$C_{1-4}$alkyl; or $R^3$ and $R^4$, together with the nitrogen atom to which they are attached form a 3- to 7-membered heterocyclyl, wherein the heterocyclyl may be optionally substituted on one or more carbon atoms with one or more $R^{15}$; and wherein when the heterocyclyl comprises one or more —NH—, the hydrogen of each —NH— group may be independently optionally replaced with $R^{16}$;

$R^{13}$, for each occurrence, is independently deutero, nitro, halo, cyano, hydroxy, carboxy, $C_{1-7}$alkyl, $C_{3-8}$cycloalkyl, $C_{1-7}$alkoxy, $C_{6-10}$aryl, $C_{6-10}$aryloxy, 3- to 10-membered heterocyclyl, 5- to 10-membered heteroaryl, amino, $C_{1-7}$alkylamino, di-$(C_{1-7}$alkyl)amino, $C_{1-7}$alkanoyl, $C_{1-7}$alkoxycarbonyl, $C_{1-7}$alkanoyloxy, $C_{1-7}$alkylamido, $C_{1-7}$alkoxyamido, carbamoyl, $N-C_{1-7}$alkylcarbamoyl, N,N-di-$(C_{1-7}$alkyl)carbamoyl, $C_{1-7}$alkylsulfonyl, $C_{1-7}$alkylsulfonyloxy, $C_{1-7}$alkylsulfonamido, sulfamoyl, $N-C_{1-7}$alkylsulfamoyl, or N,N-di-$(C_{1-7}$alkyl)sulfamoyl, wherein $R^{13}$ is optionally substituted on one or more carbon atom with one or more independently selected $R^{17}$; and wherein when $R^{13}$ is a heterocyclyl or a heteroaryl comprising one or more —NH—, the hydrogen of each —NH— group may be independently optionally replaced with $R^{20}$; or two $R^{13}$ on the same carbon atom together may form an oxo or a spiro $C_{3-8}$carbocyclyl; or two $R^{13}$ on adjacent carbon atoms together with the carbons to which they are attached may form a 3- to 7-membered heterocyclyl which may be optionally substituted on one or more carbon atom with one or more $R^{17}$ and if the heterocyclyl comprises one or more —NH— group, the hydrogen of each —NH— group may be independently optionally replaced with $R^{20}$;

$R^{14}$, for each occurrence, is independently halo, hydroxy, carboxy, $C_{1-7}$alkoxycarbonyl, $C_{1-7}$alkyl, $C_{1-7}$alkoxy, $C_{3-8}$cycloalkyl, $C_{6-10}$aryl, or 5- to 10-membered heteroaryl, wherein $R^{14}$ may be optionally substituted on one or more carbon atoms with one or more independently selected $R^{24}$; or two $R^{14}$ on the same carbon atom together may form an oxo, a spiro $C_{3-8}$carbocyclyl or a 3- to 7-membered spiro heterocyclyl; or two $R^{14}$ on adjacent carbon atoms together with the carbon atoms to which they are attached may form a phenyl which may be optionally substituted on one or more carbon atoms with one or more $R^{24}$;

$R^{15}$, for each occurrence, is independently selected from the group consisting of hydroxy, carboxy, $C_{1-7}$alkyl, $C_{1-7}$alkoxy, $C_{3-8}$carbocyclyl, phenyl, and $C_{1-7}$alkoxycarbonyl; wherein $R^{15}$ may be optionally substituted on one or more carbon atoms with one or more substituent independently selected from halo, hydroxy, $C_{1-4}$alkoxy; or two $R^{15}$ on the same carbon atom together form an oxo or together with the carbon atom to which they are attached form a $C_{2-8}$cycloalkyl or a 3- to 10-membered heterocyclyl; or two $R^{15}$ on adjacent carbon atoms together with the carbon atoms to which they are attached may form a fused phenyl;

$R^{16}$, for each occurrence, is independently selected from the group consisting of $C_{1-7}$alkyl, $C_{3-8}$carbocyclyl, $C_{1-7}$alkanoyl, $C_{1-7}$alkoxycarbonyl, or 5- to 10-membered heteroaryl;

$R^{17}$, for each occurrence, is independently selected from cyano, halo, hydroxy, carboxy, $C_{1-7}$alkyl, $C_{1-7}$alkoxy, amino, $C_{1-7}$alkylamino, di-($C_{1-7}$alkyl)amino, $C_{6-10}$arylamino, $C_{6-10}$aryl$C_{1-4}$alkylamino, $C_{1-7}$alkoxycarbonyl, $C_{1-7}$alkanoyloxy, 3- to 10-membered heterocyclyl, wherein $R^{17}$ may be optionally substituted on one or more carbon atoms with one or more independently selected halo, amino, $C_{1-7}$alkyl, $C_{1-7}$alkoxy, $C_{1-7}$haloalkyl, carboxy, or $C_{1-7}$alkyoxycarbonyl; and wherein when $R^{17}$ is a heterocyclyl comprising one or more —NH—, the hydrogen of each —NH— group may be independently optionally replaced with $R^{23}$; or two $R^{17}$ on the same carbon atom together may form an oxo;

$R^{18}$ is a $C_{1-7}$alkyl, $C_{3-8}$cycloalkyl, phenyl or a $C_{1-7}$alkoxy$C_{1-7}$alkyl;

$R^{19}$, for each occurrence, is independently hydrogen, $C_{1-7}$alkyl, $C_{1-7}$alkanoyl, tri-($C_{1-7}$alkyl)silyl, $C_{3-8}$cycloalkyl, $C_{1-7}$alkoxycarbonyl, $C_{3-8}$cycloalkoxycabonyl, carbamoyl, N—$C_{1-7}$alkylcarbamoyl, N,N-di-($C_{1-7}$alkyl)carbamoyl, or $C_{6-10}$aryl$C_{1-4}$alkyl; wherein $R^{19}$ is optionally substituted on one or more carbon atoms with one or more $R^{21}$;

$R^{20}$, $R^{21}$, $R^{22}$, and $R^{23}$, for each occurrence, are independently deutero, halo, carboxy, $C_{1-7}$alkyl, $C_{1-7}$alkoxy, $C_{6-10}$aryloxy, $C_{6-10}$aryl$C_{1-4}$alkoxy, or $C_{1-7}$alkoxycarbonyl; and $R^{24}$, for each occurrence, is independently hydroxy, halo, carboxy, $C_{1-7}$alkyl, $C_{1-7}$haloalkyl, $C_{1-7}$alkoxy, amino, N—$C_{1-7}$alkylamino, N,N-di-($C_{1-7}$alkyl)amino, $C_{1-7}$alkoxycarbonyl, $C_{1-7}$alkanoyloxy, phosphonooxy, $C_{1-7}$alkoxy(hydroxy)phosphoryloxy or di-($C_{1-7}$alkoxy)phosphoryloxy; wherein $R^{24}$ may be optionally substituted on one or more carbon atom with a group independently selected from amino, N—$C_{1-7}$alkylamino, and phenyl; provided that the compound is not ethyl 4-(2-phenyl-1H-benzo[d]imidazole-6-sulfonamido)benzoate, N-(1-hydroxy-3-phenylpropan-2-yl)-4-(naphthalene-2-sulfonamido)cyclohexanecarboxamide, 4-(naphthalene-2-sulfonamido)-N-(1-oxo-3-phenylpropan-2-yl)cyclohexanecarboxamide, or ethyl 4-(naphthalene-2-sulfonamido)cyclohexanecarboxylate.

In one embodiment, ring B is a cyclohexyl in the compounds of Formula (I), or a pharmaceutically acceptable salt thereof.

In another embodiment, $L^1$ is —SO$_2$NH—, in the compounds of Formula (I), or a pharmaceutically acceptable salt thereof.

In another embodiment, $L^1$ is —NHSO$_2$—, in the compounds of Formula (I), or a pharmaceutically acceptable salt thereof.

In another embodiment, $L^1$ is —NHSO$_2$NH—, in the compounds of Formula (I), or a pharmaceutically acceptable salt thereof.

In another embodiment, $L^1$ is —NHC(O)NH—, in the compounds of Formula (I), or a pharmaceutically acceptable salt thereof.

In another embodiment of the compounds of Formula (I), or a pharmaceutically acceptable salt thereof, ring A is a bicyclic ring system selected from the group consisting of:

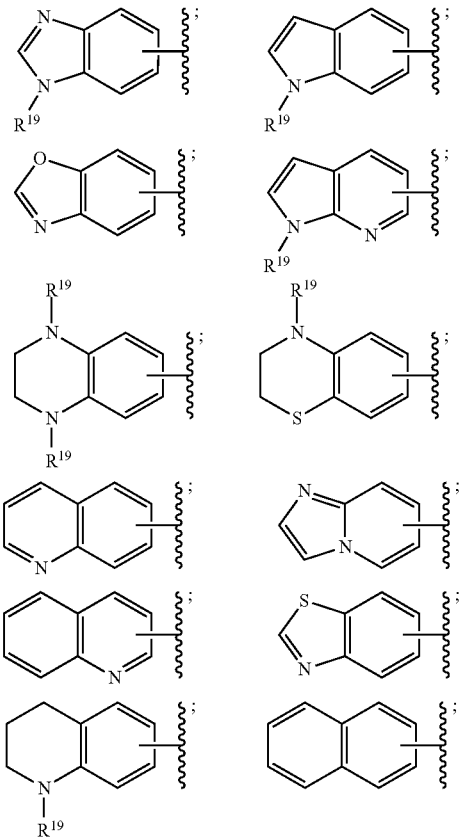

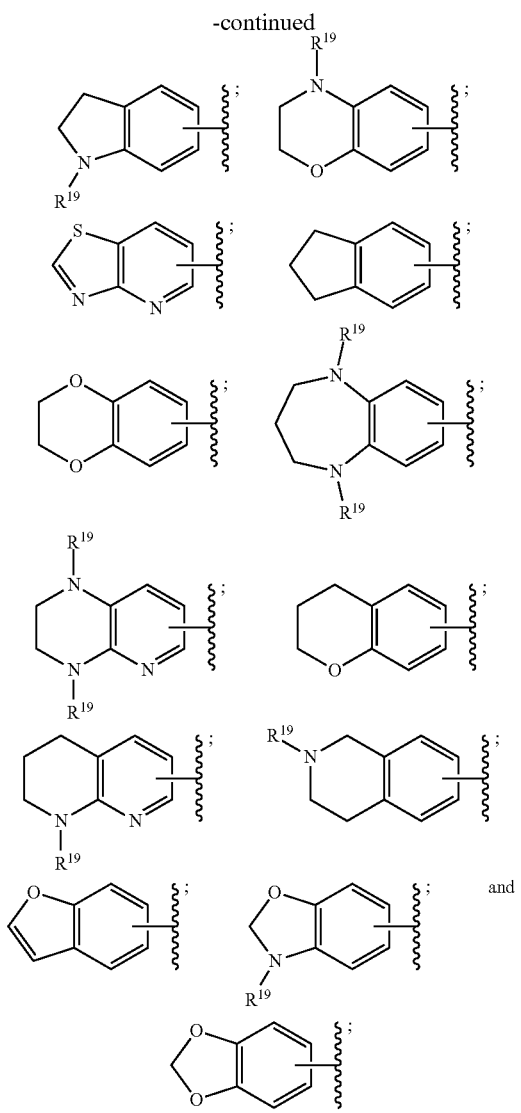

wherein $R^1$ may replace a hydrogen atom of any CH bond in ring A.

In another embodiment of the compounds of Formula (I), or a pharmaceutically acceptable salt thereof, $R^1$, for each occurrence, is independently deutro, cyano, hydroxy, carboxy, halo, $C_{1-7}$alkyl, $C_{1-7}$alkoxy, vinyl, 1-propynyl, N,N-dimethylamino, N-ethylamino, N-phenylamino, N-pyridinylamino, N-(2,3-dihydrobenzo[b][1,4]dioxin-6-ylamino, N-(benzo[c][1,2,5]thiadiazol-5-ylamino, phenyl, pyrrolidinyl, piperazinyl, piperidinyl, tetrahydro-2H-pyranyl, tetrahydrofuranyl, morpholinyl, phenylamino, cyclopropyl, cyclopentyl, pyridinyl, thiazolyl, cyclobutoxy, oxetan-3-yloxy, methoxycarbonyl, acetamido, N-ethylcarbamoyl, or benzyl, wherein $R^1$ is optionally substituted on one or more carbon atom with one or more independently selected $R^{13}$; and wherein when $R^1$ comprises a heterocyclyl or a heteroaryl comprising one or more —NH—, the hydrogen of each —NH— group may be independently optionally replaced with $R^{22}$.

In another embodiment of the compounds of Formula (I), or a pharmaceutically acceptable salt thereof, m is 1 and $R^1$ is phenyl or phenylamino, wherein $R^1$ is optionally substituted on one or more carbon atom with one or more independently selected $R^{13}$.

In another embodiment of the compounds of Formula (I), or a pharmaceutically acceptable salt thereof, m is 2 and one $R^1$ is phenyl or phenylamino and the other $R^1$ is halo, wherein $R^1$ is optionally substituted on one or more carbon atom with one or more independently selected $R^{13}$.

In another embodiment of the compounds of Formula (I), or a pharmaceutically acceptable salt thereof, $R^{19}$, for each occurrence is independently selected from the group consisting of hydrogen, methyl, ethyl, isopropyl, acetyl, hexanoyl, methoxylcarbonyl, ethoxycarbonyl, t-butoxylcarbonyl, isobutoxycarbonyl, cyclohexyloxycarbonyl, N-ethylcarbamoyl, cyclopropyl, tri-isopropylsilyl, cyclohexanoxycarbonyl, benzyl, and ethoxycarbonyl, wherein $R^{19}$ may be optionally substituted on one or more carbon atoms with one or more independently selected $R^{21}$.

In another embodiment of the compounds of Formula (I), or a pharmaceutically acceptable salt thereof, $R^{21}$, for each occurrence is independently deutero, fluoro, methoxy, carboxyl, methoxycarbonyl, or benzyloxy.

In another embodiment of the compounds of Formula (I), or a pharmaceutically acceptable salt thereof, $R^{13}$, for each occurrence, is independently halo, cyano, nitro, carboxy, hydroxy, $C_{1-4}$alkyl, $C_{1-4}$alkoxy, N,N-dimethylamino, N,N-ethylamino, methoxycarbonyl, ethoxycarbonyl, ethoxycarbonylamino, acetyl, acetamido, piperazinyl, morpholinyl, pyrrazolyl, 2-oxo-2,3-dihydrothiazolyl, methylsulfonyl, methylsulfonyloxy, sulfamoyl, or phenyloxy, wherein $R^{13}$ is optionally substituted on one or more carbon atom with one or more independently selected $R^{17}$; and wherein when $R^{13}$ is a heterocyclyl or a heteroaryl comprising one or more —NH—, the hydrogen of each —NH— group may be independently optionally replaced with $R^{20}$; or two $R^{13}$ on the same carbon atom together may form an oxo or a spiro $C_{3-8}$carbocyclyl; or two $R^{13}$ on adjacent carbon atoms together with the carbons to which they are attached may form a 3- to 7-membered heterocyclyl which may be optionally substituted on one or more carbon atom with one or more $R^{17}$ and if the heterocyclyl comprises one or more —NH— group, the hydrogen of each —NH— group may be independently optionally replaced with $R^{20}$.

In another embodiment of the compounds of Formula (I), or a pharmaceutically acceptable salt thereof, $R^{22}$, for each occurrence, is independently methyl or t-butoxycarbonyl.

In another embodiment of the compounds of Formula (I), or a pharmaceutically acceptable salt thereof, $R^{17}$, for each occurrence, is independently a halo, carboxy, hydroxy, $C_{1-4}$alkyl, $C_{1-4}$alkoxy, methoxycarbonyl, 3-methylbutanoyloxy, N-methylamino, N-benzylamino, N,N-dimethylamino, piperazinyl, or morpholinyl, wherein $R^{17}$ may be optionally substituted on one or more carbon atoms with one or more independently selected halo, amino, $C_{1-7}$alkyl, $C_{1-7}$alkoxy, $C_{1-7}$haloalkyl, carboxy, or $C_{1-7}$alkyoxycarbonyl; and wherein when $R^{17}$ is a heterocyclyl comprising one or more —NH—, the hydrogen of each —NH— group may be independently optionally replaced with $R^{23}$.

In another embodiment of the compounds of Formula (I), or a pharmaceutically acceptable salt thereof, $R^{20}$, for each occurrence, is independently methyl or t-butoxycarbonyl.

In another embodiment of the compounds of Formula (I), or a pharmaceutically acceptable salt thereof, $R^{23}$, for each occurrence, is methyl.

In another embodiment of the compounds of Formula (I), or a pharmaceutically acceptable salt thereof, Q is a group represented by the following formula:

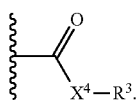

In another embodiment of the compounds of Formula (I), or a pharmaceutically acceptable salt thereof, $X^4$ is —$NR^4$—.

In another embodiment of the compounds of Formula (I), or a pharmaceutically acceptable salt thereof, $R^4$ is hydrogen.

In another embodiment of the compounds of Formula (I), or a pharmaceutically acceptable salt thereof, $R^4$ is methyl, ethyl, n-propyl, isopropyl, or methoxyethyl.

In another embodiment of the compounds of Formula (I), or a pharmaceutically acceptable salt thereof, $X^4$ is —O—.

In another embodiment of the compounds of Formula (I), or a pharmaceutically acceptable salt thereof, $R^3$ is methyl, ethyl, n-propyl, isopropyl, n-butyl, isobutyl, t-butyl, 1-methylpropyl, 1,2-dimethylpropyl, cyclopropyl, cyclohexyl, cyclopropylmethyl, cyclohexylmethyl, cycloheptylmethyl, phenyl, naphth-1-yl, benzyl, 2-phenylethyl, 1,2,3,4-tetrahydronaphth-1-yl, 2,3-dihydro-1H-inden-2-yl, azepanyl, pyridin-3-yl, pyridin-2-ylmethyl, pyridin-3-ylmethyl, pyridin-4-ylmethyl, 2-(pyridin-3-yl)-ethyl, quinolin-6-yl, or pyrazol-4-ylmethyl; wherein $R^3$ is optionally substituted on one or more carbon atom with one or more $R^{14}$; and wherein when $R^3$ comprises a heteroaryl or heterocyclyl comprising one or more —NH—, the hydrogen of each —NH— group may be independently optionally replaced with a $C_{1-7}$alkyl.

In another embodiment of the compounds of Formula (I), or a pharmaceutically acceptable salt thereof, $R^{14}$, for each occurrence, is independently halo, hydroxy, methyl, ethyl, isopropyl, t-butyl, methoxy, methoxycarbonyl, cyclopropyl, or N—N-dimethylamino; wherein $R^{14}$ may be optionally substituted on one or more carbon atoms with one or more independently selected $R^{24}$; or two $R^{14}$ on the same carbon atom together are oxo; or two $R^{14}$ on the same carbon atom together with the carbon atom to which they are attached form cyclopropyl.

In another embodiment of the compounds of Formula (I), or a pharmaceutically acceptable salt thereof, $R^{24}$, for each occurrence, is independently halo, hydroxy, carboxy, methoxy, methoxycarbonyl, t-butoxycarbonyl, propanoyloxy, 3-methylbutanoyloxy, or di-(t-butoxy)phosphoryloxy, wherein $R^{24}$ may be optionally substituted with one or more group selected from amino, methylamino, or phenyl.

In another embodiment of the compounds of Formula (I), or a pharmaceutically acceptable salt thereof, $R^3$ and $R^4$, together with the nitrogen atom to which they are attached form a 3- to 7-membered heterocyclyl, wherein the heterocyclyl may be optionally substituted on one or more carbon atoms with one or more $R^{15}$; and wherein when the heterocyclyl comprises one or more —NH—, the hydrogen of each —NH— group may be independently optionally replaced with $R^{16}$.

In another embodiment of the compounds of Formula (I), or a pharmaceutically acceptable salt thereof, $R^3$ and $R^4$, together with the nitrogen atom to which they are attached form piperazino, morpholino, piperidino, pyrrolidino, 1,4-oxazepan-4-yl, azetidin-1-yl, isoindolin-2-yl, or decahydroisoquinolin-2-yl, each of which may be optionally substituted on one or more carbon atoms with one or more $R^{15}$; and wherein the hydrogen of the —NH— of piperazino may be independently optionally replaced with $R^{16}$.

In another embodiment of the compounds of Formula (I), or a pharmaceutically acceptable salt thereof, $R^{15}$, for each occurrence, is independently selected from the group consisting of hydroxy, carboxy, methoxycarbonyl, ethoxycarbonyl, methyl, ethyl, isopropyl, t-butyl, trifluoromethyl, hydroxymethyl, methoxymethyl, 1-hydroxy-1-methyl-ethyl, 2-hydroxy-1,1-dimethyl-ethyl, cyclopropyl, phenyl, or 4-fluorophenyl; or two $R^{15}$ on the same carbon atom form oxo; or two $R^{15}$ on the same carbon atom together with the carbon atom to which they are attached form azetidinyl, oxetanyl, or 1,3-dioxanyl.

In another embodiment of the compounds of Formula (I), or a pharmaceutically acceptable salt thereof, $R^{16}$, for each occurrence, is independently selected from the group consisting of methyl, cyclopropyl, t-butoxycarbonyl, and pyrimidinyl.

In another embodiment of the compounds of Formula (I), or a pharmaceutically acceptable salt thereof, Q is a group represented by the following formula:

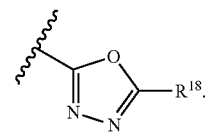

In one aspect of this embodiment, $R^{18}$ is isopropyl, t-butyl, methoxymethyl, cyclohexyl, or phenyl.

In another embodiment, the compounds of Formula (I) are represented by Formula (II), or pharmaceutically acceptable salts thereof:

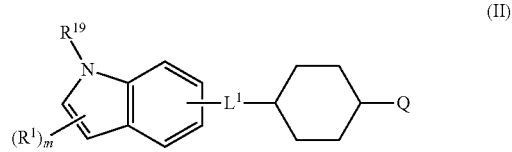

wherein m is 0, 1 or 2, and $R^1$, $R^{19}$, $L^1$, and Q are defined as in Formula (I).

In another embodiment, the compounds of Formula (I) are represented by Formula (IIa), or pharmaceutically acceptable salts thereof:

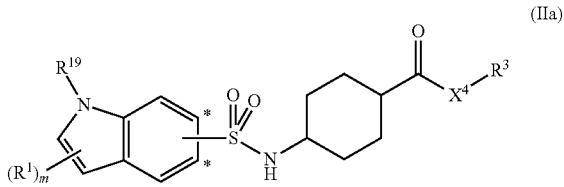

wherein "*" indicates a carbon where the sulfamoyl group may be attached, and $R^1$, $R^3$, $R^{19}$, and $X^4$ are defined as for Formula (I), and m is defined as for Formula (II).

In another embodiment of the compounds of Formula (IIa), or a pharmaceutically acceptable salt thereof, $X^4$ is —O—.

In another embodiment of the compounds of Formula (IIa), or a pharmaceutically acceptable salt thereof, $X^4$ is —$NR^4$—.

In another embodiment of the compounds of Formula (IIa), or a pharmaceutically acceptable salt thereof, $R^4$ is hydrogen.

In another embodiment of the compounds of Formula (IIa), or a pharmaceutically acceptable salt thereof, $R^4$ is a $C_{1-4}$alkyl.

In another embodiment of the compounds of Formula (IIa), or a pharmaceutically acceptable salt thereof, $R^3$ is $C_{1-4}$alkyl, 1,2-dimethyl-propyl, cyclopropylmethyl, benzyl, pyridinylmethyl, or azepanyl, wherein $R^3$ is optionally substituted on one or more carbon atom with one or more $R^{14}$; and wherein when $R^3$ is azepanyl the hydrogen of the —NH— group may be independently optionally replaced with a $C_{1-7}$alkyl. In one aspect of this embodiment, $R^{14}$, for each occurrence, is independently halo, $C_{1-4}$alkyl, $C_{1-4}$alkoxy, $C_{1-4}$alkoxycarbonyl, or cyclopropyl, wherein $R^{14}$ may be optionally substituted on one or more carbon atoms with one or more independently selected $R^{24}$; or two $R^{14}$ on the same carbon atom together are oxo. In another aspect of this embodiment, $R^{24}$, for each occurrence, is independently halo, hydroxy, carboxy, $C_{1-4}$alkoxy, or $C_{1-4}$alkoxycarbonyl.

In another embodiment of the compounds of Formula (IIa), or a pharmaceutically acceptable salt thereof, $R^3$ and $R^4$ together with the nitrogen atom to which they are attached form a 3- to 7-membered heterocyclyl, wherein the heterocyclyl may be optionally substituted on one or more carbon atoms with one or more $R^{15}$; and wherein when the heterocyclyl comprises one or more —NH—, the hydrogen of each —NH— group may be independently optionally replaced with $R^{16}$.

In another embodiment of the compounds of Formula (IIa), or a pharmaceutically acceptable salt thereof, $R^3$ and $R^4$ together with the nitrogen atom to which they are attached form piperazino, morpholino, piperidino, pyrrolidino, or azetidin-1-yl, each of which may be optionally substituted on one or more carbon atoms with one or more $R^{15}$; and wherein the hydrogen of the —NH— of piperazino may be independently optionally replaced with $R^{16}$. In one aspect of this embodiment, $R^{15}$, fore each occurrence, is independently hydroxy, carboxy, $C_{1-4}$alkyl, 1-hydroxy-1-methyl-ethyl, 2-hydroxy-1,1-dimethyl-ethyl, hydroxymethyl, methoxymethyl, cyclopropyl, trifluoromethyl, phenyl, 4-fluorophenyl, or $C_{1-4}$alkoxycarbonyl; or two $R^{15}$ on the same carbon atom together form oxo; or two $R^{15}$ on the same carbon atom together with the carbon to which they are attached form azetidinyl or oxetanyl. In another aspect of this embodiment, $R^{16}$ is $C_{1-4}$alkoxycarbonyl or cyclopropyl.

In another embodiment, the compounds of Formula (I) are represented by Formula (IIb), or pharmaceutically acceptable salts thereof:

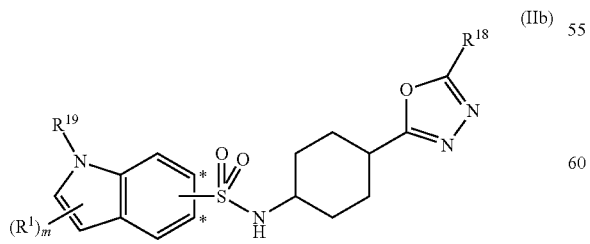

(IIb)

wherein "*" indicates a carbon where the sulfamoyl group may be attached, and $R^1$, $R^{18}$, and $R^{19}$ are defined as for Formula (I), and m is defined as for Formula (II).

In another embodiment of the compounds of Formula (IIb), or a pharmaceutically acceptable salt thereof, $R^{18}$ is isopropyl, t-butyl, methoxymethyl, cyclohexyl, or phenyl.

In another embodiment of the compounds of Formula (IIb), or a pharmaceutically acceptable salt thereof, $R^{19}$ is hydrogen.

In another embodiment of the compounds of Formula (IIb), or a pharmaceutically acceptable salt thereof, $R^{19}$ is a $C_{1-4}$alkyl.

In another embodiment of the compounds of Formula (II), (IIa), or (IIb), or a pharmaceutically acceptable salt thereof, m is 1.

In another embodiment of the compounds of Formula (II), (IIa), or (IIb), or a pharmaceutically acceptable salt thereof, m is 2.

In another embodiment of the compounds of Formula (II), (IIa), or (IIb), or a pharmaceutically acceptable salt thereof, m is zero.

In another embodiment of the compounds of Formula (II), (IIa), or (IIb), or a pharmaceutically acceptable salt thereof, $R^1$, for each occurrence, is independently halo, cyano, $C_{1-4}$alkyl, cyclopropyl, cyclopentyl, phenyl, or pyridinyl, wherein $R^1$ is optionally substituted on one or more carbon atom with one or more independently selected $R^{13}$. In one aspect of this embodiment, $R^{13}$, for each occurrence, is independently halo, hydroxy, cyano, carboxy, $C_{1-4}$alkyl, $C_{1-4}$alkoxy, $C_{1-4}$alkoxycarbonyl, or $C_{1-4}$alkylsulfonyloxy, wherein $R^{13}$ is optionally substituted on one or more carbon atom with one or more independently selected $R^{17}$. In another aspect of this embodiment, $R^{17}$, for each occurrence, is independently halo, hydroxy, carboxy, $C_{1-4}$alkoxy, $C_{1-4}$alkanoyloxy, 2-amino-3-methyl-butanoyloxy, or $C_{1-4}$alkoxycarbonyl.

In another embodiment, the compounds of Formula (I) are represented by Formula (III), or pharmaceutically acceptable salts thereof:

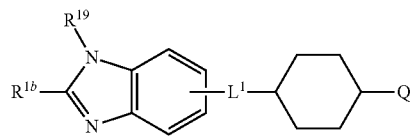

(III)

wherein $R^{1b}$ is hydrogen or $R^1$, and $R^{19}$, $L^1$ and Q are defined as for Formula (I).

In another embodiment, the compounds of Formula (I) are represented by Formula (IIIa), or pharmaceutically acceptable salts thereof:

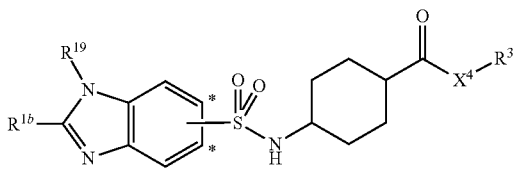

(IIIa)

wherein "*" indicates a carbon where the sulfamoyl group may be attached, $R^3$, $R^{19}$ and $X^4$ are defined as for Formula (I), and $R^{1b}$ is defined as for Formula (III).

In another embodiment of the compounds of Formula (IIIa), or a pharmaceutically acceptable salt thereof, $X^4$ is —O—.

In another embodiment of the compounds of Formula (IIIa), or a pharmaceutically acceptable salt thereof, $X^4$ is $—NR^4—$.

In another embodiment of the compounds of Formula (IIIa), or a pharmaceutically acceptable salt thereof, $R^4$ is hydrogen.

In another embodiment of the compounds of Formula (IIIa), or a pharmaceutically acceptable salt thereof, $R^4$ is a $C_{1-4}$alkyl.

In another embodiment of the compounds of Formula (IIIa), or a pharmaceutically acceptable salt thereof, $R^3$ is $C_{1-4}$alkyl, cyclopropyl, cyclohexyl, cyclopropylmethyl, cyclohexylmethyl, cycloheptylmethyl, phenyl, benzyl, 2-phenyl-ethyl, naphthyl, 1,2,3,4-tetrahydronaphthyl, 2,3-dihydro-1H-indenyl, quinolinyl, pyridinyl, pyridinylmethyl, 2-(pyridinyl)-ethyl, or azepanyl, wherein $R^3$ is optionally substituted on one or more carbon atom with one or more $R^{14}$; and wherein when $R^3$ is azepanyl the hydrogen of the —NH— group may be independently optionally replaced with a $C_{1-7}$alkyl. In one aspect of this embodiment, $R^{14}$, for each occurrence, is independently halo, hydroxy, $C_{1-4}$alkyl, $C_{1-4}$alkoxy, amino, N—$C_{1-4}$alkylamino or N,N-di-($C_{1-4}$alkyl)amino, wherein $R^{14}$ may be optionally substituted on one or more carbon atoms with one or more independently selected $R^{24}$; or two $R^{14}$ on the same carbon atom together are oxo; or two $R^{14}$ on the same carbon atom together with the carbon to which they are attached form cyclopropyl. In another aspect of this embodiment, $R^{24}$, fore each occurrence, is independently halo or hydroxy.

In another embodiment of the compounds of Formula (IIIa), or a pharmaceutically acceptable salt thereof, $R^3$ and $R^4$ together with the nitrogen atom to which they are attached form a 3- to 7-membered heterocyclyl, wherein the heterocyclyl may be optionally substituted on one or more carbon atoms with one or more $R^{15}$; and wherein when the heterocyclyl comprises one or more —NH—, the hydrogen of each —NH— group may be independently optionally replaced with $R^{16}$. In one aspect of this embodiment, $R^{15}$, for each occurrence, is independently a $C_{1-4}$alkyl; or two $R^{15}$ on the same carbon atom together with the carbon to which they are attached form 1,3-dioxanyl. In another aspect of this embodiment, $R^{16}$ is cyclohexylmethyl or phenyl.

In another embodiment of the compounds of Formula (IIIa), or a pharmaceutically acceptable salt thereof, $R^3$ and $R^4$ together with the nitrogen atom to which they are attached form piperazino, morpholino, piperidino, pyrrolidino, 1,2,3,4-tetrahydroisoquinolin-2-yl, decahydroisoquinolin-2-yl, isoindolin-2-yl, each of which may be optionally substituted on one or more carbon atoms with one or more $R^{15}$; and wherein the hydrogen of the —NH— of piperazino may be independently optionally replaced with $R^{16}$. In one aspect of this embodiment, $R^{15}$, for each occurrence, is independently a $C_{1-4}$alkyl; or two $R^{15}$ on the same carbon atom together with the carbon to which they are attached form 1,3-dioxanyl. In another aspect of this embodiment, $R^{16}$ is cyclohexylmethyl or phenyl.

In another embodiment, the compounds of Formula (I) are represented by Formula (IIIb), or pharmaceutically acceptable salts thereof:

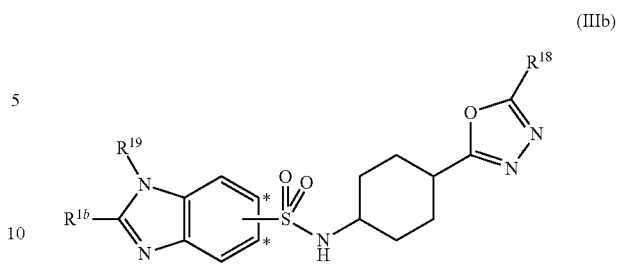

(IIIb)

wherein "*" indicates a carbon where the sulfamoyl group may be attached, $R^{18}$ and $R^{19}$ are defined as for Formula (I), and $R^{1b}$ is defined as for Formula (III).

In another embodiment of the compounds of Formula (IIIb), or a pharmaceutically acceptable salt thereof, $R^{18}$ is isopropyl, t-butyl, methoxymethyl, cyclohexyl, or phenyl.

In another embodiment of the compounds of Formula (III), (IIIa) or (IIIb), or a pharmaceutically acceptable salt thereof, $R^{19}$ is hydrogen.

In another embodiment of the compounds of Formula (III), (IIIa) or (IIIb), or a pharmaceutically acceptable salt thereof, $R^{19}$ is a $C_{1-4}$alkyl which may be optionally substituted with methoxy.

In another embodiment of the compounds of Formula (III), (IIIa) or (IIIb), or a pharmaceutically acceptable salt thereof, $R^{1b}$ is hydrogen.

In another embodiment of the compounds of Formula (III), (IIIa) or (IIIb), or a pharmaceutically acceptable salt thereof, $R^{1b}$, for each occurrence, is independently $C_{1-4}$alkyl, cyclopropyl, pyrrolidinyl, tetrahydro-2H-pyranyl, tetrahydrofuranyl, phenyl, phenylamino, phenyloxy, thiazolyl, pyridinyl, pyridinylamino, wherein $R^1$ is optionally substituted on one or more carbon atom with one or more independently selected $R^{13}$. In one aspect of this embodiment, $R^{13}$, for each occurrence, is independently halo, nitro, hydroxy, cyano, carboxy, $C_{1-4}$alkyl, $C_{1-4}$alkoxy, $C_{1-4}$alkoxycarbonyl, $C_{1-4}$alkoxyamido, amino, N,N-di-($C_{1-4}$alkyl)amino, N—$C_{1-4}$alkylamino, $C_{1-4}$alkanoyl, $C_{1-4}$alkylamido, piperazinyl, morpholinyl, 2,3-dihydrothiazolyl, pyrazolyl, $C_{1-4}$alkylsulfonyl, or sulfamoyl, wherein $R^{13}$ is optionally substituted on one or more carbon atom with one or more independently selected $R^{17}$; and wherein when $R^{13}$ is piperazinyl, morpholinyl, or pyrazolyl, the hydrogen of each —NH— group may be independently optionally replaced with $R^{20}$. In another aspect of this embodiment, $R^{17}$, for each occurrence, is independently hydroxy, N—$C_{1-4}$alkylamino, N-benzylamino, N,N-di-($C_{1-4}$alkyl)amino, piperazinyl, or morpholinyl, wherein $R^{17}$ is optionally substituted on one or more carbon atom with one or more methoxy; and wherein when $R^{17}$ is a piperazinyl, or morpholinyl, the hydrogen of each —NH— group may be independently optionally replaced with $R^{23}$; or two $R^{17}$ on the same carbon atom together form oxo. In another aspect of this embodiment, $R^{20}$ is $C_{1-4}$alkyl or $C_{1-4}$alkoxycarbonyl. In another aspect of this embodiment, $R^{23}$ is a $C_{1-4}$alkyl.

In another embodiment, the compounds of Formula (I) are represented by Formula (IV), or pharmaceutically acceptable salts thereof:

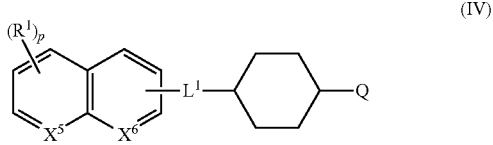

(IV)

wherein R1, L1 and Q are defined as for Formula (I); one of $X^5$ or $X^6$ is N and the other is CH; and p is 0, 1, 2, or 3.

In another embodiment, the compounds of Formula (I) are represented by Formula (IVa), or pharmaceutically acceptable salts thereof:

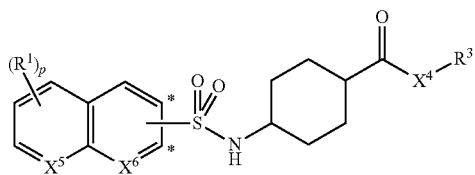

(IVa)

wherein "*" indicates a carbon where the sulfamoyl group may be attached, and $R^1$, $R^3$ and $X^4$ are defined as for Formula (I), and $X^5$, $X^6$ and p is defined as for Formula (IV).

In another embodiment of the compounds of Formula (IVa), or a pharmaceutically acceptable salt thereof, $X^4$ is —O—.

In another embodiment of the compounds of Formula (IVa), or a pharmaceutically acceptable salt thereof, $X^4$ is —$NR^4$—.

In another embodiment of the compounds of Formula (IVa), or a pharmaceutically acceptable salt thereof, $R^4$ is hydrogen.

In another embodiment of the compounds of Formula (IVa), or a pharmaceutically acceptable salt thereof, $R^4$ is a $C_{1-4}$alkyl.

In another embodiment of the compounds of Formula (IVa), or a pharmaceutically acceptable salt thereof, $R^3$ is $C_{1-4}$alkyl, benzyl, or pyrazinylmethyl, wherein $R^3$ is optionally substituted on one or more carbon atom with one or more $R^{14}$; and wherein when $R^3$ is pyrazinyl, the hydrogen of the —NH— group may be independently optionally replaced with a $C_{1-7}$alkyl. In one aspect of this embodiment, $R^{14}$, for each occurrence, is independently halo, $C_{1-4}$alkyl, wherein $R^{14}$ may be optionally substituted on one or more carbon atoms with one or more independently selected $R^{24}$. In another aspect of this embodiment, $R^{24}$, for each occurrence, is independently halo, hydroxy, carboxy, $C_{1-4}$alkoxycarbonyl, $C_{1-4}$alkanoyloxy, 2-amino-3-phenyl-propanoyloxy, 2-amino-3-methyl-butanoyloxy, phosphonooxy, or di-($C_{1-4}$alkoxy)phosphoryloxy.

In another embodiment of the compounds of Formula (IVa), or a pharmaceutically acceptable salt thereof, $R^3$ and $R^4$ together with the nitrogen atom to which they are attached form a 3- to 7-membered heterocyclyl, wherein the heterocyclyl may be optionally substituted on one or more carbon atoms with one or more $R^{15}$; and wherein when the heterocyclyl comprises one or more —NH—, the hydrogen of each —NH— group may be independently optionally replaced with $R^{16}$. In one aspect of this embodiment, $R^{15}$, for each occurrence, is independently carboxy, $C_{1-4}$alkyl, trifluoromethyl, phenyl, or $C_{1-4}$alkoxycarbonyl. In another aspect of this embodiment, $R^{16}$ is $C_{1-4}$alkoxycarbonyl.

In another embodiment of the compounds of Formula (IVa), or a pharmaceutically acceptable salt thereof, $R^3$ and $R^4$ together with the nitrogen atom to which they are attached form piperazino, morpholino, piperidino, or pyrrolidino, each of which may be optionally substituted on one or more carbon atoms with one or more $R^{15}$; and wherein the hydrogen of the —NH— of piperazino may be independently optionally replaced with $R^{16}$. In one aspect of this embodiment, $R^{15}$, for each occurrence, is independently carboxy, $C_{1-4}$alkyl, trifluoromethyl, phenyl, or $C_{1-4}$alkoxycarbonyl. In another aspect of this embodiment, $R^{16}$ is $C_{1-4}$alkoxycarbonyl.

In another embodiment, the compounds of Formula (I) are represented by Formula (IVb), or pharmaceutically acceptable salts thereof:

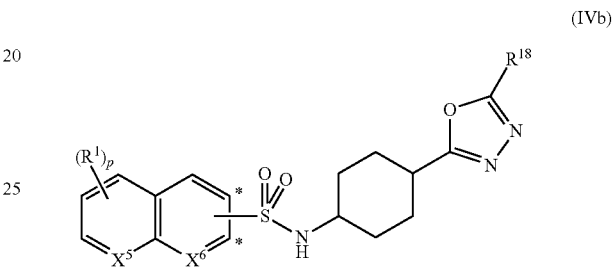

(IVb)

wherein "*" indicates a carbon where the sulfamoyl group may be attached, and $R^1$ and $R^{18}$ are defined as for formula (I) and $X^5$, $X^6$ and p are defined as for formula (IV).

In another embodiment of the compounds of Formula (IVb), or a pharmaceutically acceptable salt thereof, $R^{18}$ is isopropyl, t-butyl, methoxymethyl, cyclohexyl, or phenyl.

In another embodiment of the compounds of Formula (IVb), or a pharmaceutically acceptable salt thereof, p is 1.

In another embodiment of the compounds of Formula (IVb), or a pharmaceutically acceptable salt thereof, p is 2.

In another embodiment of the compounds of Formula (IVb), or a pharmaceutically acceptable salt thereof, p is 3.

In another embodiment of the compounds of Formula (IVb), or a pharmaceutically acceptable salt thereof, p is zero.

In another embodiment of the compounds of Formula (IVb), or a pharmaceutically acceptable salt thereof, $R^1$, for each occurrence, is independently halo, hydroxy, $C_{1-4}$alkyl, $C_{1-4}$alkenyl, $C_{1-4}$alkynyl, $C_{1-4}$alkoxy, cyclobutyloxy, oxetan-3-yloxy, amino, N—$C_{1-4}$alkylamino, N,N-di-($C_{1-4}$alkyl)amino, N—$C_{1-4}$alkylcarbamoyl, piperazinyl, piperidinyl, phenyl, or pyridinyl, wherein $R^1$ is optionally substituted on one or more carbon atom with one or more independently selected $R^{13}$; and wherein when $R^1$ is piperazinyl or piperidinyl, the hydrogen of each —NH— group may be independently optionally replaced with $R^{22}$; or two $R^1$ on the same carbon atom together with the carbon atom to which they are attached may form a spiro $C_{3-8}$carbocyclyl. In one aspect of this embodiment, $R^{13}$, for each occurrence, is independently halo, hydroxy, carboxy, $C_{1-4}$alkyl, $C_{1-4}$alkoxy, amino, N—$C_{1-4}$alkylamino, N,N-di-($C_{1-4}$alkyl)amino, wherein $R^{13}$ is optionally substituted on one or more carbon atom with one or more independently selected $R^{17}$. In another aspect of this embodiment, $R^{17}$, for each occurrence, is independently halo. In another aspect of this embodiment, $R^{22}$, for each occurrence, is independently a $C_{1-4}$alkyl.

In another embodiment of the compounds of Formula (IV), (IVa), or (IVb), or a pharmaceutically acceptable salt thereof, $X^5$ is N and $X^6$ is CH.

In another embodiment of the compounds of Formula (IV), (IVa), or (IVb), or a pharmaceutically acceptable salt thereof, $X^5$ is CH and $X^6$ is N.

In another embodiment, the compounds of Formula (I) are represented by Formula (V), or pharmaceutically acceptable salts thereof:

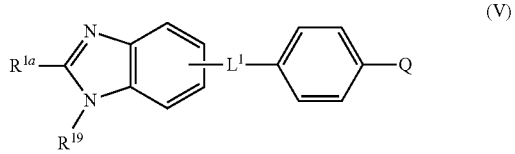

wherein $R^{1a}$, $R^{19}$, $L^1$ and Q are defined as for Formula (I).

In another embodiment, the compounds of Formula (I) are represented by Formula (Va), or pharmaceutically acceptable salts thereof:

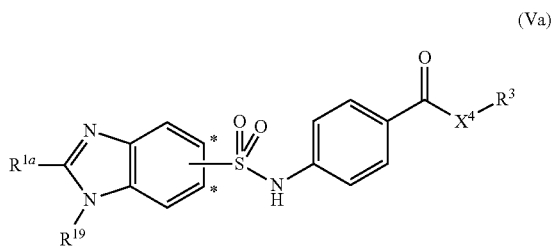

wherein "*" indicates a carbon where the sulfamoyl group may be attached; and $R^{1a}$, $R^{19}$, $R^3$ and $X^4$ are defined as for Formula (I).

In another embodiment of the compounds of Formula (Va), or a pharmaceutically acceptable salt thereof, $X^4$ is —O—.

In another embodiment of the compounds of Formula (Va), or a pharmaceutically acceptable salt thereof, $X^4$ is —$NR^4$—.

In another embodiment of the compounds of Formula (Va), or a pharmaceutically acceptable salt thereof, $R^4$ is hydrogen.

In another embodiment of the compounds of Formula (Va), or a pharmaceutically acceptable salt thereof, $R^4$ is a $C_{1-4}$alkyl.

In another embodiment of the compounds of Formula (Va), or a pharmaceutically acceptable salt thereof, $R^3$ is $C_{1-4}$alkyl or phenyl.

In another embodiment, the compounds of Formula (I) are represented by Formula (Vb), or pharmaceutically acceptable salts thereof:

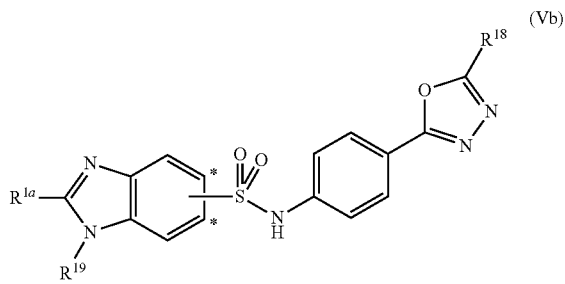

wherein "*" indicates a carbon where the sulfamoyl group may be attached; and $R^{1a}$, $R^{18}$ and $R^{19}$ are defined as for Formula (I).

In another embodiment of the compounds of Formula (Vb), or a pharmaceutically acceptable salt thereof, $R^{18}$ is isopropyl, t-butyl, methoxymethyl, cyclohexyl, or phenyl.

In another embodiment of the compounds of Formula (Vb), or a pharmaceutically acceptable salt thereof, $R^{1a}$ is phenyl, phenylamino, thiazolyl, pyridinyl, pyridinylamino, 2,3-dihydrobenzo[b][1,4]dioxinyl, benzo[c][1,2,5]oxadiazolyl, wherein $R^{1a}$ may be optionally substituted on one or more carbon atom with one or more independently selected $R^{13}$. In one aspect of this embodiment, $R^{13}$, for each occurrence, is independently halo, cyano, nitro, hydroxy, carboxy, $C_{1-4}$alkyl, $C_{1-4}$alkoxy, N,N-di-($C_{1-4}$alkyl)amino, phenoxy, $C_{1-4}$alkanoyl, $C_{1-4}$alkylamido, $C_{1-4}$alkylsulfonyl, sulfamoyl, piperazinyl, morpholinyl, pyrazolyl, wherein $R^{13}$ is optionally substituted on one or more carbon atom with one or more independently selected $R^{17}$; and wherein when $R^{13}$ is piperazinyl, morpholinyl, or pyrazolyl, the hydrogen of each —NH— group may be independently optionally replaced with $R^{20}$. In another aspect of this embodiment, $R^{17}$, for each occurrence, is independently hydroxy, or piperazinyl, wherein when $R^{17}$ is piperazinyl, the hydrogen of each —NH— group of the piperazinyl may be optionally replaced with an independently selected $C_{1-4}$alkyl. In another aspect of this embodiment, $R^{20}$ is a $C_{1-4}$alkyl.

In another embodiment of the compounds of Formula (Vb), or a pharmaceutically acceptable salt thereof, $R^{19}$ is hydrogen.

The compounds of the present invention are useful as both prophylactic and therapeutic treatments for diseases or conditions related to the inhibition of ACC, preferably ACC2.

Thus, as a further aspect, the invention relates to a method for treating a disease or condition related to the inhibition of ACC, preferably ACC2, comprising administration of an effective therapeutic amount of a compound of formula (I), (II), (IIa) (IIb), (III), (IIIa), (IIIb), (IV), (IVa), (IVb), (V), (Va), or (Vb), or a pharmaceutically acceptable salt thereof.

Compounds of formula (I), (II), (IIa) (IIb), (III), (IIIa), (IIIb), (IV), (IVa), (IVb), (V), (Va), or (Vb), or a pharmaceutically acceptable salt thereof, may be useful in the treatment of metabolic disorders, or conditions, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, hypertension, chronic heart failure, edema and hyperuricaemia.

Compounds of formula (I), (II), (IIa) (IIb), (III), (IIIa), (IIIb), (IV), (IVa), (IVb), (V), (Va), or (Vb), or a pharmaceutically acceptable salt thereof, may, for example, be used to treat various diseases or disorders such as type 1 diabetes, type 2 diabetes mellitus, hyperlipidemia, idiopathic type 1 diabetes, latent autoimmune diabetes in adults, early-onset type 2 diabetes, youth-onset atypical diabetes, maturity onset diabetes of the young, malnutrition-related diabetes and gestational diabetes, coronary heart disease, ischemic stroke, restenosis after angioplasty, peripheral vascular disease, arterial occlusive disease, intermittent claudication, myocardial infarction, dyslipidemia, mixed dyslipidemia, post-prandial lipemia, conditions of impaired glucose tolerance, conditions of impaired fasting plasma glucose, metabolic acidosis, ketosis, arthritis, osteoporosis, diabetic hypertension, familial chylomicromia syndrome, congestive heart failure, left ventricular hypertrophy, peripheral arterial disease, diabetic retinopathy, other ophthalmic complications of diabetes, macular degeneration, cataract, diabetic nephropathy, diabetic foot ulcer, glomerulosclerosis, chronic renal failure, diabetic neuropathy, peripheral angiopathy, peripheral angiopathy gangrene, microangiopathic changes that result in amputation, cancer, cancer deaths, metabolic syndrome, syndrome X, Reaven syndrome, coronary heart disease, other acute and subacute forms of coronary ischemia, angina pectoris, thrombosis, atherosclerosis, myocardial infarction, transient ischemic attacks, stroke, vascular restenosis, hypoglycemia, hyperglycemia, hyperuricemia, hyperinsulinemia, hyperlipidemia, hypertryglyceridemia, hypercholesterolemia, high blood pressure, excessive cardiovascular morbidity, and cardiovascular mortality in diabetics, elevated non-HDL cholesterol, decreased HDL cholesterol, elevated triglycerides, low high density lipoprotein, high low density lipoprotein, pancreatitis, insulin resistance, impaired glucose metabolism, conditions of impaired glucose tolerance, obesity, central obesity, nonalcoholic fatty liver disease, erectile dysfunction, skin and connective tissue disorders, foot ulcerations and ulcerative colitis, endothelial dysfunction and impaired vascular compliance, conditions characterized by low bone mass (e.g. osteopenia, osteoporosis, rheumatoid arthritis, osteoarthritis, periodontal disease, alveolar bone loss, osteotomy loss, childhood idiopathic bone loss, Paget's disease, bone loss due to metastatic cancer, osteolytic lesions, curvature of the spine, and loss of height), neurodegenerative disease, neurological disorders, seizure, peripheral sensory neuropathy, lipid disorders, cognitive impairment (learning and memory conditions) and dementia.

It is also well-established that metabolic diseases exert a negative influence on other physiological systems. Thus, there is often the codevelopment of multiple disease states (e.g. type I diabetes, type II diabetes, inadequate glucose tolerance, insulin resistance, hyperglycemia, hyperlipidemia, hypertriglyceridemia, hypercholesterolemia, dyslipidemia, obesity or cardiovascular disease in "Syndrome X") or secondary diseases which clearly occur secondary to diabetes (e.g. kidney disease, peripheral neuropathy). Thus, it is expected that effective treatment of the diabetic condition will in turn be of benefit to such interconnected disease states.

In one embodiment, compounds of formula (I), (II), (IIa) (IIb), (III), (IIIa), (IIIb), (IV), (IVa), (IVb), (V), (Va), or (Vb), or a pharmaceutically acceptable salt thereof, may be useful for treating a disorder selected from type 1 and type 2 diabetes mellitus, or complications of diabetes.

In another embodiment, the invention provides a method for treating a metabolic syndrome, such as Syndrome X, diabetes, insulin resistance, decreased glucose tolerance, non-insulin-dependent diabetes mellitus, Type II diabetes, Type I diabetes, diabetic complications, body weight disorders, or leptin related diseases, comprising administering to a mammal in need thereof a therapeutically effective amount of a compound according to formula (I), (II), (IIa) (IIb), (III), (IIIa), (IIIb), (IV), (IVa), (IVb), (V), (Va), or (Vb), or a pharmaceutically acceptable salt thereof. In another embodiment, the metabolic syndrome is dyslipidemia, obesity, insulin resistance, hypertension, microalbuminemia, hyperuricaemia, or hypercoagulability.

In another embodiment, the invention provides a method for treating insulin resistance, decreased glucose tolerance, non-insulin-dependent diabetes mellitus, Type II diabetes, or Type I diabetes, comprising administering to a mammal in need thereof a therapeutically effective amount of a compound according to formula (I), (II), (IIa) (IIb), (III), (IIIa), (IIIb), (IV), (IVa), (IVb), (V), (Va), or (Vb), or a pharmaceutically acceptable salt thereof.

In another embodiment, the invention provides a method for treating a bodyweight disorder such as obesity, overweight, cachexia or anorexia, comprising administering to a mammal in need thereof a therapeutically effective amount of a compound according to formula (I), (II), (IIa) (IIb), (III), (IIIa), (IIIb), (IV), (IVa), (IVb), (V), (Va), or (Vb), or a pharmaceutically acceptable salt thereof.

Compounds of formula (I), (II), (IIa) (IIb), (III), (IIIa), (IIIb), (IV), (IVa), (IVb), (V), (Va), or (Vb), or a pharmaceutically acceptable salt thereof, may be also suitable for preventing beta-cell degeneration such as apoptosis or necrosis of pancreatic beta cells, for improving or restoring the functionality of pancreatic cells, increasing the number and size of pancreatic beta cells, for use as diuretics or antihypertensives and for the prevention and treatment of acute renal failure.

In one embodiment, the invention provides a method of treating an HCV-associated disorder comprising administering to a subject in need thereof a therapeutically effective amount of a compound of the invention, e.g., a compound of any one according to Formula (I), (II), (IIa) (IIb), (III), (IIIa), (IIIb), (IV), (IVa), (IVb), (V), (Va), or (Vb), or a pharmaceutically acceptable salt thereof, such that the HCV-associated disorder is treated.

In another embodiment, the invention provides a method of inhibiting or preventing the activity of HCV in a subject in need thereof, comprising administering to the subject a therapeutically effective amount of a compound according to any one of Formula (I), (II), (IIa) (IIb), (III), (IIIa), (IIIb), (IV), (IVa), (IVb), (V), (Va), or (Vb), or a pharmaceutically acceptable salt thereof. In one embodiment, the compounds of the invention inhibit the activity of the ACC1, ACC2 or both ACC1 and ACC2.

In another embodiment, the invention provides a method of decreasing the HCV RNA load in a subject in need thereof comprising administering to the subject a therapeutically effective amount of a compound according to any one of Formula (I), (II), (IIa) (IIb), (III), (IIIa), (IIIb), (IV), (IVa), (IVb), (V), (Va), or (Vb), or a pharmaceutically acceptable salt thereof.

In still another embodiment, the invention provides a method of treating an HCV-associated disorder comprising administering to a subject in need thereof a therapeutically effective amount of a compound according to any one of Formula (I), (II), (IIa) (IIb), (III), (IIIa), (IIIb), (IV), (IVa), (IVb), (V), (Va), or (Vb), or a pharmaceutically acceptable salt thereof, in combination with a pharmaceutically effective amount of an additional HCV-modulating compound, such as interferon or derivatized interferon, or a cytochrome P450 monooxygenase inhibitor, such that the HCV-associated disorder is treated. In one embodiment, the additional HCV-modulating compound is selected from the group consisting of DEB025 (i.e., alisporivir, Novartis), NIM811, ITMN191, MK-7009, TMC 435350, Sch 503034 and VX-950 (i.e., telaprevir, Vertex Pharmaceuticals).

In another embodiment, the invention provides a method of inhibiting hepatitis C virus replication in a cell, comprising contacting said cell with a compound according to any one of Formula (I), (II), (IIa) (IIb), (III), (IIIa), (IIIb), (IV), (IVa), (IVb), (V), (Va), or (Vb), or a pharmaceutically acceptable salt thereof.

In yet another embodiment, the invention provides a packaged HCV-associated disorder treatment, comprising an HCV-modulating compound according to any one of Formula (I), (II), (IIa) (IIb), (III), (IIIa), (IIIb), (IV), (IVa), (IVb), (V), (Va), or (Vb), or a pharmaceutically acceptable salt thereof, packaged with instructions for using an effective amount of the HCV-modulating compound to treat an HCV-associated disorder.

In certain embodiments, the HCV-associated disorder is selected from the group consisting of HCV infection, liver cirrhosis, chronic liver disease, hepatocellular carcinoma, cryoglobulinaemia, non-Hodgkin's lymphoma, liver fibrosis and a suppressed innate intracellular immune response.

In another embodiment, the invention provides a method of treating HCV infection, liver cirrhosis, chronic liver disease, hepatocellular carcinoma, cryoglobulinaemia, non-Hodgkin's lymphoma, liver fibrosis or a suppressed innate intracellular immune response in a subject in need thereof comprising administering to the subject a therapeutically effective amount of a compound according to any one of Formula (I), (II), (IIa) (IIb), (III), (IIIa), (IIIb), (IV), (IVa), (IVb), (V), (Va), or (Vb), or a pharmaceutically acceptable salt thereof.

In one embodiment, the HCV to be treated is selected of any HCV genotype. In another embodiment, the HCV is selected from HCV genotype 1, 2, 3, and/or 4.

As the product of the ACC reaction, malonyl CoA, is a substrate for FAS, and it is expected that inhibition of ACC will result in either, the selective destruction of, or a reduction in proliferation of, cancerous cells, particularly tumors containing cells overexpressing FAS or ACC, including prostate and breast cancers. Thus, in another embodiment, the invention provides a method of treating cancer in a subject in need thereof comprising administering to the subject a therapeutically effective amount of a compound according to any one of Formula (I), (II), (IIa) (IIb), (III), (IIIa), (IIIb), (IV), (IVa), (IVb), (V), (Va), or (Vb), or a pharmaceutically acceptable salt thereof.

A compound of formula (I), (II), (IIa) (IIb), (III), (IIIa), (IIIb), (IV), (IVa), (IVb), (V), (Va), or (Vb), or a pharmaceutically acceptable salt thereof, may be usefully combined with another pharmacologically active compound, or with two or more other pharmacologically active compounds, for use in therapy. For example, a compound of the formula (I), (II), (IIa) (IIb), (III), (IIIa), (IIIb), (IV), (IVa), (IVb), (V), (Va), or (Vb), or a pharmaceutically acceptable salt thereof, may be administered simultaneously, sequentially or separately in combination with one or more agents for the treatment of disorders previously listed.

In one embodiment, the other therapeutic agent is another anti-obesity agents, anorectic agents, appetite suppressant and related agents. Diet and/or exercise can also have synergistic effects. Anti-obesity agents include, but are not limited to, apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, β3 adrenergic receptor agonists, dopamine agonists (for example, bromocriptine), melanocyte-stimulating hormone receptor analogs, cannabinoid 1 receptor antagonists [for example, compounds described in WO2006/047516), melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Where compounds of the invention are administered in conjunction with other therapies, dosages of the co-administered compounds will of course vary depending on the type of co-drug employed, on the specific drug employed, on the condition being treated and so forth. A combined preparation or pharmaceutical composition can comprise a compound of the invention as defined above or a pharmaceutical acceptable salt thereof and at least one additional active ingredient selected from:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; cholesterylester transfer protein inhibitors (CETP inhibitors); RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin— Example 1 of WO 00/34241), MK-0431, saxagliptin, GSK23A; an AGE breaker; a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid described in the patent application WO 03/043985, as compound 19 of Example 4, a non-glitazone type PPAR gamma agonist e.g. GI-262570; Monoacylglycerol O-acyltransferase 2 inhibitots (MGAT-2) inhibitors; Diacylglycerol acetyltransferase (DGAT) inhibitors such as those disclosed in WO 2005044250, WO 2005013907, WO 2004094618 and WO 2004047755;

b) hypolipidemic agents such as 3-hydroxy-3-methyl-glutaryl coenzyme A (HMG-CoA) reductase inhibitors, e.g., lovastatin and related compounds such as those disclosed in U.S. Pat. No. 4,231,938, pitavastatin, simvastatin and related compounds such as those disclosed in U.S. Pat. Nos. 4,448,784 and 4,450,171, pravastatin and related compounds such as those disclosed in U.S. Pat. No. 4,346,227, cerivastatin, mevastatin and related compounds such as those disclosed in U.S. Pat. No. 3,983,140, velostatin, fluvastatin, dalvastatin, atorvastatin, rosuvastatin and related statin compounds disclosed in U.S. Pat. No. 5,753,675, rivastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl) pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S.

Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as a CB1 activity modulator, melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a SCD-1 inhibitor as disclosed in WO2005011655, a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine;

d) anti-hypertensive agents such as loop diuretics such as ethacrynic acid, furosemide and torsemide; diuretics such as thiazide derivatives, chlorithiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren, terlakiren, ditekiren, RO 66-1132, RO-66-1168; beta-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; aldosterone synthase inhibitors; and dual ET/AII antagonist such as those disclosed in WO 00/01389;

e) a HDL increasing compound, such as niacin, fibrates (e.g., Lopid, others) and statins;

f) Cholesterol absorption modulator such as Zetia® and KT6-971;

g) Apo-A1 analogues and mimetics;

h) thrombin inhibitors such as Ximelagatran;

i) aldosterone inhibitors such as anastrazole, fadrazole, eplerenone;

j) Inhibitors of platelet aggregation such as aspirin, clopidogrel bisulfate;

k) estrogen, testosterone, a selective estrogen receptor modulator, a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, compounds decreasing the protein kinase activity such as a PDGF receptor tyrosine kinase inhibitor preferably Imatinib ({N-{5-[4-(4-methyl-piperazino-methyl)-benzoylamido]-2-methylphenyl}-4-(3-pyridyl)-2-pyrimidine-amine}) described in the European patent application EP-A-0 564 409 as example 21 or 4-Methyl-N-[3-(4-methyl-imidazol-1-yl)-5-trifluoromethyl-phenyl]-3-(4-pyridin-3-yl-pyrimidin-2-ylamino)-benzamide described in the patent application WO 04/005281 as example 92;

m) an agent interacting with a $5\text{-}HT_3$ receptor and/or an agent interacting with $5\text{-}HT_4$ receptor such as tegaserod described in the U.S. Pat. No. 5,510,353 as example 13, tegaserod hydrogen maleate, cisapride, cilansetron;

n) an agent for treating tobacco abuse, e.g., nicotine receptor partial agonists, bupropion hypochloride (also known under the tradename Zyban®) and nicotine replacement therapies;

o) an agent for treating erectile dysfunction, e.g., dopaminergic agents, such as apomorphine), ADD/ADHD agents (e.g., Ritalin®, Strattera®, Concerta® and Adderall®);

p) an agent for treating alcoholism, such as opioid antagonists (e.g., naltrexone (also known under the tradename ReVia®) and nalmefene), disulfuram (also known under the tradename Antabuse®), and acamprosate (also known under the tradename Campral®)). In addition, agents for reducing alcohol withdrawal symptoms may also be co-administered, such as benzodiazepines, beta-blockers, clonidine, carbamazepine, pregabalin, and gabapentin (Neurontin®);

q) other agents that are useful including anti-inflammatory agents (e.g., COX-2 inhibitors); antidepressants (e.g., fluoxetine hydrochloride (Prozac®)); cognitive improvement agents (e.g., donepezil hydrochloride (Aircept®) and other acetylcholinesterase inhibitors); neuroprotective agents (e.g., memantine); antipsychotic medications (e.g., ziprasidone (Geodon®), risperidone (Risperdal®), and olanzapine (Zyprexa®));

or, in each case a pharmaceutically acceptable salt thereof; and optionally a pharmaceutically acceptable carrier.

In one embodiment, the other therapeutic agent is selected from DPP4 inhibitors, renin inhibitors, angiotensin 2 receptor blockers, HMG-co-A reductase inhibitors, GLP mimetics, PPAR-agonists, beta-2 angiotensin receptor blockers, ACE inhibitors, niacin, glyburide, exendin, metformin and diuretics.

Such combinations may offer significant advantages, including synergistic activity, in therapy.

In another embodiment, the therapy is the treatment of a viral infection or disease associated with viral infection or HCV associated disease. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the other therapeutic agent is selected from second therapeutic agents that are active against viruses and, in particular, against HCV. The compound and agent may be administered in a single or separate formulations. Agents active against HCV include, but are not limited to, interferon-α, pegylated interferon-α (peginterferon-α), albinterferon-α2b (albIFN, Novartis/Human Genome Science), PEG-Interferon lambda (BMS/ZymoGenetics), ribavirin, levovirin, viramidine, a combination of interferon-α and ribavirin, a combination of peginterferon-α and ribavirin, a combination of albIFN and ribavirin, a combination of interferon-α and levovirin, a combination of peginterferon-α and levovirin, and a combination of albIFN and levovirin. Interferon-α includes, but is not limited to, recombinant interferon-α2a (such as ROFERON interferon available from Hoffman-LaRoche, Nutley, N.J.), interferon-α2b (such as Intron-A interferon available from Merck & Co., Kenilworth, N.J., USA), a consensus interferon, and a purified interferon-α product. Pegylated interferon-α includes, but is not limited to, PEG IFN-α2a (such as Pegsys available from Hoffman-LaRoche, Nutley, N.J.), PEG IFN-α2b (such as PegIntron available from Schering Corp., Kenilworth, N.J., USA), For a discussion of ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.*, 35:201-210 (2000).

The agents active against hepatitis C virus also include agents that inhibit HCV NS2 or NS3 proteases, HCV NS5B polymerase, HCV NS5A protein, HCV NS3 helicase, HCV NS4B protein, HCV p7 protein, HCV NS4A protein, HCV IRES and protein translation, HCV entry, HCV assembly, HCV egress, and inosine 5'-monophosphate dehydrogenase, cyclophilins or other host factors that are required for HCV replication. Still other compounds include those disclosed in WO 2004/014313 and WO 2004/014852 and in the references cited therein.

Specific antiviral agents include BI-201335 (Boehringer Ingelheim), telaprevir (Vertex), VX-813 (Vertex), VX-500 (Vertex), boceprevir (Schering-Plough), Sch 900518 (Schering-Plough), ITMN-191/R7227 (Intermune/Roche), ITMN-5489 (Intermune), MK-7009 (Merck), TMC435 (Tibotec), BMS-650032 (Bristol-Myers-Squibb), PHX1766 (Phenomix), GS-9256 (Gilead), VCH-916 (Vertex), VCH-759 (Vertex), VCH-222/VX-222 (Vertex), ABT-333 (Abbott), ANA-598 (Anadys), PF-868,554 (Pfizer), MK-3281 (Merck), PSI-7851 (Pharmasset), R7128 (Pharmasset/Roche), R1626 (Roche), GS9190 (Gilead), BI-207127 (Boehringer Ingelheim), JTK-652 (Japan Tobacco Inc.), IDX375 (Idenix), Valopicitabine/NM283 (Idenix), IDX-184 (Idenix), AZD2836/A-831 (Arrow/AstraZeneca), AZD7295/A-689 (Arrow/AstraZeneca), BMS-790052 (Bristol-Myers-Squibb), PPI-461 (Presidio), EDP-239 (Enanta), Ceplene (Maxim Pharmaceuticals), Civacir (Nabi Biopharmaceuticals Inc, VX-497 (Vertex Pharmaceuticals Inc.), XTL-002 (XTL Biopharmaceuticals), isatoribine and its prodrugs ANA971, ANA975 and ANA773 (Anadys), NIM811 (Novartis), DEB025 (DebioPharm/Novartis), SCY-635 (Scynexis), nitazoxanide (Romark), IDN-6556 (Idun Pharmaceuticals), IP-501 (Indevus Pharmaceuticals), and ISIS 14803 (ISIS Pharmaceuticals Inc.).

In some embodiments, the compositions and methods of the present invention contain a compound of the invention and interferon. In some aspects, the interferon is selected from the group consisting of interferon alpha 2B, pegylated interferon alpha, consensus interferon, interferon alpha 2A, and lymphoblastoid interferon tau.

In other embodiments the compositions and methods of the present invention contain a compound of the invention and a compound having anti-HCV activity is selected from the group consisting of interleukin 2, interleukin 6, interleukin 12, a compound that enhances the development of a type 1 helper T cell response, interfering RNA, anti-sense RNA, Imiquimod, ribavirin, an inosine 5'-monophospate dehydrogenase inhibitor, amantadine, and rimantadine.

In still other embodiments, the compound having anti-HCV activity is Ribavirin, levovirin, viramidine, thymosin alpha-1, an inhibitor of NS3 serine protease, and inhibitor of inosine monophosphate dehydrogenase, interferon-alpha, or pegylated interferon-alpha alone or in combination with Ribavirin or viramidine.

In another embodiments, the compound having anti-HCV activity is said agent active against HCV is interferon-alpha or pegylated interferon-alpha alone or in combination with Ribavirin or viramidine.

The present invention is also in relation to a pharmaceutical composition comprising a compound of formula (I), (II), (IIa) (IIb), (III), (IIIa), (IIIb), (IV), (IVa), (IVb), (V), (Va), or (Vb), or a pharmaceutically acceptable salt thereof, and pharmaceutically acceptable excipients.

The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 0.1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

General Synthetic Aspects

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

In general, starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl $4^{th}$ Ed. 1952, Methods of Organic Synthesis, Thieme, Volume 21).

Typically, the compounds of formula (I), (II), (IIa) (IIb), (III), (IIIa), (IIIb), (IV), (IVa), (IVb), (V), (Va), or (Vb) can be prepared according to the Schemes provided infra.

Method of Preparation

The invention provides, in another aspect, a process for preparing a compound of formula (I). The schemes detailed below show general schemes for synthesizing compounds of formula (I). In the reactions described in the schemes herein below, any reactive group present, such as hydroxyl, amino, carbonyl or imino groups may be protected during the reaction by conventional protecting groups such as trimethylsilyl, tert-butyldimethylsilyl, benzyl, acetal, ketal etc., which are cleaved again after the reaction.

The following schemes represent general procedures used to synthesize compounds in this application. Unless otherwise stated, the variables in the schemes below are as defined above for Formulas (I), (II), (IIa) (IIb), (III), (IIIa), (IIIb), (IV), (IVa), (IVb), (V), (Va), and (Vb).

Scheme A provides a method of preparing compounds of the invention in which $L^1$ is —SO$_2$NH— and Q is —C(O)X$^4$—R$^3$. In Scheme A, a trans-aminocyclohexane carboxylic acid (i) in which the amino group is protected with an amine protecting group such as a Boc protecting group, is condensed with an amine or alcohol (ii) using standard amide or ester forming conditions to produce an amino-protected trans-aminocyclohexane carboxamide or carboxylic ester (iii). The amine protecting group is removed to provide (iv) which is then condensed with an appropriate sulfonyl chloride (v) in the presence of a base to yield a compound of the invention (I-a). The sulfonyl chloride in this scheme is either commercially available or is prepared from a commercially available sulfonic acid or aniline by methods known in the art.

Scheme A

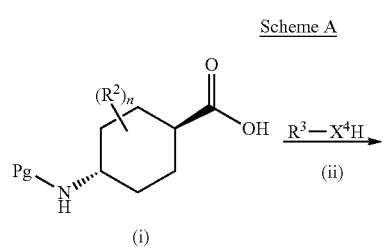

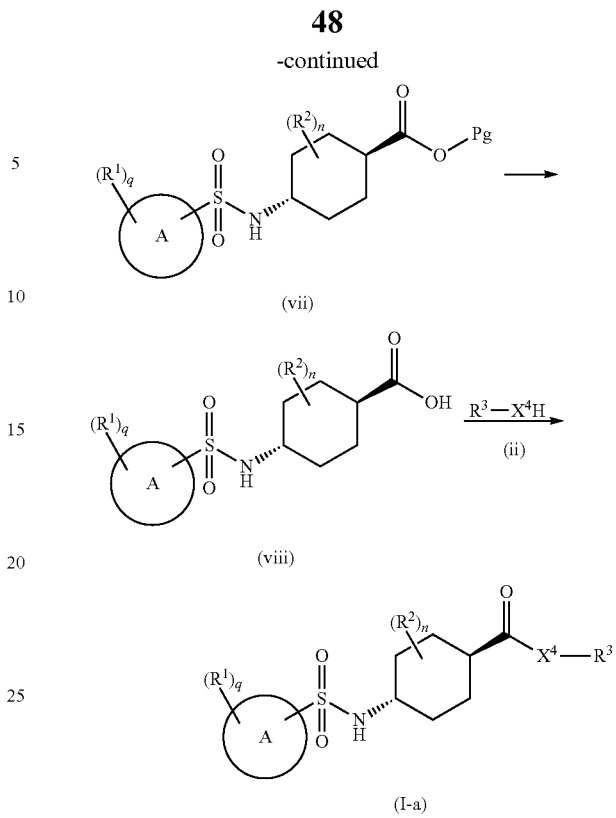

Wherein Pg is a protecting group.

Scheme B provides an alternative method of preparing compounds of the invention in which $L^1$ is —$SO_2NH$— and Q is —$C(O)X^4$—$R^3$. In Scheme B, an appropriate sulfonyl chloride (v) is condensed with a trans-aminocyclohexane carboxylic acid in which the carboxylic acid group is protected (vi) (e.g., as an ester, such as a methyl ester) to form a sulfonamide (vii). The sulfonamide (vii) is treated to remove the carboxylic acid protecting group (for example an ester can be treated with a base) to form a carboxylic acid (viii). The carboxylic acid (viii) is then condensed with an amine or alcohol (ii) using standard amide or ester forming conditions to form a compound of the invention (I-a).

Wherein Pg is a Protecting group.

Scheme 1 illustrates one method for the preparation of a series of benzimidazole derivatives. Scheme 1 is generally applicable when using commercially available benzimidazole sulfonyl chlorides or sulfonic acids or other classes of sulfonic acids or sulfonyl chlorides that may be commercially available.

Examples which contain a free basic NH or a carboxylic acid substituent may be prepared via a protected (e.g., Boc) amine followed by deprotection as a final step, or, respectively, from the corresponding ester followed by ester hydrolysis as a final step. This variation may apply for any of the following general synthetic schemes.

Scheme 1

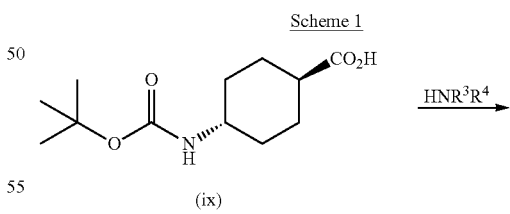

Scheme B

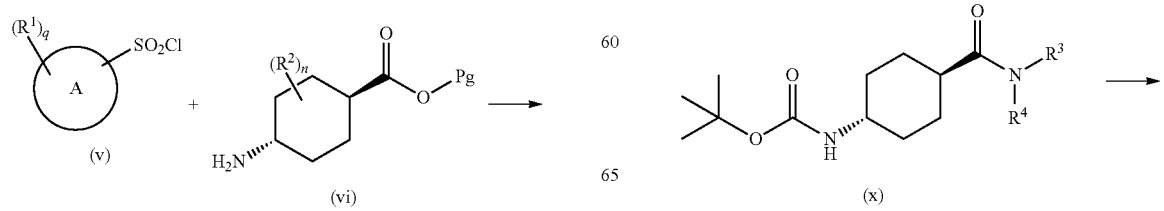

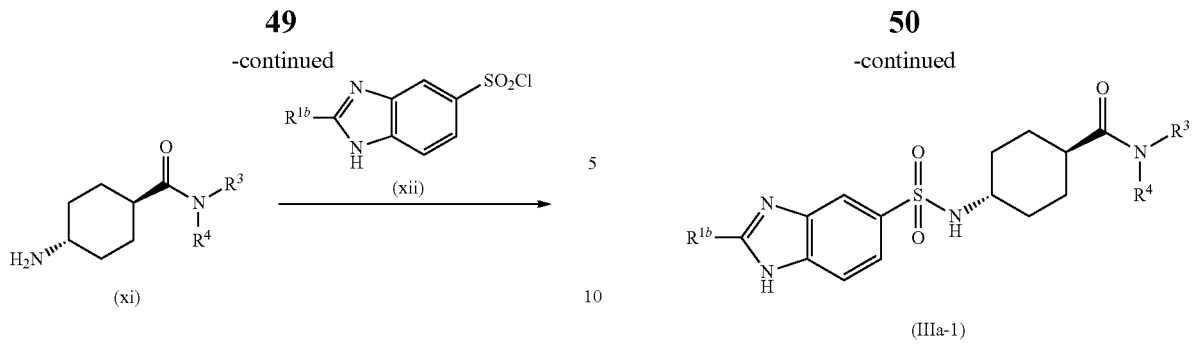

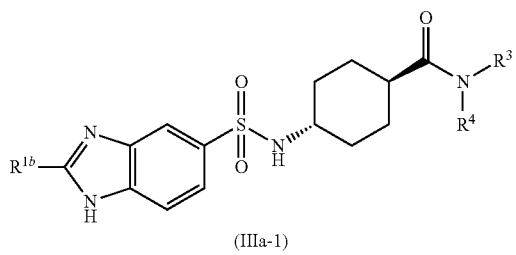

In this modification, the sulfonamide is formed first, followed by ester hydrolysis and carboxamide formation.

Another variation on Scheme 1 is shown below in Scheme 1B. This variation may be used for the preparation of compounds in which the central saturated ring is replaced by an aromatic ring.

Scheme 1B

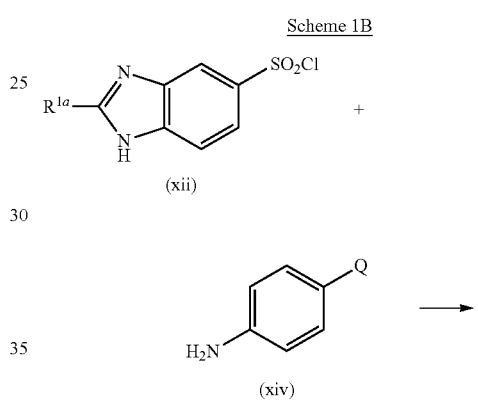

In the method of Scheme 1, a Boc-protected trans-aminocyclohexane carboxylic acid (ix) is condensed with an amine using standard amide forming conditions to produce the Boc-protected amino amide (x). Removal of the Boc protecting group, followed by condensation with an appropriate benzimidazole sulfonyl chloride (xii) yields the final product (IIIa-1). The sulfonyl chloride in this scheme is either commercially available or is prepared from a commercially available sulfonic acid.

In a variation on Scheme 1, the order of the sequence may be modified as shown below in Scheme 1A:

Scheme 1A

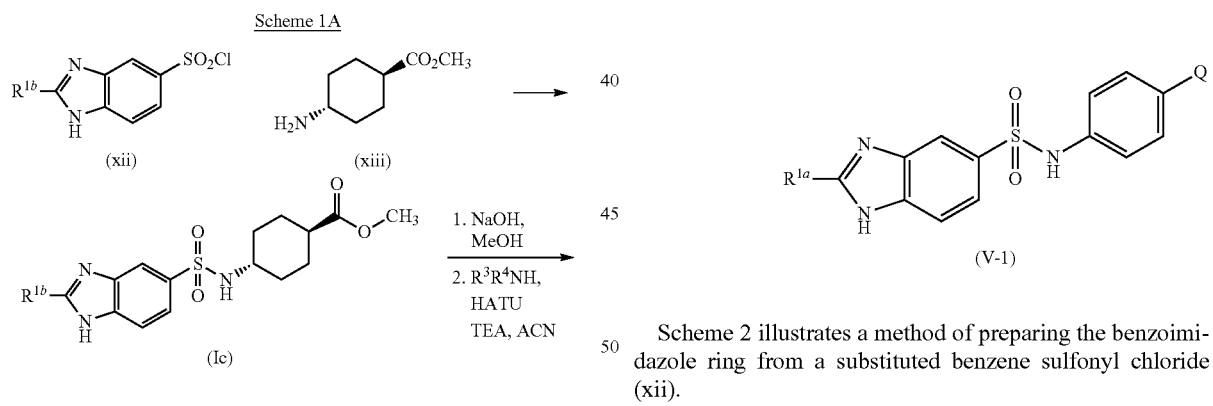

Scheme 2 illustrates a method of preparing the benzoimidazole ring from a substituted benzene sulfonyl chloride (xii).

Scheme 2

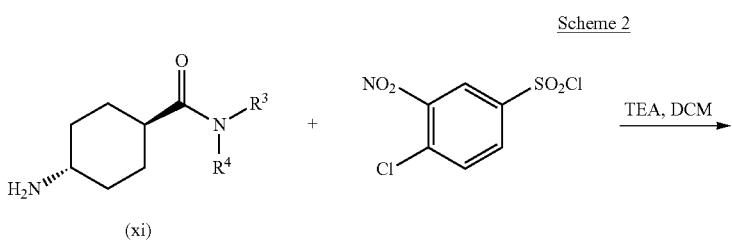

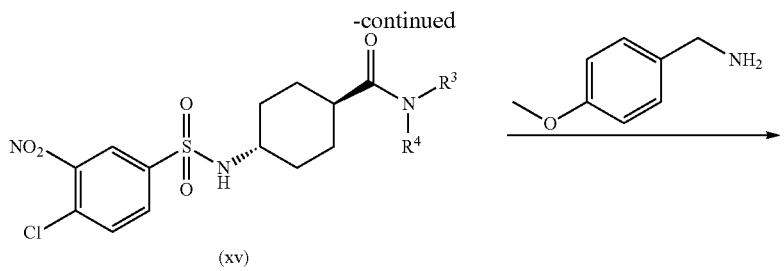

(xv)

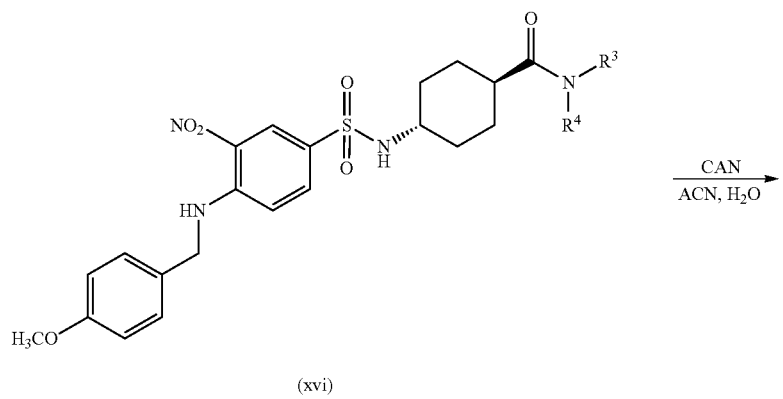

(xvi)

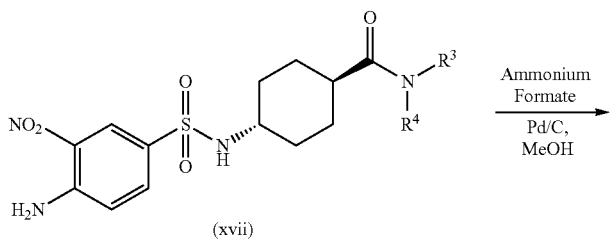

(xvii)

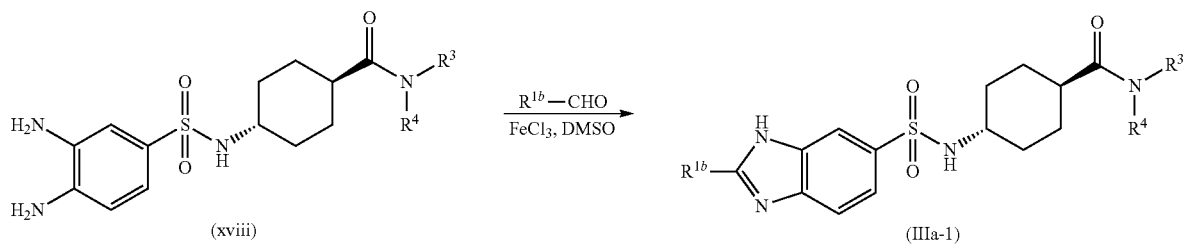

(xviii)  (IIIa-1)

The amino amide (xi) in Scheme 2 may be prepared as illustrated in Scheme 1. Condensation of the amine with the commercially available 4-chloro-3-nitrobenzene-1-sulfonyl chloride is carried out by the method of Scheme 1. The 4-chloro group is then displaced with m-methoxybenzyl amine followed by CAN-mediated oxidative removal of the p-methoxybenzyl group and reduction of the nitro group to give the diaminobenzene derivative (xviii). This diaminobenzene derivative (xviii) may then be condensed with an aldehyde under oxidative conditions (or with a carboxylic acid, followed by dehydrative cyclizing conditions) to give the substituted benzimidazole derivative (IIIa-1).

N-alkylated benzimidazoles may be prepared as shown in Scheme 3 below.

Scheme 3

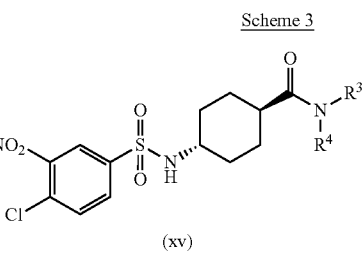

(xv)

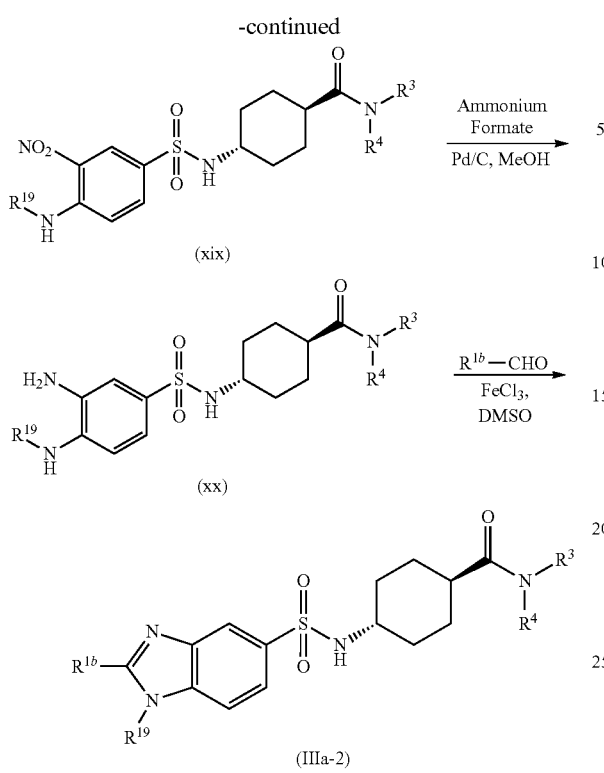

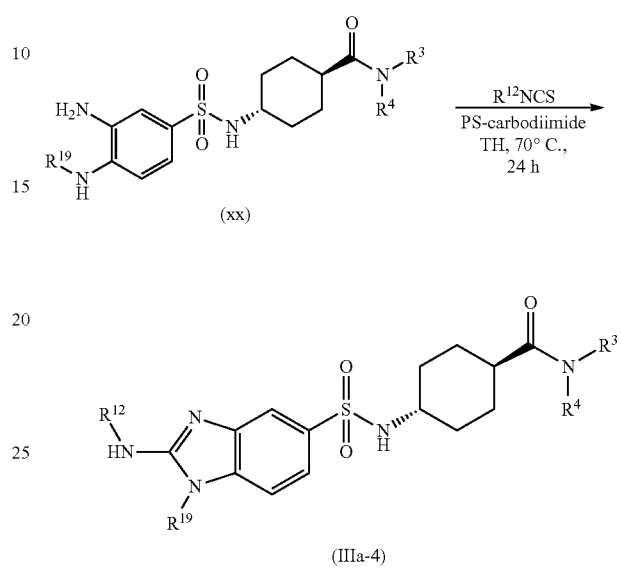

Following the procedure outlined in Scheme 3, the procedure of Scheme 4 may also be used to produce benzimidazole derivatives substituted on the benzimidazole nitrogen as shown in Scheme 4A.

This route is similar to Scheme 2 except that the amine ($R^{19}$—$NH_2$) used to displace the chlorine is left in place following the displacement, leading to formation of an alkylated diaminobenzene derivative (xx) that is subsequently condensed with an aldehyde as in Scheme 2.

Scheme 4 may be used to prepare benzimidazole derivatives in which $R^{1b}$ is an alkylamino or arylamino.

Scheme 5 can be used for the preparation of ester derivatives.

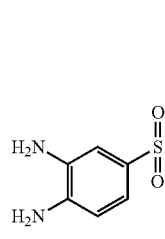

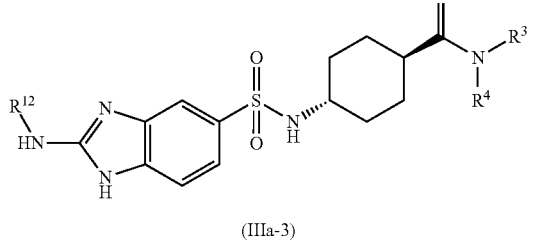

Wherein $R^{12}$ is $C_{1-7}$alkylamino, $C_{6-10}$arylamino, (3- to 10-membered heterocyclyl)amino, or (5- to 10-membered heteroaryl)amino.

In Scheme 4, the diaminobenzene derivative (xviii) (as prepared according to Scheme 2) is condensed with an isothiocyanate to form the substituted aminobenzimidazole Formula (IIIa-3).

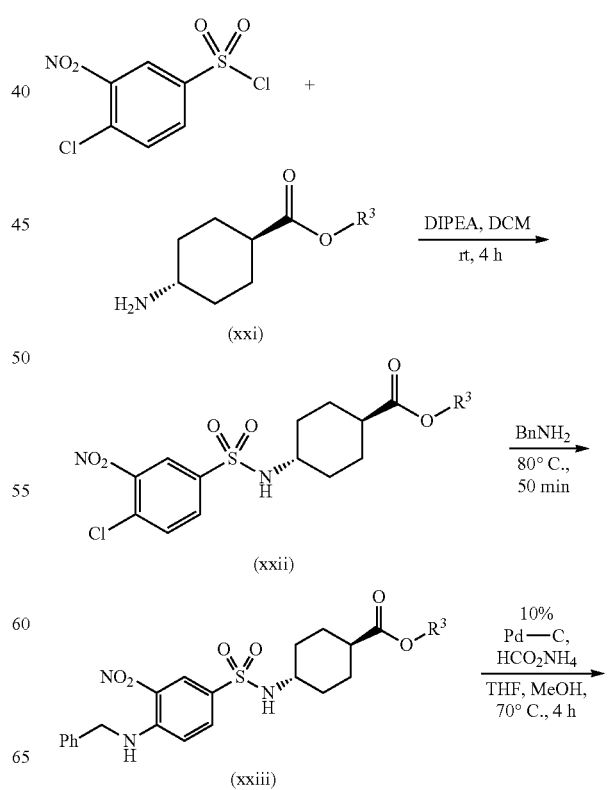

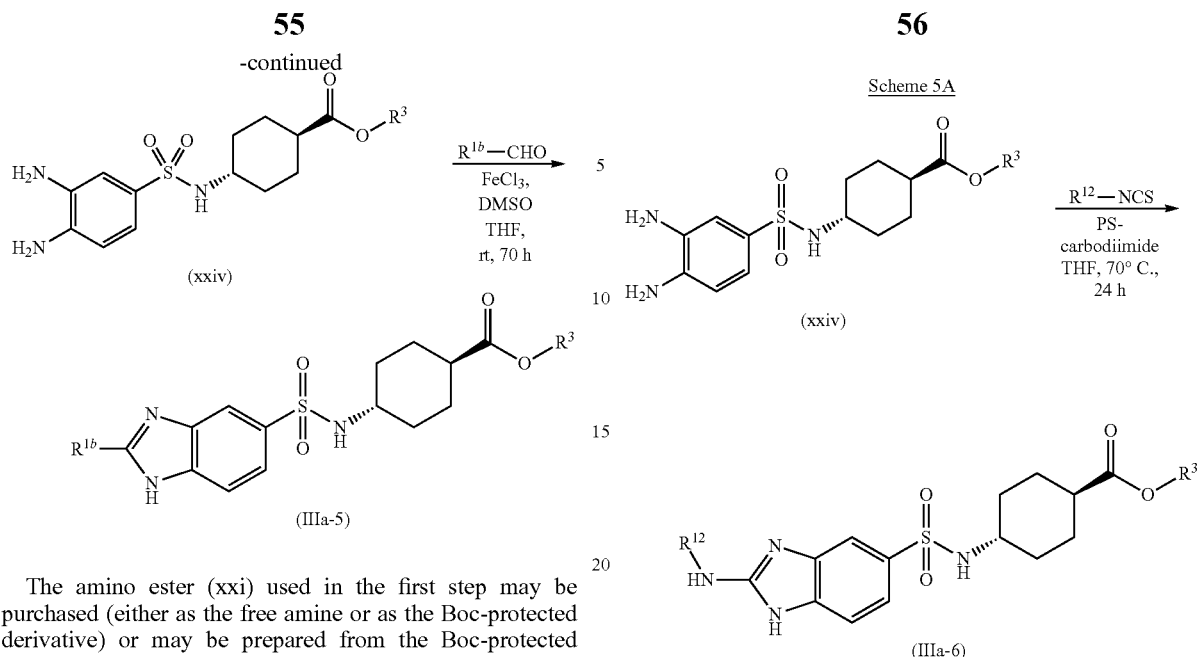

The amino ester (xxi) used in the first step may be purchased (either as the free amine or as the Boc-protected derivative) or may be prepared from the Boc-protected amine using standard methods for the preparation of esters.

A variation of Scheme 5 is shown in Scheme 5A and may be used for the preparation of ester derivatives of benzimidazoles with NH—$R^{12}$ in the 2-position:

Derivatives in which group Q is an oxadiazole are prepared according to Scheme 6.

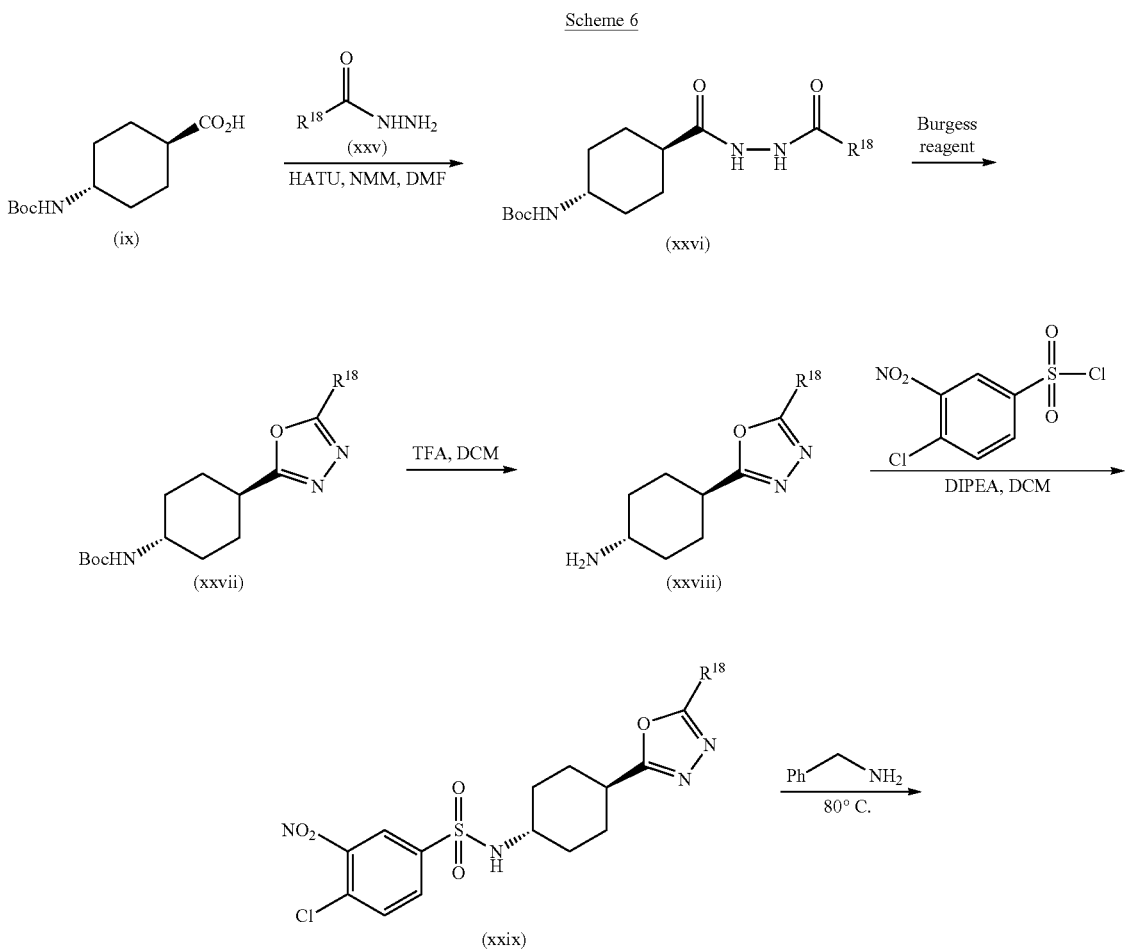

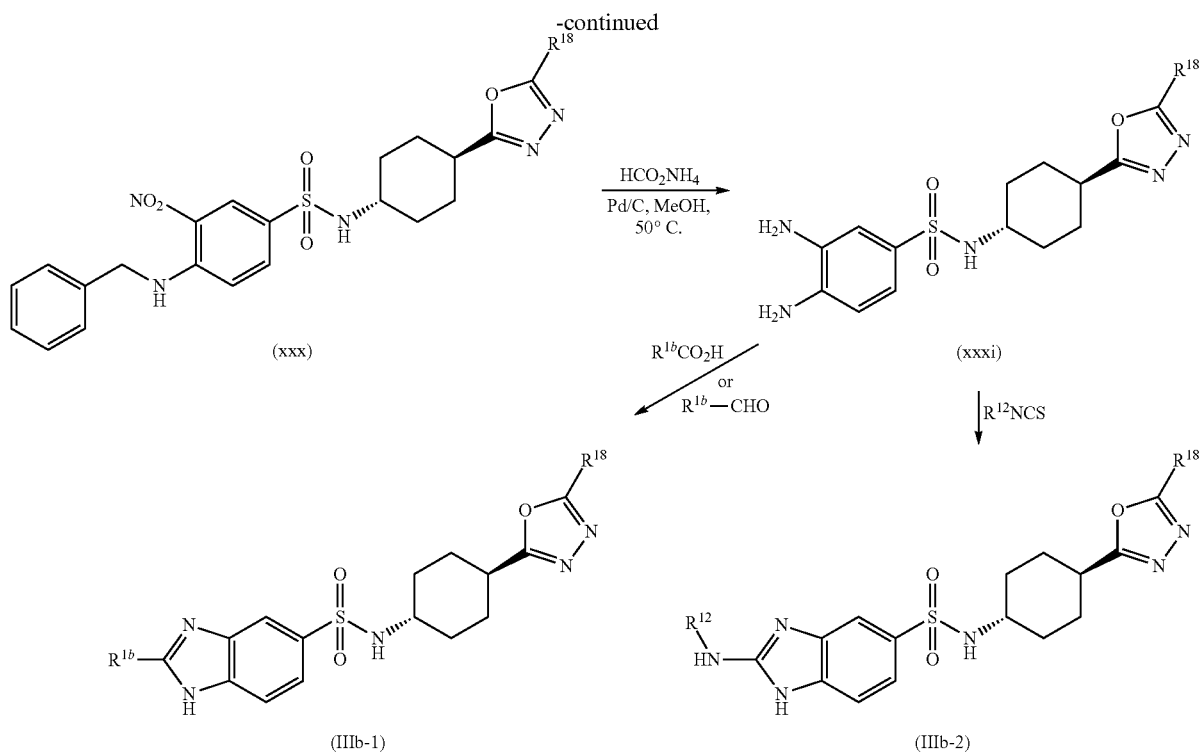

Scheme 6 is similar to the previous schemes except for the formation of the oxadiazole heterocycle. Analogs in which the benzimidazole moiety is replaced by an alternative aromatic or heterocyclic system may be prepared similarly.

As illustrated for Scheme 1, Schemes 2-6 may be applied in the preparation of analogs in which the saturated aliphatic central ring is replaced with an aromatic ring to provide compounds of the following type:

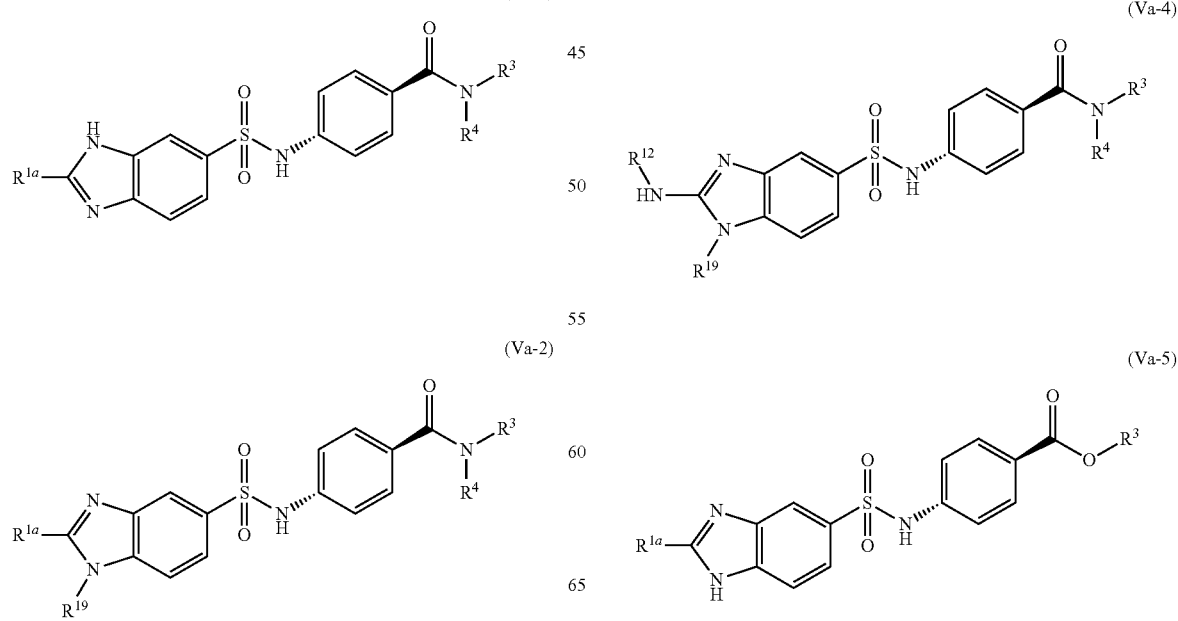

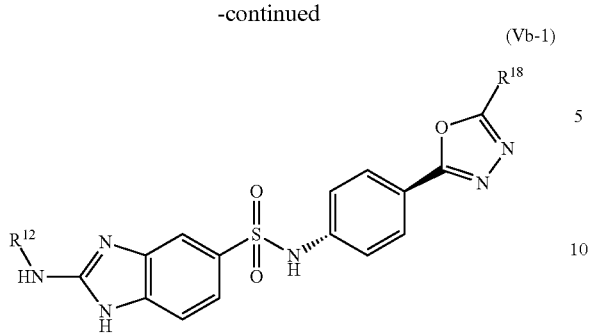

Analogs in which the benzimidazole moiety is replaced with an indole may be prepared by a number of methods as illustrated schematically below.

Indole analogs wherein the requisite indole sulfonic acid or sulfonyl chloride is commercially available may be prepared as described in Scheme 7.

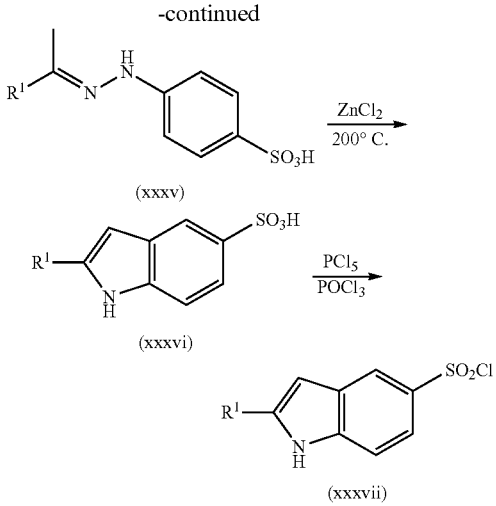

Scheme 7

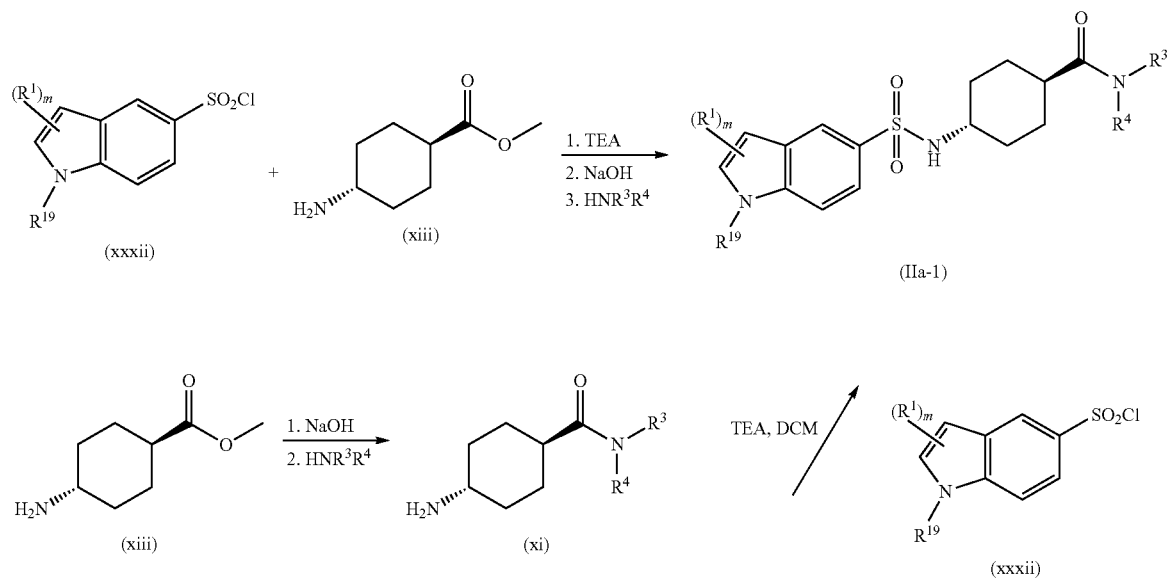

In this scheme, an indole sulfonyl chloride (xxxii) is condensed with either an amino ester (xiii) and then converted to a compound of Formula (IIa-1), or the amino ester (xiii) is first converted to an amino amide (xi) and then condensed with the indole sulfonyl chloride (xxxii) to form a compound of Formula (IIa-1). The methods used for the condensations are standard methods.

Indoles substituted with sulfonamides at the 5-position may be prepared according to Scheme 8.

Scheme 8

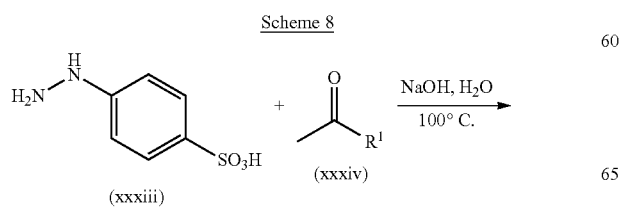

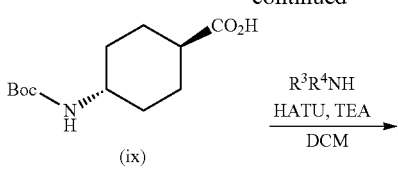

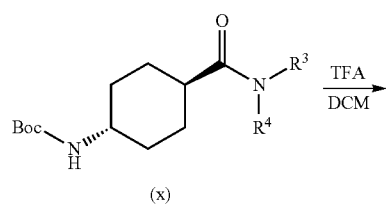

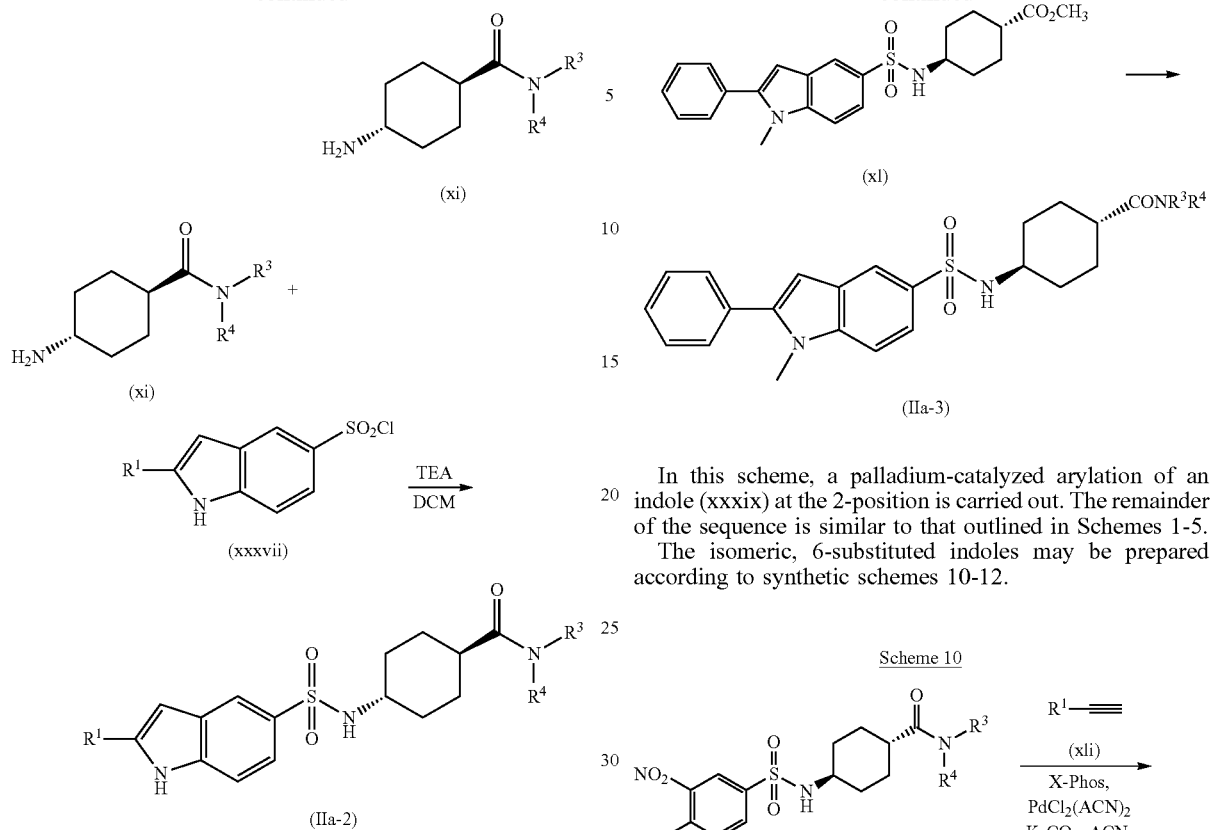

This scheme employs a variation on the Fischer indole synthesis to form the indole (xxxvii), followed by a sequence of reactions similar to those outlined in Schemes 1-5.

An alternate route to the preparation of 2-aryl substituted indoles was developed, as illustrated in Scheme 9.

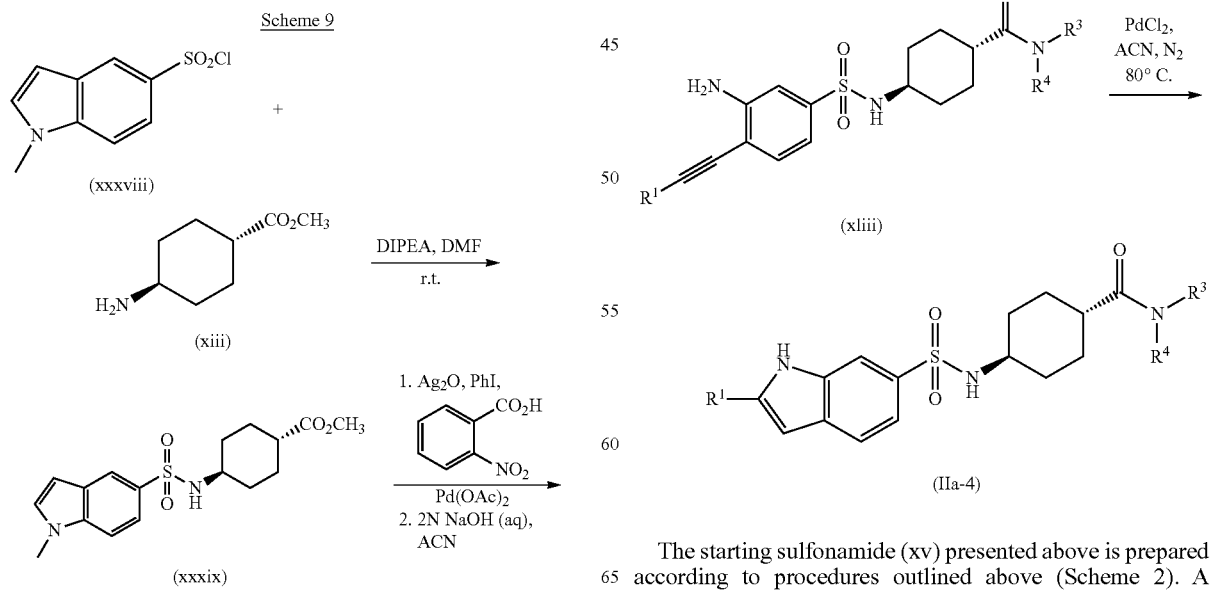

In this scheme, a palladium-catalyzed arylation of an indole (xxxix) at the 2-position is carried out. The remainder of the sequence is similar to that outlined in Schemes 1-5.

The isomeric, 6-substituted indoles may be prepared according to synthetic schemes 10-12.

Scheme 10

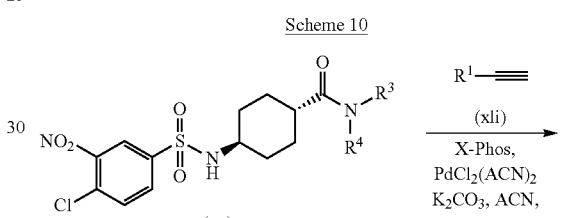

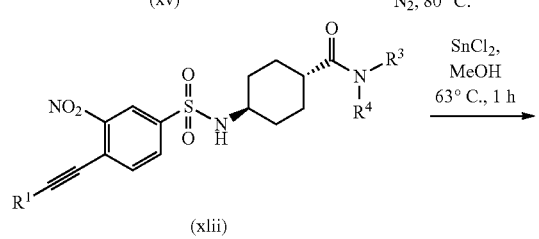

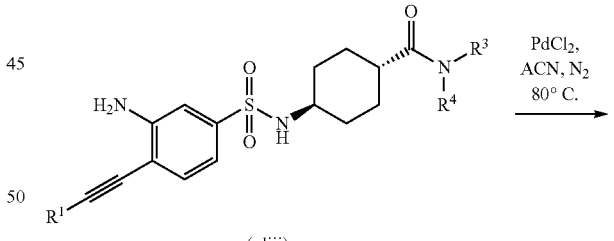

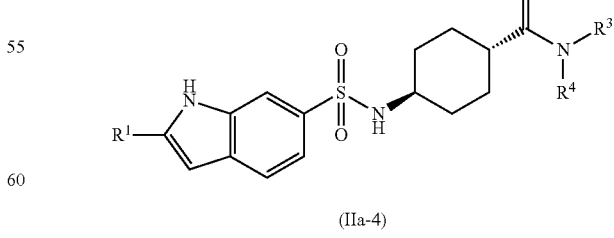

The starting sulfonamide (xv) presented above is prepared according to procedures outlined above (Scheme 2). A palladium-catalyzed addition of an aryl or an alkyl acetylene (xIi) to the aromatic ring with displacement of the chloro group, followed by selective reduction of the nitro group and palladium-catalyzed cyclization of the anilino-acetylene derivative (xliii) provides an indole (IIa-4).

Alternatively, the procedure may be modified so as to form the amide last as illustrated in Scheme 11.

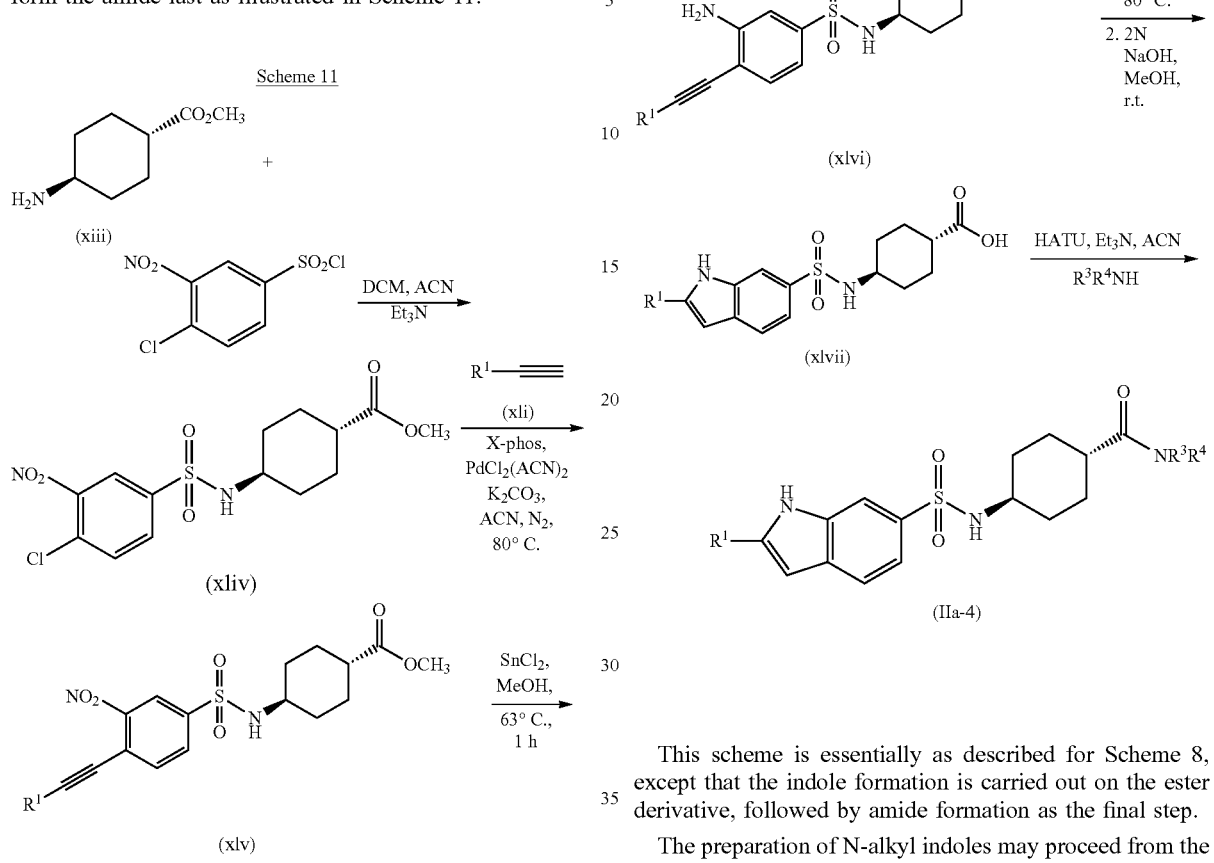

This scheme is essentially as described for Scheme 8, except that the indole formation is carried out on the ester derivative, followed by amide formation as the final step.

The preparation of N-alkyl indoles may proceed from the above acetylenic aniline as shown in Scheme 12.

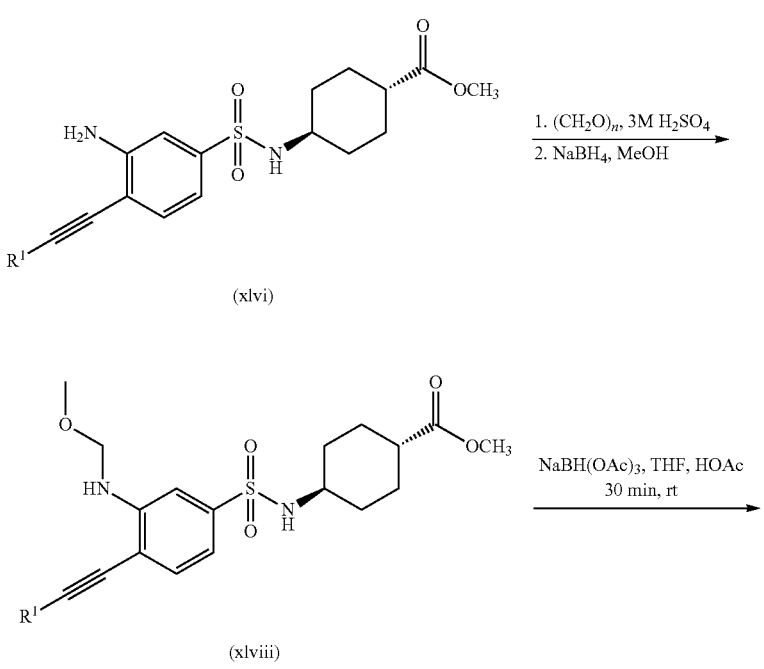

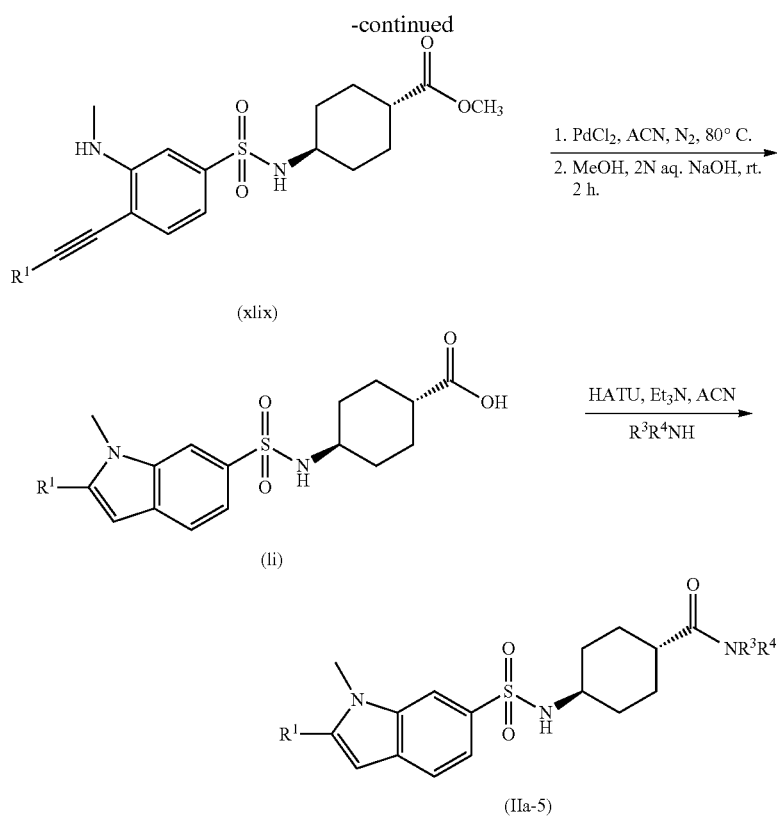

In Scheme 12, the acetylenic aniline derivative (xlvi) (prepared as outlined in either Scheme 11) is condensed with a carbonyl compound (aldehyde or ketone; paraformaldehyde in the above sequence) to form an imine which is reduced to the N-alkyl amine (xlviii). Palladium-catalyzed cyclization to the indole is then carried out to provide the indole derivative which is deprotected to give a carboxylic acid (li). The carboxylic acid (li) is then coupled with a primary or secondary amine to give a compound of the invention represented by Formula (IIa-5).

Scheme 13 illustrates the preparation of indole derivatives that are unsubstituted on the indole moiety.

Scheme 13

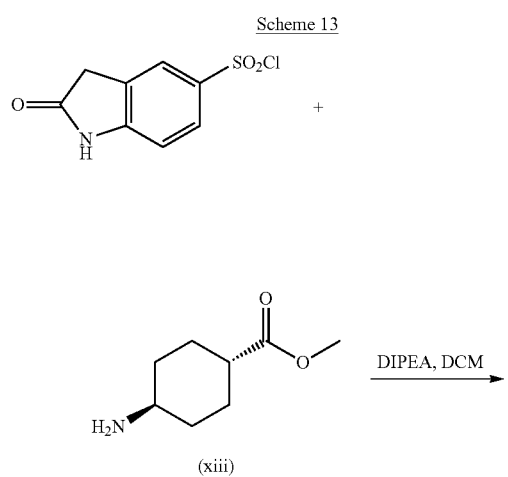

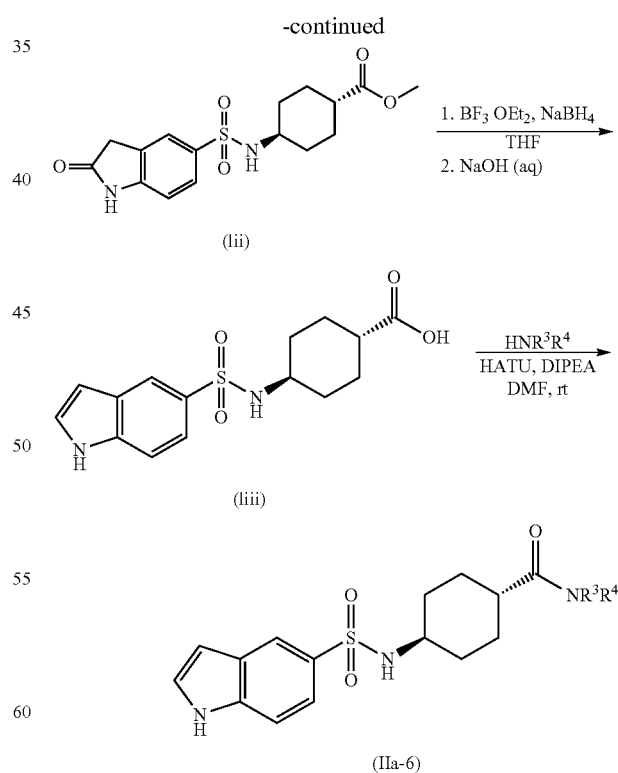

In this scheme, 2-oxoindoline-5-sulfonyl chloride is condensed with an amino ester (xiii), followed by conversion of the oxindole (lii) to an indole. The resulting ester is then hydrolyzed to a carboxylic acid (Iiii) and converted to an amide of Formula (IIa-6) using standard amide forming methods.

Preparation of 3-chloroindole derivatives is shown in Scheme 14.

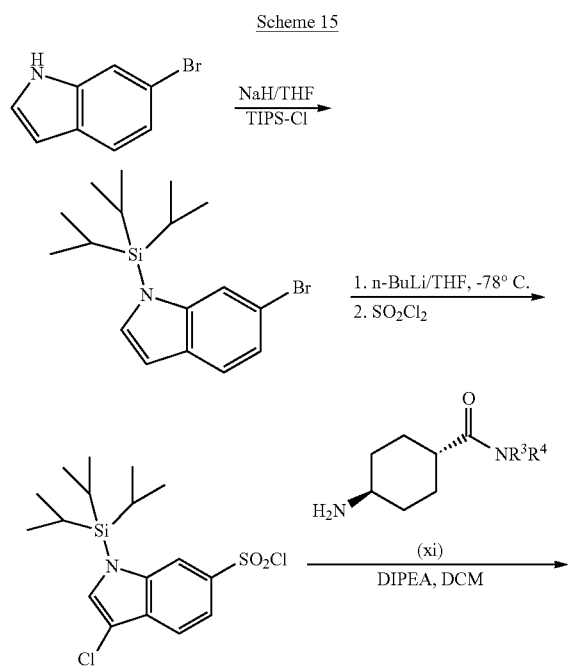

(IIa-5)

(IIa-6)

The indole derivatives, prepared by any of Schemes 7-13, may be chlorinated on the 3-position using phosphorus pentachloride in phosphoryl chloride as shown in Scheme 14.

An alternative method for the preparation of 3-chloroindoles is illustrated in Scheme 15.

Scheme 15

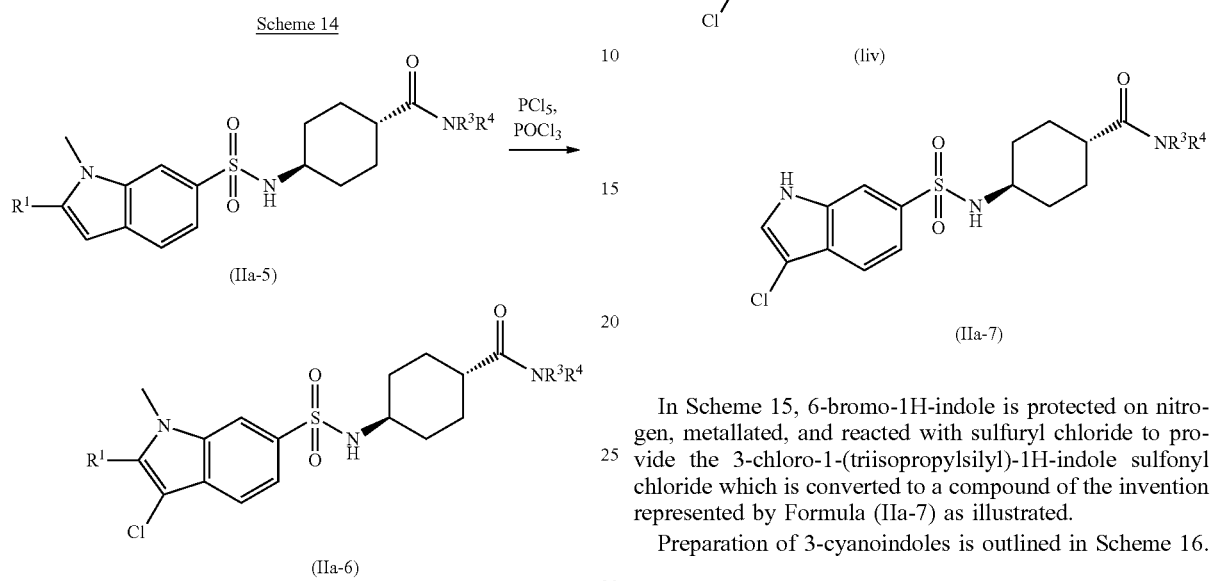

(liv)

(IIa-7)

In Scheme 15, 6-bromo-1H-indole is protected on nitrogen, metallated, and reacted with sulfuryl chloride to provide the 3-chloro-1-(triisopropylsilyl)-1H-indole sulfonyl chloride which is converted to a compound of the invention represented by Formula (IIa-7) as illustrated.

Preparation of 3-cyanoindoles is outlined in Scheme 16.

Scheme 16

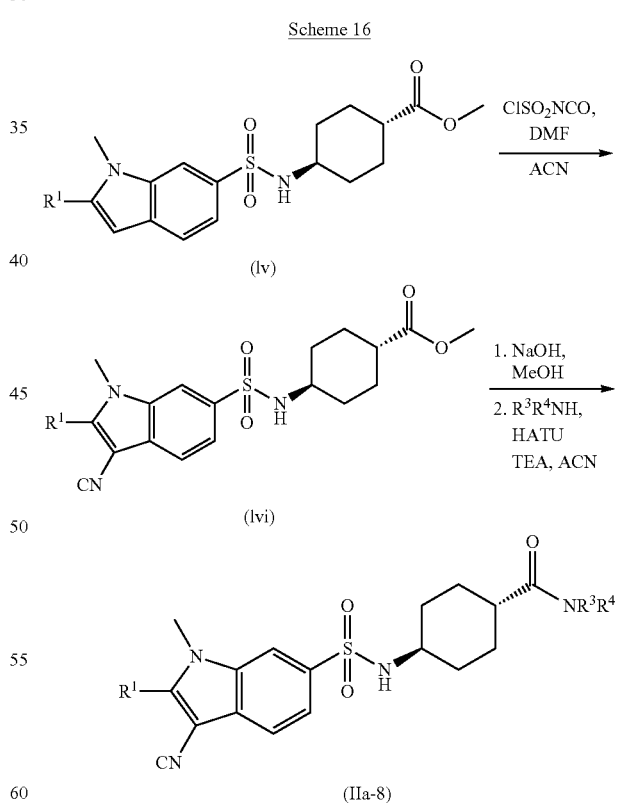

(lv)

(lvi)

(IIa-8)

Indoles prepared via Schemes 7-13 may be converted to 3-cyano derivatives using chlorosulfonylisocyanate as shown in Scheme 16.

Indoles prepared via Schemes 7-13 may be methylated in the 3-position via the method shown in Scheme 17.

Scheme 17

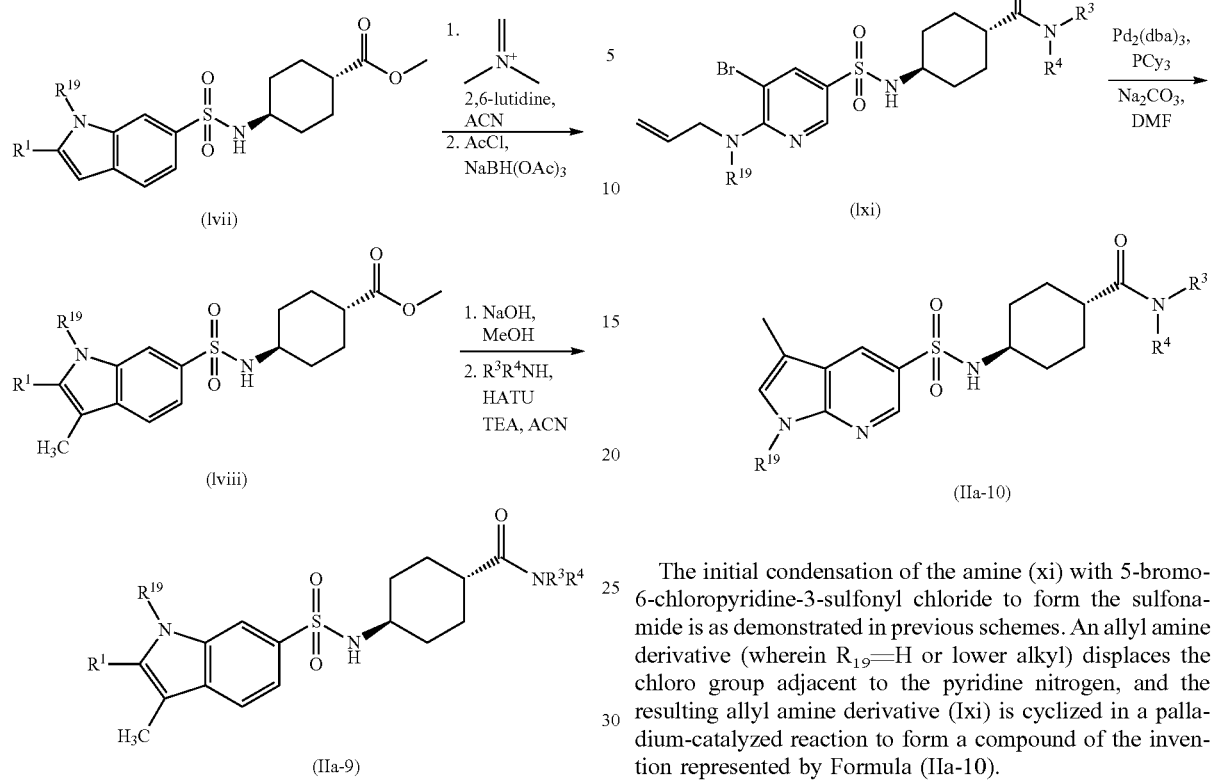

In this scheme, N-alkyl indole derivatives (lvii) are methylated in the 3-position by reaction with Eschenmoser's salt (methylenemethanaminium chloride), followed by reaction with acetyl chloride and sodium triacetoxyborohydride.

Aza indole derivatives may be prepared via Scheme 18.

Scheme 18

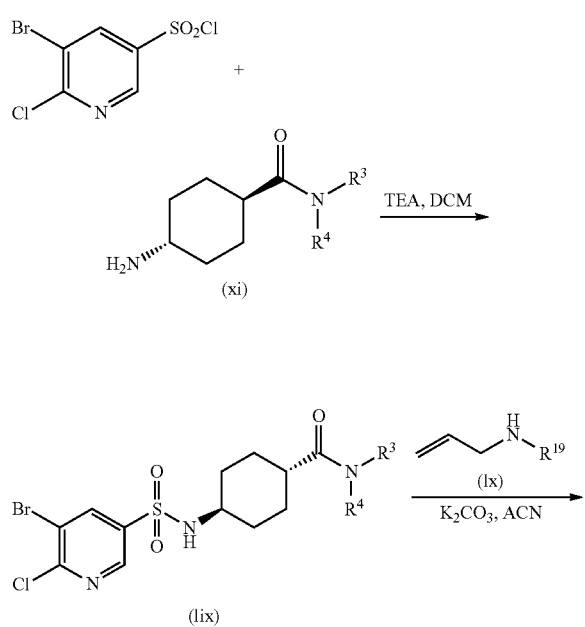

The initial condensation of the amine (xi) with 5-bromo-6-chloropyridine-3-sulfonyl chloride to form the sulfonamide is as demonstrated in previous schemes. An allyl amine derivative (wherein $R_{19}$=H or lower alkyl) displaces the chloro group adjacent to the pyridine nitrogen, and the resulting allyl amine derivative (lxi) is cyclized in a palladium-catalyzed reaction to form a compound of the invention represented by Formula (IIa-10).

Where the requisite benzoxazole or benzothiazole sulfonyl chloride is commercially available, compounds of the invention in which ring A is benzoxazole or benzothiazole can be prepared as described for Scheme 1. Otherwise, the requisite sulfonyl chlorides may be prepared as disclosed in Scheme 19.

Scheme 19

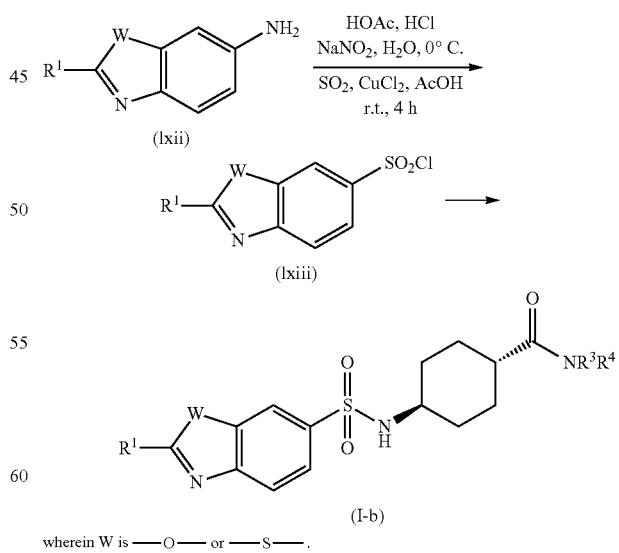

wherein W is —O— or —S—.

Compounds of the invention where $R^2$ is an alkyl, may be prepared according to Scheme 20.

Scheme 20
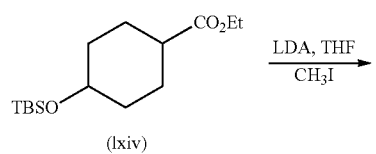
(lxiv)
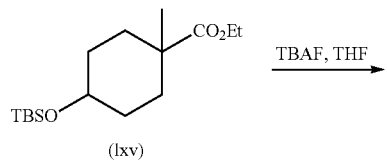
(lxv)
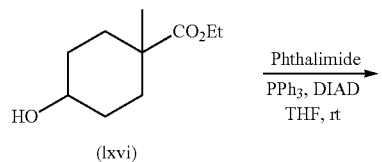
(lxvi)
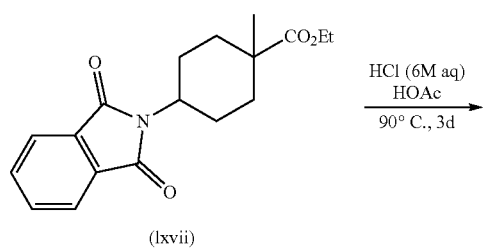
(lxvii)
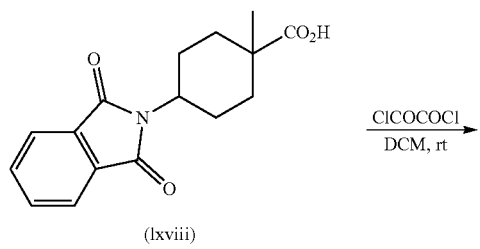
(lxviii)
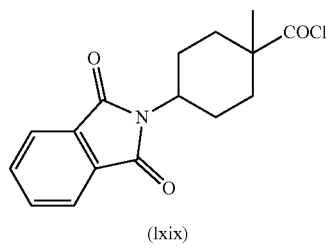
(lxix)

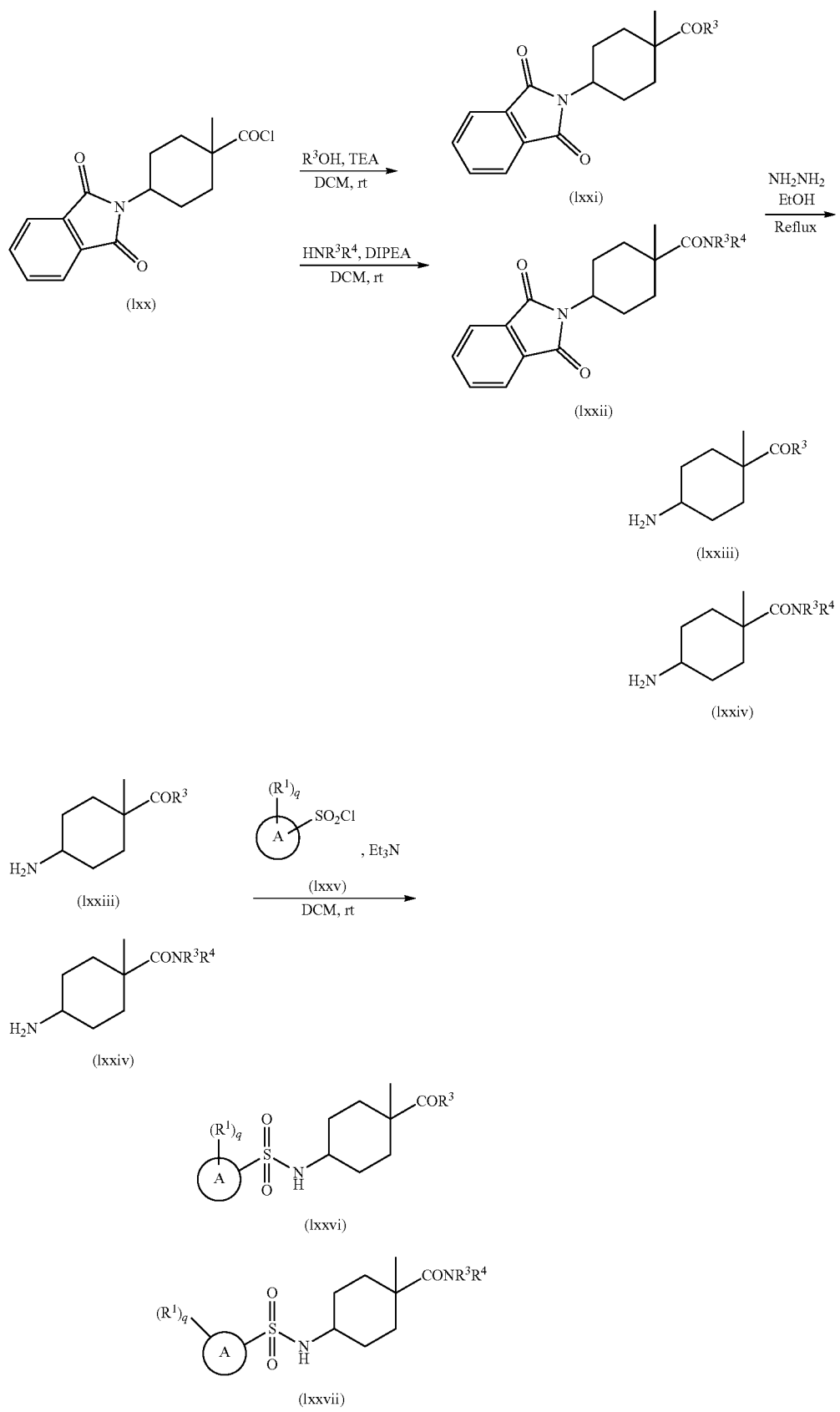

In Scheme 20, TBS-protected ethyl 4-hydroxycyclohexanecarboxylate (lxiv) is deprotonated with a strong base (LDA) and the resulting ester enolate is alkylated with an alkyl halide (e.g., methyl iodide) to form (lxv). The TBS-protected alcohol is then deprotected and converted to an amine (lxvii) via Mitsunobu reaction with phthalimide, followed by ester hydrolysis, conversion to acid chloride, coupling with an amine to form an amide (lxxii), or with an alcohol to form an ester (lxxi). The amide (lxxii) or ester (lxxi) are then treated with hydraze to remove the phthalimide group. Condensation of the resulting amine, (lxxiii) or (lxxiv), with an aryl sulfonyl chloride (lxxv) as described for previous schemes (e.g., Scheme 1) provides compounds of the invention in which R² is an alkyl. In this scheme, the aryl sulfonyl chloride (lxxv) may be a commercially available derivative, or may be an intermediate, such as described in previous schemes.

Compounds of the invention wherein ring A is a quinoline may be prepared according to Scheme 21.

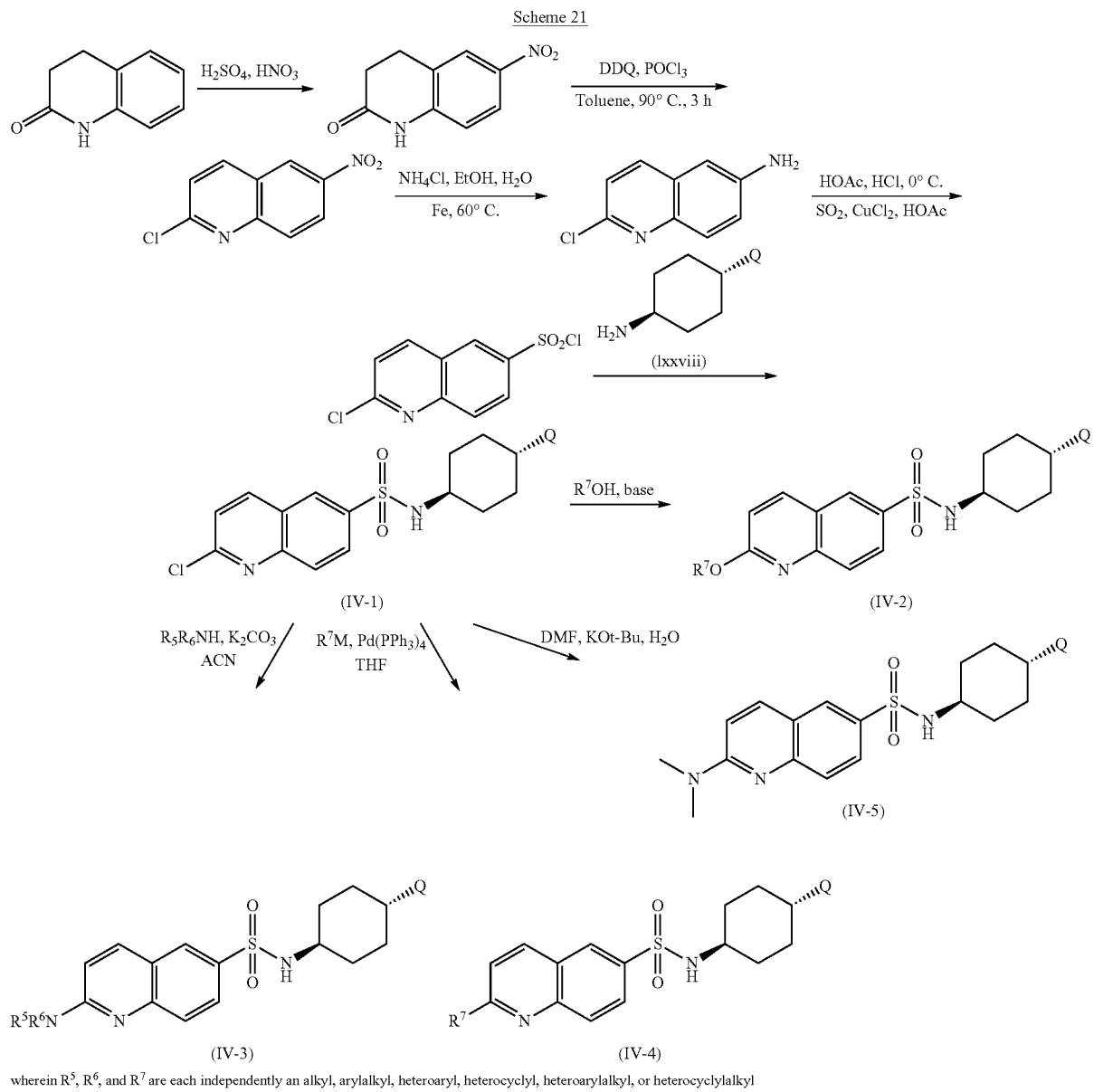

In Scheme 21, a chloroquinoline sulfonyl chloride is prepared and then condensed with the aminocyclohexane derivative (lxxviii) for form a compound of the invention represented by Formula (IV-1). Compounds of represented by Formula (IV-1) can be derivatized by displacement of the chloro group using a variety of nucleophiles to form alkoxyquinolines (IV-2), aminoquinolines (IV-3) and (IV-5), and alkyl derivatives (IV-4).

Tetrahydroquinoline derivatives may be prepared by catalytic hydrogenation of, as is shown for the 2-alkylquinoline derivative prepared as shown in Scheme 21A below:

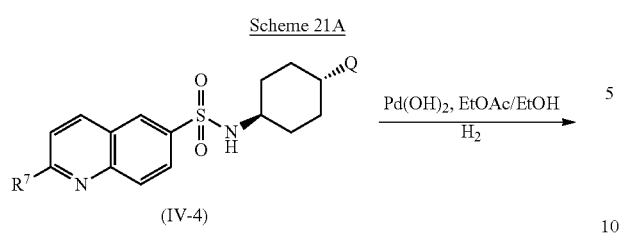
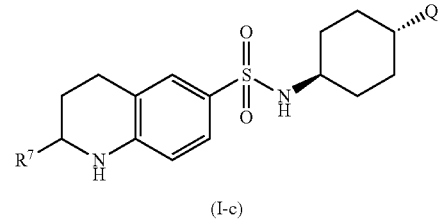
Tetrahydropyridopyrazine systems are prepared according to Scheme 22.
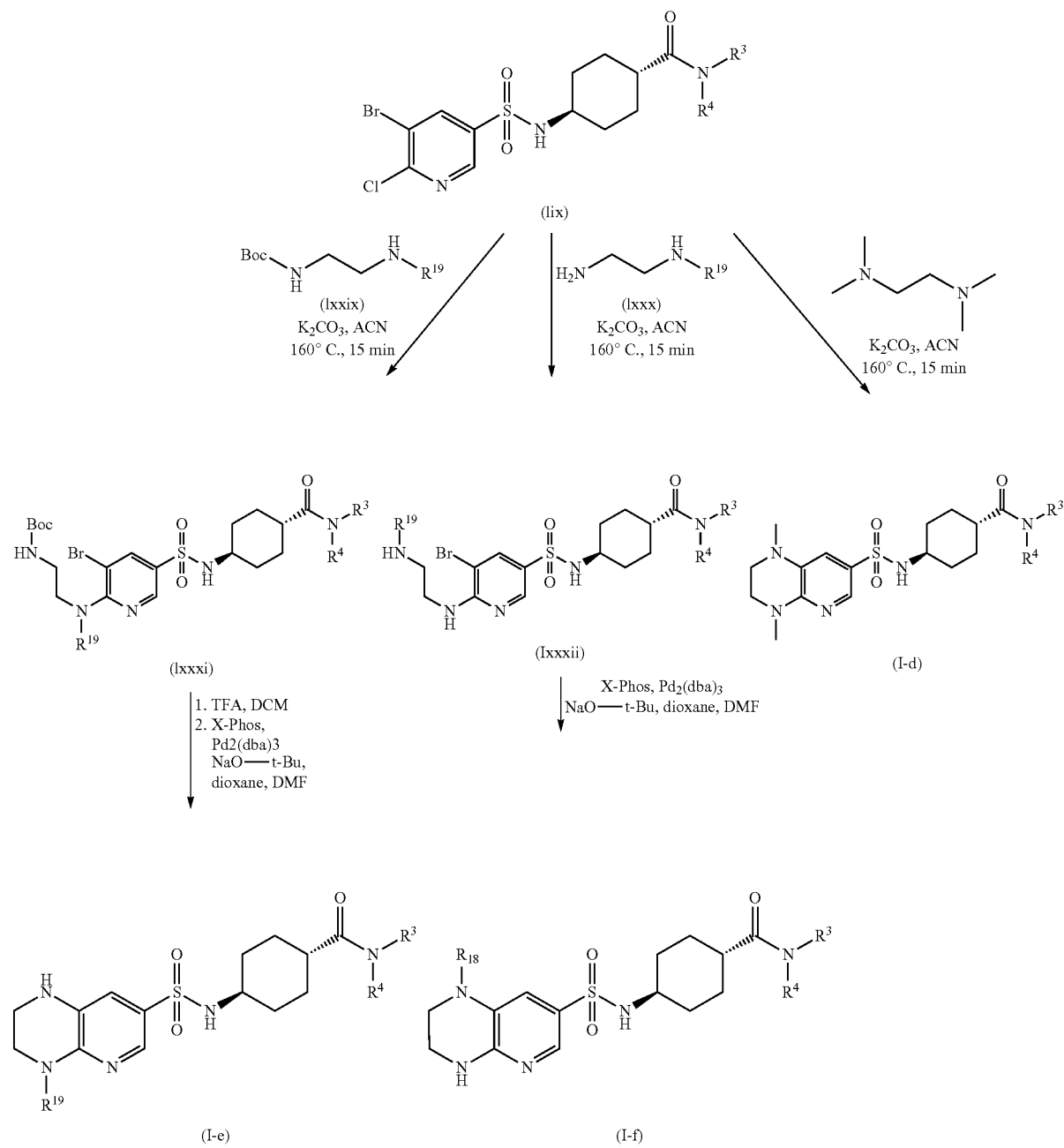

The 5-bromo-6-chloro-3-pyridinesulfonamide derivative (lix) (prepared from the commercially available 5-bromo-6-chloropyridine sulfonyl chloride as shown in Scheme 18) is condensed with diamine (lxxix), (lxxx) or $N^1,N^1,N^2,N^2$-tetramethylethane-1,2-diamine to form tetrahydropyridopyrazine derivative (I-e), (I-f) or (I-d), respectively, as shown.

The pyrazine nitrogens may also be acylated with chloroformates or acid chlorides for form amide or carbamate derivatives as shown in Scheme 22A:

Scheme 22A

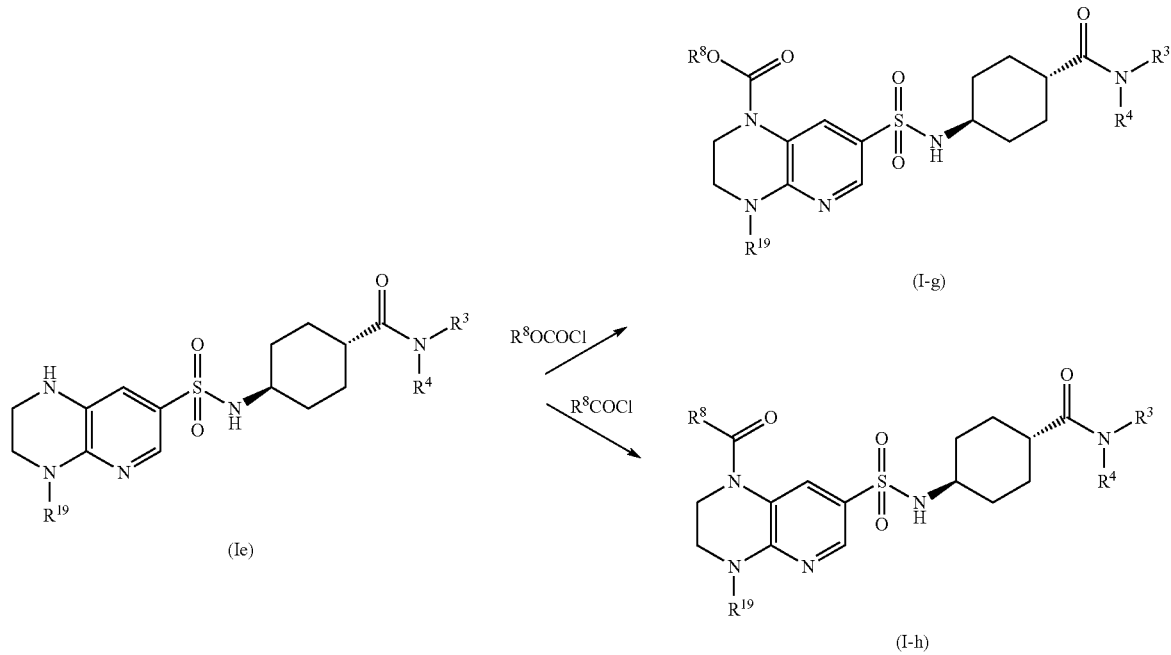

wherein $R^8$ is an alkyl or a cycloalkyl.

Pyridooxazines and pyridothiazines may be prepared by a procedure analogous to the procedure shown in Scheme 22, as illustrated by Scheme 23.

Scheme 23

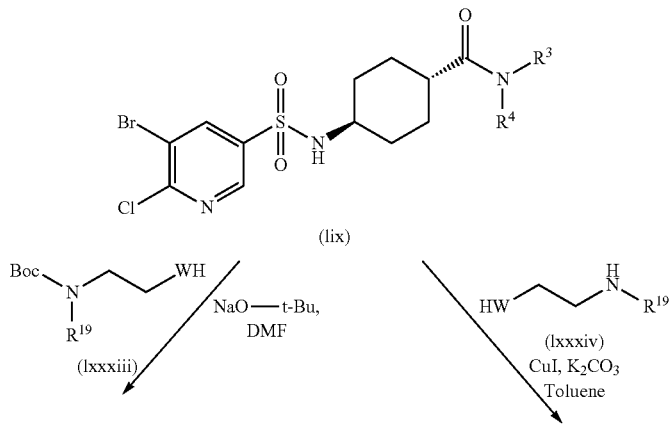

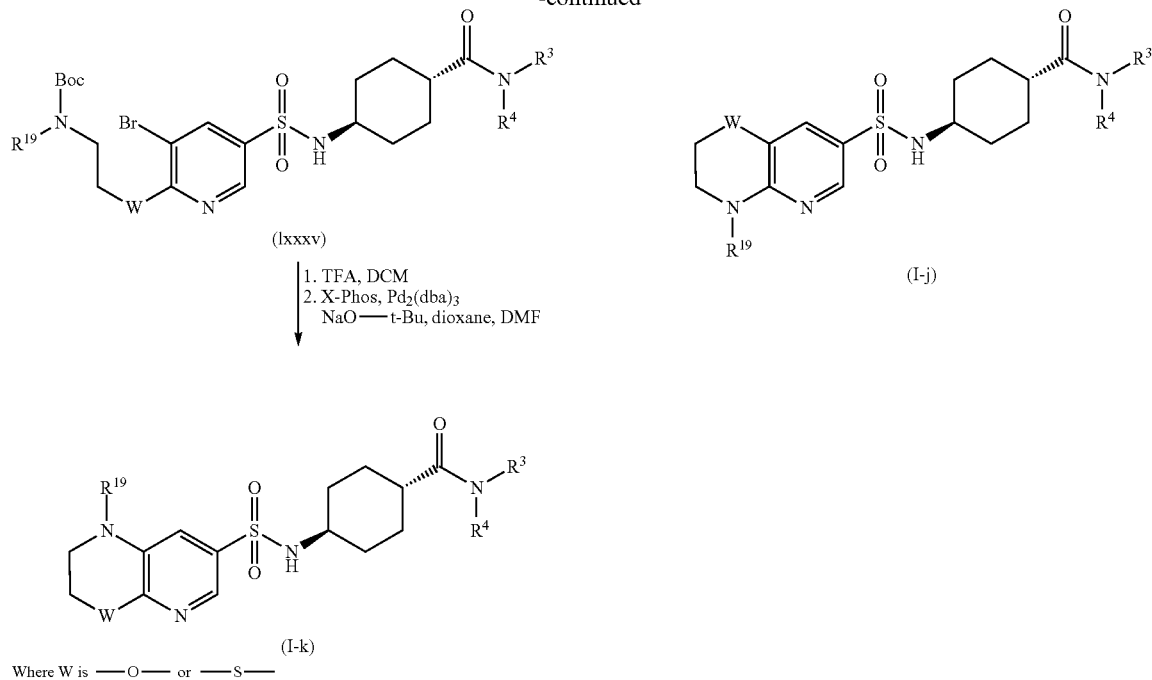

Where W is —O— or —S—

Oxazolopyridine or thiazolopyridine sulfonyl chlorides may be prepared as illustrated in Schemes 24-25, and then converted to sulfonamide compounds of the invention as in Scheme 1.

Scheme 24

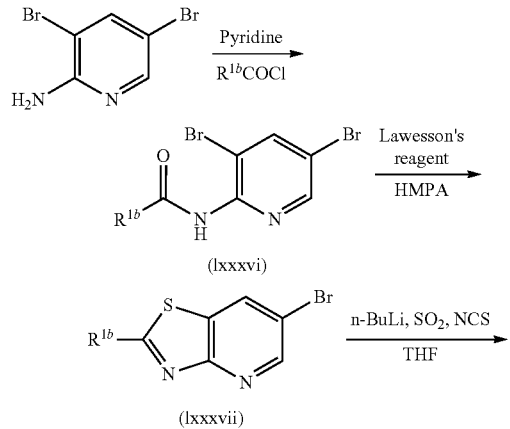

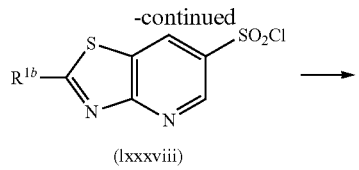

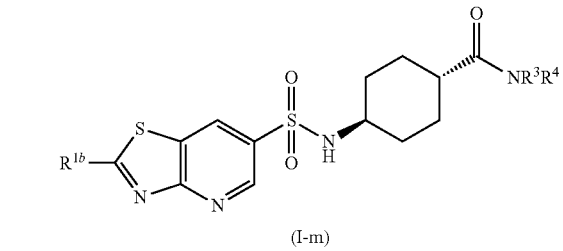

In Scheme 24, 3,5-dibromopyridin-2-amine is acylated and then cyclized using Lawesson's reagent to form a thiazolopyridine (lxxxvii). Halogen-metal exchange followed by sulfonation and chlorination with sulfur dioxide and N-chlorosuccinimide provides the requisite sulfonyl chloride (lxxxviii). The sulfonyl chloride (lxxxviii) is converted into the final sulfonamide derivatives (I-m) of the invention using standard methods as described in previous schemes.

Scheme 25

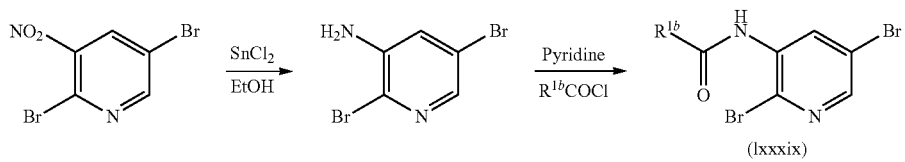

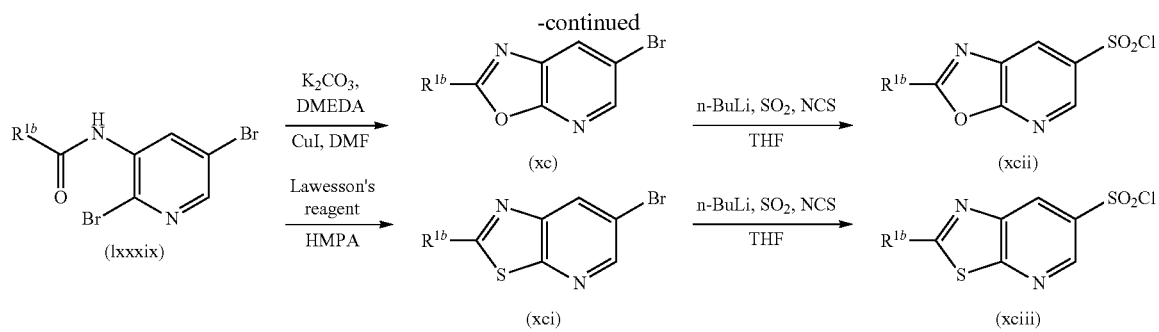

Scheme 25 is analogous to Scheme 24, but starts with an isomeric dibromoaminopyridine to provide either the thiazolopyridine (xciii) or oxazolopyridine (xcii) sulfonyl chlorides which are then converted into the final sulfonamide derivatives as described in Scheme 1.

Naphthyridine sulfonamide derivatives may be prepared as outlined in Scheme 26.

Compound (lix) is prepared as described in Scheme 18. Displacement of the chloro group with the aminobutene derivative (xciv) followed by palladium-catalyzed cyclization and subsequent aromatization provides the naphthyridine derivatives of the invention represented by Formula (I-n).

Tetrahydronaphthyridine derivatives may be prepared as disclosed in Scheme 27.

Scheme 26

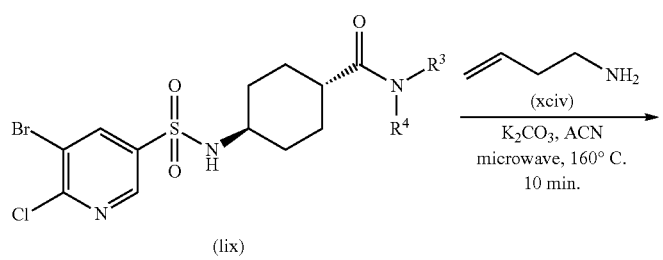

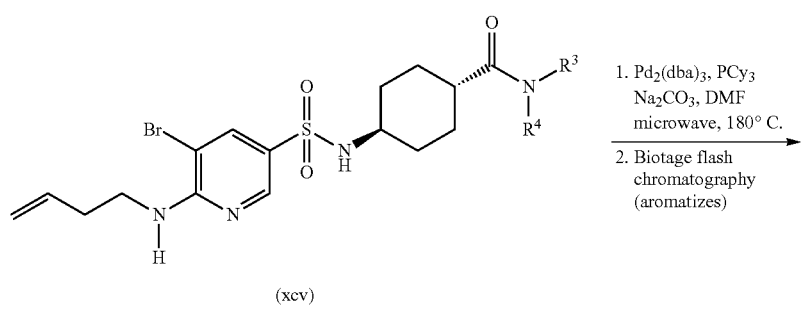

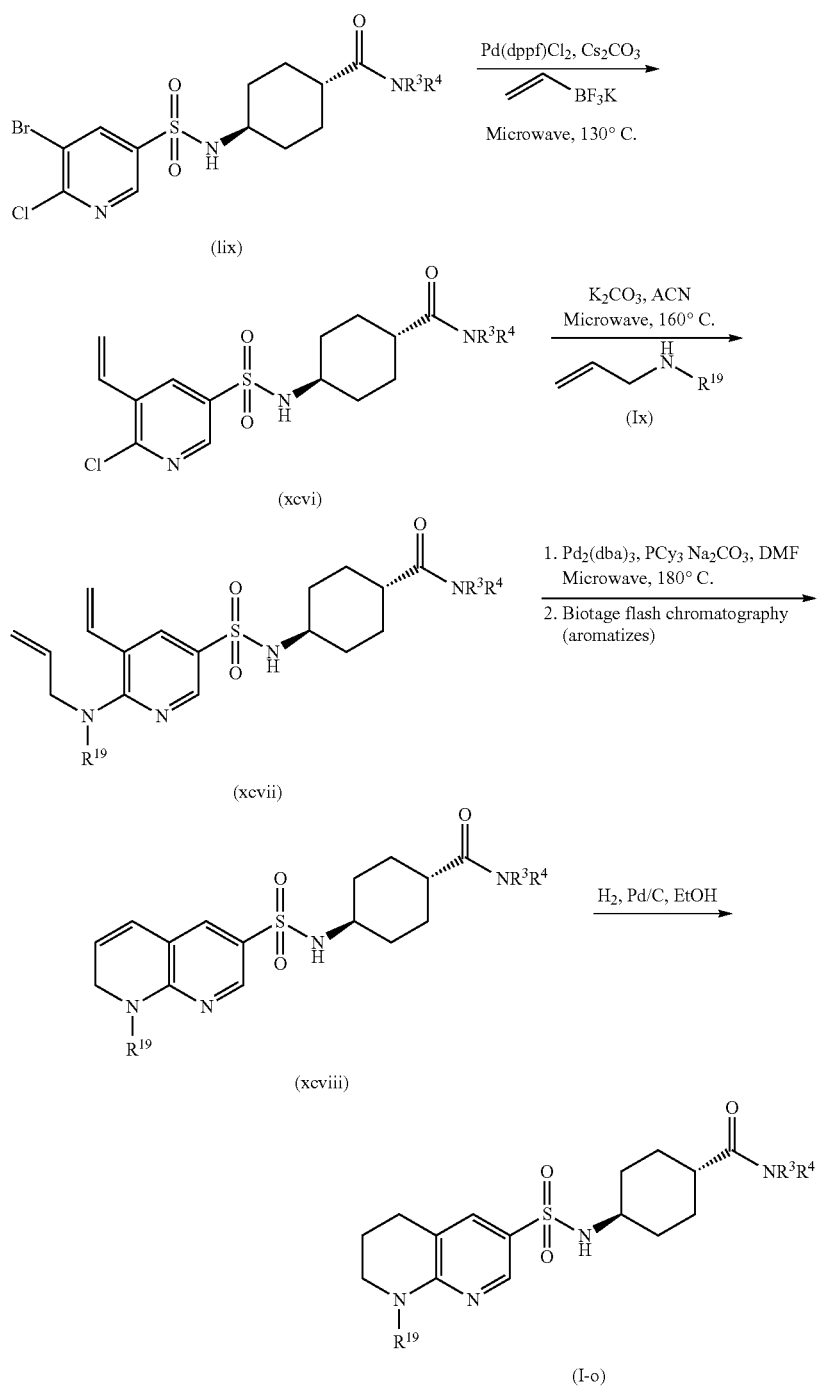
The starting sulfonamide (lix) is prepared as in Scheme 18. Ring forming metathesis reaction forms a dihydro naphthyridine (xcviii), followed by its reduction to a tetrahydronaphthyridine represented by Formula (I-o).
Tetrahydroquinoline sulfonamide derivatives may be prepared as outlined in Scheme 28.
Scheme 28
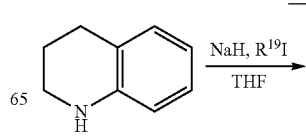

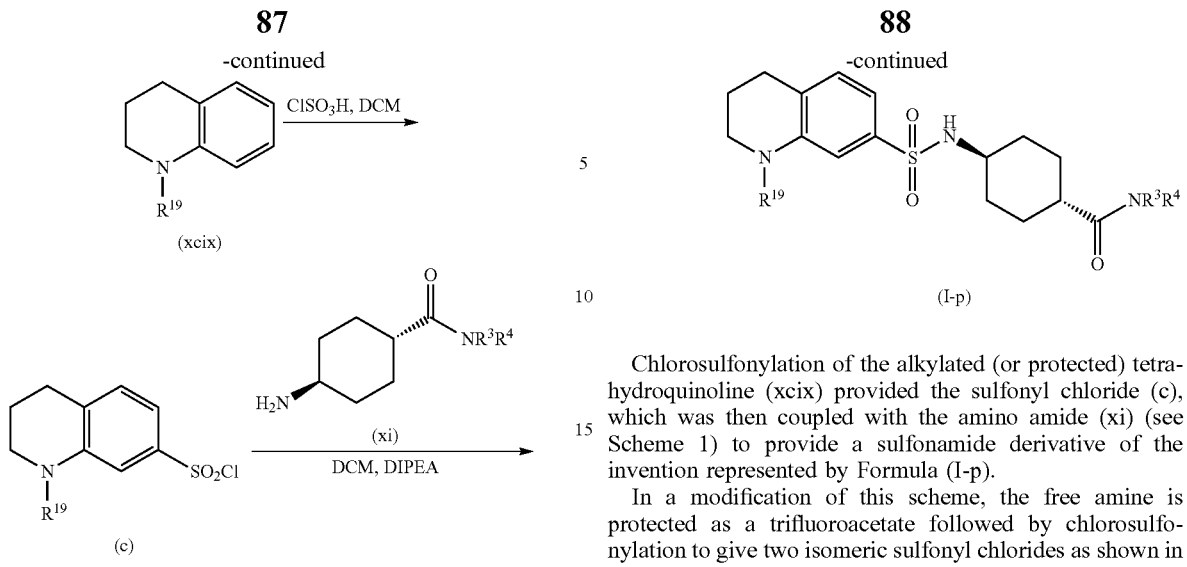

Chlorosulfonylation of the alkylated (or protected) tetra-hydroquinoline (xcix) provided the sulfonyl chloride (c), which was then coupled with the amino amide (xi) (see Scheme 1) to provide a sulfonamide derivative of the invention represented by Formula (I-p).

In a modification of this scheme, the free amine is protected as a trifluoroacetate followed by chlorosulfonylation to give two isomeric sulfonyl chlorides as shown in Scheme 28A:

Scheme 28A

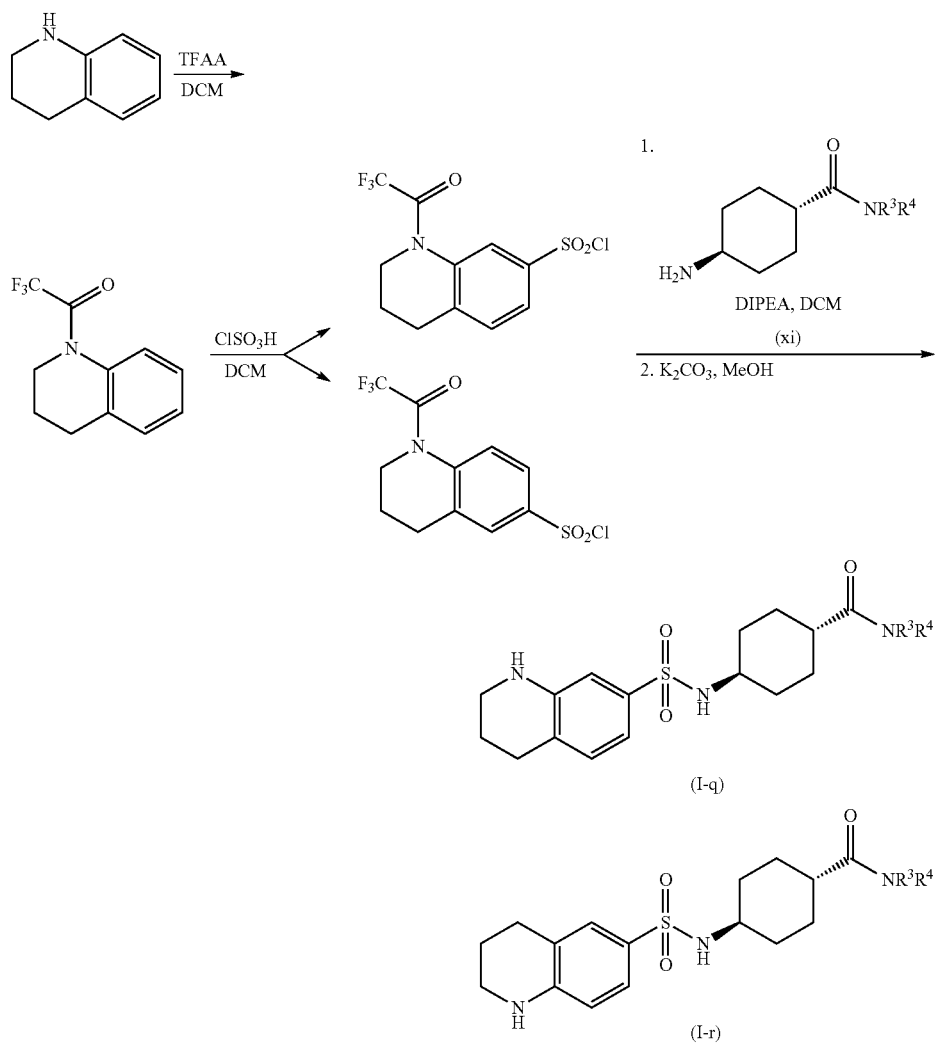

The sulfonylchlorides are coupled to the aminocyclohexane carboxamide (xi) as described above, followed by separation of the isomer mixture by chromatography. This procedure is also applicable starting from a variety of substituted tetrahydroquinolines.

The tetrahydroquinoline nitrogen may be acylated with acid chlorides, chloroformates, or isocyanates to form, respectively, amides, carbamates, or ureas as disclosed in Scheme 22A.

Quinoxaline sulfonamide derivatives may be prepared as outlined in Scheme 29.

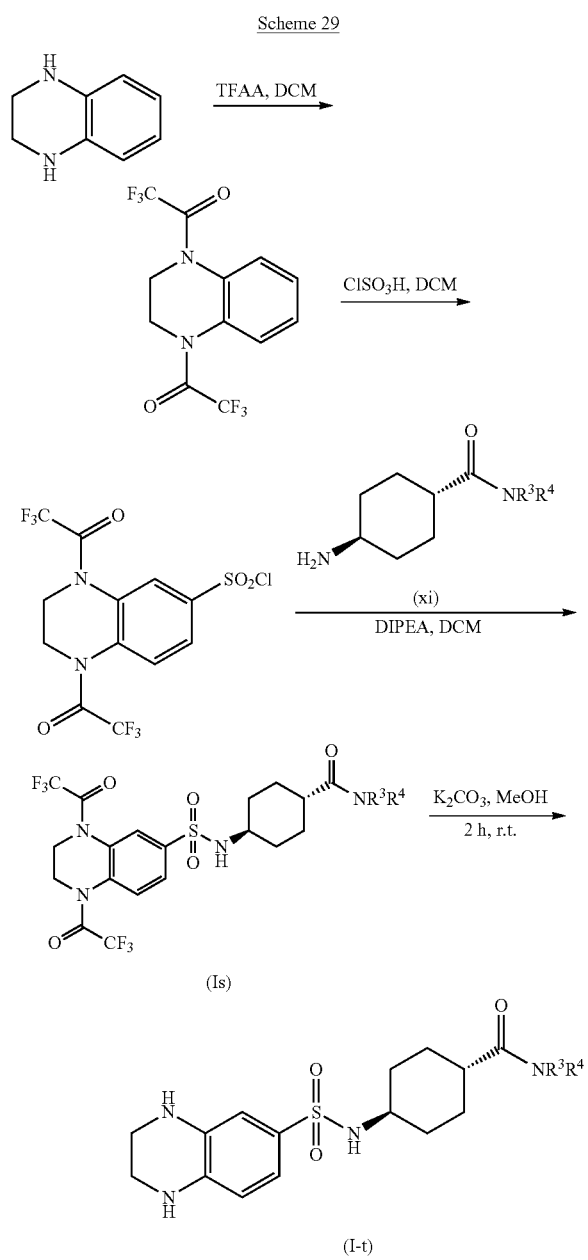

The starting unsubstituted quinoxaline is commercially available. The intermediate aminocyclohexane carboxamide is prepared and condensed with the sulfonyl chloride as disclosed in Scheme 1.

Di-N-alkylated quinoxaline derivatives are prepared as disclosed in Scheme 30.

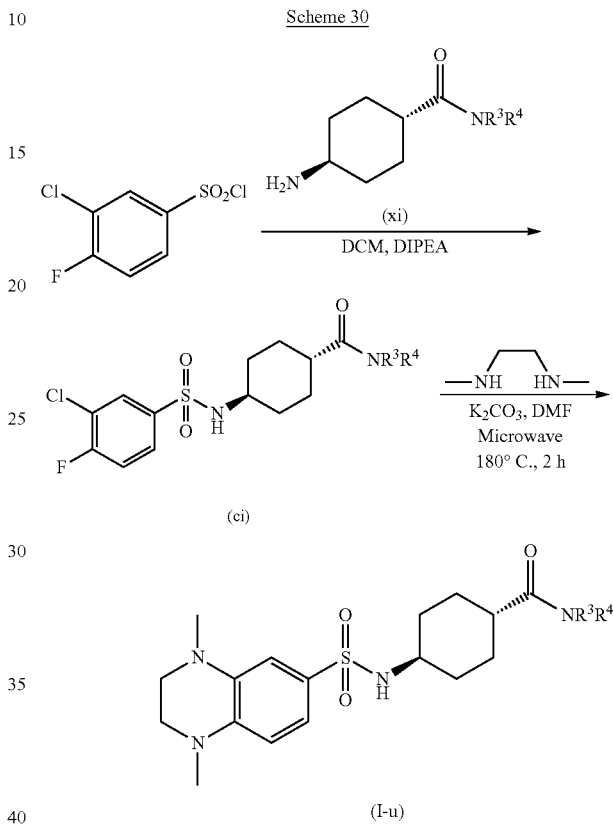

In this case, the starting sulfonyl chloride is commercially available. The intermediate aminocyclohexane carboxamide (xi) is prepared and condensed with the sulfonyl chloride as disclosed in Scheme 1.

Oxazine derivatives are prepared as described in Scheme 31.

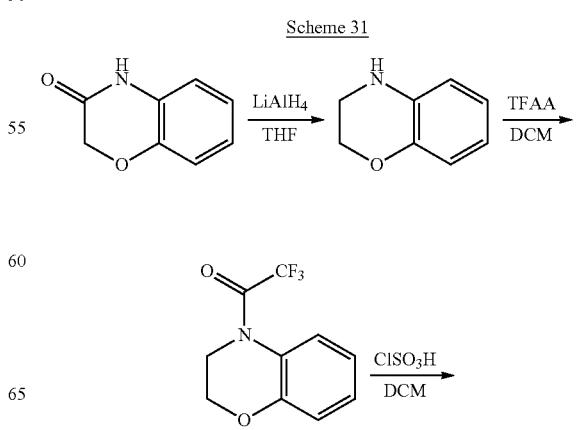

As disclosed in Scheme 22A, the pyrazine NH groups of compounds of Formula (I-t) may be acylated with acid chlorides to form amides, with chloroformates to form carbamates, or with isocyanates to form ureas.

91

-continued

1.

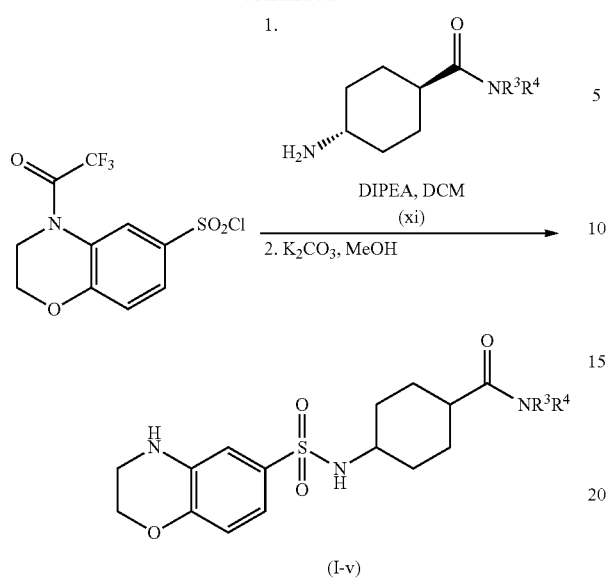

(I-v)

In Scheme 31, the starting 2H-benzo[b][1,4]oxazin-3 (4H)-one is commercially available. Protection of the nitrogen as a trifluoroacetate is followed by chlorosulfonylation, condensation with an aminocyclohexane carboxylate (xi) (see Scheme 1), and deprotection to provide a sulfonamide of the invention represented by Formula (I-v).

N-Alkylated oxazinone derivatives are prepared by a modification of this procedure, as described in Scheme 32.

Scheme 32

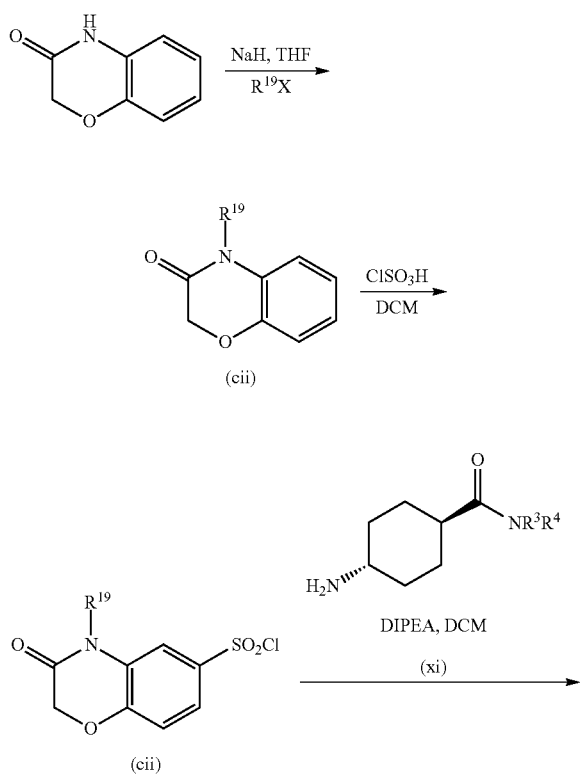

92

-continued

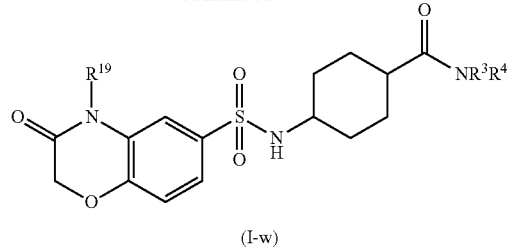

(I-w)

In Scheme 32 an oxazinone derivative is alkylated, followed by chlorosulfonylation to give a sulfonyl chloride (cii). The sulfonyl chloride (cii) is condensed with the aminocyclohexane carboxamide (xi) to provide a sulfonamide of the invention represented by Formula (I-w).

A related series of dihydroquinolinone analogs are prepared according to Scheme 33.

Scheme 33

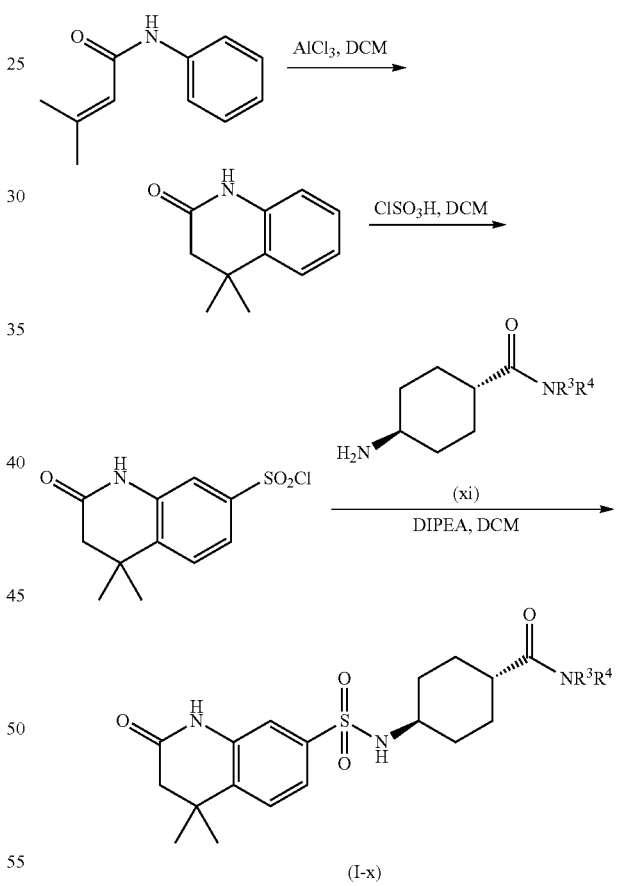

(I-x)

The dihydroquinolinone is prepared by Lewis acid-mediated cyclization of the phenylbutenamide, followed by chlorosulfonylation and condensation with the aminocyclohexanecarboxamide (xi) as outlined in Scheme 1 to afford a sulfonamide of the invention represented by Formula (I-x). As indicated below in Scheme 33A, the initially formed dihydroquinolinone may be reduced to the tetrahydroquinoline and chlorosulfonylated to provide the sulfonyl chloride which may be converted to the sulfonamide following the procedure described in Scheme 1.

Scheme 33A

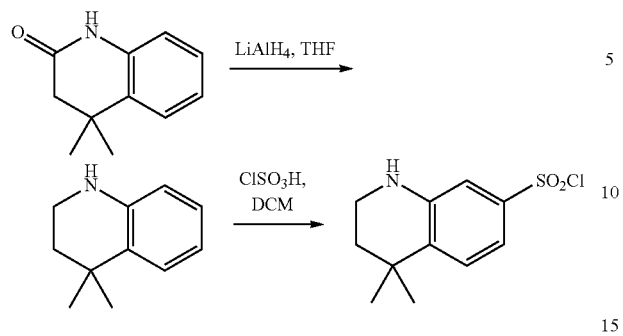

A variant of this procedure was used to prepare analogous dihydroisoquinolinone derivatives as shown in Scheme 33B:

Scheme 33B

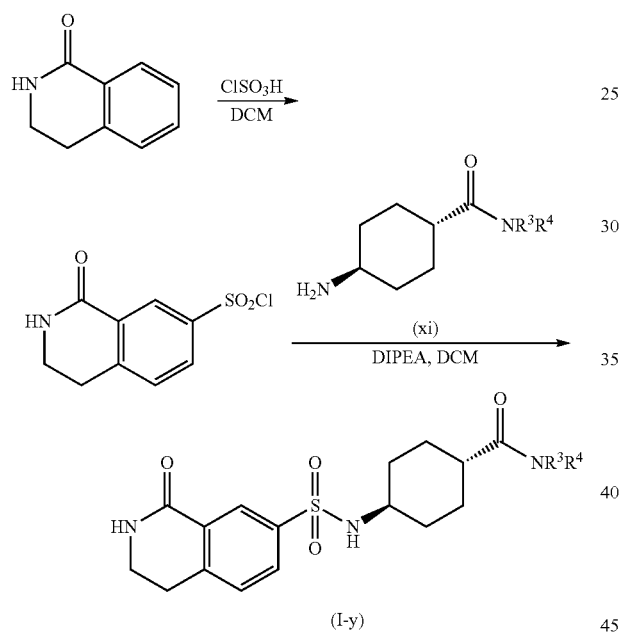

As disclosed in Scheme 22A, the free NH group of the tetrahydroquinoline in Formula (I-y) may be acylated with acid chlorides to form amides, with chloroformates to form carbamates, or with isocyanates to form ureas.

Indole derivatives may be alkylated at the 3-position using the palladium catalyzed alkylation reaction shown in Scheme 34.

Scheme 34

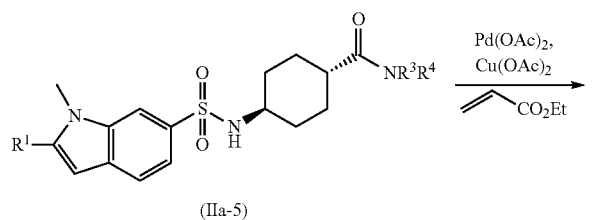

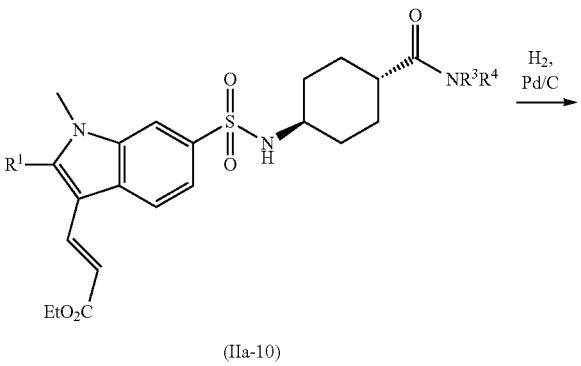

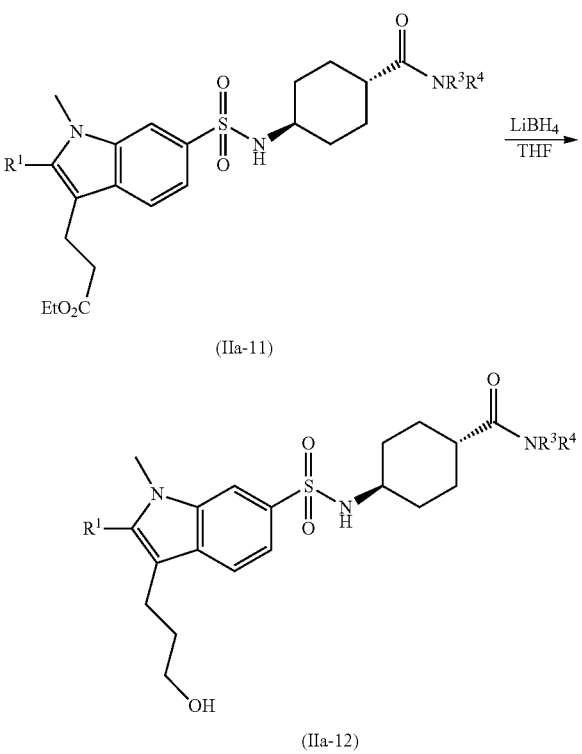

In Scheme 34, the 3-alkylated compound (IIa-10) may be transformed by reduction of the double bond of the saturated ester (IIa-11), and reduction of the ester to an alcohol (IIa-12) as shown. The method has been applied to indole derivatives of the invention in which $L^1$ is in the 5- and 6-substituted position of the indole. In a preferred embodiment, $L^1$ is —S(O)$_2$NH—.

Scheme 35

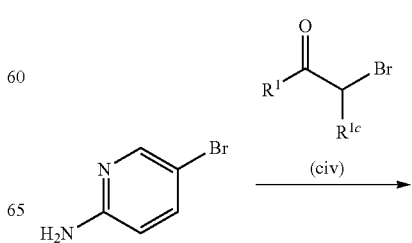

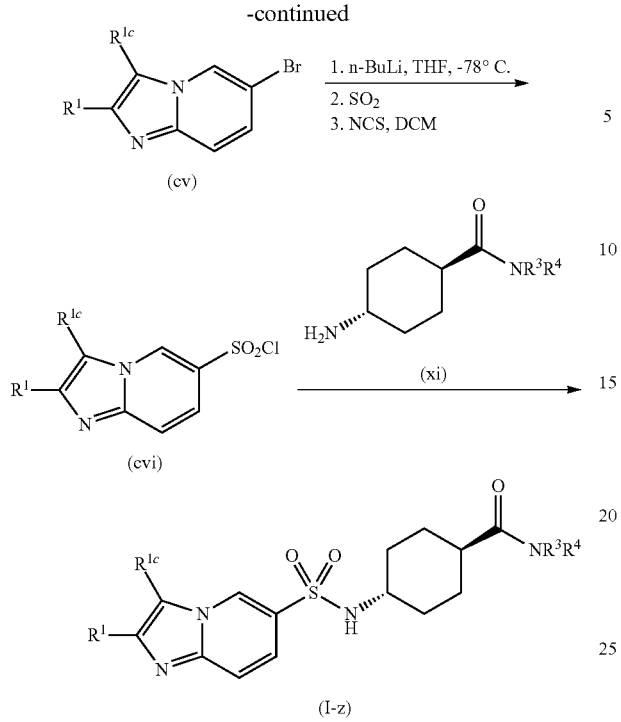

The reactions shown in Scheme 35 are employed in the preparation of analogs with an imidazopyridine sulfonamide moiety. In this class of compounds, $R^1$ and $NR^3R^4$ are as previously described; $R^{1c}$ may be hydrogen or lower alkyl. In some cases, migration of the initially formed organolithium species occurs to lead to sulfonyl chloride formation on the pyridine carbon atom adjacent to the pyridine nitrogen, leading to an isomeric analog as shown below:

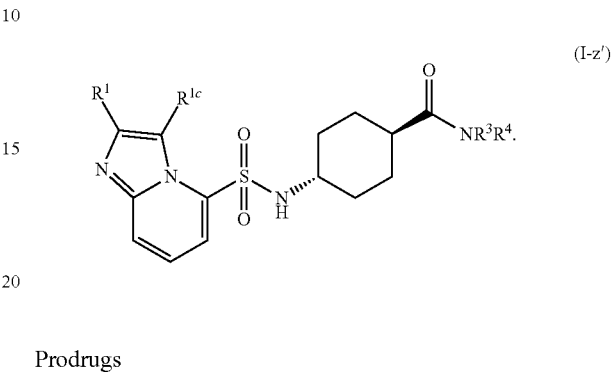

Prodrugs

Scheme 36 discloses the preparation of amino acid prodrugs which can be prepared from a compound of the invention comprising an alcohol group. Amino-protected valine is shown in the scheme below for illustration. However, any naturally occurring and non-natural amino acids can be prepared by this method.

Scheme 36

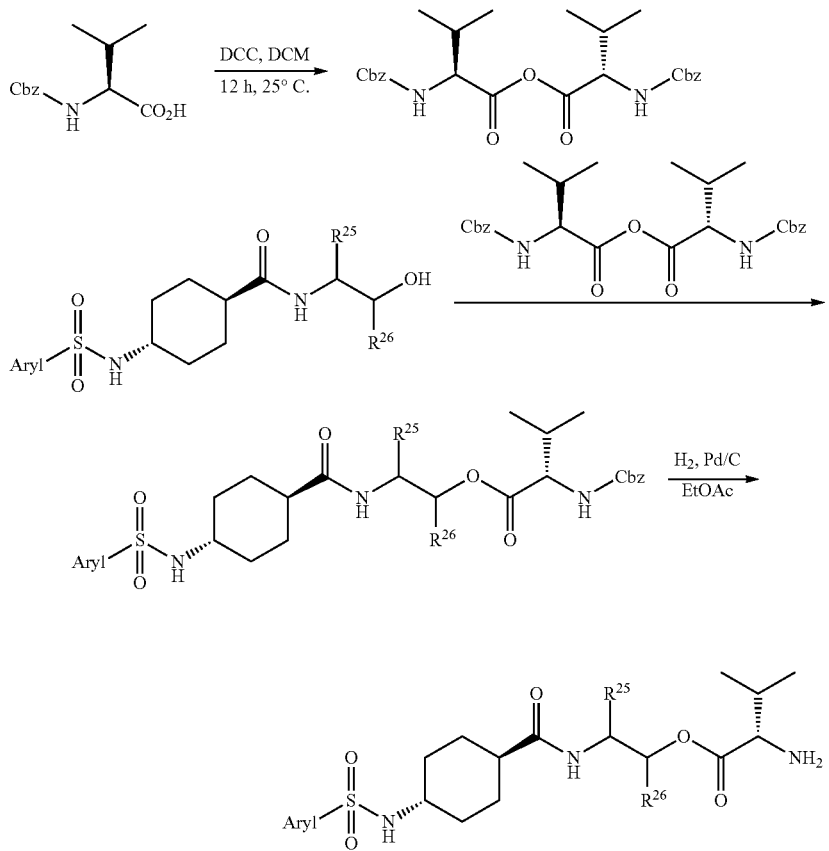

In Scheme 36, the aryl sulfonamide moiety may represent any of the aryl sulfonamides described herein. $R^{25}$ and $R^{26}$ each independently may be aryl, lower alkyl, or hydrogen. This scheme may also be employed for the preparation of amino acid ester prodrugs of alcohols in which the alcohol is appended to the aryl sulfonamide moiety in structures analogous to the above.

Scheme 37 discloses the preparation of phosphate ester prodrugs which can be prepared from compounds of the invention which have a alcohol group.

Scheme 37

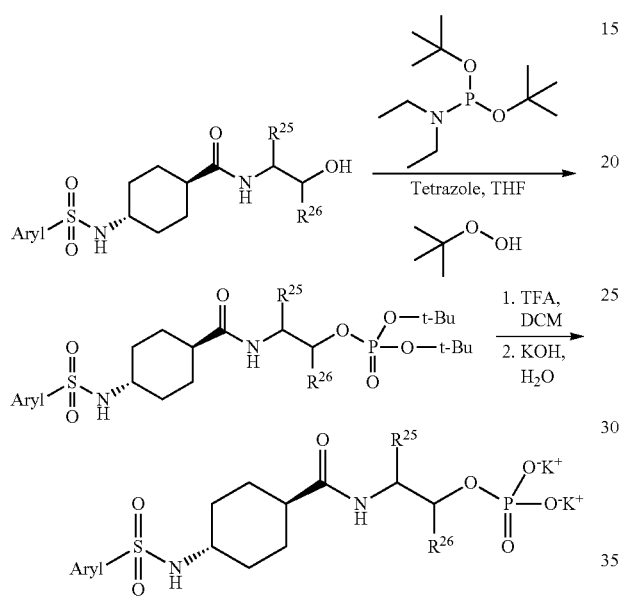

In Scheme 37, the aryl sulfonamide moiety may represent any of the aryl sulfonamides described herein. $R^{25}$ and $R^{26}$ each independently may be aryl, lower alkyl, or hydrogen. This scheme may also be employed for the preparation of phosphate ester prodrugs of alcohols in which the alcohol is appended to the aryl sulfonamide moiety in structures analogous to the above.

EXEMPLIFICATION

The following specific examples are intended to illustrate the invention without limiting the scope thereof.

Compounds prepared by these methods were analyzed by a variety of methods to determine identity and purity. These methods included NMR, mass spectroscopy, and HPLC. A variety of HPLC methods were used and these are described in the following table.

TABLE 1

HPLC Methods

| Method | | Description |
|---|---|---|
| A | Column | SunFire C18 20 × 4.6 mm, 3.5 μm |
|  | Column Temperature: | 40° C. |
|  | Eluents | A: $H_2O$, B: acetonitrile, both containing 0.1% TFA |
|  | Flow Rate: | 3.0 mL/min |
|  | Gradient: | 5-100% B in 4.0 min (A1) or 15-90% B in 4.0 min (A2) |

TABLE 1-continued

HPLC Methods

| Method | | Description |
|---|---|---|
| B | Column | SunFire C18 20 × 4.6 mm, 3.5 μm |
|  | Column Temperature: | RT |
|  | Eluents: | A: $H_2O$, B: acetonitrile, both containing 0.1% TFA |
|  | Flow Rate: | 3.0 mL/min |
|  | Gradient: | 5-50% B in 4.0 min (B1) or 10-70% B in 4.0 min (B2) |
| C | Column | Waters X Terra C18 30 × 3 mm, 2.5 μm |
|  | Column Temperature: | RT |
|  | Eluents: | A: $H_2O$ (containing 5% acetonitrile and 0.05% TFA), B: acetonitrile (containing 0.05% TFA) |
|  | Flow Rate: | 0.7 mL/min |
|  | Gradient: | 10-95% B in 1.5 min, then 95% B for 1 min |
| D | Column | Phenomenex Luna C8 50 × 5 mm, 4.6 μm |
|  | Column Temperature: | RT |
|  | Eluents: | A: $H_2O$, B: acetonitrile, both containing 0.1% TFA |
|  | Flow Rate: | 3 mL/min |
|  | Gradient: | 10-100% B in 15 min |
| E | Column | Waters Atlantis C18 150 × 4.6 mm, 5.0 μm |
|  | Column Temperature: | RT |
|  | Eluents: | A: $H_2O$, B: acetonitrile, both containing 0.1% TFA |
|  | Flow Rate: | 1.4 mL/min |
|  | Gradient: | 0-95% B in 19 min |
| F | Column | Phenomenex Gemini C18 50 × 4.6 mm, |
|  | Column Temperature: | RT |
|  | Eluents: | A: $H_2O$, B: acetonitrile, both containing 0.1% TFA |
|  | Flow Rate: | 3 mL/min |
|  | Gradient: | 10-100% B in 15 min |
| G | Column | Waters Xterra C8 100 × 4.6 mm |
|  | Column Temperature: | RT |
|  | Eluents: | A: 5 mM NH4OH in $H_2O$, B: acetonitrile, both containing 0.1% TFA |
|  | Flow Rate: | 3 mL/min |
|  | Gradient: | 5-100% B in 15 min |
| H | Column | Inertsil C8-3, 3 cm × 33 mm × 3.0 μM |
|  | Column Temperature: | 50° C. |
|  | Eluents: | Acetonitrile/methanol with 5 mM ammonium bicarbonate |
|  | Flow Rate: | 2 mL/min |
|  | Gradient: | 40-95% in 2 min |

TABLE 2

Commonly used abbreviations

| Abbreviation | Description |
|---|---|
| Bn | Benzyl |
| Boc | Tert-butoxycarbonyl |
| CAN | Ceric ammonium nitrate |
| DCC | 1,3-Dicyclohexylcarbodiimide |
| DCM | Dichloromethane |
| DIAD | Diisopropylazodicarboxylate |
| DIPEA | Diisopropylethylamine |
| DMAP | N,N-dimethylpyridin-4-amine |
| DMF | N,N-dimethylformamide |
| DMSO | Dimethyl sulfoxide |
| EDCI | 1-ethyl-3-(3'-dimethylaminopropyl)carbodiimide |
| h | Hour(s) |
| HATU | 2-(1H-7-azabenzotriazol-1-yl)-1,1,3,3,-tetramethyluronium hexafluorophosphate |
| HOBt | 1H-benzo[d][1,2,3]triazol-1-ol |
| HPLC | High performance liquid chromatography |

TABLE 2-continued

Commonly used abbreviations

| Abbreviation | Description |
|---|---|
| HV | High vacuum |
| LC-MS | Liquid chromatography - mass spectrometry |
| LDA | Lithium diisopropylamide |
| min | Minute(s) |
| mL | Milliliter(s) |
| MS-Es | Electrospray mass spectrometry |
| NMM | N-methylmorpholine |
| rt | Room temperature |
| TBAF | Tetrabutylammonium fluoride |
| TFA | Trifluoroacetic acid |
| TFAA | Trifluoroacetic anhydride |
| THF | Tetrahydrofuran |
| $t_R$ | Retention time |
| Xphos | 2-Dicyclohexylphosphino-2',4',6'-triisopropylbiphenyl |

Example 1

Preparation of (1r,4R)-4-(2-phenyl-1H-benzo[d]imidazole-5-sulfonamido)-N—((R)-1-phenylethyl)cyclohexanecarboxamide

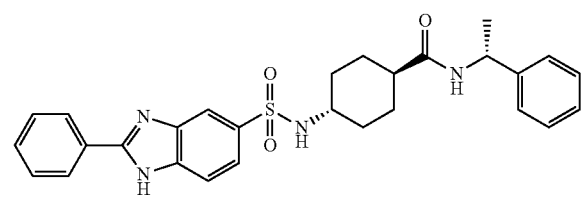 [SMILES: C[C@@H](NC(=O)[C@H]1CC[C@H](NS(=O)(=O)c2ccc3[nH]c(-c4ccccc4)nc3c2)CC1)c1ccccc1]

Step 1. Preparation of tert-butyl (1R,4r)-4-((R)-1-phenylethylcarbamoyl)cyclohexylcarbamate

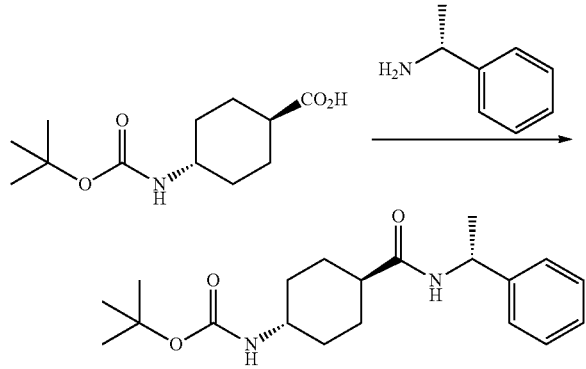

Trans 4-tert-butoxycarbonylamino-cyclohexanecarboxylic acid (5 g, 20.5 mmol) was dissolved in THF, to which triethylamine (3 mL) was added. The reaction mixture was cooled to 0° C. and a solution of isobutyl chloroformate (2.8 g, 20.7 mmol) in THF was added dropwise. The resulting white suspension was stirred at room temperature for 30 min, after which a solution of 4-fluoro-(R)-1-phenyl-ethyl-amine (2.9 g, 20.5 mmol) in THF was added dropwise. The reaction mixture was then stirred at room temperature for 4 h, after which LC-MS showed one major peak corresponding to desired product. The reaction mixture was concentrated, and the residue was diluted with water (250 mL). The resulting white precipitate was filtered, washing with ether, to afford a dry white solid {4-[(R)-1-(4-Fluoro-phenyl)-ethylcarbamoyl]-cyclohexyl}-carbamic acid tert-butyl ester (5.2 g; MS: $(M+H)^+=347.34$).

Step 2. Preparation of (1r,4R)-4-amino-N—((R)-1-phenylethyl)cyclohexanecarboxamide

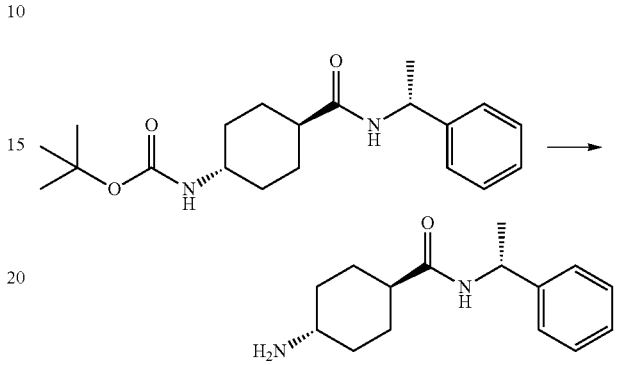

tert-Butyl (1R,4r)-4-((R)-1-phenylethylcarbamoyl)cyclohexylcarbamate (5.2 g) was dissolved in DCM (50 mL) to which TFA was added. The resulting mixture was stirred for 45 min at room temperature. LC-MS of material showed one major peak which corresponded to desired product. The reaction mixture was then concentrated to give a clear oil. The oil was then dissolved in diethyl ether (200 mL) to which HCl (2M solution in ether) (20 mL) was added. The resulting mixture was stirred at room temperature for 2 h, resulting in a white precipitate that was collected by filtration and washed with diethyl ether (4.1 g; MS: $(M+H)^+=247.25$).

Step 3. Preparation of 2-phenyl-1H-benzoimidazole-5-sulfonyl chloride

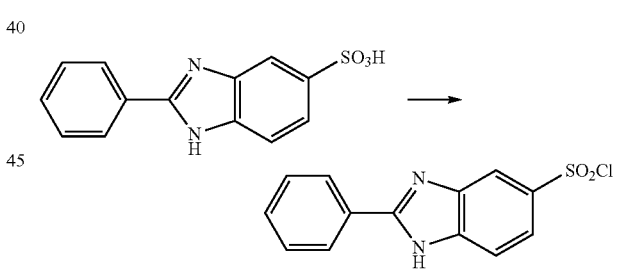

Thionyl chloride (100 mL) and 2-phenyl-1H-benzoimidazole-5-sulfonic acid (24.5 g, 89.4 mmol) were combined at room temperature. To the resulting slurry was added 2 drops of DMF. The mixture was stirred at room temperature overnight. The reaction mixture was then poured into toluene, and the resulting solid was collected by filtration, washed with toluene and dried under vacuum to provide 48.6 g of product which still contained some starting material. This crude product (43.7 g) was then treated with 250 mL of thionyl chloride and 1 mL of DMF. The resulting mixture was heated to reflux for 3.5 h, stirred at room temperature for 3 h. Considerable swelling occurs, the reaction appeared to solidify, and an additional 150 mL of thionyl chloride was added with additional stirring. The reaction mixture was then cooled, toluene was added, and the product was collected by filtration, washed with toluene, and dried undervacuum to give 51 g of a white solid (MS: $(M+H)^+=293.1$).

Step 4. Preparation of (1r,4R)-4-(2-phenyl-1H-benzo[d]imidazole-5-sulfonamido)-N—((R)-1-phenylethyl)cyclohexanecarboxamide

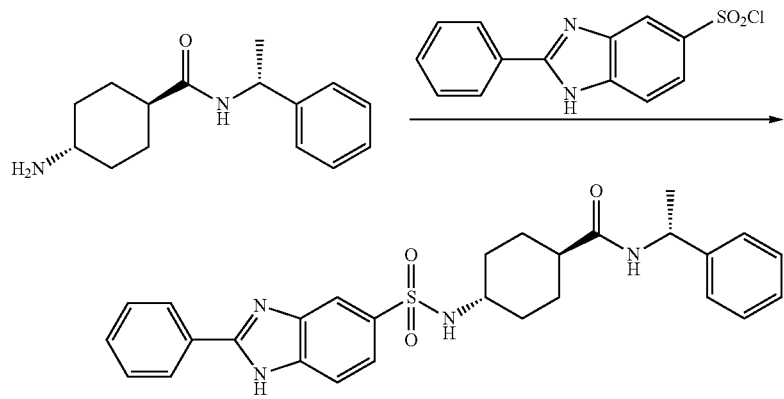

The sulfonyl chloride (118 mg, 0.4 mmol) was added to a solution of the aminoamide (100 mg, 0.4 mmol) and triethyl amine (0.228 mL, 1.6 mmol) in DCM (3 mL) at room temperature. The reaction was complete within 10 min. The reaction mixture was concentrated under vacuum, taken up in 50 mL of ethyl acetate, washed with three 50 mL portions of water, dried and concentrated to give the crude product.

Example 2

Preparation of ethyl 3-(6-(N-((1R,4r)-4-((R)-1-phenylethylcarbamoyl)cyclohexyl)sulfamoyl)-1H-benzo[d]imidazol-2-yl)benzoate

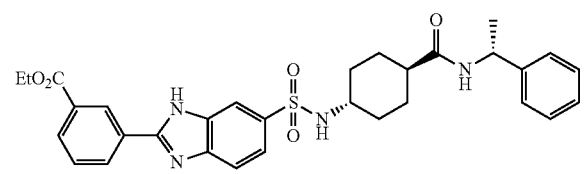 [SMILES: CCOC(=O)c1cccc(-c2nc3ccc(S(=O)(=O)N[C@H]4CC[C@H](C(=O)N[C@H](C)c5ccccc5)CC4)cc3[nH]2)c1]

Step 1. Preparation of (1r,4R)-4-(4-chloro-3-nitrophenylsulfonamido)-N—((R)-1-phenylethyl)cyclohexanecarboxamide

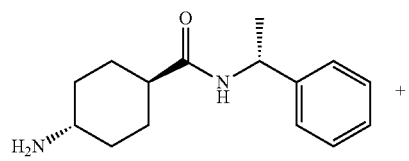

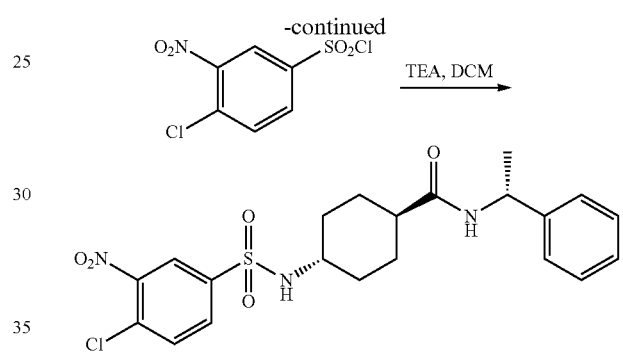

4-Chloro-3-nitro-benzenesulfonyl chloride (1.41 g, 5.5 mmol) was added to a solution of (1r,4R)-4-amino-N—((R)-1-phenylethyl)cyclohexanecarboxamide (1.133 g, 4.6 mmol; prepared as described for Example 1) and 5.12 mL (3.72 g, 36.8 mmol) in DCM (15 mL) at room temperature. The mixture was allowed to stir for 1 h, and was then concentrated in vacuo. The residue was taken up in 50 mL of ethyl acetate and washed with 50 mL of sat. aq. sodium bicarbonate, 2 portions of 50 mL 1 N aq. HCl, then dried (Na$_2$SO$_4$), and concentrated to give product. The crude product was suspended in 10 mL of ethyl acetate, agitated in an ultrasonic bath, and filtered. The light brown solid was washed with a small amount of ethyl acetate and dried to give 1.06 g of product (MS: (M+H)$^+$=466.18).

Step 2. Preparation of (1r,4R)-4-(4-(4-methoxybenzylamino)-3-nitrophenylsulfonamido)-N—((R)-1-phenylethyl)cyclohexanecarboxamide

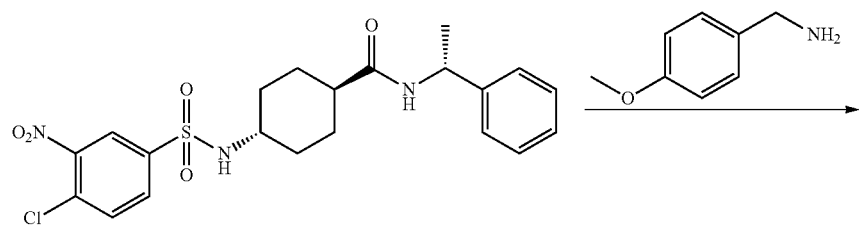

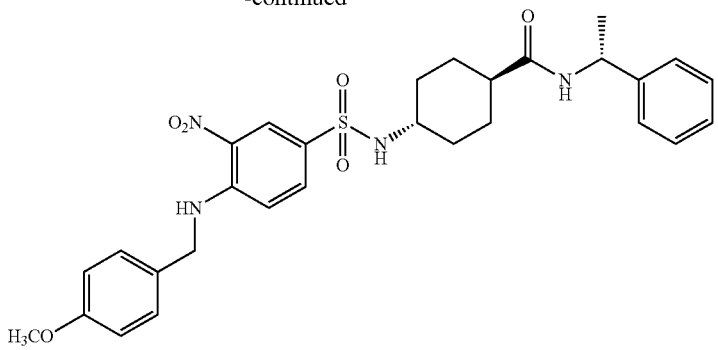

A mixture of the chloro-nitro benzenesulfonamide from the previous step (1 g, 2.15 mmol) and 4-methoxy-benzylamine (5.57 mL, 42.92 mmol) was heated to 80° C. A yellow solution was formed, followed by formation of a thick precipitate. An additional 20 mL of 4-methoxy-benzylamine and 20 mL of THF were added, and the mixture was stirred at 80° C. for an additional 25 min. Water (200 mL) was added to the mixture, and the flask was agitated in an ultrasonic bath, followed by filtration. The solid product was washed with water and a small amount of ether to give 1.2 g as a yellow solid (MS: $(M+H)^+=567.40$).

Step 3. Preparation of (1r,4R)-4-(4-amino-3-nitrophenylsulfonamido)-N—((R)-1-phenylethyl)cyclohexanecarboxamide The product from the previous step (1.2 g, 2.15 mmol) was added to a mixture of acetonitrile (40 mL) and water (1 mL). To the resulting heterogeneous mixture was added 3.53 g (6.44 mmol) of ceric ammonium nitrate (CAN). The reaction mixture became homogeneous after about 0.5 h. Ethyl acetate (200 mL) and water (100 mL) was added. The layers were separated, and the aqueous layer was extracted twice with 50 mL portions of ethyl acetate. The combined organic solutions were washed with 100 mL of sat. aq. NaCl, dried ($Na_2SO_4$). Toluene (20 mL) was added to the organic solution, and the resulting solution was concentrated under vacuum to a volume of approximately 5 mL, after which 50 mL of heptane was added to precipitate the product. The resulting heterogeneous mixture was filtered, and the solid product was rinsed with a small amount of n-heptane, resulting in 850 mg of product as a yellow solid (MS: $(M+H)^+=447.17$).

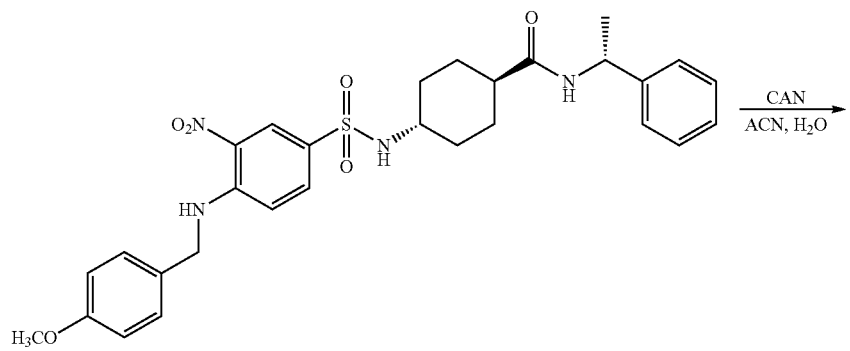

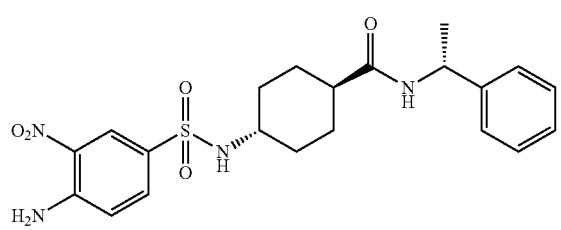

Step 4. Preparation of (1r,4R)-4-(3,4-diaminophenylsulfonamido)-N—((R)-1-phenylethyl)cyclohexanecarboxamide

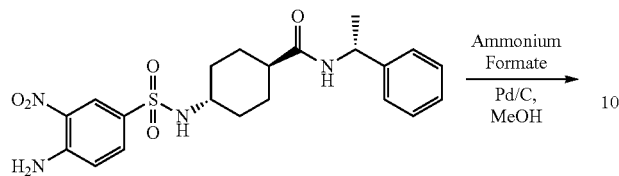

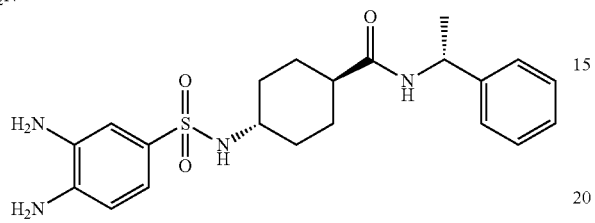

To a solution of the nitro aniline from the previous step (828 mg, 1.85 mmol) in 40 mL of methanol in a 250 mL r.b. flask was added 933 mg (14.8 mmol) of ammonium formate and 82 mg of Pd/C (10% by wt, 50% water; Degussa type). The resulting mixture was stirred under nitrogen for 2 h after which it was filtered through celite. Ethyl acetate (200 mL) was added, and the solution was washed with aqueous sodium bicarbonate (100 mL). The aqueous extracts were extracted with ethyl acetate (3×100 mL), and the combined organic solution was dried (sodium sulfate) and concentrated to give 800 mg of product as a yellow solid (MS: $(M+H)^+=417.28$).

Step 5. Preparation of ethyl 3-(6-(N-((1R,4r)-4-((R)-1-phenylethylcarbamoyl)cyclohexyl)sulfamoyl)-1H-benzo[d]imidazol-2-yl)benzoate A solution of 41 mg (0.1 mmol) in DMSO (2 mL) was added to 3-formyl-benzoic acid ethyl ester (16 mg, 0.9 mmol). Ferric chloride (2 mg) was added, and the mixture was stirred at room temperature over night. Some starting material remained, and an additional 2 mg of ferric chloride was added, followed by continued stirring up to a total of 24 h. The product was then purified by HPLC (method x) to give 26 mg of product.

Example 3

(1r,4R)—N—((R)-1-(4-fluorophenyl)ethyl)-4-(2-((S)-pyrrolidin-2-yl)-1H-benzo[d]imidazole-5-sulfonamido)cyclohexanecarboxamide

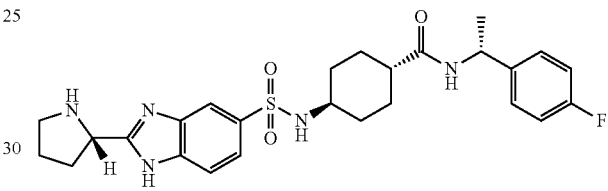

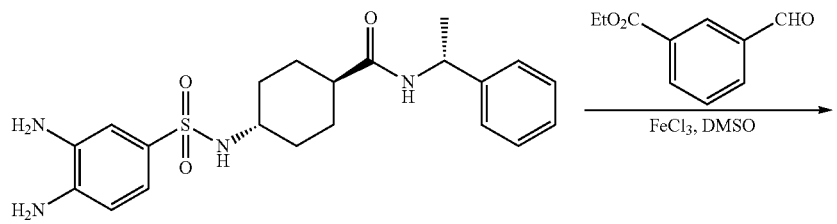

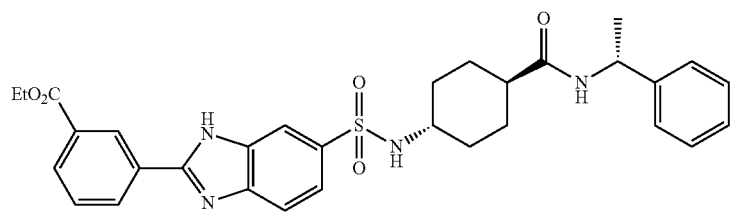

Step 1. Preparation of (S)-tert-butyl 2-(5-(N-((1R,4r)-4-((R)-1-(4-fluorophenyl)ethylcarbamoyl)cyclohexyl)sulfamoyl)-1H-benzo[d]imidazol-2-yl)pyrrolidine-1-carboxylate

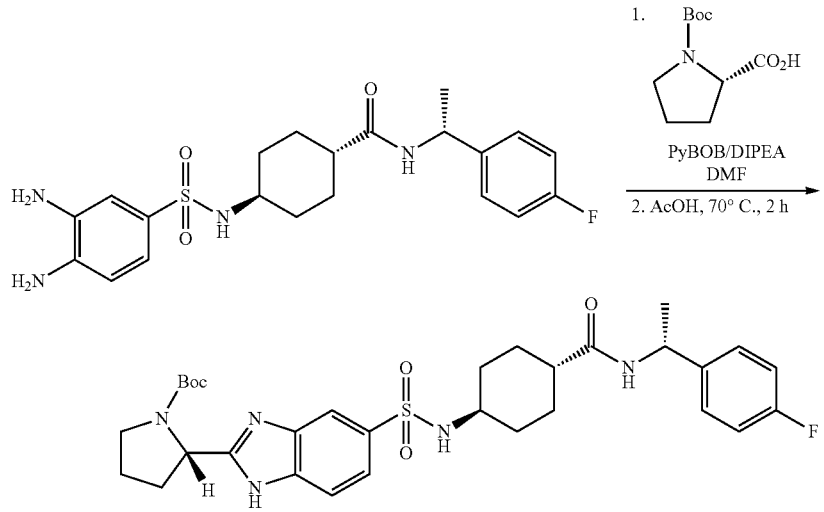

To a mixture of the diamine (0.1 g, 0.23 mmol; prepared as described for Example 2, but incorporating (R)-1-(4-fluorophenyl)ethanamine in place of the des-fluoro analog used previously) and N-Boc L-proline (49 mg, 0.22 mmol) in DMF (2 mL) was added PyBOP (115 mg, 0.23 mmol) and DIPEA (0.1 mL). The mixture was stirred at room temperature overnight. The reaction mixture was then poured onto a mixture of saturated aqueous sodium chloride and 1M hydrochloric acid and extracted with ethyl acetate. The organic solution was dried over magnesium sulfate and concentrated under vacuum to give product (0.37 g).

The crude product from the previous step was heated in 5 mL of acetic acid at 70° C. for 2 h, then cooled and concentrated under vacuum. The residue was taken up in ethyl acetate and washed with saturated aqueous sodium bicarbonate and brine, dried over magnesium sulfate and concentrated to give the crude product as a yellow solid. The crude product was purified using flash chromatography (Biotage 12S column, with 95:5 ethyl acetate/methanol as the eluent). Product was obtained as 23 mg of an orange gum.

Step 2. Preparation of (1r,4R)—N—((R)-1-(4-fluorophenyl)ethyl)-4-(2-((S)-pyrrolidin-2-yl)-1H-benzo[d]imidazole-5-sulfonamido)cyclohexanecarboxamide

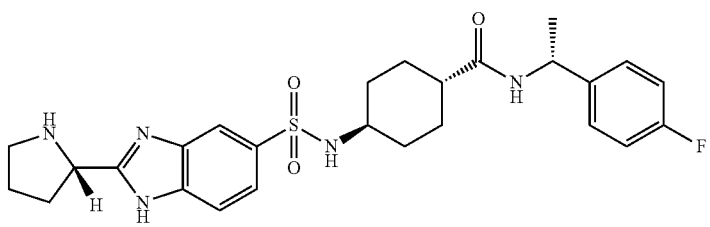

The product from Step 1 (23 mg, 0.0375 mmol) was dissolved in 2 mL of DCM to which 0.5 mL of trifluoroacetic acid was added. The reaction was stirred for 2 h at room temperature and concentrated under vacuum to a yellow residue. To this residue was added 3 mL of 2M HCl in ether. The mixture was stirred and filtered to give 8 mg of the product as its hydrochloride salt.

-continued

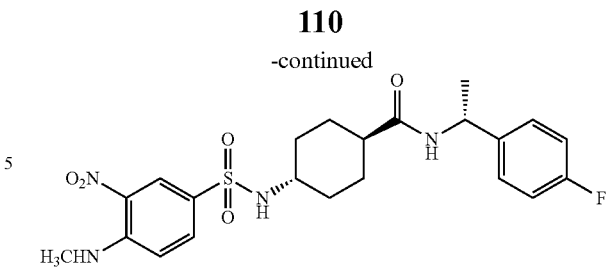

Example 4

Preparation of (1r,4R)—N—((R)-1-(4-fluorophenyl)ethyl)-4-(1-methyl-2-phenyl-1H-benzo[d]imidazole-5-sulfonamido)cyclohexanecarboxamide

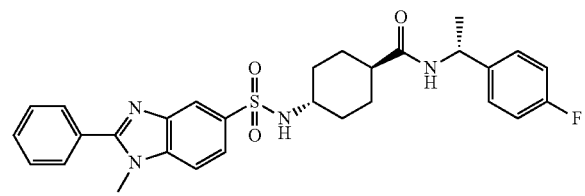 [SMILES: C[C@@H](NC(=O)[C@H]1CC[C@H](NS(=O)(=O)c2ccc3c(c2)nc(-c2ccccc2)n3C)CC1)c1ccc(F)cc1]

The chloronitrobenzenesulfonamide (0.396 g, 0.818 mmol; preparation described for Example 2) was dissolved in 1 mL of DMSO to which 1.23 mL of a 2M solution of methylamine (2.46 mmol) in THF was added. The mixture was heated to 70° C. in a sealed tube overnight. The reaction mixture was then poured into water and extracted three times with ethyl acetate. The organic solution was dried (MgSO$_4$) and concentrated to afford product as a yellow solid (0.413 g).

Step 2. Preparation of (1r,4R)-4-(3-amino-4-(methylamino)phenylsulfonamido)-N—((R)-1-(4-fluorophenyl)ethyl)cyclohexanecarboxamide

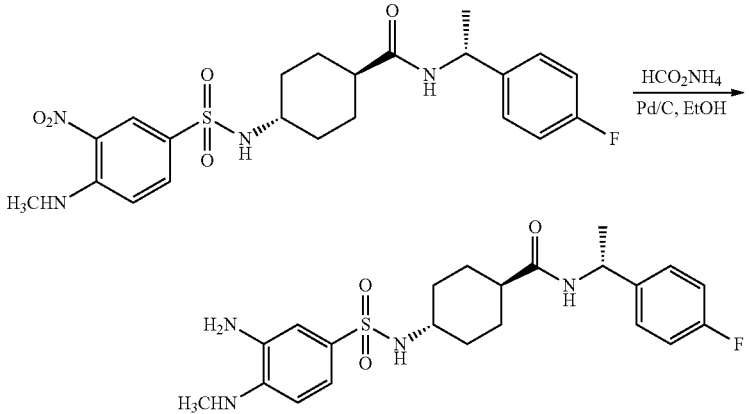

The product from the previous step was reduced following the procedure described in Step 4 of Example 2 for the preparation of (1r,4R)-4-(3,4-diaminophenylsulfonamido)-N—((R)-1-phenylethyl)cyclohexanecarboxamide. The crude product was suspended in water and filtered to provide a gray sticky solid which was then dissolved in methanol, filtered and concentrated. The resulting brown solid was taken up in ethyl acetate and washed with water, dried (MgSO$_4$) and concentrated to give a white solid. This material was triturated in hexane and filtered to afford a white solid (0.085 g). the filtrate was concentrated to afford a beige foam (0.124 g). NMR indicated that the two fractions were the same and were used as is in the next step.

Step 1. Preparation of (1r,4R)—N—((R)-1-(4-fluorophenyl)ethyl)-4-(4-(methylamino)-3-nitrophenylsulfonamido)cyclohexanecarboxamide

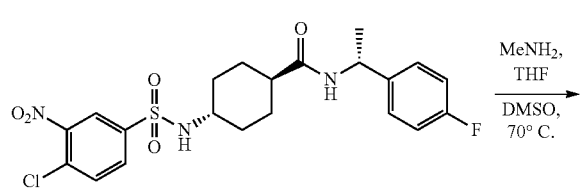

Step 3. Preparation of (1r,4R)—N—((R)-1-(4-fluorophenyl)ethyl)-4-(1-methyl-2-phenyl-1H-benzo[d]imidazole-5-sulfonamido)cyclohexanecarboxamide

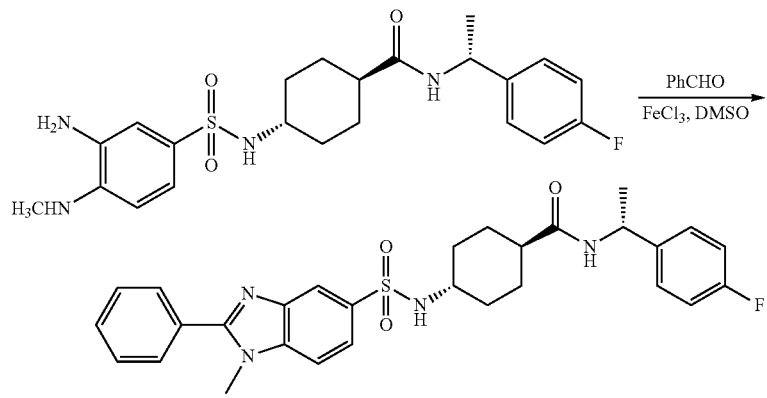

The diamine from the previous step (69 mg, 0.153 mmol) was condensed with benzaldehyde (16 mg, 0.153 mmol) with ferric chloride (1.2 mg, 0.008 mmol) in DMSO (1 mL) as described above for the preparation of ethyl 3-(6-(N-((1R,4r)-4-((R)-1-phenylethylcarbamoyl)cyclohexyl)sulfamoyl)-1H-benzo[d]imidazol-2-yl)benzoate. The product was obtained as a yellow solid (0.031 g).

Example 5

(1r,4R)-4-(1,2-dimethyl-1H-benzo[d]imidazole-5-sulfonamido)-N—((R)-1-(4-fluorophenyl)ethyl)cyclohexanecarboxamide

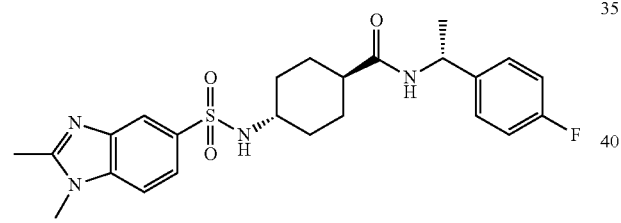

Step 1. Preparation of (1r,4R)-4-(3-amino-4-(methylamino)phenylsulfonamido)-N—((R)-1-(4-fluorophenyl)ethyl)cyclohexanecarboxamide Prepared as described in Step 2, Example 4 (above)

Step 2. Preparation of (1r,4R)-4-(1,2-dimethyl-1H-benzo[d]imidazole-5-sulfonamido)-N—((R)-1-(4-fluorophenyl)ethyl)cyclohexanecarboxamide

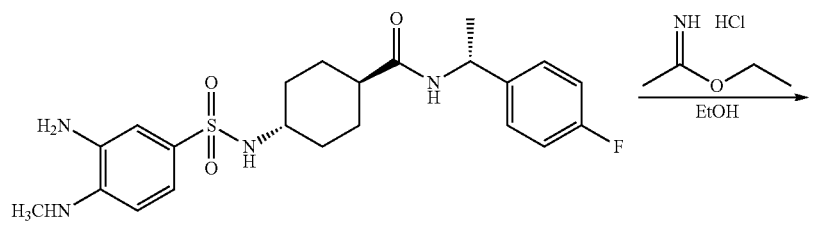

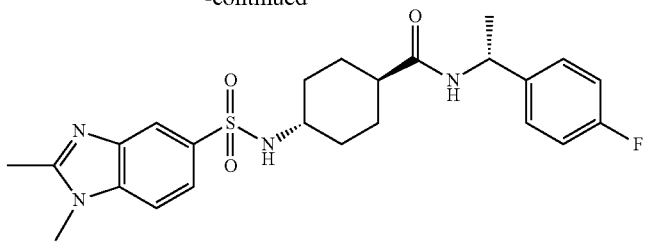

The diamine from the previous step (0.05 g, 0.111 mmol) and ethyl acetimidate hydrochloride (0.034 g, 0.279 mmol) were heated in ethanol (10 mL) at reflux overnight. The ethanol was removed under vacuum and acetic acid was added. Heating (80° C.) was continued for an additional 2 h followed by concentration of the mixture under vacuum. The product was purified by HPLC on a C8 Luna column using a water/acetonitrile gradient. The relevant fractions were combined and concentrated under vacuum to give product (21.7 mg).

Example 6

Preparation of Preparation of (1r,4R)—N—((R)-1-(4-fluorophenyl)ethyl)-4-(2-(tetrahydro-2H-pyran-4-yl)-1H-benzo[d]imidazole-6-sulfonamido)cyclohexanecarboxamide

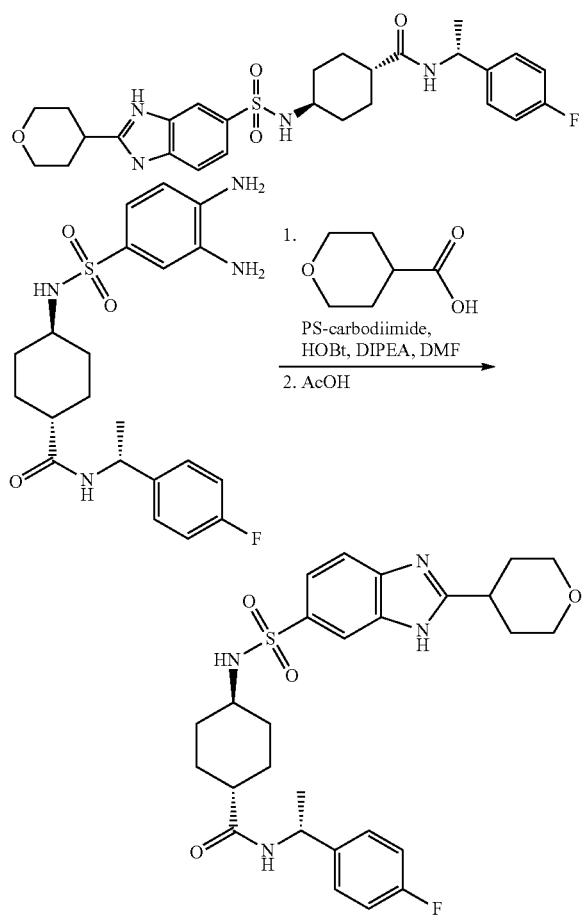

PS-carbodiimide (0.276 g, 0.345 mmol) was suspended in DMF, to which a solution of tetrahydro-2-H-pyran-4-carboxylic acid (0.1 g, 0.230 mmol) in DMF was added. A solution of HOBt (0.047 g, 0.345 mmol) in DMF was then added and the reaction mixture was shaken at RT for 20 mins. A solution of (1r,4R)-4-(3,4-diaminophenylsulfonamido)-N—((R)-1-(4-fluorophenyl)ethyl)cyclohexanecarboxamide (prepared similarly to the des-fluoro analog described in Steps 1-4 of Example 2) in DMF was then added and the reaction mixture was shaken at room temperature overnight. LC-MS then showed one major peak corresponding to desired product. The reaction mixture was then filtered and concentrated. The resulting crude brown oil —N-(2-amino-4-(N-((1R,4r)-4-((R)-1-(4-fluorophenyl)ethylcarbamoyl)cyclohexyl)sulfamoyl)phenyl)tetrahydro-2H-pyran-4-carboxamide was taken on without further purification.

The product from the previous step (0.25 g crude) was dissolved in AcOH (20 mL) and heated to 80° C. for 1 hour. LC-MS at this point showed one major peak corresponding to the desired product the reaction mixture was then concentrated and the residue was partitioned between 1M NaOH and EtOAc. The organic layer was dried over MgSO₄, filtered and concentrated to afford a mobile orange oil which was purified via Biotage flash column chromatography (2-20% EtOAc/MeOH). Relevant fractions were pooled and concentrated to afford an orange foam. This material was further purified via prep HPLC (10-45-100% Water/CAN/0.1% TFA). Relevant fractions were frozen and lyophilized to afford the product as a white powder (0.027 g-6% yield).

Example 7

Preparation of (1r,4r)-N-isopropyl-N-methyl-4-(2-(phenylamino)-1H-benzo[d]imidazole-5-sulfonamido)cyclohexanecarboxamide

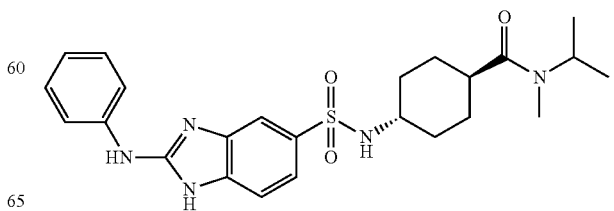

Step 1. Preparation of (1r,4r)-4-(3,4-diaminophenyl-sulfonamido)-N-isopropyl-N-methylcyclohexanecarboxamide This intermediate diaminophenyl derivative is prepared as described for Example 2.

Step 2. Preparation of (1r,40-N-isopropyl-N-methyl-4-(2-(phenylamino)-1H-benzo[d]imidazole-5-sulfonamido)cyclohexanecarboxamide

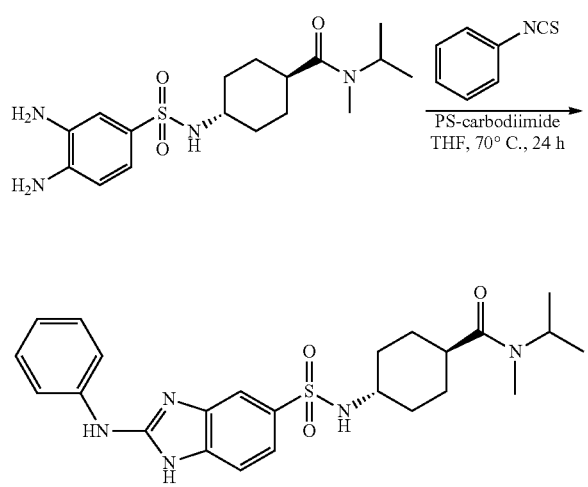

To a solution of (1r,4r)-4-(3,4-diaminophenylsulfonamido)-N-isopropyl-N-methylcyclohexanecarboxamide (54.5 mg, 0.133 mmol) in THF (2 mL) is added isothiocyanato-benzene (0.02 mL, 0.162 mmol) and polystyrene N1-cyclohexylcarbodiimide-N2-propyloxymethyl resin (187 mg, 0.266 mmol; 1.42 mmol/g). The reaction mixture is heated to 70° C. for 24 h. After cooling to rt, the resin is filtered off and rinsed with THF and MeOH. The filtrate is concentrated under reduced pressure. The residue is purified by reverse phase prep-HPLC (Waters) to afford the title compound as a white solid. HPLC: $t_R$=1.37 min (Method A1); MS-ES: (M+H)$^+$=470.

Example 8

Preparation of (1r,4r)-isopropyl 4-(2-(4-acetamidophenyl)-1H-benzo[d]imidazole-5-sulfonamido)cyclohexanecarboxylate

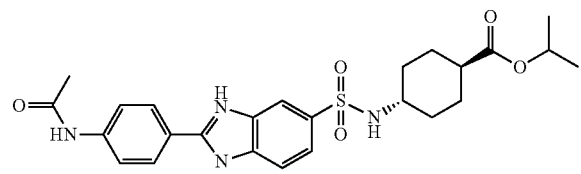

Step 1. Preparation of (1r,4r)-isopropyl 4-(4-chloro-3-nitrophenylsulfonamido)cyclohexanecarboxylate

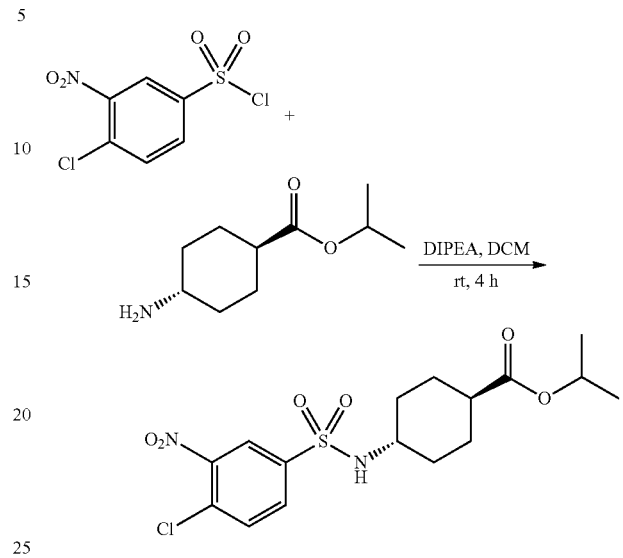

To a solution of (1r,4r)-isopropyl 4-aminocyclohexanecarboxylate (670 mg, 3.44 mmol) in DCM (20 mL) is added 4-chloro-3-nitro-benzenesulfonyl chloride (898 mg, 3.44 mmol) and DIPEA (1.20 mL, 6.87 mmol) at rt. The reaction mixture is stirred for 4 h at rt. The mixture is diluted with DCM and washed with 1 N HCl and saturated aqueous NaCl solution. The organic layer is dried over Na$_2$SO$_4$, filtered, and concentrated under reduced pressure to yield the title compound as a yellow solid.

Step 2. Preparation of (1r,4r)-isopropyl 4-(4-(benzylamino)-3-nitrophenylsulfonamido)cyclohexanecarboxylate

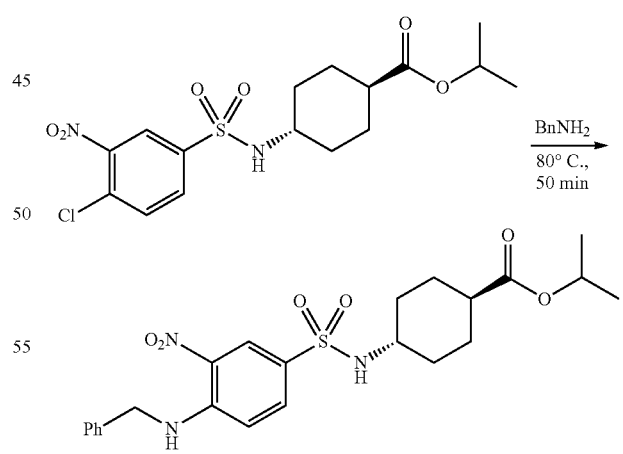

A solution of (1r,4r)-isopropyl 4-(4-chloro-3-nitrophenylsulfonamido)cyclohexanecarboxylate (1.30 g, 3.15 mmol) in benzylamine (7 mL) is heated to 80° C. for 50 min. After cooling to rt, the reaction mixture is diluted with EtOAc and the pH is adjusted to 3 with 0.5 N HCl. The organic layer is washed 0.5 N HCl (2×), saturated aqueous NaHCO$_3$ solution, and saturated aqueous NaCl solution. Then, the organic layer is dried over Na$_2$SO$_4$, filtered, and concentrated under reduced pressure. The residue is triturated with MeOH to yield the title compound as a yellow solid.

Step 3. Preparation of (1r,4r)-isopropyl 4-(3,4-diaminophenylsulfonamido)cyclohexanecarboxylate

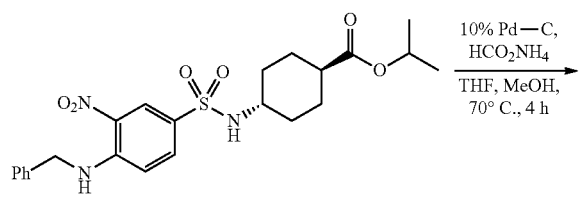

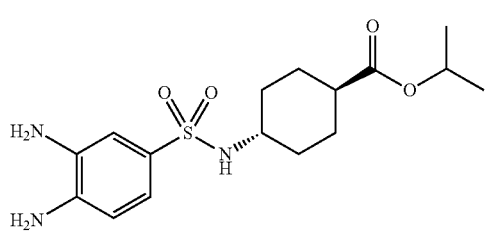

To a solution of (1r,4r)-isopropyl 4-(4-(benzylamino)-3-nitrophenylsulfonamido)cyclohexanecarboxylate (1.39 mg, 2.63 mmol) in THF (21 mL) and MeOH (6 mL) is added 10% Pd—C (440 mg, 0.410 mmol) and ammonium formate (856 mg, 13.2 mmol) at rt. The reaction mixture is heated to 70° C. for 4 h. After cooling to rt, the mixture is filtered through a Celite plug (washed with MeOH) and the filtrate is concentrated under reduce pressure to yield the title compound as an off-white foam.

Step 4. Preparation of (1r,4r)-isopropyl 4-(2-(4-acetamidophenyl)-1H-benzo[d]imidazole-5-sulfonamido)cyclohexanecarboxylate

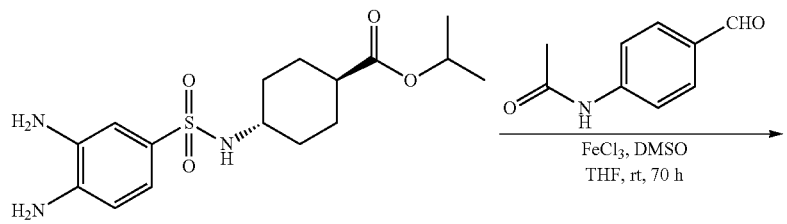

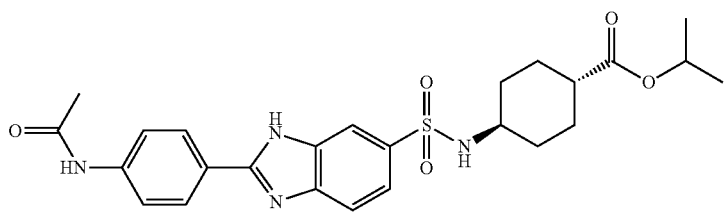

To a solution of (1r,4r)-isopropyl 4-(3,4-diaminophenylsulfonamido)cyclohexanecarboxylate (47.8 mg, 0.121 mmol) and N-(4-formyl-phenyl)-acetamide (22.2 mg, 0.133 mmol) in DMSO (1 mL) was added a suspension of anhydrous FeCl$_3$ (1.1 mg, 0.007 mmol) in THF (0.35 mL) at rt. The reaction mixture was stirred for 70 h at rt (open to air). Then, the mixture is filtered through a SiO$_2$ cartridge (230 mg, Chromafix, Macherey-Nagel) which is washed with EtOAc. The filtrate is concentrated under reduce pressure. The remaining DMSO solution is purified by reverse phase prep-HPLC (Waters) to afford the title compound as a light yellow solid. HPLC: t$_R$=1.55 min (Method A1); MS-ES: (M+H)$^+$=499.

Example 9 and 10

Preparation of N-((1r,4r)-4-(5-tert-butyl-1,3,4-oxadiazol-2-yl)cyclohexyl)-2-(4-(4-methylpiperazin-1-yl)phenylamino)-1H-benzo[d]imidazole-5-sulfonamide and N-((1r,4r)-4-(5-tert-butyl-1,3,4-oxadiazol-2-yl)cyclohexyl)-2-(4-(4-methylpiperazin-1-yl)phenyl)-1H-benzo[d]imidazole-5-sulfonamide

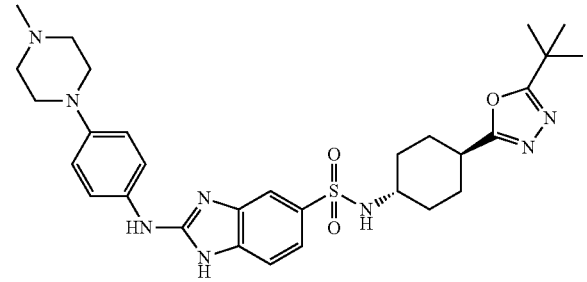

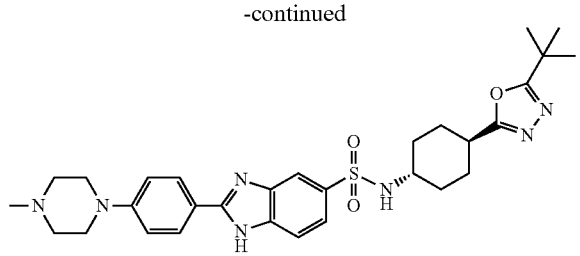

Step 1. Preparation of tert-butyl (1r,4r)-4-(2-pivaloylhydrazinecarbonyl)cyclohexylcarbamate

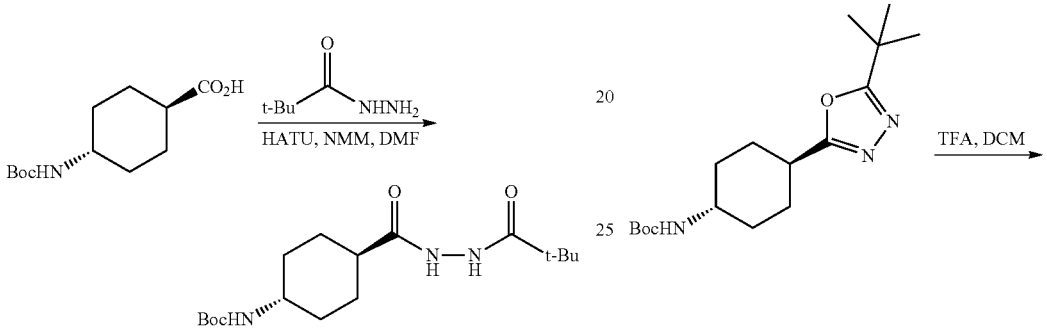

Pivaloyl hydrazide (4.98 g, 42.91 mmol) was added to a solution of trans-4-tert-butoxycarbonylamino-cyclohexanecarboxylic acid (8.70 g, 35.76 mmol), HATU (13.57 g, 35.67 mol), and NMM (9.04 g, 89.4 mmol) in 350 mL of DMF. The reaction was stirred at room temperature overnight. The reaction mixture was diluted with ethyl acetate and washed with saturated aqueous ammonium chloride, water and brine. The organic phase was dried ($Na_2SO_4$) and concentrated to give approximately 11.44 g crude (MS: $(M+H)^+=342.20$). This material was used as is in the next step.

Step 2. Preparation of tert-butyl (1r,4r)-4-(5-tert-butyl-1,3,4-oxadiazol-2-yl)cyclohexylcarbamate (Methoxycarbonylsulfamoyl)triethylammonium hydroxide inner salt (Burgess reagent, 8.43 g, 35.4 mmol) was added in one portion to room temperature solution of crude tert-butyl (1r,4r)-4-(2-pivaloylhydrazinecarbonyl)cyclohexylcarbamate (8.05 g, 23.58 mmol) in THF. The reaction was heated 70° C. for approximately two hours. Reaction cooled to room temperature, filtered over sintered funnel and concentrated to 16.6 g of crude product. The crude product was chromatographed by normal phase chromatography 5-100% ethyl acetate in heptane. Desired fractions were concentrated to give tert-butyl (1r,4r)-4-(5-tert-butyl-1,3,4-oxadiazol-2-yl)cyclohexylcarbamate (4.17 g, 12.9 mmol; MS: $(M+H)^+=324.17$).

Step 3. Preparation of (1r,4r)-4-(5-tert-butyl-1,3,4-oxadiazol-2-yl)cyclohexanamine tert-Butyl (1r,4r)-4-(5-tert-butyl-1,3,4-oxadiazol-2-yl)cyclohexylcarbamate (4.15 g, 12.84 mmol) was stirred in 20% v/v trifluoroacetic acid in DCM at room temperature overnight. The reaction mixture was then diluted with DCM, washed with water, dried ($MgSO_4$) and concentrated to give product (2.72 g, 12.19 mmol; MS: $(M+H)^+=224.26$).

Step 4. Preparation of N-((1r,4r)-4-(5-tert-butyl-1,3,4-oxadiazol-2-yl)cyclohexyl)-4-chloro-3-nitrobenzenesulfonamide

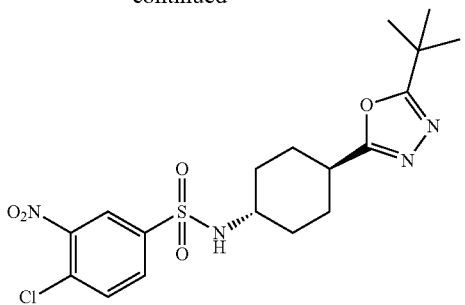

The above amine (2.72 g, 12.19 mmol) and sulfonyl chloride (3.12 g, 12.19 mmol) were coupled according to the procedure described above (Scheme 3) using diisopropylethyl amine in DCM to provide 3.89 g (8.78 mmol) of product (MS: (M+H)$^+$=443.13).

Step 5. Preparation of 4-(benzylamino)-N-((1r,4r)-4-(5-tert-butyl-1,3,4-oxadiazol-2-yl)cyclohexyl)-3-nitrobenzenesulfonamide

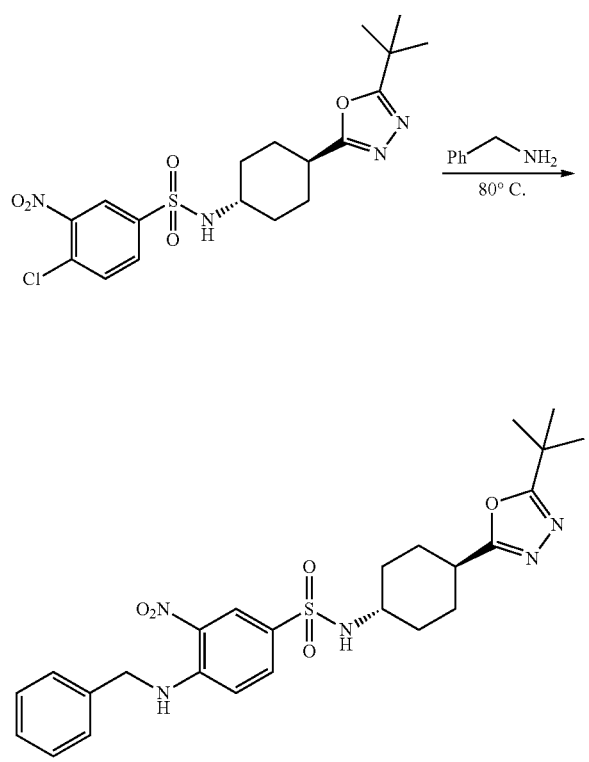 [SMILES: CC(C)(C)c1nnc([C@H]2CC[C@H](NS(=O)(=O)c3ccc(Cl)c([N+](=O)[O-])c3)CC2)o1 ; NCc1ccccc1 ; CC(C)(C)c1nnc([C@H]2CC[C@H](NS(=O)(=O)c3ccc(NCc4ccccc4)c([N+](=O)[O-])c3)CC2)o1]

N-((1r,4r)-4-(5-tert-butyl-1,3,4-oxadiazol-2-yl)cyclohexyl)-4-chloro-3-nitrobenzenesulfonamide (3.50 g, 7.90 mmol) and benzylamine (17.2 ml, 158 mmol) were combined and placed in a pre-heated 80° C. oil bath for approximately 10 minutes. The reaction was cooled to room temperature and poured on 340 ml 0.5N hydrochloric acid. The product was extracted into ethyl acetate with multiple extracts. The combined extracts rinsed successively 0.5N HCl, saturated sodium bicarbonate, and brine. The organic solution was dried over sodium sulfate, filtered, and concentrated. The crude product was triturated in 60 mL 1:1 diethyl ether:heptane to afford 4-(benzylamino)-N-((1r,4r)-4-(5-tert-butyl-1,3,4-oxadiazol-2-yl)cyclohexyl)-3-nitrobenzenesulfonamide (3.86 g, 7.51 mmol; MS: (M+H)$^+$=514.23).

Step 6. Preparation of 3,4-diamino-N-((1r,4r)-4-(5-tert-butyl-1,3,4-oxadiazol-2-yl)cyclohexyl)benzenesulfonamide

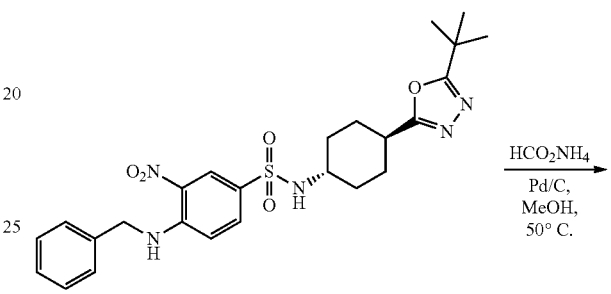

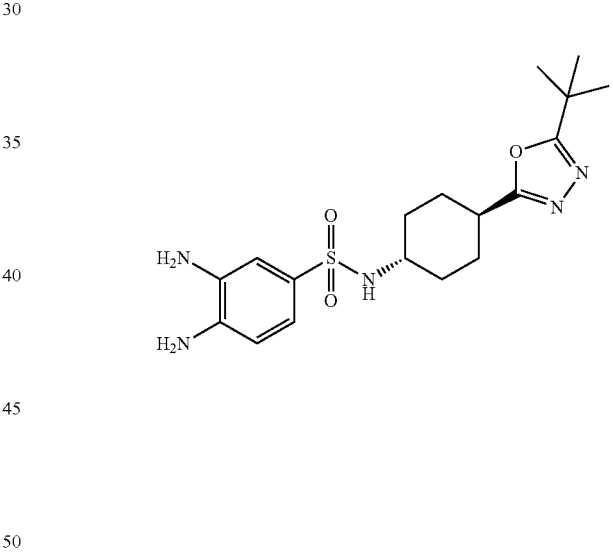

Ammonium formate (3.57 g, 56.5 mmol) was added to slurry of 4-(benzylamino)-N-((1r,4r)-4-(5-tert-butyl-1,3,4-oxadiazol-2-yl)cyclohexyl)-3-nitrobenzenesulfonamide (3.63 g, 7.07 mmol) and 10% Pd/C (3.63 g, Degussa Type E101, 50% wet) in methanol (70 ml). The reaction mixture was heated at 50° C. for two hours, then cooled to room temperature, filtered over celite, and concentrated to residue. The residue was partitioned between dichloromethane and saturated aqueous sodium bicarbonate. The organic layer was rinsed once with water, dried over sodium sulfate, filtered, and concentrated to 3,4-diamino-N-((1r,4r)-4-(5-tert-butyl-1,3,4-oxadiazol-2-yl)cyclohexyl)benzenesulfonamide (2.62 g, 6.65 mmol; MS: (M+H)$^+$=394.16).

Step 7a. Preparation of N-((1r,4r)-4-(5-tert-butyl-1,3,4-oxadiazol-2-yl)cyclohexyl)-2-(4-(4-methylpiperazin-1-yl)phenylamino)-1H-benzo[d]imidazole-5-sulfonamide

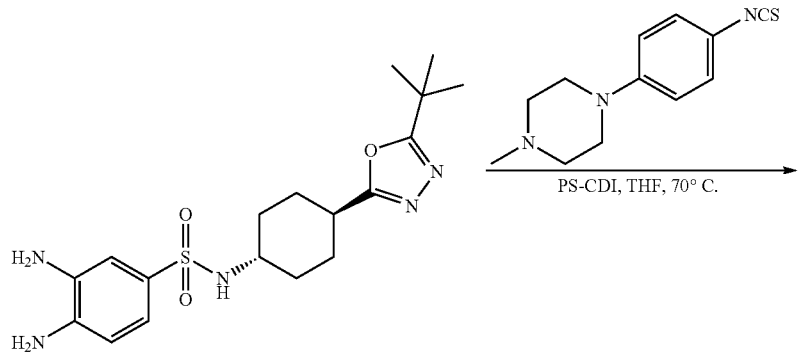

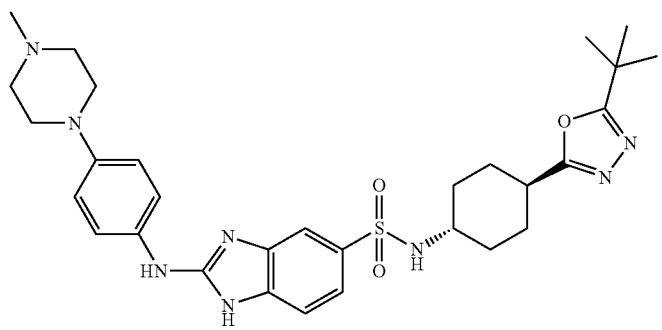

The diamine from the previous step (196 mg, 0.5 mmol) was added to 1-(4-isothiocyanatophenyl)-4-methylpiperazine (130 mg, 0.55 mmol) and polymer-supported carbodiimide (900 mg, 1 mmol) in 10 mL of THF. The mixture was heated to 70° C. for 16 h and was then concentrated under vacuum. The residue was purified by normal phase silica gel chromatography to provide the title compound (MS: (M+H)$^+$=592.7).

Step 7b. Preparation of N-((1r,4r)-4-(5-tert-butyl-1,3,4-oxadiazol-2-yl)cyclohexyl)-2-(4-(4-methylpiperazin-1-yl)phenyl)-1H-benzo[d]imidazole-5-sulfonamide

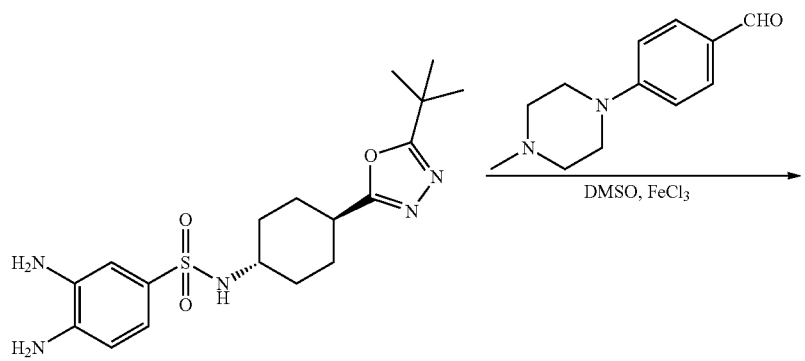

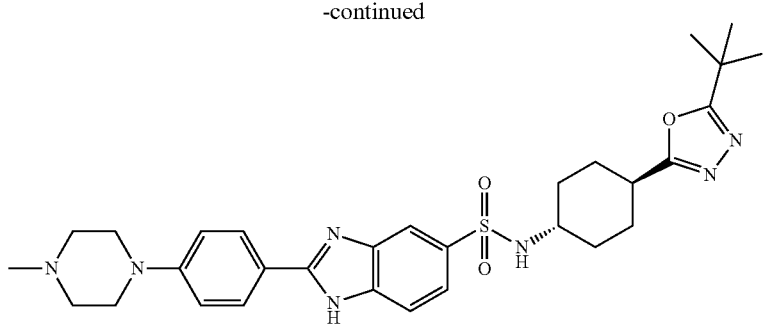

A suspension of anhydrous iron (III) chloride in DMSO (0.015 mmol) was added to a mixture of the diamine from Step 6 (60 mg, 0.152 mmol) and 4-(4-methylpiperazin-1-yl)benzaldehyde (33.5 L, 0.167 mmol) in DMSO. The mixture was stirred overnight at room temperature, then concentrated under vacuum. The residue was purified by normal phase chromatography on silica gel (MS: $(M+H)^+=578.27$).

Example 11

N—((R)-1-(4-fluorophenyl)ethyl)-4-(2-phenylbenzo[d]oxazole-6-sulfonamido)cyclohexanecarboxamide

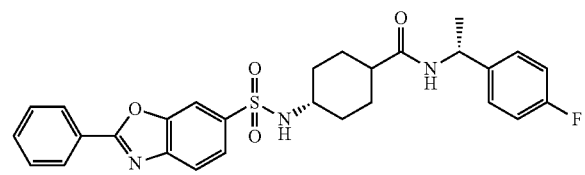

Step 1. Preparation of 2-phenylbenzo[d]oxazole-6-sulfonyl chloride

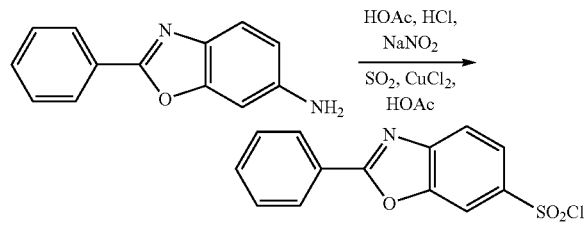

2-Phenylbenzo[d]oxazol-6-amine (250 mg, 1.19 mmol) was dissolved in acetic acid (5 mL), to which concentrated hydrochloric acid (2 mL) was added. A solution of 81.67 mg (1.19 mmol) of sodium nitrite in 1.5 mL of water was then added dropwise. The mixture was stirred at 0° C. for 15 min., after which the entire reaction mixture was poured into 42 mL of a solution prepared by bubbling 74 g of sulfur dioxide gas into 740 mL of glacial acetic acid followed by addition of 30 g of copper (II) chloride monohydrate in 35 mL of water. The reaction mixture was then stirred for 4 h at room temperature. The resulting mixture was poured onto ice and partitioned between ethyl acetate and water. The organic layer was dried over magnesium sulfate and concentrated to afford product (161 mg) as a brown solid.

Step 2. Preparation of N—((R)-1-(4-fluorophenyl)ethyl)-4-(2-phenylbenzo[d]oxazole-6-sulfonamido)cyclohexanecarboxamide

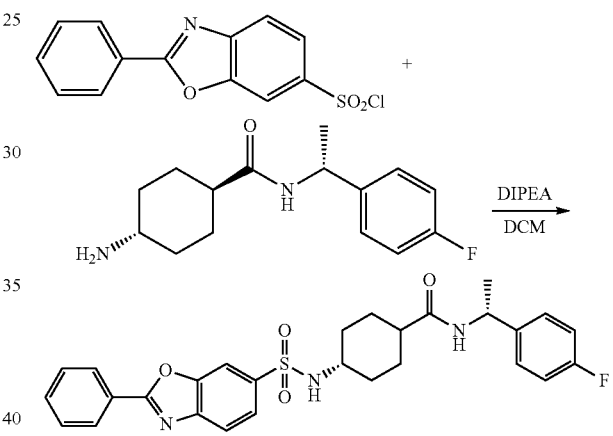

The product from the previous step was condensed with (1r,4R)-4-amino-N—((R)-1-(4-fluorophenyl)ethyl)cyclohexanecarboxamide in a manner analogous to that described for Example 1 to afford the title compound (55 mg) which was purified by HPLC.

Example 12

(1r,4R)—N—((R)-1-(4-fluorophenyl)ethyl)-4-(1-methyl-1H-indole-5-sulfonamido)cyclohexanecarboxamide

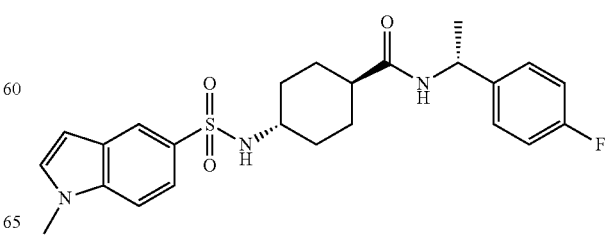

Preparation of (1r,4R)—N—((R)-1-(4-fluorophenyl)ethyl)-4-(1-methyl-1H-indole-5-sulfonamido)cyclohexanecarboxamide

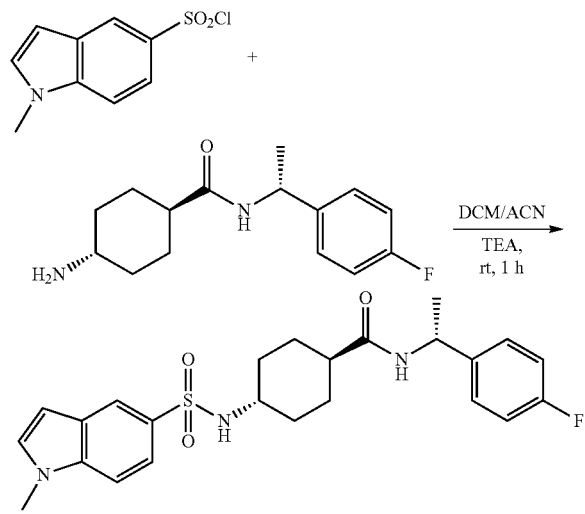

(1I,4I)-4-Amino-N—((I)-1-(4-fluorophenyl)ethyl)cyclohexanecarboxamide hydrochloride (prepared as described in Example 1, but using (R)-1-(4-fluorophenyl)ethanamine instead of the des-fluoro analog) was dissolved in a DCM/ACN mixture. Triethylamine was added followed by the commercially available 1-methyl-1I-indole-5-sulfonyl chloride. The reaction mixture was stirred overnight at room temperature and then concentrated under vacuum. The residue was purified by HPLC (MS: (M+H)⁺=458.25).

Example 13

Preparation of (1r,4R)-4-(2-phenyl-1H-indole-5-sulfonamido)-N—((R)-1-phenylethyl)cyclohexanecarboxamide

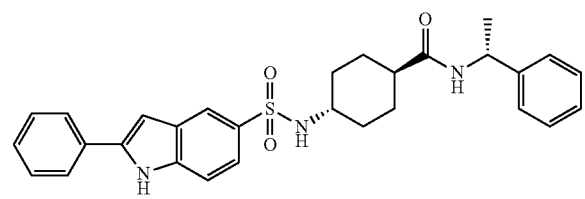 [SMILES: C[C@@H](NC(=O)[C@H]1CC[C@H](NS(=O)(=O)c2ccc3[nH]c(-c4ccccc4)cc3c2)CC1)c1ccccc1]

Step 1. Preparation of 4-{N'-[1-phenyl-eth-(E)-ylidene]-hydrazino}-benzenesulfonic acid

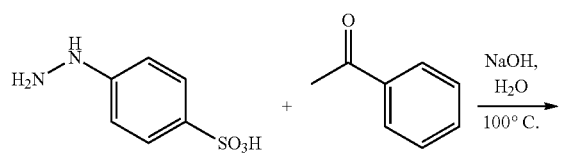

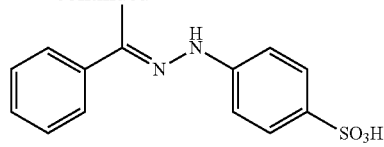

Sodium hydroxide (400 mg, 10 mmol) in 10 mL of water was added to a solution of 4-hydrazino-benzenesulfonic acid (1.88 g, 10 mmol) in 20 mL of water. Acetophenone (1.32 g, 11 mmol) was then added, and the mixture was heated to 100° C. overnight. The resulting mixture was then cooled and washed with ether. The pH of the aqueous solution was then adjusted to 4 with conc. HCl. Water was removed under vacuum, and methanol was added. The solution was filtered and concentrated to give product (680 mg) as a yellow solid (MS: (M+H)⁺=291.15).

Step 2. Preparation of 2-phenyl-1H-indole-5-sulfonic acid

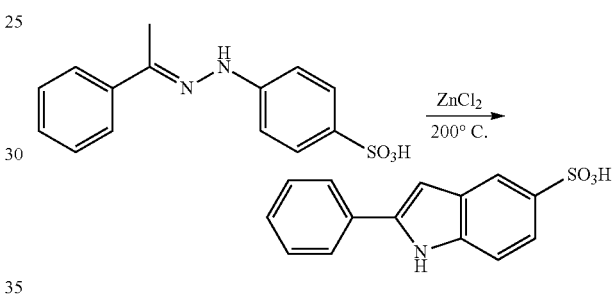

The hydrazine derivative from the previous step (600 mg, 2.07 mmol) was mixed with 3 g (22 mmol) of zinc chloride and heated to 200° C. for 2 h. The mixture was cooled, and water was added. The product (330 mg) was collected as a brown solid (MS: (M+H)⁺=274.19).

Step 3. Preparation of 2-Phenyl-1H-indole-5-sulfonyl chloride

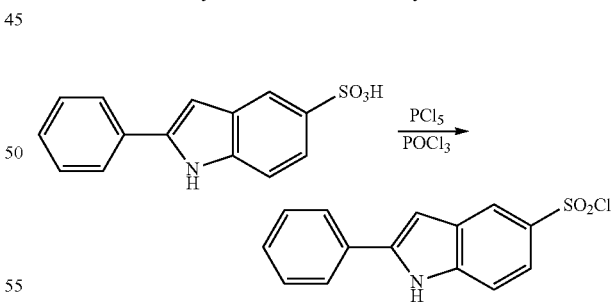

To a mixture of the indole sulfonic acid from the previous step (130 mg, 0.476 mmol) in 2 mL of phosphoryl chloride was added 100 mg (0.48 mmol) of phosphorus pentachloride. The mixture was stirred at room temperature for 60 min, then poured on ice in a beaker. DCM was added to extract the product, and the organic solution was dried (Na₂SO₄) and concentrated to give the crude product. The product was purified by flash chromatography on silica gel using a mixture of ethyl acetate (0-10% gradient) in heptane to give 11 mg (MS: (M+H)⁺=290.08).

Step 4. Preparation of (1r,4R)-4-(2-phenyl-1H-indole-5-sulfonamido)-N—((R)-1-phenylethyl)cyclohexanecarboxamide

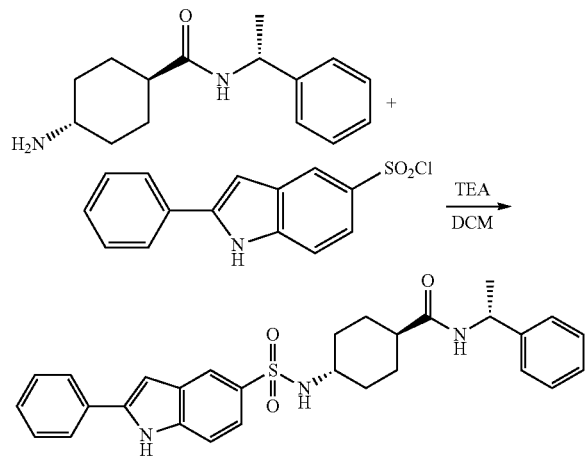

A solution of the sulfonyl chloride from the previous step (11 mg, 0.0377 mmol) in dichloromethane (0.2 mL) was added dropwise to a solution of (1r,4R)-4-amino-N—((R)-1-phenylethyl)cyclohexanecarboxamide (18.48 mg, 0.075 mmol) and triethylamine (61 mg, 0.6 mmol) in 0.3 mL of dichloromethane at room temperature. The mixture was stirred 2 h, then concentrated under vacuum. The residue was purified by flash chromatography on a silica gel column using an ethyl acetate/heptane gradient (0-100% ethyl acetate) to give 5 mg of product.

Example 14

(1r,4R)—N—((R)-1-(4-fluorophenyl)ethyl)-4-(1-methyl-2-phenyl-1H-indole-5-sulfonamido)cyclohexanecarboxamide

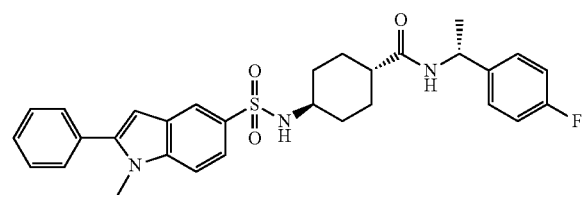 [SMILES: C[C@@H](NC(=O)[C@H]1CC[C@H](NS(=O)(=O)c2ccc3c(c2)cc(-c2ccccc2)n3C)CC1)c1ccc(F)cc1]

Step 1. Preparation of (1r,4r)-methyl 4-(1-methyl-1H-indole-5-sulfonamido)cyclohexanecarboxylate

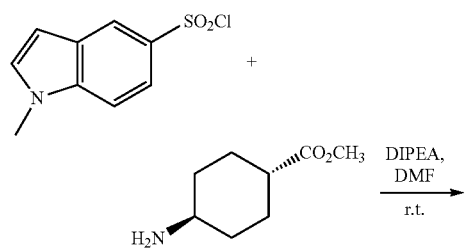

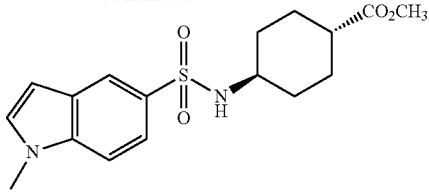

A mixture of 1-methyl-1H-indole-5-sulfonyl chloride (0.869 g, 4.48 mmol), (1r,4r)-methyl 4-aminocyclohexanecarboxylate (1.03 g, 4.48 mmol), and DIPEA (1.217 g, 1.645 mL, 9.42 mmol) in DMF (9 mL) was stirred at room temperature for 1 h. The mixture was then poured into water, filtered, washed with water and dried over $P_2O_5$ to provide the product (MS: M+351.0).

Step 2. Preparation of (1r,4r)-4-(1-methyl-2-phenyl-1H-indole-5-sulfonamido)cyclohexanecarboxylic acid

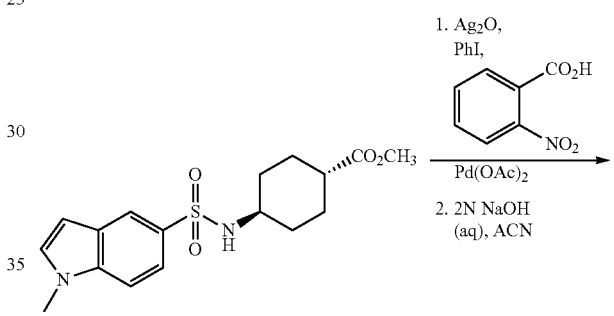

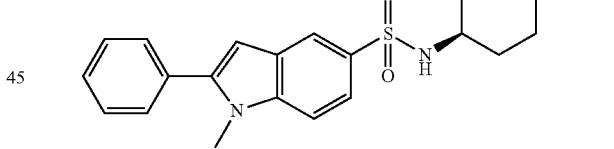

A mixture of (1r,4r)-methyl 4-(1-methyl-1H-indole-5-sulfonamido)cyclohexanecarboxylate (100 mg, 0.285 mmol), silver oxide (49.6 mg, 0.214 mmol), palladium acetate (6.41 mg, 0.029 mmol), iodobenzene (233 mg, 1.141 mmol) and 2-nitrobenzoic acid (71.5 mg, 0.428 mmol) was stirred under nitrogen at 40° C. in DMF (1.43 mL) for 16 h. The reaction mixture was added to 2M aq. sodium carbonate and extracted twice with ethyl acetate. The organic phase was washed with dilute sodium carbonate (aq.) and water, filtered and concentrated. The residue was taken up in acetonitrile and 20 eq. of 2N sodium hydroxide was added, and the mixture was stirred at room temperature for 2 h. The mixture was concentrated under vacuum to remove the acetonitrile, diluted with water, and washed twice with ether. The aqueous phase was acidified with aq. HCl to pH 4-5 and extracted twice with ethyl acetate. The organic solution was dried ($MgSO_4$) and concentrated to give product (MS: M+413.0).

Step 3. Preparation of (1r,4R)—N—((R)-1-(4-fluorophenyl)ethyl)-4-(1-methyl-2-phenyl-1H-indole-5-sulfonamido)cyclohexanecarboxamide

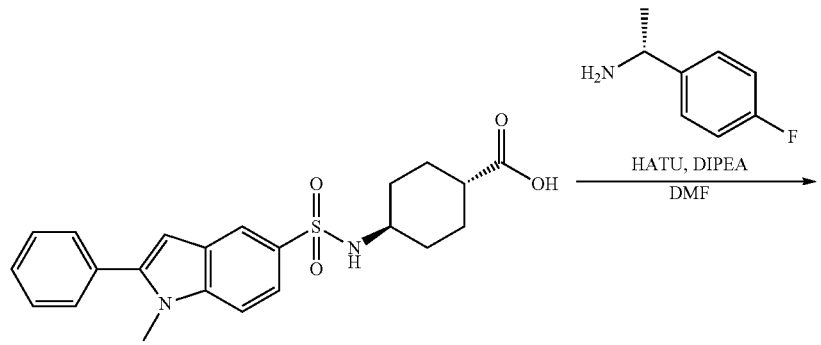

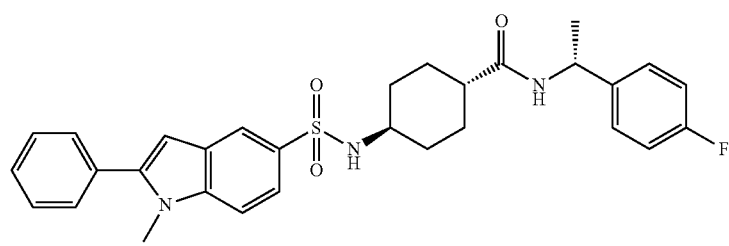

The indole carboxylic acid from the previous step (27.5 mg, 0.067 mmol), (R)-1-(4-fluorophenyl)ethanamine (9.28 mg, 0.067 mmol), and HATU (30.42 mg, 0.08 mmol) were dissolved in DMF (1 mL). Diisopropylethylamine (26 L, 19.26 mg, 0.149 mmol) was added. The mixture was then stirred at room temperature for 15 min. The reaction was filtered (with addition of ACN and water, concentrated, and purified by HPLC using 0.1% TFA in a water/ACN (20-100%) solvent gradient as eluent.

Example 15

(1r,4S)—N—((S)-2-hydroxy-2-methyl-1-phenylpropyl)-4-(1-methyl-2-phenyl-1H-indole-5-sulfonamido)cyclohexanecarboxamide

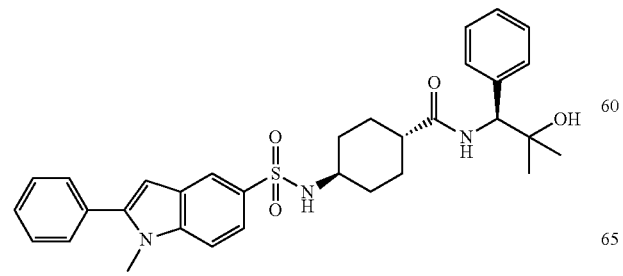

Step 1. Preparation of (S)-1-amino-2-methyl-1-phenylpropan-2-ol

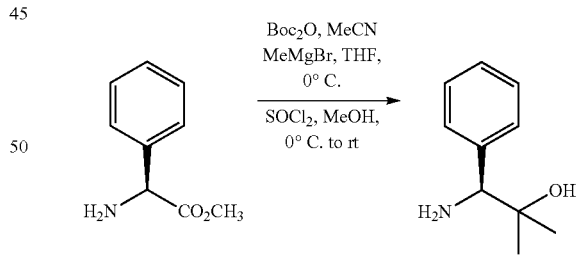

The preparation of (S)-1-amino-2-methyl-1-phenylpropan-2-ol from (S)-methyl 2-amino-2-phenylacetate was carried out according to the procedure for the preparation of this compound in Rikimaru, K., et al., *Synthesis*, 2004 (6), 909-917.

Step 2, Preparation of (1r,4S)—N—((S)-2-hydroxy-2-methyl-1-phenylpropyl)-4-(1-methyl-2-phenyl-1H-indole-5-sulfonamido)cyclohexanecarboxamide

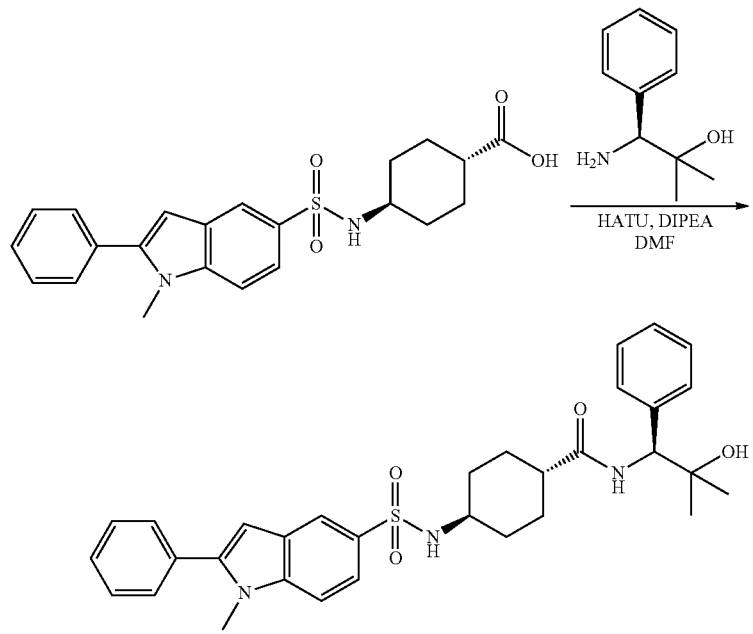

(1r,4r)-4-(1-methyl-2-phenyl-1H-indole-5-sulfonamido)cyclohexanecarboxylic acid (prepared as described for Example 14) was condensed with (S)-1-amino-2-methyl-1-phenylpropan-2-ol also according to the procedure described for Example 14 to give the title compound.

Example 16

(1r,4R)—N—((R)-1-(4-fluorophenyl)ethyl)-4-(1H-indole-5-sulfonamido)cyclohexanecarboxamide Step 1. Preparation of (1r,4r)-methyl 4-(2-oxoindoline-5-sulfonamido)cyclohexanecarboxylate

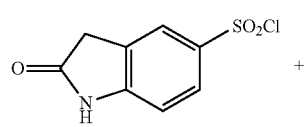

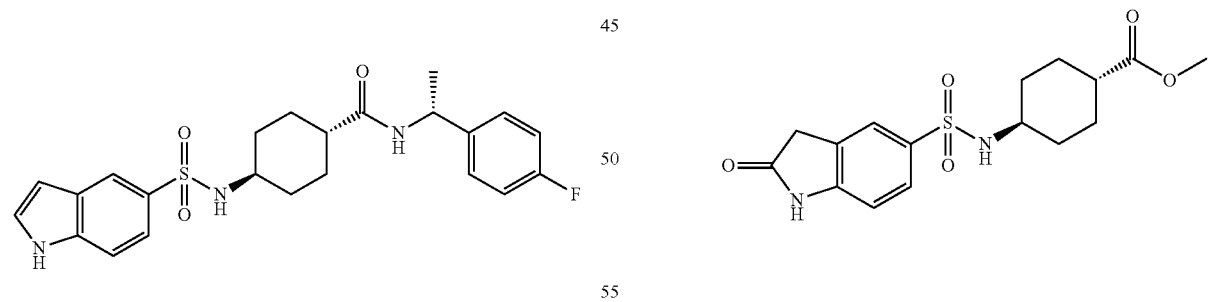

To a solution of (1r,4r)-methyl 4-aminocyclohexanecarboxylate (1.686 g, 8.7 mmol) and DIPEA (3.78 mL, 21.76 mmol) in DCM at 0° C. was added 2-oxoindoline-5-sulfonyl chloride (2.02 g, 8.7 mmol). The reaction was allowed to warm to room temperature and stirred for 2 h. The mixture was then concentrated under vacuum, and the oily residue was triturated in ethyl acetate and methanol. Product was collected by filtration (MS: (M+H)$^+$=353).

Step 2. Preparation of (1r,4r)-4-(1H-indole-5-sulfonamido)cyclohexanecarboxylic acid

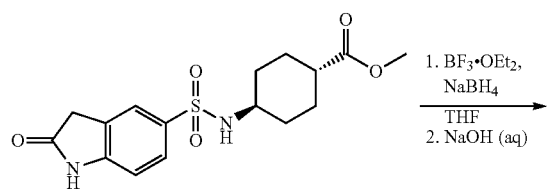

To a suspension of the oxindole (238 mg, 0.65 mmol) in THF (5 mL) at 0° C. was added boron trifluoride etherate (0.24 mL, 2.28 mmol). After stirring 10 min., sodium borohydride (40 mg, 1.04 mmol) was added. The resulting solution was allowed to warm to room temperature with stirring overnight. The reaction mixture was then quenched by slowly adding water (15 mL) at 0° C. and stirring for an additional 30 min. Acidification to pH 1 with 6N HCl was followed by stirring for 30 min., after which the pH was adjusted to 14 with 2N aq. sodium hydroxide followed by stirring for 30 min. The mixture was extracted with ethyl acetate, and the organic extracts were dried (MgSO$_4$) and concentrated under vacuum. The aqueous layer was lyophilized and purified on acidic preparative HPLC to give the acidic product (MS: (M+H)$^+$=323.18).

Step 3. Preparation of (1r,4R)—N—((R)-1-(4-fluorophenyl)ethyl)-4-(1H-indole-5-sulfonamido)cyclohexanecarboxamide

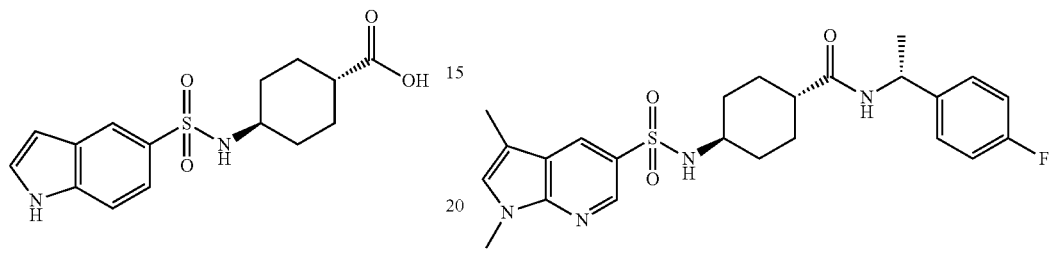

(R)-1-(4-Fluorophenyl)ethanamine (13 μL, 0.096 mmol) was added to a solution of the acid from the previous step (34 mg, 0.106 mmol), HATU (55 mg, 0.144 mmol) and DIPEA (67 μL, 0.385 mmol) in DMF (1 mL) at room temperature. The mixture was stirred overnight. The mixture was then concentrated, and the residue purified using basic HPLC to give 10 mg of product as a white solid (MS: (M+H)$^+$=444.19).

Example 17

(1r,4r)-4-(1,3-dimethyl-1H-pyrrolo[2,3-b]pyridine-5-sulfonamido)-N-(4-fluorobenzyl)cyclohexanecarboxamide

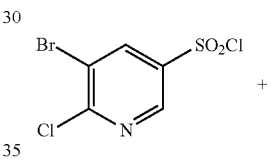

Step 1. Preparation of (1r,4R)-4-(5-bromo-6-chloropyridine-3-sulfonamido)-N—((R)-1-(4-fluorophenyl)ethyl)cyclohexanecarboxamide

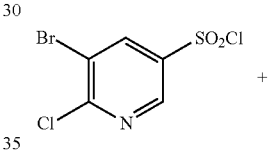

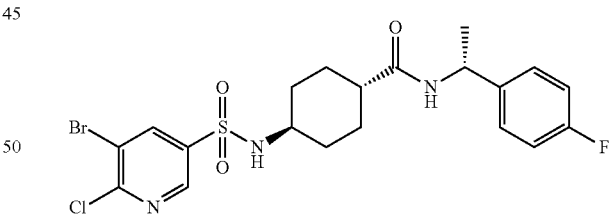

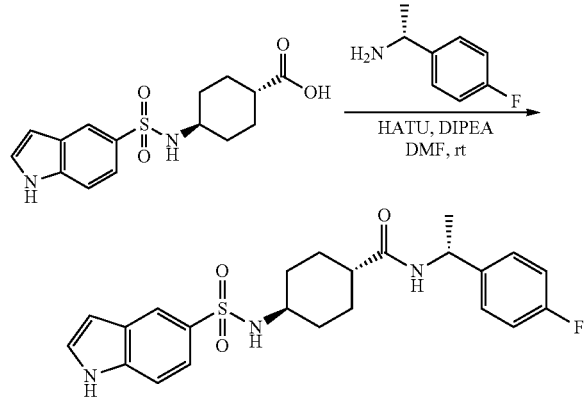

5-Bromo-6-chloropyridine-3-sulfonyl chloride (250 mg, 0.859 mmol) was dissolved in DCM (10 mL) to which a suspension of (1r,4R)-4-amino-N—((R)-1-(4-fluorophenyl)ethyl)cyclohexanecarboxamide (227 mg, 0.859 mmol) in DCM was added. The reaction mixture was stirred at room temperature overnight and then concentrated under vacuum. The residue was partitioned between ethyl acetate and 1M aq. sodium hydroxide. The aqueous layer was extracted with ethyl acetate and the combined organic layers were dried over magnesium sulfate, filtered and concentrated under vacuum to afford product as a beige solid. The crude product was triturated with hexane to afford product as a white power (220 mg).

Step 2. Preparation of (1r,4R)-4-(6-(allyl(methyl)amino)-5-bromopyridine-3-sulfonamido)-N—((R)-1-(4-fluorophenyl)ethyl)cyclohexanecarboxamide

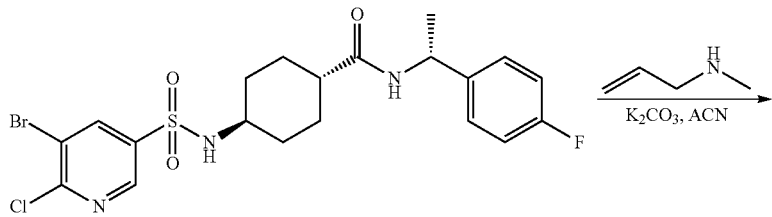

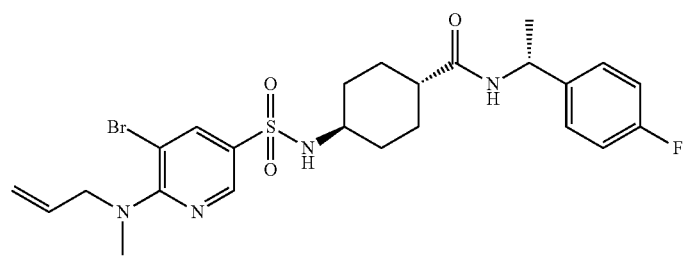

The chloropyridine (0.5 g, 0.967 mmol; as prepared in Step 1), potassium carbonate (0.401 g, 2.9 mmol), N-methylprop-2-en-1-amine (0.103 g, 1.45 mmol) and acetonitrile (10 mL) were combined and heated in a microwave reactor to 160° C. for 10 min. The reaction mixture was filtered, and the filtrate was concentrated under vacuum to afford a brown foam. After drying under high vacuum, the product (443 mg) was taken on to the next step.

Step 3. Preparation of (1r,4R)-4-(1,3-dimethyl-1H-pyrrolo[2,3-b]pyridine-5-sulfonamido)-N—((R)-1-(4-fluorophenyl)ethyl)cyclohexanecarboxamide The product from the previous step (33 mg, 0.036 mmol), tris(dibenzylideneacetone)dipalladium(0), tricyclohexylphosphine (20 mg, 0.072 mmol), sodium carbonate (134 mg, 1.26 mmol) and DMF (5 mL) were combined and heated to 180° C. for 10 min in a microwave reactor. The mixture was filtered, and the filtrate was concentrated to afford a brown oil which was dried under high vacuum. The crude product was purified by flash chromatography (Biotage 25M column, 50-100% heptane/ethyl acetate as eluent). The relevant fractions were combined and concentrated under vacuum to afford 67 mg of product.

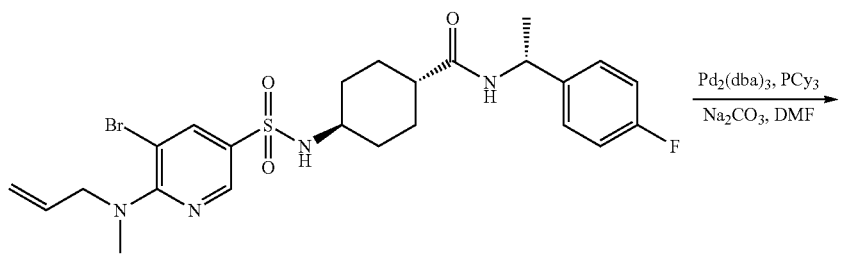

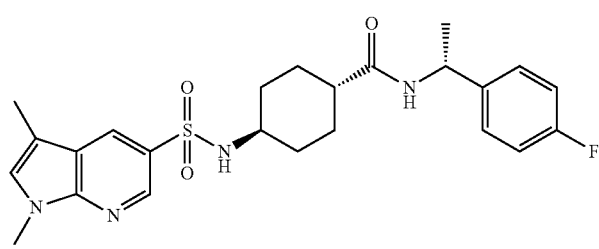 [SMILES: Cc1cn(C)c2ncc(S(=O)(=O)N[C@H]3CC[C@H](C(=O)N[C@H](C)c4ccc(F)cc4)CC3)cc12]

Example 18

(1r,4R)—N—((R)-1-(4-fluorophenyl)ethyl)-4-(2-phenyl-1H-indole-6-sulfonamido)cyclohexanecarboxamide

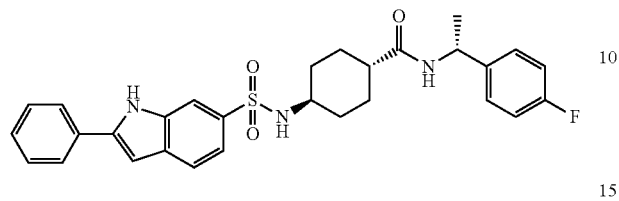

Step 1. Preparation of (1r,4R)—N—((R)-1-(4-fluorophenyl)ethyl)-4-(3-nitro-4-(phenylethynyl)phenylsulfonamido)cyclohexanecarboxamide

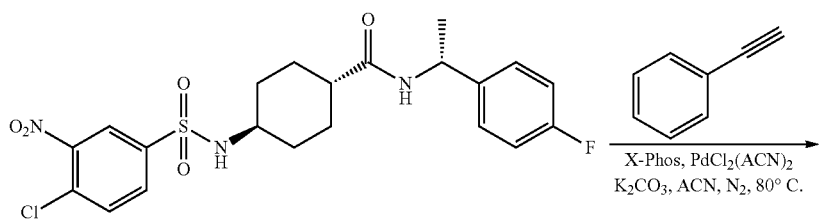

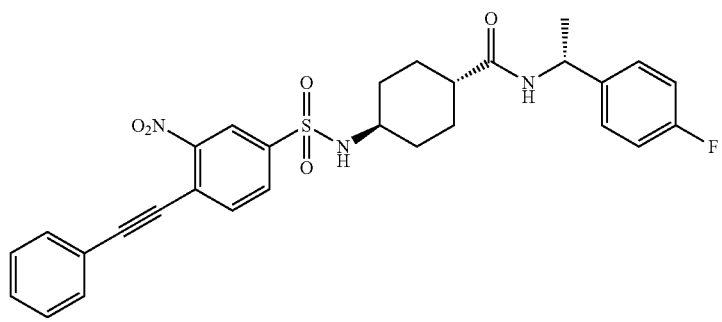

A mixture of (1r,4R)-4-(4-chloro-3-nitrophenylsulfonamido)-N—((R)-1-(4-fluorophenyl)ethyl)cyclohexanecarboxamide (1.0 g, 2.17 mmol; prepared as described in Example 2), X-Phos (59 mg, 0.12 mmol), PdCl2(ACN)$_2$ (11 mg, 0.04 mmol) and potassium carbonate (855 mg, 6.19 mmol) was placed in a flask and purged with nitrogen. Acetonitrile (8 mL) was then added, followed by additional purging with nitrogen. Phenylacetylene (0.25 mL, 2.28 mmol) was then added slowly and the reaction mixture was heated to 80° C. for 3 h. The reaction mixture was poured into ethyl acetate (100 mL) and washed with water and brine. The organic phase was dried (Na$_2$SO$_4$), filtered and concentrated to afford the product (1.15 g; MS: (M+H)$^+$=550.23).

Step 2. Preparation of (1r,4R)-4-(3-amino-4-(phenylethynyl)phenylsulfonamido)-N—((R)-1-(4-fluorophenyl)ethyl)cyclohexanecarboxamide

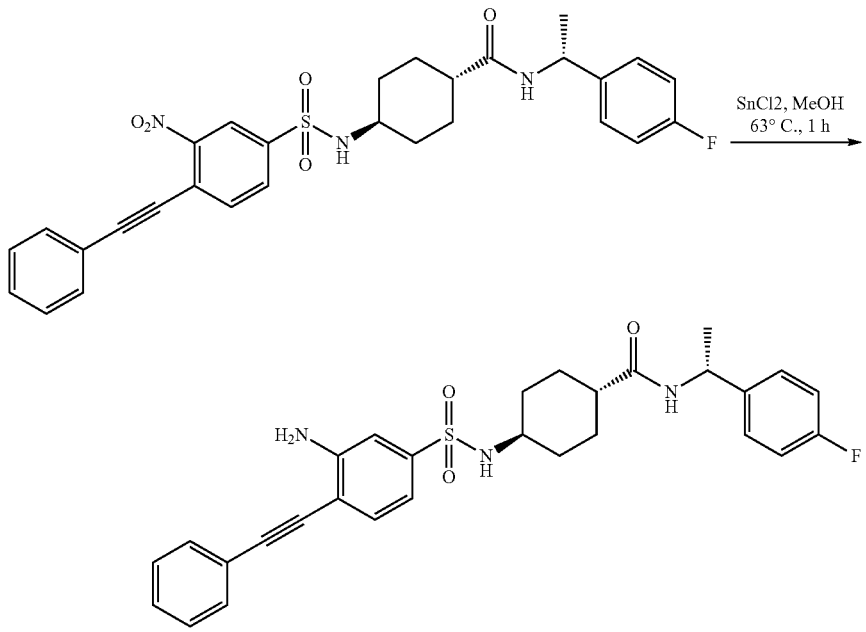

The product from the previous step (1.15 g, 2.09 mmol) was taken up in methanol (15 mL) and treated with tin(II) chloride (3.96 g, 20.9 mmol) at 63° C. for 1 h. The reaction mixture was then concentrated under vacuum, taken up in ethyl acetate (100 mL) and washed with water. The aqueous layer was extracted with ethyl acetate, and the combined organic solutions were washed with 1.0 N sodium hydroxide (aq.) and brine, dried over sodium sulfate, filtered and concentrated under vacuum to give 780 mg of product (MS: $(M+H)^+=520.23$).

Step 3. Preparation of (1r,4R)—N—((R)-1-(4-fluorophenyl)ethyl)-4-(2-phenyl-1H-indole-6-sulfonamido)cyclohexanecarboxamide

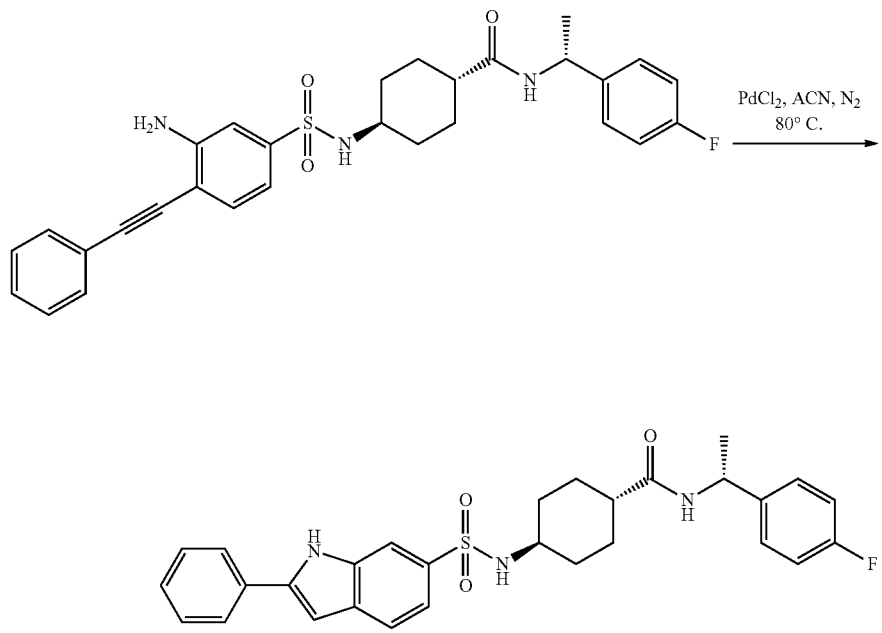 [SMILES: C[C@@H](NC(=O)[C@H]1CC[C@H](NS(=O)(=O)c2ccc(C#Cc3ccccc3)c(N)c2)CC1)c1ccc(F)cc1 ; C[C@@H](NC(=O)[C@H]1CC[C@H](NS(=O)(=O)c2ccc3cc(-c4ccccc4)[nH]c3c2)CC1)c1ccc(F)cc1]

Palladium (II) chloride (24 mg, 0.14 mmol) in anhydrous acetonitrile (10 mL) in a capped vial was purged with nitrogen and then heated to 80° C. until the mixture became homogeneous. A solution of the previously prepared compound (360 mg, 0.69 mmol) in hot anhydrous acetonitrile (10 mL, 70-80° C.) was added dropwise over about 10 min. The reaction was continued for 30 min at 80 C, followed by concentration of the reaction mixture under reduced pressure. The residue was purified by flash chromatography on silica gel using a gradient of 0-100% ethyl acetate in n-heptane as the eluent to give 200 mg of the desired indole.

Example 19

(1r,4R)-4-(2-phenyl-1H-indole-6-sulfonamido)-N—((R)-1-(pyridin-2-yl)ethyl)cyclohexanecarboxamide

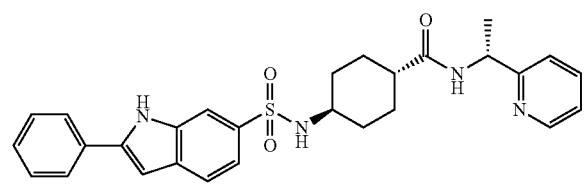 [SMILES: C[C@@H](NC(=O)[C@H]1CC[C@H](NS(=O)(=O)c2ccc3cc(-c4ccccc4)[nH]c3c2)CC1)c1ccccn1]

Step 1. Preparation of (1r,4r)-methyl 4-(4-chloro-3-nitrophenylsulfonamido)cyclohexanecarboxylate

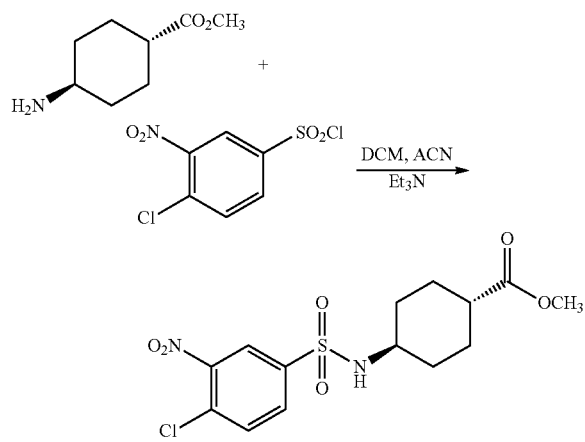

(1r,4r)-methyl 4-aminocyclohexanecarboxylate HCl salt (7.75 g, 40 mmol) was suspended in a mixture of DCM (50 mL) and then treated with triethylamine (22.31 mL, 160 mmol), followed by 4-chloro-3-nitrobenzene-1-sulfonyl chloride (11.27 g, 44 mmol). The reaction mixture was stirred at rt for 2 h and then concentrated under reduced pressure. The residue was taken up in ethyl acetate (100 mL) and washed with 1N aq. HCl (3×100 mL), brine (100 mL) and dried over sodium sulfate. Filtration and concentration of the organic solution gave product (14.1 g) as a yellow solid (MS: (M+H)$^+$=377.3).

Step 2. Preparation of (1r,4r)-methyl 4-(3-nitro-4-(phenylethynyl)phenylsulfonamido)cyclohexanecarboxylate

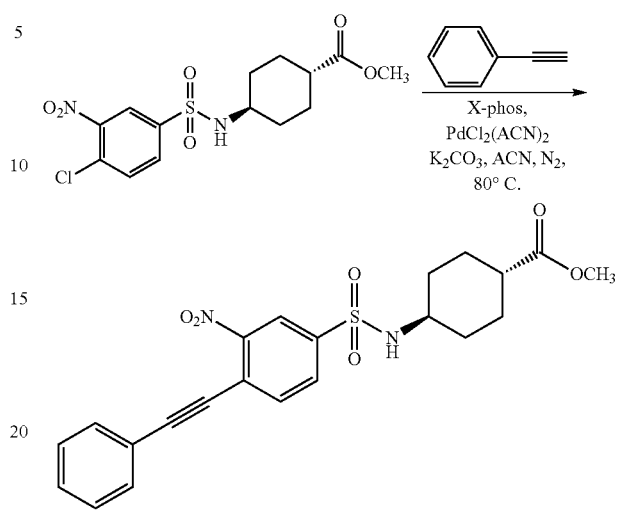

A 10 mL vial was charged with (1r,4r)-methyl 4-(4-chloro-3-nitrophenylsulfonamido)cyclohexanecarboxylate (200 mg, 0.53 mmol), X-phos (15 mg, 0.031 mmol), PdCl2(ACN)$_2$ (2.7 mg, 0.010 mmol) and potassium carbonate (220 mg, 1.6 mmol). The vial was then capped and purged with nitrogen. Anhydrous acetonitrile (2 mL) was added, and the resulting heterogeneous mixture was purged with nitrogen for 3 min., followed by addition of phenylacetylene (0.087 mL, 0.8 mmol) via syringe. The vial was then heated to 80° C. for 2 h. The mixture was then poured into ethyl acetate (20 mL) and washed with 1N aq. HCl (3×20 mL) and brine (20 mL), dried over sodium sulfate and concentrated under vacuum to afford 276 mg of crude product (MS: (M+H)$^+$=443.3) that was used directly in the next step.

Step 3. Preparation of (1r,4r)-methyl 4-(3-amino-4-(phenylethynyl)phenylsulfonamido)cyclohexanecarboxylate

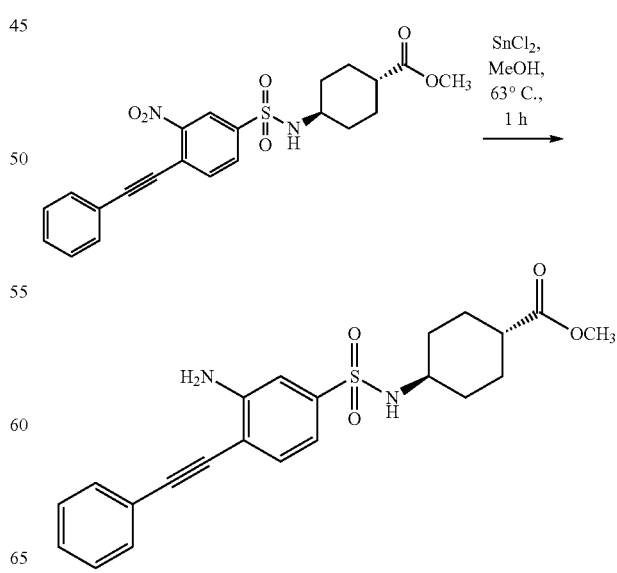

The product from the previous step (ca. 0.53 mmol) in methanol (5 mL) was treated with tin(II) chloride (1.18 g, 6.2 mmol) and heated at 63° C. for 1 h. The reaction mixture was then poured into ethyl acetate (50 mL) and washed with 1 N aq HCl (50 mL), sat. aq sodium bicarbonate (50 mL) and brine (50 mL). The acidic aqueous layer was neutralized with aqueous sodium bicarbonate and extracted with ethyl acetate (50 mL) to recover the product. The combined organic layers were then dried over sodium sulfate, filtered and concentrated. The residue was purified by chromatography (Biotage 25+M column, 0-50% ethyl acetate in n-heptane) to afford product as a brown solid (200 mg; MS: (M+H)$^+$=413.14).

Step 4. Preparation of (1r,4r)-4-(2-phenyl-1H-indole-6-sulfonamido)cyclohexanecarboxylic acid

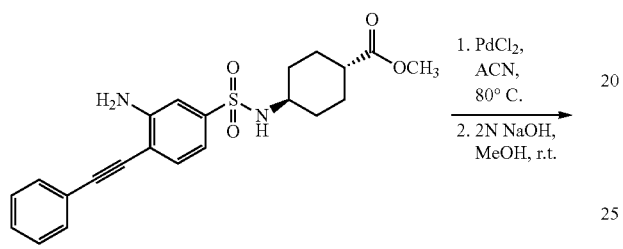

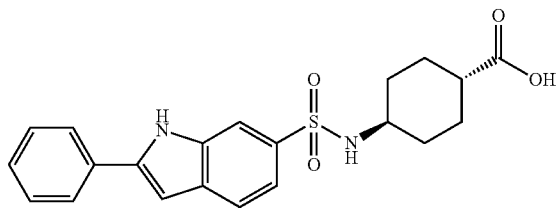

Palladium (II) chloride (17 mg, 0.096 mmol) in anhydrous acetonitrile (5 mL) in a capped 50 mL flask was purged with nitrogen for 3 min., and then heated to 80° C. to obtain a homogeneous solution. A solution of the product from the previous step (200 mg, 0.48 mmol) in hot anhydrous acetonitrile (10 mL, 70-80° C.) was added into the reaction flask dropwise via syringe over about 10 min. The reaction was continued for 30 minutes at 80° C., followed by concentration under reduced pressure. The residue was purified by flash chromatography (Biotage, 25+M column, 0-100% ethyl acetate in n-heptane) to give product (134 mg) as a yellow solid.

This product (134 mg, 0.32 mmol) was taken up in methanol (2 mL) and treated with 2N aq. sodium hydroxide (1.5 mL). The mixture was stirred at rt for 1.5 h. Hydrochloric acid (1N) was added to neutralize the mixture, and the mixture was then extracted with ethyl acetate. The organic phase was washed with brine (10 mL) and dried over sodium sulfate, filtered and concentrated to give the product (83 mg; MS: (M+H)$^+$=399.3).

Step 5. Preparation of (1r,4R)-4-(2-phenyl-1H-indole-6-sulfonamido)-N—((R)-1-(pyridin-2-yl)ethyl)cyclohexanecarboxamide

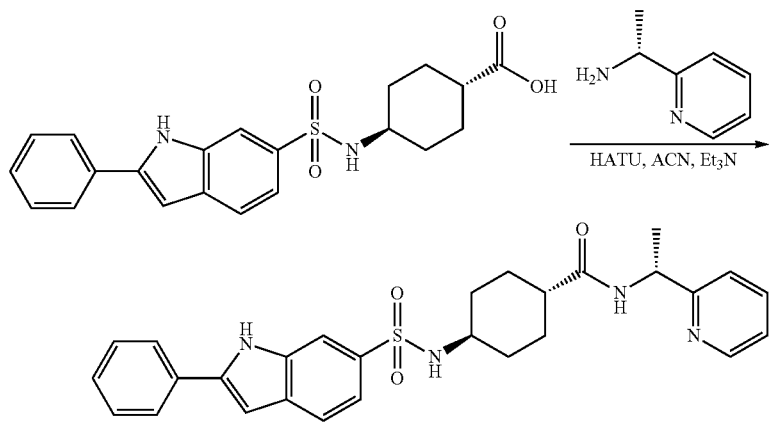

The acid from the previous step (83 mg, 0.21 mmol) in acetonitrile (2 mL) was treated with HATU (119 mg, 0.31 mmol) and triethylamine (87 µL, 0.62 mmol) and stirred at rt for 5 min. (R)-1-(Pyridin-2-yl)ethanamine (30 mg, 0.24 mmol) was added and the reaction mixture was stirred at rt overnight. The reaction mixture was then concentrated under vacuum and diluted with DMSO. The product was purified by HPLC (30-60% ACN in water with 5 mM ammonium hydroxide, Xterra C18 30-100 mm column, 0-12 min, $t_R$ —7.896 min) and then treated with hydrochloric acid to afford the product (53 mg) as its HCl salt.

Example 20

(1r,4R)—N—((R)-1-(4-fluorophenyl)ethyl)-4-(1-methyl-2-phenyl-1H-indole-6-sulfonamido)cyclohexanecarboxamide

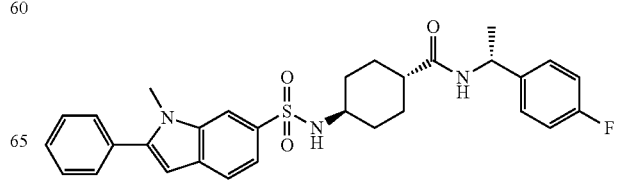

Step 1. Preparation of (1r,4r)-methyl 4-(3-(methoxymethylamino)-4-(phenylethynyl)phenylsulfonamido)cyclohexanecarboxylate

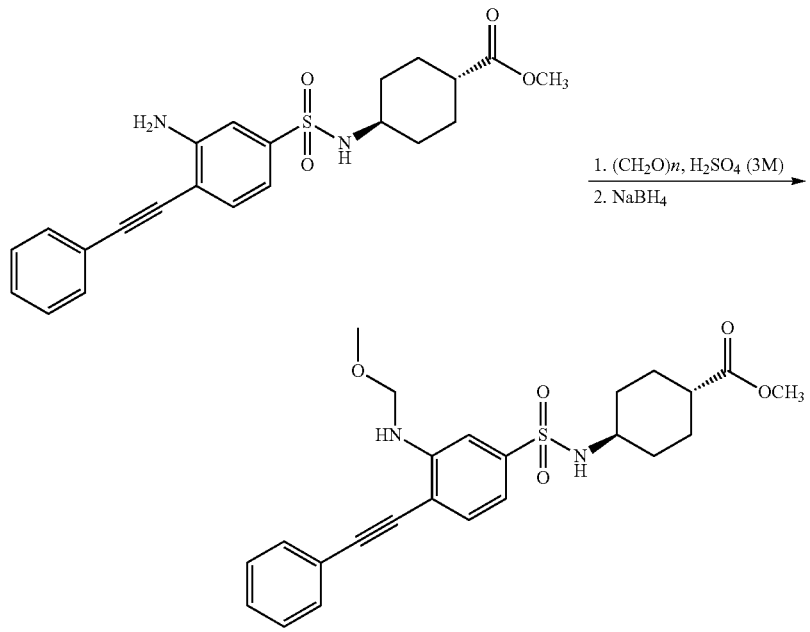

The aniline ((413 mg, 1 mmol; prepared as described in Example 19) in THF (10 mL) was mixed with paraformaldehyde (228 mg, 7.6 mmol) and then 3.0 M aq. sulfuric acid (1 mL, 3 mmol) and stirred at rt for 1.5 h. The mixture was then diluted with methanol (30 mL) and treated carefully with sodium borohydride (500 mg). After bubbling stopped, ethyl acetate (100 mL) was added, and the mixture was washed with water (100 mL) and brine. The organic solution was dried over sodium sulfate, filtered and concentrated under vacuum to give the product (260 mg) as a yellow oil (MS: $(M+H)^+=457.4$).

Step 2. Preparation of (1r,4r)-methyl 4-(3-(methylamino)-4-(phenylethynyl)phenylsulfonamido)cyclohexanecarboxylate

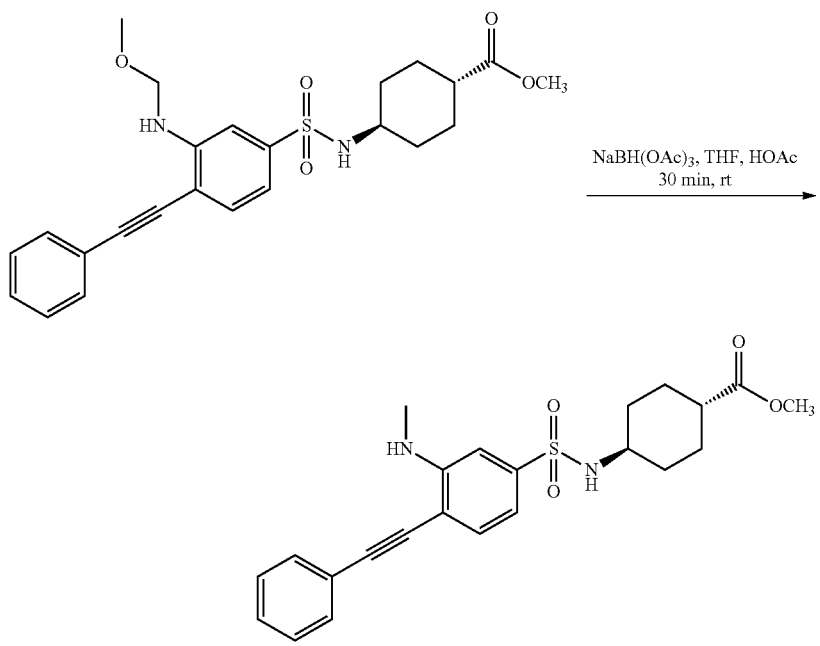

The product from the previous step (0.260 mg, 0.61 mmol) in THF (15 mL) was treated with sodium triacetoxyborohydride (519 mg, 2.45 mmol), and then acetic acid (5 mL, 87 mmol). The reaction was stirred at rt for 30 min and diluted with ethyl acetate (50 mL) and water (50 mL). The organic phase was separated, dried over sodium sulfate, filtered and concentrated under vacuum to provide 261 mg of product (MS: $(M+H)^+=427.4$) that was used as is in the next step.

Step 3. Preparation of (1r,4r)-4-(1-methyl-2-phenyl-1H-indole-6-sulfonamido)cyclohexanecarboxylic acid

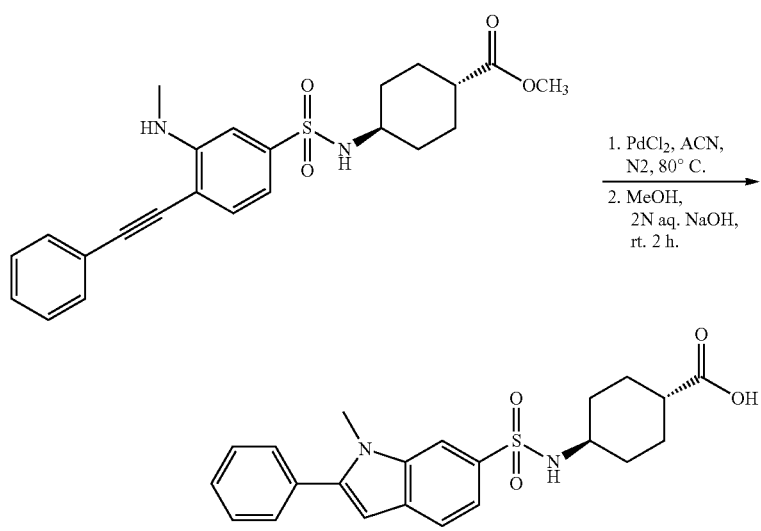

Palladium (II) chloride (22 mg, 0.122 mmol) in anhydrous acetonitrile (5 mL) in a capped 30 mL vial was purged with nitrogen and then heated to 80° C. A solution of the product from the previous step (261 mg, 0.612 mmol) in hot anhydrous acetonitrile (10 mL, 70-80° C.) was added to the reaction flask dropwise during 10 min. The reaction was stirred for an additional 30 min at 80° C. to complete the reaction. The mixture was then concentrated under vacuum, and the residue was purified by flash chromatography (ISCO, 12 g column, 0-100% ethyl acetate in n-heptane) to afford 76 mg of product.

The aforementioned product (76 mg, 0.18 mmol) was dissolved in methanol (3 mL) and treated with 2N aq. sodium hydroxide (1.7 mL). The reaction mixture was stirred at rt for 2 h, followed by addition of 1N aq. hydrochloric acid to neutralize the solution. The mixture was then extracted with ethyl acetate (30 mL) and the organic phase was washed with brine (30 mL), dried over sodium sulfate and concentrated under vacuum to give 60 mg of product (MS: $(M+H)^+=413.3$).

Step 4. Preparation of (1r,4R)—N—((R)-1-(4-fluorophenyl)ethyl)-4-(1-methyl-2-phenyl-1H-indole-6-sulfonamido)cyclohexanecarboxamide

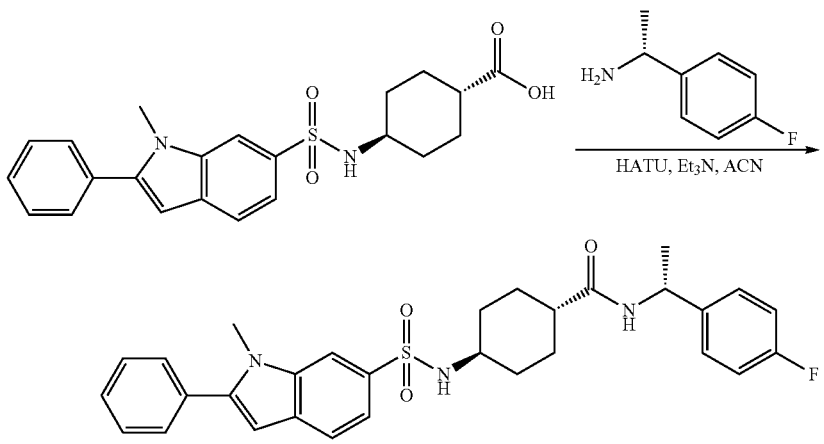

The acid from the previous step (20 mg, 0.048 mmol) in acetonitrile (2 mL) was treated with HATU (36.9 mg, 0.097 mmol) and triethylamine (41 L, 0.291 mmol) and stirred at rt for 5 min. (R)-1-(4-fluorophenyl)ethanamine (6.75 mg, 0.048 mmol) was added and the reaction mixture was stirred at rt for 30 min. The reaction mixture was then concentrated under vacuum and diluted with DMSO (1 mL). The product was purified by HPLC (40-70% ACN in water with 0.5 mM ammonium hydroxide, Xbridge C8 30×100 column, 0-12 min) to afford the product (9 mg).

Example 21

3-chloro-1-methyl-2-phenyl-N-((1S,4r)-4-((S)-3-(trifluoromethyl)piperazine-1-carbonyl)cyclohexyl)-1H-indole-6-sulfonamide

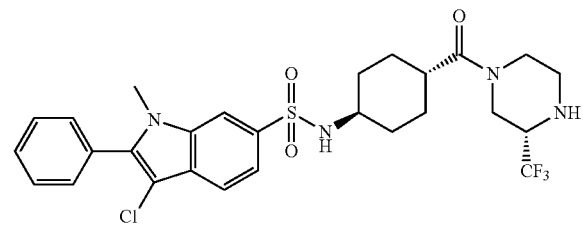 [SMILES: Cn1c(-c2ccccc2)c(Cl)c2ccc(S(=O)(=O)N[C@H]3CC[C@H](C(=O)N4CCN[C@H](C(F)(F)F)C4)CC3)cc21]

Preparation of 3-chloro-1-methyl-2-phenyl-N-((1S,4r)-4-((S)-3-(trifluoromethyl)piperazine-1-carbonyl)cyclohexyl)-1H-indole-6-sulfonamide

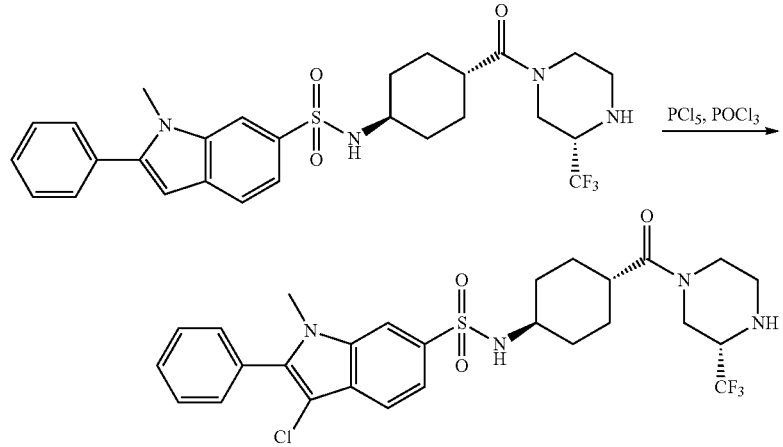

To a mixture of 1-methyl-2-phenyl-N-((1S,4r)-4-((S)-3-(trifluoromethyl)piperazine-1-carbonyl)cyclohexyl)-1H-indole-6-sulfonamide (20 mg, 0.036 mmol) in 0.5 mL of phosphoryl chloride was added 9.11 mg (0.044 mmol) of phosphorus pentachloride. The mixture was stirred for 30 min and then poured onto ice. The mixture was then neutralized with sat. aq. sodium bicarbonate and extracted with ethyl acetate (20 mL). The organic solution was dried (sodium sulfate) and concentrated under vacuum. The residue was purified by HPLC using 35-65% acetonitrile in water with 0.5% aq. ammonium hydroxide using a Waters Xbridge C8 30×100 column to give 11 mg of product.

Example 22

2-cyclopropyl-N-((1S,4r)-4-((S)-3-isopropylmorpholine-4-carbonyl)cyclohexyl)-1-methyl-1H-indole-6-sulfonamide

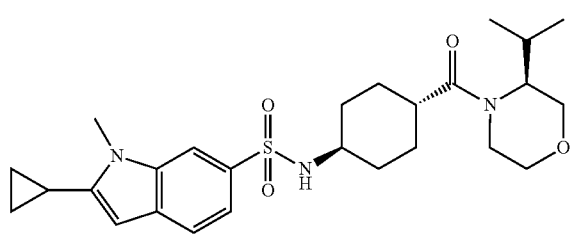 [SMILES: CC(C)[C@H]1COCCN1C(=O)[C@H]1CC[C@H](NS(=O)(=O)c2ccc3cc(C4CC4)n(C)c3c2)CC1]

Step 1. Preparation of (S)-5-isopropylmorpholin-3-one

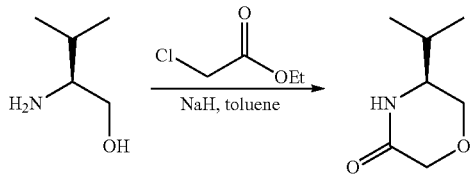

To an ice-cold, stirred suspension of sodium hydride (2.59 g, 64.8 mmol) in toluene (90 mL) was added dropwise a solution of (S)-2-amino-3-methylbutan-1-ol (3 g, 29.1 mmol) in toluene (60 mL). The reaction was then warmed to room temperature and a solution of ethyl chloroacetate (3.56 g, 29.1 mmol) in toluene (16 mL) was added dropwise. The resulting mixture was heated to reflux for 20 h under nitrogen and then concentrated under vacuum. The residue was purified by flash chromatography to afford 2.8 g of product (MS: (M+H)$^+$=144.3).

Step 2. Preparation of (S)-3-isopropylmorpholine

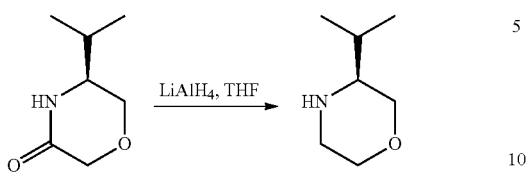

The product from the previous step (2.8 g, 19.56 mmol) in THF (12 mL) was added dropwise over 20 min. to a solution of lithium aluminum hydride (2M in THF, 19.5 mL, 39.1 mmol) in THF (30 mL) at 0° C. Following the addition, the ice bath was removed and the reaction was heated to reflux for 18 h. The reaction was cooled in an ice bath and quenched with water (1.5 mL) and 2M aq. sodium hydroxide (3 mL). The resulting mixture was stirred at room temperature for 1 h and filtered. The solid was washed with ethyl acetate, and the organic solution was concentrated under vacuum to give product (2.13 g) as an oil (MS: $(M+H)^+=130.3$).

Step 3. Preparation of 2-cyclopropyl-N-((1S,4r)-4-((S)-3-isopropylmorpholine-4-carbonyl)cyclohexyl)-1-methyl-1H-indole-6-sulfonamide

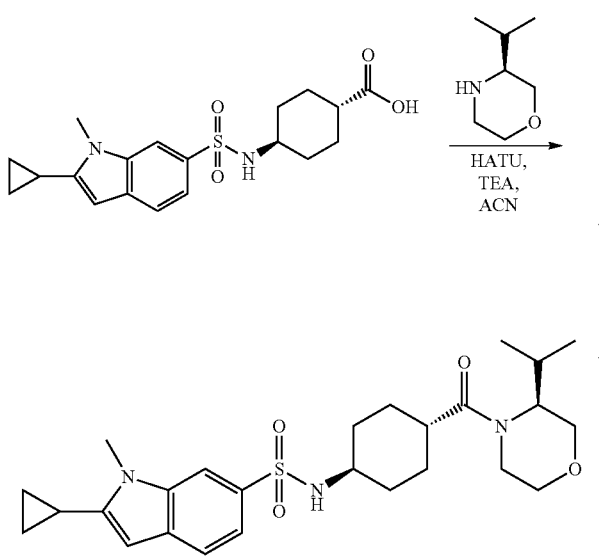

(1r,4r)-4-(2-Cyclopropyl-1-methyl-1H-indole-6-sulfonamido)cyclohexanecarboxylic acid (48.2 mg, 0.128 mmol, MS: $(M+H)^+=377.1$; prepared as described in Example 19, but using cyclopropyl acetylene in place of phenyl acetylene) was condensed with (S)-3-isopropylmorpholine (21.5 mg, 0.166 mmol) according to the procedure described for Example 20. The product (38 mg) was purified by HPLC on a Phenomenex Hydro 4u 20×100 mm column using acetonitrile in water (40-60%) containing 0.1% TFA as the eluent.

Example 23

3-cyano-2-cyclopropyl-1-methyl-N-((1r,4r)-4-(morpholine-4-carbonyl)cyclohexyl)-1H-indole-6-sulfonamide

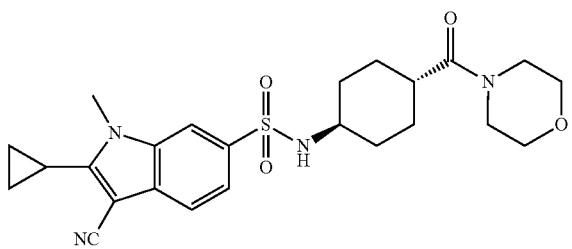 [SMILES: Cn1c(C2CC2)c(C#N)c2ccc(S(=O)(=O)N[C@H]3CC[C@H](C(=O)N4CCOCC4)CC3)cc21]

Preparation of 3-cyano-2-cyclopropyl-1-methyl-N-((1r,4r)-4-(morpholine-4-carbonyl)cyclohexyl)-1H-indole-6-sulfonamide

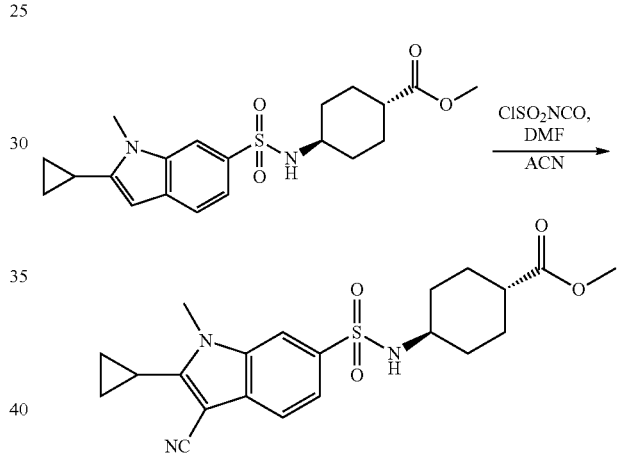

(1r,4r)-methyl 4-(2-cyclopropyl-1-methyl-1H-indole-6-sulfonamido)cyclohexanecarboxylate (50 mg, 0.128 mmol) (prepared as described in Example 19; MS: $(M+H)^+=391.0$) was treated with chlorosulfonylisocyanate (19.93 mg, 0.141 mmol) and stirred at room temperature for 1 h. DMF (18.72 mg, 0.020 mL, 0.256 mmol) was added and the mixture was stirred for an additional 30 min. The mixture was quenched with sat. aq. sodium bicarbonate and then extracted with ethyl acetate (50 mL). The organic solution was washed with water (50 mL), brine and then dried (sodium sulfate) and concentrated under vacuum to give product that was used directly in the next step. The reaction was repeated with another 50 mg of starting ester to give a total of 90 mg of product (MS: $(M+H)^+=416.0$).

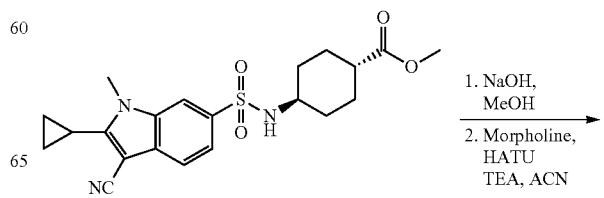

-continued

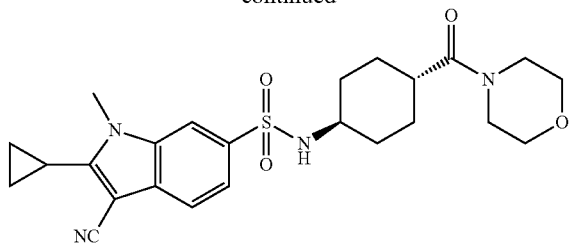

A solution of (1r,4r)-methyl 4-(3-cyano-2-cyclopropyl-1-methyl-1H-indole-6-sulfonamido)cyclohexanecarboxylate from the previous step (90 mg, 0.217 mmol) was treated with 2.166 mL of 2N aq. sodium hydroxide (4.33 mmol) in methanol (2 mL) an stirred at room temperature for 3.5 h. The mixture was then neutralized with 1N aq. hydrochloric acid and extracted with ethyl acetate (20 mL). The organic solution was washed with brine, dried (sodium sulfate) and concentrated under vacuum to give the acid.

The acid (23 mg, 0.057 mmol) in acetonitrile (2 mL) was treated with HATU (26.1 mg, 0.069 mmol) and triethylamine (11.59 mg, 0.016 mL, 0.115 mmol) and stirred for 2 min. Morpholine (7.49 mg, 7.49 μL, 0.086 mmol) was then added and the mixture was stirred for an additional 10 min at room temperature. The mixture was diluted with DMSO (1 mL) and purified using HPLC (30-55% acetonitrile in water containing 0.1% TFA; Sunfire Prep C18 5 u 30×100 mm column) to give the product (12 mg).

Example 24

2-cyclopropyl-1-methyl-N-((1r,4r)-4-methyl-4-(morpholine-4-carbonyl)cyclohexyl)-1H-indole-6-sulfonamide

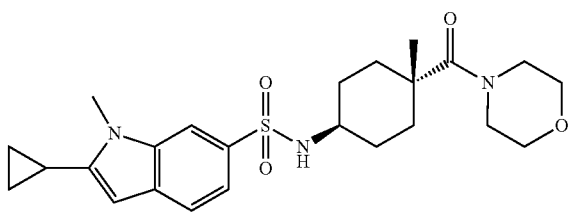 [SMILES: Cn1c(C2CC2)cc2ccc(S(=O)(=O)N[C@H]3CC[C@](C)(C(=O)N4CCOCC4)CC3)cc21]

Step 1 Preparation of ethyl 4-(tert-butyldimethylsilyloxy)-1-methylcyclohexanecarboxylate

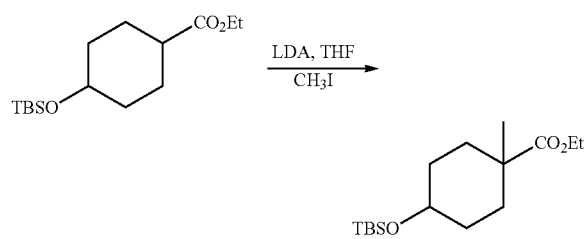

Ethyl 4-(tert-butyldimethylsilyloxy)cyclohexanecarboxylate (3 g, 10.47 mmol) in THF (20 mL) was added to a freshly prepared solution of LDA (prepared from n-butyllithium (26.2 mmol) in hexane and diisopropylamine (3.73 mL, 26.2 mmol) in 7 mL of THF) at −78° C. the reaction was stirred for 1 h, warmed to 0° C. for 5 min, cooled again to −78° C. followed by addition of methyl iodide (2.292 mL, 36.7 mmol). The reaction mixture was allowed to warm to room temperature overnight, quenched with aqueous ammonium chloride, and concentrated under vacuum to remove volatile solvents. The residual aqueous mixture was extracted with ether, and the ether solution was dried and concentrated under vacuum to give the crude product as an oil which was further purified via normal phase chromatography on silica gel (Biotage SP1, 40+S column) to give product (2.7 g; MS: (M+H)$^+$=301.3) as a clear oil.

Step 2. Preparation of ethyl 4-hydroxy-1-methylcyclohexanecarboxylate

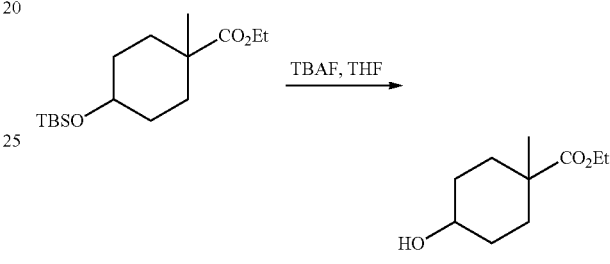

The product from the previous step (2.7 g, 8.98 mmol) was mixed with a solution of TBAF (15 mL, 15 mmol) in THF at 0° C. and stirred at room temperature overnight. The reaction mixture was then concentrated under vacuum, and the crude oil was taken up in water and extracted with ether (3×250 mL). The combined organic layers were dried (MgSO$_4$) and concentrated under vacuum to give the crude product as an oil. This crude product was further purified via chromatography on silica gel using 20% ethyl acetate in heptane as the eluent to provide 1.43 g of product as a clear oil (MS: (M+H)$^+$=186.7).

Step 3. Preparation of ethyl 4-(1,3-dioxoisoindolin-2-yl)-1-methylcyclohexanecarboxylate

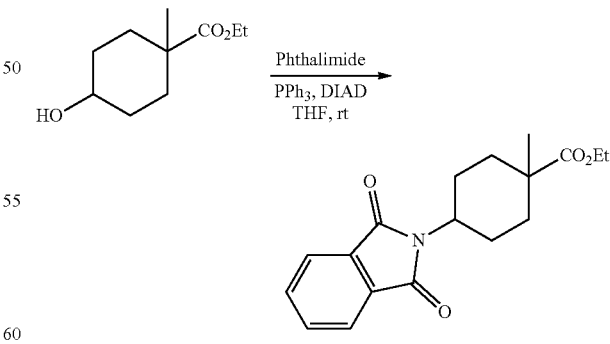

The hydroxy ester from the previous step (930 mg, 4.99 mmol), triphenylphosphine (3.143 g, 11.98 mmol), and phthalimide (882 mg, 5.99 mmol) were dissolved in 60 mL of THF. DIAD (2.33 mL, 11.98 mmol) was then added and the reaction mixture was stirred overnight at room temperature. The mixture was concentrated under vacuum, and the

Step 4. Preparation of 4-(1,3-dioxoisoindolin-2-yl)-1-methylcyclohexanecarboxylic acid

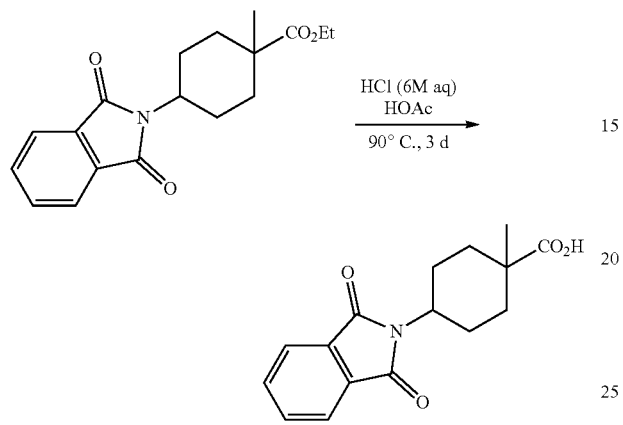

The ethyl ester from the previous step (900 mg, 2.85 mmol) was added to 6M aq. hydrochloric acid (0.951 mL, 5.71 mmol) in acetic acid (5 mL). The reaction mixture was heated to 90° C. for 48 h and then concentrated under vacuum. The residue was taken up in a minimal volume of ethyl acetate and a white solid precipitated. The product was collected by filtration, washed with acetonitrile and dried to provide the product acid (475 mg). as a white solid (MS: $(M+H)^+=288.2$).

Step 5. Preparation of 4-(1,3-dioxoisoindolin-2-yl)-1-methylcyclohexanecarbonyl chloride

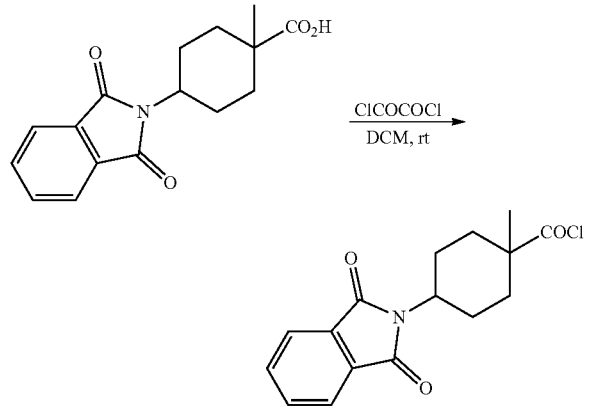

The acid from the previous step (220 mg, 0.786 mmol) was dissolved in DCM (5 mL). Oxalyl chloride (146 mg, 0.1 mL, 1.149 mmol) was added slowly, followed by addition of a drop of DMF. Stirring was continued at room temperature for 20 min and concentrated under vacuum to provide the product as a yellow solid that was used as is in the next step.

Step 6. Preparation of 2-(4-methyl-4-(morpholine-4-carbonyl)cyclohexyl)isoindoline-1,3-dione

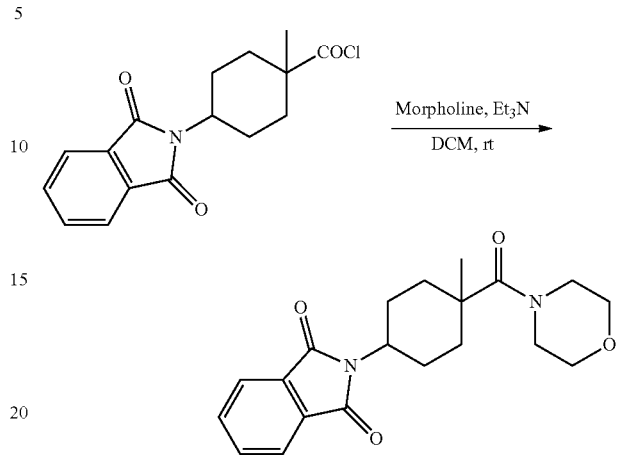

The acid chloride from the previous step (0.234 g, 0.766 mmol) in DCM (5 mL) was added to a mixture of morpholine (0.087 g, 0.996 mmol) and triethylamine (0.233 g, 2.298 mmol) in DCM (5 mL). The mixture was stirred at room temperature for 1 h and was then concentrated under vacuum. The residue was taken up in ethyl acetate (50 mL) as washed with 1N aq. hydrochloric acid (3×50 mL), dried with sodium sulfate and concentrated to afford the product as a yellow oil (0.273 g; MS: $(M+H)^+=357.2$).

Step 7. Preparation of (4-amino-1-methylcyclohexyl)(morpholino)methanone

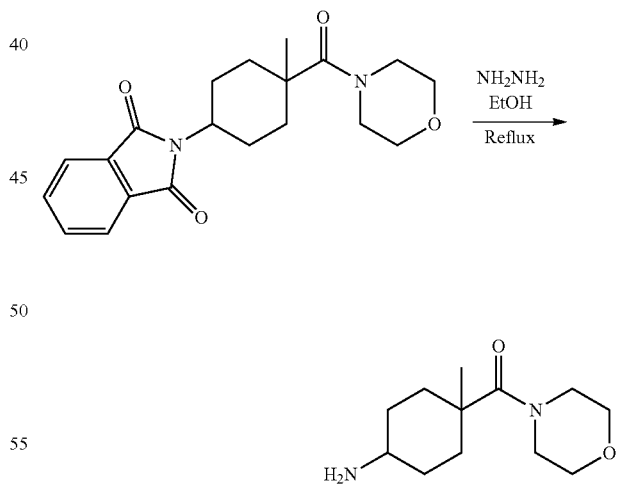

Hydrazine (192 mg, 0.188 mL, 3.83 mmol) was added to the product from the previous step (0.273 g, 0.766 mmol) in ethanol (25 mL) and heated to 80° C. for 16 h. The mixture was then cooled to room temperature (a white precipitate formed) and concentrated under vacuum. DCM was added and the mixture was filtered. The white solid was washed with DCM, and the organic solution was concentrated under vacuum to afford product as a yellow solid (0.173 g; MS: $(M+H)^+=227.3$).

Step 8. Preparation of 4-chloro-N-(4-methyl-4-(morpholine-4-carbonyl)cyclohexyl)-3-nitrobenzenesulfonamide

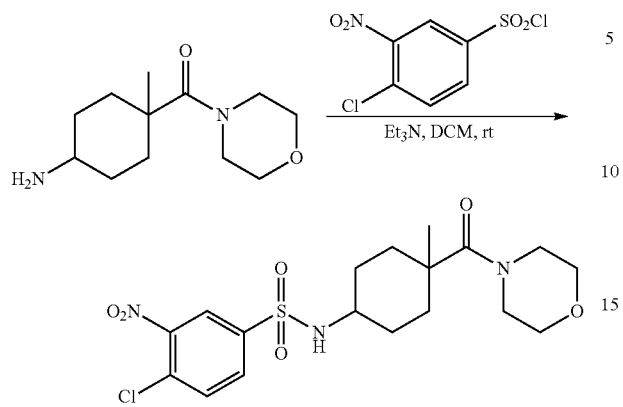

4-Chloro-3-nitrobenzene-1-sulfonyl chloride (118 mg, 0.461 mmol) was added to a solution of the amine from the previous step (87 mg, 0.384 mmol) and triethylamine (117 mg, 0.161 mL, 1.153 mmol) in acetonitrile (3 mL). The mixture was then stirred for 30 min at room temperature. The reaction mixture was diluted with ethyl acetate (30 mL) and washed with 3×30 mL of 1N hydrochloric acid and 30 mL of brine, dried (sodium sulfate) and concentrated under vacuum to afford product (146 mg) as a sticky yellow solid (MS: (M+H)$^+$=446.1).

Step 9. Preparation of 4-(cyclopropylethynyl)-N-(4-methyl-4-(morpholine-4-carbonyl)cyclohexyl)-3-nitrobenzenesulfonamide

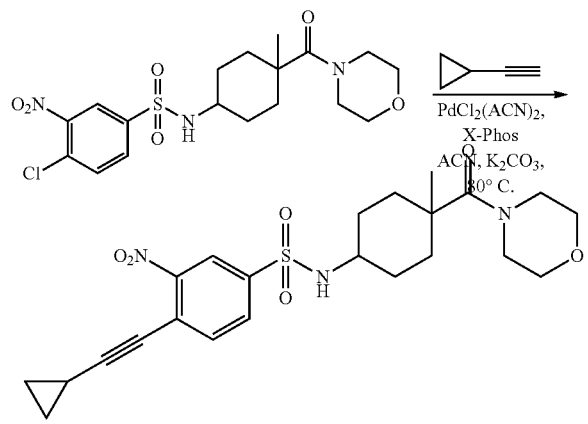

A dried vial was charged with the chloronitrosulfonamide from the previous step (146 mg, 0.327 mmol), bis(acetonitrile)dichloropalladium (3.4 mg, 0.013 mmol), X-Phos (18.73 mg, 0.039 mmol) and potassium carbonate (136 mg, 0.982 mmol). The vial was purged with nitrogen and acetonitrile (3 mL) was added, followed by addition of cyclopropylacetylene (32.5 mg, 0.491 mmol). The vial was heated to 80° C. for 2 h. The reaction mixture was then poured into 50 mL of ethyl acetate and washed with 1N hydrochloric acid (50 mL) and brine. The organic solution was dried (sodium sulfate) and concentrated under vacuum to afford 156 mg of product MS: (M+H)$^+$=476.2).

Step 10. Preparation of 3-amino-4-(cyclopropylethynyl)-N-(4-methyl-4-(morpholine-4-carbonyl)cyclohexyl)benzenesulfonamide

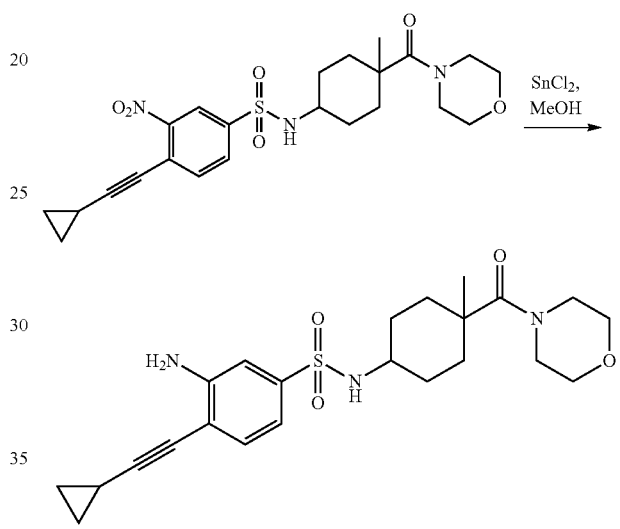

The product of the previous step (156 mg, 0.328 mmol) was treated with tin(II) chloride (622 mg, 3.28 mmol) in methanol (7 mL) at 63° C. with stirring for 1 h. The mixture was then poured into ethyl acetate (30 mL) and washed with 1N hydrochloric acid (3×30 mL) and brine (30 mL), dried (sodium sulfate) and concentrated under vacuum to give the crude product. The crude product was purified by flash chromatography (ISCO, 12 g silica gel column, 0-100% ethyl acetate/heptane) to give 80 mg of product as a brown oil MS: (M+H)$^+$=446.2).

Step 11. Preparation of 4-(cyclopropylethynyl)-N-(4-methyl-4-(morpholine-4-carbonyl)cyclohexyl)-3-(methylamino)benzenesulfonamide

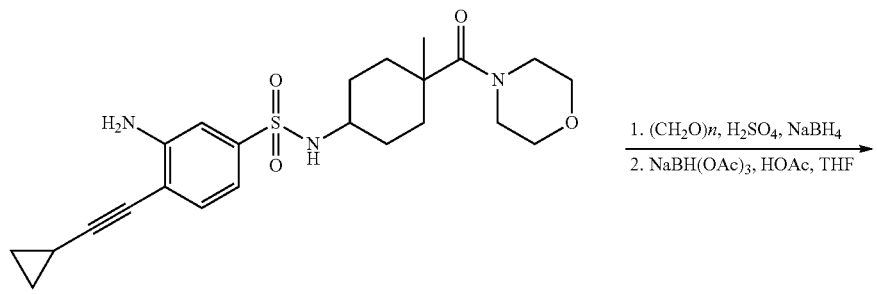

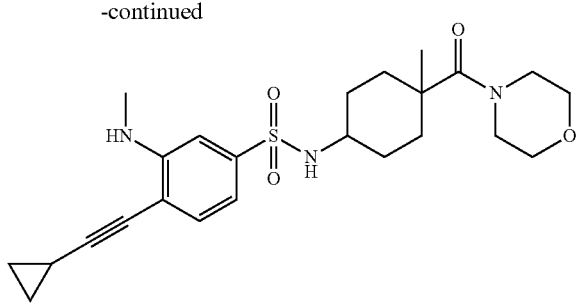

The product from the previous step (80 mg, 0.180 mmol) in THF (2 mL) was mixed with paraformaldehyde (62 mg, 2.065 mmol) and then sulfuric acid (0.180 mL) and stirred at room temperature for 2 h. An additional 24 mg of paraformaldehyde was added. Stirring was continued for 1 h and an additional 48 mg of paraformaldehyde was added. After an additional 30 min at room temperature, sodium borohydride (120 mg) was added. Once the bubbling had stopped, ethyl acetate (50 mL) was added, and the mixture was washed with water (2×50 mL) and brine. The organic phase was dried (sodium sulfate) and concentrated under vacuum to give product (82 mg) as a yellow solid.

The aforementioned yellow solid (82 mg, 0.180 mmol) in THF (2 mL) was treated with sodium triacetoxyborohydride (153 mg, 0.720 mmol) followed by acetic acid (600 mg, 0.763 mL, 13.32 mmol) and stirred at room temperature for 15 min. Ethyl acetate (30 mL) was added together with water (30 mL). The organic phase was separated, washed with water (30 mL) and brine (100 mL), dried (sodium sulfate) and concentrated under vacuum. The residue was diluted with toluene (5 mL) and concentrated again under vacuum (to remove traces of acetic acid) to afford product (58 mg) as a yellow solid MS: (M+H)$^+$=460.2).

Step 12. Preparation of 2-cyclopropyl-1-methyl-N-((1r,4r)-4-methyl-4-(morpholine-4-carbonyl)cyclohexyl)-1H-indole-6-sulfonamide

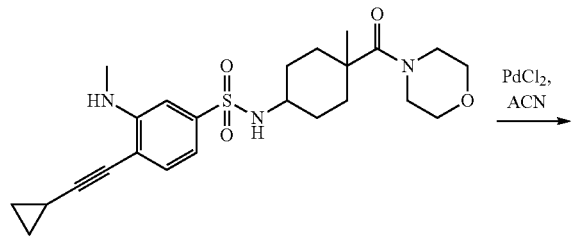

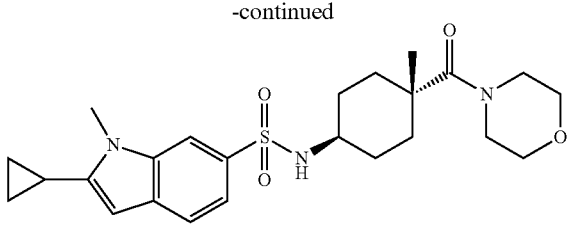

A mixture of palladium dichloride (4.48 mg) in 1 mL of acetonitrile was purged with nitrogen while heating to 80° C. until the palladium dichloride was dissolved, after which the product from the previous step (58 mg, 0.126 mmol) in hot acetonitrile (3 mL) was added over 10 min. Stirring was continued for 30 min. The mixture was then concentrated under vacuum and the residue was purified by HPLC (Sunfire Prep C18 column, 35-70% acetonitrile in water as eluent) to provide the product (0.8 mg).

Example 25

3-(4-(3-chloro-6-(N-((1S,4r)-4-((S)-3-isopropylmorpholine-4-carbonyl)cyclohexyl)sulfamoyl)-1-methyl-1H-indol-2-yl)phenyl)propanoic acid

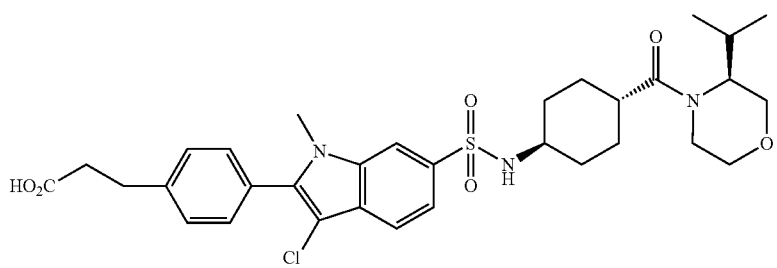 [SMILES: CC(C)[C@H]1COCCN1C(=O)[C@H]1CC[C@H](NS(=O)(=O)c2ccc3c(Cl)c(-c4ccc(CCC(=O)O)cc4)n(C)c3c2)CC1]

Step 1. Preparation of tert-butyl (1S,4r)-4-((S)-3-isopropylmorpholine-4-carbonyl)cyclohexylcarbamate

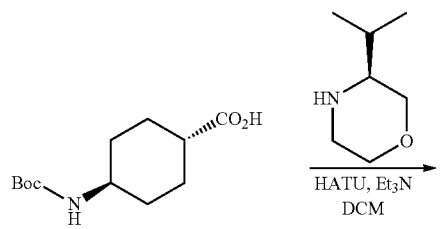

Step 3. Preparation of 4-chloro-N-((1S,4r)-4-((S)-3-isopropylmorpholine-4-carbonyl)cyclohexyl)-3-nitrobenzenesulfonamide

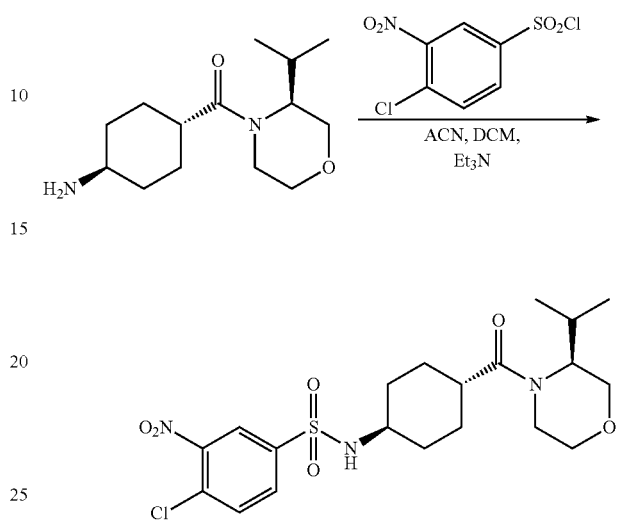

HATU (1.031 g, 2.71 mmol) and triethylamine (0.499 g, 0.687 mL, 4.93 mmol) were added to (1r,4r)-4-(tert-butoxycarbonylamino)cyclohexanecarboxylic acid (0.6 g, 2.466 mmol) in DCM (10 mL) at room temperature. Stirring was continued for 5 min, followed by addition of (S)-3-isopropylmorpholine (0.382 g, 2.96 mmol; prepared as described for Example 22). Stirring was continued for an additional 1 h. The reaction was then concentrated under vacuum and diluted with ethyl acetate (100 mL) and water (100 mL). The layers were separated, and the organic phase was washed with water (2×100 mL) and brine, dried (sodium sulfate) and concentrated under vacuum to give product (1.07 g; MS: $(M+H)^+=355.2$) as an oil that was used as is in the next step.

Step 2. Preparation of ((1r,4S)-4-aminocyclohexyl)((S)-3-isopropylmorpholino)methanone

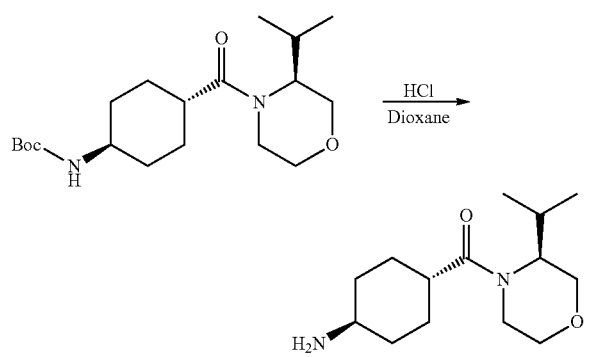

A solution of the product from the previous step in 4M HCl in 1,4-dioxane was stirred at room temperature for 1 h. The mixture was concentrated under vacuum, and the product obtained (MS: $(M+H)^+=255.2$) was used as is in the next step.

Triethylamine (990 mg, 1.375 mL, 9.96 mmol) and 4-chloro-3-nitrobenzene-1-sulfonyl chloride (695 mg, 2.71 mmol) were added sequentially to a solution of the product from the previous step in a mixture of acetonitrile (3 mL) and DCM (6 mL). The mixture was stirred at room temperature for 1 h, then diluted with ethyl acetate (50 mL) and washed with 1N aq. HCl (3×50 mL), sat. aq. sodium bicarbonate (50 mL) and brine (50 mL). The organic phase was dried (sodium sulfate) and concentrated under vacuum to provide the crude product. The product was purified by flash chromatography (ISCO 40 g silica gel column using a 0-100% ethyl acetate-heptane gradient as the eluent to afford 400 mg of product (MS: $(M+H)^+=474.1$).

Step 4. Preparation of methyl 3-(4-bromophenyl)propanoate

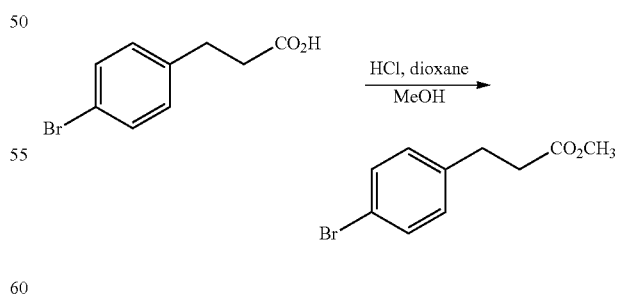

HCl in dioxane (4M, 61.1 mL) was added to a solution of 3-(4-bromophenyl)propanoic acid in methanol (60 mL) at room temperature. The reaction was stirred 18 h and then concentrated under vacuum. The crude product was purified by flash chromatography on silica gel using a 0-50% ethyl acetate-n-heptane gradient to afford 5.1 g of product as a colorless oil.

Step 5. Preparation of methyl 3-(4-((trimethylsilyl)ethynyl)phenyl)propanoate

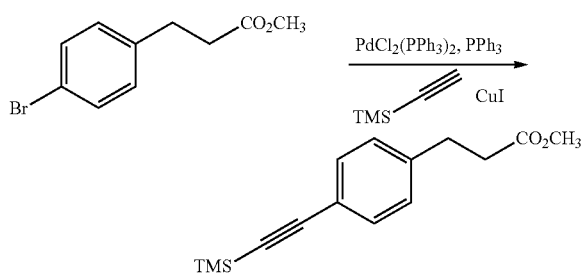

The ester from the previous step (5.1 g, 20.98 mmol), copper(I) iodide (0.08 g, 0.42 mmol), bis(triphenylphosphine)palladium dichloride (0.295 g, 0.42 mmol) and triphenylphosphine (0.275 g, 1.049 mmol) were mixed in 25 mL of piperidine and purged with nitrogen. Ethynyltrimethylsilane (3.09 g, 31.5 mmol) was then added, and the mixture was heated to 100° C. for 1 h under nitrogen. The mixture was concentrated under vacuum, diluted with ethyl acetate and filtered. The filtrate was concentrated under vacuum and purified by flash chromatography on silica gel using a 0-35% ethyl acetate-n-heptane gradient to afford 4.2 g of product as a brown oil (MS: $(M+H)^+=261.2$).

Step 6. Preparation of methyl 3-(4-ethynylphenyl)propanoate

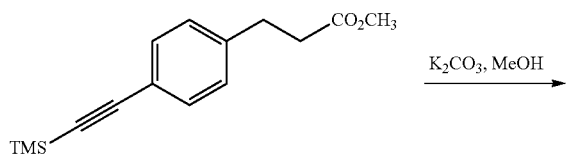

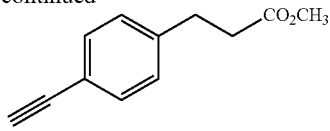

Potassium carbonate (2.229 g, 16.13 mmol) was added to a solution of the product from the previous step (4.2 g, 16.13 mmol) in methanol (30 mL). The mixture was concentrated under vacuum, and the residue was taken up in ethyl acetate (100 mL) and washed with 1N aq. HCl (100 mL). The aqueous layer was extracted with ethyl acetate, and the combined organic phase was washed with brine (50 mL), dried (sodium sulfate) and concentrated. The residue was then purified by flash chromatography on silica gel using a 0-35% ethyl acetate-n-heptane gradient as the eluent to provide 2.6 g of product.

Step 7. Preparation of methyl 3-(4-((4-(N-((1S,4r)-4-((S)-3-isopropylmorpholine-4-carbonyl)cyclohexyl)sulfamoyl)-2-nitrophenyl)ethynyl)phenyl)propanoate

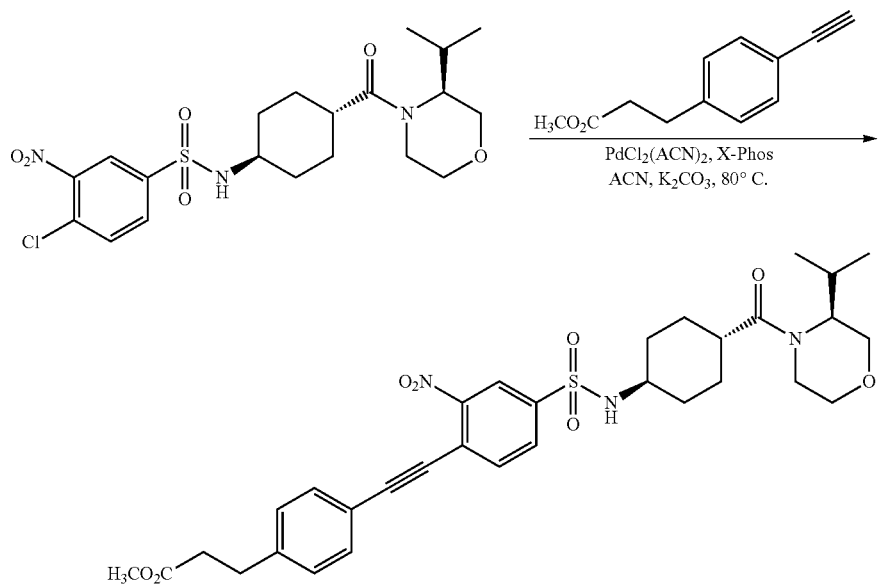

A mixture of the product from Step 3 (400 mg, 0.844 mmol), bis(acetonitrile)dichloropalladium(II) (8.76 mg, 0.034 mmol), X-Phos (48.3 mg, 0.101 mmol) and potassium carbonate (350 mg, 2.53 mmol) was flushed with nitrogen. Acetonitrile (7 mL) was added, followed by addition of methyl 3-(4-ethynylphenyl)propanoate (191 mg, 1.013 mmol). The flask was then heated to 80° C. for 2.5 h under nitrogen. The reaction mixture was then cooled and poured into 50 mL of ethyl acetate and washed with water (2×50 mL). The organic phase was separated, dried (sodium sulfate) and concentrated under vacuum to provide the crude product (MS: $(M+H)^+=626.3$) which was used as is in the next step.

Step 8. Preparation of methyl 3-(4-((2-amino-4-(N-((1S,4r)-4-((S)-3-isopropylmorpholine-4-carbonyl)cyclohexyl)sulfamoyl)phenyl)ethynyl)phenyl)propanoate

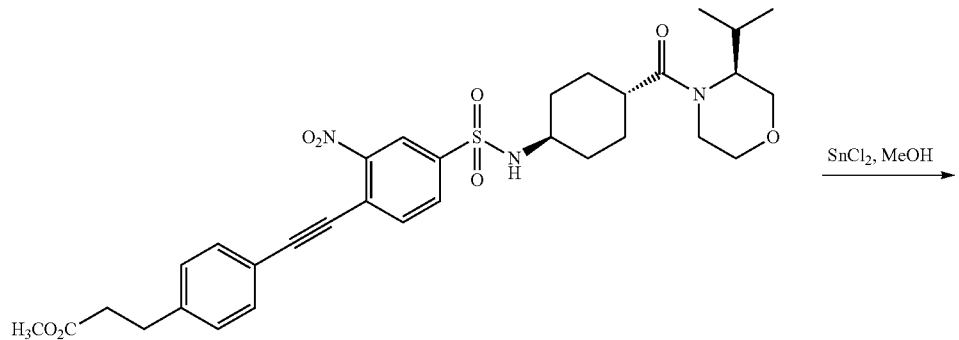

The nitro group of the product from the previous step was reduced with tin(II) chloride in methanol as described in Step 2 of Example 18. The product (MS: (M+H)$^+$=596.4) was used as is in the next step.

Step 9. Preparation of methyl 3-(4-((4-(N-((1S,4r)-4-((S)-3-isopropylmorpholine-4-carbonyl)cyclohexyl)sulfamoyl)-2-(methylamino)phenyl)ethynyl)phenyl)propanoate

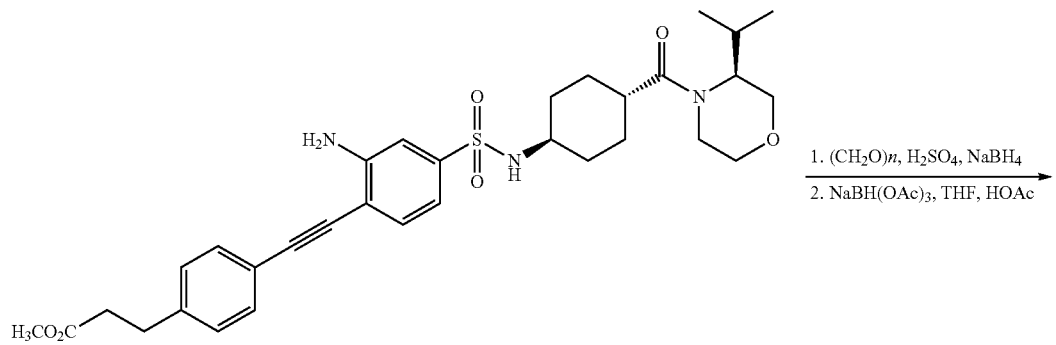

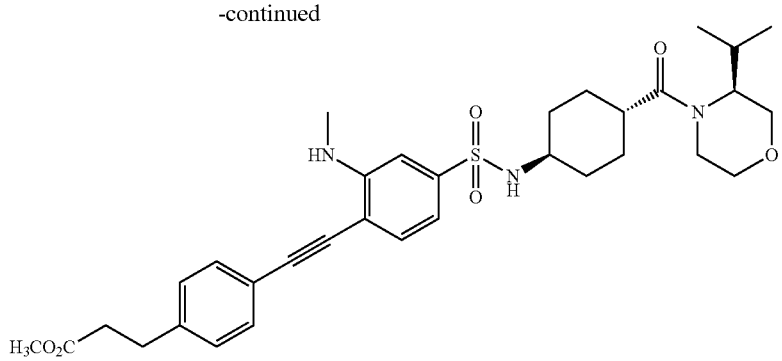

The N-methyl derivative of the aniline from the previous step was prepared according to the procedure of Example 20 to provide 400 mg (0.656 mmol) of crude product (MS: $(M+H)^+=610.4$) that was used as is in the next step.

Step 10. Preparation of methyl 3-(4-(6-(N-((1S,4r)-4-((S)-3-isopropylmorpholine-4-carbonyl)cyclohexyl)sulfamoyl)-1-methyl-1H-indol-2-yl)phenyl)propanoate

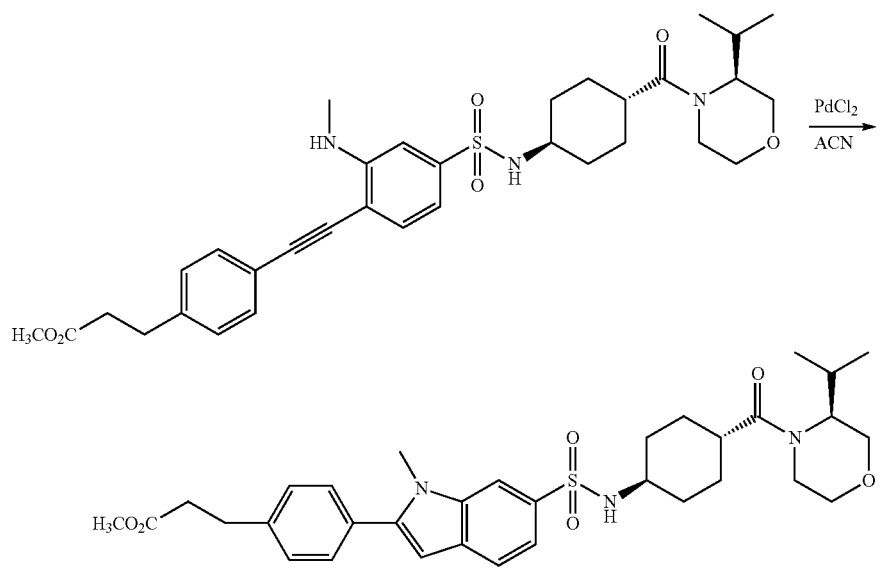

Cyclization of the aminoacetylene to the indole was carried out as described in Example 20. The crude product was purified by flash chromatography on silica gel using a 0-100% ethyl acetate-n-heptane gradient as the eluent to afford 170 mg of the desired product (MS: $(M+H)^+=610.2$).

Step 11. Preparation of methyl 3-(4-(3-chloro-6-(N-((1S,4r)-4-((S)-3-isopropylmorpholine-4-carbonyl)cyclohexyl)sulfamoyl)-1-methyl-1H-indol-2-yl)phenyl)propanoate

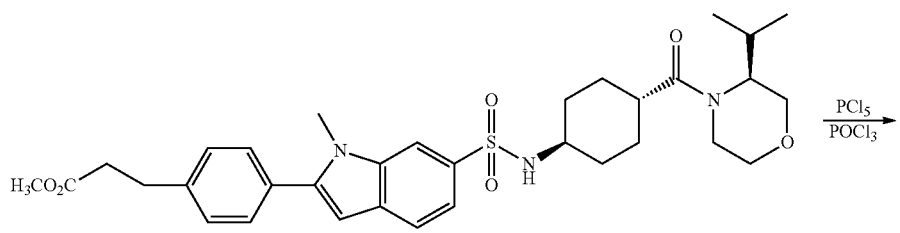

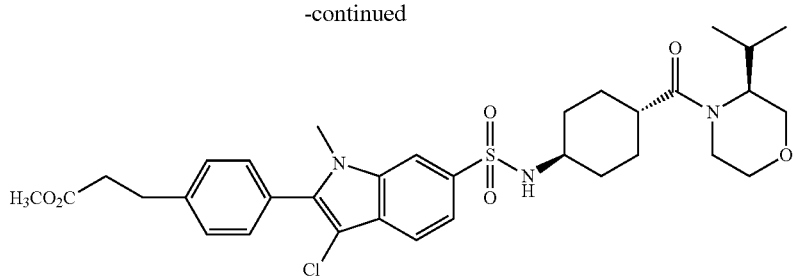

Phosphorus pentachloride (44.4 mg, 0.213 mmol) was added to a solution of the product from the previous step (100 mg, 0.164 mmol) in phosphoryl chloride (2 mL) at room temperature. The mixture was stirred 30 min, then poured onto ice and extracted with ethyl acetate (2×20 mL). The organic solution was washed with brine and concentrated under vacuum to afford the product (MS: (M+H)$^+$=644.3) which was used as is in the next step.

Step 12. Preparation of 3-(4-(3-chloro-6-(N-((1S, 4r)-4-((S)-3-isopropylmorpholine-4-carbonyl)cyclohexyl)sulfamoyl)-1-methyl-1H-indol-2-yl)phenyl) propanoic acid

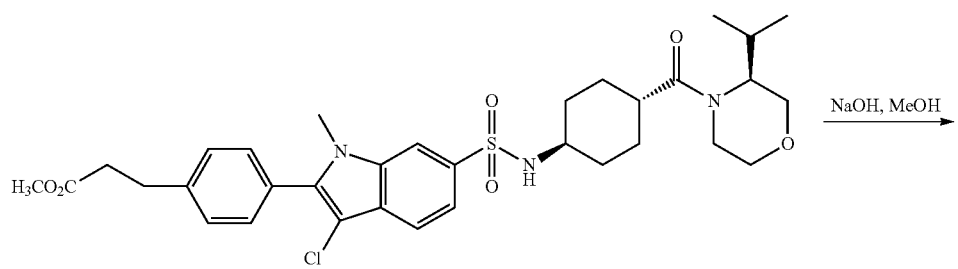

Sodium hydroxide (2.05 mL, 4.1 mmol of 2M aq. solution) was added to the ester from the previous step in methanol (2.5 mL). The mixture was stirred at room temperature for 30 min, and then neutralized with 1N aq. HCl. The mixture was extracted with ethyl acetate, dried (sodium sulfate) and concentrated under vacuum to provide the crude product. The crude product was purified by HPLC using a 40-70% acetonitrile/water gradient containing 0.1% TFA to afford 51 mg of the desired product.

Example 26

(1r,4R)-4-(3-chloro-1H-indole-6-sulfonamido)-N—((R)-1-(4-fluorophenyl)ethyl)cyclohexanecarboxamide

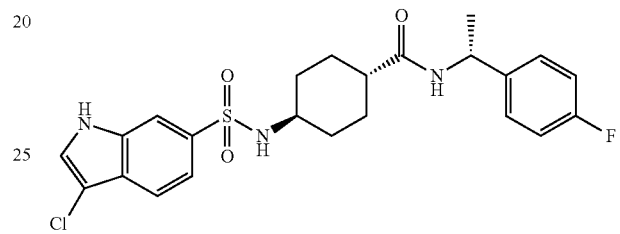

Step 1. Preparation of 6-bromo-1-(triisopropylsilyl)-1H-indole

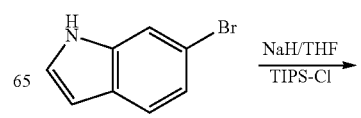

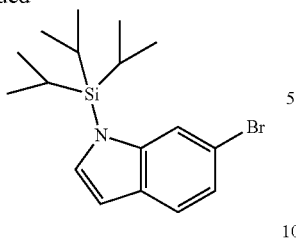

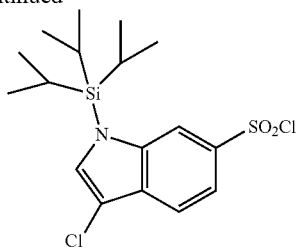

To a solution of 6-bromo-1H-indole (2 g, 10.2 mmol) in THF (20 mL) at 0° C. was added 0.46 g of sodium hydride (12 mmol) in 3 portions. The mixture was stirred 30 min followed by addition of chlorotriisopropylsilane (2 g, 10.4 mmol). The reaction was allowed to warm to room temperature and stirring was continued overnight. The mixture was then poured into sat. aq. sodium bicarbonate and extracted with ethyl acetate. The organic phase was washed with brine, dried (magnesium sulfate) and concentrate under vacuum to afford the crude product as an orange oil that was purified by flash chromatography on silica gel using a 4:1 ethyl acetate/heptane mixture as the eluent. The purified product (2.8 g) was a light orange oil.

Step 2. Preparation of 3-chloro-1-(triisopropylsilyl)-1H-indole-6-sulfonyl chloride

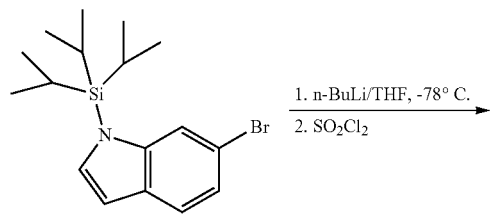

n-Butyllithium (2.7 mL of a 2.7 M solution in heptane) was added dropwise to a solution of the bromo indole from the previous step (2.3 g, 6.53 mmol) at −78° C. The mixture was stirred 1 h and then poured into 1.3 mL of sulfuryl chloride in cyclohexane (45 mL) at 0° C. The reaction was then allowed to warm to room temperature with stirring overnight. Water (30 mL) was then added followed by stirring for 30 min. The layers were separated, and the organic phase was dried over magnesium sulfate and concentrated under vacuum to provide the crude product as a deep orange oil. Purification by flash chromatography on silica gel using 9/1 heptane/ethyl acetate as the eluent afforded 1.3 g of product.

Step 3. Preparation of (1r,4R)-4-(3-chloro-1-(triisopropylsilyl)-1H-indole-6-sulfonamido)-N—((R)-1-(4-fluorophenyl)ethyl)cyclohexanecarboxamide

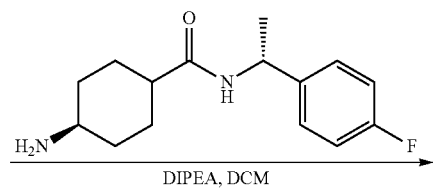

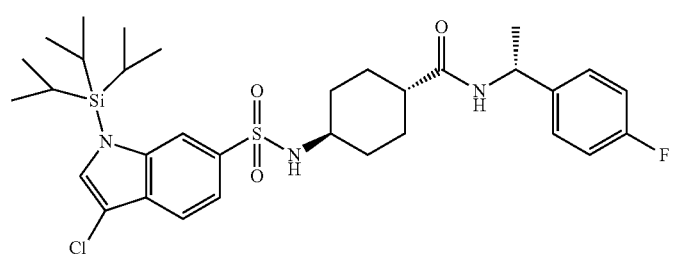

A mixture of the sulfonyl chloride from the previous step (0.1 g, 0.246 mmol) and 4-amino-N—((R)-1-(4-fluorophenyl)ethyl)cyclohexanecarboxamide (75 mg, 0.25 mmol; prepared as described in Example 1, but using (R)-1-(4-fluorophenyl)ethanamine in place of the des-fluoro analog) and diisopropylethylamine (0.1 mL) in DMF was stirred at room temperature overnight. The mixture was then concentrated under vacuum, and 1N aq. hydrochloric acid was added. The mixture was extracted with ethyl acetate, and the organic layer was washed with brine, dried (magnesium sulfate) and concentrated under vacuum to afford 0.15 g of crude product which was purified by flash chromatography on silica gel using a 65:35 heptane-ethyl acetate mixture as eluent to yield 52 mg of product.

Step 4. Preparation of (1r,4R)-4-(3-chloro-1H-indole-6-sulfonamido)-N—((R)-1-(4-fluorophenyl)ethyl)cyclohexanecarboxamide

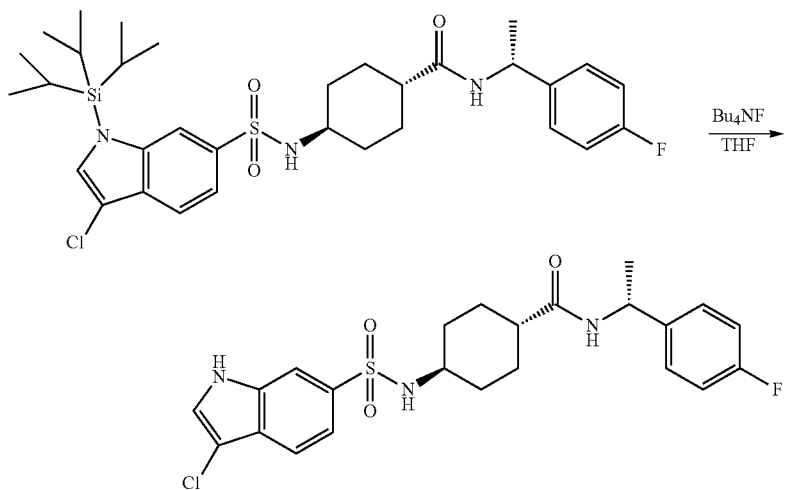

The product from the previous step (32 mg, 0.0584 mmol) and tetrabutylammonium fluoride (0.1 mL of a 1M solution in THF) were stirred in 2 mL of THF at room temperature overnight. The mixture was then poured into aqueous sodium bicarbonate and extracted with ethyl acetate. The organic phase was dried over magnesium sulfate and concentrated under vacuum to give the crude product. The product was triturated with ether and filtered to provide 13 mg of product as a beige powder.

Example 27

(S)-4-(6-(N-((1R,4r)-4-((R)-1-(4-fluorophenyl)ethylcarbamoyl)cyclohexyl)sulfamoyl)-1H-indol-2-yl)benzyl 2-amino-3-methylbutanoate

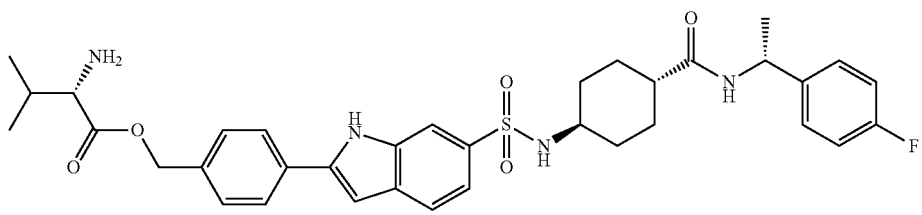 [SMILES: CC(C)[C@H](N)C(=O)OCc1ccc(-c2cc3ccc(S(=O)(=O)N[C@H]4CC[C@H](C(=O)N[C@H](C)c5ccc(F)cc5)CC4)cc3[nH]2)cc1]

Step 1. Preparation of (S)-4-(6-(N-((1R,4i)-4-((R)-1-(4-fluorophenyl)ethylcarbamoyl)cyclohexyl)sulfamoyl)-1H-indol-2-yl)benzyl 2-(tert-butoxycarbonylamino)-3-methylbutanoate

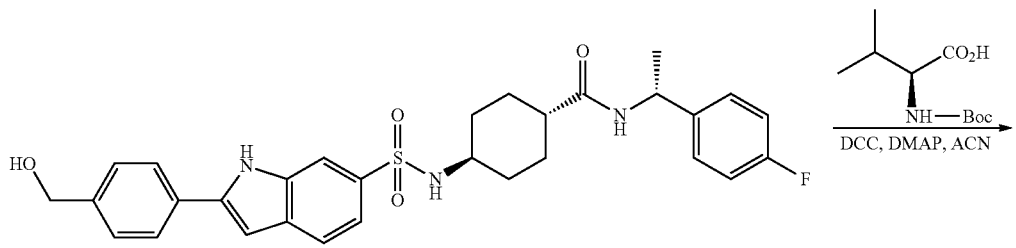

-continued

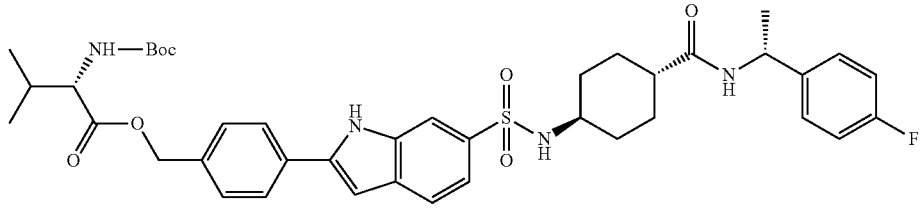

Boc-valine (89 mg, 0.41 mmol) in acetonitrile (10 mL) was treated with DCC (113 mg, 0.55 mmol) followed by addition of (1r,4R)—N—((R)-1-(4-fluorophenyl)ethyl)-4-(2-(4-(hydroxymethyl)phenyl)-1H-indole-6-sulfonamido)cyclohexanecarboxamide (150 mg, 0.27 mmol; (MS: (M+H)+=550.2) prepared as described for Example 18, but with (4-ethynylphenyl)methanol used in place of phenyl acetylene) in acetonitrile (5 mL) followed by addition of DMAP (3 mg, 0.025 mmol). The mixture was stirred overnight at room temperature, then ethyl acetate (50 mL) and water (50 mL) were added. The layers were separated, and the organic phase was dried (sodium sulfate) and concentrated under vacuum to give the crude product as a yellow solid (MS: (M+H)+=749.3).

Step 2. Preparation of (S)-4-(6-(N-((1R,4r)-4-((R)-1-(4-fluorophenyl)ethylcarbamoyl)cyclohexyl)sulfamoyl)-1H-indol-2-yl)benzyl 2-amino-3-methylbutanoate

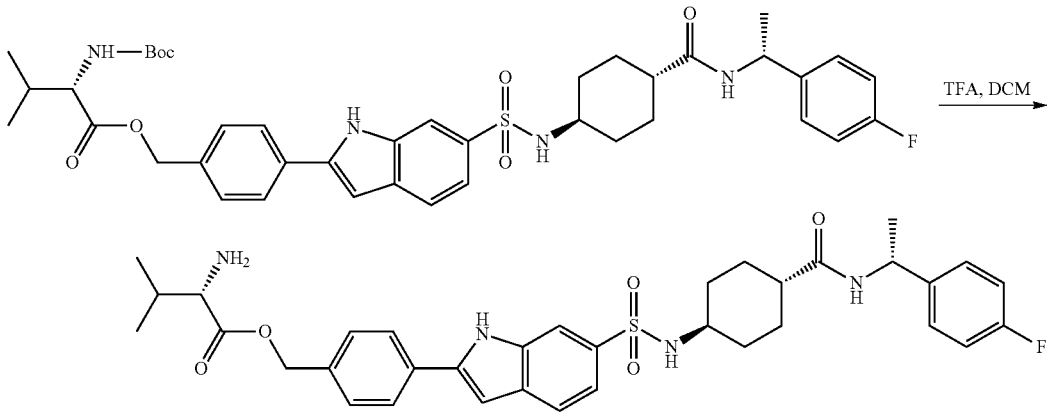

The crude product from the previous step was stirred in a solution of DCM (5 mL) and TFA (5 mL) at room temperature for 0.5 h and then concentrated under vacuum. DMSO was added and the product was purified by HPLC using a Waters Xbridge C8 column with a 40-60% acetonitrile/water solvent system in which the water contained 5 mM ammonium hydroxide. Approximately 70 mg of product was obtained.

Example 28

3-(4-(3-chloro-6-(N-((1S,4r)-4-((S)-3-cyclopropylmorpholine-4-carbonyl)cyclohexyl)sulfamoyl)-1-methyl-1H-indol-2-yl)phenyl)propanoic acid

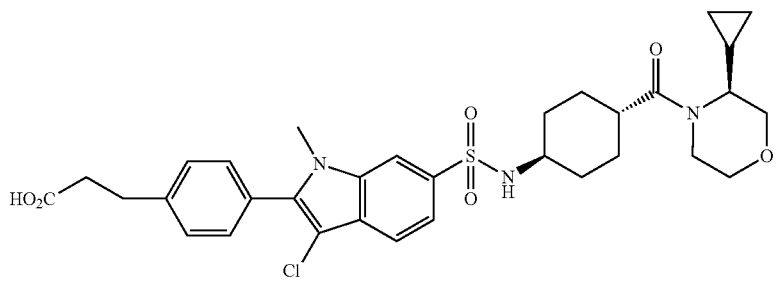 [SMILES: Cn1c(-c2ccc(CCC(=O)O)cc2)c(Cl)c2ccc(S(=O)(=O)N[C@H]3CC[C@H](C(=O)N4CCOC[C@@H]4C4CC4)CC3)cc21]

Step 1. Preparation of (S)-3-cyclopropylmorpholine

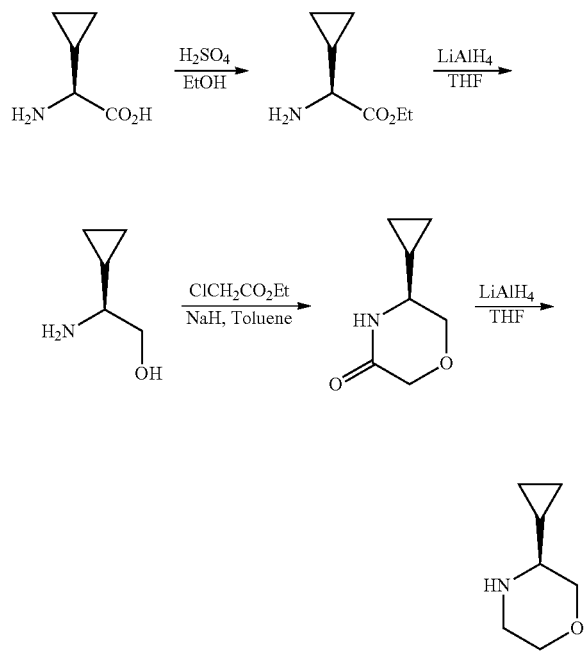

Sulfuric acid (conc., 1.704 g, 0.926 mL, 17.37 mmol) was added to a solution of (S)-2-amino-2-cyclopropylacetic acid (1 g, 8.69 mmol) in ethanol (12 mL) and heated to reflux for 5 h, then cooled to rt. The reaction mixture was concentrated under vacuum to remove solvent and water (10 mL) was added. The pH of the mixture was adjusted to 10 using 2M aq. sodium hydroxide and was then extracted with DCM (3×15 mL). The organic phase was dried with sodium sulfate and concentrated under vacuum to provide (S)-ethyl 2-amino-2-cyclopropylacetate (862 mg) which was used as is.

(S)-ethyl 2-amino-2-cyclopropylacetate (644 mg, 4.5 mmol) in THF (7.5 mL) was added dropwise to 6.75 mL of a 2M solution of lithium aluminum hydride in THF at 0° C. under a nitrogen atmosphere. The mixture was stirred for 10 min at 0° C. and then allowed to warm to room temperature, followed by stirring for an additional 1 h. The mixture was then cooled to 0° C. and water (0.6 mL) was added slowly, followed by 1.2 mL of 2 M aq. sodium hydroxide and an additional 1.2 mL of water. The resulting mixture was stirred at rt for 10 min. Celite was added and the mixture was filtered through a celite pad. The solid was washed twice with warm THF. The filtrate was dried with sodium sulfate and concentrated under vacuum to afford (S)-2-amino-2-cyclopropylethanol (420 mg) as a light yellow oil.

To a cold, stirred suspension of sodium hydride (600 mg, 14.99 mmol) in toluene (20 mL) was added dropwise a solution of (S)-2-amino-2-cyclopropylethanol (680 mg, 6.72 mmol)) in toluene (12 mL). The reaction mixture was then allowed to warm to room temperature and a solution of ethyl chloroacetate (824 mg, 6.72 mmol) in toluene (4 mL) was added dropwise. The resulting mixture was stirred for 3 h at room temperature. The mixture was then quenched with the addition of 10 mL of 1N aq. hydrochloric acid and concentrated under vacuum. The residue was diluted with THF, dried with magnesium sulfate, concentrated under vacuum and filtered through a pad of silica gel, flushing with additional THF. The resulting filtrate was concentrated under vacuum, and the residue was further purified by flash chromatography (ISCO, 12 g silica gel column, using a 0-100% ethyl acetate in n-heptane gradient as the eluent to afford 208 mg of (S)-5-cyclopropylmorpholin-3-one as a white solid (MS: (M+H)⁺=142.2).

A solution of (S)-5-cyclopropylmorpholin-3-one (208 mg, 1.473 mmol) in THF (5 mL) was added dropwise to a suspension of lithium aluminum hydride (112 mg, 2.95 mmol) in THF (6 mL) at 0° C. Following completion of the addition, the ice bath was removed, and the reaction was allowed to warm to room temperature and then heated to reflux for 3 h. The reaction mixture was then cooled and water (0.3 mL) was slowly added, followed by 1N aq. sodium hydroxide (0.6 mL). The resulting mixture was stirred at rt for 1 h and filtered, washing the solid with warm THF and DCM. The filtrate was dried with magnesium sulfate, filtered and concentrated under vacuum to provide (S)-3-cyclopropylmorpholine (110 mg) as a yellow oil (MS: (M+H)⁺=128.3).

Step 2. Preparation of tert-butyl (1S,4r)-4-((S)-3-cyclopropylmorpholine-4-carbonyl)cyclohexylcarbamate

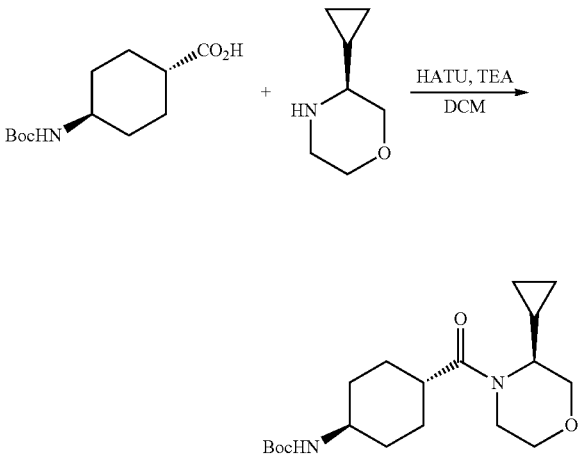

(1r,4r)-4-(tert-butoxycarbonylamino)cyclohexanecarboxylic acid (0.6 g, 2.466 mmol) in DCM (10 mL) was treated with HATU (0.345 g, 2.71 mmol) and TEA (0.499 g, 0.687 mL, 4.93 mmol) and stirred at rt for 5 min, followed by addition of (S)-3-cyclopropylmorpholine (0.345 g, 2.71 mmol). Stirring was continued for 2 h, and the mixture was then concentrated under vacuum. The residue was diluted with 50 mL of ethyl acetate and 50 mL of water. The organic layer was separated and washed with water (3×50 mL) and brine, dried (sodium sulfate), filtered and concentrated to give product (870 mg) as a solid (MS: (M+H)⁺=353.3).

Step 3. Preparation of ((1r,4S)-4-aminocyclohexyl)((S)-3-cyclopropylmorpholino)methanone hydrochloride salt

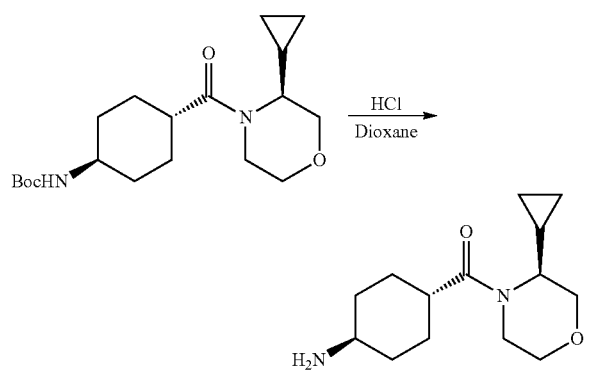

The product from the previous reaction (870 mg, 2.468 mmol) was stirred in 4M HCl in dioxane (12.3 mL, 49.2 mmol) at rt for 1 h. The mixture was then concentrated under vacuum to give product as a solid that was used in the next step as is.

Step 4. Preparation of 4-chloro-N-((1S,4r)-4-((S)-3-cyclopropylmorpholine-4-carbonyl)cyclohexyl)-3-nitrobenzenesulfonamide

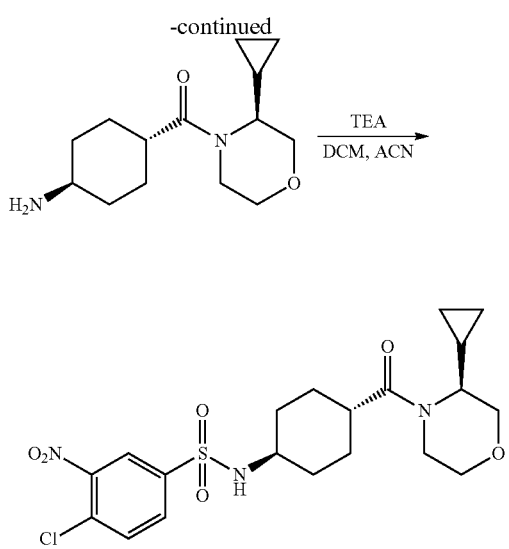

The condensation of the amine (713 mg, 2.468 mmol) and the sulfonyl chloride (695 mg, 2.71 mmol) was carried out as described for Example 2, except that a mixture of DCM (3 mL) and ACN (3 mL) was used as the solvent. The product was purified by flash chromatography on silica gel (ISCO, 40 g column, 0-100% ethyl acetate in n-heptane) to afford 740 mg of the sulfonamide (MS: (M+H)$^+$=472.0).

Step 5. Preparation of methyl 3-(4-((4-(N-((1S,4r)-4-((S)-3-cyclopropylmorpholine-4-carbonyl)cyclohexyl)sulfamoyl)-2-nitrophenyl)ethynyl)phenyl)propanoate

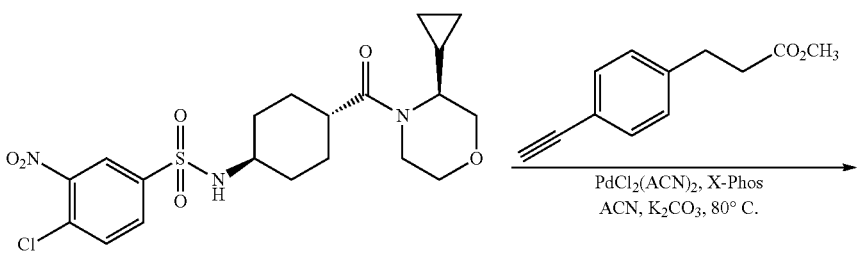

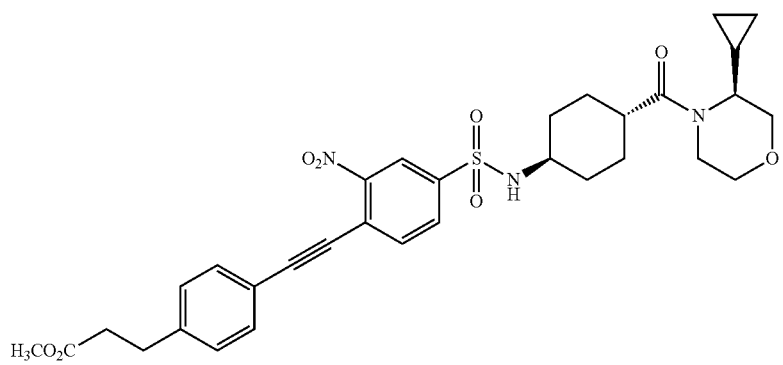 [SMILES: COC(=O)CCc1ccc(C#Cc2ccc(S(=O)(=O)N[C@H]3CC[C@H](C(=O)N4CCOC[C@@H]4C4CC4)CC3)cc2N)cc1]

The chlorosulfonamide from the previous step (740 mg, 1.568 mmol) and methyl 3-(4-ethynylphenyl)propanoate (354 mg, 1.882 mmol; prepared as described in Example 25) were coupled as described for Example 25 to provide the title compound (MS: (M+H)$^+$=624.3) which was used as is in the next step.

Step 6. Preparation of methyl 3-(4-((2-amino-4-(N-((1S,4r)-4-((S)-3-cyclopropylmorpholine-4-carbonyl)cyclohexyl)sulfamoyl)phenyl)ethynyl)phenyl)propanoate

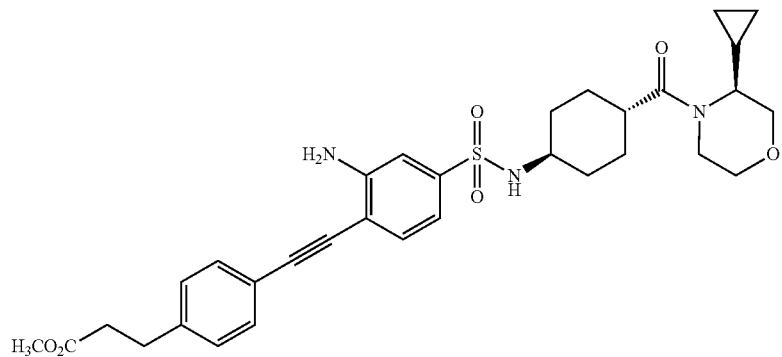

The nitro compound from the previous step (0.978 mg, 1.568 mmol) was reduced to the aniline derivative using tin(II) chloride as described in Example 18 to afford the product (MS: (M+H)$^+$=594.2) which was used as is in the next step.

Step 7. Preparation of methyl 3-(4-((4-(N-((1S,4r)-4-((S)-3-cyclopropylmorpholine-4-carbonyl)cyclohexyl)sulfamoyl)-2-(methylamino)phenyl)ethynyl)phenyl)propanoate

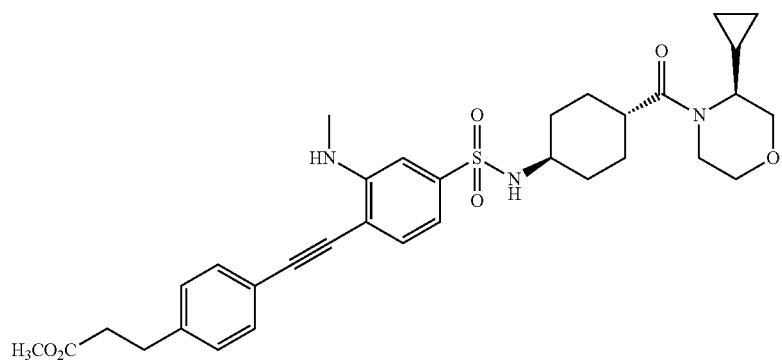 [SMILES: CNc1cc(S(=O)(=O)N[C@H]2CC[C@H](C(=O)N3CCOC[C@@H]3C3CC3)CC2)ccc1C#Cc1ccc(CCC(=O)OC)cc1]

The aniline derivative from the previous step was methylated following the procedure described for Example 20. The product was purified by flash chromatography on silica gel (ISCO, 40 g column, 0-100% ethyl acetate in n-heptane as eluent) to afford 425 mg of the product as a yellow solid (MS: (M+H)$^+$=608.3).

Step 8. Preparation of methyl 3-(4-(6-(N-((1S,4r)-4-
((S)-3-cyclopropylmorpholine-4-carbonyl)cyclo-
hexyl)sulfamoyl)-1-methyl-1H-indol-2-yl)phenyl)
propanoate

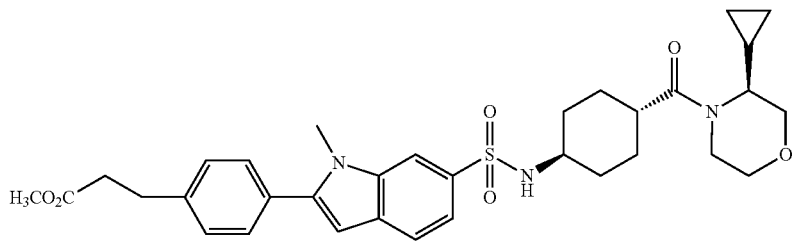 [SMILES: COC(=O)CCc1ccc(-c2cc3ccc(S(=O)(=O)N[C@H]4CC[C@H](C(=O)N5CCOC[C@@H]5C5CC5)CC4)cc3n2C)cc1]

The product from the previous step (425 mg, 0.699 mmol) was cyclized to the indole derivative following the procedure described for Example 20. The crude product was taken up in 10 mL of ACN of which 6 mL was used for HPLC purification using a Sunfire Prep C18 30×100 mm column with 40-65% ACN in water containing 0.1% TFA for both solvents. Retention time was 9.509 min., and 90 mg was obtained (MS: $(M+H)^+=608.3$).

Step 9. Preparation of methyl 3-(4-(3-chloro-6-(N-
((1S,4r)-4-((S)-3-cyclopropylmorpholine-4-carbo-
nyl)cyclohexyl)sulfamoyl)-1-methyl-1H-indol-2-yl)
phenyl)propanoate

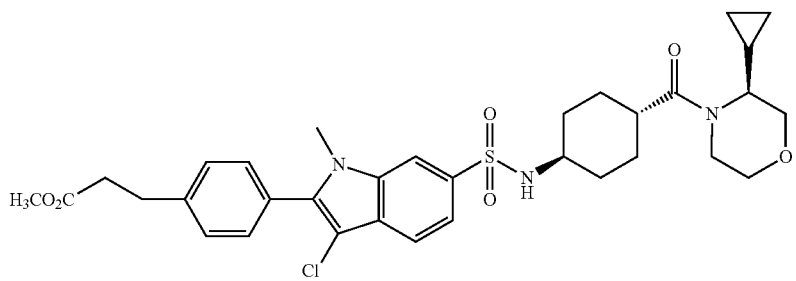 [SMILES: COC(=O)CCc1ccc(-c2c(Cl)c3ccc(S(=O)(=O)N[C@H]4CC[C@H](C(=O)N5CCOC[C@@H]5C5CC5)CC4)cc3n2C)cc1]

The indole from Step 8 (80 mg, 0.132 mmol) was chlorinated using the procedure described for Example 21 to afford the desired 3-chloro derivative (MS: $(M+H)^+=642.4$) which was used directly as is in the next step.

Step 10. Preparation of 3-(4-(3-chloro-6-(N-((1S,
4r)-4-((S)-3-cyclopropylmorpholine-4-carbonyl)
cyclohexyl)sulfamoyl)-1-methyl-1H-indol-2-yl)phe-
nyl)propanoic acid

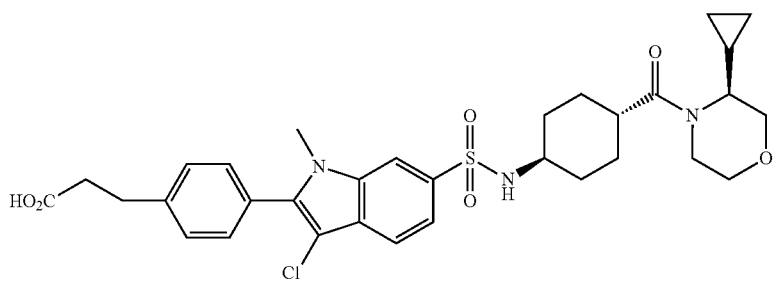 [SMILES: Cn1c(-c2ccc(CCC(=O)O)cc2)c(Cl)c2ccc(S(=O)(=O)N[C@H]3CC[C@H](C(=O)N4CCOC[C@@H]4C4CC4)CC3)cc21]

The ester from the previous step (80 mg, 0.121 mmol) was hydrolyzed as described for Example 25. The product was purified by HPLC (40-60% ACN in water containing 0.1% TFA for both solvents; Sunfire Prep C18 30×100 mm column; $t_R$=8.253 min.; 76 mg obtained). The purified acid was converted to a potassium salt using potassium bicarbonate (1.0 equivalent) in a mixture of water and ACN followed by lyophilization to afford 80 mg of the potassium salt.

Example 29

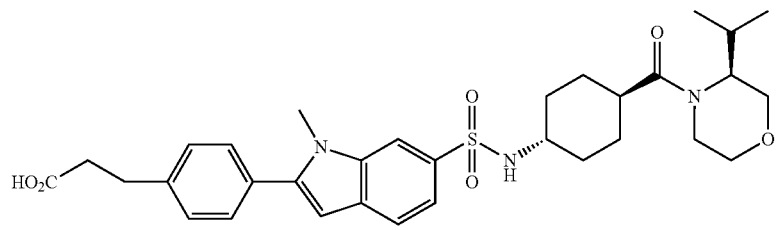 [SMILES: CC(C)[C@H]1COCCN1C(=O)[C@H]1CC[C@H](NS(=O)(=O)c2ccc3cc(-c4ccc(CCC(=O)O)cc4)n(C)c3c2)CC1]

3-(4-(6-(N-((1S,4r)-4-((S)-3-isopropylmorpholine-4-carbonyl)cyclohexyl)sulfamoyl)-1-methyl-1H-indol-2-yl)phenyl)propanoic acid

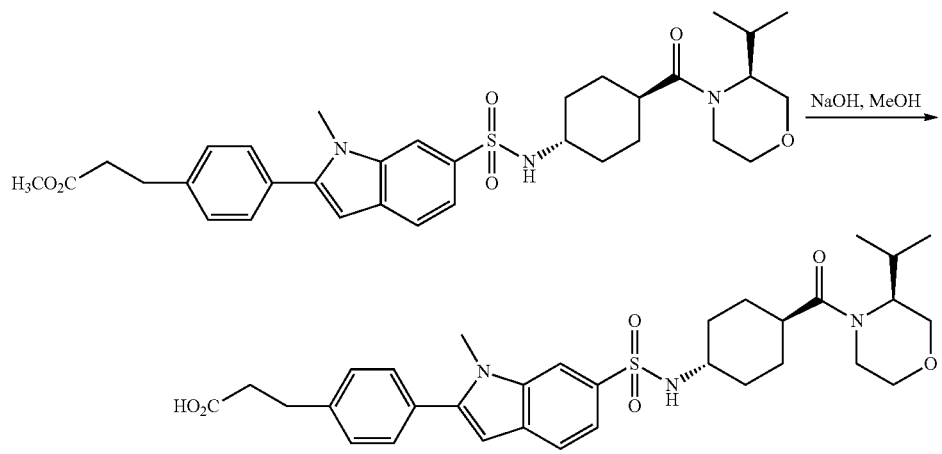

The title compound was prepared and purified by the hydrolysis of the product of Step 10 of Example 25 according to the procedure of Step 12 of Example 25 to afford 40 mg of the acidic product. This product was converted to its potassium salt by treatment with 1.0 equivalents (6.7 mg) of potassium bicarbonate in a mixture of acetonitrile and water. Lyophilization provided 42 mg of the product as its potassium salt.

Example 30

2-(4-(2-methoxyethyl)phenyl)-N-((1S,4r)-4-((S)-3-methylmorpholine-4-carbonyl)cyclohexyl)-1H-indole-6-sulfonamide

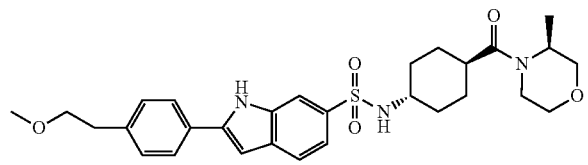 [SMILES: COCCc1ccc(-c2cc3ccc(S(=O)(=O)N[C@H]4CC[C@H](C(=O)N5CCOC[C@@H]5C)CC4)cc3[nH]2)cc1]

Step 1. Preparation of ((4-(2-methoxyethyl)phenyl)ethynyl)trimethylsilane

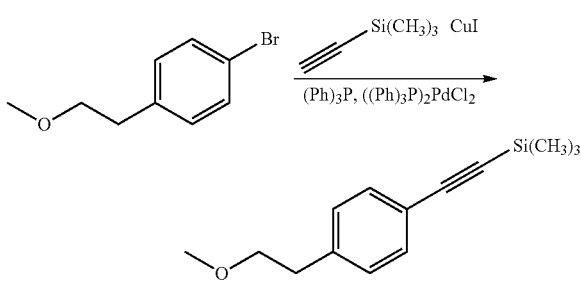

Ethynyltrimethylsilane (3.42 g, 34.9 mmol) was added via syringe to a mixture of 1-bromo-4-(2-methoxyethyl)benzene (5 g, 23.25 mmol), bis(triphenylphosphine)palladium dichloride (0.326 g, 0.465 mmol), triphenylphosphine (0.305 g, 1.162 mmol) and copper(I) iodide (0.089 g, 0.465 mmol) in piperidine (25 mL). The mixture was heated to 100° C. for 1 h under a nitrogen atmosphere, then cooled and concentrated under vacuum. The residue was taken up in ethyl acetate (70 mL), filtered and concentrated to give the crude product that was then purified by flash chromatography on silica gel (ISCO 120 g column, 0-20% ethyl acetate in n-heptane as the eluent). Product (4.36 g) was obtained as a brown oil (MS: (M+H)⁺=233.3).

Step 2. Preparation of 1-ethynyl-4-(2-methoxyethyl)benzene

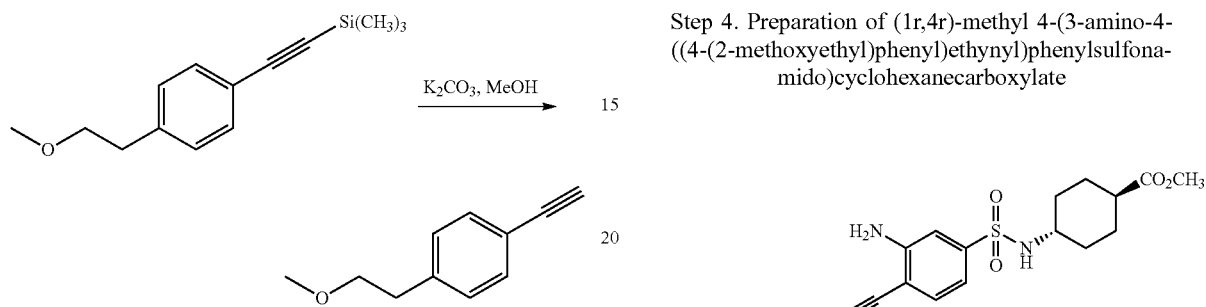

The product from the previous step (4.36 g, 18.76 mmol) and potassium carbonate (2.59 g, 18.76 mmol) was stirred in methanol (30 mL) at room temperature for 1 h and then concentrated under vacuum. The residue was taken up in ethyl acetate (100 mL) and washed with 100 mL of 1.0N HCl. The aqueous fraction was extracted with ethyl acetate (50 mL), and the combined organic solutions were washed with brine (50 mL), dried (sodium sulfate) and concentrated under vacuum to provide the crude product. The product was purified by flash chromatography on silica gel (ISCO 120 g column, with 0-50% ethyl acetate in n-heptane as the eluent) to give 2.34 g of product as a brown oil.

Step 3. Preparation of (1r,4r)-methyl 4-(4-((4-(2-methoxyethyl)phenyl)ethynyl)-3-nitrophenylsulfonamido)cyclohexanecarboxylate

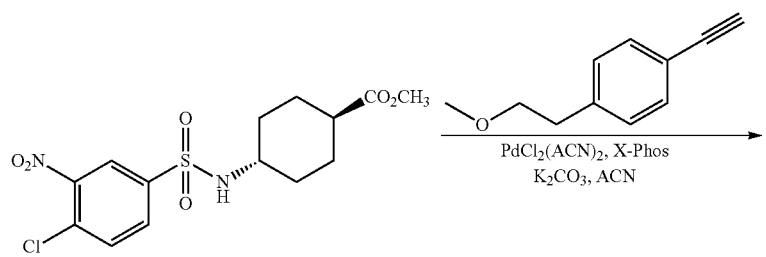

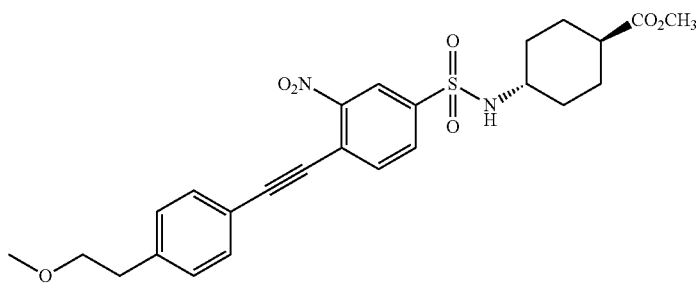

The product from the previous step (0.385 g, 2.4 mmol) was condensed with (1r,4r)-methyl 4-(4-chloro-3-nitrophenylsulfonamido)cyclohexanecarboxylate (0.754 g, 2 mmol; prepared as described in Example 19) following the procedure outlined for Example 19. The crude product (MS: (M+H)⁺=501.3) was isolated as described and used as is in the next step.

Step 4. Preparation of (1r,4r)-methyl 4-(3-amino-4-((4-(2-methoxyethyl)phenyl)ethynyl)phenylsulfonamido)cyclohexanecarboxylate

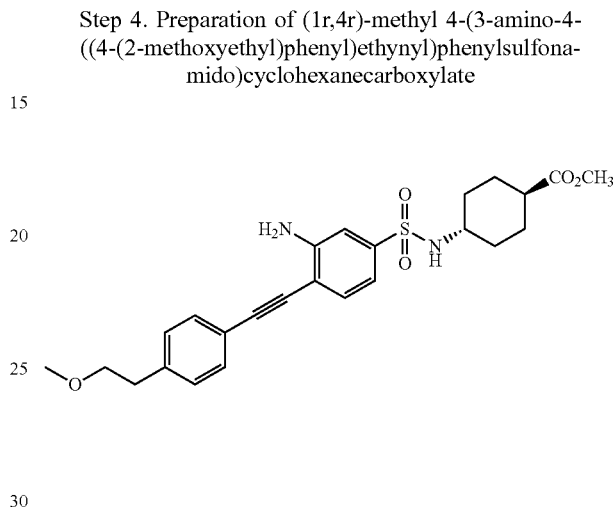

The nitro compound from the previous step (1 g, 2 mmol) was reduced to the corresponding aniline derivative with tin(II) chloride (3.79 g, 20 mmol) following the procedure described for Example 18. The crude product was purified by flash chromatography on silica gel (ISCO 40 g column, with 0-100% ethyl acetate in n-heptane as the eluent) to afford 1.01 g of the title compound (MS: (M+H)⁺=471.3).

Step 5. Preparation of (1r,4r)-methyl 4-(2-(4-(2-methoxyethyl)phenyl)-1H-indole-6-sulfonamido)cyclohexanecarboxylate

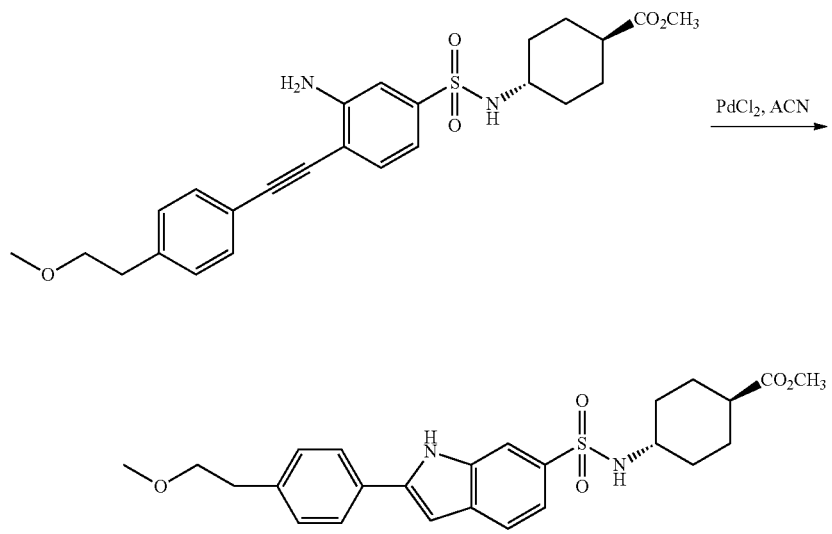

The product from the previous step (1.01 g, 2.146 mmol) was cyclized to the indole derivative following the procedure described for Example 18. The crude product so obtained was purified by flash chromatography on silica gel (ISCO 40 g column, using 0-100% ethyl acetate in n-heptane as the eluent) to afford 560 mg of the title compound (MS: $(M+H)^+=471.1$).

Step 6. Preparation of 2-(4-(2-methoxyethyl)phenyl)-N-((1S,4r)-4-((S)-3-methylmorpholine-4-carbonyl)cyclohexyl)-1H-indole-6-sulfonamide

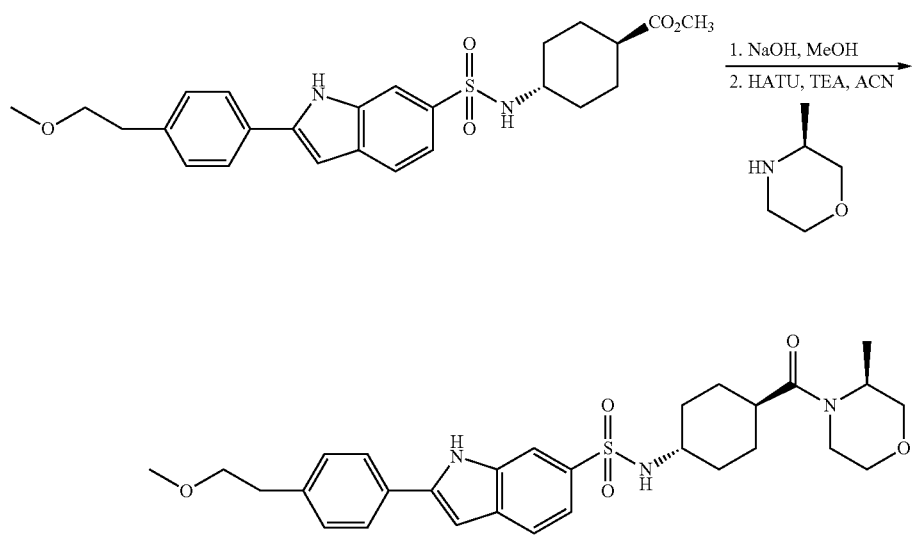

The ester from the previous step (280 mg, 0.595 mmol) was hydrolyzed in methanol (6 mL) with 5.95 mL of 2M aq. sodium hydroxide as described for Example 19 to afford 230 mg of the corresponding acid. The resulting acid (60 mg, 0.131 mmol) was condensed with (S)-3-methylmorpholine (15.95 mg, 0.158 mmol) as described for Example 19. The crude product was purified by HPLC using a Sunfire Prep C18 5u 30×100 mm column with 35-65% acetonitrile containing 0.1% TFA to afford 43 mg of the title compound after lyophilization.

Example 31

3-chloro-2-(4-(2-methoxyethyl)phenyl)-N-((1S,4r)-4-((S)-3-methylmorpholine-4-carbonyl)cyclohexyl)-1H-indole-6-sulfonamide

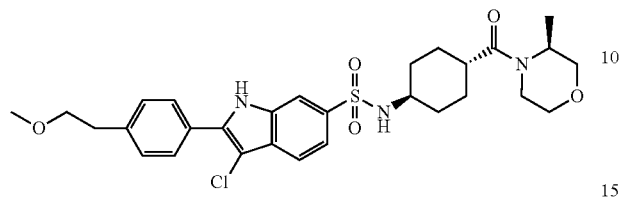

Step 1. Preparation of (1r,4r)-methyl 4-(3-chloro-2-(4-(2-methoxyethyl)phenyl)-1H-indole-6-sulfonamido)cyclohexanecarboxylate

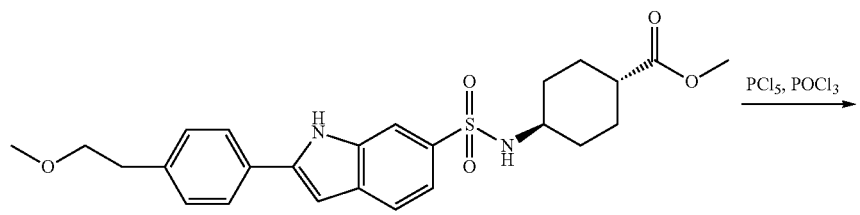

Phosphorus pentachloride (0.526 g, 2.52 mmol) was added to a solution of (1r,4r)-methyl 4-(2-(4-(2-methoxyethyl)phenyl)-1H-indole-6-sulfonamido)cyclohexanecarboxylate (1.08 g, 2.295 mmol; prepared as described in Step 5 of Example 30) in phosphoryl chloride (10 mL) at room temperature. After 30 min, an additional 278 mg of phosphorus pentachloride was added and stirring was continued for an additional 15 min. The mixture was then poured onto ice and then extracted with ethyl acetate (50 mL). The organic solution was washed with water (2×50 mL) and brine (50 mL), dried (sodium sulfate) and concentrated to provide 810 mg of the title compound (MS: (M+H)$^+$=505.1).

Step 2. Preparation of (1r,4r)-4-(3-chloro-2-(4-(2-methoxyethyl)phenyl)-1H-indole-6-sulfonamido)cyclohexanecarboxylic acid

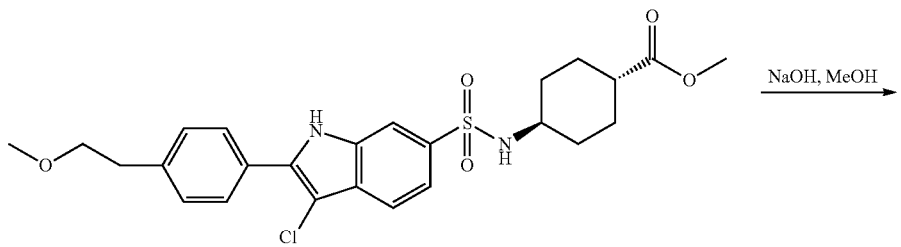

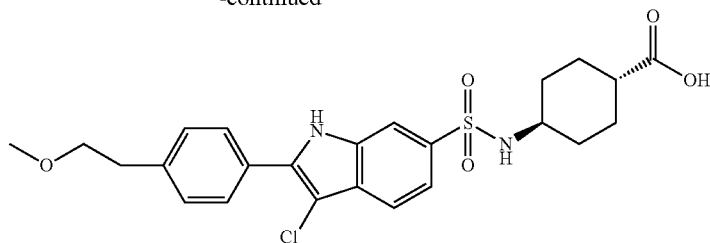

A solution of the product from the previous step (810 mg, 1.604 mmol) in methanol (20 mL) was treated with 2M aq. sodium hydroxide (16.04 mL, 32.1 mmol). The mixture was stirred for 1 h at room temperature, then neutralized with 1N aq. hydrochloric acid and extracted with ethyl acetate (100 mL). The organic phase was washed with brine (50 mL), dried (sodium sulfate) and concentrated to provide the product (810 mg; (MS: (M+H)+=491.0) which was used as is in the next step.

Step 4. Preparation of 3-chloro-2-(4-(2-methoxyethyl)phenyl)-N-((1S,4r)-4-((S)-3-methylmorpholine-4-carbonyl)cyclohexyl)-1H-indole-6-sulfonamide

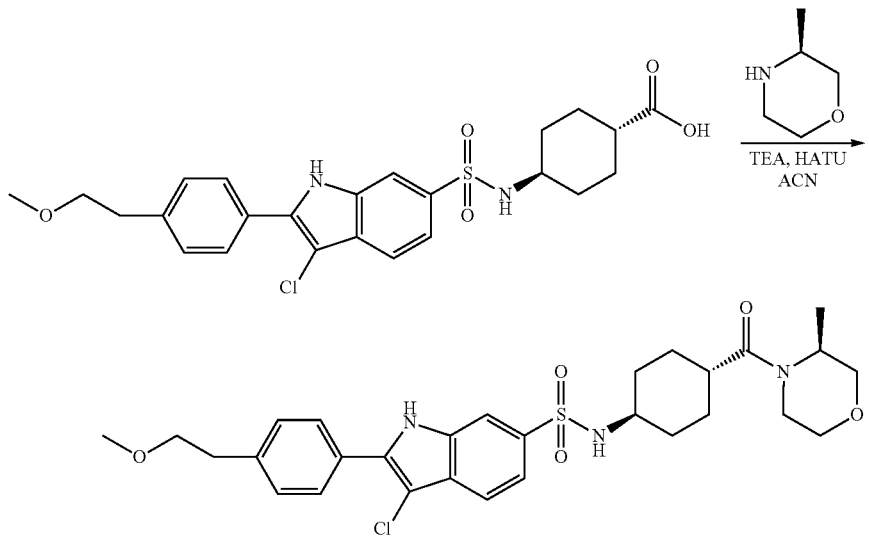

A solution of the product of the previous step (450 mg, 0.916 mmol), TEA (185 mg, 0.255 mL, 1.833 mmol) and HATU (383 mg, 1.008 mmol) in acetonitrile (4 mL) was stirred for 2 min at room temperature, followed by addition of (S)-3-methylmorpholine (93 mg, 0.916 mmol). Stirring was continued at room temperature for 30 min., followed by dilution with DMSO (1 mL). The resulting mixture was purified by HPLC using a Sunfire Prep C18 5u 30×100 mm column with 40-70% acetonitrile containing 0.1% TFA as the eluent to provide the product (145 mg) following lyophilization; $t_R$=8.013 min.

Formulations:
Microemulsion Preparation:
50 grams of Cremophor RH 40 was added to 30 grams of Propylene Glycol and 20 grams of Labrafil M2125 CS. The mixture was stirred at 50° C. until a clear, slightly yellow, completely homogeneous solution was achieved with no phase separation.

Oral Dosing Solution:
16.75 mg of Example 31 was added to 3.35 mL of Microemulsion prepare above. The mixture was sonicated/stirred at room temperature until Example 31 was completely dissolve and the solution was homogeneous. Final concentration of Example 31 was 5.0 mg/mL. Prior to dosing, the solution was diluted 1:10 with water and allow to stir until a clear, homogeneous solution was achieved.

IV Dosing Solution:
7.00 mg of Example 31 was added to 0.7 mL N-methyl pyrollidone (NMP) and 6.3 mL PEG 300. The mixtured was stirred/sonicated at room temperature until full dissolution of Example 31 to give a homogeneous solution. The solution was I.V. dosed neat with a final concentration was 1.0 mg/mL Example 32

2-cyclopropyl-1,3-dimethyl-N-((1S,4r)-4-((S)-3-methylmorpholine-4-carbonyl)cyclohexyl)-1H-indole-6-sulfonamide

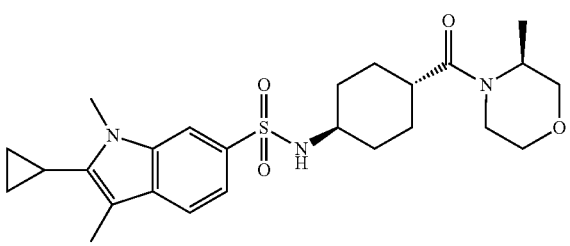 [SMILES: Cc1c(C2CC2)n(C)c2cc(S(=O)(=O)N[C@H]3CC[C@H](C(=O)N4CCOC[C@@H]4C)CC3)ccc12]

Step 1. Preparation of (1r,4r)-methyl 4-(2-cyclopropyl-1,3-dimethyl-1H-indole-6-sulfonamido)cyclohexanecarboxylate

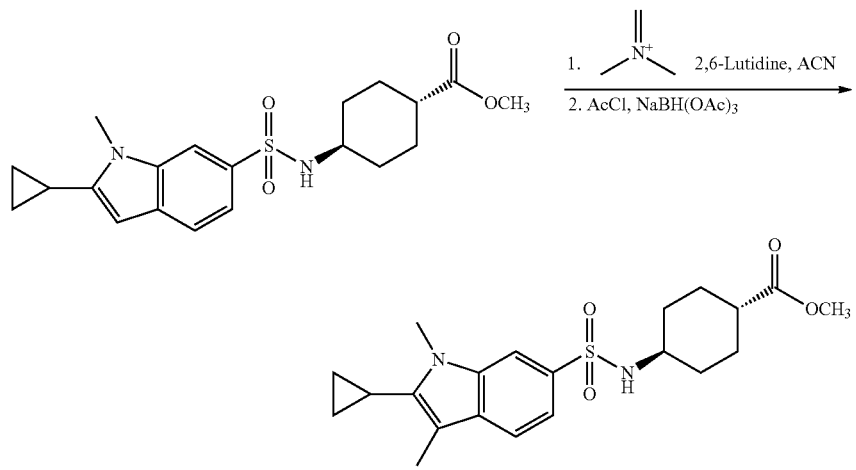

A mixture of (1r,4r)-methyl 4-(2-cyclopropyl-1-methyl-1H-indole-6-sulfonamido)cyclohexanecarboxylate (30 mg, 0.077 mmol) and N-methyl-N-methylenemethanaminium chloride (14.37 mg, 0.154 mmol) in acetonitrile (5 mL) was stirred for 10 min at room temperature followed by addition of 2,6-lutidine (8.23 mg, 8.95 L, 0.077 mmol). The reaction was then stirred overnight at room temperature. To this mixture was added THF (1 mL) followed by sodium triacetoxyborohydride (100 mg, 0.472 mmol). Acetyl chloride (221 mg, 200 L, 2.81 mmol) was then added dropwise, and stirring was continued for an additional 10 min. The mixture was quenched with 1.0 N aq. hydrochloric acid (2 mL) and extracted with ethyl acetate (4 mL). The organic phase was washed with brine, dried (sodium sulfate) and concentrated to provide the crude product (MS: $(M+H)^+=405.1$) that was used as is for the next step.

Step 2. Preparation of 2-cyclopropyl-1,3-dimethyl-N-((1S,4r)-4-((S)-3-methylmorpholine-4-carbonyl)cyclohexyl)-1H-indole-6-sulfonamide

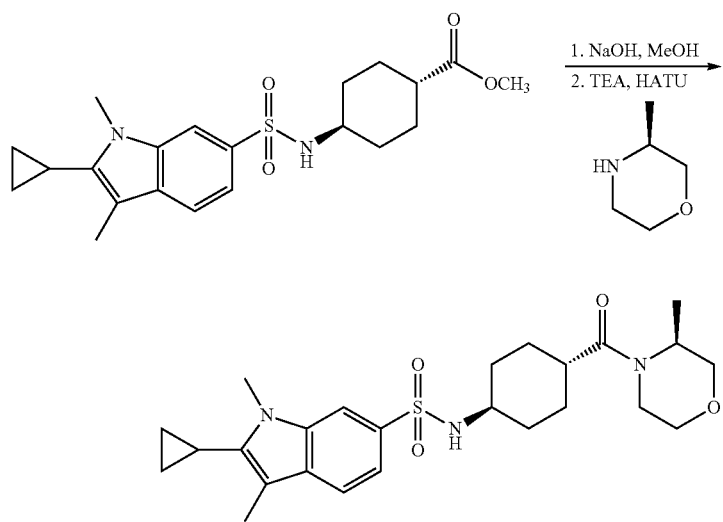

The product from the previous step (31 mg, 0.077 mmol) was taken up in methanol (1 mL) to which 2M aq. sodium hydroxide (0.958 mL, 1.016 mmol) was added. The mixture was stirred 2 h at room temperature and then neutralized with the addition of 1.0N aq. hydrochloric acid. The resulting mixture was extracted with ethyl acetate, and the organic phase was washed with brine, dried with sodium sulfate and concentrated to give the crude acid.

The crude hydrolysis product was taken up in acetonitrile (1 mL) and triethylamine and HATU were added. This mixture was stirred for 2 min., followed by addition of (S)-3-methylmorpholine (9.01 mg, 0.089 mmol). The resulting mixture was stirred 30 min., diluted with DMSO and purified by HPLC using a Sunfire Prep C18 5u 30×100 mm column, with 40-70% acetonitrile in water containing 0.1% TFA as the eluent. Following lyophilization, 10 mg of product was isolated.

Example 33

(1r,4R)—N—((R)-1-(4-fluorophenyl)ethyl)-4-(1,2,3,4-tetrahydropyrido[3,2-b]pyrazine-7-sulfonamido)cyclohexanecarboxamide

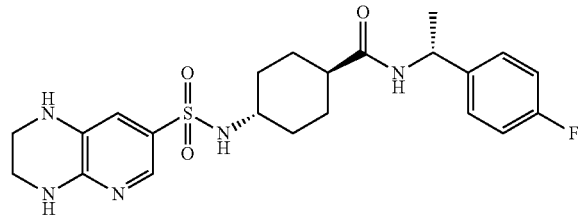 [SMILES: C[C@@H](NC(=O)[C@H]1CC[C@H](NS(=O)(=O)c2cnc3c(c2)NCCN3)CC1)c1ccc(F)cc1]

Step 1. Preparation of (1r,4R)-4-(5-bromo-6-chloropyridine-3-sulfonamido)-N—((R)-1-(4-fluorophenyl)ethyl)cyclohexanecarboxamide

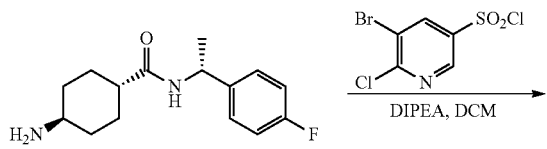

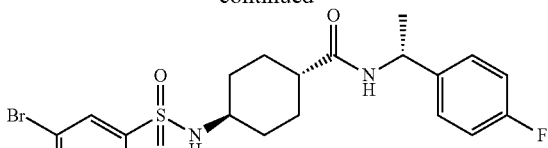

DIPEA (4.3 g, 5.81 mL, 33.2 mmol) was added to a suspension of (1r,4R)-4-amino-N—((R)-1-(4-fluorophenyl)ethyl)cyclohexanecarboxamide (5 g, 16.62 mmol; prepared as described in Example 1) in DCM (200 mL) at room temperature. 5-Bromo-6-chloropyridine-3-sulfonyl chloride (4.84 g, 16.62 mmol) in DCM (100 mL) was then added and the reaction mixture was stirred overnight at room temperature. The reaction mixture was concentrated, and the residue was taken up in ethyl acetate and washed with sat. aq. sodium carbonate, dried (magnesium sulfate) and concentrated to afford a yellow solid. The yellow solid was triturated with hexane and filtered to afford a beige powder (6.74 g).

Step 2. Preparation of (1r,4R)-4-(6-(2-aminoethylamino)-5-bromopyridine-3-sulfonamido)-N—((R)-1-(4-fluorophenyl)ethyl)cyclohexanecarboxamide

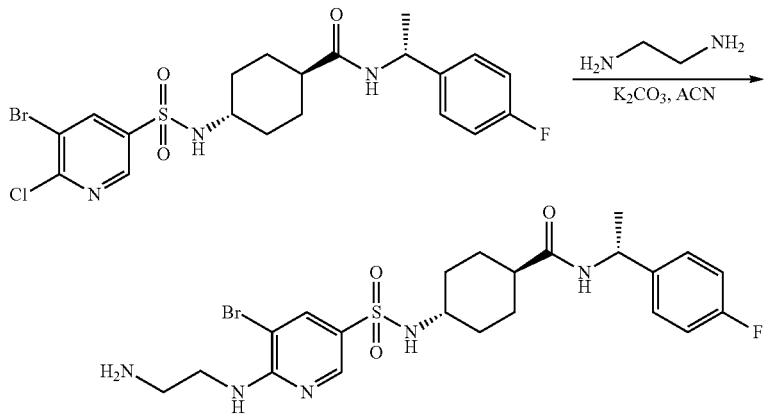

The product from the previous step (0.6 g, 1.156 mmol), potassium carbonate (0.479 g, 3.47 mmol) acetonitrile (1.5 mL) and ethylenediamine (0.22085 g, 0.22343 mL, 3.47 mmol) were heated in a microwave oven at 160° C. for 10 min. The reaction was performed on this scale 10 times, and the resulting reaction mixtures were filtered and combined. The filtrate was concentrated to afford a beige foam (5.15 g; M+H: 544.1, 545.5).

Step 3. Preparation of (1r,4R)—N—((R)-1-(4-fluorophenyl)ethyl)-4-(1,2,3,4-tetrahydropyrido[3,2-b]pyrazine-7-sulfonamido)cyclohexanecarboxamide

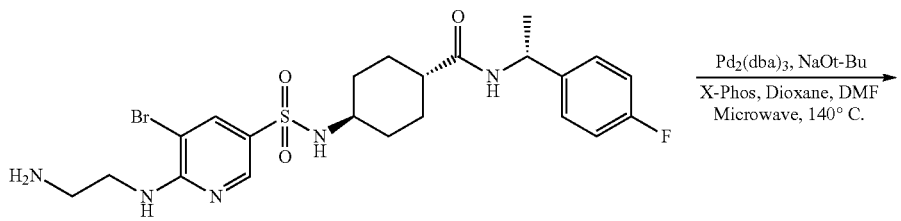

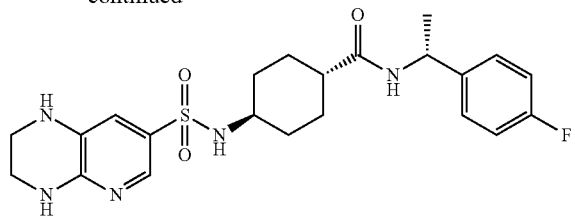

The product from the previous step (50 mg, 0.092 mmol), X Phos (21.97 mg, 0.046 mmol), Pd2(dba)3 (16.88 mg, 0.018 mmol) and sodium tert-butoxide (39.9 mg, 0.415 mmol) were added to a dry microwave vial, to which dioxane (3 ml) and DMF (2 ml) were then added. The reaction mixture was heated at 140° C. for 15 min in a microwave oven, after which the reaction mixture was concentrated. The resulting brown oil was dried under high vacuum and then adsorbed onto silica and purified via Biotage automated flash column chromatography, 25M, eluting with 2-20% ethyl acetate in methanol. Relevant fractions were pooled and concentrated to afford an off white solid, which was dried under a high vacuum to give 48 mg of product as a white solid.

Example 34

(1r,4R)-4-(1,4-dimethyl-1,2,3,4-tetrahydropyrido[3,2-b]pyrazine-7-sulfonamido)-N—((R)-1-(4-fluorophenyl)ethyl)cyclohexanecarboxamide (1r,4R)-4-(5-bromo-6-chloropyridine-3-sulfonamido)-N—((R)-1-(4-fluorophenyl)ethyl)cyclohexanecarboxamide (500 mg, 0.964 mmol; prepared as described in Step 1 of Example 33) and potassium carbonate (400 mg, 2.89 mmol) were added to a dry microwave vial, to which acetonitrile (15 mL) was then added. $N^1,N^2$-dimethylethane-1,2-diamine (0.311 ml, 2.89 mmol) was then added to this solution and the reaction mixture was then heated in a microwave oven at 160° C. for 15 min. The reaction mixture was filtered, and the filtrate was concentrated to afford a sticky brown solid that was purified via Biotage automated flash column chromatography 40M, eluting with 2-20% ethyl acetate in methanol. Relevant fractions were pooled and concentrated to afford a white solid, which was dried under high vacuum. This material was triturated with hexanes and filtered to afford a white solid, which was itself dried under high vacuum to give 243 mg of product.

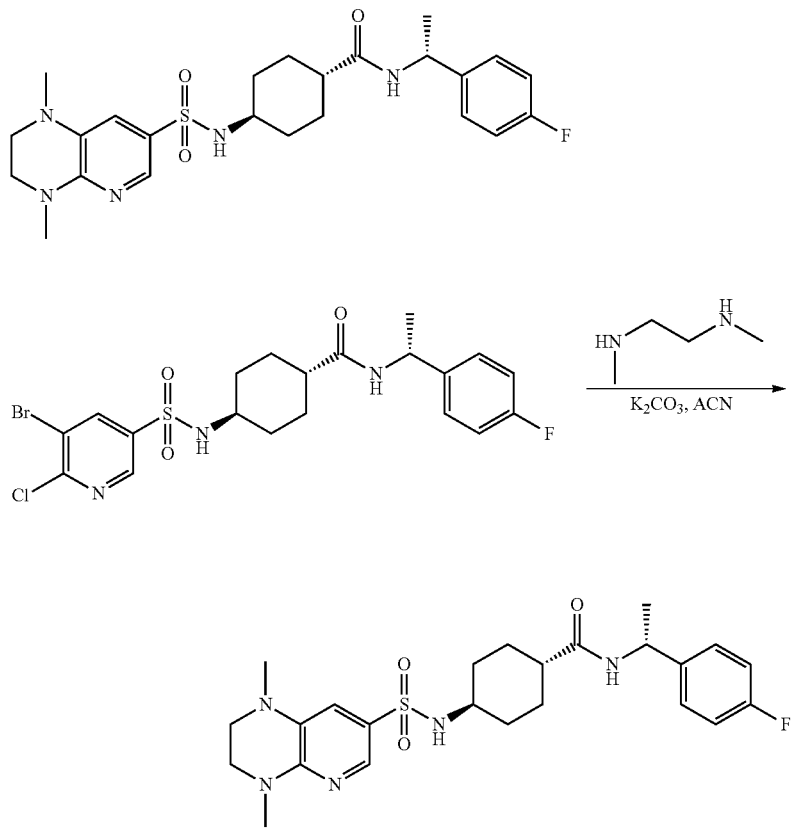

Example 35

(1r,4R)-4-(2,3-dihydro-1H-pyrido[2,3-b][1,4]thiaz-ine-7-sulfonamido)-N—((R)-1-(4-fluorophenyl)ethyl)cyclohexanecarboxamide

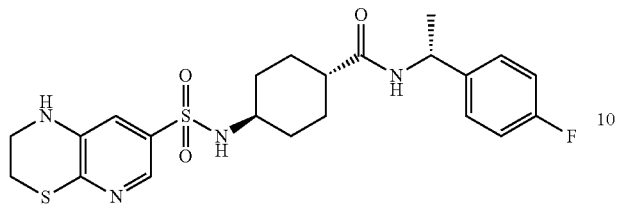

Step 1. Preparation of tert-butyl 2-(3-bromo-5-(N-((1R,4r)-4-((R)-1-(4-fluorophenyl)ethylcarbamoyl)cyclohexyl)sulfamoyl)pyridin-2-ylthio)ethylcarbamate

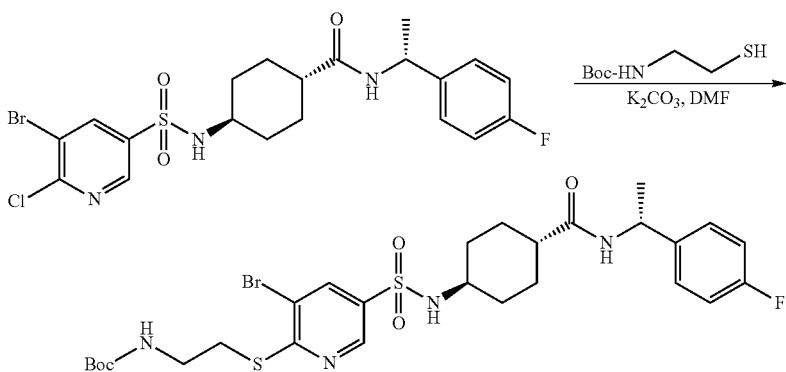

A mixture of (1r,4R)-4-(5-bromo-6-chloropyridine-3-sulfonamido)-N—((R)-1-(4-fluorophenyl)ethyl)cyclohexanecarboxamide (1 g, 1.927 mmol: prepared as described in Step 1 of Example 33), potassium carbonate (0.533 g, 3.85 mmol) and tert-butyl 2-mercaptoethylcarbamate (0.512 g, 0.489 mL, 2.89 mmol) in DMF (10 mL) was stirred overnight at room temperature. The reaction mixture was then poured into brine and extracted with ethyl acetate. The organic phase was dried (magnesium sulfate) and concentrated to provide product (1.1 g) as a yellow foam.

Step 2. Preparation of (1r,4R)-4-(6-(2-aminoethylthio)-5-bromopyridine-3-sulfonamido)-N—((R)-1-(4-fluorophenyl)ethyl)cyclohexanecarboxamide

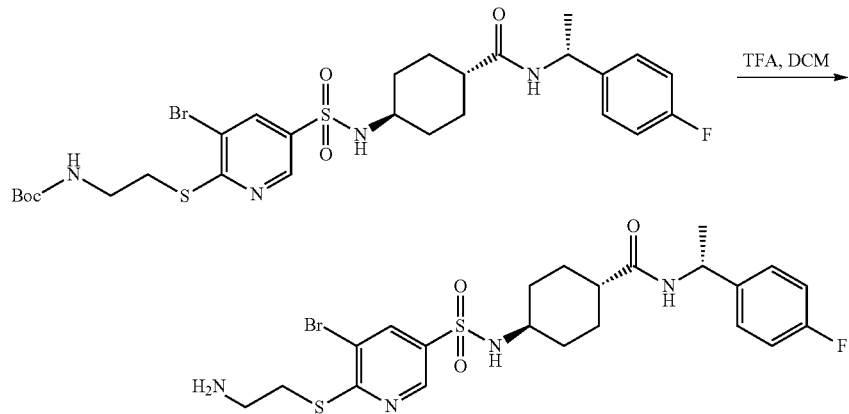

The product from the previous step (1.1 g, 1.668 mmol) and trifluoroacetic acid (4.44 g, 3 mL, 38.9 mmol) in DCM (15 mL) were stirred at room temperature for 3 h. The mixture was then concentrated, treated with sat. aq. sodium bicarbonate and extracted with ethyl acetate. The organic phase was dried (magnesium sulfate) and concentrated to provide 240 mg of product as a yellow powder.

Step 3. Preparation of (1r,4R)-4-(2,3-dihydro-1H-pyrido[2,3-b][1,4]thiazine-7-sulfonamido)-N—((R)-1-(4-fluorophenyl)ethyl)cyclohexanecarboxamide

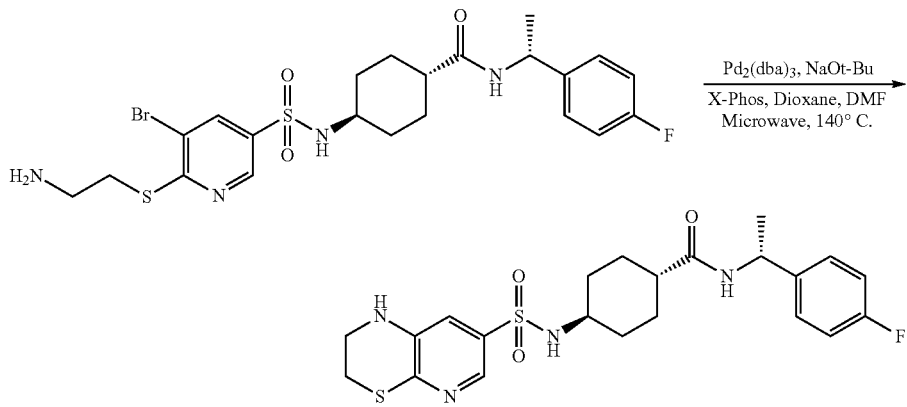

The product from the previous step (220 mg, 0.393 mmol) was cyclized following the procedure described in Step 3 of Example 33. The crude product was purified by flash chromatography on silica gel on a Biogage 25S column with 1:1 ethyl acetate/heptane followed by 95:5 ethyl acetate/methanol as eluents to provide an orange oil. Trituration with ether and filtration afforded 74 mg of a yellow solid.

Example 36

(1r,4R)-4-(2-ethoxyquinoline-6-sulfonamido)-N—((R)-1-(4-fluorophenyl)ethyl)cyclohexanecarboxamide

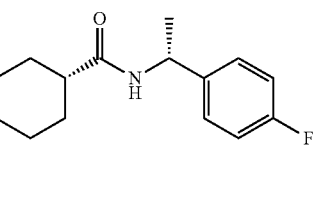

Step 1. Preparation of 6-nitro-3,4-dihydroquinolin-2(1H)-one

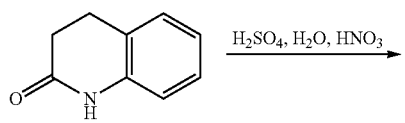

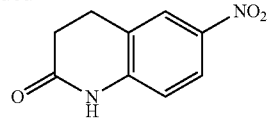

3,4-Dihydro-1H-quinolin-2-one (7.2 g, 48.9 mmol) was dissolved in sulfuric acid (150 mL) and cooled to 0° C. Water (35 mL) was added dropwise, followed by nitric acid (3.5 mL, 78 mmol) dropwise following this, retaining temperature below 0° C. The reaction mixture was stirred at 0° C. for 15 min after which LC-MS showed one major peak corresponding to desired product. The reaction mixture was then poured into ice water and extracted with EtOAc (3×); the combined organic phases were dried over MgSO$_4$, filtered and concentrated to afford a brown solid-6-nitro-3,4-Dihydro-1H-quinolin-2-one-8.56 g (91% yield).

Step 2. Preparation of 2-chloro-6-nitroquinoline

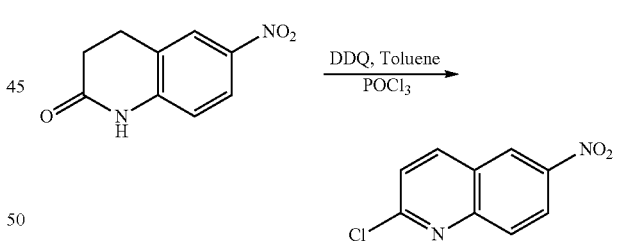

6-Nitro-3,4-dihydro-1H-quinolin-2-one (12.56 g, 65.4 mmol) was suspended in toluene (200 mL), to which DDQ (15.06 g, 66.3 mmol) was added. Phosphoryl trichloride (30.5 mL, 327 mmol) was then added dropwise and the reaction mixture was then heated at 90° C. for 3 hours. It was then observed that the deep red semi-solution had become an orange free flowing suspension, which LC-MS confirmed contained desired product. The reaction mixture was then poured slowly into ice water (1 L), keeping temperature below 10° C. This solution was then neutralized to pH 7 via slow addition of 2.5M aq. sodium hydroxide, keeping temperature below 10° C. This brown suspension was then extracted with ethyl acetate. The aqueous layer was back extracted further with ethyl acetate, and the combined organic layers were washed with brine. The resulting orange/brown solution was dried over MgSO₄, filtered and concentrated to afford a brown/orange solid, which was dried under high vacuum overnight. The mass of dry material (2-chloro-6-nitro-quinoline) was 7.2 g (50% yield).

Step 3. Preparation of 2-chloroquinolin-6-amine

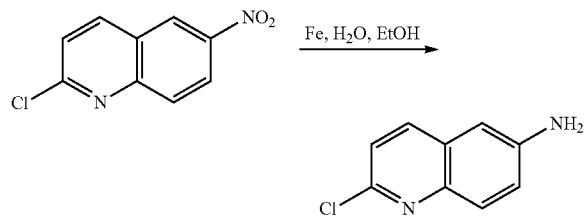

2-chloro-6-nitro-quinoline (12.5 g, 59.9 mmol) and ammonium chloridel (9.78 g, 183 mmol) were suspended in ethanol (175 mL) and water (50 mL). The resulting mixture was heated to 60° C. and iron powder (15.06 g, 270 mmol) was added as a solid in portions. The reaction mixture was stirred at 60° C. for 2 hours. LC-MS at this point showed one major peak corresponding to desired product. The reaction mixture was then concentrated to remove the majority of ethanol, and the residue was diluted with ethyl acetate and filtered to remove brown solids. The filter cake was washed with ethyl acetate. The filtrate was then dried over MgSO₄, filtered and concentrated to afford a brown solid. This material was adsorbed onto silica and purified via Biotage automated flash column chromatography, eluting with 10-100% ethyl acetate/heptane. Relevant fractions were pooled and concentrated to afford a creamy yellow soft fluffy solid, which was dried under high vacuum to provide 6.45 g (60% yield) of product.

Step 4. Preparation of 2-chloroquinoline-6-sulfonyl chloride

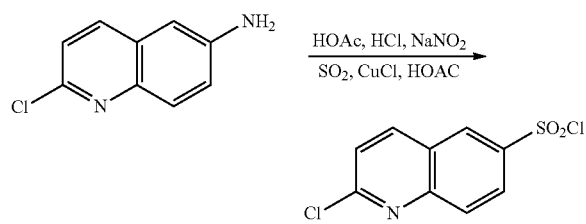

2-Chloroquinolin-6-amine (6.45 g, 36.1 mmol) was dissolved in acetic acid (50 mL) and hydrochloric acid, 37% (14 mL) and cooled to 0° C. A solution of sodium nitrite (2.74 g, 39.7 mmol) in water (8 mL) was then added dropwise, and the reaction mixture was then stirred at 0° C. for 15 min. the entire reaction mixture was then poured into a 0° C. solution of sulfur dioxide, copper(II) chloride and acetic acid (1 L, 36.1 mmol; solution prepared as described for Example 11). The reaction mixture was allowed to warm to room temperature overnight. LC-MS at this time showed reaction had progressed to completion. The reaction mixture was then concentrated, and the residue was partitioned between ethyl acetate and water. The aqueous phase was back extracted, and the combined organic phases were dried over MgSO₄, filtered and concentrated to afford a creamy orange solid, which was dried under high vacuum to provide 8.21 g (87% yield) of product.

Step 5. Preparation of (1r,4R)-4-(2-chloroquinoline-6-sulfonamido)-N—((R)-1-(4-fluorophenyl)ethyl) cyclohexanecarboxamide

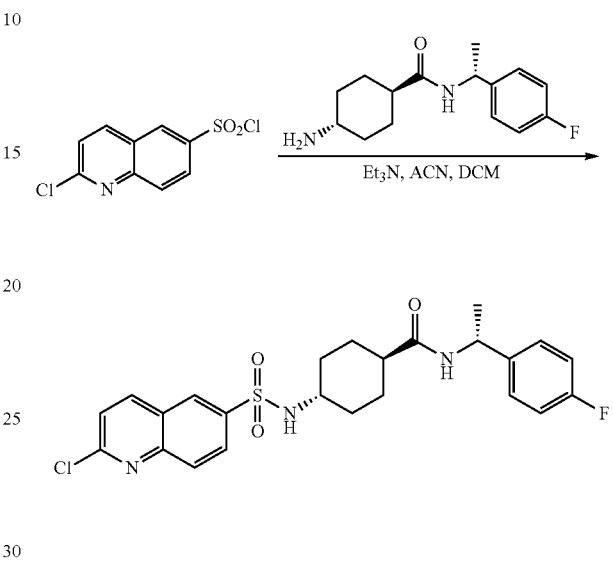

The sulfonyl chloride from the previous step (700 mg, 2.67 mmol) and (1r,4R)-4-amino-N—((R)-1-(4-fluorophenyl)ethyl)cyclohexanecarboxamide (964 mg, 3.2 mmol; prepared as described in Example 1) were condensed as described in Example 1 to provide 320 mg of the title compound.

Step 6. Preparation of (1r,4R)-4-(2-ethoxyquinoline-6-sulfonamido)-N—((R)-1-(4-fluorophenyl)ethyl)cyclohexanecarboxamide

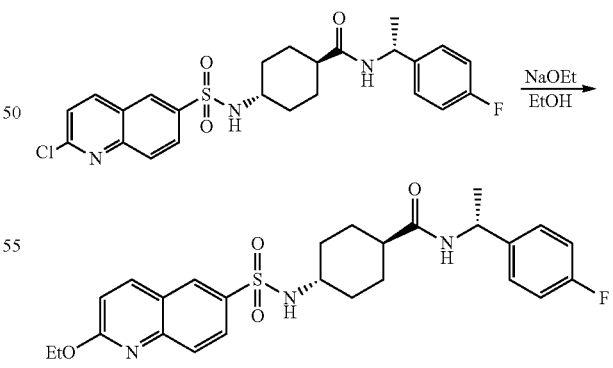

Ethanol (1 mL, anhydrous) and sodium ethoxide (43 L of a 21% solution in ethanol) were added to the chloroquinoline derivative. The reaction was heated to 60 C overnight, then concentrated under vacuum. The residue was purified by flash chromatography using a 1:1 mixture of ethyl acetate and heptane as the eluent to afford 10 mg of product.

Example 37

(1r,4S)-4-(2-ethoxyquinoline-6-sulfonamido)-N-((1S,2R)-2-hydroxy-1-phenylpropyl)cyclohexanecarboxamide

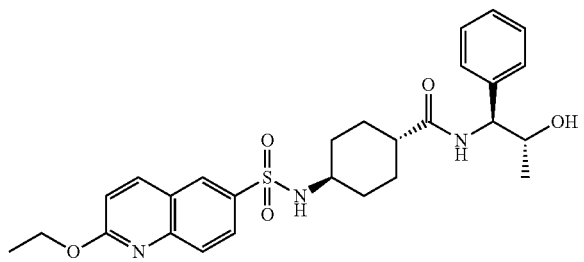 [SMILES: CCOc1ccc2cc(S(=O)(=O)N[C@H]3CC[C@H](C(=O)N[C@@H](c4ccccc4)[C@@H](C)O)CC3)ccc2n1]

Step 1. Preparation of (1R,2R)-1-phenylpropane-1,2-diol

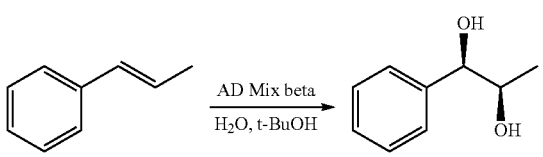

AD Mix beta (Aldrich; 12.88 g, 9.22 mmol) was suspended in water (50 mL) and t-butanol (50 mL), and the resulting slurry was cooled to 0° C. (E)-prop-1-enylbenzene (1.203 g, 9.22 mmol) was then added and the reaction mixture was stirred at 0° C. (with careful temperature monitoring) for 6 h. The reaction was then allowed to warm to room temperature and stirred overnight. The reaction was quenched by addition of solid sodium sulfite (6 g). Water was then added, and the mixture was extracted with ethyl acetate. The organic phase was washed with brine, dried (MgSO$_4$) and concentrated to afford the crude product which was purified by flash chromatography (Biotage 40 M column, 10-100% ethyl acetate/heptane as eluent). The relevant fractions were combined and concentrated to afford the product (8.48 g, ca. 96% pure, ca. 92% de).

Step 2. Preparation of (4R,5R)-4-methyl-5-phenyl-[1,3,2]dioxathiolane 2-oxide

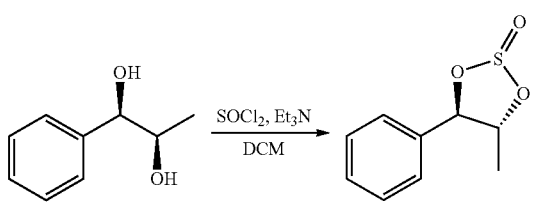

The diol from the previous step (4.86 g, 31.9 mmol) was dissolved in triethylamine (15 mL, 108 mmol) and DCM (75 mL) and cooled to 0° C. Thionyl chloride (3.5 mL, 47.9 mmol) was then added dropwise (vigorous gas evolution). Stirring was continued at 0° C. for 45 min., after which the mixture was concentrated. The residue was partitioned between cold water and diethyl ether, and the organic phase was washed with 1N aq. hydrochloric acid, saturated aq. sodium bicarbonate and brine, dried (MgSO$_4$) and concentrated to afford the crude product as a brown oil. Further drying under high vacuum gave 5.029 g of a brown oil.

Step 3. Preparation of (1S,2R)-1-azido-1-phenylpropan-2-ol

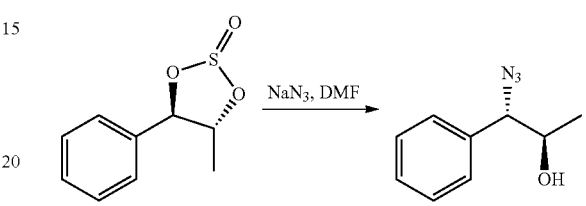

The product from the previous step (2.51 g, 12.66 mmol) was dissolved in DMF, to which solid sodium azide (3.29 g, 50.6 mmol) was added. The mixture was then heated to 90° C. for 6 h, and then cooled and poured into water and extracted with diethyl ether (3×). The combined organic phase was washed with brine, dried (MgSO$_4$) and concentrated to afford the crude product as a yellow oil (3.5 g) which was used as is in the next step.

Step 4. Preparation of tert-butyl (1S,2R)-2-hydroxy-1-phenylpropylcarbamate

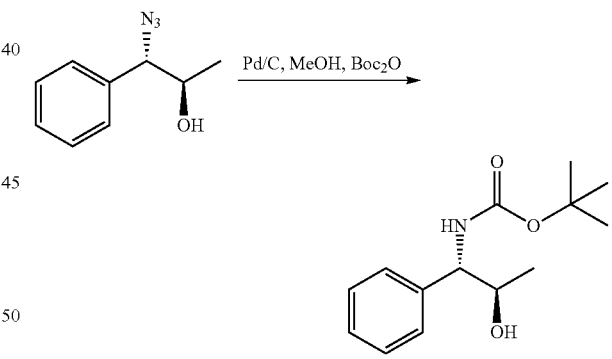

The product from the previous step (2.244 g, 12.66 mmol) was dissolved in methanol (100 mL) to which di-tert-butyl dicarbonate (5.88 mL, 25.3 mmol) was added. The reaction mixture was then stirred for 5 min at room temperature and then flushed with nitrogen. Palladium on carbon (0.658 g, 6.18 mmol) was then added, and the mixture was stirred under a hydrogen atmosphere overnight. The mixture was then filtered through celite and concentrated to afford a clear oil which solidified on standing. The product was purified by flash chromatography on silica gel (Biotage column) with 10-100% ethyl acetate/heptane as the eluent. The relevant fractions were combined and concentrated to afford product as a white solid. The mass of dry material following two runs of this reaction at this scale was 4.15 g.

Step 5. Preparation of (1S,2R)-1-amino-1-phenylpropan-2-ol

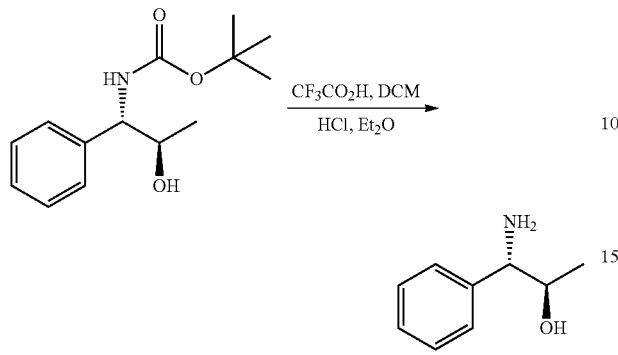

The product from multiple runs of the previous reaction (7.85 g, 31.2 mmol) was dissolved in DCM (25 mL) to which trifluoroacetic acid (25 mL, 324 mmol) was added. The reaction mixture was stirred at room temperature for 15 min., after which it was concentrated under vacuum. The residue was dissolved in ether (50 mL) to which 2M hydrogen chloride in ether (30 mL) was added. A white precipitate formed, and the resulting suspension was stirred at room temperature for 1 h. The mixture was filtered, and the solid was washed with ether and dried under high vacuum to afford 5.7 g of a white powder.

Step 6. Preparation of (1r,4r)-methyl 4-(2-chloroquinoline-6-sulfonamido)cyclohexanecarboxylate

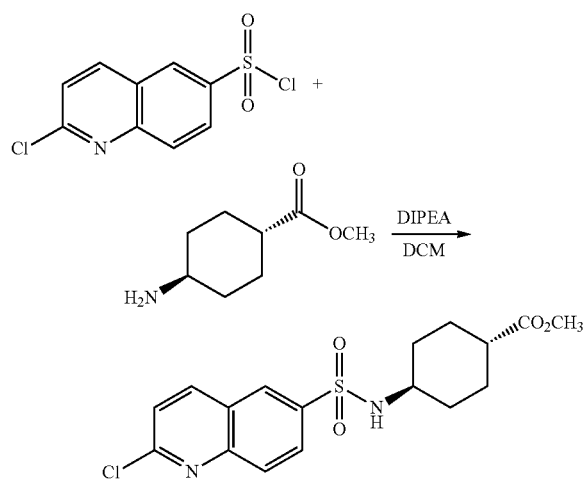

A suspension of (1r,4r)-methyl 4-aminocyclohexanecarboxylate hydrochloride (2.032 g, 10.49 mmol) in DCM (25 mL) was treated with DIPEA (3.08 g, 4.16 mL, 23.84 mmol), followed by addition of 2-chloroquinoline-6-sulfonyl chloride (2.5 g, 9.54 mmol; prepared as described in Example 36). the resulting mixture was stirred overnight at room temperature and then concentrated under vacuum. The residue was treated with 1N aq. hydrochloric acid and extracted with ethyl acetate. The organic phase was washed with brine, dried (MgSO$_4$) and concentrated to provide a reddish powder which was triturated with ether and filtered to provide 2.3 g of the product.

Step 7. Preparation of (1r,4r)-4-(2-ethoxyquinoline-6-sulfonamido)cyclohexanecarboxylic acid

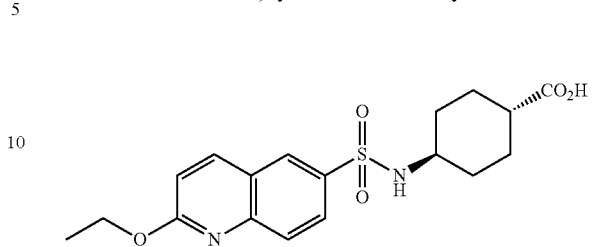

Sodium (2.88 g, 125 mmol) was dissolved in ethanol (150 mL), followed by addition of the ester from the previous step (4.8 g, 12.54 mmol; from multiple preparations). The mixture was stirred at 45° C. overnight followed by addition of 2 mL of water. Stirring was continued to complete the saponification. After 3 h, the mixture was concentrated under vacuum and 200 mL of water was added. The residue was acidified with 1N aq. hydrochloric acid and extracted with ethyl acetate. The organic phased was dried (MgSO$_4$) and concentrated to give the product as a tan solid (3.6 g)

Step 8. Preparation of (1r,4S)-4-(2-ethoxyquinoline-6-sulfonamido)-N-((1S,2R)-2-hydroxy-1-phenylpropyl)cyclohexanecarboxamide

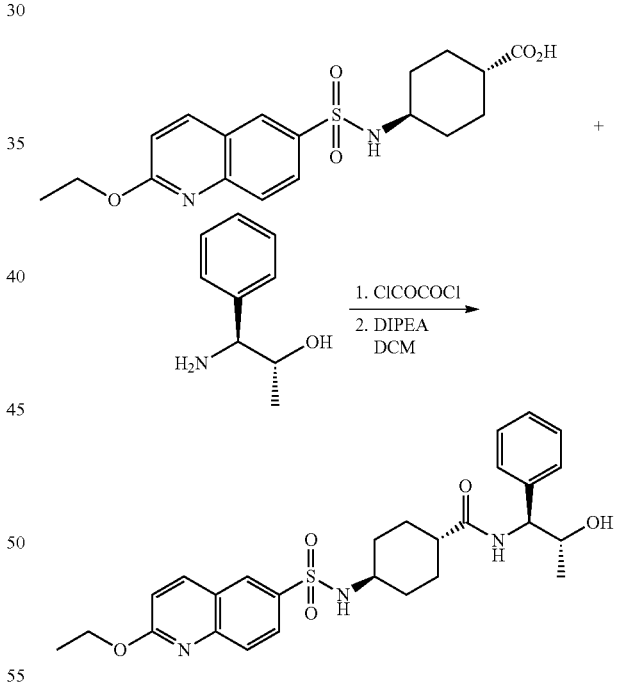

A mixture of the acid from the previous step (250 mg, 0.661 mmol) in DCM was treated with oxalyl chloride (495 L, 0.991 mmol) and DMF (1 drop) and stirred at 35° C. until a clear solution was formed. The mixture was concentrated under vacuum to provide 280 mg of a yellow solid. This was added to a solution of (1S,2R)-1-amino-1-phenylpropan-2-ol (hydrochloride salt; 124 mg, 0.661 mmol) in DCM to which DIPEA (85 mg, 115 L, 0.661 mmol) was added. Stirring was continued for 1 h, followed by concentration under vacuum. The residue was taken up in ethyl acetate and washed with saturated aqueous sodium bicarbonate and brine, dried (MgSO$_4$) and concentrated to provide the product as a white solid (150 mg).

Example 38

(1r,4R)—N—((R)-1-(4-fluorophenyl)ethyl)-4-(2-(4-methylpiperazin-1-yl)quinoline-6-sulfonamido)cyclohexanecarboxamide

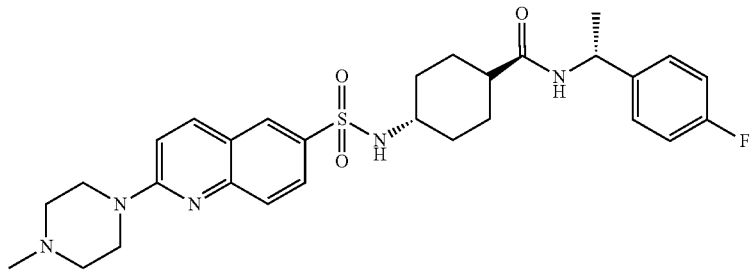

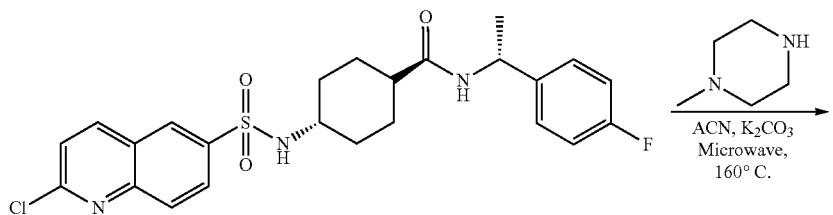

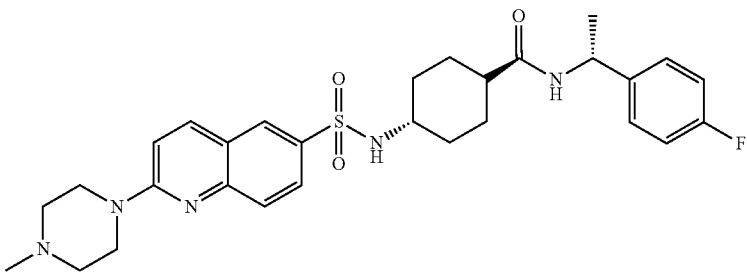

(1r,4R)-4-(2-chloroquinoline-6-sulfonamido)-N—((R)-1-(4-fluorophenyl)ethyl)cyclohexanecarboxamide (100 mg, 0.204 mmol) and potassium carbonate (85 mg, 0.612 mmol) were added to a dry microwave vial, to which acetonitrile (5 mL) and then N-methyl piperazine (0.068 mL, 0.612 mmol) were then added. The vial was then heated at 160° C. for 40 min in a microwave reactor. LC-MS at this point showed 95% desired product. The reaction mixture was then filtered and concentrated to afford an orange oil. This material was adsorbed onto silica and purified via Biotage automated flash column chromatography 12M, eluting with 2-20% EtOAc/MeOH. Relevant fractions were pooled and concentrated to afford an off white foam, which was dried under high vacuum to give 57.50 mg (50% yield) of product.

Example 39

(1r,4R)—N—((R)-1-(4-fluorophenyl)ethyl)-4-(2-(pyridin-4-yl)quinoline-6-sulfonamido)cyclohexanecarboxamide

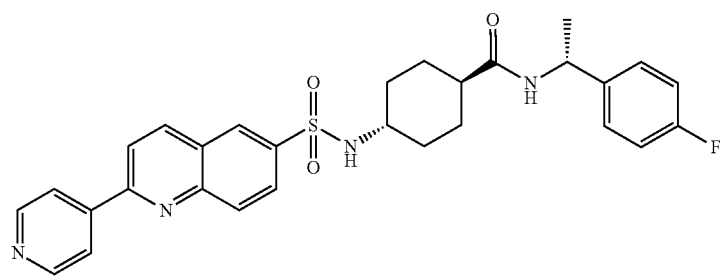

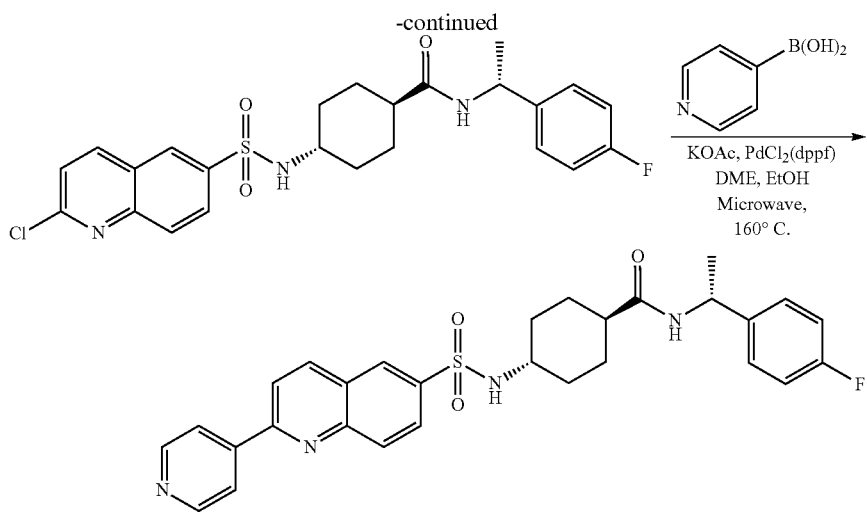

(1r,4R)-4-(2-chloroquinoline-6-sulfonamido)-N—((R)-1-(4-fluorophenyl)ethyl)cyclohexanecarboxamide (100 mg, 0.204 mmol), 4 pyridine boronic acid (37.6 mg, 0.306 mmol), potassium acetate (70.1 mg, 0.714 mmol) and PdCl2 (dppf) (14.93 mg, 0.020 mmol) were added to a dry microwave vial, to which DME (3 mL) and then EtOH (2 mL) were then added. The vial was then capped and sealed, and the reaction mixture was heated at 160° C. for 10 min in microwave. LC-MS at this point showed one major peak corresponding to desired product. The reaction mixture was then filtered, and the filtrate was concentrated. The residue was adsorbed onto silica and purified via Biotage automated flash column chromatography 12M, eluting with 2-20% EtOAc/MeOH. Relevant fractions were pooled and concentrated to afford an off white foam, which was dried under high vacuum to give 27.38 mg (25% yield) of product.

Example 40

(1r,4R)—N—((R)-1-(4-fluorophenyl)ethyl)-4-(2-(trifluoromethyl)imidazo[1,2-a]pyridine-6-sulfonamido)cyclohexanecarboxamide

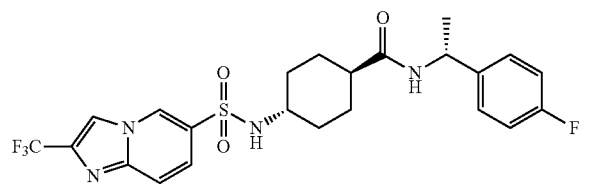 [SMILES: C[C@@H](NC(=O)[C@H]1CC[C@H](NS(=O)(=O)c2ccc3nc(C(F)(F)F)cn3c2)CC1)c1ccc(F)cc1]

Step 1. Preparation of 6-bromo-2-(trifluoromethyl)imidazo[1,2-a]pyridine

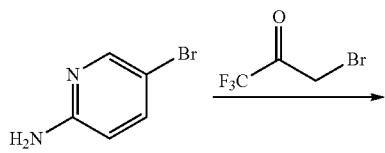

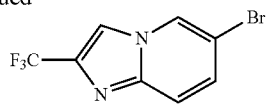

A mixture of 5-bromopyridin-2-amine (2 g, 11.56 mmol), 3-bromo-1,1,1-trifluoropropan-2-one (1.44 mL, 2.65 g, 13.87 mmol) and potassium carbonate (2.4 g, 17.34 mmol) and 15 mL of ethanol was heated in a microwave vial to 120° C. for 30 min. The mixture was concentrated, and the residue was partitioned between DCM and water. The organic phase was concentrated and purified by flash chromatography on silica gel using MBTE/heptane as the eluent. Product was isolated as an off-white solid.

Step 2. Preparation of 2-(trifluoromethyl)imidazo[1,2-a]pyridine-6-sulfonyl chloride

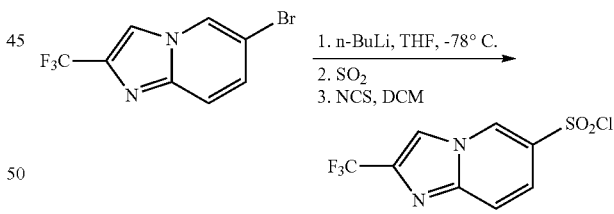

n-Butyl lithium (495 L, 1.6M in hexane) was added to a THF (4 mL) solution of the product from the previous step (200 mg, 0.75 mmol) at −78° C. The mixture was stirred for 45 min., after which sulfur dioxide was bubbled into the solution for about 2 min. The mixture was then allowed to warm to room temperature, and stirring was continued for 2 h. Solvent was removed under vacuum, and the residue was triturated with a DCM/heptane mixture to provide a light green solid. This material was dissolved in DCM (3 mL) and N-chlorosuccinimide (119.7 mg, 0.9 mmol) was added. The mixture was stirred 30 min at room temperature and concentrated under vacuum. The residue was purified by flash chromatography (MBTE/heptane) to afford 66 mg of an off-white solid.

Step 3. Preparation of (1r,4R)—N—((R)-1-(4-fluorophenyl)ethyl)-4-(2-(trifluoromethyl)imidazo[1,2-a]pyridine-6-sulfonamido)cyclohexanecarboxamide

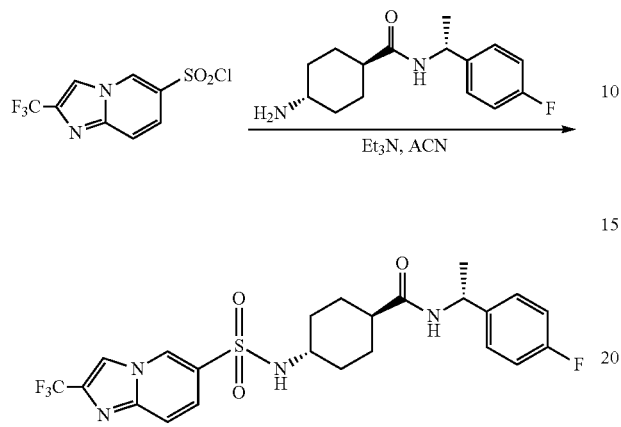

A solution of (1r,4R)-4-amino-N—((R)-1-(4-fluorophenyl)ethyl)cyclohexanecarboxamide (74 mg, 0.28 mmol) in acetonitrile was added to a mixture of the sulfonyl chloride from the previous step (66 mg, 0.23 mmol) and triethylamine (71 L, 0.51 mmol) in acetonitrile (1 mL). The mixture was stirred at 0° C. for 15 min, then overnight at room temperature. The reaction mixture was concentrated under vacuum, and the residue was purified by HPLC to afford 4.6 mg of the title compound.

Example 41

(1r,4R)—N—((R)-1-(4-fluorophenyl)ethyl)-4-(3-(2-phenyl-1H-benzo[d]imidazol-5-yl)ureido)cyclohexanecarboxamide

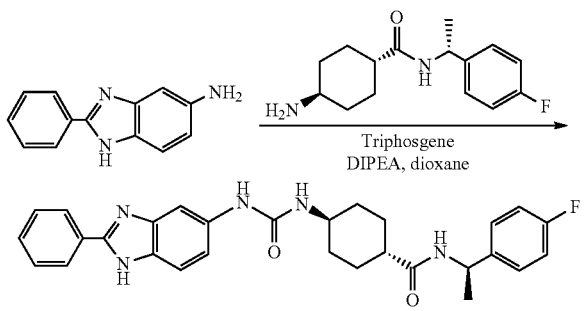

To a suspension of 2-phenyl-1H-benzo[d]imidazol-5-amine (0.1 g, 0.478 mmol) in dioxane (5 mL) and DIPEA (0.167 mL, 0.124 g, 0.956 mmol) was added triphosgene (0.284 g, 0.956 mmol). The reaction was heated to 50° C. for 1 h, after which a suspension of (1r,4R)-4-amino-N—((R)-1-(4-fluorophenyl)ethyl)cyclohexanecarboxamide (144 mg, 0.478 mmol) and DIPEA in dioxane was added. The reaction mixture was stirred for 1 h and then concentrated under vacuum. the residue was purified by flash chromatography (Biotage 25M column, 2-20% ethyl acetate/methanol as eluent). The resulting material was further purified by HPLC to afford product.

The compounds in the Table below were prepared by the method indicated in the column labeled "Synthetic Scheme" which corresponds to a synthetic scheme shown in the section labeled "Method of Preparation".

| Ex. | Synthetic Scheme | HPLC RT | HPLC Method | MS | NMR | Name |
|---|---|---|---|---|---|---|
| 1 | 1 | 10.60 min | E | 557.2797 (M + H+) | 1H NMR (400 MHz, MeOD) d ppm 1.15-1.49 (m, 7H) 1.62-1.86 (m, 4H) 2.02-2.18 (m, 1H) 2.95-3.07 (m, 1H) 7.13-7.19 (m, 1H) 7.20-7.29 (m, 4H) 7.69-7.82 (m, 3H) 7.91-7.96 (m, 1H) 7.99-8.05 (m, 1H) 8.10-8.17 (m, 2H) 8.26 (d, J = 1.01 Hz, 1H) | (1r,4R)-4-(2-phenyl-1H-benzo[d]imidazole-5-sulfonamido)-N-((R)-1-phenylethyl)cyclohexanecarboxamide |
| 2 | 2 | 11.92 | E | 575.2346 (M + H+) | 1H NMR (400 MHz, DMSO-d6) d ppm 1.05-1.32 (m, 7H) 1.38 (t, J = 7.20 Hz, 3H) 1.54-1.69 (m, 4H) 1.93-2.08 (m, 1H) 2.81-2.96 (m, 1H) 4.40 (q, J = 7.24 Hz, 2H) 4.81 (quin, J = 7.26 Hz, 1H) 7.11-7.32 (m, 5H) 7.62 (d, J = 7.07 Hz, 1H) 7.69 (dd, J = 8.46, 1.64 Hz, 1H) 7.72-7.83 (m, 1H) 8.02-8.15 (m, 2H) 8.40-8.51 (m, 1H) 8.80 (t, J = 1.52 Hz, 1H) | ethyl 3-(5-(N-((1R,4r)-4-((R)-1-phenylethylcarbamoyl)cyclohexyl)sulfamoyl)-1H-benzo[d]imidazol-2-yl)benzoate |
| 3 | 2 | 6.49 | D | 514 (M + H+) | 1H NMR (400 MHz, DMSO-d6) d ppm 1.09 (t, J = 7.01 Hz, 5H) 1.26 (d, J = 6.95 Hz, 4H) 1.60 (br. s., 4H) 2.09 (br. s., 3H) 2.23 (br. s., 1H) 2.85 (br. s., 1H) 3.38 (d, J = 6.95 Hz, 2H) 4.81 (br. s., 1H) 4.99 (br. s., 1H) 7.06-7.14 (m, 1H) 7.26 (br. s., 2H) 7.61 (br. s., 1H) 7.71 (br. s., 1H) 7.77 (s, 1H) 8.05 (s, 2H) 9.31 (br. s., 1H) 10.18 (br. s., 1H) | (1r,4R)-N-((R)-1-(4-fluorophenyl)ethyl)-4-(2-((S)-pyrrolidin-2-yl)-1H-benzo[d]imidazole-5-sulfonamido)cyclohexanecarboxamide |
| 4 | 3 | 7.616 | D | 535.36 (M + H+) | 1H NMR (400 MHz, DMSO-d6) d ppm 1.08-1.21 (m, 3H) 1.26 (d, J = 7.07 Hz, 4H) 1.56-1.68 (m, 2H) 1.62 (d, J = 8.08 Hz, 2H) 1.99 (dd, J = 19.83, 3.41 Hz, 1H) 2.88 (dt, J = 7.39, 3.76 Hz, 1H) 3.93 (s, 3H) 4.82 (qd, J = 7.24, 7.07 Hz, 1H) 7.05-7.13 (m, 2H) 7.26 (dd, J = 8.59, 5.56 Hz, 2H) 7.56 (d, J = 7.33 Hz, 1H) 7.59-7.62 (m, 1H) 7.60 (d, J = 2.78 Hz, 2H) 7.77 (d, J = 1.77 Hz, 1H) 7.81-7.86 (m, 1H) 7.88 (dd, J = 6.69, 3.16 Hz, 2H) 8.05 (d, J = 8.08 Hz, 1H) 8.11 (d, J = 1.26 Hz, 1H) | (1r,4R)-N-((R)-1-(4-fluorophenyl)ethyl)-4-(1-methyl-2-phenyl-1H-benzo[d]imidazole-5-sulfonamido)cyclohexanecarboxamide |

| Ex. | Synthetic Scheme | HPLC RT | HPLC Method | MS | NMR | Name |
|---|---|---|---|---|---|---|
| 5 | 3 | 6.475 | D | 473.33 (M + H+) | 1H NMR (400 MHz, DMSO-d6) δ ppm 1.09-1.23 (m, 4H) 1.26 (d, J = 6.82 Hz, 3H) 1.60 (br. s., 4H) 1.98 (d, J = 3.03 Hz, 1H) 2.69 (s, 3H) 2.86 (br. s., 1H) 3.86 (s, 3H) 4.82 (t, J = 7.33 Hz, 1H) 7.06-7.12 (m, 1H) 7.09 (t, J = 8.84 Hz, 1H) 7.26 (dd, J = 8.59, 5.56 Hz, 2H) 7.64 (d, J = 7.33 Hz, 1H) 7.78-7.89 (m, 2H) 8.03-8.09 (m, 2H) | (1r,4R)-4-(1,2-dimethyl-1H-benzo[d]imidazole-5-sulfonamido)-N-((R)-1-(4-fluorophenyl)ethyl)cyclohexanecarboxamide |
| 6 | 2 | 6.656 | D | 529.33 (M + H+) | 1H NMR (400 MHz, DMSO-d6) δ ppm 1.05-1.23 (m, 4H) 1.26 (d, J = 6.95 Hz, 3H) 1.62 (d, J = 9.60 Hz, 3H) 1.58 (d, J = 1.64 Hz, 2H) 1.89 (td, J = 12.13, 8.08 Hz, 2H) 1.96-2.04 (m, 1H) 2.00 (d, J = 2.27 Hz, 2H) 2.86 (ddd, J = 7.14, 3.85, 3.66 Hz, 1H) 3.28-3.37 (m, 1H) 3.50 (td, J = 11.62, 2.02 Hz, 2H) 3.98 (dt, J = 9.57, 2.10 Hz, 2H) 4.76-4.86 (m, J = 7.28, 7.17, 6.95 Hz, 1H) 7.04-7.13 (m, 1H) 7.09 (t, J = 8.84 Hz, 1H) 7.26 (dd, J = 8.65, 5.62 Hz, 2H) 7.70 (d, J = 7.20 Hz, 1H) 7.78 (q, J = 8.46 Hz, 1H) 7.74-7.82 (m, 1H) 8.03 (d, J = 1.01 Hz, 1H) 8.10 (d, J = 7.96 Hz, 1H) | (1r,4R)-N-((R)-1-(4-fluorophenyl)ethyl)-4-(2-(tetrahydro-2H-pyran-4-yl)-1H-benzo[d]imidazole-5-sulfonamido)cyclohexanecarboxamide |
| 7 | 4 | 1.37 | A1 | 470 (M + H+) | 1H NMR (600 MHz, DMSO-d6) δ ppm 1.11 (d, 6H), 1.12-1.18 (m, 4H), 1.57-1.62 (m, 2H), 1.74-1.78 (m, 2H), 2.03-2.08 (m, 1H), 2.10 (s, 3H), 2.85-2.95 (m, 1H), 4.78-4.83 (m, 1H), 7.60 (d, 1H), 7.65 (d, 1H), 7.72 (br s, 1H), 7.78 (d, 2H), 7.98 (br s, 1H), 8.13 (d, 2H), 10.25 (s, 1H), 13.20 (br s, 1H) | (1r,4r)-N-isopropyl-N-methyl-4-(2-(phenylamino)-1H-benzo[d]imidazole-5-sulfonamido)cyclohexanecarboxamide |
| 8 | 5 | 1.55 | A1 | 499 (M + H+) | | (1r,4r)-isopropyl 4-(2-(4-acetamidophenyl)-1H-benzo[d]imidazole-5-sulfonamido)cyclohexanecarboxylate |
| 9 | 6 | 1.19 | E | 593.31 (M + H+) | | N-((1r,4r)-4-(5-tert-butyl-1,3,4-oxadiazol-2-yl)cyclohexyl)-2-(4-(4-methylpiperazin-1-yl)phenylamino)-1H-benzo[d]imidazole-5-sulfonamide |
| 10 | 6 | 8.704 | D | 578.36 (M + H+) | 1H NMR (400 MHz, DMSO-d6) δ ppm 0.98-1.32 (m, 7H) 1.58 (br. s., 4H) 1.97 (br. s., 1H) 2.08 (s, 1H) 2.80 (br. s., 1H) 3.85 (s, 3H) 4.72-4.89 (m, 1H) 6.62 (dd, J = 3.09, 0.69 Hz, 1H) 7.03-7.16 (m, 1H) 7.19-7.31 (m, 2H) | N-((1r,4r)-4-(5-tert-butyl-1,3,4-oxadiazol-2-yl)cyclohexyl)-2-(4-(4-methylpiperazin-1-yl)phenyl)-1H-benzo[d]imidazole-5-sulfonamide |

| Ex. | Synthetic Scheme | HPLC RT | HPLC Method | MS | NMR | Name |
|---|---|---|---|---|---|---|
| 11 | 19 | 9.856 | D | 522.16 (M + H+) | 7.39 (d, J = 7.20 Hz, 1H) 7.51 (d, J = 3.16 Hz, 1H) 7.54-7.66 (m, 2H) 7.98-8.14 (m, 2H) | (1r,4R)-N-((R)-1-(4-fluorophenyl)ethyl)-4-(2-phenylbenzo[d]oxazole-6-sulfonamido)cyclohexanecarboxamide |
| 12 | 7 | 5.815 | G | 458.24 (M + H+) | 1H NMR (400 MHz, DMSO-d6) d ppm 1.11-1.21 (m, 3H), 1.26 (d, 4H), 1.64 (br.s., 4H), 1.99 (br.s., 1H), 2.95 (br.s., 1H), 4.81 (d, 1H), 7.09 (t, 1H), 7.26 (dd, 2H), 7.64-7.73 (m, 3H), 7.79 (d, 1H), 7.87 (dd, 1H), 8.01 (d, 1H), 8.09 (d, 1H), 8.21-8.28 (m, 3H) 1H NMR (400 MHz, MeOD) d ppm 1.06-1.46 (m, 7H) 1.61-1.82 (m, 3H) 2.07 (tt, J = 11.94, 3.41 Hz, 1H) 2.76-3.05 (m, 2H) 4.90 (q, J = 6.95 Hz, 2H) 6.61 (dd, J = 3.22, 0.82 Hz, 1H) 6.93-7.05 (m, 2H) 7.19-7.32 (m, 2H) 7.35-7.45 (m, 1H) 7.48-7.55 (m, 1H) 7.55-7.63 (m, 1H) 8.12 (d, J = 1.39 Hz, 1H) | (1r,4R)-N-((R)-1-(4-fluorophenyl)ethyl)-4-(1-methyl-1H-indole-5-sulfonamido)cyclohexanecarboxamide |
| 13 | 8 | 13.65 | E | 502.2174 (M + H+) | 1H NMR (400 MHz, ACETONITRILE-d3) d ppm 1.03-1.42 (m, 7H) 1.60-1.78 (m, 4H) 1.87-2.04 (m, 1H) 2.90-3.09 (m, 1H) 4.80-4.92 (m, 1H) 5.42 (d, J = 7.33 Hz, 1H) 6.62 (d, J = 7.83 Hz, 1H) 6.98 (d, J = 2.53 Hz, 1H) 7.13-7.32 (m, 5H) 7.34-7.42 (m, 1H) 7.44-7.64 (m, 4H) 7.74-7.81 (m, 2H) 8.08-8.13 (m, 1H) 10.17 (br. s., 1H) | (1r,4R)-4-(2-phenyl-1H-indole-5-sulfonamido)-N-((R)-1-phenylethyl)cyclohexanecarboxamide |
| 14 | 9 | 1.36 | H | 534.3 (M+) | 1H NMR (400 MHz, MeOD) d ppm 0.73-0.91 (m, 2H) 1.17-1.30 (m, 2H) 1.31-1.40 (d, 3H) 1.65-1.77 (m, 4H) 2.05-2.09 (m, 1H) 2.93-2.98 (m, 1H) 3.35 (s, 1H) 3.81 (s, 3H) 6.69 (s, 1H) 6.99 (t, 2H) 7.26 (dd, 2H) 7.44-7.46 (m, 1H) 7.47 (t, 2H) 7.57-7.59 (m, 2H) 7.69 (dd, 1H) 8.13 (d, 1H) 8.22 (d, 1H) | (1r,4R)-N-((R)-1-(4-fluorophenyl)ethyl)-4-(1-methyl-2-phenyl-1H-indole-5-sulfonamido)cyclohexanecarboxamide |
| 15 | 9 | 1.29 | H | 560.3 (M+) | 1H NMR (400 MHz, MeOD) d ppm 0.39 (s, 1H) 1.42 (s, 3H) 1.57 (s, 3H) 1.60-1.77 (m, 4H) 1.99-2.18 (m, 4H) 2.38 (s, 1H) 2.61 (t, 1H) 3.35 (t, 1H) 3.74 (s, 1H) 4.18 (s, 3H) 5.10-5.12 (m, 1H) 7.06 (s, 1H) 7.59-7.61 (m, 1H) 7.64 (t, 1H) 7.69-7.71 (m, 2H) 7.84-7.86 (m, 1H) 7.91 (t, 2H) 7.94-7.97 (m, 3H) | (1r,4S)-N-((S)-2-hydroxy-2-methyl-1-phenylpropyl)-4-(1-methyl-2-phenyl-1H-indole-5-sulfonamido)cyclohexanecarboxamide |

| Ex. | Synthetic Scheme | HPLC RT | HPLC Method | MS | NMR | Name |
|---|---|---|---|---|---|---|
| 16 | 13 | 8.565 | D | 444.19 (M + H+) | 8.08 (dd, 2H) 8.38-8.40 (m, 1H) 8.52 (d, 1H) | (1r,4R)-N-((R)-1-(4-fluorophenyl)ethyl)-4-(1H-indole-5-sulfonamido)cyclohexanecarboxamide |
| 17 | 18 | 8.491 | D | 473 (M + H+) | 1H NMR (400 MHz, DMSO-d6) δ ppm 1.17 (t, J = 7.14 Hz, 2H) 1.07-1.20 (m, 1H) 1.26 (d, J = 7.07 Hz, 4H) 1.62 (d, J = 10.48 Hz, 4H) 1.93-2.05 (m, 1H) 2.30 (d, J = 0.88 Hz, 3H) 2.91 (d, J = 2.65 Hz, 1H) 3.81 (s, 3H) 4.82 (qd, J = 7.28, 7.07 Hz, 1H) 7.05-7.14 (m, 2H) 7.26 (dd, J = 8.46, 5.56 Hz, 2H) 7.48 (d, J = 1.01 Hz, 1H) 7.61 (d, J = 7.33 Hz, 1H) 8.08 (d, J = 7.96 Hz, 1H) 8.33 (d, J = 2.15 Hz, 1H) 8.65 (d, J = 2.02 Hz, 1H) | (1r,4R)-4-(1,3-dimethyl-1H-pyrrolo[2,3-b]pyridine-5-sulfonamido)-N-((R)-1-(4-fluorophenyl)ethyl)cyclohexanecarboxamide |
| 18 | 10 | 13.91 | E | 520.2056 (M + H+) | 1H NMR (400 MHz, DMSO-d6) d ppm 1.03-1.33 (m, 7H) 1.54-1.71 (m, 4H) 1.92-2.03 (m, 1H) 2.80-2.93 (m, 1H) 4.76-4.86 (m, J = 7.45, 7.45, 7.33, 7.07 Hz, 1H) 7.02-7.13 (m, 3H) 7.22-7.29 (m, 2H) 7.35-7.47 (m, 2H) 7.48-7.55 (m, 3H) 7.69 (d, J = 8.34 Hz, 1H) 7.86 (s, 1H) 7.90 (d, J = 8.59 Hz, 2H) 8.08 (d, J = 8.08 Hz, 1H) | (1r,4R)-N-((R)-1-(4-fluorophenyl)ethyl)-4-(2-phenyl-1H-indole-6-sulfonamido)cyclohexanecarboxamide |
| 19 | 11 | 10.61 | E | 503.2128 (M + H+) | 1H NMR (400 MHz, DMSO-d6) d ppm 1.07-1.31 (m, 4H) 1.36 (d, J = 7.07 Hz, 3H) 1.59-1.72 (m, 4H) 2.01-2.12 (m, 1H) 2.79-2.93 (m, 1H) 4.92 (quin, J = 7.14 Hz, 1H) 7.04 (d, J = 1.26 Hz, 1H) 7.34-7.46 (m, 2H) 7.47-7.59 (m, 5H) 7.69 (d, J = 8.34 Hz, 1H) 7.86 (s, 1H) 7.89 (d, J = 8.34 Hz, 1H) 8.09 (br. s., 1H) 8.34 (d, J = 6.32 Hz, 1H) 8.61 (d, J = 4.29 Hz, 1H) 11.99 (s, 1H) | (1r,4R)-N-((R)-1-(4-fluorophenyl)ethyl)-N-((R)-1-(pyridin-2-yl)ethyl)cyclohexanecarboxamide |
| 20 | 12 | 12.83 | E | 534.22391 (M + H+) | 1H NMR (400 MHz, DMSO-d6) d ppm 1.04-1.33 (m, 7H) 1.53-1.72 (m, 4H) 1.94-2.06 (m, 1H) 2.82-3.00 (m, 1H) 3.82 (s, 3H) 4.76-4.88 (m, 1H) 6.71 (s, 1H) 7.05-7.13 (m, 2H) 7.22-7.30 (m, 2H) 7.45-7.60 (m, 5H) 7.61-7.68 (m, 2H) 7.74 (d, J = 8.34 Hz, 1H) 7.97 (s, 1H) 8.09 (d, J = 8.08 Hz, 1H) 12.02 (s, 1H) | (1r,4R)-N-((R)-1-(4-fluorophenyl)ethyl)-4-(1-methyl-2-phenyl-1H-indole-6-sulfonamido)cyclohexanecarboxamide |

| Ex. | Synthetic Scheme | HPLC RT | HPLC Method | MS | NMR | Name |
|---|---|---|---|---|---|---|
| 21 | 12 + 14 | 12.27 | E | 583.17716 (M + H+) | 1H NMR (400 MHz, ACETONITRILE-d3) δ ppm 1.13-1.45 (m, 4H) 1.57-1.76 (m, 4H) 2.21-3.31 (m, 8H) 3.60-4.32 (m, 2H) 3.74 (s, 3H) 5.58 (d, J = 7.58 Hz, 1H) 7.53-7.63 (m, 5H) 7.65 (dd, J = 8.34, 1.52 Hz, 1H) 7.75 (d, J = 8.34, 1H) 8.04 (d, J = 1.77 Hz, 1H) | 3-chloro-1-methyl-2-phenyl-N-((1S,4r)-4-((S)-3-(trifluoromethyl)piperazine-1-carbonyl)cyclohexyl)-1H-indole-6-sulfonamide |
| 22 | 12 | 14.85 | E | 488.2577 (M + H+) | 1H NMR (400 MHz, ACETONITRILE-d3) δ ppm 0.66-0.81 (m, 5H) 0.89-1.09 (m, 5H) 1.11-1.44 (m, 4H) 1.44-1.72 (m, 4H) 2.12-4.22 (m, 11H) 3.86 (s, 3H) 5.41 (d, J = 7.33 Hz, 1H) 6.19-6.21 (m, 1H) 7.42-7.47 (m, 1H) 7.57 (d, J = 8.34 Hz, 1H) 7.86 (s, 1H) | 2-cyclopropyl-N-((1S,4r)-4-((S)-3-isopropylmorpholine-4-carbonyl)cyclohexyl)-1-methyl-1H-indole-6-sulfonamide |
| 23 | 12 + 16 | 12.49 | E | 471.2056 (M + H+) | 1H NMR (400 MHz, ACETONITRILE-d3) δ ppm 1.07-1.44 (m, 8H) 1.57-1.73 (m, 4H) 1.80-2.50 (m, 2H) 3.00-3.12 (m, 1H) 3.39-3.49 (m, 4H) 3.50-3.60 (m, 4H) 3.91 (s, 3H) 5.58 (d, J = 7.58 Hz, 1H) 7.62-7.74 (m, 2H) 7.99 (s, 1H) | 3-cyano-2-cyclopropyl-1-methyl-N-((1r,4r)-4-(morpholine-4-carbonyl)cyclohexyl)-1H-indole-6-sulfonamide |
| 24 | 20 | 14.2 | E | 460.2275 (M + H+) | 1H NMR (400 MHz, ACETONITRILE-d3) δ ppm 0.73-0.79 (m, 2H) 0.98-1.08 (m, 2H) 1.16 (s, 3H) 1.27-1.71 (m, 7H) 3.02-3.13 (m, 1H) 3.46-3.57 (m, 8H) 3.86 (s, 3H) 5.43 (d, J = 7.07 Hz, 1H) 6.20 (s, 1H) 7.39-7.48 (m, 1H) 7.57 (d, J = 8.34 Hz, 1H) 7.80-7.87 (m, 1H) | 2-cyclopropyl-1-methyl-N-((1r,4r)-4-(morpholine-4-carbonyl)cyclohexyl)-1H-indole-6-sulfonamide |
| 25 | 12 + 14 | 15.66 | E | 630.2398 (M + H+) | 1H NMR (400 MHz, ACETONITRILE-d3) δ ppm 0.65-1.03 (m, 6H) 1.13-1.75 (m, 8H) 2.15-4.23 (m, 10H) 2.69 (t, J = 7.71 Hz, 2H) 3.01 (t, J = 7.58 Hz, 2H) 3.73 (s, 3H) 5.58 (d, J = 7.58 Hz, 1H) 7.43-7.53 (m, 4H) 7.57-7.67 (m, 1H) 7.72 (d, J = 8.34 Hz, 1H) 8.00-8.06 (m, 1H) | 3-(4-(3-chloro-6-(N-((1S,4r)-4-((S)-3-isopropylmorpholine-4-carbonyl)cyclohexyl)sulfamoyl)-1-methyl-1H-indol-2-yl)phenyl)propanoic acid |
| 26 | 15 | | | | 1H NMR (400 MHz, DMSO-d6) δ ppm 1.06-1.20 (m, 3H) 1.26 (d, J = 7.07 Hz, 4H) 1.60 (br. s., 4H) 1.92-2.04 (m, 1H) 2.84 (br. s., 1H) 4.81 (t, J = 7.33 Hz, 1H) 7.09 (t, J = 8.91 Hz, 2H) 7.22-7.29 (m, 2H) 7.55 (dd, J = 9.92, 7.89 Hz, 1H) | (1r,4R)-4-(3-chloro-1H-indole-6-sulfonamido)-N-((R)-1-(4-fluorophenyl)ethyl)cyclohexanecarboxamide |

| Ex. | Synthetic Scheme | HPLC RT | HPLC Method | MS | NMR | Name |
|---|---|---|---|---|---|---|
| 27 | 11 + 35 | 11.65 | E | 648.2804 (M + H+) | 7.51-7.58 (m, 1H) 7.66 (d, J = 8.46 Hz, 1H) 7.81 (d, J = 2.78 Hz, 1H) 7.90 (d, J = 1.01 Hz, 1H) 8.07 (d, J = 8.08 Hz, 1H) 11.85 (d, J = 2.15 Hz, 1H) | (S)-4-(6-(N-((1R,4r)-4-((R)-1-(4-fluorophenyl)ethyl)carbamoyl)cyclohexyl)sulfamoyl)-1H-indol-2-yl)benzyl 2-amino-3-methylbutanoate |
| 28 | 12 + 14 | 15.34 | E | 628.2233 (M + H+) | 1H NMR (400 MHz, DMSO-d6) d ppm 0.16-0.35 (m, 2H) 0.40-0.50 (m, 2H) 1.08-1.73 (m, 10H) 2.37-2.47 (m, 2H) 2.83-2.99 (m, 1H) 2.88 (t, J = 7.58 Hz, 2H) 3.11-3.86 (m, 7H) 3.74 (s, 3H) 7.40-7.54 (m, 4H) 7.60-7.65 (m, 2H) 7.70 (d, J = 8.34 Hz, 1H) 8.04 (s, 1H) | 3-(4-(3-chloro-6-(N-((1S,4r)-4-((S)-3-cyclopropylmorpholine-4-carbonyl)cyclohexyl)sulfamoyl)-1-methyl-1H-indol-2-yl)phenyl)propanoic acid |
| 29 | 12 | 14.49 | E | 596.279 (M + H+) | 1H NMR (400 MHz, DMSO-d6) d ppm 0.60-0.75 (m, 3H) 0.85-1.00 (m, 3H) 1.03-1.71 (m, 8H) 2.05-2.26 (m, 1H) 2.36-2.97 (m, 6H) 3.08-4.13 (m, 7H) 3.81 (s, 3H) 6.65 (s, 1H) 7.39 (d, J = 8.34 Hz, 2H) 7.47-7.56 (m, 4H) 7.70 (d, J = 8.34 Hz, 1H) 7.95 (s, 1H) | 3-(4-(6-(N-((1S,4r)-4-((S)-3-isopropylmorpholine-4-carbonyl)cyclohexyl)sulfamoyl)-1-methyl-1H-indol-2-yl)phenyl)propanoic acid |
| 30 | 11 | 15.27 | E | 540.2508 (M + H+) | 1H NMR (400 MHz, ACETONITRILE-d3) d ppm 1.04-1.76 (m, 11H) 2.29-2.42 (m, 1H) 2.89 (t, J = 6.69 Hz, 2H) 2.98-3.10 (m, 1H) 3.17-4.46 (m, 7H) 3.82 Hz, 1H) 3.17-4.46 (m, 7H) 3.30 (s, 3H) 3.62 (t, J = 6.69 Hz, 2H) 5.50 (d, J = 7.58 Hz, 1H) 6.91 (d, J = 1.26 Hz, 1H) 7.37 (d, J = 8.08 Hz, 2H) 7.50 (dd, J = 8.46, 1.64 Hz, 1H) 7.68-7.76 (m, 3H) 7.71-7.76 (m, 1H) 7.92 (s, 1H) 10.13 (br. s., 1H) | 2-(4-(2-methoxyethyl)phenyl)-N-((1S,4r)-4-((S)-3-methylmorpholine-4-carbonyl)cyclohexyl)-1H-indole-6-sulfonamide |

| Ex. | Synthetic Scheme | HPLC RT | HPLC Method | MS | NMR | Name |
|---|---|---|---|---|---|---|
| 31 | 11 + 14 | 16.58 | E | 574.2115 (M + H+) | 1H NMR (400 MHz, ACETONITRILE-d3) d ppm 1.03-1.73 (m, 11H) 2.27-2.43 (m, 1H) 2.81-4.48 (m, 7H) 2.92 (t, J = 6.69 Hz, 2H) 2.99-3.11 (m, 1H) 3.31 (s, 3H) 3.63 (t, J = 6.57 Hz, 2H) 5.58 (d, J = 7.33 Hz, 1H) 7.39-7.46 (m, 2H) 7.57-7.64 (m, 1H) 7.71 (d, J = 8.34 Hz, 1H) 7.79-7.84 (m, 2H) 7.92-7.96 (m, 1H) 10.19 (s, 1H) | 3-chloro-2-(4-(2-methoxyethyl)phenyl)-N-((1S,4r)-4-((S)-3-methylmorpholine-4-carbonyl)cyclohexyl)-1H-indole-6-sulfonamide |
| 32 | 12 + 17 | 14.83 | E | 474.2406 (M + H+) | 1H NMR (400 MHz, ACETONITRILE-d3) d ppm 0.69-0.84 (m, 2H) 1.04-1.73 (m, 14H) 2.31-2.40 (m, 1H) 2.32 (s, 3H) 2.96-3.09 (m, 1H)3.20-3.54 (m, 3H) 3.60 (d, J = 11.37 Hz, 1H) 3.72-4.44 (m, 3H) 3.87 (s, 3H) 5.42 (d, J = 7.58 Hz, 1H) 7.46 (dd, J = 8.34, 1.52 Hz, 1H) 7.58 (d, J = 8.34 Hz, 1H) 7.82 (d, J = 1.52 Hz, 1H) | 2-cyclopropyl-1,3-dimethyl-N-((1S,4r)-4-((S)-3-methylmorpholine-4-carbonyl)cyclohexyl)-1H-indole-6-sulfonamide |
| 33 | 22 | 6.155 | D | 462.1 (M + H+) | 1H NMR (400 MHz, DMSO-d6) d ppm 1.07-1.25 (m, 1H) 1.15 (d, J = 15.79 Hz, 2H) 1.28 (d, J = 6.95 Hz, 4H) 1.68 (br. s., 4H) 1.99 (s, 1H) 2.79 (br. s., 1H) 3.17 (br. s., 2H) 3.34-3.39 (m, 2H) 4.84 (t, J = 7.39 Hz, 1H) 6.04 (s, 1H) 6.82 (d, J = 2.02 Hz, 1H) 7.11 (t, J = 8.91 Hz, 2H) 7.08-7.15 (m, 1H) 7.28 (dd, J = 8.65, 5.62 Hz, 2H) 7.62 (d, J = 2.15 Hz, 1H) 7.95 (s, 1H) 8.10 (d, J = 7.96 Hz, 1H) | (1r,4R)-N-((R)-1-(4-fluorophenyl)ethyl)-4-(1,2,3,4-tetrahydropyrido[3,2-b]pyrazine-7-sulfonamido)cyclohexanecarboxamide |
| 34 | 22 | 6.443 | D | 490.1 (M + H+) | 1H NMR (400 MHz, DMSO-d6) d ppm 1.28 (d, J = 6.95 Hz, 4H) 1.08-1.31 (m, 3H) 1.61 (br. s., 1H) 1.70 (d, J = 15.28 Hz, 3H) 1.95-2.05 (m, 1H) 2.79 (s, 4H) 3.07 (d, J = 0.88 Hz, 3H) 3.23 (t, J = 4.86 Hz, 2H) 3.54 (t, J = 4.86 Hz, 2H) 4.84 (t, J = 7.33 Hz, 1H) 6.74 (d, J = 1.01 Hz, 1H) 7.07-7.14 (m, 1H) 7.10 (d, J = 0.76 Hz, 1H) 7.28 (t, J = 8.08 Hz, 2H) 7.28 (d, J = 8.72 Hz, 1H) 7.77 (dd, J = 1.89, 0.88 Hz, 1H) 8.10 (d, J = 7.96 Hz, 1H) | (1r,4R)-4-(1,4-dimethyl-1,2,3,4-tetrahydropyrido[3,2-b]pyrazine-7-sulfonamido)-N-((R)-1-(4-fluorophenyl)ethyl)cyclohexanecarboxamide |

| Ex. | Synthetic Scheme | HPLC RT | HPLC Method | MS | NMR | Name |
|---|---|---|---|---|---|---|
| 35 | 23 | 10.82 | E | 479 (M + H+) | | (1r,4R)-4-(2,3-dihydro-1H-pyrido[2,3-b][1,4]thiazine-7-sulfonamido)-N-((R)-1-(4-fluorophenyl)ethyl)cyclohexanecarboxamide |
| 36 | 21 | | | | 1H NMR (400 MHz, DMSO-d6) d ppm 1.10 (d, J = 7.07 Hz, 1H) 1.14-1.22 (m, 2H) 1.26 (d, J = 7.07 Hz, 4H) 1.40 (t, J = 7.07 Hz, 3H) 1.62 (d, J = 9.73 Hz, 4H) 1.99 (s, 1H) 2.92 (d, J = 3.79 Hz, 1H) 4.50 (q, J = 7.03 Hz, 2H) 4.82 (t, J = 7.33 Hz, 1H) 7.13 (d, J = 8.84 Hz, 1H) 7.09 (t, J = 8.91 Hz, 2H) 7.26 (dd, J = 8.46, 5.68 Hz, 2H) 7.73 (d, J = 7.45 Hz, 1H) 7.97 (d, J = 2.15 Hz, 1H) 7.99 (d, J = 2.02 Hz, 1H) 8.08 (d, J = 8.08 Hz, 1H) 8.41 (d, J = 1.89 Hz, 1H) 8.45 (d, J = 8.84 Hz, 1H) | (1r,4R)-4-(2-ethoxyquinoline-6-sulfonamido)-N-((R)-1-(4-fluorophenyl)ethyl)cyclohexanecarboxamide |
| 37 | 21 | | | 512.2 (M + H+) | | (1r,4S)-4-(2-ethoxyquinoline-6-sulfonamido)-N-((1S,2R)-2-hydroxy-1-phenylpropyl)cyclohexanecarboxamide |
| 38 | 21 | 6.293 | D | 554 (M + H+) | 1H NMR (400 MHz, DMSO-d6) d ppm 1.15 (d, J = 14.02 Hz, 3H) 1.20 (br. s., 1H) 1.26 (d, J = 6.95 Hz, 3H) 1.60 (br. s., 4H) 1.92-2.04 (m, 1H) 2.23 (s, 3H) 2.42 (t, J = 4.80 Hz, 4H) 2.89 (d, J = 7.45 Hz, 1H) 3.75 (d, J = 4.80 Hz, 4H) 4.77-4.86 (m, 1H) 7.04-7.13 (m, 1H) 7.09 (t, J = 8.91 Hz, 1H) 7.25 (dd, J = 8.53, 5.62 Hz, 2H) 7.36 (d, J = 9.35 Hz, 1H) 7.63 (d, J = 8.97 Hz, 1H) 7.58 (d, J = 7.45 Hz, 1H) 7.82 (dd, J = 8.91, 2.21 Hz, 1H) 8.09 (d, J = 8.08 Hz, 1H) 8.21 (d, J = 9.35 Hz, 1H) 8.19 (d, J = 2.15 Hz, 1H) | (1r,4R)-N-((R)-1-(4-fluorophenyl)ethyl)-4-(2-(4-methylpiperazin-1-yl)quinoline-6-sulfonamido)cyclohexanecarboxamide |
| 39 | 21 | 7.008 | D | 533 (M + H+) | 1H NMR (400 MHz, DMSO-d6) d ppm 1.14 (d, J = 7.20 Hz, 2H) 1.18 (d, J = 7.20 Hz, 2H) 1.25 (d, J = 6.95 Hz, 4H) 1.63 (br. s., 4H) 1.99 (s, 1H) 2.98 (br. s., 1H) 4.81 (t, J = 7.33 Hz, 1H) 7.05-7.12 (m, 1H) 7.08 (t, J = 8.91 Hz, 1H) 7.22-7.30 (m, 2H) 7.91 (d, J = 7.58 Hz, 1H) 8.08 (d, J = 8.08 Hz, 1H) 8.13 (dd, J = 8.91, 2.08 Hz, 1H) 8.24-8.33 (m, 3H) 8.42 (d, J = 8.72 Hz, 1H) 8.60 (d, J = 2.02 Hz, 1H) 8.77-8.87 (m, 3H) | (1r,4R)-N-((R)-1-(4-fluorophenyl)ethyl)-4-(2-(pyridin-4-yl)quinoline-6-sulfonamido)cyclohexanecarboxamide |

| Ex. | Synthetic Scheme | HPLC RT | HPLC Method | MS | NMR | Name |
|---|---|---|---|---|---|---|
| 40 | 37 | | | | | (1r,4R)-N-((R)-1-(4-fluorophenyl)ethyl)-4-(2-(trifluoromethyl)imidazo[1,2-a]pyridine-6-sulfonamido)cyclohexanecarboxamide |
| 41 | | | | 500.22 (M + H+) | | (1r,4R)-N-((R)-1-(4-fluorophenyl)ethyl)-4-(3-(2-phenyl-1H-benzo[d]imidazol-5-yl)ureido)cyclohexanecarboxamide |
| 42 | 1 | 1.37 | H | 490.13691 (M + H+) | | (1r,4R)-4-(2-chloroquinoline-6-sulfonamido)-N-((R)-1-(4-fluorophenyl)ethyl)cyclohexanecarboxamide |
| 43 | 1 | 12.38 | E | 464.2 (M + H+) | | N-((1r,4r)-4-(2-phenylpyrrolidine-1-carbonyl)cyclohexyl)quinoline-3-sulfonamide |
| 44 | 1 | 12.1 | E | 456.1 (M + H+) | | (1r,4r)-N-(1-(3-fluorophenyl)ethyl)-4-(quinoline-3-sulfonamido)cyclohexanecarboxamide |
| 45 | 1 | | | | | (1r,4r)-4-(quinoline-3-sulfonamido)-N-(1-(4-(trifluoromethyl)phenyl)ethyl)cyclohexanecarboxamide |
| 46 | 1 | | | | | (1r,4R)-4-(quinoline-3-sulfonamido)-N-((R)-1-(2-(trifluoromethyl)phenyl)ethyl)cyclohexanecarboxamide |
| 47 | 1 | | | | | N-((1r,4r)-4-(4-methyl-2-phenylpiperazine-1-carbonyl)cyclohexyl)quinoline-3-sulfonamide |
| 48 | 1 | | | | | N-((1r,4r)-4-(2-(trifluoromethyl)pyrrolidine-1-carbonyl)cyclohexyl)quinoline-3-sulfonamide |
| 49 | 21 | 1.39 | H | 486.18686 (M + H+) | | (1r,4R)-N-((R)-1-(4-fluorophenyl)ethyl)-4-(2-methoxyquinoline-6-sulfonamido)cyclohexanecarboxamide |
| 50 | 21 | | | | | (1r,4R)-N-((R)-1-(4-fluorophenyl)ethyl)-4-(2-(2,2,2-trifluoroethoxy)quinoline-6-sulfonamido)cyclohexanecarboxamide |
| 51 | 21 | 1.49 | H | 526.21896 (M + H+) | | (1r,4R)-4-(2-cyclobutoxyquinoline-6-sulfonamido)-N-((R)-1-(4-fluorophenyl)ethyl)cyclohexanecarboxamide |
| 52 | 24 | 1.29 | H | 539 (M+) | | (1r,4R)-N-((R)-1-(4-fluorophenyl)ethyl)-4-(2-phenylthiazolo[4,5-b]pyridine-6-sulfonamido)cyclohexanecarboxamide |
| 53 | 21 | 1.28 | H | 499.21829 (M + H+) | | (1r,4R)-4-(2-(dimethylamino)quinoline-6-sulfonamido)-N-((R)-1-(4-fluorophenyl)ethyl)cyclohexanecarboxamide |
| 54 | 21 | 1.08 | H | 472.17052 (M + H+) | | (1r,4R)-N-((R)-1-(4-fluorophenyl)ethyl)-4-(2-hydroxyquinoline-6-sulfonamido)cyclohexanecarboxamide |
| 55 | 1 | 11.81 | E | 438.2 (M + H+) | | (1r,4R)-N-((R)-1-phenylethyl)-4-(quinoline-3-sulfonamido)cyclohexanecarboxamide |
| 56 | 1 | 12.46 | E | 452.3 (M + H+) | | (1r,4R)-N-((R)-1-phenylpropyl)-4-(quinoline-3-sulfonamido)cyclohexanecarboxamide |
| 57 | 1 | 12.83 | E | 472.1 (M + H+) | | (1r,4R)-N-((R)-1-(4-chlorophenyl)ethyl)-4-(quinoline-3-sulfonamido)cyclohexanecarboxamide |
| 58 | 1 | 12.06 | E | 456.1 (M + H+) | | (1r,4R)-N-((R)-1-(2-fluorophenyl)ethyl)-4-(quinoline-3-sulfonamido)cyclohexanecarboxamide |
| 59 | 1 | 13.51 | E | 478.2 (M + H+) | | N-((1r,4r)-4-(2-phenylpiperidine-1-carbonyl)cyclohexyl)quinoline-3-sulfonamide |

-continued

| Ex. | Synthetic Scheme | HPLC RT | HPLC Method | MS | NMR | Name |
|---|---|---|---|---|---|---|
| 60 | 1 | 13.87 | E | 579.3 (M + H+) | | tert-butyl 3-phenyl-4-((1r,4r)-4-(quinoline-3-sulfonamido)cyclohexanecarbonyl)piperazine-1-carboxylate |
| 61 | 1 | 8.97 | E | 479.2 (M + H+) | | N-((1r,4r)-4-(2-phenylpiperazine-1-carbonyl)cyclohexyl)quinoline-3-sulfonamide |
| 62 | 1 | | | | | (1r,4r)-N-(1-(1-methyl-1H-pyrazol-4-yl)ethyl)-4-(quinoline-3-sulfonamido)cyclohexanecarboxamide |
| 63 | 37 | | | | | (1r,4R)-N-((R)-1-(4-fluorophenyl)ethyl)-4-(3-methyl-2-(trifluoromethyl)imidazo[1,2-a]pyridine-5-sulfonamido)cyclohexanecarboxamide |
| 64 | 21 | 1.27 | H | 528.1975 (M + H+) | | (1r,4R)-N-((R)-1-(4-fluorophenyl)ethyl)-4-(2-(oxetan-3-yloxy)quinoline-6-sulfonamido)cyclohexanecarboxamide |
| 65 | 37 | | | | | (1r,4R)-N-((R)-1-(4-fluorophenyl)ethyl)-4-(2-phenylimidazo[1,2-a]pyridine-5-sulfonamido)cyclohexanecarboxamide |
| 66 | 1 | 12.4 | E | 473.9 (M + H+) | | (1r,4r)-N-(1-(3,4-difluorophenyl)ethyl)-4-(quinoline-3-sulfonamido)cyclohexanecarboxamide |
| 67 | 1 | 12.34 | E | 473.9 (M + H+) | | (1r,4r)-N-(1-(2,4-difluorophenyl)ethyl)-4-(quinoline-3-sulfonamido)cyclohexanecarboxamide |
| 68 | 21 | 1.28 | H | 530.2139 (M + H+) | | (1r,4R)-N-((R)-1-(4-fluorophenyl)ethyl)-4-(2-methoxyethoxy)quinoline-6-sulfonamido)cyclohexanecarboxamide |
| 69 | 21 | 0.97 | H | 543.24467 (M + H+) | | (1r,4R)-4-(2-(2-(dimethylamino)ethoxy)quinoline-6-sulfonamido)-N-((R)-1-(4-fluorophenyl)ethyl)cyclohexanecarboxamide |
| 70 | 37 | 1.32 | H | 535.21862 (M + H+) | | (1r,4R)-N-((R)-1-(4-fluorophenyl)ethyl)-4-(3-methyl-2-phenylimidazo[1,2-a]pyridine-6-sulfonamido)cyclohexanecarboxamide |
| 71 | 21 | 1.28 | H | 482.19272 (M + H+) | | (1r,4R)-N-((R)-1-(4-fluorophenyl)ethyl)-4-(2-vinylquinoline-6-sulfonamido)cyclohexanecarboxamide |
| 72 | 21 | 1.19 | H | 470.19226 (M + H+) | | (1r,4R)-N-((R)-1-(4-fluorophenyl)ethyl)-4-(2-methylquinoline-6-sulfonamido)cyclohexanecarboxamide |
| 73 | 21 | 1.36 | H | 558.20734 (M + H+) | | ethyl 2-(6-(N-((1R,4r)-4-((R)-1-(4-fluorophenyl)ethylcarbamoyl)cyclohexyl)sulfamoyl)quinolin-2-yloxy)acetate |
| 74 | 21 | 1.27 | H | 484.20783 (M + H+) | | (1r,4R)-4-(2-ethylquinoline-6-sulfonamido)-N-((R)-1-(4-fluorophenyl)ethyl)cyclohexanecarboxamide |
| 75 | 25 | 1.46 | H | 553 (M+) | | (1r,4R)-N-((R)-1-(4-fluorophenyl)ethyl)-4-(2-o-tolylthiazolo[5,4-b]pyridine-6-sulfonamido)cyclohexanecarboxamide |
| 76 | 25 | 1.42 | H | 537 (M+) | | (1r,4R)-N-((R)-1-(4-fluorophenyl)ethyl)-4-(2-o-tolyloxazolo[5,4-b]pyridine-6-sulfonamido)cyclohexanecarboxamide |

-continued

| Ex. | Synthetic Scheme | HPLC RT | HPLC Method | MS | NMR | Name |
|---|---|---|---|---|---|---|
| 77 | 21 | 1.35 | H | 488.2391 (M + H+) | | (1r,4R)-4-(2-ethyl-1,2,3,4-tetrahydroquinoline-6-sulfonamido)-N-((R)-1-(4-fluorophenyl)ethyl)cyclohexanecarboxamide |
| 78 | 21 | 0.96 | H | 530.17642 (M + H+) | | 2-(6-(N-((1R,4r)-4-((R)-1-(4-fluorophenyl)ethylcarbamoyl)cyclohexyl)sulfamoyl)quinolin-2-yloxy)acetic acid |
| 79 | 37 | 1.3 | H | 521.20315 (M + H+) | | (1r,4R)-4-N-((R)-1-(4-fluorophenyl)ethyl)-4-(2-phenylimidazo[1,2-a]pyridine-6-sulfonamido)cyclohexanecarboxamide |
| 80 | 21 | 1.3 | H | 544.22903 (M + H+) | | (1r,4R)-4-N-((R)-1-(4-fluorophenyl)ethyl)-4-(2-(1-hydroxy-2-methylpropan-2-yloxy)quinoline-6-sulfonamido)cyclohexanecarboxamide |
| 81 | 21 | | | | | (1r,4R)-4-N-((R)-1-(4-fluorophenyl)ethyl)-4-(2-(2-hydroxy-2-methylpropoxy)quinoline-6-sulfonamido)cyclohexanecarboxamide |
| 82 | 21 | 1.19 | H | 483 (M + H+) | | (1r,4R)-4-(2-ethoxyquinoline-6-sulfonamido)-N-((R)-1-(pyridin-2-yl)ethyl)cyclohexanecarboxamide |
| 83 | 21 | 1.06 | H | 511 (M + H+) | | (1r,4R)-4-(2-(oxetan-3-yloxy)quinoline-6-sulfonamido)-N-((R)-1-(pyridin-2-yl)ethyl)cyclohexanecarboxamide |
| 84 | 1 | 1.33 | H | 579 (M + H+) | | (S)-tert-butyl 3-phenyl-4-((1r,4S)-4-(quinoline-3-sulfonamido)cyclohexanecarbonyl)piperazine-1-carboxylate |
| 85 | 1 | 0.96 | H | 479 (M + H+) | | N-((1S,4r)-4-((S)-2-phenylpiperazine-1-carbonyl)cyclohexyl)quinoline-3-sulfonamide |
| 86 | 9 | | | | | 1-methyl-2-phenyl-N-((1S,4r)-4-((S)-3-(trifluoromethyl)piperazine-1-carbonyl)cyclohexyl)-1H-indole-5-sulfonamide |
| 87 | 9 | | | | | 1-methyl-2-phenyl-N-((1R,4r)-4-((R)-3-(trifluoromethyl)piperazine-1-carbonyl)cyclohexyl)-1H-indole-5-sulfonamide |
| 88 | 7 + 16 | | | | | (1r,4R)-4-(3-cyano-1-methyl-1H-indole-5-sulfonamido)-N-((R)-1-(4-fluorophenyl)ethyl)cyclohexanecarboxamide |
| 89 | 7 + 16 | | | | | (1r,4S)-4-(3-cyano-1-methyl-1H-indole-5-sulfonamido)-N-((S)-2-hydroxy-2-methyl-1-phenylpropyl)cyclohexanecarboxamide |
| 90 | 9 | | | | | 1-((1r,4r)-4-(1-methyl-2-phenyl-1H-indole-5-sulfonamido)cyclohexanecarbonyl)-6-phenylpiperidine-3-carboxylic acid |
| 91 | 9 | | | | | 1-((1r,4r)-4-(1-methyl-2-phenyl-1H-indole-5-sulfonamido)cyclohexanecarbonyl)-6-phenylpiperidine-3-carboxylic acid |
| 92 | 9 | | | | | 1-((1r,4r)-4-(1-methyl-2-phenyl-1H-indole-5-sulfonamido)cyclohexanecarbonyl)-6-phenylpiperidine-3-carboxylic acid |
| 93 | 9 | | | | | 1-((1r,4r)-4-(1-methyl-2-phenyl-1H-indole-5-sulfonamido)cyclohexanecarbonyl)-6-phenylpiperidine-3-carboxylic acid |

-continued

| Ex. | Synthetic Scheme | HPLC RT | HPLC Method | MS | NMR | Name |
|---|---|---|---|---|---|---|
| 94 | 9 | | | | | (R)-tert-butyl 3-((1r,4R)-4-(1-methyl-2-phenyl-1H-indole-5-sulfonamido)cyclohexanecarboxamido)-3-phenylpropanoate |
| 95 | 9 | | | | | (R)-3-(((1r,4R)-4-(1-methyl-2-phenyl-1H-indole-5-sulfonamido)cyclohexanecarboxamido)-3-phenylpropanoic acid |
| 96 | 1 | 14.17 | E | 481 (M + H+) | | (1r,4S)-N-((S)-2-hydroxy-2-methyl-1-phenylpropyl)-4-(naphthalene-2-sulfonamido)cyclohexanecarboxamide |
| 97 | 9 | | | | | (S)-2,2-dimethyl-3-((1r,4S)-4-(1-methyl-2-phenyl-1H-indole-5-sulfonamido)cyclohexanecarboxamido)-3-phenylpropanoic acid |
| 98 | 5 | | | | 1H NMR (400 MHz, DMSO-d6) d ppm 1.11-1.28 (m, 4H) 1.66 (br. s., 2H) 1.77 (br. s., 2H) 2.15 (ddd, J = 11.62, 8.08, 3.28 Hz, 1H) 2.92 (dd, J = 10.74, 3.66 Hz, 1H) 3.53 (s, 3H) 7.53-7.63 (m, 4H) 7.68 (br. s., 2H) 8.07 (br. s., 1H) 8.20 (dd, J = 8.21, 1.39 Hz, 2H) 13.32 (br. s., 1H) | (1r,4r)-methyl 4-(2-phenyl-1H-benzo[d]imidazole-6-sulfonamido)cyclohexanecarboxylate |
| 99 | 5 | 8.171 | D | 490.2 (M + H+) | 1H NMR (400 MHz, DMSO-d6) d ppm 1.12-1.31 (m, 4H) 1.63 (br. s., 2H) 1.80 (br. s., 2H) 2.22 (t, J = 11.49 Hz, 1H) 2.93 (ddd, J = 7.17, 3.92, 3.69 Hz, 1H) 5.03 (s, 2H) 7.27-7.37 (m, 2H) 7.31 (d, J = 7.83 Hz, 3H) 7.53-7.74 (m, 6H) 7.96 (br. s., 1H) 8.21 (s, 1H) 8.20 (d, J = 6.69 Hz, 1H) 13.35 (br. s., 1H | (1r,4r)-benzyl 4-(2-phenyl-1H-benzo[d]imidazole-6-sulfonamido)cyclohexanecarboxylate |
| 100 | 5 | 8.235 | D | 520.19 (M + H+) | 1H NMR (400 MHz, DMSO-d6) d ppm 1.21 (s, 3H) 1.27 (br. s., 1H) 1.62 (br. s., 2H) 1.80 (br. s., 2H) 2.22 (br. s., 1H) 2.90 (br. s., 1H) 3.86 (s, 3H) 5.02 (s, 2H) 7.14 (d, J = 8.72 Hz, 1H) 7.14 (s, 1H) 7.27-7.36 (m, 2H) 7.31 (d, J = 8.08 Hz, 3H) 7.56-7.68 (m, 3H) 7.58 (d, J = 7.07 Hz, 1H) 8.14 (d, J = 8.72 Hz, 2H) 13.19 (s, 1H) | (1r,4r)-benzyl 4-(2-(4-methoxyphenyl)-1H-benzo[d]imidazole-6-sulfonamido)cyclohexanecarboxylate |
| 101 | 5 | | | 548.19 (M + H+) | | methyl 4-(((1r,4r)-4-(2-phenyl-1H-benzo[d]imidazole-6-sulfonamido)cyclohexanecarbonyloxy)methyl)benzoate |
| 102 | 8 | 13.62 | E | 520 (M + H+) | 1H NMR (400 MHz, DMSO-d6) δ ppm 1.12 (br. s., 3H) 1.25 (d, J = 6.95 Hz, 4H) 1.61 (d, J = 5.43 Hz, 4H) 1.91-2.04 (m, 1H) 2.84 (br. s., 1H) 4.81 (t, J = 7.26 Hz, 1H) 7.10 (q, J = 8.76 Hz, 3H) 7.25 (dd, J = 8.46, | (1r,4R)-N-((R)-1-(4-fluorophenyl)ethyl)-4-(2-phenyl-1H-indole-5-sulfonamido)cyclohexanecarboxamide |

-continued

| Ex. | Synthetic Scheme | HPLC RT | HPLC Method | MS | NMR | Name |
|---|---|---|---|---|---|---|
| 103 | 2 | 11.15 | E | 653.48 (M + H+) | 1H NMR (400 MHz, DMSO-d6) d ppm 1.18-1.24 (m, 4H) 1.43 (s, 9H) 1.53 (br. s., 2H) 1.61 (d, J = 8.46 Hz, 2H) 2.40 (br. s., 2H) 2.88 (br. s., 1H) 3.30 (d, J = 6.19 Hz, 3H) 3.30 (br. s., 1H) 3.36 (d, J = 4.42 Hz, 2H) 3.44 (br. s., 2H) 3.48 (d, J = 5.18 Hz, 8H) 7.12 (dd, J = 9.03, 2.21 Hz, 2H) 7.56-7.65 (m, 3H) 8.06 (d, J = 1.26 Hz, 1H) 7.99-8.08 (m, 1H) 13.04 (d, J = 18.19 Hz, 1H) 5.68 Hz, 2H) 7.34-7.43 (m, 1H) 7.38 (d, J = 9.73 Hz, 1H) 7.50 (t, J = 7.71 Hz, 2H) 7.54 (s, 2H) 7.89 (d, J = 7.45 Hz, 2H) 8.07 (d, J = 8.08 Hz, 1H) 8.04 (s, 1H) 12.02 (s, 1H) | tert-butyl 4-(4-(5-(N-((1r,4r)-4-(morpholine-4-carbonyl)cyclohexyl)sulfamoyl)-1H-benzo[d]imidazol-2-yl)phenyl)piperazine-1-carboxylate |
| 104 | 2 | 7.2 | E | 553.23 (M + H+) | 1H NMR (400 MHz, DMSO-d6) d ppm 1.23 (br. s., 4H) 1.50-1.67 (m, 4H) 2.41 (br. s., 1H) 2.91 (br. s., 1H) 3.24 (br. s., 4H) 3.36 (d, J = 4.04 Hz, 2H) 3.42 (br. s., 2H) 3.48 (d, J = 5.68 Hz, 4H) 3.66 (br. s., 1H) 3.65 (d, J = 4.80 Hz, 3H) 7.26 (d, J = 8.97 Hz, 2H) 7.80-7.91 (m, 1H) 7.84 (d, J = 3.79 Hz, 2H) 8.09 (s, 1H) 8.25 (d, J = 8.72 Hz, 2H) 9.21 (br. s., 2H) | N-((1r,4r)-4-(morpholine-4-carbonyl)cyclohexyl)-2-(4-(piperazin-1-yl)phenyl)-1H-benzo[d]imidazole-5-sulfonamide |
| 105 | 1 | 8.651 | D | 456.35 (M + H+) | 1H NMR (400 MHz, DMSO-d6) d ppm 1.09-1.31 (m, 3H) 1.26 (d, J = 7.07 Hz, 4H) 1.66 (br. s., 1H) 1.63 (d, J = 8.46 Hz, 3H) 1.80 (br. s., 1H) 2.00 (t, J = 11.68 Hz, 1H) 3.05 (dd, J = 7.45, 3.79 Hz, 1H) 4.82 (dq, J = 7.64, 7.43 Hz, 1H) 7.05-7.15 (m, 2H) 7.22-7.30 (m, 1H) 7.26 (dd, J = 8.65, 5.62 Hz, 1H) 7.78 (dd, J = 15.03, 1.01 Hz, 1H) 8.01 (d, J = 7.33 Hz, 1H) 7.96 (ddd, J = 8.43, 6.98, 1.39 Hz, 1H) 8.14 (d, J = 8.46 Hz, 1H) 8.09 (d, J = 8.08 Hz, 1H) 8.25 (d, J = 7.71 Hz, 1H) 8.89 (d, J = 2.27 Hz, 1H) 9.21 (d, J = 2.27 Hz, 1H) | (1r,4R)-N-((R)-1-(4-fluorophenyl)ethyl)-4-(quinoline-3-sulfonamido)cyclohexanecarboxamide |
| 106 | 1 | 8.235 | D | 488.43 (M + H+) | 1H NMR (400 MHz, DMSO-d6) δ ppm 1.19 (br. s., 1H) 1.17 (d, J = 6.82 Hz, 2H) 1.27 (d, J = 6.82 Hz, 4H) 1.63 (br. s., 4H) 1.99 (s, 2H) 2.19 (br. s., 2H) 2.83 (br. s., 1H) 3.20 (br. s., 2H) 4.16 (br. s., 2H) 4.83 (br. s., 1H) 7.11 (d, J = 8.97 Hz, 2H) | (1r,4R)-4-(1-acetylindoline-5-sulfonamido)-N-((R)-1-(4-fluorophenyl)ethyl)cyclohexanecarboxamide |

| Ex. | Synthetic Scheme | HPLC RT | HPLC Method | MS | NMR | Name |
|---|---|---|---|---|---|---|
| 107 | 2 | | | | 7.27 (dd, J = 8.46, 5.56 Hz, 2H) 7.48 (br. s., 1H) 7.62 (br. s., 2H) 8.12 (br. s., 2H) | (1r,4R)-4-(1H-benzo[d]imidazole-5-sulfonamido)-N-((R)-1-(4-fluorophenyl)ethyl)cyclohexanecarboxamide |
| 108 | 2 | | | 529.41 (M + H+) | 1H NMR (400 MHz, DMSO-d6) δ ppm 1.13 (dd, J = 13.20, 11.56 Hz, 3H) 1.21-1.29 (m, 4H) 1.26 (d, J = 6.95 Hz, 3H) 1.60 (br. s., 4H) 1.98 (d, J = 2.91 Hz, 1H) 2.88 (d, J = 7.33 Hz, 1H) 4.81 (t, J = 7.39 Hz, 1H) 7.06-7.13 (m, 1H) 7.09 (t, J = 8.91 Hz, 1H) 7.21-7.29 (m, 1H) 7.26 (dd, J = 8.53, 5.62 Hz, 2H) 7.67 (d, J = 7.33 Hz, 1H) 7.77 (d, J = 1.64 Hz, 1H) 7.82-7.87 (m, 1H) 8.09 (d, J = 8.08 Hz, 1H) 8.11 (d, J = 1.26 Hz, 1H) 8.83 (s, 1H) | (1r,4R)-N-((R)-1-(4-fluorophenyl)ethyl)-4-(2-((S)-piperazin-2-yl)-1H-benzo[d]imidazole-5-sulfonamido)cyclohexanecarboxamide |
| 109 | 3 | | | | 1H NMR (400 MHz, DMSO-d6) δ ppm 1.07-1.25 (m, 4H) 1.26 (d, J = 7.07 Hz, 3H) 1.60 (t, J = 10.36 Hz, 4H) 1.98 (t, J = 11.49 Hz, 1H) 2.87 (td, J = 7.33, 3.54 Hz, 1H) 3.94 (s, 3H) 4.82 (qd, J = 7.24, 7.07 Hz, 1H) 7.06-7.12 (m, 1H) 7.09 (t, J = 8.97 Hz, 1H) 7.26 (dd, J = 8.59, 5.56 Hz, 2H) 7.61 (d, J = 7.07 Hz, 1H) 7.78-7.88 (m, 2H) 8.05 (d, J = 7.83 Hz, 1H) 8.12 (d, J = 1.26 Hz, 1H) 8.68 (s, 1H) | (1r,4R)-N-((R)-1-(4-fluorophenyl)ethyl)-4-(1-methyl-1H-benzo[d]imidazole-5-sulfonamido)cyclohexanecarboxamide |
| 110 | 1 | 7.605 | D | 474 (M + H+) | 1H NMR (400 MHz, DMSO-d6) δ ppm 1.15 (br. s., 5H) 1.27 (d, J = 6.95 Hz, 4H) 1.63 (br. s., 4H) 2.00 (br. s., 1H) 2.84 (br. s., 1H) 2.95 (t, J = 7.52 Hz, 2H) 4.83 (t, J = 7.33 Hz, 1H) 6.96 (d, J = 8.21 Hz, 1H) 7.10 (t, J = 8.91 Hz, 2H) 7.27 (dd, J = 8.53, 5.62 Hz, 2H) 7.46 (d, J = 7.33 Hz, 1H) 7.54-7.63 (m, 1H) 7.58 (d, J = 8.21 Hz, 1H) 8.10 (d, J = 7.96 Hz, 1H) 10.44 (s, 1H) | (1r,4R)-N-((R)-1-(4-fluorophenyl)ethyl)-4-(2-oxo-1,2,3,4-tetrahydroquinoline-6-sulfonamido)cyclohexanecarboxamide |
| 111 | 1 | 7.115 | D | 456 (M + H+) | 1H NMR (400 MHz, DMSO-d6) δ ppm 1.19 (br. s., 1H) 1.17 (d, J = 7.20 Hz, 2H) 1.25 (d, J = 6.95 Hz, 4H) 1.63 (br. s., 4H) 1.99 (s, 1H) 2.96 (br. s., 1H) 4.80 (d, J = 7.58 Hz, 1H) 7.09 (t, J = 8.84 Hz, 2H) 7.25 (dd, J = 8.53, 5.62 Hz, 2H) 7.69 (dd, J = 8.34, 4.17 Hz, | (1r,4R)-N-((R)-1-(4-fluorophenyl)ethyl)-4-(quinoline-6-sulfonamido)cyclohexanecarboxamide |

-continued

| Ex. | Synthetic Scheme | HPLC RT | HPLC Method | MS | NMR | Name |
|---|---|---|---|---|---|---|
| 112 | 1 | 7.701 | D | 476 (M + H+) | 1H NMR (400 MHz, DMSO-d6) δ ppm 1.09-1.23 (m, 4H) 1.25 (d, J = 2.53 Hz, 3H) 1.24 (br. s., 1H) 1.65 (br. s., 3H) 1.95-2.05 (m, 1H) 2.85 (d, J = 10.86 Hz, 1H) 3.14 (dd, J = 7.45, 4.42 Hz, 1H) 3.62 (dd, J = 6.44, 3.92 Hz, 1H) 4.85 (d, J = 7.07 Hz, 1H) 7.11 (d, J = 8.84 Hz, 2H) 7.08 (d, J = 2.02 Hz, 1H) 7.28 (dd, J = 8.46, 5.68 Hz, 2H) 7.36 (d, J = 2.27 Hz, 1H) 7.34 (s, 1H) 7.57 (d, J = 7.58 Hz, 1H) 7.86 (d, J = 7.33 Hz, 1H) 8.08 (d, J = 8.59 Hz, 2H) 8.20 (d, J = 8.84 Hz, 1H) 8.54 (d, J = 1.89 Hz, 1H) 8.62 (s, 1H) 9.05 (dd, J = 4.23, 1.58 Hz, 1H) | (1r,4R)-N-((R)-1-(4-fluorophenyl)ethyl)-4-(3-oxo-3,4-dihydro-2H-benzo[b][1,4]oxazine-6-sulfonamido)cyclohexanecarboxamide |
| 113 | 1 | | | | 1H NMR (400 MHz, DMSO-d6) δ ppm 1.08-1.21 (m, 3H) 1.26 (d, J = 7.07 Hz, 4H) 1.63 (d, J = 10.11 Hz, 4H) 1.99 (d, J = 1.77 Hz, 1H) 2.96 (dt, J = 7.39, 3.76 Hz, 1H) 4.82 (qd, J = 7.24, 7.07 Hz, 1H) 7.05-7.13 (m, 1H) 7.09 (t, J = 8.84 Hz, 1H) 7.26 (dd, J = 8.59, 5.56 Hz, 2H) 7.75 (d, J = 7.33 Hz, 1H) 7.94 (dd, J = 8.59, 1.77 Hz, 1H) 8.06 (d, J = 8.08 Hz, 1H) 8.26 (d, J = 8.59 Hz, 1H) 8.71 (d, J = 1.77 Hz, 1H) 9.61 (s, 1H) | (1r,4R)-4-(benzo[d]thiazole-6-sulfonamido)-N-((R)-1-(4-fluorophenyl)ethyl)cyclohexanecarboxamide |
| 114 | 2 | 6.83 | D | 515 (M + H+) | 1H NMR (400 MHz, DMSO-d6) δ ppm 1.12 (br. s., 3H) 1.19 (br. s., 2H) 1.26 (d, J = 7.07 Hz, 3H) 1.60 (br. s., 4H) 1.98 (qd, J = 6.86, 6.69 Hz, 3H) 2.16-2.25 (m, 1H) 2.21 (d, J = 7.83 Hz, 1H) 2.32-2.42 (m, 2H) 2.84 (br. s., 1H) 4.83 (d, J = 7.58 Hz, 1H) 5.18 (dd, J = 7.71, 5.94 Hz, 1H) 7.06-7.13 (m, 1H) 7.09 (t, J = 8.97 Hz, 1H) 7.26 (dd, J = 8.34, 5.56 Hz, 2H) 7.56 (d, J = 7.07 Hz, 1H) 7.64-7.72 (m, 1H) 7.67 (d, J = 4.55 Hz, 1H) 7.97 (s, 1H) 8.05 (d, J = 7.83 Hz, 1H) | (1r,4R)-N-((R)-1-(4-fluorophenyl)ethyl)-4-(2-((S)-tetrahydrofuran-2-yl)-1H-benzo[d]imidazole-5-sulfonamido)cyclohexanecarboxamide |
| 115 | 1 | | | 484 (M + H+) | | N-((1R,4r)-4-((R)-1-(4-fluorophenyl)ethyl)carbamoyl)cyclohexyl)-2-phenyl-1H-indole-6-carboxamide |
| 116 | 15 | | | | 1H NMR (400 MHz, DMSO-d6) δ ppm 1.02-1.16 (m, 1H) 1.08 (d, J = 7.45 Hz, 20H) 1.25 (d, J = 6.95 Hz, | (1r,4R)-4-(3-chloro-1-(triisopropylsilyl)-1H-indole-6-sulfonamido)-N-((R)-1-(4-fluorophenyl)ethyl)cyclohexanecarboxamide |

| Ex. | Synthetic Scheme | HPLC RT | HPLC Method | MS | NMR | Name |
|---|---|---|---|---|---|---|
| 117 | 2 | 6.97 | D | 515 (M + H+) | 4H) 1.55 (dd, J = 9.47, 3.03 Hz, 3H) 1.59 (br. s., 1H) 1.71-1.83 (m, J = 7.48, 7.48, 7.48, 7.48, 7.33 Hz, 3H) 1.92-2.01 (m, 1H) 2.76 (br. s., 1H) 4.80 (qd, J = 7.22, 7.01 Hz, 1H) 7.06-7.13 (m, 2H) 7.25 (dd, J = 8.72, 5.56 Hz, 2H) 7.63 (d, J = 1.14 Hz, 1H) 7.70 (t, J = 7.89 Hz, 1H) 7.80 (s, 1H) 7.97 (s, 1H) 8.08 (d, J = 8.08 Hz, 1H) 1H NMR (400 MHz, DMSO-d6) δ ppm 1.16 (s, 2H) 1.11 (d, J = 14.02 Hz, 1H) 1.24-1.28 (m, 1H) 1.26 (d, J = 6.95 Hz, 3H) 1.60 (br. s., 4H) 1.93-2.03 (m, J = 6.88, 6.88, 6.88, 6.88 Hz, 2H) 1.99 (s, 2H) 2.20 (dd, J = 12.69, 6.13 Hz, 1H) 2.31-2.41 (m, 1H) 2.34 (d, J = 7.33 Hz, 1H) 2.83 (br. s., 1H) 3.88 (d, J = 7.07 Hz, 1H) 4.82 (t, J = 7.33 Hz, 1H) 5.13 (br. s., 1H) 7.06-7.12 (m, 1H) 7.09 (t, J = 8.91 Hz, 1H) 7.22-7.29 (m, 1H) 7.26 (dd, J = 8.53, 5.62 Hz, 2H) 7.60 (s, 2H) 7.89 (s, 1H) 8.07 (d, J = 7.96 Hz, 1H) 12.79 (d, J = 8.46 Hz, 1H) | (1r,4R)-N-((R)-1-(4-fluorophenyl)ethyl)-4-(2-((R)-tetrahydrofuran-2-yl)-1H-benzo[d]imidazole-5-sulfonamido)cyclohexanecarboxamide |
| 118 | 2 | | | 550 (M + H+) | | (1r,4R)-4-(2-((S)-4,4-difluoropyrrolidin-2-yl)-1H-benzo[d]imidazole-5-sulfonamido)-N-((R)-1-(4-fluorophenyl)ethyl)cyclohexanecarboxamide |
| 119 | 1 | 14.7 | E | 445 (M + H+) | 1H NMR (400 MHz, DMSO-d6) δ ppm 1.07-1.23 (m, 3H) 1.27 (d, J = 6.95 Hz, 4H) 1.57-1.69 (m, 4H) 1.96-2.10 (m, J = 7.45, 7.45, 7.45, 7.45 Hz, 2H) 1.96-2.10 (m, 1H) 2.84 (dd, J = 11.12, 3.79 Hz, 1H) 2.92 (t, J = 7.45 Hz, 4H) 4.83 (qd, J = 7.24, 7.07 Hz, 1H) 7.07-7.15 (m, 2H) 7.27 (dd, J = 8.53, 5.62 Hz, 2H) 7.40 (d, J = 7.83 Hz, 1H) 7.51 (d, J = 7.20 Hz, 1H) 7.57 (dd, J = 7.83, 1.64 Hz, 1H) 7.64 (s, 1H) 8.09 (d, J = 8.08 Hz, 1H) | (1r,4R)-4-(2,3-dihydro-1H-indene-5-sulfonamido)-N-((R)-1-(4-fluorophenyl)ethyl)cyclohexanecarboxamide |
| 120 | 19 | | | | 1H NMR (400 MHz, DMSO-d6) δ ppm 1.17 (d, J = 9.09 Hz, 2H) 1.13 (br. s., 1H) 1.26 (d, J = 7.07 Hz, 4H) 1.59 (br. s., 1H) 1.65 (br. s., 3H) 2.00 (d, J = 2.91 Hz, 1H) 2.96 (d, J = 3.92 Hz, 1H) 4.82 (t, J = 7.33 Hz, 1H) 7.09 (t, J = 8.91 Hz, 2H) 7.23-7.29 (m, 2H) | (1r,4R)-N-((R)-1-(4-fluorophenyl)ethyl)-4-(2-phenylbenzo[d]thiazole-6-sulfonamido)cyclohexanecarboxamide |

| Ex. | Synthetic Scheme | HPLC RT | HPLC Method | MS | NMR | Name |
|---|---|---|---|---|---|---|
| 121 | 1 | 8.096 | D | 509.38 (M + H+) | 7.59-7.67 (m, 3H) 7.79 (d, J = 7.45 Hz, 1H) 7.94 (dd, J = 8.59, 1.77 Hz, 1H) 8.09 (d, J = 7.96 Hz, 1H) 8.14 (dd, J = 7.58, 1.89 Hz, 2H) 8.23 (d, J = 8.59 Hz, 1H) 8.70 (d, J = 1.64 Hz, 1H) | (1r,4R)-N-((R)-1-cyclohexylethyl)-4-(2-phenyl-1H-benzo[d]imidazole-5-sulfonamido)cyclohexanecarboxamide |
| 122 | 1 | 8.715 | D | 476 (M + H+) | 1H NMR (400 MHz, DMSO-d6) d ppm 0.82 (d, J = 6.57 Hz, 2H) 0.90 (d, J = 6.69 Hz, 3H) 0.99-1.17 (m, 6H) 1.23 (d, J = 12.51 Hz, 2H) 1.62 (br. s., 9H) 1.89-1.97 (m, 1H) 2.89 (br. s., 1H) 3.50 (dt, J = 8.53, 6.85 Hz, 1H) 7.35 (d, J = 8.59 Hz, 1H) 7.58 (td, J = 11.46, 8.53 Hz, 3H) 7.53-7.63 (m, 1H) 7.70 (s, 1H) 8.09 (s, 1H) 8.20 (d, J = 7.83 Hz, 2H) 13.34 (d, J = 15.66 Hz, 1H) | (1r,4R)-N-((R)-1-(4-fluorophenyl)ethyl)-4-(4-methyl-3,4-dihydro-2H-benzo[b][1,4]oxazine-7-sulfonamido)cyclohexanecarboxamide |
| 123 | 1 | 8.715 | D | 463 (M + H+) | 1H NMR (400 MHz, DMSO-d6) d ppm 1.07-1.19 (m, 1H) 1.14 (t, J = 12.00 Hz, 1H) 1.21-1.32 (m, 1H) 1.28 (d, J = 6.95 Hz, 4H) 1.60-1.73 (m, 2H) 1.68 (t, J = 8.21 Hz, 3H) 1.97-2.05 (m, 1H) 2.82 (ddd, J = 14.84, 7.33, 7.14 Hz, 1H) 3.11 (s, 3H) 3.54 (t, J = 4.48 Hz, 2H) 4.23 (t, J = 4.55 Hz, 2H) 4.84 (qd, J = 7.26, 7.01 Hz, 1H) 7.08-7.15 (m, 3H) 7.28 (dd, J = 8.53, 5.62 Hz, 2H) 7.42 (d, J = 7.07 Hz, 1H) 8.02 (d, J = 2.15 Hz, 1H) 8.10 (d, J = 8.08 Hz, 1H) | (1r,4R)-4-(2,3-dihydrobenzo[b][1,4]dioxine-6-sulfonamido)-N-((R)-1-(4-fluorophenyl)ethyl)cyclohexanecarboxamide |
| 124 | 15 | 9.48 | D | 492.1524 (M + H+) | 1H NMR (400 MHz, DMSO-d6) δ ppm 1.13 (d, J = 15.54 Hz, 3H) 1.26 (d, J = 7.07 Hz, 4H) 1.59 (br. s., 4H) 1.92-2.03 (m, 1H) 2.23 (s, 3H) 2.83 (br. s., 1H) 4.82 (t, J = 7.39 Hz, 1H) 7.09 (t, J = 8.91 Hz, 2H) 7.22-7.31 (m, 2H) 7.42 (dd, J = 7.96, 3.66 Hz, 1H) | (1r,4R)-4-(2-chloro-3-methyl-1H-indole-5-sulfonamido)-N-((R)-1-(4-fluorophenyl)ethyl)cyclohexanecarboxamide |

| Ex. | Synthetic Scheme | HPLC RT | HPLC Method | MS | NMR | Name |
|---|---|---|---|---|---|---|
| 125 | 1 | 6.539 | D | 467.13 (M + H+) | 1H NMR (400 MHz, DMSO-d6) δ ppm 0.99 (d, J = 6.32 Hz, 2H) 1.18 (t, J = 7.14 Hz, 5H) 1.44 (dd, J = 4.93, 3.41 Hz, 1H) 1.53-1.66 (m, 3H) 1.59 (d, J = 9.47 Hz, 2H) 1.73-1.91 (m, 3H) 2.89 (br. s., 1H) 3.17-3.25 (m, 1H) 3.40-3.47 (m, 1H) 7.53-7.62 (m, 1H) 7.58 (ddd, J = 7.99, 3.28, 3.13 Hz, 3H) 7.66 (d, J = 8.59 Hz, 1H) 7.70 (s, 1H) 8.10 (s, 1H) 8.20 (d, J = 1.01 Hz, 1H) 8.21 (s, 1H) 13.35 (d, J = 14.27 Hz, 1H) 2H) 7.55 (dd, J = 8.59, 1.77 Hz, 1H) 7.93 (d, J = 1.39 Hz, 1H) 8.08 (d, J = 7.96 Hz, 1H) 12.13 (s, 1H) | N-((1R,4r)-4-((R)-2-methylpyrrolidine-1-carbonyl)cyclohexyl)-2-phenyl-1H-benzo[d]imidazole-5-sulfonamide |
| 126 | 2 | 8.224 | D | 579.3 (M + H+) | 1H NMR (400 MHz, DMSO-d6) δ ppm 1.17 (t, J = 7.14 Hz, 3H) 1.26 (d, J = 7.07 Hz, 4H) 1.64 (br. s., 4H) 1.99 (s, 1H) 2.90 (d, J = 5.94 Hz, 1H) 3.08 (s, 3H) 3.67 (t, J = 5.24 Hz, 2H) 4.51 (t, J = 5.18 Hz, 2H) 4.82 (t, J = 7.39 Hz, 1H) 7.06-7.12 (m, 1H) 7.09 (t, J = 8.91 Hz, 1H) 7.26 (dd, J = 8.53, 5.49 Hz, 2H) 7.60 (dd, J = 5.68, 2.40 Hz, 3H) 7.57-7.62 (m, 1H) 7.74 (dd, J = 8.59, 1.77 Hz, 1H) 7.85 (ddd, J = 3.98, 2.65, 1.58 Hz, 2H) 7.89 (d, J = 8.59 Hz, 1H) 8.11 (d, J = 1.39 Hz, 1H) 8.08 (d, J = 7.96 Hz, 1H) | (1r,4R)-N-((R)-1-(4-fluorophenyl)ethyl)-4-(1-(2-methoxyethyl)-2-phenyl-1H-benzo[d]imidazole-5-sulfonamido)cyclohexanecarboxamide |
| 127 | 23 | 6.976 | D | 477.1 (M + H+) | 1H NMR (400 MHz, DMSO-d6) δ ppm 1.16 (d, J = 2.91 Hz, 1H) 1.14 (br. s., 1H) 1.21-1.34 (m, 1H) 1.28 (d, J = 7.07 Hz, 4H) 1.67 (br. s., 4H) 2.01 (t, J = 11.81 Hz, 1H) 2.81 (dd, J = 7.45, 3.54 Hz, 1H) 3.11 (s, 3H) 3.54 (t, J = 4.48 Hz, 2H) 4.22 (t, J = 4.48 Hz, 2H) 4.84 (t, J = 7.39 Hz, 1H) 7.08-7.15 (m, 3H) 7.28 (dd, J = 8.59, 5.56 Hz, 2H) 7.42 (d, J = 6.95 Hz, 2H) 8.02 (d, J = 2.15 Hz, 1H) 8.10 (d, J = 8.08 Hz, 1H) | (1r,4R)-N-((R)-1-(4-fluorophenyl)ethyl)-4-(4-methyl-3,4-dihydro-2H-pyrido[3,2-b][1,4]oxazine-7-sulfonamido)cyclohexanecarboxamide |
| 128 | 22 | 6.773 | D | 504.2 (M + H+) | 1H NMR (400 MHz, DMSO-d6) δ ppm 1.63-1.80 (m, 3H) 1.83 (d, J = 6.95 Hz, 4H) 2.14-2.32 (m, 4H) 2.41-2.50 (m, J = 6.32, 6.06, 5.94, 5.94 Hz, 2H) 2.57 (td, J = 11.72, 3.22 Hz, 1H) 3.31 (s, 1H) | (1r,4R)-4-(1,5-dimethyl-2,3,4,5-tetrahydro-1H-pyrido[2,3-b][1,4]diazepine-8-sulfonamido)-N-((R)-1-(4-fluorophenyl)ethyl)cyclohexanecarboxamide |

-continued

| Ex. | Synthetic Scheme | HPLC RT | HPLC Method | MS | NMR | Name |
|---|---|---|---|---|---|---|
| 129 | 30 | | | 436 (M + H+) | 3H) 3.41 (dd, J = 11.05, 7.26 Hz, 1H) 3.64 (s, 3H) 3.76 (t, J = 6.44 Hz, 2H) 4.16-4.22 (m, 1H) 4.19 (d, J = 5.68 Hz, 1H) 5.39 (qd, J = 7.24, 7.07 Hz, 1H) 7.62-7.69 (m, 3H) 7.83 (dd, J = 8.59, 5.56 Hz, 2H) 8.18 (br. s., 1H) 8.39 (d, J = 1.77 Hz, 1H) 8.69 (d, J = 8.08 Hz, 1H) | 1,4-dimethyl-N-((1R,4r)-4-((R)-2-methylpyrrolidine-1-carbonyl)cyclohexyl)-1,2,3,4-tetrahydropyrido[3,2-b]pyrazine-7-sulfonamide |
| 130 | 22 | 6.432 | D | 476 (M + H+) | 1H NMR (400 MHz, DMSO-d6) d ppm 1.07-1.23 (m, 2H) 1.23-1.33 (m, 2H) 1.29 (t, J = 3.54 Hz, 3H) 1.62 (br. s., 1H) 1.68 (br. s., 2H) 1.71 (d, J = 3.79 Hz, 1H) 1.96-2.06 (m, 1H) 2.79 (s, 4H) 3.14 (t, J = 4.80 Hz, 2H) 3.46 (t, J = 5.81 Hz, 2H) 4.84 (qd, J = 7.24, 7.07 Hz, 1H) 6.78 (d, J = 1.52 Hz, 1H) 7.07-7.14 (m, 1H) 7.11 (t, J = 8.91 Hz, 1H) 7.23-7.31 (m, 1H) 7.27 (td, J = 8.56, 6.25 Hz, 2H) 7.37 (s, 1H) 7.68 (d, J = 2.02 Hz, 1H) 8.10 (d, J = 7.96 Hz, 1H) | (1r,4R)-N-((R)-1-(4-fluorophenyl)ethyl)-4-(1-methyl-1,2,3,4-tetrahydropyrido[3,2-b]pyrazine-7-sulfonamido)cyclohexanecarboxamide |
| 131 | 23 | 11.07 | D | 477 (M + H+) | 1H NMR (400 MHz, DMSO-d6) d ppm 1.15 (br. s., 2H) 1.22-1.35 (m, 1H) 1.28 (d, J = 7.07 Hz, 4H) 1.62 (br. s., 1H) 1.65-1.74 (m, 3H) 2.01 (t, J = 11.81 Hz, 1H) 2.84-2.94 (m, 4H) 3.32 (br. s., 2H) 4.44 (br. s., 1H) 4.42 (d, J = 4.55 Hz, 1H) 4.84 (t, J = 7.26 Hz, 1H) 7.07-7.14 (m, 1H) 7.11 (t, J = 8.84 Hz, 1H) 7.19 (d, J = 2.15 Hz, 1H) 7.28 (dd, J = 8.59, 5.68 Hz, 2H) 7.57 (d, J = 7.07 Hz, 1H) 7.79 (d, J = 2.02 Hz, 1H) 8.10 (d, J = 8.08 Hz, 1H) | (1r,4R)-N-((R)-1-(4-fluorophenyl)ethyl)-4-(1-methyl-2,3-dihydro-1H-pyrido[2,3-b][1,4]oxazine-7-sulfonamido)cyclohexanecarboxamide |
| 132 | 22 | 6.997 | D | 516 (M + H+) | 1H NMR (400 MHz, DMSO-d6) d ppm 0.49 (dd, J = 3.47, 2.34 Hz, 2H) 0.83 (dd, J = 6.51, 1.96 Hz, 2H) 1.17 (t, J = 7.14 Hz, 3H) 1.25-1.34 (m, 1H) 1.28 (d, J = 7.07 Hz, 3H) 1.60-1.76 (m, 4H) 2.01 (t, J = 3.28 Hz, 1H) 2.22-2.30 (m, J = 6.55, 6.55, 3.66, 3.32 Hz, 1H) 2.76-2.86 (m, 1H) 3.06 (s, 3H) 3.26 (t, J = 4.93 Hz, 2H) 3.49 (t, J = 4.93 Hz, 2H) 4.84 (t, J = 7.39 Hz, 1H) 7.07-7.15 (m, 2H) | (1r,4R)-4-(1-cyclopropyl-4-methyl-1,2,3,4-tetrahydropyrido[3,2-b]pyrazine-7-sulfonamido)-N-((R)-1-(4-fluorophenyl)ethyl)cyclohexanecarboxamide |

-continued

| Ex. | Synthetic Scheme | HPLC RT | HPLC Method | MS | NMR | Name |
|---|---|---|---|---|---|---|
| 133 | 30 | 8.139 | D | 489 (M + H+) | 1H NMR (400 MHz, DMSO-d6) δ ppm 1.05-1.25 (m, 4H) 1.27 (d, J = 6.95 Hz, 3H) 1.60 (d, J = 2.65 Hz, 1H) 1.66 (br. s., 2H) 1.69 (d, J = 3.41 Hz, 1H) 2.00 (dd, J = 14.72, 8.53 Hz, 1H) 2.76 (d, J = 7.58 Hz, 1H) 2.73 (d, J = 0.63 Hz, 1H) 2.81 (s, 3H) 2.88 (s, 3H) 3.26 (t, J = 4.86 Hz, 1H) 3.40 (d, J = 5.31 Hz, 1H) 4.79-4.87 (m, J = 7.26, 7.26, 7.26 Hz, 1H) 6.47 (d, J = 8.34 Hz, 1H) 6.76 (d, J = 2.02 Hz, 1H) 7.01 (dd, J = 8.34, 2.02 Hz, 1H) 7.07-7.18 (m, 3H) 7.24-7.31 (m, 1H) 7.27 (dd, J = 8.53, 5.62 Hz, 2H) 8.11 (d, J = 7.96 Hz, 1H) 7.20 (d, J = 2.15 Hz, 1H) 7.28 (dd, J = 8.53, 5.62 Hz, 2H) 7.40 (d, J = 7.07 Hz, 1H) 7.83 (d, J = 2.15 Hz, 1H) 8.10 (d, J = 8.08 Hz, 1H) | (1r,4R)-4-(1,4-dimethyl-1,2,3,4-tetrahydroquinoxaline-6-sulfonamido)-N-((R)-1-(4-fluorophenyl)ethyl)cyclohexanecarboxamide |
| 134 | 22 | 7.435 | D | 544.3 (M + H+) | 1H NMR (400 MHz, DMSO-d6) δ ppm 1.12 (br. s., 1H) 1.17 (t, J = 7.07 Hz, 3H) 1.28 (d, J = 6.95 Hz, 6H) 1.23 (br. s., 1H) 1.65 (br. s., 6H) 1.99-2.05 (m, 1H) 2.33 (d, J = 1.64 Hz, 2H) 2.60-2.72 (m, 4H) 2.80 (dd, J = 10.99, 3.92 Hz, 1H) 3.08 (s, 3H) 3.15 (ddd, J = 11.37, 8.27, 3.35 Hz, 1H) 4.84 (t, J = 7.39 Hz, 1H) 6.87 (d, J = 2.02 Hz, 1H) 7.07-7.14 (m, 1H) 7.10 (t, J = 8.91 Hz, 1H) 7.25-7.33 (m, 3H) 7.82 (d, J = 2.02 Hz, 1H) 8.09 (d, J = 7.96 Hz, 1H) | (1r,4R)-4-(5,10-dimethyl-5,5a,6,7,8,9,9a,10-octahydropyrido[3,2-b]quinoxaline-3-sulfonamido)-N-((R)-1-(4-fluorophenyl)ethyl)cyclohexanecarboxamide |
| 135 | 22 | 7.328 | D | 558.2 (M + H+) | 1H NMR (400 MHz, DMSO-d6) δ ppm 1.06-1.24 (m, 3H) 1.28 (d, J = 7.07 Hz, 4H) 1.60 (br. s., 1H) 1.67 (br. s., 2H) 1.70 (d, J = 3.79 Hz, 1H) 2.00 (td, J = 11.65, 3.09 Hz, 1H) 2.81 (dd, J = 10.99, 4.04 Hz, 1H) 3.07 (s, 3H) 3.48 (s, 4H) 4.16 (q, J = 9.64 Hz, 2H) 4.83 (qd, J = 7.24, 7.07 Hz, 2H) 7.05 (s, 1H) 7.07-7.14 (m, 1H) 7.10 (t, J = 8.91 Hz, 1H) 7.28 (dd, J = 7.83, 6.06 Hz, 3H) 7.83 (d, J = 1.89 Hz, 1H) 8.10 (d, J = 8.08 Hz, 1H) | (1r,4R)-N-((R)-1-(4-fluorophenyl)ethyl)-4-(4-methyl-1-(2,2,2-trifluoroethyl)-1,2,3,4-tetrahydropyrido[3,2-b]pyrazine-7-sulfonamido)cyclohexanecarboxamide |

-continued

| Ex. | Synthetic Scheme | HPLC RT | HPLC Method | MS | NMR | Name |
|---|---|---|---|---|---|---|
| 136 | 11 | | | | 1H NMR (400 MHz, CHLOROFORM-d) δ ppm 1.25 (br. s., 1H) 1.32 (d, J = 0.88 Hz, 1H) 1.58 (br. s., 1H) 1.65 (br. s., 3H) 1.76 (br. s., 2H) 2.05 (br. s., 2H) 2.41 (t, J = 11.49 Hz, 1H) 2.59 (s, 3H) 2.89 (s, 2H) 3.21 (d, J = 7.20 Hz, 1H) 3.52 (br. s., 2H) 3.64 (br. s., 2H) 3.71 (br. s., 3H) 4.41 (d, J = 6.95 Hz, 1H) 6.77 (d, J = 1.01 Hz, 1H) 7.58 (d, J = 6.69 Hz, 1H) 7.66 (d, J = 8.46 Hz, 1H) 7.81 (d, J = 8.34 Hz, 1H) 8.10 (s, 1H) 8.74 (s, 1H) | N-((1r,4r)-4-(morpholine-4-carbonyl)cyclohexyl)-2-o-tolyl-1H-indole-6-sulfonamide |
| 137 | 11 | | | | 1H NMR (400 MHz, CHLOROFORM-d) δ ppm 1.65 (d, J = 8.59 Hz, 3H) 1.79 (br. s., 3H) 1.95-2.03 (m, 2H) 2.06 (br. s., 3H) 2.13 (s, 3H) 2.43 (s, 1H) 2.59 (s, 3H) 3.27 (br. s., 1H) 3.50 (br. s., 1H) 3.57 (s, 2H) 4.20 (d, J = 7.20 Hz, 1H) 4.23 (s, 1H) 6.74 (d, J = 1.26 Hz, 1H) 7.35-7.41 (m, 3H) 7.64 (dd, J = 8.40, 1.45 Hz, 1H) 7.56-7.66 (m, 1H) 7.78 (d, J = 8.46 Hz, 1H) 8.19 (br. s., 1H) 9.14 (br. s., 1H) | N-((1R,4r)-4-((R)-2-methylpyrrolidine-1-carbonyl)cyclohexyl)-2-o-tolyl-1H-indole-6-sulfonamide |
| 138 | 18 | 8.491 | D | 459.1 (M + H+) | 1H NMR (400 MHz, DMSO-d6) δ ppm 1.14 (br. s., 3H) 1.26 (d, J = 7.07 Hz, 4H) 1.61 (br. s., 4H) 1.99 (br. s., 1H) 2.30 (s, 3H) 2.79 (br. s., 1H) 4.81 (d, J = 7.07 Hz, 1H) 7.09 (t, J = 8.91 Hz, 2H) 7.26 (dd, J = 8.53, 5.62 Hz, 2H) 7.44 (s, 1H) 7.58 (d, J = 7.20 Hz, 1H) 8.08 (d, J = 7.96 Hz, 1H) 8.31 (d, J = 1.89 Hz, 1H) 8.60 (d, J = 2.15 Hz, 1H) 11.86 (s, 1H) | (1r,4R)-N-((R)-1-(4-fluorophenyl)ethyl)-4-(3-methyl-1H-pyrrolo[2,3-b]pyridine-5-sulfonamido)cyclohexanecarboxamide |
| 139 | 22 | 7.413 | D | 544 (M + H+) | 1H NMR (400 MHz, DMSO-d6) d ppm 1.14-1.35 (m, 3H) 1.28 (d, J = 6.95 Hz, 8H) 1.62-1.84 (m, 7H) 2.03 (t, J = 11.68 Hz, 1H) 2.35 (br. s., 1H) 2.33 (dd, J = 3.60, 1.71 Hz, 1H) 2.76 (s, 4H) 2.85 (d, J = 10.61 Hz, 1H) 3.16 (s, 3H) 3.26 (d, J = 2.40 Hz, 1H) 3.57-3.63 (m, J = 6.35, 4.09, 1.99, 1.99, 1.99 Hz, 1H) 4.84 (t, J = 7.33 Hz, 1H) 6.97 (d, J = 1.64 Hz, 1H) 7.07-7.14 (m, 1H) 7.11 (t, J = 8.91 Hz, 1H) 7.28 (dd, J = 8.59, 5.56 Hz, 2H) 7.60 (br. s., 1H) 7.71 (d, J = 1.77 Hz, 1H) 8.14 (d, J = 7.96 Hz, 1H) | (1R,4R)-4-((5aR,9aR)-5,10-dimethyl-5,5a,6,7,8,9,9a,10-octahydropyrido[3,2-b]quinoxaline-3-sulfonamido)-N-((R)-1-(4-fluorophenyl)ethyl)cyclohexanecarboxamide |

| Ex. | Synthetic Scheme | HPLC RT | HPLC Method | MS | NMR | Name |
|---|---|---|---|---|---|---|
| 140 | 26 | 7.051 | D | 471 (M + H+) | 1H NMR (400 MHz, DMSO-d6) d ppm 1.20 (d, J = 8.34 Hz, 2H) 1.26 (d, J = 6.82 Hz, 5H) 1.65 (br. s., 4H) 2.00 (d, J = 3.28 Hz, 1H) 2.80 (s, 3H) 3.07 (br. s., 1H) 4.83 (d, J = 7.33 Hz, 1H) 7.08 (t, J = 8.84 Hz, 2H) 7.23-7.28 (m, 2H) 7.66 (d, J = 4.55 Hz, 1H) 8.07 (dd, J = 7.71, 4.67 Hz, 2H) 8.91 (d, J = 2.53 Hz, 1H) 9.09 (d, J = 4.55 Hz, 1H) 9.38 (d, J = 2.53 Hz, 1H) | (1r,4R)-N-((R)-1-(4-fluorophenyl)ethyl)-4-(5-methyl-1,8-naphthyridine-3-sulfonamido)cyclohexanecarboxamide |
| 141 | 22 | 7.04 | D | 504.2 (M + H+) | 1H NMR (400 MHz, DMSO-d6) d ppm 1.16 (d, J = 6.44 Hz, 8H) 1.13 (d, J = 3.92 Hz, 1H) 1.28 (d, J = 7.07 Hz, 5H) 1.65 (br. s., 2H) 1.75 (d, J = 4.04 Hz, 2H) 2.03 (t, J = 3.28 Hz, 1H) 2.85 (dd, J = 7.07, 3.79 Hz, 1H) 3.16 (t, J = 4.86 Hz, 2H) 3.95 (dt, J = 13.14, 6.57 Hz, 2H) 4.84 (qd, J = 7.26, 7.01 Hz, 1H) 7.01 (d, J = 1.39 Hz, 1H) 7.08-7.14 (m, 1H) 7.11 (t, J = 8.97 Hz, 1H) 7.28 (dd, J = 8.46, 5.56 Hz, 2H) 7.53 (d, J = 6.82 Hz, 1H) 7.64 (d, J = 1.89 Hz, 1H) 8.12 (d, J = 8.08 Hz, 1H) 8.28 (br. s., 1H) | (1r,4R)-N-((R)-1-(4-fluorophenyl)ethyl)-4-(1-isopropyl-1,2,3,4-tetrahydropyrido[3,2-b]pyrazine-7-sulfonamido)cyclohexanecarboxamide |
| 142 | 22 | 6.155 | D | 476.2 (M + H+) | 1H NMR (400 MHz, DMSO-d6) d ppm 1.17 (t, J = 7.07 Hz, 3H) 1.28 (d, J = 7.07 Hz, 4H) 1.68 (br. s., 4H) 1.99-2.05 (m, 1H) 2.79 (d, J = 4.17 Hz, 1H) 3.05 (s, 3H) 3.27 (br. s., 2H) 3.43 (t, J = 4.74 Hz, 2H) 4.84 (t, J = 7.39 Hz, 1H) 6.15 (s, 1H) 6.81 (d, J = 2.15 Hz, 1H) 7.11 (t, J = 8.91 Hz, 1H) 7.29 (d, J = 9.09, 4.55 Hz, 2H) 7.25-7.31 (m, 1H) 7.71 (d, J = 2.15 Hz, 1H) 8.10 (d, J = 8.08 Hz, 1H) | (1r,4R)-N-((R)-1-(4-fluorophenyl)ethyl)-4-(4-methyl-1,2,3,4-tetrahydropyrido[3,2-b]pyrazine-7-sulfonamido)cyclohexanecarboxamide |
| 143 | 22 | 7.563 | D | 546 (M + H+) | 1H NMR (400 MHz, DMSO-d6) d ppm 1.12 (dd, J = 10.80, 6.63 Hz, 14H) 1.24 (d, J = 2.53 Hz, 1H) 1.28 (d, J = 6.95 Hz, 4H) 1.64 (t, J = 12.32 Hz, 2H) 1.67 (br. s., 1H) 1.73 (d, J = 3.92 Hz, 1H) 1.97-2.06 (m, 1H) 2.80 (dd, J = 11.05, 4.11 Hz, 1H) 3.10 (t, J = 4.80 Hz, 2H) 3.40 (t, J = 4.80 Hz, 2H) 3.89 (dt, J = 13.11, 6.52 Hz, 1H) 4.83 (t, J = 7.39 Hz, 1H) 5.03-5.12 (m, 1H) 6.79, 6.79, 6.79 Hz, 1H) | (1r,4R)-4-(1,4-diisopropyl-1,2,3,4-tetrahydropyrido[3,2-b]pyrazine-7-sulfonamido)-N-((R)-1-(4-fluorophenyl)ethyl)cyclohexanecarboxamide |

-continued

| Ex. | Synthetic Scheme | HPLC RT | HPLC Method | MS | NMR | Name |
|---|---|---|---|---|---|---|
| 144 | 1 | | | | 6.88 (d, J = 1.77 Hz, 1H) 7.07-7.14 (m, 1H) 7.10 (t, J = 8.91 Hz, 1H) 7.28 (dd, J = 5.43, 3.28 Hz, 2H) 7.25-7.30 (m, 1H) 7.73 (d, J = 1.89 Hz, 1H) 8.09 (d, J = 7.96 Hz, 1H) 1H NMR (400 MHz, DMSO-d6) δ ppm 1.10-1.22 (m, J = 18.62, 9.54, 9.23, 9.23 Hz, 1H) 1.10-1.22 (m, 1H) 1.36 (s, 6H) 1.41-1.60 (m, 2H) 1.45 (d, J = 6.95 Hz, 3H) 1.80-2.00 (m, 4H) 1.85 (dq, J = 7.07, 6.82 Hz, 3H) 2.82 (t, J = 6.69 Hz, 2H) 2.99-3.09 (m, J = 11.35, 7.46, 7.46, 3.79 Hz, 1H) 4.24 (d, J = 7.20 Hz, 1H) 5.03-5.11 (m, J = 7.11, 7.11, 7.11, 7.11 Hz, 1H) 5.57 (d, J = 7.58 Hz, 1H) 6.84 (d, J = 8.59 Hz, 1H) 7.00 (t, J = 8.65 Hz, 2H) 7.22-7.26 (m, 2H) 7.55 (dd, J = 8.59, 2.27 Hz, 1H) 7.60 (d, J = 2.15 Hz, 1H) | (1r,4R)-4-(2,2-dimethylchroman-6-sulfonamido)-N-((R)-1-(4-fluorophenyl)ethyl)cyclohexanecarboxamide |
| 145 | 27 | 6.347 | D | 475.3 (M + H+) | 1H NMR (400 MHz, DMSO-d6) δ ppm 1.08-1.22 (m, 1H) 1.15 (d, J = 3.79 Hz, 1H) 1.22-1.33 (m, 1H) 1.28 (d, J = 7.07 Hz, 4H) 1.62 (br. s., 1H) 1.68 (br. s., 2H) 1.71 (d, J = 4.04 Hz, 1H) 1.82-1.89 (m, 2H) 2.01 (t, J = 11.81 Hz, 1H) 2.74 (t, J = 6.13 Hz, 2H) 2.82 (dd, J = 11.05, 3.85 Hz, 1H) 3.10 (s, 3H) 3.44 (t, J = 5.62 Hz, 2H) 4.83 (d, J = 7.33 Hz, 1H) 7.07-7.14 (m, 1H) 7.11 (t, J = 8.91 Hz, 1H) 7.24-7.31 (m, 2H) 7.36 (d, J = 7.20 Hz, 1H) 7.45 (d, J = 2.27 Hz, 1H) 8.11 (d, J = 8.08 Hz, 1H) 8.18 (d, J = 2.40 Hz, 1H) | (1r,4R)-N-((R)-1-(4-fluorophenyl)ethyl)-4-(8-methyl-5,6,7,8-tetrahydro-1,8-naphthyridine-3-sulfonamido)cyclohexanecarboxamide |
| 146 | 1 | 8.427 | D | 401.2 (M + H+) | 1H NMR (400 MHz, DMSO-d6) δ ppm 0.99 (d, J = 6.32 Hz, 2H) 1.05 (d, J = 6.44 Hz, 1H) 1.13-1.27 (m, 4H) 1.44 (dd, J = 4.99, 3.35 Hz, 1H) 1.56 (t, J = 7.14 Hz, 2H) 1.63 (br. s., 2H) 1.70-1.92 (m, 3H) 2.17 (td, J = 11.27, 8.27 Hz, 1H) 2.96 (br. s., 1H) 3.20 (dt, J = 8.78, 6.60 Hz, 1H) 3.36-3.46 (m, 1H) 3.91 (td, J = 6.57, 2.65 Hz, 1H) 7.68 (td, J = 7.86, 1.45 Hz, 2H) 7.79 (d, J = 7.33 Hz, 1H) 7.86 (t, J = 1.96 Hz, 1H) 8.04 (d, J = 7.83 Hz, | N-((1S,4r)-4-((S)-2-methylpyrrolidine-1-carbonyl)cyclohexyl)naphthalene-2-sulfonamide |

-continued

| Ex. | Synthetic Scheme | HPLC RT | HPLC Method | MS | NMR | Name |
|---|---|---|---|---|---|---|
| 147 | 1 | | | 455.1 (M + H+) | 1H) 8.12 (d, J = 8.72 Hz, 1H) 8.17 (d, J = 7.71 Hz, 1H) 8.46 (s, 1H) | (1s,4S)-N-((R)-1-(4-fluorophenyl)ethyl)-4-(naphthalene-2-sulfonamido)cyclohexanecarboxamide |
| 148 | 28 | 9.024 | D | 474.3 (M + H+) | 1H NMR (400 MHz, DMSO-d6) δ ppm 1.27 (d, J = 7.07 Hz, 4H) 1.08-1.30 (m, 3H) 1.61 (d, J = 2.40 Hz, 1H) 1.67 (br. s., 2H) 1.70 (d, J = 3.28 Hz, 1H) 1.84-1.91 (m, 1H) 1.88 (d, J = 6.19 Hz, 1H) 1.95-2.05 (m, 1H) 2.70-2.88 (m, 6H) 3.26 (s, 1H) 3.24 (d, J = 5.81 Hz, 1H) 4.83 (t, J = 7.39 Hz, 1H) 6.88-6.93 (m, 1H) 6.90 (t, J = 1.83 Hz, 1H) 7.03 (d, J = 7.58 Hz, 1H) 7.07-7.14 (m, 1H) 7.10 (t, J = 8.91 Hz, 1H) 7.27 (dd, J = 8.59, 5.56 Hz, 2H) 7.42 (d, J = 7.20 Hz, 1H) 8.10 (d, J = 8.08 Hz, 1H) | (1r,4R)-N-((R)-1-(4-fluorophenyl)ethyl)-4-(1-methyl-1,2,3,4-tetrahydroquinoline-7-sulfonamido)cyclohexanecarboxamide |
| 149 | 29 | 10.31 | E | 461 (M + H+) | 1H NMR (400 MHz, DMSO-d6) δ ppm 1.04-1.25 (m, 3H) 1.16 (d, J = 11.75 Hz, 1H) 1.28 (d, J = 6.95 Hz, 3H) 1.65 (d, J = 7.96 Hz, 3H) 1.68 (br. s., 1H) 2.00 (t, J = 11.68 Hz, 1H) 2.74 (d, J = 7.20 Hz, 1H) 3.19 (d, J = 2.53 Hz, 2H) 3.26 (d, J = 2.40 Hz, 2H) 4.84 (t, J = 7.39 Hz, 1H) 5.74 (s, 1H) 6.12 (s, 1H) 6.38 (d, J = 7.96 Hz, 1H) 6.80 (d, J = 2.15 Hz, 1H) 6.78 (s, 1H) 7.02 (d, J = 7.20 Hz, 1H) 7.11 (t, J = 8.91 Hz, 2H) 7.28 (dd, J = 8.40, 5.62 Hz, 2H) 8.10 (d, J = 7.96 Hz, 1H) | (1r,4R)-N-((R)-1-(4-fluorophenyl)ethyl)-4-(1,2,3,4-tetrahydroquinoxaline-6-sulfonamido)cyclohexanecarboxamide |
| 150 | 31 | 11.57 | E | 462 (M + H+) | 1H NMR (400 MHz, DMSO-d6) δ ppm 1.11 (d, J = 11.62 Hz, 1H) 1.16-1.32 (m, 1H) 1.28 (d, J = 6.95 Hz, 5H) 1.59-1.71 (m, 1H) 1.65 (d, J = 8.08 Hz, 3H) 2.00 (t, J = 11.75 Hz, 1H) 2.79 (dd, J = 11.05, 3.85 Hz, 1H) 3.30 (br. s., 2H) 4.17 (t, J = 4.17 Hz, 2H) 4.84 (t, J = 7.39 Hz, 1H) 6.25 (s, 1H) 6.76 (d, J = 8.34 Hz, 1H) 6.89 (dd, J = 8.34, 2.15 Hz, 1H) 7.01 (d, J = 2.27 Hz, 1H) 7.11 (t, J = 8.91 Hz, 2H) 7.25-7.35 (m, 1H) 7.28 (dd, J = 8.53, 5.62 Hz, 2H) 8.11 (d, J = 7.96 Hz, 1H) | (1r,4R)-4-(3,4-dihydro-2H-benzo[b][1,4]oxazine-6-sulfonamido)-N-(R)-1-(4-fluorophenyl)ethyl)cyclohexanecarboxamide |

| Ex. | Synthetic Scheme | HPLC RT | HPLC Method | MS | NMR | Name |
|---|---|---|---|---|---|---|
| 151 | 28 | 7.467 | D | 460.2 (M + H+) | 1H NMR (400 MHz, DMSO-d6) d ppm 1.07-1.32 (m, 2H) 1.28 (d, J = 6.95 Hz, 5H) 1.67 (t, J = 13.20 Hz, 2H) 1.60-1.73 (m, 2H) 1.74-1.82 (m, J = 6.00, 5.78, 5.67, 5.67 Hz, 2H) 2.01 (t, J = 11.62 Hz, 1H) 2.69 (t, J = 6.19 Hz, 2H) 2.81 (dd, J = 10.93, 3.85 Hz, 1H) 3.21 (br. s., 1H) 3.19 (d, J = 5.56 Hz, 1H) 4.84 (qd, J = 7.24, 7.07 Hz, 1H) 6.81 (dd, J = 7.71, 1.52 Hz, 1H) 6.88 (d, J = 1.52 Hz, 1H) 6.99 (d, J = 7.83 Hz, 1H) 7.11 (t, J = 8.84 Hz, 2H) 7.28 (dd, J = 8.65, 5.62 Hz, 2H) 7.37 (d, J = 7.20 Hz, 1H) 8.11 (d, J = 8.08 Hz, 1H) | (1r,4R)-N-((R)-1-(4-fluorophenyl)ethyl)-4-(1,2,3,4-tetrahydroquinoline-7-sulfonamido)cyclohexanecarboxamide |
| 152 | 28 | 8.224 | D | 460.2 (M + H+) | 1H NMR (400 MHz, DMSO-d6) d ppm 1.28 (d, J = 6.95 Hz, 4H) 1.07-1.30 (m, 3H) 1.58-1.70 (m, 2H) 1.65 (d, J = 8.08 Hz, 2H) 1.73-1.82 (m, 1H) 1.78 (d, J = 5.31 Hz, 1H) 1.95-2.05 (m, 1H) 2.68 (t, J = 6.06 Hz, 2H) 2.73 (br. s., 1H) 3.24 (br. s., 1H) 3.21 (d, J = 5.68 Hz, 1H) 4.84 (qd, J = 7.24, 7.07 Hz, 1H) 6.46 (d, J = 8.08 Hz, 1H) 7.01-7.15 (m, 3H) 7.22-7.32 (m, 4H) 8.10 (d, J = 8.08 Hz, 1H) | (1r,4R)-N-((R)-1-(4-fluorophenyl)ethyl)-4-(1,2,3,4-tetrahydroquinoline-6-sulfonamido)cyclohexanecarboxamide |
| 153 | 22 | 7.093 | D | 504 (M + H+) | 1H NMR (400 MHz, DMSO-d6) d ppm 0.91 (s, 6H) 1.10-1.33 (m, 7H) 1.68 (br. s., 4H) 2.01 (br. s., 1H) 2.87 (d, J = 3.79 Hz, 3H) 3.02 (d, J = 4.29 Hz, 2H) 4.85 (d, J = 7.20 Hz, 1H) 5.45-5.51 (m, 1H) 6.40-6.47 (m, 1H) 7.03 (d, J = 2.02 Hz, 1H) 7.08-7.15 (m, 2H) 7.23-7.39 (m, 1H) 7.28 (dd, J = 8.72, 5.56 Hz, 2H) 7.73 (d, J = 2.02 Hz, 1H) 8.11 (d, J = 8.08 Hz, 1H) | (1r,4R)-4-(3,3-dimethyl-2,3,4,5-tetrahydro-1H-pyrido[2,3-b][1,4]diazepine-8-sulfonamido)-N-((R)-1-(4-fluorophenyl)ethyl)cyclohexanecarboxamide |
| 154 | 22 | | | 504 (M + H+) | | (1s,4S)-4-(3,3-dimethyl-2,3,4,5-tetrahydro-1H-pyrido[2,3-b][1,4]diazepine-8-sulfonamido)-N-((R)-1-(4-fluorophenyl)ethyl)cyclohexanecarboxamide |
| 155 | 32 | 11.55 | E | 493 (M + H+) | (1r,4R)-N-((R)-1-(4-(trideuteriomethyl)-4-fluorophenyl)ethyl)-4-(3,4-dihydro-2H-benzo[b][1,4]oxazine-6-sulfonamido)cyclohexanecarboxamide | (1r,4R)-N-((R)-1-(4-fluorophenyl)ethyl)-4-(3-oxo-4-(trideuteriomethyl)-3,4-dihydro-2H-benzo[b][1,4]oxazine-6-sulfonamido)cyclohexanecarboxamide |

| Ex. | Synthetic Scheme | HPLC RT | HPLC Method | MS | NMR | Name |
|---|---|---|---|---|---|---|
| 156 | 32 | 11.57 | E | 490 (M + H+) | 1H NMR (400 MHz, DMSO-d6) d ppm 1.16 (d, J = 11.75 Hz, 2H) 1.21-1.33 (m, 1H) 1.27 (d, J = 6.95 Hz, 4H) 1.61 (br. s., 1H) 1.67 (br. s., 2H) 1.69 (d, J = 3.66 Hz, 1H) 2.01 (t, J = 11.75 Hz, 1H) 2.88 (dd, J = 10.93, 3.85 Hz, 1H) 3.30 (s, 3H) 4.77 (s, 2H) 4.83 (qd, J = 7.26, 7.01 Hz, 1H) 7.07-7.17 (m, 3H) 7.27 (dd, J = 8.53, 5.62 Hz, 2H) 7.43-7.50 (m, 2H) 7.60 (d, J = 7.20 Hz, 1H) 8.10 (d, J = 8.08 Hz, 1H) | (1r,4R)-N-((R)-1-(4-fluorophenyl)ethyl)-4-(4-methyl-3-oxo-3,4-dihydro-2H-benzo[b][1,4]oxazine-6-sulfonamido)cyclohexanecarboxamide |
| 157 | 32 | 12.42 | E | 476 (M + H+) | 1H NMR (400 MHz, DMSO-d6) d ppm 1.07-1.31 (m, 3H) 1.28 (d, J = 7.07 Hz, 4H) 1.59-1.71 (m, 2H) 1.66 (d, J = 8.34 Hz, 2H) 1.95-2.06 (m, 1H) 2.81 (ddd, J = 10.99, 7.39, 3.47 Hz, 1H) 2.86 (s, 3H) 3.29 (d, J = 4.42 Hz, 1H) 3.28 (br. s., 1H) 4.30 (br. s., 1H) 4.28 (d, J = 4.55 Hz, 1H) 4.84 (qd, J = 7.26, 7.01 Hz, 1H) 6.79 (d, J = 8.21 Hz, 1H) 6.98-7.04 (m, 2H) 7.07-7.14 (m, 1H) 7.11 (t, J = 8.91 Hz, 1H) 7.28 (dd, J = 8.65, 5.62 Hz, 2H) 7.37 (d, J = 7.07 Hz, 1H) 8.10 (d, J = 8.08 Hz, 1H) | (1r,4R)-N-((R)-1-(4-fluorophenyl)ethyl)-4-(4-methyl-3,4-dihydro-2H-benzo[b][1,4]oxazine-6-sulfonamido)cyclohexanecarboxamide |
| 158 | 32 | 12.39 | E | 479 (M + H+) | (R)-N-(1-(4-fluorophenyl)ethyl)-4-(2,2,3,3-tetradeuterio-1,2,3,4-tetrahydropyrido[3,2-b]pyrazine-7-sulfonamido)cyclohexanecarboxamide | (1r,4R)-N-((R)-1-(4-fluorophenyl)ethyl)-4-(4-(trideuteriomethyl)-3,4-dihydro-2H-benzo[b][1,4]oxazine-6-sulfonamido)cyclohexanecarboxamide |
| 159 | 28 | 5.6 | D | 457.3 (M + H+) | 1H NMR (400 MHz, DMSO-d6) d ppm 1.32 (d, J = 7.07 Hz, 4H) 1.10-1.33 (m, 3H) 1.63-1.73 (m, 4H) 1.84-1.91 (m, 1H) 1.88 (d, J = 6.06 Hz, 1H) 2.07 (dd, J = 14.78, 8.59 Hz, 1H) 2.73 (d, J = 12.63 Hz, 1H) 2.73 (s, 1H) 2.83 (dd, J = 7.33, 3.79 Hz, 1H) 2.86 (s, 3H) 3.26 (s, 1H) 3.24 (d, J = 5.68 Hz, 1H) 4.87 (t, J = 7.39 Hz, 1H) 6.88-6.94 (m, 2H) 7.04 (d, J = 7.58 Hz, 1H) 7.20-7.27 (m, 2H) 7.42 (d, J = 7.07 Hz, 1H) 7.72 (td, J = 7.71, 1.77 Hz, 1H) 8.12 (d, J = 7.96 Hz, 1H) 8.48 (d, J = 4.04 Hz, 1H) | (1r,4r)-4-(1-methyl-1,2,3,4-tetrahydroquinoline-7-sulfonamido)-N-(1-(pyridin-2-yl)ethyl)cyclohexanecarboxamide |

| Ex. | Synthetic Scheme | HPLC RT | HPLC Method | MS | NMR | Name |
|---|---|---|---|---|---|---|
| 160 | 28 | 5.525 | D | 457.3 (M + H+) | 1H NMR (400 MHz, DMSO-d6) δ ppm 1.10-1.34 (m, 7H) 1.61 (br. s., 1H) 1.67 (br. s., 2H) 1.70 (d, J = 3.28 Hz, 1H) 1.84-1.91 (m, 1H) 1.88 (d, J = 6.06 Hz, 1H) 1.99-2.05 (m, 1H) 2.73 (d, J = 12.63 Hz, 2H) 2.78-2.88 (m, 1H) 2.86 (s, 3H) 3.26 (s, 1H) 3.24 (d, J = 5.68 Hz, 1H) 4.87 (t, J = 7.26 Hz, 1H) 6.88-6.93 (m, 2H) 7.03 (d, J = 7.58 Hz, 1H) 7.32 (dd, J = 7.83, 4.80 Hz, 1H) 7.42 (d, J = 6.95 Hz, 1H) 7.64 (dt, J = 7.86, 1.94 Hz, 1H) 8.18 (d, J = 7.83 Hz, 1H) 8.41 (dd, J = 4.74, 1.58 Hz, 1H) 8.47 (d, J = 2.15 Hz, 1H) | (1r,4r)-4-(1-methyl-1,2,3,4-tetrahydroquinoline-7-sulfonamido)-N-(1-(pyridin-3-yl)ethyl)cyclohexanecarboxamide |
| 161 | 28 | 5.515 | D | 457.3 (M + H+) | 1H NMR (400 MHz, DMSO-d6) δ ppm 1.15 (dd, J = 10.80, 9.28 Hz, 3H) 1.26 (br. s., 1H) 1.29 (d, J = 7.07 Hz, 3H) 1.63-1.73 (m, 4H) 1.84-1.91 (m, 1H) 1.88 (d, J = 6.06 Hz, 1H) 2.04 (br. s., 1H) 2.73 (t, J = 6.32 Hz, 2H) 2.86 (s, 4H) 3.26 (s, 1H) 3.24 (d, J = 5.81 Hz, 1H) 4.81 (t, J = 7.26 Hz, 1H) 6.89-6.93 (m, 1H) 6.90 (t, J = 1.83 Hz, 1H) 7.04 (d, J = 7.58 Hz, 1H) 7.23 (d, J = 6.06 Hz, 2H) 7.43 (d, J = 7.07 Hz, 1H) 8.20 (d, J = 7.83 Hz, 1H) 8.46 (d, J = 6.06 Hz, 1H) 8.46 (d, J = 2.91 Hz, 1H) | (1r,4r)-4-(1-methyl-1,2,3,4-tetrahydroquinoline-7-sulfonamido)-N-(1-(pyridin-4-yl)ethyl)cyclohexanecarboxamide |
| 162 | 22 | 7.072 | D | 516.3 (M + H+) | 1H NMR (400 MHz, DMSO-d6) δ ppm 1.17 (t, J = 7.14 Hz, 3H) 1.09-1.19 (m, 1H) 1.22-1.35 (m, 2H) 1.28 (d, J = 6.95 Hz, 2H) 1.65 (br. s., 2H) 1.68 (d, J = 2.91 Hz, 4H) 1.86-2.05 (m, 3H) 2.66 (ddd, J = 11.21, 7.93, 3.81 Hz, 1H) 2.79 (dt, J = 7.42, 3.81 Hz, 1H) 2.87-2.94 (m, 1H) 4.84 (t, J = 7.33 Hz, 1H) 6.03 (s, 1H) 6.85 (d, J = 2.02 Hz, 1H) 7.12 (d, J = 8.84 Hz, 2H) 7.23-7.32 (m, 1H) 7.27 (d, J = 7.20 Hz, 2H) 7.65 (d, J = 2.15 Hz, 1H) 8.11 (d, J = 8.08 Hz, 1H) | (1S,4R)-N-((R)-1-(4-fluorophenyl)ethyl)-4-((5aS,9aS)-5,5a,6,7,8,9,9a,10-octahydropyrido[3,2-b]quinoxaline-3-sulfonamido)cyclohexanecarboxamide |
| 163 | 1 | | | 445.2 (M + H+) | | (R)-1-((1r,4R)-4-(naphthalene-2-sulfonamido)cyclohexanecarbonyl)piperidine-3-carboxylic acid |

| Ex. | Synthetic Scheme | HPLC RT | HPLC Method | MS | NMR | Name |
|---|---|---|---|---|---|---|
| 164 | 28 | 9.301 | F | 532.3 (M + H+) | | methyl 2-(7-(N-((1R,4r)-4-((R)-1-(4-fluorophenyl)ethyl)carbamoyl)cyclohexyl)sulfamoyl)-3,4-dihydroquinolin-1(2H)-yl)acetate |
| 165 | 1 | | | 470 (M + H+) | | (1r,4R)-N-((R)-1-(4-fluorophenyl)ethyl)-4-(3-methylquinoline-8-sulfonamido)cyclohexanecarboxamide |
| 166 | 28 | 8.736 | F | 518.2 (M + H+) | | 2-(7-(N-((1R,4r)-4-((R)-1-(4-fluorophenyl)ethyl)carbamoyl)cyclohexyl)sulfamoyl)-3,4-dihydroquinolin-1(2H)-yl)acetic acid |
| 167 | 28 | 10.539 | F | 516.3 (M + H+) | | (1r,4R)-N-((R)-1-(4-fluorophenyl)ethyl)-4-(2-isobutyl-1,2,3,4-tetrahydroquinoline-6-sulfonamido)cyclohexanecarboxamide |
| 168 | 28 | 8.245 | F | 474.3 (M + H+) | | (1r,4R)-N-((R)-1-(4-fluorophenyl)ethyl)-4-(2-methyl-1,2,3,4-tetrahydroquinoline-7-sulfonamido)cyclohexanecarboxamide |
| 169 | 28 | 8.928 | F | 474.3 (M + H+) | | (1r,4R)-N-((R)-1-(4-fluorophenyl)ethyl)-4-(2-methyl-1,2,3,4-tetrahydroquinoline-6-sulfonamido)cyclohexanecarboxamide |
| 170 | 28 | 9.557 | F | 488.4 (M + H+) | | (1r,4R)-4-((S)-2-ethyl-1,2,3,4-tetrahydroquinoline-6-sulfonamido)-N-((R)-1-(4-fluorophenyl)ethyl)cyclohexanecarboxamide |
| 171 | 28 | 9.557 | F | 488.4 (M + H+) | | (1r,4R)-4-((R)-2-ethyl-1,2,3,4-tetrahydroquinoline-6-sulfonamido)-N-((R)-1-(4-fluorophenyl)ethyl)cyclohexanecarboxamide |
| 172 | 22 | 6.352 | F | 476.3 (M + H+) | | (1R,4R)-N-((R)-1-(4-fluorophenyl)ethyl)-4-((R)-2-methyl-1,2,3,4-tetrahydropyrido[3,2-b]pyrazine-7-sulfonamido)cyclohexanecarboxamide |
| 173 | 28 | 9.643 | F | 581.3 (M + H+) | | tert-butyl 3-phenyl-4-((1r,4r)-4-(1,2,3,4-tetrahydroquinoline-6-sulfonamido)cyclohexanecarbonyl)piperazine-1-carboxylate |
| 174 | 28 | 9.003 | F | 583.2 (M + H+) | | tert-butyl 3-phenyl-4-((1r,4r)-4-(1,2,3,4-tetrahydroquinoline-7-sulfonamido)cyclohexanecarbonyl)piperazine-1-carboxylate |
| 175 | 28 | 5.952 | F | 483.2 (M + H+) | | N-((1r,4r)-4-(2-phenylpiperazine-1-carbonyl)cyclohexyl)-1,2,3,4-tetrahydroquinoline-6-sulfonamide |
| 176 | 28 | 5.493 | F | 483.2 (M + H+) | | N-((1r,4r)-4-(2-phenylpiperazine-1-carbonyl)cyclohexyl)-1,2,3,4-tetrahydroquinoline-7-sulfonamide |
| 177 | 28 | 8.203 | F | 484.4 (M + H+) | | N-((1r,4r)-4-(3-phenylmorpholine-4-carbonyl)cyclohexyl)-1,2,3,4-tetrahydroquinoline-6-sulfonamide |
| 178 | 28 | 7.467 | F | 484.4 (M + H+) | | N-((1r,4r)-4-(3-phenylmorpholine-4-carbonyl)cyclohexyl)-1,2,3,4-tetrahydroquinoline-7-sulfonamide |
| 179 | 28 | 10.475 | F | 651.5 (M + H+) | | tert-butyl 3-phenyl-4-((1r,4r)-4-(2-(trifluoromethyl)-1,2,3,4-tetrahydroquinoline-6-sulfonamido)cyclohexanecarbonyl)piperazine-1-carboxylate |

| Ex. | Synthetic Scheme | HPLC RT | HPLC Method | MS | NMR | Name |
|---|---|---|---|---|---|---|
| 180 | 22 | 8.053 | F | 647.3 (M + H+) | | benzyl 4-((1r,4r)-4-(1,4-dimethyl-1,2,3,4-tetrahydropyrido[3,2-b]pyrazine-7-sulfonamido)cyclohexanecarbonyl)-3-phenylpiperazine-1-carboxylate |
| 181 | 22 | 7.808 | F | 619.3 (M + H+) | | benzyl 3-phenyl-4-((1r,4r)-4-(1,2,3,4-tetrahydropyrido[3,2-b]pyrazine-7-sulfonamido)cyclohexanecarbonyl)piperazine-1-carboxylate |
| 182 | 28 | 7.061 | F | 551.2 (M + H+) | | N-((1r,4r)-4-(2-phenylpiperazine-1-carbonyl)cyclohexyl)-2-(trifluoromethyl)-1,2,3,4-tetrahydroquinoline-6-sulfonamide |
| 183 | 22 | 6.53 | E | 513.2 (M + H+) | | 1,4-dimethyl-N-((1r,4r)-4-(2-phenylpiperazine-1-carbonyl)cyclohexyl)-1,2,3,4-tetrahydropyrido[3,2-b]pyrazine-7-sulfonamide |
| 184 | 29 | | | 667.2 (M + H+) | | (1r,4R)-N-((R)-1-(4-fluorophenyl)ethyl)-4-(4-(2,2,2-trifluoroacetyl)-1-(2,2,2-trifluoroacetamido)-1,2,3,4-tetrahydroquinoline-6-sulfonamido)cyclohexanecarboxamide |
| 185 | 29 | | | 571.2 (M + H+) | | (1r,4R)-N-((R)-1-(4-fluorophenyl)ethyl)-4-(4-(2,2,2-trifluoroacetamido)-1,2,3,4-tetrahydroquinoline-6-sulfonamido)cyclohexanecarboxamide |
| 186 | 22 | 5.92 | E | 485.2 (M + H+) | | N-((1r,4r)-4-(2-phenylpiperazine-1-carbonyl)cyclohexyl)-1,2,3,4-tetrahydropyrido[3,2-b]pyrazine-7-sulfonamide |
| 187 | 28 | 7.371 | F | 551.2 (M + H+) | | N-((1r,4r)-4-(2-phenylpiperazine-1-carbonyl)cyclohexyl)-2-(trifluoromethyl)-1,2,3,4-tetrahydroquinoline-7-sulfonamide |
| 188 | 28 | 6.923 | F | 474.1 (M + H+) | | (1r,4R)-N-((R)-1-(4-fluorophenyl)ethyl)-4-(6-methyl-1,2,3,4-tetrahydroquinoline-7-sulfonamido)cyclohexanecarboxamide |
| 189 | 23 | 13.53 | E | 569 (M + H+) | | 4-((S)-2-benzyl-2,3-dihydro-1H-pyrido[2,3-b][1,4]thiazine-7-sulfonamido)-N-((R)-1-(4-fluorophenyl)ethyl)cyclohexanecarboxamide |
| 190 | 23 | 13.51 | E | 569 (M + H+) | | 4-((R)-2-benzyl-2,3-dihydro-1H-pyrido[2,3-b][1,4]thiazine-7-sulfonamido)-N-((R)-1-(4-fluorophenyl)ethyl)cyclohexanecarboxamide |
| 191 | 22 | 6.18 | E | 485.2 (M + H+) | | N-((1S,4r)-4-((S)-2-phenylpiperazine-1-carbonyl)cyclohexyl)-1,2,3,4-tetrahydropyrido[3,2-b]pyrazine-7-sulfonamide |
| 192 | 23 | 8.52 | E | 502 (M + H+) | | N-((1S,4r)-4-((S)-2-phenylpiperazine-1-carbonyl)cyclohexyl)-2,3-dihydro-1H-pyrido[2,3-b][1,4]thiazine-7-sulfonamide |
| 193 | 23 | 12.26 | E | 503 (M + H+) | | N-((1r,4r)-4-(3-phenylmorpholine-4-carbonyl)cyclohexyl)-2,3-dihydro-1H-pyrido[2,3-b][1,4]thiazine-7-sulfonamide |
| 194 | 22 | 5.771 | F | 486.1 (M + H+) | | N-((1r,4r)-4-(3-phenylmorpholine-4-carbonyl)cyclohexyl)-1,2,3,4-tetrahydropyrido[3,2-b]pyrazine-7-sulfonamide |

-continued

| Ex. | Synthetic Scheme | HPLC RT | HPLC Method | MS | NMR | Name |
|---|---|---|---|---|---|---|
| 195 | 33 | 8.043 | E | 502.1 (M + H+) | | (1r,4R)-4-(4,4-dimethyl-2-oxo-1,2,3,4-tetrahydroquinoline-7-sulfonamido)-N-((R))-1-(4-fluorophenyl)ethyl)cyclohexanecarboxamide |
| 196 | 33 | 8.907 | D | 488.4 (M + H+) | | (1r,4R)-4-(4,4-dimethyl-1,2,3,4-tetrahydroquinoline-7-sulfonamido)-N-((R))-1-(4-fluorophenyl)ethyl)cyclohexanecarboxamide |
| 197 | 22 | 6.389 | F | 476.1 (M + H+) | | (1r,4R)-4-N-((R)-1-(4-fluorophenyl)ethyl)-1-methyl-4-(1,2,3,4-tetrahydropyrido[3,2-b]pyrazine-7-sulfonamido)cyclohexanecarboxamide |
| 198 | 29 | | | 462 (M + H+) | | (1s,4S)-N-((R)-1-(4-fluorophenyl)ethyl)-4-(1,2,3,4-tetrahydropyrido[3,2-b]pyrazine-7-sulfonamido)cyclohexanecarboxamide |
| 119 | 22 | 9.02 | E | 466 (M + H+) | | (R)-N-(1-(4-fluorophenyl)ethyl)-4-(2,2,3,3-tetradeuterio-1,2,3,4-tetrahydropyrido[3,2-b]pyrazine-7-sulfonamido)cyclohexanecarboxamide |
| 200 | 22 | 11.67 | E | 562 (M + H+) | | isobutyl 7-(N-((1R,4r)-4-((R)-1-(4-fluorophenyl)ethyl)carbamoyl)cyclohexyl)sulfamoyl)-3,4-dihydropyrido[3,2-b]pyrazine-1(2H)-carboxylate |
| 201 | 21 | 6.859 | D | 529 (M + H+) | | (1r,4R)-N-((R)-1-(4-fluorophenyl)ethyl)-4-(2-(2-methoxyethylamino)quinoline-6-sulfonamido)cyclohexanecarboxamide |
| 202 | 21 | 9.397 | D | 532.2 (M + H+) | | (1r,4R)-N-((R)-1-(4-fluorophenyl)ethyl)-4-(2-phenylquinoline-6-sulfonamido)cyclohexanecarboxamide |
| 203 | 21 | 6.464 | D | 543 (M + H+) | | 3-(6-(N-((1R,4r)-4-((R)-1-(4-fluorophenyl)ethyl)carbamoyl)cyclohexyl)sulfamoyl)quinolin-2-ylamino)propanoic acid |
| 204 | 21 | 14.06 | E | 523 (M + H+) | | 2-ethoxy-N-((1r,4)-4-(2-phenylpiperazine-1-carbonyl)cyclohexyl)quinoline-6-sulfonamide |
| 205 | 21 | 15.06 | E | 498 (M + H+) | | (1r,4S)-4-(2-ethoxyquinoline-6-sulfonamido)-N-((S)-2-hydroxy-1-phenylethyl)cyclohexanecarboxamide |
| 206 | 21 | 15.84 | E | 526 (M + H+) | | (1r,4S)-4-(2-ethoxyquinoline-6-sulfonamido)-N-((S)-2-hydroxy-2-methyl-1-phenylpropyl)cyclohexanecarboxamide |
| 207 | 21 | 8.331 | D | 557.3 (M + H+) | | 6-(N-((1R,4r)-4-((R)-1-(4-fluorophenyl)ethyl)carbamoyl)cyclohexyl)sulfamoyl)-N-(2-methoxyethyl)quinoline-2-carboxamide |
| 208 | 22 | 14.32 | E | 640 (M + H+) | | 2-(benzyloxy)ethyl 7-(N-((1R,4r)-4-((R)-1-(4-fluorophenyl)ethyl)carbamoyl)cyclohexyl)sulfamoyl)-3,4-dihydropyrido[3,2-b]pyrazine-1(2H)-carboxylate |
| 209 | 22 | 12.41 | E | 554 (M + H+) | | ethyl 7-(N-((1R,4r)-4-((R)-1-(4-fluorophenyl)ethyl)carbamoyl)cyclohexyl)sulfamoyl)-3,4-dihydropyrido[3,2-b]pyrazine-1(2H)-carboxylate |

-continued

| Ex. | Synthetic Scheme | HPLC RT | HPLC Method | MS | NMR | Name |
|---|---|---|---|---|---|---|
| 210 | 22 | 14.74 | E | 588 (M + H+) | | cyclohexyl 7-(N-((1R,4r)-4-((R)-1-(4-fluorophenyl)ethyl)carbamoyl)cyclohexyl)sulfamoyl)-3,4-dihydropyrido[3,2-b]pyrazine-1(2H)-carboxylate |
| 211 | 21 | 17.43 | E | 482 (M + H+) | | (R)-tert-butyl 3-((1r,4R)-4-(2-ethoxyquinoline-6-sulfonamido)cyclohexanecarboxamido)-3-phenylpropanoate |
| 212 | 33 | 11.051 | D | 588 (M + H+) | | isobutyl 7-(N-((1R,4r)-4-((R)-1-(4-fluorophenyl)ethyl)carbamoyl)cyclohexyl)sulfamoyl)-4,4-dimethyl-3,4-dihydroquinoline-1(2H)-carboxylate |
| 213 | 21 | 6.848 | D | 541 (M + H+) | | (1r,4R)-N-((R)-1-(4-fluorophenyl)ethyl)-4-(2-morpholinoquinoline-6-sulfonamido)cyclohexanecarboxamide |
| 214 | 29 | 11.2 | D | 661.1 (M + H+) | | diisobutyl 6-(N-((1R,4r)-4-((R)-1-(4-fluorophenyl)ethyl)carbamoyl)cyclohexyl)sulfamoyl)-2,3-dihydroquinoxaline-1,4-dicarboxylate |
| 215 | 21 | 6.219 | D | 542.1 (M + H+) | | (1r,4R)-4-(2-(dimethylamino)ethylamino)quinoline-6-sulfonamido)-N-((R)-1-(4-fluorophenyl)ethyl)cyclohexanecarboxamide |
| 216 | 21 | 7.2 | D | 539.2 (M + H+) | | (1r,4R)-N-((R)-1-(4-fluorophenyl)ethyl)-4-(2-(piperidin-1-yl)quinoline-6-sulfonamido)cyclohexanecarboxamide |
| 217 | 29 | 9.365 | D | 561 (M + H+) | | isobutyl 7-(N-((1R,4r)-4-((R)-1-(4-fluorophenyl)ethyl)carbamoyl)cyclohexyl)sulfamoyl)-3,4-dihydroquinoxaline-1(2H)-carboxylate |
| 218 | 21 | 7.072 | D | 533.2 (M + H+) | | (1r,4R)-N-((R)-1-(4-fluorophenyl)ethyl)-4-(2-(pyridin-3-yl)quinoline-6-sulfonamido)cyclohexanecarboxamide |
| 219 | 21 | 6.827 | D | 528.2 (M + H+) | | 3-(6-(N-((1R,4r)-4-((R)-1-(4-fluorophenyl)ethyl)carbamoyl)cyclohexyl)sulfamoyl)quinolin-2-yl)propanoic acid |
| 220 | 22 | 8.363 | D | 560 (M + H+) | | (1r,4R)-N-((R)-1-(4-fluorophenyl)ethyl)-4-(1-(4-methyl)pentanoyl)-1,2,3,4-tetrahydropyrido[3,2-b]pyrazine-7-sulfonamido)cyclohexanecarboxamide |
| 221 | 29 | 8.107 | D | 519.2 (M + H+) | | methyl 7-(N-((1R,4r)-4-((R)-1-(4-fluorophenyl)ethyl)carbamoyl)cyclohexyl)sulfamoyl)-3,4-dihydroquinoxaline-1(2H)-carboxylate |
| 222 | 22 | 6.987 | D | 520 (M + H+) | | methyl 7-(N-((1R,4r)-4-((R)-1-(4-fluorophenyl)ethyl)carbamoyl)cyclohexyl)sulfamoyl)-3,4-dihydropyrido[3,2-b]pyrazine-1(2H)-carboxylate |
| 223 | 33 | 7.381 | F | 474.2 (M + H+) | | (1r,4R)-N-((R)-1-(4-fluorophenyl)ethyl)-4-(1-oxo-1,2,3,4-tetrahydroisoquinoline-7-sulfonamido)cyclohexanecarboxamide |
| 224 | 28 | 9.163 | F | 532 (M + H+) | | methyl 7-(N-((1R,4r)-4-((R)-1-(4-fluorophenyl)ethyl)carbamoyl)cyclohexyl)sulfamoyl)-1-methyl-1,2,3,4-tetrahydroquinoline-2-carboxylate |

-continued

| Ex. | Synthetic Scheme | HPLC RT | HPLC Method | MS | NMR | Name |
|---|---|---|---|---|---|---|
| 225 | 28 | 8.309 | D | 518.2 (M + H+) | | 7-(N-((1R,4r)-4-((R)-1-(4-fluorophenyl)ethyl)carbamoyl)cyclohexyl)sulfamoyl)-1-methyl-1,2,3,4-tetrahydroquinoline-2-carboxylic acid |
| 226 | 1 | 15.72 | E | 493 (M + H+) | | (1r,4R)-4-(9H-fluorene-2-sulfonamido)-N-((R)-1-(4-fluorophenyl)ethyl)cyclohexanecarboxamide |
| 227 | 21 | 7.211 | D | 561.3 (M + H+) | | (1r,4R)-4-(2,6-dimethylpyridin-4-yl)quinoline-6-sulfonamido)-N-((R)-1-(4-fluorophenyl)ethyl)cyclohexanecarboxamide |
| 228 | 21 | 13.92 | E | 526 (M + H+) | | (R)-3-((1r,4R)-4-(2-ethoxyquinoline-6-sulfonamido)cyclohexanecarboxamido)-3-phenylpropanoic acid |
| 229 | 21 | 7.093 | D | 547.2 (M + H+) | | (1r,4R)-N-((R)-1-(4-fluorophenyl)ethyl)-4-(2-(2-methylpyridin-4-yl)quinoline-6-sulfonamido)cyclohexanecarboxamide |
| 230 | 21 | 7.488 | D | 533.2 (M + H+) | | (1r,4R)-N-((R)-1-(4-fluorophenyl)ethyl)-4-(2-(pyridin-2-yl)quinoline-6-sulfonamido)cyclohexanecarboxamide |
| 231 | 21 | 10.208 | D | 514.2 (M + H+) | | (1r,4R)-4-(2-ethoxyquinoline-6-sulfonamido)-N-((R)-1-(4-fluorophenyl)ethyl)-1-methylcyclohexanecarboxamide |
| 232 | 21 | 8.053 | D | 640.3 (M + H+) | | tert-butyl 4-(6-(N-((1R,4r)-4-((R)-1-(4-fluorophenyl)ethyl)carbamoyl)cyclohexyl)sulfamoyl)quinolin-2-yl)piperazine-1-carboxylate |
| 233 | 22 | 13.31 | E | 610 (M + H+) | | (1r,4R)-4-(1-(2-(benzyloxy)acetyl)-1,2,3,4-tetrahydropyrido[3,2-b]pyrazine-7-sulfonamido)-N-((R)-1-(4-fluorophenyl)ethyl)cyclohexanecarboxamide |
| 234 | 21 | 12.89 | E | 523 (M + H+) | | 2-ethoxy-N-((1S,4r)-4-((S)-2-phenylpiperazine-1-carbonyl)cyclohexyl)quinoline-6-sulfonamide |
| 235 | 21 | 15.56 | E | 605 (M + H+) | | (R)-1-tert-butyl 4-methyl 4-((1r,4R)-4-(2-ethoxyquinoline-6-sulfonamido)cyclohexanecarbonyl)piperazine-1,3-dicarboxylate |
| 236 | 21 | 11.99 | E | 505 (—C4H9) (M + H+) | | (R)-methyl 1-((1r,4R)-4-(2-ethoxyquinoline-6-sulfonamido)cyclohexanecarbonyl)piperazine-2-carboxylate |
| 237 | 21 | 6.347 | D | 566.2 (M + H+) | | (1r,4R)-4-(2-(4,7-diazaspiro[2.5]octan-7-yl)quinoline-6-sulfonamido)-N-((R)-1-(4-fluorophenyl)ethyl)cyclohexanecarboxamide |
| 238 | 21 | 6.229 | D | 540.2 (M + H+) | | (1r,4R)-N-((R)-1-(4-fluorophenyl)ethyl)-4-(2-(piperazin-1-yl)quinoline-6-sulfonamido)cyclohexanecarboxamide |
| 239 | 22 | 7.659 | D | 532.1 (M + H+) | | N-ethyl-7-(N-((1R,4r)-4-((R)-1-(4-fluorophenyl)ethyl)carbamoyl)cyclohexyl)sulfamoyl)-3,4-dihydroquinoxaline-1(2H)-carboxamide |
| 240 | 1 | 17.3 | E | 616 (M + H+) | | (S)-tert-butyl 4-((1r,4S)-4-(9H-fluorene-2-sulfonamido)cyclohexanecarbonyl)-3-phenylpiperazine-1-carboxylate |

-continued

| Ex. | Synthetic Scheme | HPLC RT | HPLC Method | MS | NMR | Name |
|---|---|---|---|---|---|---|
| 241 | 1 | 14.51 | E | 568 (M + H+) | | (S)-tert-butyl 4-((1r,4S)-4-(2,3-dihydro-1H-indene-5-sulfonamido)cyclohexanecarbonyl)-3-phenylpiperazine-1-carboxylate |
| 242 | 21 | 6.731 | D | 598.2 (M + H+) | | methyl 4-(6-(N-((1R,4r)-4-((R)-1-(4-fluorophenyl)ethyl)carbamoyl)cyclohexyl)sulfamoyl)quinolin-2-yl)piperazine-2-carboxylate |
| 243 | 1 | 15.91 | E | 495 (M + H+) | | (1r,4R)-4-(dibenzo[b,d]furan-2-sulfonamido)-N-((R)-1-(4-fluorophenyl)ethyl)cyclohexanecarboxamide |
| 244 | 1 | 13.38 | E | 516 (M + H+) | | N-((1S,4r)-4-((S)-2-phenylpiperazine-1-carbonyl)cyclohexyl)-9H-fluorene-2-sulfonamide |
| 245 | 1 | 12 | E | 468 (M + H+) | | N-((1S,4r)-4-((S)-2-phenylpiperazine-1-carbonyl)cyclohexyl)-2,3-dihydro-1H-indene-5-sulfonamide |
| 246 | 21 | | | 491.1 (M + H+) | | (R)-1-((1r,4R)-4-(2-ethoxyquinoline-6-sulfonamido)cyclohexanecarbonyl)piperazine-2-carboxylic acid |
| 247 | 21 | 6.763 | D | 578.2 (M + H+) | | (1r,4R)-N-((R)-1-(4-fluorophenyl)ethyl)-4-(2-(3-(piperazin-1-yl)prop-1-ynyl)quinoline-6-sulfonamido)cyclohexanecarboxamide |
| 248 | 21 | 7.147 | D | 608.2 (M + H+) | | (1r,4R)-N-((R)-1-(4-fluorophenyl)ethyl)-4-(2-(3-(trifluoromethyl)piperazin-1-yl)quinoline-6-sulfonamido)cyclohexanecarboxamide |
| 249 | 21 | 8.736 | D | 576.2 (M + H+) | | 3-(6-(N-((1R,4r)-4-((R)-1-(4-fluorophenyl)ethylcarbamoyl)cyclohexyl)sulfamoyl)quinolin-2-yl)benzoic acid |
| 250 | 28 | 8.309 | D | 518 (M + H+) | | (S)-7-(N-((1R,4S)-4-((R)-1-(4-fluorophenyl)ethyl)carbamoyl)cyclohexyl)sulfamoyl)-1-methyl-1,2,3,4-tetrahydroquinoline-2-carboxylic acid |
| 251 | 28 | 8.309 | D | 518 (M + H+) | | (R)-7-(N-((1R,4R)-4-((R)-1-(4-fluorophenyl)ethyl)carbamoyl)cyclohexyl)sulfamoyl)-1-methyl-1,2,3,4-tetrahydroquinoline-2-carboxylic acid |
| 252 | 21 | | | 454.2 (M + H+) | | (1r,4r)-methyl 4-(2-(2,6-dimethylpyridin-4-yl)quinoline-6-sulfonamido)cyclohexanecarboxylate |
| 253 | 21 | 6.645 | D | 587 (M + H+) | | (1r,4r)-4-(2-(2,6-dimethylpyridin-4-yl)quinoline-6-sulfonamido)-N-(4-hydroxy-2-methyl-1-phenylpropyl)cyclohexanecarboxamide |
| 254 | 21 | 5.685 | D | 584 (M + H+) | | 2-(2,6-dimethylpyridin-4-yl)-N-((1r,4r)-4-(2-phenylpiperazine-1-carbonyl)cyclohexyl)quinoline-6-sulfonamide |
| 255 | 1 | 17.25 | E | 618 (M + H+) | | (S)-tert-butyl 4-((1r,4S)-4-(dibenzo[b,d]furan-2-sulfonamido)cyclohexanecarbonyl)-3-phenylpiperazine-1-carboxylate |
| 256 | 1 | 13.26 | E | 518 (M + H+) | | N-((1S,4r)-4-((S)-2-phenylpiperazine-1-carbonyl)cyclohexyl)dibenzo[b,d]furan-2-sulfonamide |

-continued

| Ex. | Synthetic Scheme | HPLC RT | HPLC Method | MS | NMR | Name |
|---|---|---|---|---|---|---|
| 257 | 21 | 5.611 | D | 584 (M + H+) | | 2-(2,6-dimethylpyridin-4-yl)-N-((1R,4r)-4-((R)-2-phenylpiperazine-1-carbonyl)cyclohexyl)quinoline-6-sulfonamide |
| 258 | 21 | 5.771 | D | 580.4 (M + H+) | | (1r,4R)-N-((R)-2-hydroxy-2-methyl-1-phenylpropyl)-4-(2-(4-methylpiperazin-1-yl)quinoline-6-sulfonamido)cyclohexanecarboxamide |
| 259 | 21 | | | 577.2 (M + H+) | | 2-(4-methylpiperazin-1-yl)-N-((1r,4r)-4-(2-phenylpiperazine-1-carbonyl)cyclohexyl)quinoline-6-sulfonamide |
| 260 | 21 | | | 544.3 (M + H+) | | N-((1S,4r)-4-((S)-3-isopropylmorpholine-4-carbonyl)cyclohexyl)-2-(4-methylpiperazin-1-yl)quinoline-6-sulfonamide |
| 261 | 21 | | | 551.3 (M + H+) | | 2-(2,6-dimethylpyridin-4-yl)-N-((1S,4r)-4-((S)-3-isopropylmorpholine-4-carbonyl)cyclohexyl)quinoline-6-sulfonamide |
| 262 | 22 | | | 514.3 (M + H+) | | 4-(1,2,3,4-Tetrahydro-pyrido[2,3-b] pyrazine-7-sulfonylamino)-adamantane-1-carboxylic acid [(R)-1-(4-fluoro-phenyl)-ethyl]-amide |
| 263 | 1 | | | 618.3 (M + H+) | | (S)-tert-butyl 4-((1r,4S)-4-(dibenzo[b,d]furan-3-sulfonamido)cyclohexanecarbonyl)-3-phenylpiperazine-1-carboxylate |
| 264 | 1 | | | 518.1 (M + H+) | | N-((1S,4r)-4-((S)-2-phenylpiperazine-1-carbonyl)cyclohexyl)dibenzo[b,d]furan-3-sulfonamide |
| 265 | 1 | | | 440 (M + H+) | | 4-(Dibenzofuran-2-sulfonylamino)-adamantane-1-carboxylic acid methyl ester |
| 266 | 21 + 37 | | | 597.4 (M + H+) | | (S)-(S)-2-((1r,4S)-4-(2-ethoxyquinoline-6-sulfonamido)cyclohexanecarboxamido)-2-phenylethyl) 2-amino-3-methylbutanoate |
| 267 | 1 | | | 402.1 (M + H+) | | (1r,4r)-methyl 4-((dibenzo[b,d]furan-2-sulfonamido)methyl)cyclohexanecarboxylate |
| 268 | 21 + 36 | | | 690.3 (M + H+) | | di-tert-butyl (S)-2-((1r,4S)-4-(2-ethoxyquinoline-6-sulfonamido)cyclohexanecarboxamido)-2-phenylethyl phosphate |
| 269 | 21 + 36 | | | 578.1 (M + H+) | | (S)-2-((1r,4S)-4-(2-ethoxyquinoline-6-sulfonamido)cyclohexanecarboxamido)-2-phenylethyl dihydrogen phosphate |
| 270 | 22 | | | 488.4 (M + H+) | | (R)-N-(1-(4-fluorophenyl)ethyl)-4-(1,2,3,4-tetrahydropyrido[3,2-b]pyrazine-7-sulfonamido)bicyclo[2.2.2]octane-1-carboxamide |
| 271 | 21 + 35 | | | 611.3 (M + H+) | | (S)-((1S,2S)-1-((1r,4S)-4-(2-ethoxyquinoline-6-sulfonamido)cyclohexanecarboxamido)-1-phenylpropan-2-yl) 2-amino-3-methylbutanoate |
| 272 | 21 + 35 | | | 611.2 (M + H+) | | (S)-(S)-2-((1r,4S)-4-(2-ethoxyquinoline-6-sulfonamido)cyclohexanecarboxamido)-2-phenylethyl) 3-methyl-2-(methylamino)butanoate |
| 273 | 21 + 35 | | | 645.1 (M + H+) | | (S)-(S)-2-((1r,4S)-4-(2-ethoxyquinoline-6-sulfonamido)cyclohexanecarboxamido)-2-phenylethyl) 2-amino-3-phenylpropanoate |

| Ex. | Synthetic Scheme | HPLC RT | HPLC Method | MS | NMR | Name |
|---|---|---|---|---|---|---|
| 274 | 1 | 17.78 | E | 557.1814 (M + H+) | | (1r,4S)-4-(2-phenyl-1H-benzo[d]imidazole-5-sulfonamido)-N-((S)-2,2,2-trifluoro-1-phenylethyl)cyclohexanecarboxamide |
| 275 | 2 | 11.35 | E | 561.2146 (M + H+) | | methyl 4-(5-(N-((1R,4r)-4-((R)-1-phenylethylcarbamoyl)cyclohexyl)sulfamoyl)-1H-benzo[d]imidazol-2-yl)benzoate |
| 276 | 2 | 10.87 | E | 521.2004 (M + H+) | | (1r,4R)-4-(2-(4-fluorophenyl)-1H-benzo[d]imidazole-5-sulfonamido)-N-((R)-1-phenylethyl)cyclohexanecarboxamide |
| 277 | 2 | 9.36 | E | 467.2114 (M + H+) | | (1r,4R)-4-(2-cyclopropyl-1H-benzo[d]imidazole-5-sulfonamido)-N-((R)-1-phenylethyl)cyclohexanecarboxamide |
| 278 | 2 | 10.28 | E | 547.202 (M + H+) | | 4-(5-(N-((1R,4r)-4-((R)-1-phenylethylcarbamoyl)cyclohexyl)sulfamoyl)-1H-benzo[d]imidazol-2-yl)benzoic acid |
| 279 | 2 | 10.32 | E | 547.2015 (M + H+) | | 3-(5-(N-((1R,4r)-4-((R)-1-phenylethylcarbamoyl)cyclohexyl)sulfamoyl)-1H-benzo[d]imidazol-2-yl)benzoic acid |
| 280 | 2 | 9.43 | E | 504.2076 (M + H+) | | (1r,4R)-N-((R)-1-phenylethyl)-4-(2-(pyridin-4-yl)-1H-benzo[d]imidazole-5-sulfonamido)cyclohexanecarboxamide |
| 281 | 2 | 9.65 | E | 504.2065 (M + H+) | | (1r,4R)-N-((R)-1-phenylethyl)-4-(2-(pyridin-3-yl)-1H-benzo[d]imidazole-5-sulfonamido)cyclohexanecarboxamide |
| 282 | 11 | 13.9 | E | 502.217 (M + H+) | | (1r,4R)-4-(2-phenyl-1H-indole-6-sulfonamido)-N-((R)-1-phenylethyl)cyclohexanecarboxamide |
| 283 | 8 | 6.93 | E | 504.2072 (M + H+) | | (1r,4r)-4-(2-(pyridin-3-yl)-1H-indole-5-sulfonamido)-N-(1-(pyridin-4-yl)ethyl)cyclohexanecarboxamide |
| 284 | 8 | 9.96 | E | 503.2121 (M + H+) | 1H NMR (400 MHz, DMSO-d6) d ppm 1.00-1.34 (m, 7H) 1.52-1.70 (m, 4H) 1.91-2.06 (m, 1H) 2.76-2.93 (m, 1H) 4.73-4.87 (m, 1H) 7.12-7.32 (m, 6H) 7.39-7.47 (m, 1H) 7.50-7.55 (m, 1H) 7.57 (d, J = 1.01 Hz, 2H) 7.99-8.13 (m, 1H) 8.17-8.31 (m, 1H) 8.49-8.59 (m, 1H) 9.03-9.21 (m, 1H) 12.15 (br. s., 1H) | (1r,4R)-N-((R)-1-phenylethyl)-4-(2-(pyridin-3-yl)-1H-indole-5-sulfonamido)cyclohexanecarboxamide |
| 285 | 8 | 10.15 | E | 521.2029 (M + H+) | | (1r,4R)-N-((R)-1-(4-fluorophenyl)ethyl)-4-(2-(pyridin-3-yl)-1H-indole-5-sulfonamido)cyclohexanecarboxamide |
| 286 | 8 | 8.73 | E | 455.2126 (M + H+) | | (1r,4r)-N-sec-butyl-4-(2-(pyridin-3-yl)-1H-indole-5-sulfonamido)cyclohexanecarboxamide |
| 287 | 8 | 8.73 | E | 455.2119 (M + H+) | | (1r,4R)-N-sec-butyl-4-(2-(pyridin-3-yl)-1H-indole-5-sulfonamido)cyclohexanecarboxamide |
| 288 | 8 | 8.89 | E | 455.2123 (M + H+) | | (1r,4r)-N-isopropyl-N-methyl-4-(2-(pyridin-3-yl)-1H-indole-5-sulfonamido)cyclohexanecarboxamide |

| Ex. | Synthetic Scheme | HPLC RT | HPLC Method | MS | NMR | Name |
|---|---|---|---|---|---|---|
| 289 | 8 | 9.37 | E | 469.2276 (M + H+) | | (1r,4R)-N-((R)-3-methylbutan-2-yl)-4-(2-(pyridin-3-yl)-1H-indole-5-sulfonamido)cyclohexanecarboxamide |
| 290 | 10 | 12.93 | E | 484.2064 (M + H+) | 1H NMR (400 MHz, DMSO-d6) d ppm 0.78-0.88 (m, 2H) 0.98-1.05 (m, 2H) 1.06-1.30 (m, 4H) 1.26 (d, J = 7.07 Hz, 3H) 1.52-1.68 (m, 4H) 1.92-2.02 (m, 1H) 2.03-2.13 (m, 1H) 2.74-2.88 (m, 1H) 4.72-4.90 (m, 1H) 6.17-6.25 (m, 1H) 7.03-7.15 (m, 2H) 7.21-7.30 (m, 2H) 7.31-7.43 (m, 2H) 7.50 (d, J = 8.34 Hz, 1H) 7.67-7.73 (m, 1H) 8.08 (d, J = 8.08 Hz, 1H) 11.35 (br. s., 1H) | (1r,4R)-4-(2-cyclopropyl-1H-indole-6-sulfonamido)-N-((R)-1-(4-fluorophenyl)ethyl)cyclohexanecarboxamide |
| 291 | 10 | 14.22 | E | 554.1669 (M + H+) | 1H NMR (400 MHz, DMSO-d6) d ppm 1.05-1.32 (m, 4H) 1.26 (d, J = 7.07 Hz, 3H) 1.55-1.72 (m, 4H) 1.92-2.05 (m, 1H) 2.79-2.94 (m, 1H) 4.74-4.88 (m, 1H) 6.98 (dd, J = 2.27, 1.01 Hz, 1H) 7.03-7.14 (m, 2H) 7.21-7.30 (m, 2H) 7.40-7.57 (m, 4H) 7.64 (dd, J = 7.96, 1.39 Hz, 1H) 7.72-7.79 (m, 2H) 7.87-7.91 (m, 1H) 8.08 (d, J = 8.08 Hz, 1H) 11.93 (br. s., 1H) | (1r,4R)-4-(2-(2-chlorophenyl)-1H-indole-6-sulfonamido)-N-((R)-1-(4-fluorophenyl)ethyl)cyclohexanecarboxamide |
| 292 | 10 | 14.16 | E | 534.224 (M + H+) | 1H NMR (400 MHz, DMSO-d6) d ppm 1.05-1.30 (m, 4H) 1.26 (d, J = 7.07 Hz, 3H) 1.54-1.72 (m, 4H) 1.94-2.04 (m, 1H) 2.48 (s, 3H) 2.78-2.94 (m, 1H) 4.71-4.92 (m, 1H) 6.70-6.75 (m, 1H) 7.04-7.15 (m, 2H) 7.22-7.29 (m, 2H) 7.31-7.40 (m, 3H) 7.45 (dd, J = 8.34, 1.52 Hz, 1H)7.49 (d, J = 7.33 Hz, 1H) 7.54-7.60 (m, 1H) 7.71 (d, J = 8.34 Hz, 1H) 7.85-7.88 (m, 1H) 8.08 (d, j = 8.08 Hz, 1H) 11.77 (br. s., 1H) | (1r,4R)-N-((R)-1-(4-fluorophenyl)ethyl)-4-(2-o-tolyl-1H-indole-6-sulfonamido)cyclohexanecarboxamide |
| 293 | 10 | 15.35 | E | 550.2185 (M + H+) | | (1r,4R)-N-((R)-1-(4-fluorophenyl)ethyl)-4-(2-(2-methoxyphenyl)-1H-indole-6-sulfonamido)cyclohexanecarboxamide |
| 294 | 10 | 9.4 | E | 467.2102 (M + H+) | | (1r,4R)-4-(2-cyclopropyl-1H-indole-6-sulfonamido)-N-((R)-1-(pyridin-2-yl)ethyl)cyclohexanecarboxamide |
| 295 | 10 | 15.05 | E | 586.115 (M + H+) | | (1r,4R)-4-(2-(2,6-dichlorophenyl)-1H-indole-6-sulfonamido)-N-((R)-1-(4-fluorophenyl)ethyl)cyclohexanecarboxamide |

| Ex. | Synthetic Scheme | HPLC RT | HPLC Method | MS | NMR | Name |
|---|---|---|---|---|---|---|
| 296 | 10 | 12.57 | E | 549.2105 (M + H+) | 1H NMR (400 MHz, DMSO-d6) δ ppm 1.03-1.34 (m, 7H) 1.63 (br. s., 4H) 1.98 (br. s., 1H) 2.79-2.94 (m, 1H) 4.55 (d, J = 5.81 Hz, 2H) 4.75-4.87 (m, 1H) 5.27 (t, J = 5.68 Hz, 1H) 7.01 (d, J = 1.26 Hz, 1H) 7.04-7.12 (m, 2H) 7.21-7.29 (m, 2H) 7.40-7.47 (m, 3H) 7.49 (d, J = 7.33 Hz, 1H) 7.68 (d, J = 8.34 Hz, 1H) 7.81-7.89 (m, 3H) 8.07 (d, J = 8.08 Hz, 1H) 11.96 (s, 1H) | (1r,4R)-N-((R)-1-(4-fluorophenyl)ethyl)-4-(2-(4-(hydroxymethyl)phenyl)-1H-indole-6-sulfonamido)cyclohexanecarboxamide |
| 297 | 10 | 14.83 | E | 563.2272 (M + H+) | | (1r,4R)-N-((R)-1-(4-fluorophenyl)ethyl)-4-(2-(4-methoxy-2-methylphenyl)-1H-indole-6-sulfonamido)cyclohexanecarboxamide |
| 298 | 10 | 15.57 | E | 547.2316 (M + H+) | | (1r,4R)-4-(2-(2,5-dimethylphenyl)-1H-indole-6-sulfonamido)-N-((R)-1-(4-fluorophenyl)ethyl)cyclohexanecarboxamide |
| 299 | 10 | 13.19 | E | 549.21 (M + H+) | | (1r,4R)-N-((R)-1-(4-fluorophenyl)ethyl)-4-(2-(2-(hydroxymethyl)phenyl)-1H-indole-6-sulfonamido)cyclohexanecarboxamide |
| 300 | 10 | 14.56 | E | 591.2206 (M + H+) | | methyl 4-(6-(N-((1R,4r)-4-((R)-1-(4-fluorophenyl)ethylcarbamoyl)cyclohexyl)sulfamoyl)-1H-indol-2-yl)-3-methylbenzoate |
| 301 | 10 | 12.85 | E | 577.2046 (M + H+) | | 4-(6-(N-((1R,4r)-4-((R)-1-(4-fluorophenyl)ethylcarbamoyl)cyclohexyl)sulfamoyl)-1H-indol-2-yl)-3-methylbenzoic acid |
| 302 | 10 | 12.7 | E | 563.2256 (M + H+) | 1H NMR (400 MHz, DMSO-d6) δ ppm 1.05-1.33 (m, 7H) 1.64 (br, 4H) 1.93-2.05 (m, 1H) 2.48 (s, 3 H) 2.80-2.94 (m, 1H) 4.54 (s, 2 H) 4.77-4.88 (m, 1H) 6.70 (d, J = 1.52 Hz, 1H) 7.06-7.14 (m, 2 H) 7.21-7.35 (m, 4H) 7.39-7.60 (m, 4H) 7.41-7.58 (m, 3H) 7.71 (d, J = 8.34 Hz, 1H) 7.86 (s, 1H) 8.09 (d, J = 8.08 Hz, 1H) 11.74 (br. s., 1H) | (1r,4R)-N-((R)-1-(4-fluorophenyl)ethyl)-4-(2-(4-(hydroxymethyl)phenyl)-2-methylphenyl)-1H-indole-6-sulfonamido)cyclohexanecarboxamide |
| 303 | 10 | 14.36 | E | 499.2319 (M + H+) | | (1r,4R)-N-((R)-1-(4-fluorophenyl)ethyl)-4-(2-isobutyl-1H-indole-6-sulfonamido)cyclohexanecarboxamide |
| 304 | 10 | 14.62 | E | 511.2316 (M + H+) | | (1r,4R)-4-(2-cyclopentyl-1H-indole-6-sulfonamido)-N-((R)-1-(4-fluorophenyl)ethyl)cyclohexanecarboxamide |
| 305 | 10 | 10.97 | E | 487.1951 (M + H+) | | (1r,4R)-N-((R)-1-(4-fluorophenyl)ethyl)-4-(2-(2-hydroxyethyl)-1H-indole-6-sulfonamido)cyclohexanecarboxamide |
| 306 | 10 | 12.07 | E | 565.1722 (M + H+) | | 2-(6-(N-((1R,4r)-4-((R)-1-(4-fluorophenyl)ethylcarbamoyl)cyclohexyl)sulfamoyl)-1H-indol-2-yl)ethyl methanesulfonate |

| Ex. | Synthetic Scheme | HPLC RT | HPLC Method | MS | NMR | Name |
|---|---|---|---|---|---|---|
| 307 | 10 | 13.49 | E | 545.20182 (M + H+) | 1H NMR (400 MHz, DMSO-d6) d ppm 1.00-1.36 (m, 9H) 1.51-1.75 (m, 4H) 1.99 (br. s., 1H) 2.87 (br. s., 1H) 4.67-4.93 (m, 1H) 6.99-7.14 (m, 2H) 7.18-7.34 (m, 3H) 7.49 (dd, J = 8.46, 1.64 Hz, 1H) 7.54-7.68 (m, 2H) 7.76-7.98 (m, 3H) 7.96-8.16 (m, 2H) | (1r,4R)-4-(2-(2-cyanophenyl)-1H-indole-6-sulfonamido)-N-(R)-1-(4-fluorophenyl)ethyl)cyclohexanecarboxamide |
| 308 | 11 | | | | 1H NMR (400 MHz, DMSO-d6) d ppm 1.12-1.31 (m, 4H) 1.48-1.73 (m, 4H) 2.35-2.49 (m, 1H) 2.48 (s, 3H) 2.80-2.92 (m, 1H) 3.25-3.56 (m, 8H) 4.54 (s, 2H) 5.27 (br. s., 1H) 6.70 (s, 1H) 7.25-7.34 (m, 2H) 7.40-7.48 (m, 1H) 7.54 (d, J = 7.83 Hz, 1H) 7.70 (d, J = 8.34 Hz, 1H) 7.86 (s, 1H) 11.74 (br. s., 1H) | 2-(4-(hydroxymethyl)-2-methylphenyl)-N-((1r,4r)-4-(morpholine-4-carbonyl)cyclohexyl)-1H-indole-6-sulfonamide |
| 309 | 11 | 14.07 | E | 687.321 (M + H+) | | (S)-tert-butyl 4-((1r,4S)-4-(2-(4-(hydroxymethyl)-2-methylphenyl)-1H-indole-6-sulfonamido)cyclohexanecarbonyl)-3-phenylpiperazine-1-carboxylate |
| 310 | 11 | 12.6 | E | 611.29038 (M + H+) | | tert-butyl 4-((1r,4r)-4-(2-(4-(hydroxymethyl)-2-methylphenyl)-1H-indole-6-sulfonamido)cyclohexanecarbonyl)piperazine-1-carboxylate |
| 311 | 11 | 12.52 | E | 588.25271 (M + H+) | | 2-(4-(hydroxymethyl)-2-methylphenyl)-N-((1r,4r)-4-(3-phenylmorpholine-4-carbonyl)cyclohexyl)-1H-indole-6-sulfonamide |
| 312 | 11 | 8.96 | E | 511.23902 (M + H+) | | 2-(4-(hydroxymethyl)-2-methylphenyl)-N-((1r,4r)-4-(piperazine-1-carbonyl)cyclohexyl)-1H-indole-6-sulfonamide |
| 313 | 11 | 10.09 | E | 587.26931 (M + H+) | | 2-(4-(hydroxymethyl)-2-methylphenyl)-N-((1S,4r)-4-((S)-2-phenylpiperazine-1-carbonyl)cyclohexyl)-1H-indole-6-sulfonamide |
| 314 | 11 | 11.93 | E | 510.24365 (M + H+) | | 2-(4-(hydroxymethyl)-2-methylphenyl)-N-((1r,4r)-4-(piperidine-1-carbonyl)cyclohexyl)-1H-indole-6-sulfonamide |
| 315 | 12 | 13.02 | E | 578.24929 (M + H+) | | (1r,4R)-N-((R)-1-(4-fluorophenyl)ethyl)-4-(2-(4-(hydroxymethyl)-2-methylphenyl)-1-methyl-1H-indole-6-sulfonamido)cyclohexanecarboxamide |
| 316 | 10 | 11.34 | E | 502.2184 (M + H+) | | (1r,4R)-N-((R)-1-(4-fluorophenyl)ethyl)-4-(2-(2-hydroxypropyl)-1H-indole-6-sulfonamido)cyclohexanecarboxamide |
| 317 | 11 | 9.6 | E | 579.22732 (M + H+) | | 2-(4-(hydroxymethyl)-2-methylphenyl)-N-((1r,4r)-4-(3-(trifluoromethyl)piperazine-1-carbonyl)cyclohexyl)-1H-indole-6-sulfonamide |
| 318 | 12 | 9.98 | E | 593.24279 (M + H+) | | 2-(4-(hydroxymethyl)-2-methylphenyl)-N-((1r,4r)-4-(3-(trifluoromethyl)piperazine-1-carbonyl)cyclohexyl)-1-methyl-1H-indole-6-sulfonamide |

| Ex. | Synthetic Scheme | HPLC RT | HPLC Method | MS | NMR | Name |
|---|---|---|---|---|---|---|
| 319 | 10 | 11.23 | E | 502.21868 (M + H+) | 1H NMR (400 MHz, DMSO-d6) d ppm 0.93-1.33 (m, 9H) 1.61 (d, J = 9.73 Hz, 4H) 1.71-1.90 (m, 2H) 1.98 (br. s., 1H) 2.80 (t, J = 7.64 Hz, 3H) 3.47 (t, J = 5.87 Hz, 2H) 4.81 (t, J = 7.39 Hz, 1H) 6.27 (s, 1H) 6.97-7.16 (m, 2H) 7.18-7.29 (m, 2H) 7.37 (dd, J = 8.27, 1.58 Hz, 2H) 7.55 (d, J = 8.34 Hz, 1H) 7.73 (s, 1H) 8.07 (d, J = 8.08 Hz, 1H) | (1r,4R)-N-((R)-1-(4-fluorophenyl)ethyl)-4-(2-(3-hydroxypropyl)-1H-indole-6-sulfonamido)cyclohexanecarboxamide |
| 320 | 11 | 10.75 | E | 549.21606 (M + H+) | | 2-o-tolyl-N-((1r,4r)-4-(3-(trifluoromethyl)piperazine-1-carbonyl)cyclohexyl)-1H-indole-6-sulfonamide |
| 321 | 11 | 14.15 | E | 548.22025 (M + H+) | | 2-o-tolyl-N-((1r,4r)-4-(3-(trifluoromethyl)piperidine-1-carbonyl)cyclohexyl)-1H-indole-6-sulfonamide |
| 322 | 11 | 15.2 | E | 657.3116 (M + H+) | | (S)-tert-butyl 3-phenyl-4-((1r,4S)-4-(2-o-tolyl-1H-indole-6-sulfonamido)cyclohexanecarbonyl)piperazine-1-carboxylate |
| 323 | 11 | 9.93 | E | 535.20098 (M + H+) | | 2-phenyl-N-((1r,4r)-4-(3-(trifluoromethyl)piperazine-1-carbonyl)cyclohexyl)-1H-indole-6-sulfonamide |
| 324 | 12 | 9.48 | E | 549.21682 (M + H+) | | 1-methyl-2-phenyl-N-((1r,4r)-4-(3-(trifluoromethyl)piperazine-1-carbonyl)cyclohexyl)-1H-indole-6-sulfonamide |
| 325 | 11 | 9.7 | E | 557.2604 (M + H+) | 1H NMR (400 MHz, DMSO-d6) d ppm 1.03-1.48 (m, 6H) 1.54-1.88 (m, 5H) 2.84-3.05 (m, 4H) 3.35 (s, 3H) 3.41-3.54 (m, 2H) 3.62-3.79 (m, 1H) 3.87-4.05 (m, 1H) 6.73 (s, 1H) 7.21 (br. s., 3H) 7.36 (m, 7H) 7.53-7.62 (m, 1H) 7.72 (d, J = 8.21 Hz, 1H) 7.88 (s, 1H) | N-((1S,4r)-4-((S)-2-phenylpiperazine-1-carbonyl)cyclohexyl)-2-o-tolyl-1H-indole-6-sulfonamide |
| 326 | 11 | 14.48 | E | 558.24347 (M + H+) | | N-((1S,4r)-4-((S)-3-phenylmorpholine-4-carbonyl)cyclohexyl)-2-o-tolyl-1H-indole-6-sulfonamide |
| 327 | 11 | 14.48 | E | 558.2442 (M + H+) | 1H NMR (400 MHz, DMSO-d6) d ppm 1.17-1.45 (m, 5H) 1.51-1.77 (m, 4H) 2.79-3.00 (m, 1H) 3.04-3.14 (m, 1H) 3.17 (s, 3H) 3.38-3.47 (m, 1H) 3.54-3.89 (m, 3H) 4.11 (q, J = 5.31 Hz, 1H) 4.37 (d, J = 12.13 Hz, 1H) 5.42 (br. s., 1H) 6.72 (s, 1H) 7.13-7.42 (m, 8H) 7.42-7.51 (m, 1H) 7.53-7.62 (m, 2H) 7.72 (d, J = 8.34 Hz, 1H) 7.88 (br. s., 1H) | N-((1S,4r)-4-((S)-3-phenylmorpholine-4-carbonyl)cyclohexyl)-2-o-tolyl-1H-indole-6-sulfonamide |

| Ex. | Synthetic Scheme | HPLC RT | HPLC Method | MS | NMR | Name |
|---|---|---|---|---|---|---|
| 328 | 11 | 15.36 | E | 711.28333 (M + H+) | | (S)-tert-butyl 3-phenyl-4-((1r,4S)-4-(2-(2-(trifluoromethyl)phenyl)-1H-indole-6-sulfonamido)cyclohexanecarbonyl)piperazine-1-carboxylate |
| 329 | 10 | 14.05 | E | 588.19567 (M + H+) | | (1r,4R)-N-((R)-1-(4-fluorophenyl)ethyl)-4-(2-(2-(trifluoromethyl)phenyl)-1H-indole-6-sulfonamido)cyclohexanecarboxamide |
| 330 | 11 | 14.32 | E | 602.19258 (M + H+) | | 2-(2-(trifluoromethyl)phenyl)-N-((1r,4r)-4-(3-(trifluoromethyl)piperidine-1-carbonyl)cyclohexyl)-1H-indole-6-sulfonamide |
| 331 | 12 | | | | 1H NMR (400 MHz, DMSO-d6) d ppm 1.11-1.73 (m, 8H) 2.31-4.12 (m, 10H) 3.83 (s, 3H) 6.71 (d, J = 0.76 Hz, 1H) 7.46-7.59 (m, 5H) 7.62-7.68 (m, 2H) 7.73 (d, J = 8.34 Hz, 1H) 7.98 (d, J = 1.01 Hz, 1H) | 1-methyl-2-phenyl-N-((1S,4r)-4-((S)-3-(trifluoromethyl)piperazine-1-carbonyl)cyclohexyl)-1H-indole-6-sulfonamide |
| 332 | 12 | | | | 1H NMR (400 MHz, DMSO-d6) d ppm 1.11-1.73 (m, 8H) 2.31-4.12 (m, 10H) 3.83 (s, 3H) 6.71 (d, J = 0.76 Hz, 1H) 7.46-7.59 (m, 5H) 7.62-7.68 (m, 2H) 7.73 (d, J = 8.34 Hz, 1H) 7.98 (d, J = 1.01 Hz, 1H) | 1-methyl-2-phenyl-N-((1R,4r)-4-((R)-3-(trifluoromethyl)piperazine-1-carbonyl)cyclohexyl)-1H-indole-6-sulfonamide |
| 333 | 11 | 12.58 | E | 611.23154 (M + H+) | | N-((1S,4r)-4-((S)-2-phenylpiperazine-1-carbonyl)cyclohexyl)-2-(2-(trifluoromethyl)phenyl)-1H-indole-6-sulfonamide |
| 334 | 11 | 12.77 | E | 487.15025 (M + H+) | | 2-(2-(trifluoromethyl)phenyl)-N-((1r,4r)-4-(3-(trifluoromethyl)piperazine-1-carbonyl)cyclohexyl)-1H-indole-6-sulfonamide |
| 335 | 11 | 15.12 | E | 542.24871 (M + H+) | | N-((1r,4r)-4-(2-phenylpyrrolidine-1-carbonyl)cyclohexyl)-2-o-tolyl-1H-indole-6-sulfonamide |
| 336 | 12 | 11.94 | E | 512.22167 (M + H+) | | 2-(4-(hydroxymethyl)phenyl)-1-methyl-N-((1r,4r)-4-(morpholine-4-carbonyl)cyclohexyl)-1H-indole-6-sulfonamide |
| 337 | 12 | | | | 1H NMR (400 MHz, ACETONITRILE-d3) d ppm 1.14-1.45 (m, 4H) 1.54-1.74 (m, 4H) 1.75-3.23 (m, 8H) 3.34 (t, J = 5.94 Hz, 1H) 3.59-4.30 (m, 2H) 3.81-3.83 (m, 3H) 4.67 (d, J = 5.81 Hz, 2H) 5.51 (d, J = 7.58 Hz, 1H) 6.67 (s, 1H) 7.47-7.61 (m, 5H) 7.69-7.76 (m, 1H) 7.96-8.00 (m, 1H) | 2-(4-(hydroxymethyl)phenyl)-1-methyl-N-((1S,4r)-4-(S)-3-(trifluoromethyl)piperazine-1-carbonyl)cyclohexyl)-1H-indole-6-sulfonamide |
| 338 | 12 | | | | 1H NMR (400 MHz, ACETONITRILE-d3) d ppm 1.15-1.47 (m, 4H) 1.57-1.76 (m, 4H) 1.76-1.81 (m, 1H) 1.86-3.24 (m, 8H) 3.33 (t, J = 5.94 Hz, 1H) | 2-(4-(hydroxymethyl)phenyl)-1-methyl-N-((1R,4r)-4-(R)-3-(trifluoromethyl)piperazine-1-carbonyl)cyclohexyl)-1H-indole-6-sulfonamide |

| Ex. | Synthetic Scheme | HPLC RT | HPLC Method | MS | NMR | Name |
|---|---|---|---|---|---|---|
| 339 | 12 | 13.35 | E | 593.24151 (M + H+) | 3.60-4.29 (m, 1H) 3.83 (s, 3H) 4.68 (d, J = 5.81 Hz, 1H) 5.50 (d, J = 7.58 Hz, 1H) 6.68 (s, 1H) 7.48-7.62 (m, 5H) 7.74 (d, J = 8.34 Hz, 1H) 7.99 (s, 1H) | 2-(4-(methoxymethyl)phenyl)-1-methyl-N-((1r,4r)-4-(3-(trifluoromethyl)piperazine-1-carbonyl)cyclohexyl)-1H-indole-6-sulfonamide |
| 340 | 11 | 14.4 | E | 582.26368 (M + H+) | | ethyl 1-((1r,4r)-4-(2-(4-(methoxymethyl)phenyl)-1H-indole-6-sulfonamido)cyclohexanecarbonyl)piperidine-2-carboxylate |
| 341 | 12 | 14.68 | E | 596.28 (M + H+) | | ethyl 1-((1r,4r)-4-(2-(4-(methoxymethyl)phenyl)-1-methyl-1H-indole-6-sulfonamido)cyclohexanecarbonyl)piperidine-2-carboxylate |
| 342 | 11 | 13.92 | E | 549.21537 (M + H+) | | 2-o-tolyl-N-((1S,4r)-4-((S)-3-(trifluoromethyl)piperazine-1-carbonyl)cyclohexyl)-1H-indole-6-sulfonamide |
| 343 | 11 | 13.96 | E | 549.21501 (M + H+) | | 2-o-tolyl-N-((1R,4r)-4-((R)-3-(trifluoromethyl)piperazine-1-carbonyl)cyclohexyl)-1H-indole-6-sulfonamide |
| 344 | 12 | 14.11 | E | 567.20497 (M + H+) | | 2-(4-fluorophenyl)-1-methyl-N-((1r,4r)-4-(3-(trifluoromethyl)piperazine-1-carbonyl)cyclohexyl)-1H-indole-6-sulfonamide |
| 345 | 12 | 19.75 | E | 570.2429 (M + H+) | | ethyl 1-((1r,4r)-4-(2-(4-fluorophenyl)-1-methyl-1H-indole-6-sulfonamido)cyclohexanecarbonyl)piperidine-3-carboxylate |
| 346 | 12 | 17.22 | E | 542.2125 (M + H+) | | 1-((1r,4r)-4-(2-(4-fluorophenyl)-1-methyl-1H-indole-6-sulfonamido)cyclohexanecarbonyl)piperidine-3-carboxylic acid |
| 347 | 12 | 13 | E | 525.2172 (M + H+) | | 2-(4-(hydroxymethyl)phenyl)-1-methyl-N-((1r,4r)-4-(3-oxopiperazine-1-carbonyl)cyclohexyl)-1H-indole-6-sulfonamide |
| 348 | 11 | 15.24 | E | 553.18931 (M + H+) | | 2-(4-fluorophenyl)-N-((1r,4r)-4-(3-(trifluoromethyl)piperazine-1-carbonyl)cyclohexyl)-1H-indole-6-sulfonamide |
| 349 | 12 | 15.4 | E | 484.22686 (M + H+) | | (1r,4r)-N-ethyl-4-(2-(4-(hydroxymethyl)phenyl)-1-methyl-1H-indole-6-sulfonamido)-N-methylcyclohexanecarboxamide |
| 350 | 12 + 14 | 17.21 | E | 629.19759 (M + H+) | | 3-chloro-2-(4-fluorophenyl)-1-isopropyl-N-((1r,4r)-4-(3-(trifluoromethyl)piperazine-1-carbonyl)cyclohexyl)-1H-indole-6-sulfonamide |
| 351 | 12 | 14.28 | E | 560.22186 (M + H+) | | (S)-methyl 2-((1r,4S)-4-(1-methyl-2-phenyl-1H-indole-6-sulfonamido)cyclohexanecarboxamido)-2-phenylacetate |
| 352 | 12 | 13.78 | E | 560.2585 (M + H+) | 1H NMR (400 MHz, DMSO-d6) d ppm 0.94 (s, 3H) 1.03 (s, 3H) 1.07-1.35 (m, 5H) | (1r,4S)-N-((S)-2-hydroxy-2-methyl-1-phenylpropyl)-4-(1-methyl-2-phenyl-1H-indole-6-sulfonamido)cyclohexanecarboxamide |

| Ex. | Synthetic Scheme | HPLC RT | HPLC Method | MS | NMR | Name |
|---|---|---|---|---|---|---|
| 353 | 12 | 13 | E | 532.22639 (M + H+) | 1.39-1.55 (m, 1H) 1.58-1.73 (m, 2H) 2.04-2.24 (m, 1H) 2.82-2.97 (m, 1H) 3.82 (s, 3H) 4.41 (s, 1H) 4.65 (d, J = 9.35 Hz, 1H) 6.70 (s, 1H) 7.10-7.35 (m, 5H) 7.42-7.59 (m, 5H) 7.61-7.68 (m, 2H) 7.73 (d, J = 8.34 Hz, 1H) 7.89 (d, J = 9.47 Hz, 1H) 7.97 (s, 1H) | (1r,4S)-N-((S)-2-hydroxy-1-phenylethyl)-4-(1-methyl-2-phenyl-1H-indole-6-sulfonamido)cyclohexanecarboxamide |
| 354 | 12 | 13.07 | E | 571.23831 (M + H+) | | 1-methyl-N-((1S,4r)-4-((S)-5-oxo-2-phenylpiperazine-1-carbonyl)cyclohexyl)-2-phenyl-1H-indole-6-sulfonamide |
| 355 | 12 | | | | 1H NMR (400 MHz, ACETONITRILE-d3) d ppm 0.71-0.78 (m, 2H) 0.95 (s, 3H) 0.99-1.08 (m, 2H) 1.08-1.39 (m, 7H) 1.52-1.79 (m, 4H) 1.93-2.02 (m, 1H) 2.08-2.12 (m, 1H) 2.74 (s, 1H) 2.93-3.06 (m, 1H) 3.85 (s, 3H) 4.63 (d, J = 9.09 Hz, 1H) 5.39 (d, J = 7.33 Hz, 1H) 6.19 (s, 1H) 6.84 (d, J = 9.50 Hz, 1H) 7.19-7.31 (m, 5H) 7.40-7.46 (m, 1H) 7.56 (d, J = 8.34 Hz, 1H) 7.84 (s, 1H) | (1r,4S)-4-(2-cyclopropyl-1-methyl-1H-indole-6-sulfonamido)-N-(S)-2-hydroxy-2-methyl-1-phenylpropyl)cyclohexanecarboxamide |
| 356 | 12 | 10.47 | E | 513.21578 (M + H+) | | 2-cyclopropyl-1-methyl-N-((1r,4r)-4-(3-(trifluoromethyl)piperazine-1-carbonyl)cyclohexyl)-1H-indole-6-sulfonamide |
| 357 | 12 | 14.11 | E | 566.26839 (M + H+) | | methyl 3-(4-(1-methyl-6-(N-((1r,4r)-4-(piperidine-1-carbonyl)cyclohexyl)sulfamoyl)-1H-indol-2-yl)phenyl)propanoate |
| 358 | 11 | 12.09 | E | 538.23719 (M + H+) | | 3-(4-(6-(N-((1r,4r)-4-(piperidine-1-carbonyl)cyclohexyl)sulfamoyl)-1H-indol-2-yl)phenyl)propanoic acid |
| 359 | 12 | 12.49 | E | 552.25324 (M + H+) | | 3-(4-(1-methyl-6-(N-((1r,4r)-4-(piperidine-1-carbonyl)cyclohexyl)sulfamoyl)-1H-indol-2-yl)phenyl)propanoic acid |
| 360 | 12 + 14 | 14.81 | E | 600.23031 (M + H+) | | methyl 3-(4-(3-chloro-1-methyl-6-(N-((1r,4r)-4-(piperidine-1-carbonyl)cyclohexyl)sulfamoyl)-1H-indol-2-yl)phenyl)propanoate |
| 361 | 12 + 14 | | | | 1H NMR (400 MHz, DMSO-d6) d ppm 1.11-1.73 (m, 14H) 2.36 (t, J = 7.83 Hz, 2H) 2.38-2.43 (m, 1H) 2.87 (t, J = 7.58 Hz, 2H) 2.91-2.98 (m, 1H) 3.31-3.39 (m, 4H) 3.74 (s, 3H) 7.39-7.53 (m, 4H) 7.59-7.73 (m, 3H) 8.01-8.08 (m, 1H) | 3-(4-(3-chloro-1-methyl-6-(N-((1r,4r)-4-(piperidine-1-carbonyl)cyclohexyl)sulfamoyl)-1H-indol-2-yl)phenyl)propanoic acid |

-continued

| Ex. | Synthetic Scheme | HPLC RT | HPLC Method | MS | NMR | Name |
|---|---|---|---|---|---|---|
| 362 | 12 + 14 | 13.48 | E | 547.17488 (M + H+) | | 3-chloro-2-cyclopropyl-1-methyl-N-((1R,4r)-4-((R)-3-(trifluoromethyl)piperazine-1-carbonyl)cyclohexyl)-1H-indole-6-sulfonamide |
| 363 | 12 + 14 | 14.6 | E | 480.17171 (M + H+) | | 3-chloro-2-cyclopropyl-1-methyl-N-((1r,4r)-4-(morpholine-4-carbonyl)cyclohexyl)-1H-indole-6-sulfonamide |
| 364 | 12 | 15.08 | E | 540.2536 (M + H+) | | methyl 3-(4-(6-(N-((1r,4r)-4-(ethyl(methyl)carbamoyl)cyclohexyl)sulfamoyl)-1-methyl-1H-indol-2-yl)phenyl)propanoate |
| 365 | 12 | 15.46 | E | 526.2383 (M + H+) | | 3-(4-(6-(N-((1r,4r)-4-(ethyl(methyl)carbamoyl)cyclohexyl)sulfamoyl)-1-methyl-1H-indol-2-yl)phenyl)propanoic acid |
| 366 | 12 + 14 | 14.52 | E | 560.1992 (M + H+) | | 3-(4-(3-chloro-6-(N-((1r,4r)-4-(ethyl(methyl)carbamoyl)cyclohexyl)sulfamoyl)-1-methyl-1H-indol-2-yl)phenyl)propanoic acid |
| 367 | 12 + 14 | 15.98 | E | 574.2145 (M + H+) | | methyl 3-(4-(3-chloro-6-(N-((1r,4r)-4-(ethyl(methyl)carbamoyl)cyclohexyl)sulfamoyl)-1-methyl-1H-indol-2-yl)phenyl)propanoate |
| 368 | 12 | 15.59 | E | 502.275 (M + H+) | | 2-cyclopropyl-N-((1r,4r)-4-(3-(2-hydroxypropan-2-yl)piperidine-1-carbonyl)cyclohexyl)-1-methyl-1H-indole-6-sulfonamide |
| 369 | 12 | 15.75 | E | 584.2583 (M + H+) | | ethyl 3-(6-(N-((1r,4r)-4-(2-(4-fluorophenyl)pyrrolidine-1-carbonyl)cyclohexyl)sulfamoyl)-1-methyl-1H-indol-2-yl)propanoate |
| 370 | 12 | 14.02 | E | 556.2274 (M + H+) | | 3-(6-(N-((1r,4r)-4-(2-(4-fluorophenyl)pyrrolidine-1-carbonyl)cyclohexyl)sulfamoyl)-1-methyl-1H-indol-2-yl)propanoic acid |
| 371 | 12 + 14 | 16.8 | E | 618.2193 (M + H+) | | ethyl 3-(3-chloro-6-(N-((1r,4r)-4-(2-(4-fluorophenyl)pyrrolidine-1-carbonyl)cyclohexyl)sulfamoyl)-1-methyl-1H-indol-2-yl)propanoate |
| 372 | 12 + 14 | 14.48 | E | 590.1885 (M + H+) | | 3-(3-chloro-6-(N-((1r,4r)-4-(2-(4-fluorophenyl)pyrrolidine-1-carbonyl)cyclohexyl)sulfamoyl)-1-methyl-1H-indol-2-yl)propanoic acid |
| 373 | 11 + 14 | 16.95 | E | 500.1762 (M + H+) | | 3-chloro-2-phenyl-N-((1r,4r)-4-(piperidine-1-carbonyl)cyclohexyl)-1H-indole-6-sulfonamide |
| 374 | 12 + 14 | 16.96 | E | 515 (M + H+) | | 3-chloro-1-methyl-2-phenyl-N-((1r,4r)-4-(piperidine-1-carbonyl)cyclohexyl)-1H-indole-6-sulfonamide |
| 375 | 11 | 15.29 | E | 466.2153 (M + H+) | | 2-phenyl-N-((1r,4r)-4-(piperidine-1-carbonyl)cyclohexyl)-1H-indole-6-sulfonamide |
| 376 | 12 | 15.78 | E | 480.2313 (M + H+) | | 1-methyl-2-phenyl-N-((1r,4r)-4-(piperidine-1-carbonyl)cyclohexyl)-1H-indole-6-sulfonamide |
| 377 | 12 | 14.88 | E | 510.2417 (M + H+) | | (1r,4S)-4-(2-cyclopropyl-1-methyl-1H-indole-6-sulfonamido)-N-((S)-2-methoxy-1-phenylethyl)cyclohexanecarboxamide |
| 378 | 12 | 15.64 | E | 538.2727 (M + H+) | | N-((1r,4r)-4-(3-(2-hydroxypropan-2-yl)piperidine-1-carbonyl)cyclohexyl)-1-methyl-2-phenyl-1H-indole-6-sulfonamide |

| Ex. | Synthetic Scheme | HPLC RT | HPLC Method | MS | NMR | Name |
|---|---|---|---|---|---|---|
| 379 | 20 | 16 | E | 471 (M + H+) | | 4-methoxybenzyl 1-methyl-4-(1-methyl-1H-indole-5-sulfonamido)cyclohexanecarboxylate |
| 380 | 12 + 16 | 11.62 | E | 538.2061 (M + H+) | | 3-cyano-2-cyclopropyl-1-methyl-N-((1R,4r)-4-((R)-3-(trifluoromethyl)piperazine-1-carbonyl)cyclohexyl)-1H-indole-6-sulfonamide |
| 381 | 12 + 16 | 14.01 | E | 469.2205 (M + H+) | | 3-cyano-2-cyclopropyl-1-methyl-N-((1r,4r)-4-(piperidine-1-carbonyl)cyclohexyl)-1H-indole-6-sulfonamide |
| 382 | 12 + 16 | | | | 1H NMR (400 MHz, ACETONITRILE-d3) d ppm 0.93-1.74 (m, 21H) 1.99-4.78 (m, 6H) 3.90 (s, 3H) 5.58 (d, J = 7.33 Hz, 1H) 7.59-7.75 (m, 2H) 7.99 (d, J = 1.77 Hz, 1H) | 3-cyano-2-cyclopropyl-1-methyl-N-((1S,4r)-4-((S)-2-methylpiperidine-1-carbonyl)cyclohexyl)-1H-indole-6-sulfonamide |
| 383 | 11 + 14 | 16.42 | E | 558.2183 (M + H+) | | 3-chloro-N-((1r,4r)-4-(3-(2-hydroxypropan-2-yl)piperidine-1-carbonyl)cyclohexyl)-2-phenyl-1H-indole-6-sulfonamide |
| 384 | 12 + 14 | 16.48 | E | 572.235 (M + H+) | | 3-chloro-N-((1r,4r)-4-(3-(2-hydroxypropan-2-yl)piperidine-1-carbonyl)cyclohexyl)-1-methyl-2-phenyl-1H-indole-6-sulfonamide |
| 385 | 20 | 11.64 | E | 420.2 (M + H+) | | 1-methyl-N-(4-methyl-4-(morpholine-4-carbonyl)cyclohexyl)-1H-indole-5-sulfonamide |
| 386 | 12 | 16.91 | E | 646.2753 (M + H+) | | methyl 3-(4-(6-(N-((1r,4r)-4-(2-(4-fluorophenyl)pyrrolidine-1-carbonyl)cyclohexyl)sulfamoyl)-1-methyl-1H-indol-2-yl)phenyl)propanoate |
| 387 | 12 | 15.81 | E | 632.257 (M + H+) | | 3-(4-(6-(N-((1r,4r)-4-(2-(4-fluorophenyl)pyrrolidine-1-carbonyl)cyclohexyl)sulfamoyl)-1-methyl-1H-indol-2-yl)phenyl)propanoic acid |
| 388 | 20 | 15.25 | E | 393.3 (M + H+) | | isopropyl 1-methyl-4-(1-methyl-1H-indole-5-sulfonamido)cyclohexanecarboxylate |
| 389 | 12 + 16 | | | | 1H NMR (400 MHz, ACETONITRILE-d3) d ppm 1.02-1.45 (m, 8H) 1.58-1.73 (m, 4H) 1.75-2.66 (m, 6H) 2.94-3.66 (m, 3H) 3.91 (s, 3H) 4.52-4.79 (m, 1H) 5.57 (d, J = 7.33 Hz, 1H) 7.63-7.75 (m, 2H) 7.99 (s, 1H) | 3-cyano-2-cyclopropyl-1-methyl-N-((1R,4r)-4-((R)-2-(trifluoromethyl)pyrrolidine-1-carbonyl)cyclohexyl)-1H-indole-6-sulfonamide |
| 390 | 12 + 16 | 15.87 | E | 511.2741 (M + H+) | | N-((1r,4r)-4-(2-tert-butylpyrrolidine-1-carbonyl)cyclohexyl)-3-cyano-2-cyclopropyl-1-methyl-1H-indole-6-sulfonamide |
| 391 | 20 | 14.15 | E | 379.2 (M + H+) | | ethyl 1-methyl-4-(1-methyl-1H-indole-5-sulfonamido)cyclohexanecarboxylate |
| 392 | 12 | 15.64 | E | 632.2646 (M + H+) | | 3-(4-(6-(N-((1R,4r)-4-((R)-2-(4-fluorophenyl)pyrrolidine-1-carbonyl)cyclohexyl)sulfamoyl)-1-methyl-1H-indol-2-yl)phenyl)propanoic acid |

| Ex. | Synthetic Scheme | HPLC RT | HPLC Method | MS | NMR | Name |
|---|---|---|---|---|---|---|
| 393 | 12 | 15.64 | E | 632.2621 (M + H+) | | 3-(4-(6-(N-((1S,4r)-4-((S)-2-(4-fluorophenyl)pyrrolidine-1-carbonyl)cyclohexyl)sulfamoyl)-1-methyl-1H-indol-2-yl)phenyl)propanoic acid |
| 394 | 12 | | | | 1H NMR (600 MHz, DMSO-d6) d ppm 0.92 (d, 3H), 1.07 (d, 3H), 1.10-1.13 (m, 4H), 1.47-1.58 (m, 2H), 1.60-1.66 (m, 2H), 2.30-2.42 (m, 1H), 2.57 (s, 3H, rotamer), 2.76 (s, 3H, rotamer), 2.81-2.92 (m, 1H), 4.05-4.11 (m, 1H, rotamer), 4.53-4.60 (m, 1H, rotamer), 7.18 (br s, 1H), 7.41-7.45 (m, 1H), 7.47-7.50 (d, 1H), 7.57-7.68 (m, 3H), 7.76 (s, 1H), 10.50 (br s, 1H), 12.50 (br s, 1H) | methyl 3-(4-(6-(N-((1r,4r)-4-(2-tert-butyl)pyrrolidine-1-carbonyl)cyclohexyl)sulfamoyl)-1-methyl-1H-indol-2-yl)phenyl)propanoate |
| 395 | 12 | 16.44 | E | 594.3019 (M + H+) | | 3-(4-(6-(N-((1r,4r)-4-(2-tert-butylpyrrolidine-1-carbonyl)cyclohexyl)sulfamoyl)-1-methyl-1H-indol-2-yl)phenyl)propanoic acid |
| 396 | 12 | 16.19 | E | 566.267 (M + H+) | 1H NMR (400 MHz CHLOROFORM-d) d ppm 0.64-0.88 (m, 2H) 0.96 (s, 3H) 1.15-1.21 (m, 2H) 1.25 (s, 3H) 1.32-1.45 (m, 3H) 1.67-2.15 (m, 6H) 2.85-3.20 (m, 1H) 3.65 (s, 3H) 3.87 (s, 3H) 4.25 (d, J = 7.33 Hz, 1H) 4.85 (d, J = 9.22 Hz, 1H) 6.18 (s, 1H) 7.01-7.17 (m, 2H) 7.19-7.30 (m, 5H) 7.39-7.66 (m, 2H) 7.85 (s, 1H) | (S)-methyl 3-((1r,4S)-4-(2-cyclopropyl-1-methyl-1H-indole-6-sulfonamido)cyclohexanecarboxamido)-2,2-dimethyl-3-phenylpropanoate |
| 397 | 12 | | | | 1H NMR (400 MHz DMSO-d6) d ppm 1.03-1.73 (m, 8H) 1.78-2.07 (m, 4H) 2.36 (t, J = 7.83 Hz, 2H) 2.26-2.39 (m, 1H) 2.85 (t, J = 7.83 Hz, 2H) 2.88-3.01 (m, 1H) 3.45-3.66 (m, 2H) 3.81 (s, 3H) 4.63-5.05 (m, 1H) 6.65 (s, 1H) 7.38 (d, J = 8.08 Hz, 2H) 7.48-7.57 (m, 4H) 7.71 (d, J = 8.34 Hz, 1H) 7.96 (s, 1H) | 3-(4-(1-methyl-6-(N-((1R,4r)-4-((R)-2-(trifluoromethyl)pyrrolidine-1-carbonyl)cyclohexyl)sulfamoyl)-1H-indol-2-yl)phenyl)propanoic acid |
| 398 | 20 | 16.61 | E | 455.2 (M + H+) | | (R)-1-phenylethyl 1-methyl-4-(1-methyl-1H-indole-5-sulfonamido)cyclohexanecarboxylate |
| 399 | 12 | 16.73 | E | 594.3023 (M + H+) | | 3-(4-(6-(N-((1S,4r)-4-((S)-2-tert-butylpyrrolidine-1-carbonyl)cyclohexyl)sulfamoyl)-1-methyl-1H-indol-2-yl)phenyl)propanoic acid |

| Ex. | Synthetic Scheme | HPLC RT | HPLC Method | MS | NMR | Name |
|---|---|---|---|---|---|---|
| 400 | 12 | | | | 1H NMR (400 MHz, ACETONITRILE-d3) d ppm 0.80-0.88 (m, 9H) 1.08-2.22 (m, 12H) 2.30-2.42 (m, 1H) 2.68 (t, J = 7.58 Hz, 2H) 2.97 (t, J = 7.83 Hz, 2H) 3.02-3.14 (m, 1H) 3.26-3.36 (m, 1H) 3.56-3.67 (m, 1H) 3.82 (s, 3H) 4.05-4.13 (m, 1H) 5.47 (d, J = 7.58 Hz, 1H) 6.65 (s, 1H) 7.41 (d, J = 8.34 Hz, 2H) 7.49-7.58 (m, 3H) 7.72 (d, J = 8.59 Hz, 1H) 7.95-8.01 (m, 1H) | 3-(4-(6-(N-((1R,4r)-4-((R)-2-tert-butylpyrrolidine-1-carbonyl)cyclohexyl)sulfamoyl)-1-methyl-1H-indol-2-yl)phenyl)propanoic acid |
| 401 | 12 + 16 | 13.03 | E | 485.2216 (M + H+) | | 3-cyano-2-cyclopropyl-1-methyl-N-((1r,4r)-4-(3-methylmorpholine-4-carbonyl)cyclohexyl)-1H-indole-6-sulfonamide |
| 402 | 12 | 14.71 | E | 496.2259 (M + H+) | | N-((1r,4r)-4-(1,4-oxazepane-4-carbonyl)cyclohexyl)-1-methyl-2-phenyl-1H-indole-6-sulfonamide |
| 403 | 12 | 15.38 | E | 538.2623 (M + H+) | 1H NMR (400 MHz, CHLOROFORM-d) d ppm 0.69-0.95 (m, 1H) 1.08-1.30 (m, 10H) 1.32-1.44 (m, 2H) 1.63-1.77 (m, 2H) 1.86-2.06 (m, 3H) 2.22-2.48 (m, 2H) 2.63-2.96 (m, 1H) 3.03-3.23 (m, 1H) 3.75-3.80 (m, 1H) 3.83 (s, 3H) 4.26 (d, J = 4.55 Hz, 1H) 4.51-4.79 (m, 1H) 6.63 (s, 2H) 7.38-7.62 (m, 7H) 7.72 (d, J = 8.34 Hz, 1H) 7.97 (s, 1H) | N-((1R,4r)-4-((R)-3-(2-hydroxypropan-2-yl)piperidine-1-carbonyl)cyclohexyl)-1-methyl-2-phenyl-1H-indole-6-sulfonamide |
| 404 | 12 | 15.37 | E | 538.2724 (M + H+) | 1H NMR (400 MHz, CHLOROFORM-d) d ppm 1.13-1.3 (m, 6H) 1.37-1.49 (m, 5H) 1.5-1.73 (m, 4H) 1.81-2.00 (m, 3H) 2.24-2.51 (m, 2H) 2.64-2.99 (m, 1H) 3.11 (qd, J = 7.28, 4.93 Hz, 2H) 3.83 (s, 3H) 3.8-4.2 (m, 1H) 4.35 (br. s., 1H) 4.57-4.75 (m, 1H) 6.63 (s, 1H) 7.37-7.53 (m, 6H) 7.58 (dd, J = 8.34, 1.26 Hz, 1H) 7.72 (d, J = 8.34 Hz, 1H) 7.98 (s, 1H) | N-((1S,4r)-4-((S)-3-(2-hydroxypropan-2-yl)piperidine-1-carbonyl)cyclohexyl)-1-methyl-2-phenyl-1H-indole-6-sulfonamide |
| 405 | 12 | 16.33 | E | 494.2471 (M + H+) | | 1-methyl-N-((1S,4r)-4-((S)-2-methylpiperidine-1-carbonyl)cyclohexyl)-2-phenyl-1H-indole-6-sulfonamide |
| 406 | 12 | 13.18 | E | 521.2603 (M + H+) | | N-((1r,4r)-4-(4-cyclopropylpiperazine-1-carbonyl)cyclohexyl)-1-methyl-2-phenyl-1H-indole-6-sulfonamide |

| Ex. | Synthetic Scheme | HPLC RT | HPLC Method | MS | NMR | Name |
|---|---|---|---|---|---|---|
| 407 | 12 | 16.67 | E | 602.2722 (M + H+) | 1H NMR (400 MHz, CHLOROFORM-d) d ppm 1.07 (s, 3H) 1.10-1.23 (m, 2H) 1.29 (s, 3H) 1.32-1.49 (m, 2H) 1.73-2.12 (m, 4H) 3.00-3.26 (m, 1H) 3.63 (s, 3H) 3.82 (s, 3H) 4.29 (d, J = 7.45 Hz, 1H) 4.85 (d, J = 9.22 Hz, 1H) 6.63 (s, 1H) 7.08-7.18 (m, 3H) 7.19-7.25 (m, 3H) 7.43-7.64 (m, 7H) 7.71 (d, J = 8.34 Hz, 1H) 7.97 (s, 1H) | (S)-methyl 2,2-dimethyl-3-((1r,4S)-4-(1-methyl-2-phenyl-1H-indole-6-sulfonamido)cyclohexanecarboxamido)-3-phenylpropanoate |
| 408 | 12 | 15.42 | E | 510.2427 (M + H+) | | N-((1R,4r)-4-((R)-2-(methoxymethyl)pyrrolidine-1-carbonyl)cyclohexyl)-1-methyl-2-phenyl-1H-indole-6-sulfonamide |
| 409 | 12 | 14.91 | E | 552.2505 (M + H+) | | (S)-3-((1r,4S)-4-(2-cyclopropyl-1-methyl-1H-indole-6-sulfonamido)cyclohexanecarboxamido)-2,2-dimethyl-3-phenylpropanoic acid |
| 410 | 12 | | | | 1H NMR (400 MHz, DMSO-d6) d ppm 0.86-1.71 (m, 17H) 2.24-2.40 (m, 3H) 2.42-4.74 (m, 6H) 3.81 (s, 3H) 6.64 (s, 1H) 7.37 (d, J = 8.34 Hz, 2H) 7.46-7.59 (m, 4H) 7.70 (d, J = 0.51 Hz, 1H) 7.95 (d, J = 0.51 Hz, 1H) | 3-(4-(1-methyl-6-(N-((1S,4r)-4-((S)-2-methylpiperidine-1-carbonyl)cyclohexyl)sulfamoyl)-1H-indol-2-yl)phenyl)propanoic acid |
| 411 | 12 | 15.86 | E | 588.2 (M + H+) | | (S)-2,2-dimethyl-3-((1r,4S)-4-(1-methyl-2-phenyl-1H-indole-6-sulfonamido)cyclohexanecarboxamido)-3-phenylpropanoic acid |
| 412 | 12 | 13.25 | E | 509.2568 (M + H+) | | N-((1S,4r)-4-((S)-2,4-dimethylpiperazine-1-carbonyl)cyclohexyl)-1-methyl-2-phenyl-1H-indole-6-sulfonamide |
| 413 | 12 + 16 | 12.73 | E | 485.2203 (M + H+) | | 3-cyano-2-cyclopropyl-1-methyl-N-((1R,4r)-4-((R)-3-methylmorpholine-4-carbonyl)cyclohexyl)-1H-indole-6-sulfonamide |
| 414 | 12 + 16 | 12.73 | E | 485.2201 (M + H+) | | 3-cyano-2-cyclopropyl-1-methyl-N-((1S,4r)-4-((S)-3-methylmorpholine-4-carbonyl)cyclohexyl)-1H-indole-6-sulfonamide |
| 415 | 12 + 16 | | | | 1H NMR (400 MHz, DMSO-d6) d ppm 0.87-1.73 (m, 17H) 2.25-2.43 (m, 3H) 2.82-3.07 (m, 3H) 3.10-4.77 (m, 3H) 3.85 (s, 3H) 7.49 (d, J = 8.34 Hz, 2H) 7.60 (d, J = 8.08 Hz, 2H) 7.70-7.79 (m, 2H) 7.86 (d, J = 8.34 Hz, 1H) 8.15 (s, 1H) | 3-(4-(3-cyano-1-methyl-6-(N-((1S,4r)-4-((S)-2-methylpiperidine-1-carbonyl)cyclohexyl)sulfamoyl)-1H-indol-2-yl)phenyl)propanoic acid |

-continued

| Ex. | Synthetic Scheme | HPLC RT | HPLC Method | MS | NMR | Name |
|---|---|---|---|---|---|---|
| 416 | 12 + 16 | | | | 1H NMR (400 MHz, DMSO-d6) d ppm 0.88-1.73 (m, 17H) 2.29-2.46 (m, 3H) 2.80-3.05 (m, 3H) 3.19-4.74 (m, 3H) 3.73 (s, 3H) 7.40-7.53 (m, 4H) 7.58-7.66 (m, 2H) 7.70 (d, J = 8.34 Hz, 1H) 8.04 (s, 1H) | 3-(4-(3-chloro-1-methyl-6-(N-((1S,4r)-4-((S)-2-methylpiperidine-1-carbonyl)cyclohexyl)sulfamoyl)-1H-indol-2-yl)phenyl)propanoic acid |
| 417 | 12 + 16 | | | | 1H NMR (400 MHz, ACETONITRILE-d3) d ppm 1.03-1.43 (m, 14H) 1.54-1.72 (m, 4H) 1.85-2.48 (m, 3H) 2.64 (dd, J = 13.14, 10.86 Hz, 1H) 2.97-3.10 (m, 1H) 3.31-3.49 (m, 2H) 3.69 (d, J = 13.14 Hz, 1H) 3.91 (s, 3H) 4.26 (d, J = 13.39 Hz, 1H) 5.59 (d, J = 7.58 Hz, 1H) 7.63-7.74 (m, 2H) 7.98-8.01 (m, 1H) | 3-cyano-2-cyclopropyl-N-((1R,4r)-4-((2S,6R)-2,6-dimethylmorpholine-4-carbonyl)cyclohexyl)-1-methyl-1H-indole-6-sulfonamide |
| 418 | 12 + 16 | 13.32 | E | 499.2393 (M + H+) | | 3-cyano-2-cyclopropyl-N-((1R,4r)-4-((R)-2-(methoxymethyl)pyrrolidine-1-carbonyl)cyclohexyl)-1-methyl-1H-indole-6-sulfonamide |
| 419 | 12 | 15.48 | E | 510.2407 (M + H+) | 1H NMR (400 MHz, CHLOROFORM-d) d ppm 1.19 (dd, J = 13.71, 6.25 Hz, 6H) 1.63-1.72 (m, 2H) 1.89-2.04 (m, 3H) 2.20-2.41 (m, 2H) 2.68-2.82 (m, 2H) 3.12 (dd, J = 11.24, 4.04 Hz, 1H) 3.48 (dd, J = 6.51, 4.36 Hz, 3H) 3.52-3.61 (m, 1H) 3.83 (s, 3H) 4.26-4.47 (m, 2H) 6.63 (s, 1H) 7.41-7.56 (m, 6H) 7.56-7.62 (m, 1H) 7.72 (d, J = 8.34 Hz, 1H) 7.98 (s, 1H) | N-((1R,4r)-4-((2S,6R)-2,6-dimethylmorpholine-4-carbonyl)cyclohexyl)-1-methyl-2-phenyl-1H-indole-6-sulfonamide |
| 420 | 12 | 15.54 | E | 538.2354 (M + H+) | | (R)-ethyl 1-((1r,4R)-4-(1-methyl-2-phenyl-1H-indole-6-sulfonamido)cyclohexanecarbonyl)pyrrolidine-2-carboxylate |
| 421 | 12 + 16 | | | | 1H NMR (400 MHz, ACETONITRILE-d3) d ppm 1.01-1.74 (m, 15H) 2.02-2.15 (m, 1H) 2.28-2.41 (m, 1H) 2.81-4.44 (m, 8H) 3.90 (s, 3H) 5.57 (d, J = 7.58 Hz, 1H) 7.57-7.76 (m, 2 H) 7.95-8.03 (m, 1H) | 3-cyano-2-cyclopropyl-1-methyl-N-((1S,4r)-4-((S)-3-methylmorpholine-4-carbonyl)cyclohexyl)-1H-indole-6-sulfonamide |
| 422 | 12 | 13.7 | E | 460.2277 (M + H+) | | 2-cyclopropyl-1-methyl-N-((1S,4r)-4-((S)-3-methylmorpholine-4-carbonyl)cyclohexyl)-1H-indole-6-sulfonamide |

| Ex. | Synthetic Scheme | HPLC RT | HPLC Method | MS | NMR | Name |
|---|---|---|---|---|---|---|
| 423 | 12 | 15.9 | E | 546.1 (M + H+) | | (1r,4S)-N-((S)-2-methoxy-1-phenylethyl)-4-(1-methyl-2-phenyl-1H-indole-6-sulfonamido)cyclohexanecarboxamide |
| 424 | 12 | 16.45 | E | 538.2736 (M + H+) | | N-((1r,4r)-4-(2,2-diethylmorpholine-4-carbonyl)cyclohexyl)-1-methyl-2-phenyl-1H-indole-6-sulfonamide |
| 425 | 12 | 14.97 | E | 496.2268 (M + H+) | 1H NMR (400 MHz, DICHLOROMETHANE-d2) d ppm 0.93-1.25 (m, 6H) 1.49 (s, 3H) 1.80 (m, 2H) 2.12-2.25 (m, 1H) 2.78-2.91 (m, 1H) 2.92-3.09 (m, 1H) 3.19-3.34 (m, 2H) 3.40 (d, J = 11.12 Hz, 1H) 3.54 (d, J = 11.24 Hz, 1H) 3.70 (s, 3H) 4.29-4.45 (m, 2H) 6.56 (s, 1H) 7.31-7.50 (m, 7H) 7.60-7.69 (m, 1H) 7.88 (s, 1H) | 1-methyl-N-((1S,4r)-4-((S)-3-methylmorpholine-4-carbonyl)cyclohexyl)-2-phenyl-1H-indole-6-sulfonamide |
| 426 | 12 + 14 | 15.23 | E | 494.1878 (M + H+) | | 3-chloro-2-cyclopropyl-1-methyl-N-((1S,4r)-4-((S)-3-methylmorpholine-4-carbonyl)cyclohexyl)-1H-indole-6-sulfonamide |
| 427 | 12 | | | | 1H NMR (400 MHz, ACETONITRILE-d3) d ppm 1.02-1.75 (m, 11H) 2.30-2.44 (m, 3H) 2.68 (t, J = 7.58 Hz, 2H) 2.78-4.46 (m, 8H) 3.01 (t, J = 7.58 Hz, 2H) 3.82 (s, 3H) 5.49 (d, J = 7.58 Hz, 1H) 6.66 (s, 1H) 7.41 (d, J = 8.08 Hz, 2H) 7.50-7.59 (m, 3H) 7.72 (d, J = 8.34 Hz, 1H) 7.95-8.01 (m, 1H) | 3-(4-(1-methyl-6-(N-((1S,4r)-4-((S)-3-methylmorpholine-4-carbonyl)cyclohexyl)sulfamoyl)-1H-indol-2-yl)phenyl)propanoic acid |
| 428 | 12 + 14 | | | | 1H NMR (400 MHz, DMSO-d6) d ppm 0.96-1.75 (m, 11H) 2.24-2.41 (m, 3H) 2.78-3.00 (m, 3H) 3.12-4.39 (m, 7H) 3.75 (s, 3H) 7.40-7.53 (m, 4H) 7.60-7.67 (m, 2H) 7.72 (d, J = 8.59 Hz, 1H) 8.05 (s, 1H) | 3-(4-(3-chloro-1-methyl-6-(N-((1S,4r)-4-((S)-3-methylmorpholine-4-carbonyl)cyclohexyl)sulfamoyl)-1H-indol-2-yl)phenyl)propanoic acid |
| 429 | 12 + 16 | 15.66 | E | 619.2946 (M + H+) | | 3-(4-(6-(N-((1S,4r)-4-((S)-2-tert-butylpyrrolidine-1-carbonyl)cyclohexyl)sulfamoyl)-3-cyano-1-methyl-1H-indol-2-yl)phenyl)propanoic acid |
| 430 | 12 + 16 | | | | 1H NMR (400 MHz, ACETONITRILE-d3) d ppm 0.77-0.94 (m, 9H) 1.11-2.26 (m, 12H) 1.22-1.23 (m, 1H) 2.31-2.44 (m, 1H) 2.71 (t, J = 7.83 Hz, 2H) 3.02 (t, J = 7.58 Hz, 2H) 3.06-3.14 (m, 1H) 3.30-3.37 (m, 1H) 3.55-3.68 (m, 1H) 3.81 (s, 3H) 3.97-4.13 (m, 1H) 5.62 (d, J = 7.58 Hz, 1H) 7.52 (d, J = 8.34 Hz, 2H) 7.60 (d, J = 8.34 Hz, 2H) | 3-(4-(6-(N-((1R,4r)-4-((R)-2-tert-butylpyrrolidine-1-carbonyl)cyclohexyl)sulfamoyl)-3-cyano-1-methyl-1H-indol-2-yl)phenyl)propanoic acid |

| Ex. | Synthetic Scheme | HPLC RT | HPLC Method | MS | NMR | Name |
|---|---|---|---|---|---|---|
| 431 | 12 | 15.32 | E | 559.2482 (M + H+) | 7.77 (dd, J = 8.34, 1.26 Hz, 1H) 7.86 (d, J = 8.59 Hz, 1H) 8.08-8.14 (m, 1H) | 1-methyl-2-phenyl-N-((1r,4r)-4-(4-(pyrimidin-2-yl)piperazine-1-carbonyl)cyclohexyl)-1H-indole-6-sulfonamide |
| 432 | 12 | 14.42 | E | 496.2266 (M + H+) | | N-((1R,4r)-4-((R)-2-(hydroxymethyl)pyrrolidine-1-carbonyl)cyclohexyl)-1-methyl-2-phenyl-1H-indole-6-sulfonamide |
| 433 | 12 | 13.88 | E | 482.2 (M + H+) | | N-((1r,4r)-4-(3-hydroxypyrrolidine-1-carbonyl)cyclohexyl)-1-methyl-2-phenyl-1H-indole-6-sulfonamide |
| 434 | 12 | 15.99 | E | 524.2575 (M + H+) | 1H NMR (400 MHz, DMSO-d6) d ppm 0.64 (d, J = 6.82 Hz, 2H) 0.73 (d, J = 6.82 Hz, 1H) 0.89 (d, J = 6.57 Hz, 2H) 0.92-1.00 (d, J = 6.57, 1H) 1.10-1.34 (m, 4H) 1.55-1.65 (m, 4H) 2.11-2.15 (m, 1H) 2.92 (d, J = 4.29 Hz, 1H) 3.11-3.28 (m, 4H) 3.59 (s, 1H) 3.69-3.79 (m, 1H) 3.82 (s, 3H) 3.85-3.95 (m, 1H) 4.03-4.17 (m, 1H) 6.71 (s, 1H) 7.44-7.60 (m, 5H) 7.61-7.68 (m, 2H) 7.73 (d, J = 8.34 Hz, 1H) 7.98 (s, 1H) | N-((1S,4r)-4-((S)-3-isopropylmorpholine-4-carbonyl)cyclohexyl)-1-methyl-2-phenyl-1H-indole-6-sulfonamide |
| 435 | 12 | 14.79 | E | 510.2427 (M + H+) | | (1r,4r)-4-(1-methyl-2-phenyl-1H-indole-6-sulfonamido)-N-(2-oxoazepan-3-yl)cyclohexanecarboxamide |
| 436 | 12 | 14.3 | E | 526.2369 (M + H+) | | 2-(4-(methoxymethyl)phenyl)-N-((1S,4r)-4-((S)-3-methylmorpholine-4-carbonyl)cyclohexyl)-1H-indole-6-sulfonamide |
| 437 | 12 | | | | 1H NMR (400 MHz, ACETONITRILE-d3) d ppm 1.07-1.77 (m, 11H) 2.31-2.45 (m, 1H) 2.81-4.46 (m, 8H) 3.42 (s, 3H) 3.85 (s, 3H) 4.54 (s, 2H) 5.51 (d, J = 7.58 Hz, 2H) 6.73 (s, 1H) 7.51 (d, J = 8.59 Hz, 2H) 7.54-7.66 (m, 3H) 7.75 (d, J = 8.34 Hz, 1H) 7.97-8.03 (m, 1H) | 2-(4-(methoxymethyl)phenyl)-1-methyl-N-((1S,4r)-4-((S)-3-methylmorpholine-4-carbonyl)cyclohexyl)-1H-indole-6-sulfonamide |
| 438 | 12 | | | | 1H NMR (400 MHz, ACETONITRILE-d3) d ppm 0.61-1.03 (m, 6H) 1.11-1.73 (m, 9H) 2.13-4.24 (m, 9H) 3.39 (s, 3H) 3.81 (s, 3H) 4.51 (s, 2H) 5.46 (d, J = 7.58 Hz, 1H) 6.66 (s, 1H) 7.45-7.60 (m, 5H) 7.71 (d, J = 8.34 Hz, 1H) 7.96 (s, 1H) | N-((1S,4r)-4-((S)-3-isopropylmorpholine-4-carbonyl)cyclohexyl)-2-(4-(methoxymethyl)phenyl)-1-methyl-1H-indole-6-sulfonamide |
| 439 | 12 | 16.19 | E | 574.2735 (M + H+) | 1H NMR (400 MHz, DICHLOROMETHANE-d2) d ppm 0.72 (s, 3H) 0.97 (s, 3H) | (1r,4S)-N-((S)-3-hydroxy-2,2-dimethyl-1-phenylpropyl)-4-(1-methyl-2-phenyl-1H-indole-6-sulfonamido)cyclohexanecarboxamide |

| Ex. | Synthetic Scheme | HPLC RT | HPLC Method | MS | NMR | Name |
|---|---|---|---|---|---|---|
| 440 | 12 | | | | 1.10-1.30 (m, 2H) 1.31-1.53 (m, 2H) 1.69-1.97 (m, 5H) 2.05 (tt, J = 12.03, 3.51 Hz, 1H) 3.01-3.23 (m, 2H) 3.35-3.50 (m, 1H) 3.85 (s, 3H) 4.42 (d, J = 7.07 Hz, 1H) 4.83 (d, J = 8.84 Hz, 1H) 6.68 (s, 1H) 6.86 (d, J = 8.59 Hz, 1H) 7.18-7.41 (m, 5H) 7.43-7.65 (m, 6H) 7.76 (d, J = 8.08 Hz, 1H) 7.99 (s, 1H) | 2-(4-methoxyphenyl)-1-methyl-N-((1S,4r)-4-((S)-3-methylmorpholine-4-carbonyl)cyclohexyl)-1H-indole-6-sulfonamide |
| 441 | 12 | | | | 1H NMR (400 MHz, ACETONITRILE-d3) d ppm 0.97-1.82 (m, 11H) 2.28-2.42 (m, 1H) 2.80-4.47 (m, 8H) 3.80 (s, 3H) 3.87 (s, 3H) 5.50 (d, J = 7.58 Hz, 1H) 6.61 (d, J = 1.01 Hz, 1H) 7.01-7.19 (m, 2H) 7.47-7.61 (m, 3H) 7.70 (d, J = 8.34 Hz, 1H) 7.92-8.02 (m, 1H) | N-((1S,4r)-4-((S)-3-isopropylmorpholine-4-carbonyl)cyclohexyl)-2-(4-methoxyphenyl)-1-methyl-1H-indole-6-sulfonamide |
| 442 | 12 | 15.32 | E | 510.2425 (M + H+) | 1H NMR (400 MHz, ACETONITRILE-d3) d ppm 0.63-1.01 (m, 6H) 1.09-1.74 (m, 8H) 2.24-3.38 (m, 6H) 3.47-4.23 (m, 4H) 3.78 (s, 3H) 3.85 (s, 3H) 5.49 (d, J = 0.76 Hz, 1H) 6.58 (d, J = 7.58 Hz, 1H) 7.03-7.10 (m, 2H) 7.47-7.55 (m, 3H) 7.68 (d, J = 8.34 Hz, 1H) 7.92-7.96 (m, 1H) | N-((1r,4r)-4-(2,2-dimethylmorpholine-4-carbonyl)cyclohexyl)-2-(4-methoxyphenyl)-1-methyl-2-phenyl-1H-indole-6-sulfonamide |
| 443 | 12 | 15.36 | E | 524.2579 (M + H+) | 1H NMR (400 MHz, DICHLOROMETHANE-d2) d ppm 1.03 (s, 3H) 1.09 (s, 3H) 1.29-1.51 (m, 5H) 1.51-1.68 (m, 2H) 1.72-1.88 (m, 2H) 2.10-2.38 (m, 1H) 2.91-3.06 (m, 1H) 3.11 (s, 1H) 3.23 (s, 1H) 3.28 (t, J = 4.93 Hz, 1H) 3.34 (s, 1H) 3.38 (t, J = 4.93 Hz, 1H) 3.74 (s, 3H) 4.32 (d, J = 7.07 Hz, 1H) 6.57 (s, 1H) 7.32-7.54 (m, 6H) 7.59-7.71 (m, 1H) 7.88 (s, 1H) | N-((1R,4r)-4-((R)-2-(2-hydroxypropan-2-yl)pyrrolidine-1-carbonyl)cyclohexyl)-1-methyl-2-phenyl-1H-indole-6-sulfonamide |
| 444 | 12 | 14.74 | E | 540.2524 (M + H+) | | 2-(4-(2-methoxyethyl)phenyl)-1-methyl-N-((1S,4r)-3-methylmorpholine-4-carbonyl)cyclohexyl)-1H-indole-6-sulfonamide |
| 445 | 11 | 14.58 | E | 526.2351 (M + H+) | | (1r,4R)-N-((R)-1-cyclopropyl-2-hydroxyethyl)-4-(2-(4-methoxyphenyl)-1-methyl-1H-indole-6-sulfonamido)cyclohexanecarboxamide |

| Ex. | Synthetic Scheme | HPLC RT | HPLC Method | MS | NMR | Name |
|---|---|---|---|---|---|---|
| 446 | 12 | 13.18 | E | 460.2246 (M + H+) | | (1r,4R)-4-(2-cyclopropyl-1-methyl-1H-indole-6-sulfonamido)-N-((R)-1-cyclopropyl-2-hydroxyethyl)cyclohexanecarboxamide |
| 447 | 12 | 16.13 | E | 598.4 (M + H+) | | N-((1S,4r)-4-((S)-3-isopropylmorpholine-4-carbonyl)cyclohexyl)-2-(4-(2-methoxyethoxy)phenyl)-1-methyl-1H-indole-6-sulfonamide |
| 448 | 12 | 15.22 | E | 570.3 (M + H+) | | 2-(4-(2-methoxyethoxy)phenyl)-1-methyl-N-((1S,4r)-4-((S)-3-methylmorpholine-4-carbonyl)cyclohexyl)-1H-indole-6-sulfonamide |
| 449 | 12 | 14.83 | E | 570.3 (M + H+) | | (1r,4S)-N-((S)-1-cyclopropyl-2-hydroxyethyl)-4-(2-(4-(2-methoxyethoxy)phenyl)-1-methyl-1H-indole-6-sulfonamido)cyclohexanecarboxamide |
| 450 | 12 | 15.54 | E | 584.3 (M + H+) | | N-((1r,4r)-4-(2,2-dimethylmorpholine-4-carbonyl)cyclohexyl)-2-(4-(2-methoxyethoxy)phenyl)-1-methyl-1H-indole-6-sulfonamide |
| 451 | 12 | 15.78 | E | 598.4 (M + H+) | | N-((1R,4r)-4-((R)-2-(2-hydroxypropan-2-yl)pyrrolidine-1-carbonyl)cyclohexyl)-2-(4-(2-methoxyethoxy)phenyl)-1-methyl-1H-indole-6-sulfonamide |
| 452 | 12 | 16.4 | E | 608.3 (M + H+) | | (1r,4R)-N-((R)-1-(4-fluorophenyl)ethyl)-4-(2-(4-(2-methoxyethoxy)phenyl)-1-methyl-1H-indole-6-sulfonamido)cyclohexanecarboxamide |
| 453 | 12 | 15.8 | E | 582.3 (M + H+) | | (1r,4R)-4-(2-(4-(2-methoxyethoxy)phenyl)-1-methyl-1H-indole-6-sulfonamido)-N-((R)-1,1,1-trifluoropropan-2-yl)cyclohexanecarboxamide |
| 454 | 12 | 16.2 | E | 552.2514 (M + H+) | | N-((1S,4r)-4-((S)-3-cyclopropylmorpholine-4-carbonyl)cyclohexyl)-2-(4-methoxyphenyl)-1-methyl-1H-indole-6-sulfonamide |
| 455 | 12 | 15.45 | E | 552.252 (M + H+) | | N-((1S,4r)-4-((S)-3-cyclopropylmorpholine-4-carbonyl)cyclohexyl)-2-(4-(methoxymethyl)phenyl)-1H-indole-6-sulfonamide |
| 456 | 12 | 15.81 | E | 566.2681 (M + H+) | | N-((1S,4r)-4-((S)-3-cyclopropylmorpholine-4-carbonyl)cyclohexyl)-2-(4-(methoxymethyl)phenyl)-1-methyl-1H-indole-6-sulfonamide |
| 457 | 12 | 16.18 | E | 580.2839 (M + H+) | | N-((1S,4r)-4-((S)-3-cyclopropylmorpholine-4-carbonyl)cyclohexyl)-2-(4-(2-methoxyethyl)phenyl)-1-methyl-1H-indole-6-sulfonamide |
| 458 | 12 | 14.88 | E | 486.2431 (M + H+) | | 2-cyclopropyl-N-((1S,4r)-4-((S)-3-cyclopropylmorpholine-4-carbonyl)cyclohexyl)-1-methyl-1H-indole-6-sulfonamide |
| 459 | 12 | 15.55 | E | 470.2475 (M + H+) | | (1r,4r)-4-(2-cyclopropyl-1-methyl-1H-indole-6-sulfonamido)-N-(dicyclopropylmethyl)cyclohexanecarboxamide |
| 460 | 11 | 16.18 | E | 568.2821 (M + H+) | | N-((1S,4r)-4-((S)-3-isopropylmorpholine-4-carbonyl)cyclohexyl)-2-(4-(2-methoxyethyl)phenyl)-1H-indole-6-sulfonamide |

-continued

| Ex. | Synthetic Scheme | HPLC RT | HPLC Method | MS | NMR | Name |
|---|---|---|---|---|---|---|
| 461 | 11 + 14 | 17.38 | E | 602.2436 (M + H+) | | 3-chloro-N-((1S,4r)-4-((S)-3-isopropylmorpholine-4-carbonyl)cyclohexyl)-2-(4-(2-methoxyethyl)phenyl)-1H-indole-6-sulfonamide |
| 462 | 11 | 14.94 | E | 482.3 (M + H+) | | N-((1S,4r)-4-((S)-3-methylmorpholine-4-carbonyl)cyclohexyl)-2-phenyl-1H-indole-6-sulfonamide |
| 463 | 11 | 15.93 | E | 510.2 (M + H+) | | N-((1S,4r)-4-((S)-3-isopropylmorpholine-4-carbonyl)cyclohexyl)-2-phenyl-1H-indole-6-sulfonamide |
| 464 | 11 | 15.27 | E | 496.3 (M + H+) | | N-((1r,4r)-4-(2,2-dimethylmorpholine-4-carbonyl)cyclohexyl)-2-phenyl-1H-indole-6-sulfonamide |
| 465 | 11 | 15.52 | E | 510.4 (M + H+) | | N-((1R,4r)-4-((R)-2-(2-hydroxypropan-2-yl)pyrrolidine-1-carbonyl)cyclohexyl)-2-phenyl-1H-indole-6-sulfonamide |
| 466 | 11 | 14.48 | E | 509.3 (M + H+) | | (1r,4r)-N-(2-oxoazepan-3-yl)-4-(2-phenyl-1H-indole-6-sulfonamido)cyclohexanecarboxamide |
| 467 | 11 + 14 | 16.05 | E | 516.3, 518.2 (M + H+) | | 3-chloro-N-((1S,4r)-4-((S)-3-methylmorpholine-4-carbonyl)cyclohexyl)-2-phenyl-1H-indole-6-sulfonamide |
| 468 | 11 + 14 | 16.93 | E | 544.3, 546.3 (M + H+) | | 3-chloro-N-((1S,4r)-4-((S)-3-isopropylmorpholine-4-carbonyl)cyclohexyl)-2-phenyl-1H-indole-6-sulfonamide |
| 469 | 11 + 14 | 16.37 | E | 530.3, 532.2 (M + H+) | | 3-chloro-N-((1r,4r)-4-(2,2-dimethylmorpholine-4-carbonyl)cyclohexyl)-2-phenyl-1H-indole-6-sulfonamide |
| 470 | 11 | 15.48 | E | 566.2665 (M + H+) | | N-((1S,4r)-4-((S)-3-cyclopropylmorpholine-4-carbonyl)cyclohexyl)-2-(4-(2-methoxyethyl)phenyl)-1H-indole-6-sulfonamide |
| 471 | 11 + 14 | 16.74 | E | 600.2277 (M + H+) | | 3-chloro-N-((1S,4r)-4-((S)-3-cyclopropylmorpholine-4-carbonyl)cyclohexyl)-2-(4-(2-methoxyethyl)phenyl)-1H-indole-6-sulfonamide |
| 472 | 11 | 15.21 | E | 508.1 (M + H+) | | N-((1S,4r)-4-((S)-3-cyclopropylmorpholine-4-carbonyl)cyclohexyl)-2-phenyl-1H-indole-6-sulfonamide |
| 473 | 12 | 15.77 | E | 608.2775 (M + H+) | | methyl 3-(4-(6-(N-((1S,4r)-4-((S)-3-cyclopropylmorpholine-4-carbonyl)cyclohexyl)sulfamoyl)-1-methyl-1H-indol-2-yl)phenyl)propanoate |
| 474 | 11 + 14 | 16.39 | E | 542.1, 544.0 (M + H+) | | 3-chloro-N-((1S,4r)-4-((S)-3-cyclopropylmorpholine-4-carbonyl)cyclohexyl)-2-phenyl-1H-indole-6-sulfonamide |
| 475 | 11 | 14.86 | E | 496.1 (M + H+) | | N-((1R,4r)-4-((2S,6R)-2,6-dimethylmorpholine-4-carbonyl)cyclohexyl)-2-phenyl-1H-indole-6-sulfonamide |

| Ex. | Synthetic Scheme | HPLC RT | HPLC Method | MS | NMR | Name |
|---|---|---|---|---|---|---|
| 476 | 12 | 14.51 | E | 594.262 (M + H+) | | 3-(4-(6-(N-((1S,4r)-4-((S)-3-cyclopropylmorpholine-4-carbonyl)cyclohexyl)sulfamoyl)-1-methyl-1H-indol-2-yl)phenyl)propanoic acid |
| 477 | 11 + 14 | 16.19 | E | 530.1, 532.0 (M + H+) | | 3-chloro-N-((1R,4r)-4-((2S,6R)-2,6-dimethylmorpholine-4-carbonyl)cyclohexyl)-2-phenyl-1H-indole-6-sulfonamide |
| 478 | 11 + 14 | 17.26 | E | 594.3, 596.3 (M + H+) | | (1r,4S)-4-(3-chloro-2-phenyl-1H-indole-6-sulfonamido)-N-((S)-3-hydroxy-2,2-dimethyl-1-phenylpropyl)cyclohexanecarboxamide |
| 479 | 12 | 15.99 | E | 522.4 (M + H+) | | N-((1S,4r)-4-((S)-3-cyclopropylmorpholine-4-carbonyl)cyclohexyl)-1-methyl-2-phenyl-1H-indole-6-sulfonamide |
| 480 | 11 + 14 | 16.86 | E | 586.2123 (M + H+) | | 3-chloro-N-((1S,4r)-4-((S)-3-cyclopropylmorpholine-4-carbonyl)cyclohexyl)-2-(4-(methoxymethyl)phenyl)-1H-indole-6-sulfonamide |
| 481 | 11 | 15.75 | E | 522.2402 (M + H+) | | N-((1S,4r)-4-((S)-3-cyclopropylmorpholine-4-carbonyl)cyclohexyl)-2-o-tolyl-1H-indole-6-sulfonamide |
| 482 | 11 | 15.04 | E | 496.225 (M + H+) | | N-((1S,4r)-4-((S)-3-methylmorpholine-4-carbonyl)cyclohexyl)-2-o-tolyl-1H-indole-6-sulfonamide |
| 483 | 11 | 15.59 | E | 593.5 (M + H+) | | tert-butyl 6-((1r,4r)-4-(1-methyl-2-phenyl-1H-indole-6-sulfonamido)cyclohexanecarbonyl)-2,6-diazaspiro[3.3]heptane-2-carboxylate |
| 484 | 12 + 17 | 17.26 | E | 594.3, 596.3 (M + H+) | | 3-(4-(6-(N-((1S,4r)-4-((S)-3-cyclopropylmorpholine-4-carbonyl)cyclohexyl)sulfamoyl)-1,3-dimethyl-1H-indol-2-yl)phenyl)propanoic acid |
| 485 | 11 + 14 | 15.71 | E | 600.3, 602.3 (M + H+) | | N-((1r,4r)-4-(2-oxa-7-azaspiro[3.5]nonane-7-carbonyl)cyclohexyl)-3-chloro-2-(4-(2-methoxyethyl)phenyl)-1H-indole-6-sulfonamide |
| 486 | 12 | 15.33 | E | 510.1 (M + H+) | | 1-ethyl-N-((1S,4r)-4-((S)-3-methylmorpholine-4-carbonyl)cyclohexyl)-2-phenyl-1H-indole-6-sulfonamide |
| 487 | 34 | 14.08 | E | 558.1 (M + H+) | | ethyl 3-(5-(N-((1R,4r)-4-((R)-1-(4-fluorophenyl)ethylcarbamoyl)cyclohexyl)sulfamoyl)-1-methyl-1H-indol-3-yl)propanoate |
| 488 | 5 | | | 436.2 (M + H+) | | isopropyl 4-(2-phenyl-1H-benzo[d]imidazole-5-sulfonamido)benzoate |
| 489 | 5 | | | 450.1 (M + H+) | | tert-butyl 4-(2-phenyl-1H-benzo[d]imidazole-5-sulfonamido)benzoate |
| 490 | 1 | | | 469.2 (M + H+) | | N-phenyl-4-(2-phenyl-1H-benzo[d]imidazole-5-sulfonamido)benzamide |
| 491 | 5 | | | 450.1 (M + H+) | | butyl 4-(2-phenyl-1H-benzo[d]imidazole-6-sulfonamido)benzoate |
| 492 | 5 | | | 466.1 (M + H+) | | isopropyl 4-(2-(2-methoxyphenyl)-1H-benzo[d]imidazole-6-sulfonamido)benzoate |
| 493 | 1 | | | 437.1 (M + H+) | | propyl 4-(2-phenyl-1H-benzo[d]imidazol-6-ylsulfonyloxy)benzoate |

| Ex. | Synthetic Scheme | HPLC RT | HPLC Method | MS | NMR | Name |
|---|---|---|---|---|---|---|
| 494 | 5 | | | 478.1 (M + H+) | | isopropyl 4-(2-(3-acetylphenyl)-1H-benzo[d]imidazole-6-sulfonamido)benzoate |
| 495 | 5 | 2.03 | A1 | 478 (M + H+) | | isopropyl 4-(2-(4-acetylphenyl)-1H-benzo[d]imidazole-6-sulfonamido)benzoate |
| 496 | 5 | | | 454.1 (M + H+) | | isopropyl 4-(2-(3-fluorophenyl)-1H-benzo[d]imidazole-6-sulfonamido)benzoate |
| 497 | 5 | 2.8 | A2 | 466 (M + H+) | | isopropyl 4-(2-(4-methoxyphenyl)-1H-benzo[d]imidazole-6-sulfonamido)benzoate |
| 498 | 5 | 2.5 | A2 | 493 (M + H+) | | isopropyl 4-(2-(4-acetamidophenyl)-1H-benzo[d]imidazole-6-sulfonamido)benzoate |
| 499 | 5 | | | 454.1 (M + H+) | | isopropyl 4-(2-(4-fluorophenyl)-1H-benzo[d]imidazole-6-sulfonamido)benzoate |
| 500 | 5 | | | 466.1 (M + H+) | | isopropyl 4-(2-(3-methoxyphenyl)-1H-benzo[d]imidazole-6-sulfonamido)benzoate |
| 501 | 5 | | | 450.1 (M + H+) | | isopropyl 4-(2-m-tolyl-1H-benzo[d]imidazole-6-sulfonamido)benzoate |
| 502 | 5 | | | 454.1 (M + H+) | | isopropyl 4-(2-(2-fluorophenyl)-1H-benzo[d]imidazole-6-sulfonamido)benzoate |
| 503 | 5 | 2.57 | A2 | 452 (M + H+) | | isopropyl 4-(2-(4-hydroxyphenyl)-1H-benzo[d]imidazole-6-sulfonamido)benzoate |
| 504 | 5 | | | 450.1 (M + H+) | | isopropyl 4-(2-p-tolyl-1H-benzo[d]imidazole-6-sulfonamido)benzoate |
| 505 | 5 | | | 494.1 (M + H+) | | isopropyl 4-(2-(4-isopropoxyphenyl)-1H-benzo[d]imidazole-6-sulfonamido)benzoate |
| 506 | 5 | | | 478.1 (M + H+) | | isopropyl 4-(2-(4-isopropylphenyl)-1H-benzo[d]imidazole-6-sulfonamido)benzoate |
| 507 | 1 | | | 528.1 (M + H+) | | isopropyl 4-(2-(4-phenoxyphenyl)-1H-benzo[d]imidazole-6-sulfonamido)benzoate |
| 508 | 5 | | | 479.1 (M + H+) | | isopropyl 4-(2-(4-(dimethylamino)phenyl)-1H-benzo[d]imidazole-6-sulfonamido)benzoate |
| 509 | 5 | 2.87 | A2 | 480 (M + H+) | | 4-(6-(N-(4-(isopropoxycarbonyl)phenyl)sulfamoyl)-1H-benzo[d]imidazol-2-yl)benzoic acid |
| 510 | 5 | | | 443 (M + H+) | | isopropyl 4-(2-(thiazol-5-yl)-1H-benzo[d]imidazole-6-sulfonamido)benzoate |
| 511 | 5 | | | 452 (M + H+) | | isopropyl 4-(2-(3-hydroxyphenyl)-1H-benzo[d]imidazole-6-sulfonamido)benzoate |
| 512 | 5 | | | 492.1 (M + H+) | | isopropyl 4-(2-(4-tert-butylphenyl)-1H-benzo[d]imidazole-6-sulfonamido)benzoate |
| 513 | 6 | | | 474.1 (M + H+) | | N-(4-(5-tert-butyl-1,3,4-oxadiazol-2-yl)phenyl)-2-phenyl-1H-benzo[d]imidazole-6-sulfonamide |
| 514 | 5 | 2.98 | A2 | 514 (M + H+) | | isopropyl 4-(2-(4-(methylsulfonyl)phenyl)-1H-benzo[d]imidazole-6-sulfonamido)benzoate |
| 515 | 2 | | | 437.1 (M + H+) | | isopropyl 4-(2-(pyridin-4-yl)-1H-benzo[d]imidazole-6-sulfonamido)benzoate |
| 516 | 5 | | | 496.1 (M + H+) | | isopropyl 4-(2-(3,4-dimethoxyphenyl)-1H-benzo[d]imidazole-6-sulfonamido)benzoate |
| 517 | 5 | 2.65 | A2 | 480 (M + H+) | | isopropyl 4-(2-(4-(1-hydroxyethyl)phenyl)-1H-benzo[d]imidazole-6-sulfonamido)benzoate |
| 518 | 6 | | | 494 (M + H+) | | 2-phenyl-N-(4-(5-phenyl-1,3,4-oxadiazol-2-yl)phenyl)-1H-benzo[d]imidazole-6-sulfonamide |

| Ex. | Synthetic Scheme | HPLC RT | HPLC Method | MS | NMR | Name |
|---|---|---|---|---|---|---|
| 519 | 6 | | | 500.1 (M + H+) | | N-(4-(5-cyclohexyl-1,3,4-oxadiazol-2-yl)phenyl)-2-phenyl-1H-benzo[d]imidazole-6-sulfonamide |
| 520 | 6 | | | 462 (M + H+) | | N-(4-(5-(methoxymethyl)-1,3,4-oxadiazol-2-yl)phenyl)-2-phenyl-1H-benzo[d]imidazole-6-sulfonamide |
| 521 | 5 | 1.74 | A1 | 451 (M + H+) | | isopropyl 4-(2-(phenylamino)-1H-benzo[d]imidazole-5-sulfonamido)benzoate |
| 522 | 5 | 1.78 | A1 | 469 (M + H+) | | isopropyl 4-(2-(4-fluorophenylamino)-1H-benzo[d]imidazole-5-sulfonamido)benzoate |
| 523 | 5 | 1.77 | A1 | 481 (M + H+) | | isopropyl 4-(2-(4-methoxyphenylamino)-1H-benzo[d]imidazole-5-sulfonamido)benzoate |
| 524 | 5 | 1.49 | C | 481 (M + H+) | | isopropyl 4-(2-(3-methoxyphenylamino)-1H-benzo[d]imidazole-5-sulfonamido)benzoate |
| 525 | 5 | 1.58 | C | 476 (M + H+) | | isopropyl 4-(2-(3-cyanophenylamino)-1H-benzo[d]imidazole-5-sulfonamido)benzoate |
| 526 | 5 | 1.52 | C | 509 (M + H+) | | isopropyl 4-(2-(2,3-dihydrobenzo[b][1,4]dioxin-6-ylamino)-1H-benzo[d]imidazole-5-sulfonamido)benzoate |
| 527 | 4 | 1.63 | C | 509 (M + H+) | | isopropyl 4-(2-(benzo[c][1,2,5]thiadiazol-5-ylamino)-1H-benzo[d]imidazole-5-sulfonamido)benzoate |
| 528 | 5 | 1.5 | C | 530 (M + H+) | | isopropyl 4-(2-(4-sulfamoylphenylamino)-1H-benzo[d]imidazole-5-sulfonamido)benzoate |
| 529 | 5 | 1.61 | C | 485 (M + H+) | | isopropyl 4-(2-(4-chlorophenylamino)-1H-benzo[d]imidazole-5-sulfonamido)benzoate |
| 530 | 5 | 1.58 | C | 511 (M + H+) | | isopropyl 4-(2-(3,5-dimethoxyphenylamino)-1H-benzo[d]imidazole-5-sulfonamido)benzoate |
| 531 | 5 | 1.52 | C | 511 (M + H+) | | isopropyl 4-(2-(3,4-dimethoxyphenylamino)-1H-benzo[d]imidazole-5-sulfonamido)benzoate |
| 532 | 5 | 1.52 | C | 536 (M + H+) | | isopropyl 4-(2-(4-morpholinophenylamino)-1H-benzo[d]imidazole-5-sulfonamido)benzoate |
| 533 | 5 | 1.6 | C | 487 (M + H+) | | isopropyl 4-(2-(2,3-difluorophenylamino)-1H-benzo[d]imidazole-5-sulfonamido)benzoate |
| 534 | 5 | 1.52 | C | 538 (M + H+) | | isopropyl 4-(2-(4-(ethoxycarbonylamino)phenylamino)-1H-benzo[d]imidazole-5-sulfonamido)benzoate |
| 535 | 5 | 1.6 | C | 469 (M + H+) | | isopropyl 4-(2-(3-fluorophenylamino)-1H-benzo[d]imidazole-5-sulfonamido)benzoate |
| 536 | 5 | 1.6 | C | 465 (M + H+) | | isopropyl 4-(2-(m-tolylamino)-1H-benzo[d]imidazole-5-sulfonamido)benzoate |
| 537 | 5 | 1.46 | C | 522 (M + H+) | | isopropyl 4-(2-(4-(diethylamino)phenylamino)-1H-benzo[d]imidazole-5-sulfonamido)benzoate |
| 538 | 5 | 1.66 | C | 496 (M + H+) | | isopropyl 4-(2-(3-nitrophenylamino)-1H-benzo[d]imidazole-5-sulfonamido)benzoate |
| 539 | 5 | 1.47 | C | 537 (M + H+) | | isopropyl 4-(2-(6-morpholinopyridin-3-ylamino)-1H-benzo[d]imidazole-5-sulfonamido)benzoate |
| 540 | 5 | | | 479.1 (M + H+) | | isopropyl 4-(2-(2,6-dimethylphenylamino)-1H-benzo[d]imidazole-5-sulfonamido)benzoate |
| 541 | 5 | 1.56 | C | 493 (M + H+) | | isopropyl 4-(2-(3-acetylphenylamino)-1H-benzo[d]imidazole-5-sulfonamido)benzoate |

-continued

| Ex. | Synthetic Scheme | HPLC RT | HPLC Method | MS | NMR | Name |
|---|---|---|---|---|---|---|
| 542 | 5 | 1.65 | C | 503 (M + H+) | | isopropyl 4-(2-(3-chloro-4-fluorophenylamino)-1H-benzo[d]imidazole-5-sulfonamido)benzoate |
| 543 | 5 | 1.55 | C | 541 (M + H+) | | isopropyl 4-(2-(3,4,5-trimethoxyphenylamino)-1H-benzo[d]imidazole-5-sulfonamido)benzoate |
| 544 | 5 | 1.55 | C | 564 (M + H+) | | isopropyl 4-(2-(4-chloro-3-sulfamoylphenylamino)-1H-benzo[d]imidazole-5-sulfonamido)benzoate |
| 545 | 5 | 1.57 | C | 517 (M + H+) | | isopropyl 4-(2-(4-(1H-pyrazol-1-yl)phenylamino)-1H-benzo[d]imidazole-5-sulfonamido)benzoate |
| 546 | 5 | 1.57 | C | 469 (M + H+) | | isopropyl 4-(2-(2-fluorophenylamino)-1H-benzo[d]imidazole-5-sulfonamido)benzoate |
| 547 | 5 | 1.64 | C | 485 (M + H+) | | isopropyl 4-(2-(3-chlorophenylamino)-1H-benzo[d]imidazole-5-sulfonamido)benzoate |
| 548 | 5 | 1.6 | C | 493 (M + H+) | | isopropyl 4-(2-(4-acetylphenylamino)-1H-benzo[d]imidazole-5-sulfonamido)benzoate |
| 549 | 5 | 1.58 | C | 550 (M + H+) | | isopropyl 4-(2-(3-(2-oxothiazol-3(2H)-yl)phenylamino)-1H-benzo[d]imidazole-5-sulfonamido)benzoate |
| 550 | 5 | 1.73 | C | 496 (M + H+) | | isopropyl 4-(2-(4-nitrophenylamino)-1H-benzo[d]imidazole-5-sulfonamido)benzoate |
| 551 | 5 | 1.48 | C | 494 (M + H+) | | isopropyl 4-(2-(4-(dimethylamino)phenylamino)-1H-benzo[d]imidazole-5-sulfonamido)benzoate |
| 552 | 5 | 1.66 | C | 476 (M + H+) | | isopropyl 4-(2-(4-cyanophenylamino)-1H-benzo[d]imidazole-5-sulfonamido)benzoate |
| 553 | 5 | 1.52 | C | 495 (M + H+) | | isopropyl 4-(2-(3-(1-hydroxyethyl)phenylamino)-1H-benzo[d]imidazole-5-sulfonamido)benzoate |
| 554 | 4 | 1.63 | A1 | 457 (M + H+) | | (1r,4r)-isopropyl 4-(2-(phenylamino)-1H-benzo[d]imidazole-5-sulfonamido)cyclohexanecarboxylate |
| 555 | 5 | 1.67 | A1 | 487 (M + H+) | | (1r,4r)-isopropyl 4-(2-(4-methoxyphenylamino)-1H-benzo[d]imidazole-5-sulfonamido)cyclohexanecarboxylate |
| 556 | 5 | 1.58 | A1 | 486 (M + H+) | | (1r,4r)-isopropyl 4-(2-(4-(1-hydroxyethyl)phenyl)-1H-benzo[d]imidazole-5-sulfonamido)cyclohexanecarboxylate |
| 557 | 5 | 1.35 | A1 | 540 (M + H+) | | (1r,4r)-isopropyl 4-(2-(4-(4-methylpiperazin-1-yl)phenyl)-1H-benzo[d]imidazole-5-sulfonamido)cyclohexanecarboxylate |
| 558 | 5 | 1.54 | A1 | 493 (M + H+) | | isopropyl 4-(2-(4-((dimethylamino)methyl)phenyl)-1H-benzo[d]imidazole-5-sulfonamido)benzoate |
| 559 | 5 | 1.54 | A1 | 478 (M + H+) | | isopropyl 4-(2-(4-((methylamino)methyl)phenyl)-1H-benzo[d]imidazole-5-sulfonamido)benzoate |
| 560 | 5 | 1.72 | A1 | 555 (M + H+) | | isopropyl 4-(2-(4-((benzylamino)methyl)phenyl)-1H-benzo[d]imidazole-5-sulfonamido)benzoate |
| 561 | 5 | 1.54 | A1 | 548 (M + H+) | | isopropyl 4-(2-(4-(4-methylpiperazin-1-yl)methyl)phenyl)-1H-benzo[d]imidazole-5-sulfonamido)benzoate |

| Ex. | Synthetic Scheme | HPLC RT | HPLC Method | MS | NMR | Name |
|---|---|---|---|---|---|---|
| 562 | 5 | 1.58 | A1 | 535 (M + H+) | | isopropyl 4-(2-(4-(morpholinomethyl)phenyl)-1H-benzo[d]imidazole-5-sulfonamido)benzoate |
| 563 | 5 | 1.78 | A1 | 615 (M + H+) | | isopropyl 4-(2-(4-((3,4-dimethoxybenzylamino)methyl)phenyl)-1H-benzo[d]imidazole-5-sulfonamido)benzoate |
| 564 | 2 | 1.16 | A1 | 553 (M + H+) | | (1r,4R)-N-isopropyl-N-methyl-4-(2-(4-(4-methylpiperazin-1-yl)phenyl)-1H-benzo[d]imidazole-5-sulfonamido)cyclohexanecarboxamide |
| 565 | 2 | 1.16 | A1 | 553 (M + H+) | | (1r,4r)-N-methyl-4-(2-(4-(4-methylpiperazin-1-yl)phenyl)-1H-benzo[d]imidazole-5-sulfonamido)-N-propylcyclohexanecarboxamide |
| 566 | 4 | 1.38 | A1 | 470 (M + H+) | | (1r,4r)-N-methyl-4-(2-(phenylamino)-1H-benzo[d]imidazole-5-sulfonamido)-N-propylcyclohexanecarboxamide |
| 567 | 2 | 2.58 | B1 | 539 (M + H+) | | (1r,4r)-N-ethyl-N-methyl-4-(2-(4-(4-methylpiperazin-1-yl)phenyl)-1H-benzo[d]imidazole-5-sulfonamido)cyclohexanecarboxamide |
| 568 | 4 | 2.26 | B2 | 456 (M + H+) | | (1r,4r)-N-ethyl-N-methyl-4-(2-(phenylamino)-1H-benzo[d]imidazole-5-sulfonamido)cyclohexanecarboxamide |
| 569 | 4 | 1.58 | A1 | 518 (M + H+) | | (1r,4R)-4-(2-(phenylamino)-1H-benzo[d]imidazole-5-sulfonamido)-N-((R)-1-phenylethyl)cyclohexanecarboxamide |
| 570 | 4 | 1.63 | A1 | 543 (M + H+) | | (1r,4R)-4-(2-(3-cyanophenylamino)-1H-benzo[d]imidazole-5-sulfonamido)-N-((R)-1-phenylethyl)cyclohexanecarboxamide |
| 571 | 4 | 1.36 | A1 | 604 (M + H+) | | (1r,4R)-4-(2-(6-morpholinopyridin-3-ylamino)-1H-benzo[d]imidazole-5-sulfonamido)-N-((R)-1-phenylethyl)cyclohexanecarboxamide |
| 572 | 4 | 1.61 | A1 | 560 (M + H+) | | (1r,4R)-4-(2-(4-acetylphenylamino)-1H-benzo[d]imidazole-5-sulfonamido)-N-((R)-1-phenylethyl)cyclohexanecarboxamide |
| 573 | 2 | 1.51 | A1 | 547 (M + H+) | | (1r,4R)-4-(2-(4-(1-hydroxyethyl)phenyl)-1H-benzo[d]imidazole-5-sulfonamido)-N-((R)-1-phenylethyl)cyclohexanecarboxamide |
| 574 | 4 | 1.52 | A1 | 603 (M + H+) | | (1r,4R)-4-(2-(4-morpholinophenylamino)-1H-benzo[d]imidazole-5-sulfonamido)-N-((R)-1-phenylethyl)cyclohexanecarboxamide |
| 575 | 2 | 1.32 | A1 | 601 (M + H+) | | (1r,4R)-4-(2-(4-(4-methylpiperazin-1-yl)phenyl)-1H-benzo[d]imidazole-5-sulfonamido)-N-((R)-1-phenylethyl)cyclohexanecarboxamide |
| 576 | 2 | 1.32 | A1 | 615 (M + H+) | | (1r,4R)-4-(2-(4-(4-methylpiperazin-1-yl)methyl)phenyl)-1H-benzo[d]imidazole-5-sulfonamido)-N-((R)-1-phenylethyl)cyclohexanecarboxamide |
| 577 | 2 | 1.33 | A1 | 602 (M + H+) | | (1r,4R)-4-(2-(4-(morpholinomethyl)phenyl)-1H-benzo[d]imidazole-5-sulfonamido)-N-((R)-1-phenylethyl)cyclohexanecarboxamide |

| Ex. | Synthetic Scheme | HPLC RT | HPLC Method | MS | NMR | Name |
|---|---|---|---|---|---|---|
| 578 | 1 | 1.74 | A1 | 517 (M + H+) | | (1r,4R)-N-methyl-4-(2-phenyl-1H-benzo[d]imidazole-5-sulfonamido)-N-((R)-1-phenylethyl)cyclohexanecarboxamide |
| 579 | 2 | 1.33 | A1 | 519 (M + H+) | | (1r,4S)-N-((S)-2-hydroxy-1-phenylethyl)-4-(2-phenyl-1H-benzo[d]imidazole-5-sulfonamido)cyclohexanecarboxamide |
| 580 | 1 | | | 503 (M + H+) | | (1r,4S)-4-(2-phenyl-1H-benzo[d]imidazole-5-sulfonamido)-N-((S)-1-phenylethyl)cyclohexanecarboxamide |
| 581 | 1 | 1.61 | A1 | 515 (M + H+) | | (1r,4r)-4-(2-phenyl-1H-benzo[d]imidazole-5-sulfonamido)-N-(1-phenylcyclopropyl)cyclohexanecarboxamide |
| 582 | 1 | 1.73 | A1 | 517 (M + H+) | 1H NMR (400 MHz, DMSO-d6) d ppm 1.21 (br. s., 1H) 1.18 (d, J = 7.20 Hz, 4H) 1.53 (br. s., 4H) 2.24 (s, 3H) 2.38 (br. s., 1H) 2.47 (br. s., 4H) 2.88 (br. s., 1H) 3.31 (br. s., 4H) 3.37 (br. s., 2H) 3.38-3.44 (m, 2H) 3.48 (d, J = 5.05 Hz, 4H) 7.10 (dd, J = 9.09, 2.78 Hz, 2H) 7.55-7.65 (m, 3H) 8.03 (dd, J = 8.97, 1.52 Hz, 2H) 13.02 (d, J = 18.32 Hz, 1H) | (1r,4r)-4-(2-phenyl-1H-benzo[d]imidazole-5-sulfonamido)-N-(2-phenylpropan-2-yl)cyclohexanecarboxamide |
| 583 | 2 | 0.93 | A1 | 567 (M + H+) | | 2-(4-(4-methylpiperazin-1-yl)phenyl)-N-((1r,4r)-4-(morpholine-4-carbonyl)cyclohexyl)-1H-benzo[d]imidazole-5-sulfonamide |
| 584 | 4 | 1.1 | A1 | 484 (M + H+) | | N-((1r,4r)-4-(morpholine-4-carbonyl)cyclohexyl)-2-(phenylamino)-1H-benzo[d]imidazole-5-sulfonamide |
| 585 | 6 | 4.898 | F | 480.23 (M + H+) | | N-((1r,4r)-4-(5-tert-butyl-1,3,4-oxadiazol-2-yl)cyclohexyl)-2-phenyl-1H-benzo[d]imidazole-5-sulfonamide |
| 586 | 6 | | | 466.14 (M + H+) | | N-((1r,4r)-4-(5-isopropyl-1,3,4-oxadiazol-2-yl)cyclohexyl)-2-phenyl-1H-benzo[d]imidazole-5-sulfonamide |
| 587 | 1 | 8.85 | E | 564.35 (M + H+) | | N-((1r,4r)-4-(5-isopropyl-1,3,4-oxadiazol-2-yl)cyclohexyl)-2-(4-(4-methylpiperazin-1-yl)phenyl)-1H-benzo[d]imidazole-5-sulfonamide |
| 588 | 6 | 10.97 | E | 565.24 (M + H+) | | N-((1r,4r)-4-(5-tert-butyl-1,3,4-oxadiazol-2-yl)cyclohexyl)-2-(4-morpholinophenyl)-1H-benzo[d]imidazole-5-sulfonamide |
| 589 | 6 | 10.46 | E | 551.24 (M + H+) | | N-((1r,4r)-4-(5-isopropyl-1,3,4-oxadiazol-2-yl)cyclohexyl)-2-(4-morpholinophenyl)-1H-benzo[d]imidazole-5-sulfonamide |
| 590 | 6 | | | 558.19 (M + H+) | | N-(4-(5-isopropyl-1,3,4-oxadiazol-2-yl)phenyl)-2-(4-(4-methylpiperazin-1-yl)phenyl)-1H-benzo[d]imidazole-5-sulfonamide |
| 591 | 6 | 9.53 | E | 558.19 (M + H+) | | N-(4-(5-isopropyl-1,3,4-oxadiazol-2-yl)phenyl)-2-(4-morpholinophenyl)-1H-benzo[d]imidazole-5-sulfonamide |

| Ex. | Synthetic Scheme | HPLC RT | HPLC Method | MS | NMR | Name |
|---|---|---|---|---|---|---|
| 592 | 6 | 9.99 | E | 572.23 (M + H+) | | N-(4-(5-tert-butyl-1,3,4-oxadiazol-2-yl)phenyl)-2-(4-(4-methylpiperazin-1-yl)phenyl)-1H-benzo[d]imidazole-5-sulfonamide |
| 593 | 6 | 11.55 | E | 559.18 (M + H+) | | N-(4-(5-tert-butyl-1,3,4-oxadiazol-2-yl)phenyl)-2-(4-morpholinophenyl)-1H-benzo[d]imidazole-5-sulfonamide |
| 594 | 6 | 10.14 | E | 511.19 (M + H+) | | N-((1r,4r)-4-(5-isopropyl-1,3,4-oxadiazol-2-yl)cyclohexyl)-2-(4-methoxyphenylamino)-1H-benzo[d]imidazole-5-sulfonamide |
| 595 | 6 | 9.84 | E | 481.2 (M + H+) | | N-((1r,4r)-4-(5-isopropyl-1,3,4-oxadiazol-2-yl)cyclohexyl)-2-(phenylamino)-1H-benzo[d]imidazole-5-sulfonamide |
| 596 | 6 | 10.7 | E | 525.22 (M + H+) | | N-((1r,4r)-4-(5-tert-butyl-1,3,4-oxadiazol-2-yl)cyclohexyl)-2-(4-methoxyphenylamino)-1H-benzo[d]imidazole-5-sulfonamide |
| 597 | 6 | 4.95 | F | 495.23 (M + H+) | | N-((1r,4r)-4-(5-tert-butyl-1,3,4-oxadiazol-2-yl)cyclohexyl)-2-(phenylamino)-1H-benzo[d]imidazole-5-sulfonamide |
| 598 | 6 | 8.64 | E | 579.28 (M + H+) | | N-((1r,4r)-4-(5-isopropyl-1,3,4-oxadiazol-2-yl)cyclohexyl)-2-(4-(4-methylpiperazin-1-yl)phenylamino)-1H-benzo[d]imidazole-5-sulfonamide |
| 599 | 6 | 9.63 | E | 566.26 (M + H+) | | N-((1r,4r)-4-(5-isopropyl-1,3,4-oxadiazol-2-yl)cyclohexyl)-2-(4-morpholinophenylamino)-1H-benzo[d]imidazole-5-sulfonamide |
| 600 | 6 | 10.22 | E | 580.25 (M + H+) | | N-((1r,4r)-4-(5-tert-butyl-1,3,4-oxadiazol-2-yl)cyclohexyl)-2-(4-morpholinophenylamino)-1H-benzo[d]imidazole-5-sulfonamide |
| 601 | 6 | no data | | 475.16 (M + H+) | | N-(4-(5-isopropyl-1,3,4-oxadiazol-2-yl)phenyl)-2-(phenylamino)-1H-benzo[d]imidazole-5-sulfonamide |
| 602 | 6 | 10.81 | E | 505.17 (M + H+) | | N-(4-(5-isopropyl-1,3,4-oxadiazol-2-yl)phenyl)-2-(4-methoxyphenylamino)-1H-benzo[d]imidazole-5-sulfonamide |
| 603 | 6 | 10.36 | E | 560.21 (M + H+) | | N-(4-(5-isopropyl-1,3,4-oxadiazol-2-yl)phenyl)-2-(4-morpholinophenylamino)-1H-benzo[d]imidazole-5-sulfonamide |
| 604 | 6 | 11.34 | E | 519.19 (M + H+) | | N-(4-(5-tert-butyl-1,3,4-oxadiazol-2-yl)phenyl)-2-(4-methoxyphenylamino)-1H-benzo[d]imidazole-5-sulfonamide |
| 605 | 6 | 9.37 | E | 573.3 (M + H+) | | N-(4-(5-isopropyl-1,3,4-oxadiazol-2-yl)phenyl)-2-(4-(4-methylpiperazin-1-yl)phenylamino)-1H-benzo[d]imidazole-5-sulfonamide |
| 606 | 4 | 7.861 | D | 616.35 (M + H+) | | (1r,4R)-4-(2-(4-(4-methylpiperazin-1-yl)phenylamino)-1H-benzo[d]imidazole-5-sulfonamido)-N-((R)-1-phenylethyl)cyclohexanecarboxamide |
| 607 | 6 | | | 498.3 (M + H+) | | N-((1r,4r)-4-(5-tert-butyl-1,3,4-oxadiazol-2-yl)cyclohexyl)-2-(4-fluorophenyl)-1H-benzo[d]imidazole-5-sulfonamide |

-continued

| Ex. | Synthetic Scheme | HPLC RT | HPLC Method | MS | NMR | Name |
|---|---|---|---|---|---|---|
| 608 | 6 | 4.88 | F | 538.35 (M + H+) | | methyl 3-(5-(N-((1r,4r)-4-(5-tert-butyl-1,3,4-oxadiazol-2-yl)cyclohexyl)sulfamoyl)-1H-benzo[d]imidazol-2-yl)benzoate |
| 609 | 6 | | | 514.14 (M + H+) | | N-((1r,4r)-4-(5-tert-butyl-1,3,4-oxadiazol-2-yl)cyclohexyl)-2-(4-chlorophenyl)-1H-benzo[d]imidazole-5-sulfonamide |
| 610 | 6 | | | 524.3 (M + H+) | | 3-(5-(N-((1r,4r)-4-(5-tert-butyl-1,3,4-oxadiazol-2-yl)cyclohexyl)sulfamoyl)-1H-benzo[d]imidazol-2-yl)benzoic acid |
| 611 | 1 | 10.997 | D | 521.31 (M + H+) | | (1r,4R)-N-((R)-1-(4-fluorophenyl)ethyl)-4-(2-phenyl-1H-benzo[d]imidazol-5-sulfonamido)cyclohexanecarboxamide |
| 612 | 1 | 9.845 | D | 510.3 (M + H+) | | (1r,4S)-N-((S)-2-oxoazepan-3-yl)-4-(2-phenyl-1H-benzo[d]imidazol-5-sulfonamido)cyclohexanecarboxamide |
| 613 | 6 | | | 404.2 (M + H+) | | N-((1r,4r)-4-(5-isopropyl-1,3,4-oxadiazol-2-yl)cyclohexyl)-2-methyl-1H-benzo[d]imidazole-5-sulfonamide |
| 614 | 2 | 4.038 | F | 441.24 (M + H+) | | (1r,4R)-4-(2-methyl-1H-benzo[d]imidazole-5-sulfonamido)-N-(R)-1-phenylethyl)cyclohexanecarboxamide |
| 615 | 6 | | | 418.24 (M + H+) | | N-((1r,4r)-4-(5-tert-butyl-1,3,4-oxadiazol-2-yl)cyclohexyl)-2-methyl-1H-benzo[d]imidazole-5-sulfonamide |
| 616 | 1 | 7.616 | D | 515.31 (M + H+) | | 2-phenyl-N-((1r,4r)-4-(1,2,3,4-tetrahydroisoquinoline-2-carbonyl)cyclohexyl)-1H-benzo[d]imidazole-5-sulfonamide |
| 617 | 1 | 6.763 | D | 544.33 (M + H+) | | 2-phenyl-N-((1r,4r)-4-(4-phenylpiperazine-1-carbonyl)cyclohexyl)-1H-benzo[d]imidazole-5-sulfonamide |
| 618 | 1 | 7.744 | D | 495.31 (M + H+) | | (1r,4r)-N-cyclohexyl-N-methyl-4-(2-phenyl-1H-benzo[d]imidazol-5-sulfonamido)cyclohexanecarboxamide |
| 619 | 1 | 7.552 | D | 503.29 (M + H+) | | (1r,4r)-N-benzyl-N-methyl-4-(2-phenyl-1H-benzo[d]imidazol-5-sulfonamido)cyclohexanecarboxamide |
| 620 | 1 | 6.517 | D | 497.31 (M + H+) | | N-((1r,4r)-4-(2,6-dimethylmorpholine-4-carbonyl)cyclohexyl)-2-phenyl-1H-benzo[d]imidazole-5-sulfonamide |
| 621 | 1 | | | 443.17 (M + H+) | | (1r,4r)-N-(2-hydroxyethyl)-4-(2-phenyl-1H-benzo[d]imidazol-5-sulfonamido)cyclohexanecarboxamide |
| 622 | 1 | 6.336 | D | 539.21 (M + H+) | | N-((1r,4r)-4-(1,5-dioxa-9-azaspiro[5.5]undecane-9-carbonyl)cyclohexyl)-2-phenyl-1H-benzo[d]imidazole-5-sulfonamide |
| 623 | 1 | 7.563 | D | 501.17 (M + H+) | | N-((1r,4r)-4-(isoindoline-2-carbonyl)cyclohexyl)-2-phenyl-1H-benzo[d]imidazole-5-sulfonamide |
| 624 | 1 | 8.416 | D | 521.25 (M + H+) | | N-((1r,4r)-4-(decahydroisoquinoline-2-carbonyl)cyclohexyl)-2-phenyl-1H-benzo[d]imidazole-5-sulfonamide |

| Ex. | Synthetic Scheme | HPLC RT | HPLC Method | MS | NMR | Name |
|---|---|---|---|---|---|---|
| 625 | 1 | 8.043 | D | 495.35 (M + H+) | | (1r,4r)-N-(cyclopropylmethyl)-4-(2-phenyl-1H-benzo[d]imidazole-5-sulfonamido)-N-propylcyclohexanecarboxamide |
| 626 | 1 | 8.107 | D | 495.35 (M + H+) | | N-((1r,4r)-4-(3,5-dimethylpiperidine-1-carbonyl)cyclohexyl)-2-phenyl-1H-benzo[d]imidazole-5-sulfonamide |
| 627 | 1 | | | 564.45 (M + H+) | | N-((1r,4r)-4-(4-(cyclohexylmethyl)piperazine-1-carbonyl)cyclohexyl)-2-phenyl-1H-benzo[d]imidazole-5-sulfonamide |
| 628 | 1 | 5.39 | G | 503.29 (M + H+) | | (1r,4r)-N-phenethyl-4-(2-phenyl-1H-benzo[d]imidazole-5-sulfonamido)cyclohexanecarboxamide |
| 629 | 1 | | | 455.3 (M + H+) | | (1r,4r)-N-isobutyl-4-(2-phenyl-1H-benzo[d]imidazole-5-sulfonamido)cyclohexanecarboxamide |
| 630 | 1 | 5.401 | G | 469.33 (M + H+) | | (1r,4r)-N-isopentyl-4-(2-phenyl-1H-benzo[d]imidazole-5-sulfonamido)cyclohexanecarboxamide |
| 631 | 1 | | | 470.29 (M + H+) | | (1r,4r)-N-(2-(dimethylamino)ethyl)-4-(2-phenyl-1H-benzo[d]imidazole-5-sulfonamido)cyclohexanecarboxamide |
| 632 | 1 | 5.388 | G | 481.32 (M + H+) | | (1r,4r)-N-cyclohexyl-4-(2-phenyl-1H-benzo[d]imidazole-5-sulfonamido)cyclohexanecarboxamide |
| 633 | 1 | | | 455.19 (M + H+) | | (1r,4r)-N-butyl-4-(2-phenyl-1H-benzo[d]imidazole-5-sulfonamido)cyclohexanecarboxamide |
| 634 | 1 | | | 457.23 (M + H+) | | (1r,4r)-N-(2-methoxyethyl)-4-(2-phenyl-1H-benzo[d]imidazole-5-sulfonamido)cyclohexanecarboxamide |
| 635 | 1 | 4.491 | G | 439.18 (M + H+) | | (1r,4r)-N-cyclopropyl-4-(2-phenyl-1H-benzo[d]imidazole-5-sulfonamido)cyclohexanecarboxamide |
| 636 | 1 | | | 529.23 (M + H+) | | (1r,4r)-4-(2-phenyl-1H-benzo[d]imidazole-5-sulfonamido)-N-(1,2,3,4-tetrahydronaphthalen-1-yl)cyclohexanecarboxamide |
| 637 | 1 | 4.855 | G | 453.22 (M + H+) | | (1r,4r)-N-(cyclopropylmethyl)-4-(2-phenyl-1H-benzo[d]imidazole-5-sulfonamido)cyclohexanecarboxamide |
| 638 | 1 | 5.546 | G | 515.22 (M + H+) | | (1r,4r)-N-(2,3-dihydro-1H-inden-2-yl)-4-(2-phenyl-1H-benzo[d]imidazole-5-sulfonamido)cyclohexanecarboxamide |
| 639 | 1 | 5.69 | G | 495.25 (M + H+) | | (1r,4r)-N-(cyclohexylmethyl)-4-(2-phenyl-1H-benzo[d]imidazole-5-sulfonamido)cyclohexanecarboxamide |
| 640 | 1 | 4.433 | G | 490.17 (M + H+) | | (1r,4r)-4-(2-phenyl-1H-benzo[d]imidazole-5-sulfonamido)-N-(pyridin-3-ylmethyl)cyclohexanecarboxamide |
| 641 | 1 | 5.931 | G | 509.33 (M + H+) | | (1r,4r)-N-(cycloheptylmethyl)-4-(2-phenyl-1H-benzo[d]imidazole-5-sulfonamido)cyclohexanecarboxamide |

| Ex. | Synthetic Scheme | HPLC RT | HPLC Method | MS | NMR | Name |
|---|---|---|---|---|---|---|
| 642 | 1 | | | 471.27 (M + H+) | | (1r,4r)-N-(3-methoxypropyl)-4-(2-phenyl-1H-benzo[d]imidazole-5-sulfonamido)cyclohexanecarboxamide |
| 643 | 1 | 4.498 | G | 504.25 (M + H+) | | (1r,4r)-4-(2-phenyl-1H-benzo[d]imidazole-5-sulfonamido)-N-(2-(pyridin-3-yl)ethyl)cyclohexanecarboxamide |
| 644 | 1 | no data | | 525.26 (M + H+) | | (1r,4r)-N-(3,5-difluorobenzyl)-4-(2-phenyl-1H-benzo[d]imidazole-5-sulfonamido)cyclohexanecarboxamide |
| 645 | 1 | | | 525.26 (M + H+) | | (1r,4r)-N-(naphthalen-1-yl)-4-(2-phenyl-1H-benzo[d]imidazole-5-sulfonamido)cyclohexanecarboxamide |
| 646 | 1 | | | 511.21 (M + H+) | | (1r,4r)-N-(3,5-difluorophenyl)-4-(2-phenyl-1H-benzo[d]imidazole-5-sulfonamido)cyclohexanecarboxamide |
| 647 | 6 | 9.109 | D | 526.26 (M + H+) | | (1r,4r)-4-(2-phenyl-1H-benzo[d]imidazole-5-sulfonamido)-N-(quinolin-6-yl)cyclohexanecarboxamide |
| 648 | 1 | | | 543.26 (M + H+) | | (1r,4r)-4-(2-phenyl-1H-benzo[d]imidazole-5-sulfonamido)-N-(3-(trifluoromethyl)phenyl)cyclohexanecarboxamide |
| 649 | 1 | 8.853 | D | 476.23 (M + H+) | | (1r,4r)-4-(2-phenyl-1H-benzo[d]imidazole-5-sulfonamido)-N-(pyridin-3-yl)cyclohexanecarboxamide |
| 650 | 1 | 10.389 | D | 469.25 (M + H+) | | N-((1r,4r)-4-(morpholine-4-carbonyl)cyclohexyl)-2-phenyl-1H-benzo[d]imidazole-5-sulfonamide |
| 651 | 6 | | D | 444.24 (M + H+) | | N-((1r,4r)-4-(5-tert-butyl-1,3,4-oxadiazol-2-yl)cyclohexyl)-2-cyclopropyl-1H-benzo[d]imidazole-5-sulfonamide |
| 652 | 6 | 9.525 | D | 538.26 (M + H+) | | methyl 4-(5-(N-((1r,4r)-4-(5-tert-butyl-1,3,4-oxadiazol-2-yl)cyclohexyl)sulfamoyl)-1H-benzo[d]imidazol-2-yl)benzoate |
| 653 | 6 | | D | 481.23 (M + H+) | | N-((1r,4r)-4-(5-tert-butyl-1,3,4-oxadiazol-2-yl)cyclohexyl)-2-(pyridin-3-yl)-1H-benzo[d]imidazole-5-sulfonamide |
| 654 | 6 | 8.651 | D | 496.23 (M + H+) | | N-((1r,4r)-4-(5-tert-butyl-1,3,4-oxadiazol-2-yl)cyclohexyl)-2-(pyridin-3-ylamino)-1H-benzo[d]imidazole-5-sulfonamide |
| 655 | 6 | 6.411 | D | 564.37 (M + H+) | | N-((1r,4r)-4-(5-tert-butyl-1,3,4-oxadiazol-2-yl)cyclohexyl)-2-(4-(piperazin-1-yl)phenyl)-1H-benzo[d]imidazole-5-sulfonamide |
| 656 | 6 | 7.189 | D | 524.25 (M + H+) | | 4-(5-(N-((1r,4r)-4-(5-tert-butyl-1,3,4-oxadiazol-2-yl)cyclohexyl)sulfamoyl)-1H-benzo[d]imidazol-2-yl)benzoic acid |
| 657 | 6 | | | 508.23 (M + H+) | | 1-benzyl-N-((1r,4r)-4-(5-tert-butyl-1,3,4-oxadiazol-2-yl)cyclohexyl)-2-methyl-1H-benzo[d]imidazole-5-sulfonamide |
| 658 | 1 | | | 424.15 (M + H+) | | 2-methyl-N-((1r,4r)-4-(morpholine-4-carbonyl)cyclohexyl)benzo[d]thiazole-6-sulfonamide |

-continued

| Ex. | Synthetic Scheme | HPLC RT | HPLC Method | MS | NMR | Name |
|---|---|---|---|---|---|---|
| 659 | 1 | | | 462.22 (M + H+) | | (1r,4R)-N-((R)-1-(4-fluorophenyl)ethyl)-4-(2-oxo-2,3-dihydrobenzo[d]oxazole-6-sulfonamido)cyclohexanecarboxamide |
| 660 | 1 | | | 476.22 (M + H+) | | (1r,4R)-N-((R)-1-(4-fluorophenyl)ethyl)-4-(2-methylbenzo[d]thiazole-6-sulfonamido)cyclohexanecarboxamide |
| 661 | 1 | | | 449.2 (M + H+) | | (1r,4R)-4-(benzo[d][1,3]dioxole-5-sulfonamido)-N-((R)-1-(4-fluorophenyl)ethyl)cyclohexanecarboxamide |
| 662 | 1 | | | 485.27 (M + H+) | | N-((1R,4r)-4-((R)-1-(4-fluorophenyl)ethylcarbamoyl)cyclohexyl)-2-phenyl-1H-benzo[d]imidazole-5-carboxamide |
| 663 | 2 | 6.315 | D | 459.2 (M + H+) | | (1r,4R)-N-((R)-1-(4-fluorophenyl)ethyl)-4-(2-methyl-1H-benzo[d]imidazole-5-sulfonamido)cyclohexanecarboxamide |
| 664 | 1 | 6.24 | D | 497.24 (M + H+) | | N-((1R,4r)-4-((2S,6R)-2,6-dimethylmorpholine-4-carbonyl)cyclohexyl)-2-phenyl-1H-benzo[d]imidazole-5-sulfonamide |
| 665 | 1 | 7.605 | D | 495.27 (M + H+) | | N-((1S,4r)-4-((3S,5S)-3,5-dimethylpiperidine-1-carbonyl)cyclohexyl)-2-phenyl-1H-benzo[d]imidazole-5-sulfonamide |
| 666 | 1 | 7.787 | D | 495.27 (M + H+) | | N-((1R,4r)-4-((3S,5R)-3,5-dimethylpiperidine-1-carbonyl)cyclohexyl)-2-phenyl-1H-benzo[d]imidazole-5-sulfonamide |
| 667 | 2 | 7.029 | D | 531.26 (M + H+) | | ethyl 2-(5-(N-((1R,4r)-4-((R)-1-(4-fluorophenyl)ethylcarbamoyl)cyclohexyl)sulfamoyl)-1H-benzo[d]imidazol-2-yl)acetate |
| 668 | 2 | 6.528 | D | 503.37 (M + H+) | | 2-(5-(N-((1R,4r)-4-((R)-1-(4-fluorophenyl)ethylcarbamoyl)cyclohexyl)sulfamoyl)-1H-benzo[d]imidazol-2-yl)acetic acid |
| 669 | 1 | 6.155 | D | 497.2 (M + H+) | | N-((1r,4r)-4-(4-methoxypiperidine-1-carbonyl)cyclohexyl)-2-phenyl-1H-benzo[d]imidazole-5-sulfonamide |
| 670 | 7 | 7.776 | D | 456.23 (M + H+) | | (1r,4S)-N-((S)-2-hydroxy-1-phenylethyl)-4-(1-methyl-1H-indole-5-sulfonamido)cyclohexanecarboxamide |
| 671 | 7 | | | 456.23 (M + H+) | | (1r,4R)-N-((R)-2-hydroxy-1-phenylethyl)-4-(1-methyl-1H-indole-5-sulfonamido)cyclohexanecarboxamide |
| 672 | 7 | 6.923 | D | 447.24 (M + H+) | | (1r,4S)-4-(1-methyl-1H-indole-5-sulfonamido)-N-((S)-2-oxoazepan-3-yl)cyclohexanecarboxamide |
| 673 | 7 | 10.64 | E | 470.16 (M + H+) | | (1r,4R)-N-((R)-3-hydroxy-1-phenylpropyl)-4-(1-methyl-1H-indole-5-sulfonamido)cyclohexanecarboxamide |
| 674 | 7 | 8.928 | D | 470.16 (M + H+) | | (1r,4S)-N-((S)-2-methoxy-1-phenylethyl)-4-(1-methyl-1H-indole-5-sulfonamido)cyclohexanecarboxamide |
| 675 | 1 | 6.795 | D | 499.33 (M + H+) | | (1r,4r)-N-isopropyl-N-(2-methoxyethyl)-4-(2-phenyl-1H-benzo[d]imidazole-5-sulfonamido)cyclohexanecarboxamide |

-continued

| Ex. | Synthetic Scheme | HPLC RT | HPLC Method | MS | NMR | Name |
|---|---|---|---|---|---|---|
| 676 | 1 | 7.957 | D | 539.37 (M + H+) | | (1r,4r)-N-cyclohexyl-N-(2-methoxyethyl)-4-(2-phenyl-1H-benzo[d]imidazole-5-sulfonamido)cyclohexanecarboxamide |
| 677 | 1 | | | 455.2 (M + H+) | | (1r,4R)-N-((R)-1-(4-fluorophenyl)ethyl)-4-(naphthalene-2-sulfonamido)cyclohexanecarboxamide |
| 678 | 1 | | | 455.2 (M + H+) | | (1r,4R)-N-((R)-1-(4-fluorophenyl)ethyl)-4-(naphthalene-1-sulfonamido)cyclohexanecarboxamide |
| 679 | 7 | 8.704 | D | 484.13 (M + H+) | | (1r,4R)-N-((R)-3-methoxy-1-phenylpropyl)-4-(1-methyl-1H-indole-5-sulfonamido)cyclohexanecarboxamide |
| 680 | 1 | | | 438.14 (M + H+) | | (1r,4r)-4-(naphthalene-2-sulfonamido)-N-(1-(pyridin-3-yl)ethyl)cyclohexanecarboxamide |
| 681 | 1 | | | 472.08 (M + H+) | | (1r,4r)-4-(6-chloronaphthalene-2-sulfonamido)-N-(1-(pyridin-3-yl)ethyl)cyclohexanecarboxamide |
| 682 | 1 | | | 438.14 (M + H+) | | (1r,4R)-4-(naphthalene-2-sulfonamido)-N-(R)-1-(pyridin-3-yl)ethyl)cyclohexanecarboxamide |
| 683 | 1 | | | 438.14 (M + H+) | | (1r,4S)-4-(naphthalene-2-sulfonamido)-N-((S)-1-(pyridin-3-yl)ethyl)cyclohexanecarboxamide |
| 684 | 1 | | | 472.08 (M + H+) | | (1r,4R)-4-(6-chloronaphthalene-2-sulfonamido)-N-((R)-1-(pyridin-3-yl)ethyl)cyclohexanecarboxamide |
| 685 | 6 | | | 445.13 (M + H+) | | N-((1r,4r)-4-(5-cyclohexyl-1,3,4-oxadiazol-2-yl)cyclohexyl)-1,2,3,4-tetrahydroisoquinoline-7-sulfonamide |

Example 686

Preparation of N-((1S,4r)-4-((S)-3-cyclopropylmorpholine-4-carbonyl)cyclohexyl)-3-methyl-2-phenyl-1H-indole-6-sulfonamide

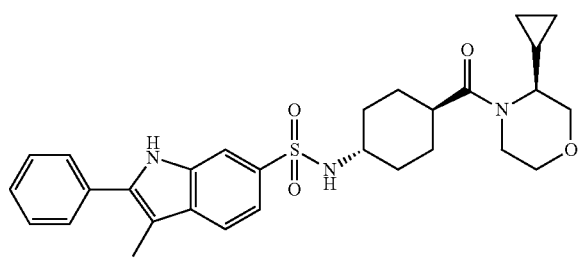

Step 1. Preparation of N-((1S,4r)-4-((S)-3-cyclopropylmorpholine-4-carbonyl)cyclohexyl)-3-formyl-2-phenyl-1H-indole-6-sulfonamide

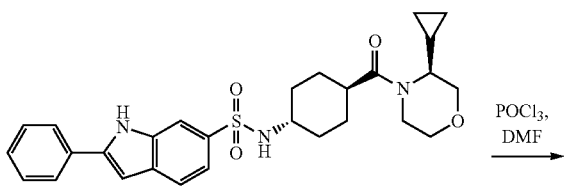

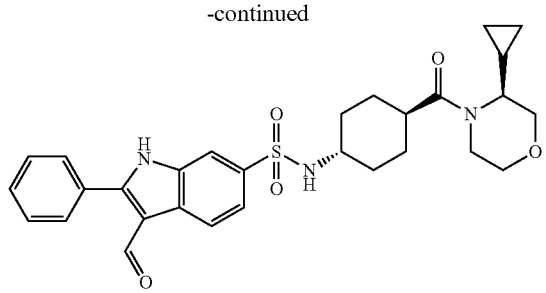

Phosphorus oxychloride (0.5 mL, 823 mg, 5.36 mmol) was added to DMF (1.5 mL) at 0° C. To this mixture was added 50 mg (0.098 mmol) of N-((1S,4r)-4-((S)-3-cyclopropylmorpholine-4-carbonyl)cyclohexyl)-2-phenyl-1H-indole-6-sulfonamide (prepared using the procedure described for scheme 12) in one portion as a solution in 1.5 mL of DMF. The reaction was heated to 45° C. for 45 minutes, and then poured into ice with stirring. To this mixture was added a saturated sodium acetate solution, and stirring was continued for 30 minutes. The solution was then extracted with ethyl acetate, and the organic phase was dried (Na$_2$SO$_4$) and concentrated under vacuum to afford a crude product that was used as is in the next step.

Step 2. Preparation of N-((1S,4r)-4-((S)-3-cyclopropylmorpholine-4-carbonyl)cyclohexyl)-3-methyl-2-phenyl-1H-indole-6-sulfonamide

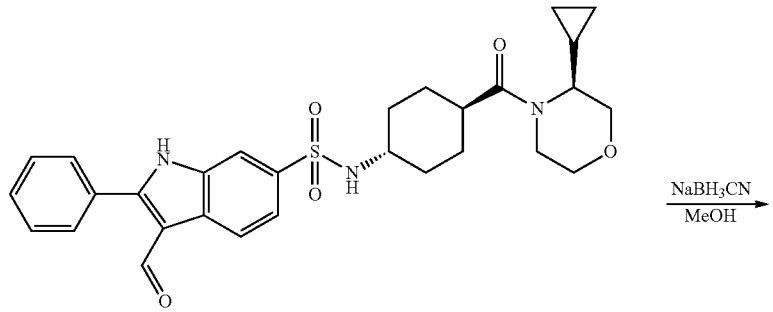

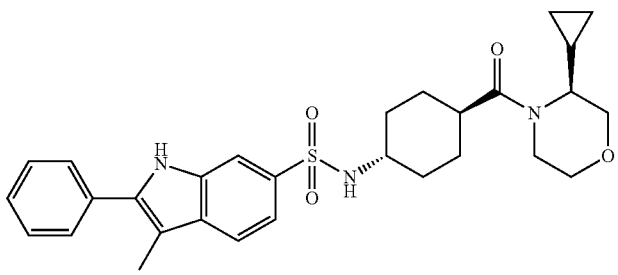 [SMILES: Cc1c(-c2ccccc2)[nH]c2cc(S(=O)(=O)N[C@H]3CC[C@H](C(=O)N4CCOC[C@@H]4C4CC4)CC3)ccc12]

The crude product from the previous step was dissolved in methanol, and sodium cyanoborohydride was added in one portion with stirring. 1N aq. hydrochloride was added to adjust the pH of the solution to approximately 3. The resulting solution was stirred for 1 hour, after which the mixture was concentrated under vacuum. The residue was suspended in water and extracted with ethyl acetate. The organic solution was concentrated and further purified by HPLC to afford 8 mg of the desired product.

Example 687

Preparation of N-((1S,4r)-4-((S)-3-cyclopropylmorpholine-4-carbonyl)cyclohexyl)-3-fluoro-2-phenyl-1H-indole-6-sulfonamide 0.098 mmol; prepared using the procedure described for scheme 12) was dissolved in DMSO (2 mL) and acetonitrile (2 mL). The solution was cooled to 0° C., and 0.5 eq. of Selectfluor reagent was added. After the addition, the cooling bath was removed and the reaction mixture was stirred at room temperature for 30 minutes. Additional fluorinating agent was added until half of the starting material was consumed. The reaction was stirred overnight and then partitioned between ethyl acetate and water. The organic layer was washed with saturated aqueous sodium bicarbonate, dried over sodium sulfate, and concentrated under vacuum to afford the crude product. The crude product was purified by HPLC to afford 6.1 mg of the purified product.

The compounds in the Table below were prepared by the method indicated in the column labeled "Synthetic Scheme"

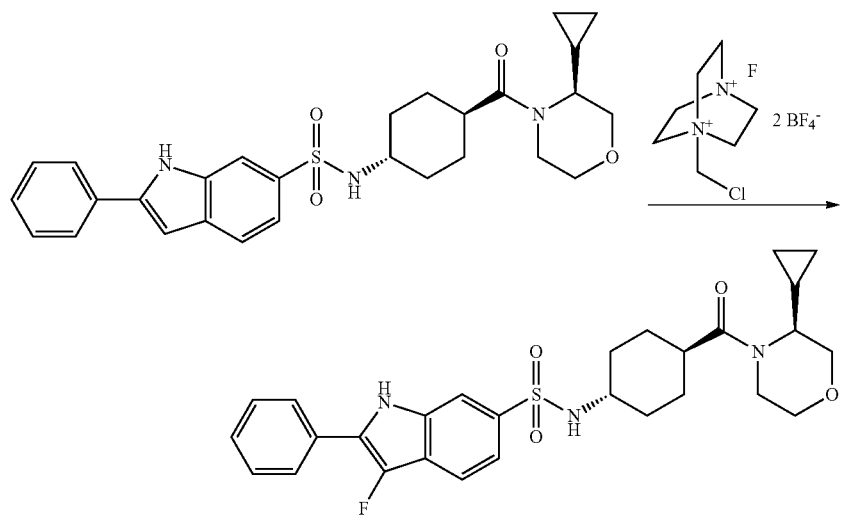

N-((1S,4r)-4-((S)-3-cyclopropylmorpholine-4-carbonyl)cyclohexyl)-2-phenyl-1H-indole-6-sulfonamide (50 mg, which corresponds to a synthetic scheme shown in the section labeled "Method of Preparation".

| Ex. | Synthetic Scheme | HPLC RT | HPLC Method | MS | NMR | Name |
|---|---|---|---|---|---|---|
| 686 | 12 + 686 | 15.73 | E | 521.67 (M+)<br>522.3 (M + H)+ | | N-((1S,4r)-4-((S)-3-cyclopropylmorpholine-4-carbonyl)cyclohexyl)-3-methyl-2-phenyl-1H-indole-6-sulfonamide |
| 687 | 12 + 687 | 13.11 | E | 525.63 (M+) | | N-((1S,4r)-4-((S)-3-cyclopropylmorpholine-4-carbonyl)cyclohexyl)-3-fluoro-2-phenyl-1H-indole-6-sulfonamide |
| 688 | 12 + 17 | 15.46 | E | 568.28 (M + H)+ | 1H NMR (400 MHz, ACETONITRILE-d3) d ppm 0.87-1.41 (m, 7H) 1.42-1.66 (m, 4H) 2.16 (s, 3H) 2.22-2.33 (m, 1H) 2.86 (t, J = 6.69 Hz, 2H) 2.93-3.03 (m, 1H) 3.23 (s, 3H) 3.57 (t, J = 6.69 Hz, 2H) 3.58 (s, 3H) 3.20-4.40 (m, 7H) 5.39 (d, J = 7.58 Hz, 1H) 7.29-7.35 (m, 4H) 7.46 (dd, J = 8.34, 1.52 Hz, 1H) 7.60 (d, J = 8.08 Hz, 1H) 7.84 (d, J = 1.01 Hz, 1H) | 2-(4-(2-methoxyethyl)phenyl)-1,3-dimethyl-N-((1S,4r)-4-((S)-3-methylmorpholine-4-carbonyl)cyclohexyl)-1H-indole-6-sulfonamide |
| 689 | 34 | 12.87 | E | 515.64 (M+)<br>516.3 (M + H)+ | | (1r,4R)-N-((R)-1-(4-fluorophenyl)ethyl)-4-(3-(3-hydroxypropyl)-1-methyl-1H-indole-5-sulfonamido)cyclohexanecarboxamide |
| 690 | 34 | 12.81 | E | 529.62 (M+)<br>530.3 (M + H)+ | | 3-(5-(N-((1R,4r)-4-((R)-1-(4-fluorophenyl)ethylcarbamoyl)cyclohexyl)sulfamoyl)-1-methyl-1H-indol-3-yl)propanoic acid |

| Ex. | Synthetic Scheme | HPLC RT | HPLC Method | MS | NMR | Name |
|---|---|---|---|---|---|---|
| 691 | 12 + 17 | 15.92 | E | 580.28 (M + H)+ | | N-((1S,4r)-4-((S)-3-cyclopropylmorpholine-4-carbonyl)cyclohexyl)-2-(4-(2-methoxyethyl)phenyl)-3-methyl-1H-indole-6-sulfonamide |
| 692 | 7 | 12.13 | E | 445.56 (M+)<br>446.1 (M + H)+ | | N-((1S,4r)-4-((S)-3-cyclopropylmorpholine-4-carbonyl)cyclohexyl)-1-methyl-1H-indole-5-sulfonamide |
| 693 | 34 | 11.57 | E | 545.69 (M+)<br>546.3 (M + H)+ | | ethyl 3-(5-(N-((1S,4r)-4-((S)-3-cyclopropylmorpholine-4-carbonyl)cyclohexyl)sulfamoyl)-1-methyl-1H-indol-3-yl)propanoate |
| 694 | 34 | 9.83 | E | 503.65 (M+)<br>504.3 (M + H)+ | | N-((1S,4r)-4-((S)-3-cyclopropylmorpholine-4-carbonyl)cyclohexyl)-3-(3-hydroxypropyl)-1-methyl-1H-indole-5-sulfonamide |
| 695 | 34 | 9.81 | E | 517.64 (M+)<br>518.3 (M + H)+ | | 3-(5-(N-((1S,4r)-4-((S)-3-cyclopropylmorpholine-4-carbonyl)cyclohexyl)sulfamoyl)-1-methyl-1H-indol-3-yl)propanoic acid |

Example 528: Acetyl-CoA Carboxylase Enzyme Assay

The inhibitory effect of compounds on the acetyl-CoA carboxylase enzyme may be demonstrated using the following test procedures.

The cDNA encoding amino acids 144 to 2458 of human acetyl-CoA carboxylase 2 (ACC2, GenBank Accession # NM_001093) was cloned into the SalI and NotI sites of pFastBac1 (Invitrogen; Carlsbad, Calif.). The resulting plasmid was used to generate a recombinant ACC2 baculovirus that was amplified and titered according to the protocols in the Bac-to-Bac baculovirus expression system manual (Invitrogen). The titered virus was used to infect Sf9 cells grown in Ex-Cell 420 serum-free medium (JRH Biosciences; Lenexa, Kans.). At 48 hours post-infection, the cells were harvested and stored at −80° C. until purification. ACC2 was purified using ammonium sulfate precipitation and anion exchange chromatography.

The enzymatic assay was run as follows: 30 μL of reaction buffer (100 mM HEPES pH 7.5, 20 mM MgCl$_2$, 20 mM potassium citrate, 2 mM DTT) was added to a 384-well microtiter plate followed by 2 μL of the test compound (or 100% DMSO control). ACC2 protein (10 μL of a 50 nM working solution) was added to plate, which was incubated at room temperature for 15 minutes. A 30 μL addition of substrate solution (50 μM acetyl-CoA, 120 μM ATP, 2 mM KHCO$_3$) was used to initiate the reactions which were quenched with 6% acetic acid (40 μL). ACC catalyzed malonyl-CoA formation was detected by LC/MS/MS using a Cohesive Technologies LX Series multiplex LC/MS/MS system configured with four binary pumps (Agilent Technologies; Palo Alto, Calif.), a dual arm autosampler (Leap Technologies; Cary, N.C.), and one Quattro Micro triple quadrupole mass spectrometer (Waters, Milford, Mass.), all run by Aria Software version 1.5 (Cohesive Technologies; Franklin, Mass.). Four samples were injected (20 μL) onto four Phenosphere NEXT C18 30×2 mm 5 μm columns (Phenomenex; Torrance, Calif.), eluted by four separate pumps, running identical gradients, through a column switching manifold with the one outlet fitted to the electrospray (ESI) source. Malonyl-CoA was eluted with 5 mM ammonium acetate, pH 4.5 (Buffer A) and 100% acetonitrile (Buffer B) via a step gradient. Argon was used as the collision gas and the following species were monitored via MRM detection: malonyl-CoA (853.8>346.9), internal standard (A: [$^{13}$C3]-malonyl-CoA, 857>350). The lower limit of detection is 0.3 uM for malonyl-CoA in this assay.

The compounds according to the invention may for example have IC$_{50}$ values below 1000 nM, particularly below 100 nM, most preferably below 10 nM. The Examples in the Table below were evaluated in the above described assay, the results of which are collated below.

| Example No. | IC$_{50}$ ACC2 (μM) |
|---|---|
| 1 | 0.013 |
| 2 | 0.019 |
| 3 | 0.507 |
| 4 | 0.013 |
| 5 | 0.244 |
| 6 | 0.156 |
| 7 | 0.071 |
| 8 | 0.045 |
| 9 | 0.047 |
| 10 | 0.115 |
| 11 | 0.048 |
| 12 | 0.055 |
| 13 | 0.065 |
| 14 | 0.010 |
| 15 | <0.01 |
| 16 | 0.051 |
| 17 | 0.065 |
| 18 | 0.011 |
| 19 | 0.056 |
| 20 | <0.01 |
| 21 | <0.01 |
| 22 | 0.070 |
| 23 | 0.150 |
| 24 | 0.230 |
| 25 | <0.01 |
| 26 | 0.020 |
| 27 | <0.01 |
| 28 | <0.01 |
| 29 | <0.01 |
| 30 | 0.010 |
| 31 | <0.01 |
| 32 | 0.245 |
| 33 | 0.140 |
| 34 | 0.138 |
| 35 | 0.010 |
| 36 | 0.050 |
| 37 | 0.075 |
| 38 | 0.050 |
| 39 | 0.025 |
| 40 | 34.150 |
| 41 | 4.635 |

| Example No. | IC$_{50}$ ACC2 (μM) |
|---|---|
| 42 | 0.094 |
| 43 | 0.412 |
| 44 | 0.450 |
| 45 | >35 |
| 46 | 9.040 |
| 47 | 4.220 |
| 48 | 32.800 |
| 49 | 0.043 |
| 50 | >35 |
| 51 | 0.101 |
| 52 | 0.435 |
| 53 | 0.093 |
| 54 | 0.193 |
| 55 | 0.134 |
| 56 | 0.189 |
| 57 | 0.112 |
| 58 | 0.185 |
| 59 | 0.339 |
| 60 | 0.131 |
| 61 | 0.098 |
| 62 | >35 |
| 63 | >35 |
| 64 | 0.042 |
| 65 | 0.149 |
| 66 | 0.205 |
| 67 | 0.240 |
| 68 | 0.070 |
| 69 | 0.050 |
| 70 | 0.165 |
| 71 | 0.405 |
| 72 | 0.115 |
| 73 | 0.175 |
| 74 | 0.160 |
| 75 | 0.095 |
| 76 | 0.590 |
| 77 | 0.050 |
| 78 | 0.470 |
| 79 | 0.115 |
| 80 | 0.040 |
| 81 | 0.095 |
| 82 | 0.845 |
| 83 | 0.855 |
| 84 | 0.045 |
| 85 | 0.143 |
| 86 | 0.075 |
| 87 | 0.100 |
| 88 | 0.050 |
| 89 | 0.020 |
| 90 | 0.260 |
| 91 | 0.030 |
| 92 | <0.01 |
| 93 | 0.545 |
| 94 | 0.075 |
| 95 | 0.030 |
| 96 | 0.010 |
| 97 | <0.01 |
| 98 | 4.300 |
| 99 | 0.494 |
| 100 | 0.760 |
| 101 | 1.790 |
| 102 | 0.045 |
| 103 | 0.038 |
| 104 | 0.020 |
| 105 | 0.252 |
| 106 | 0.388 |
| 107 | 0.205 |
| 108 | 1.265 |
| 109 | 0.321 |
| 110 | 0.290 |
| 111 | 0.139 |
| 112 | 0.344 |
| 113 | 0.212 |
| 114 | 0.296 |
| 115 | 29.100 |
| 116 | 0.013 |
| 117 | 0.574 |
| 118 | 1.750 |
| 119 | 0.161 |
| 120 | 0.034 |
| 121 | 0.017 |
| 122 | 0.016 |
| 123 | 0.450 |
| 124 | 0.032 |
| 125 | 0.058 |
| 126 | 0.071 |
| 127 | 0.391 |
| 128 | 0.146 |
| 129 | 10.400 |
| 130 | 0.059 |
| 131 | 0.173 |
| 132 | 0.068 |
| 133 | 0.046 |
| 134 | 0.028 |
| 135 | 0.157 |
| 136 | 0.187 |
| 137 | 0.162 |
| 138 | 0.147 |
| 139 | 0.016 |
| 140 | 0.986 |
| 141 | 0.579 |
| 142 | 0.068 |
| 143 | 0.325 |
| 144 | 0.314 |
| 145 | 0.128 |
| 146 | 0.952 |
| 147 | >35 |
| 148 | 0.010 |
| 149 | 0.290 |
| 150 | 0.105 |
| 151 | 0.047 |
| 152 | 0.060 |
| 153 | 0.440 |
| 154 | 1.990 |
| 155 | 0.175 |
| 156 | 0.183 |
| 157 | 0.038 |
| 158 | 0.020 |
| 159 | 0.345 |
| 160 | 0.080 |
| 161 | 0.340 |
| 162 | 0.125 |
| 163 | 8.520 |
| 164 | 0.350 |
| 165 | 0.675 |
| 166 | 0.910 |
| 167 | 0.205 |
| 168 | 0.040 |
| 169 | 0.110 |
| 170 | 0.090 |
| 171 | 0.289 |
| 172 | 0.212 |
| 173 | 0.075 |
| 174 | 0.045 |
| 175 | 0.120 |
| 176 | 0.105 |
| 177 | 0.090 |
| 178 | 0.055 |
| 179 | 0.433 |
| 180 | 0.138 |
| 181 | 0.115 |
| 182 | 0.685 |
| 183 | 0.135 |
| 184 | >35 |
| 185 | >35 |
| 186 | 0.245 |
| 187 | 0.245 |
| 188 | 0.375 |
| 189 | 0.075 |
| 190 | 0.035 |
| 191 | 0.150 |
| 192 | 0.015 |
| 193 | 0.015 |
| 194 | 0.210 |
| 195 | 0.335 |

| Example No. | IC$_{50}$ ACC2 (μM) |
|---|---|
| 196 | 0.220 |
| 197 | 0.040 |
| 198 | >35 |
| 199 | 0.075 |
| 200 | 0.060 |
| 201 | 0.080 |
| 202 | 0.020 |
| 203 | 0.305 |
| 204 | 0.080 |
| 205 | 0.020 |
| 206 | 0.020 |
| 207 | 0.355 |
| 208 | 0.595 |
| 209 | 0.020 |
| 210 | 0.225 |
| 211 | 0.180 |
| 212 | 0.165 |
| 213 | 0.095 |
| 214 | 0.365 |
| 215 | 0.125 |
| 216 | 0.180 |
| 217 | 0.015 |
| 218 | 0.020 |
| 219 | 0.495 |
| 220 | 0.875 |
| 221 | <0.01 |
| 222 | 0.040 |
| 223 | 0.205 |
| 224 | 0.060 |
| 225 | 0.085 |
| 226 | 0.010 |
| 227 | 0.015 |
| 228 | 0.213 |
| 229 | 0.020 |
| 230 | 0.060 |
| 231 | 0.010 |
| 232 | 0.765 |
| 233 | 0.965 |
| 234 | 0.020 |
| 235 | 0.095 |
| 236 | 0.385 |
| 237 | 0.085 |
| 238 | 0.065 |
| 239 | 0.130 |
| 240 | <0.01 |
| 241 | 0.025 |
| 242 | 0.195 |
| 243 | 0.015 |
| 244 | <0.01 |
| 245 | 0.035 |
| 246 | >35 |
| 247 | 0.030 |
| 248 | 0.210 |
| 249 | 0.010 |
| 250 | 0.595 |
| 251 | 0.035 |
| 252 | >35 |
| 253 | 0.020 |
| 254 | 0.020 |
| 255 | 0.015 |
| 256 | 0.020 |
| 257 | 0.050 |
| 258 | 0.080 |
| 259 | 0.450 |
| 260 | 2.960 |
| 261 | 0.460 |
| 262 | 0.020 |
| 263 | 0.030 |
| 264 | 0.020 |
| 265 | 0.685 |
| 266 | 0.140 |
| 267 | >35 |
| 268 | 0.435 |
| 269 | 25.225 |
| 270 | 0.165 |
| 271 | 0.195 |
| 272 | 0.175 |
| 273 | 0.039 |
| 274 | 4.025 |
| 275 | 0.018 |
| 276 | <0.01 |
| 277 | 0.080 |
| 278 | 0.066 |
| 279 | 0.100 |
| 280 | 0.012 |
| 281 | 0.011 |
| 282 | 0.018 |
| 283 | 0.256 |
| 284 | 0.014 |
| 285 | 0.012 |
| 286 | 0.342 |
| 287 | 0.196 |
| 288 | 0.400 |
| 289 | 0.234 |
| 290 | 0.028 |
| 291 | 0.017 |
| 292 | 0.012 |
| 293 | 0.038 |
| 294 | 0.279 |
| 295 | 0.475 |
| 296 | <0.01 |
| 297 | 0.017 |
| 298 | 0.024 |
| 299 | 0.011 |
| 300 | 0.010 |
| 301 | <0.01 |
| 302 | <0.01 |
| 303 | 0.575 |
| 304 | 0.180 |
| 305 | 0.060 |
| 306 | 0.050 |
| 307 | 0.010 |
| 308 | 0.060 |
| 309 | 0.020 |
| 310 | 0.062 |
| 311 | <0.01 |
| 312 | 0.599 |
| 313 | <0.01 |
| 314 | 0.060 |
| 315 | 0.020 |
| 316 | 0.110 |
| 317 | 0.025 |
| 318 | 0.515 |
| 319 | 0.025 |
| 320 | 0.085 |
| 321 | 0.250 |
| 322 | <0.01 |
| 323 | 0.055 |
| 324 | 0.040 |
| 325 | <0.01 |
| 326 | 0.325 |
| 327 | <0.01 |
| 328 | 0.055 |
| 329 | 0.120 |
| 330 | 3.605 |
| 331 | 0.025 |
| 332 | 0.025 |
| 333 | 0.065 |
| 334 | 1.420 |
| 335 | 0.025 |
| 336 | 0.035 |
| 337 | 0.020 |
| 338 | 0.015 |
| 339 | 0.030 |
| 340 | 0.255 |
| 341 | 0.240 |
| 342 | 0.135 |
| 343 | 0.170 |
| 344 | 0.060 |
| 345 | 0.255 |
| 346 | 0.265 |
| 347 | 0.120 |
| 348 | 0.045 |
| 349 | 0.100 |

| Example No. | IC$_{50}$ ACC2 (μM) |
|---|---|
| 350 | 0.470 |
| 351 | 0.095 |
| 352 | <0.01 |
| 353 | <0.01 |
| 354 | <0.01 |
| 355 | <0.01 |
| 356 | 0.560 |
| 357 | 0.120 |
| 358 | 0.035 |
| 359 | 0.095 |
| 360 | 0.035 |
| 361 | 0.010 |
| 362 | 0.075 |
| 363 | 0.120 |
| 364 | 0.140 |
| 365 | 0.410 |
| 366 | 0.015 |
| 367 | 0.030 |
| 368 | 0.145 |
| 369 | 0.180 |
| 370 | 0.270 |
| 371 | 0.115 |
| 372 | 0.045 |
| 373 | 0.075 |
| 374 | 0.020 |
| 375 | 0.075 |
| 376 | 0.095 |
| 377 | 0.010 |
| 378 | 0.010 |
| 379 | 0.580 |
| 380 | 0.075 |
| 381 | 0.210 |
| 382 | 0.095 |
| 383 | <0.01 |
| 384 | <0.01 |
| 385 | 0.920 |
| 386 | 0.025 |
| 387 | <0.01 |
| 388 | 0.110 |
| 389 | 0.015 |
| 390 | 0.010 |
| 391 | 0.760 |
| 392 | 0.115 |
| 393 | <0.01 |
| 394 | 0.015 |
| 395 | <0.01 |
| 396 | 0.010 |
| 397 | <0.01 |
| 398 | <0.01 |
| 399 | 0.340 |
| 400 | <0.01 |
| 401 | 0.025 |
| 402 | 0.130 |
| 403 | 0.010 |
| 404 | <0.01 |
| 405 | 0.035 |
| 406 | 0.985 |
| 407 | <0.01 |
| 408 | 0.020 |
| 409 | <0.01 |
| 410 | 0.020 |
| 411 | <0.01 |
| 412 | 0.240 |
| 413 | 0.050 |
| 414 | 0.080 |
| 415 | <0.01 |
| 416 | <0.01 |
| 417 | 0.080 |
| 418 | 0.065 |
| 419 | 0.035 |
| 420 | 0.720 |
| 421 | 0.050 |
| 422 | 0.285 |
| 423 | 0.040 |
| 424 | 0.050 |
| 425 | 0.030 |
| 426 | 0.055 |
| 427 | 0.015 |
| 428 | <0.01 |
| 429 | 0.075 |
| 430 | <0.01 |
| 431 | 0.130 |
| 432 | 0.095 |
| 433 | 0.445 |
| 434 | 0.010 |
| 435 | 0.020 |
| 436 | 0.020 |
| 437 | 0.040 |
| 438 | <0.01 |
| 439 | <0.01 |
| 440 | 0.020 |
| 441 | <0.01 |
| 442 | 0.040 |
| 443 | 0.030 |
| 444 | 0.020 |
| 445 | 0.015 |
| 446 | 0.365 |
| 447 | 0.025 |
| 448 | 0.065 |
| 449 | 0.075 |
| 450 | 0.130 |
| 451 | 0.080 |
| 452 | 0.010 |
| 453 | 0.165 |
| 454 | <0.01 |
| 455 | <0.01 |
| 456 | <0.01 |
| 457 | <0.01 |
| 458 | 0.035 |
| 459 | 0.630 |
| 460 | <0.01 |
| 461 | <0.01 |
| 462 | 0.015 |
| 463 | <0.01 |
| 464 | 0.030 |
| 465 | 0.020 |
| 466 | 0.010 |
| 467 | <0.01 |
| 468 | <0.01 |
| 469 | 0.090 |
| 470 | <0.01 |
| 471 | <0.01 |
| 472 | <0.01 |
| 473 | <0.01 |
| 474 | <0.01 |
| 475 | 0.015 |
| 476 | <0.01 |
| 477 | <0.01 |
| 478 | <0.01 |
| 479 | 0.010 |
| 480 | <0.01 |
| 481 | 0.020 |
| 482 | 0.090 |
| 483 | 0.075 |
| 484 | <0.01 |
| 485 | 0.043 |
| 486 | 0.075 |
| 487 | 0.091 |
| 488 | 1.030 |
| 489 | 1.115 |
| 490 | >138.8 |
| 491 | 1.130 |
| 492 | 1.350 |
| 493 | >138.8 |
| 494 | 1.890 |
| 495 | 0.990 |
| 496 | 2.335 |
| 497 | 0.762 |
| 498 | 0.495 |
| 499 | 2.115 |
| 500 | 1.490 |
| 501 | 1.655 |
| 502 | 1.280 |
| 503 | 0.819 |

| Example No. | IC$_{50}$ ACC2 (μM) |
|---|---|
| 504 | 1.735 |
| 505 | 1.775 |
| 506 | 1.950 |
| 507 | 22.150 |
| 508 | 1.380 |
| 509 | 0.678 |
| 510 | 1.805 |
| 511 | 1.049 |
| 512 | 2.285 |
| 513 | 2.885 |
| 514 | 0.838 |
| 515 | 2.860 |
| 516 | 1.210 |
| 517 | 0.247 |
| 518 | 3.580 |
| 519 | 32.000 |
| 520 | 9.345 |
| 521 | 0.239 |
| 522 | 0.320 |
| 523 | 0.463 |
| 524 | 0.360 |
| 525 | 0.166 |
| 526 | 0.178 |
| 527 | 0.169 |
| 528 | 0.041 |
| 529 | 0.644 |
| 530 | 0.612 |
| 531 | 0.248 |
| 532 | 0.109 |
| 533 | 0.641 |
| 534 | 0.524 |
| 535 | 0.225 |
| 536 | 0.412 |
| 537 | 0.290 |
| 538 | 0.077 |
| 539 | 0.221 |
| 540 | >138.8 |
| 541 | 0.086 |
| 542 | 0.575 |
| 543 | 0.280 |
| 544 | 0.035 |
| 545 | 0.623 |
| 546 | 0.845 |
| 547 | 0.374 |
| 548 | 0.075 |
| 549 | 0.737 |
| 550 | 0.240 |
| 551 | 0.282 |
| 552 | 0.334 |
| 553 | 0.119 |
| 554 | 0.028 |
| 555 | 0.030 |
| 556 | 0.025 |
| 557 | 0.013 |
| 558 | 0.337 |
| 559 | 0.163 |
| 560 | 0.397 |
| 561 | 0.316 |
| 562 | 0.676 |
| 563 | 0.351 |
| 564 | 0.027 |
| 565 | 0.048 |
| 566 | 0.118 |
| 567 | 0.065 |
| 568 | 0.126 |
| 569 | <0.01 |
| 570 | <0.01 |
| 571 | <0.01 |
| 572 | <0.01 |
| 573 | <0.01 |
| 574 | <0.01 |
| 575 | <0.01 |
| 576 | <0.01 |
| 577 | 0.015 |
| 578 | 0.061 |
| 579 | 0.010 |
| 580 | 1.745 |
| 581 | 0.309 |
| 582 | 0.250 |
| 583 | 0.055 |
| 584 | 0.119 |
| 585 | 0.781 |
| 586 | 1.305 |
| 587 | 0.294 |
| 588 | 0.267 |
| 589 | 0.516 |
| 590 | 0.430 |
| 591 | 1.134 |
| 592 | 0.415 |
| 593 | 1.008 |
| 594 | 0.202 |
| 595 | 0.259 |
| 596 | 0.180 |
| 597 | 0.162 |
| 598 | 0.088 |
| 599 | 0.270 |
| 600 | 0.139 |
| 601 | 0.539 |
| 602 | 0.536 |
| 603 | 0.323 |
| 604 | 0.676 |
| 605 | 0.138 |
| 606 | <0.01 |
| 607 | 1.093 |
| 608 | 0.971 |
| 609 | 1.220 |
| 610 | 1.735 |
| 611 | <0.01 |
| 612 | 0.016 |
| 613 | 39.550 |
| 614 | 0.142 |
| 615 | 11.480 |
| 616 | 0.370 |
| 617 | 0.996 |
| 618 | 0.080 |
| 619 | 0.558 |
| 620 | 0.058 |
| 621 | 1.525 |
| 622 | 0.411 |
| 623 | 0.560 |
| 624 | 0.246 |
| 625 | 0.080 |
| 626 | 0.078 |
| 627 | 2.055 |
| 628 | 0.408 |
| 629 | 1.755 |
| 630 | 0.781 |
| 631 | 10.350 |
| 632 | 0.145 |
| 633 | 1.170 |
| 634 | 1.680 |
| 635 | 0.256 |
| 636 | 1.715 |
| 637 | 0.372 |
| 638 | 0.125 |
| 639 | 0.352 |
| 640 | 0.960 |
| 641 | 0.276 |
| 642 | 1.345 |
| 643 | 0.283 |
| 644 | 0.588 |
| 645 | 1.060 |
| 646 | 1.345 |
| 647 | 0.726 |
| 648 | 1.840 |
| 649 | 0.387 |
| 650 | 0.304 |
| 651 | 6.355 |
| 652 | 0.869 |
| 653 | 2.030 |
| 654 | 0.158 |
| 655 | 0.141 |
| 656 | 0.870 |
| 657 | >35 |

| Example No. | IC$_{50}$ ACC2 (µM) |
|---|---|
| 658 | 71.700 |
| 659 | 0.378 |
| 660 | 0.242 |
| 661 | 0.733 |
| 662 | 32.500 |
| 663 | 0.252 |
| 664 | 0.054 |
| 665 | 0.040 |
| 666 | 0.030 |
| 667 | 0.615 |
| 668 | 0.124 |
| 669 | 0.362 |
| 670 | 0.066 |
| 671 | >35 |
| 672 | 0.639 |
| 673 | 0.138 |
| 674 | 0.771 |
| 675 | 0.105 |
| 676 | 0.023 |
| 677 | 0.010 |
| 678 | 0.433 |
| 679 | 0.110 |
| 680 | 0.240 |
| 681 | 0.142 |
| 682 | 0.144 |
| 683 | >35 |
| 684 | 0.180 |
| 685 | >35 |

Example 529: HCV Assay

The effect of compounds on HCV infection was determined in vitro using cell cultured (HCVcc) genotype 2a (JFH-1 strain) virus. A *renilla* luciferase reporter gene was inserted in the viral genome, the expression of which was under the control of HCV 5'UTR (JFH-1$^{rLuc}$). Thus, the inhibition of HCV infection or replication can be indirectly measured by the reduction of luciferase activity in the cells. A specifically adapted hepatoma cell line, Huh 7.5, which allowed higher infectivity of HCV in vitro, was cultured in Dulbecco's modified Eagle's medium (DMEM) supplemented with 2 mM L-glutamine, 0.1 mM non-essential amino acids and 10% heat-inactivated fetal bovine serum. The cells were infected with JFH-1$^{rLuc}$ virus at an M01=0.01 and were treated at the same time with serially diluted compounds. After 72 hours, luciferase activities in compound-treated cells were measured using the *Renilla* Luciferase Assay System (Promega) and were compared to those in untreated control cells. Concentration-dependent inhibition curves were generated, from which EC$_{50}$ values, the concentrations of compounds at which luciferase activities were reduced by 50% relative to untreated control, were calculated. In parallel, cytotoxicity of compounds was determine by measuring the viability of compound-treated cells using CellTiter 96® AQueous One Solution Cell Proliferation Assay (Promega). CC$_{50}$ represented the concentration of the compound at which cell viability was reduced by 50% compared to untreated control.

| Example | EC$_{50}$ (µM) | CC$_{50}$ (µM) |
|---|---|---|
| 25 | 0.68 | >33 |
| 28 | 0.51 | >33 |
| 29 | 2.42 | >33 |
| 30 | 0.71 | >33 |
| 31 | 0.14 | 24 |
| 208 | 4.74 | >16.7 |
| 272 | 14.12 | >16.7 |
| 431 | 2.23 | >33 |
| 458 | 0.24 | >33 |
| 459 | 0.21 | 26 |
| 474 | 0.029 | >67 |
| 477 | 0.04 | 12 |
| 479 | 1.27 | >33 |
| 473 | 0.20 | >33 |
| 483 | 0.04 | 16 |

It can be seen that the compounds of the invention are useful as inhibitors of ACC2 and therefore useful in the treatment of diseases and conditions mediated by ACC2 such as the metabolic disorders disclosed herein.

It will be understood that the invention has been described by way of example only and modifications may be made whilst remaining within the scope and spirit of the invention.

We claim:
1. A compound, or a pharmaceutically acceptable salt thereof, wherein the compound is represented by formula (IV):

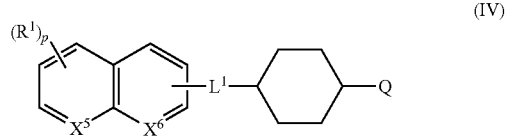

(IV)

wherein:
one of $X^5$ or $X^6$ is N and the other is CH; and
p is 0, 1, 2, or 3
Q is selected from the group consisting of:

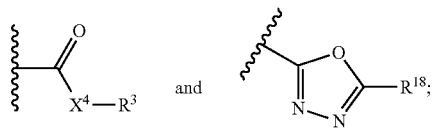

and wherein the symbol

indicates the point of attachment to ring B;
$X^4$ is —NR$^4$— or —O—;
q and n are each, independently, 0, 1, 2, 3, or 4;
$L_1$ is —NHSO$_2$—, —SO$_2$NH—, —NHSO$_2$NH— or —NHC(O)NH—;
$R^1$ may replace a hydrogen atom of any CH bond in ring A and, for each occurrence, is independently deutero, hydroxy, nitro, halo, cyano, carboxy, formyl, C$_{1-7}$alkyl, C$_{3-8}$ carbocyclyl, C$_{2-7}$alkenyl, C$_{2-7}$alkynyl, C$_{1-7}$alkoxy, C$_{1-7}$alkylthio, C$_{3-8}$cycloalkoxy, C$_{6-10}$aryl, C$_{6-10}$aryl C$_{1-4}$alkyl, C$_{6-10}$aryloxy, amino, N—C$_{1-7}$alkylamino, N,N-di-(C$_{1-7}$alkyl)amino, N—C$_{6-10}$arylamino, 3- to 10-membered heterocyclyl, N-(3- to 10-membered heterocyclyl)amino, (3- to 10-membered heterocyclyl)

oxy, 5- to 10-membered heteroaryl, (5- to 10-membered heteroaryl)$C_{1-4}$alkyl, N-(5- to 10-membered heteroaryl)amino, (5- to 10-membered heteroaryl)oxy, $C_{1-7}$alkanoyl, $C_{1-7}$alkoxycarbonyl, $C_{1-7}$alkanoyloxy, $C_{1-7}$alkylamido, $C_{6-10}$arylamido, (3- to 10-membered heterocyclyl)amido, carbamoyl, N—$C_{1-7}$alkylcarbamoyl, N,N-di-($C_{1-7}$alkyl)carbamoyl, $C_{1-7}$alkoxyamido, $C_{1-7}$alkylureido, and $C_{6-10}$arylureido, wherein $R^1$ is optionally substituted on one or more carbon atom with one or more independently selected $R^{13}$; and wherein when $R^1$ comprises a heterocyclyl or a heteroaryl comprising one or more —NH—, the hydrogen of each —NH— group may be independently optionally replaced with $R^{22}$; or two $R^1$ on the same carbon atom together may form an oxo; or two $R^1$ on the same carbon atom together with the carbon to which they are attached form a spiro $C_{3-8}$carbocyclyl; or two $R^1$ on adjacent carbon atoms together with the carbon atoms to which they are attached may form a fused $C_{3-8}$carbocyclyl or phenyl which may be optionally substituted with one or more $R^{13}$; and $R^3$ is selected from the group consisting of a $C_{1-7}$alkyl, $C_{3-8}$carbocyclyl, $C_{3-8}$carbocyclyl$C_{1-4}$alkyl, $C_{6-10}$aryl, $C_{6-10}$aryl$C_{1-4}$alkyl, a 5- to 10-membered heteroaryl, a (5- to 10-membered heteroaryl)$C_{1-4}$alkyl, a 3- to 10-membered heterocyclyl, and a (3- to 10-membered heterocyclyl)$C_{1-4}$alkyl, wherein $R^3$ is optionally substituted on one or more carbon atom with one or more $R^{14}$; and wherein when $R^3$ comprises a heteroaryl or heterocyclyl comprising one or more —NH—, the hydrogen of each —NH— group may be independently optionally replaced with a $C_{1-7}$alkyl;

$R^4$ is hydrogen, $C_{1-7}$ alkyl, or $C_{1-4}$alkoxy$C_{1-4}$alkyl; or $R^3$ and $R^4$, together with the nitrogen atom to which they are attached form a 3- to 7-membered heterocyclyl, wherein the heterocyclyl may be optionally substituted on one or more carbon atoms with one or more $R^{15}$; and wherein when the heterocyclyl comprises one or more —NH—, the hydrogen of each —NH— group may be independently optionally replaced with $R^{16}$;

$R^{13}$, for each occurrence, is independently deutero, nitro, halo, cyano, hydroxy, carboxy, $C_{1-7}$alkyl, $C_{3-8}$cycloalkyl, $C_{1-7}$alkoxy, $C_{6-10}$aryl, $C_{6-10}$aryloxy, 3- to 10-membered heterocyclyl, 5- to 10-membered heteroaryl, amino, $C_{1-7}$alkylamino, di-($C_{1-7}$alkyl)amino, $C_{1-7}$alkanoyl, $C_{1-7}$alkoxycarbonyl, $C_{1-7}$alkanoyloxy, $C_{1-7}$alkylamido, $C_{1-7}$alkoxyamido, carbamoyl, N—$C_{1-7}$alkylcarbamoyl, N,N-di-($C_{1-7}$alkyl)carbamoyl, $C_{1-7}$alkylsufonyl, $C_{1-7}$alkylsulfonyloxy, $C_{1-7}$alkylsulfonamido, sulfamoyl, N—$C_{1-7}$alkylsulfamoyl, or N,N-di-($C_{1-7}$alkyl)sulfamoyl, wherein $R^{13}$ is optionally substituted on one or more carbon atom with one or more independently selected $R^{17}$; and wherein when $R^{13}$ is a heterocyclyl or a heteroaryl comprising one or more —NH—, the hydrogen of each —NH— group may be independently optionally replaced with $R^{20}$; or two $R^{13}$ on the same carbon atom together may form an oxo or a spiro $C_{3-8}$carbocyclyl; or two $R^{13}$ on adjacent carbon atoms together with the carbons to which they are attached may form a 3- to 7-membered heterocyclyl which may be optionally substituted on one or more carbon atom with one or more $R^{17}$ and if the heterocyclyl comprises one or more —NH— group, the hydrogen of each —NH— group may be independently optionally replaced with $R^{20}$;

$R^{14}$, for each occurrence, is independently halo, hydroxy, carboxy, $C_{1-7}$alkoxycarbonyl, $C_{1-7}$alkyl, $C_{1-7}$alkoxy, $C_{3-8}$cycloalkyl, $C_{6-10}$aryl, or 5- to 10-membered heteroaryl, wherein $R^{14}$ may be optionally substituted on one or more carbon atoms with one or more independently selected $R^{24}$; or two $R^{14}$ on the same carbon atom together may form an oxo, a spiro $C_{3-8}$carbocyclyl or a 3- to 7-membered spiro heterocyclyl; or two $R^{14}$ on adjacent carbon atoms together with the carbon atoms to which they are attached may form a phenyl which may be optionally substituted on one or more carbon atoms with one or more $R^{24}$;

$R^{15}$, for each occurrence, is independently selected from the group consisting of hydroxy, carboxy, $C_{1-7}$alkyl, $C_{1-7}$alkoxy, $C_{3-8}$carbocyclyl, phenyl, and $C_{1-7}$alkoxycarbonyl; wherein $R^{15}$ may be optionally substituted on one or more carbon atoms with one or more substituent independently selected from halo, hydroxy, $C_{1-4}$alkoxy; or two $R^{15}$ on the same carbon atom together form an oxo or together with the carbon atom to which they are attached form a $C_{2-8}$cycloalkyl or a 3- to 10-membered heterocyclyl; or two $R^{15}$ on adjacent carbon atoms together with the carbon atoms to which they are attached may form a fused phenyl;

$R^{16}$, for each occurrence, is independently selected from the group consisting of $C_{1-7}$alkyl, $C_{3-8}$carbocyclyl, $C_{1-7}$alkanoyl, $C_{1-7}$alkoxycarbonyl, or 5- to 10-membered heteroaryl;

$R^{17}$, for each occurrence, is independently selected from cyano, halo, hydroxy, carboxy, $C_{1-7}$alkyl, $C_{1-7}$alkoxy, amino, $C_{1-7}$alkylamino, di-($C_{1-7}$alkyl)amino, $C_{6-10}$arylamino, $C_{6-10}$aryl$C_{1-4}$alkylamino, $C_{1-7}$alkoxycarbonyl, $C_{1-7}$alkanoyloxy, 3- to 10-membered heterocyclyl, wherein $R^{17}$ may be optionally substituted on one or more carbon atoms with one or more independently selected halo, amino, $C_{1-7}$alkyl, $C_{1-7}$alkoxy, $C_{1-7}$haloalkyl, carboxy, or $C_{1-7}$alkyoxycarbonyl; and wherein when $R^{17}$ is a heterocyclyl comprising one or more —NH—, the hydrogen of each —NH— group may be independently optionally replaced with $R^{23}$; or two $R^{17}$ on the same carbon atom together may form an oxo;

$R^{18}$ is a $C_{1-7}$alkyl, $C_{3-8}$cycloalkyl, phenyl or a $C_{1-7}$alkoxy$C_{1-7}$alkyl;

$R^{20}$, $R^{22}$, and $R^{23}$, for each occurrence, are independently deutero, halo, carboxy, $C_{1-7}$alkyl, $C_{1-7}$alkoxy, $C_{6-10}$aryloxy, $C_{6-10}$aryl$C_{1-4}$alkoxy, or $C_{1-7}$alkoxycarbonyl; and $R^{24}$, for each occurrence, is independently hydroxy, halo, carboxy, $C_{1-7}$alkyl, $C_{1-7}$haloalkyl, $C_{1-7}$alkoxy, amino, N—$C_{1-7}$alkylamino, N,N-di-($C_{1-7}$alkyl)amino, $C_{1-7}$alkoxycarbonyl, $C_{1-7}$alkanoyloxy, phosphonooxy, $C_{1-7}$alkoxy(hydroxy)phosphoryloxy or di-($C_{1-7}$alkoxy) phosphoryloxy; wherein $R^{24}$ may be optionally substituted on one or more carbon atom with a group independently selected from amino, N—$C_{1-7}$alkylamino, and phenyl.

2. The compound according to claim 1, or a pharmaceutically acceptable salt thereof, wherein the compound is represented by formula (IVa):

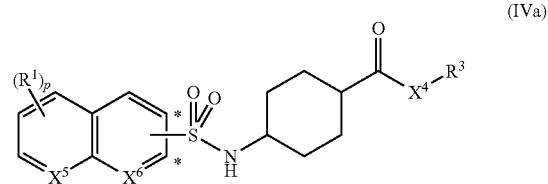

(IVa)

wherein "*" indicates a carbon where the sulfamoyl group may be attached.

3. The compound according to claim 2, or a pharmaceutically acceptable salt thereof, wherein $X^4$ is —$NR^4$—.

4. The compound according to claim 3, or a pharmaceutically acceptable salt thereof, wherein $R^4$ is hydrogen.

5. The compound according to claim 2, or a pharmaceutically acceptable salt thereof, wherein $R^3$ is $C_{1-4}$alkyl, benzyl, or pyrazinylmethyl, wherein $R^3$ is optionally substituted on one or more carbon atom with one or more $R^{14}$; and wherein when $R^3$ is pyrazinyl, the hydrogen of the —NH— group may be independently optionally replaced with a $C_{1-7}$alkyl.

6. The compound according to claim 5, or a pharmaceutically acceptable salt thereof, wherein $R^{14}$, for each occurrence, is independently halo, $C_{1-4}$alkyl, wherein $R^{14}$ may be optionally substituted on one or more carbon atoms with one or more independently selected $R^{24}$.

7. The compound according to claim 6, or a pharmaceutically acceptable salt thereof, wherein $R^{24}$, for each occurrence, is independently halo, hydroxy, carboxy, $C_{1-4}$alkoxycarbonyl, $C_{1-4}$alkanoyloxy, 2-amino-3-phenyl-propanoyloxy, 2-amino-3-methyl-butanoyloxy, phosphonooxy, or di-(C1-4alkoxy)phosphoryloxy.

8. The compound according to claim 3, or a pharmaceutically acceptable salt thereof, wherein $R^3$ and $R^4$ together with the nitrogen atom to which they are attached form a 3- to 7-membered heterocyclyl, wherein the heterocyclyl may be optionally substituted on one or more carbon atoms with one or more $R^{15}$; and wherein when the heterocyclyl comprises one or more —NH—, the hydrogen of each —NH— group may be independently optionally replaced with $R^{16}$.

9. The compound according to claim 8, or a pharmaceutically acceptable salt thereof, wherein $R^3$ and $R^4$ together with the nitrogen atom to which they are attached form piperazino, morpholino, piperidino, or pyrrolidino, each of which may be optionally substituted on one or more carbon atoms with one or more $R^{15}$; and wherein the hydrogen of the —NH— of piperazino may be independently optionally replaced with $R^{16}$.

10. The compound according to claim 2, or a pharmaceutically acceptable salt thereof, wherein p is 1.

11. The compound according to claim 2, or a pharmaceutically acceptable salt thereof, wherein $R^1$, for each occurrence, is independently halo, hydroxy, $C_{1-4}$alkyl, $C_{1-4}$alkenyl, $C_{1-4}$alkynyl, $C_{1-4}$alkoxy, cyclobutyloxy, oxetan-3-yloxy, amino, N—$C_{1-4}$alkylamino, N,N-di-($C_{1-4}$alkyl)amino, N—$C_{1-4}$alkylcarbamoyl, piperazinyl, piperidinyl, phenyl, or pyridinyl, wherein $R^1$ is optionally substituted on one or more carbon atom with one or more independently selected $R^{13}$; and wherein when $R^1$ is piperazinyl or piperidinyl, the hydrogen of each —NH— group may be independently optionally replaced with $R^{22}$; or two $R^1$ on the same carbon atom together with the carbon atom to which they are attached may form a spiro $C_{3-8}$carbocyclyl.

12. The compound according to claim 11, or a pharmaceutically acceptable salt thereof, wherein $R^{13}$, for each occurrence, is independently halo, hydroxy, carboxy, $C_{1-4}$alkyl, $C_{1-4}$alkoxy, amino, N—$C_{1-4}$alkylamino, N,N-di-($C_{1-4}$alkyl)amino, wherein $R^{13}$ is optionally substituted on one or more carbon atom with one or more independently selected $R^{17}$.

13. The compound according to claim 12, or a pharmaceutically acceptable salt thereof, wherein $R^{17}$, for each occurrence, is independently halo.

14. The compound according to claim 11, or a pharmaceutically acceptable salt thereof, wherein $R^{22}$, for each occurrence, is independently a $C_{1-4}$alkyl.

15. The compound according to claim 2, or a pharmaceutically acceptable salt thereof, wherein $X^5$ is N and $X^6$ is CH.

16. A compound according to claim 1, or a pharmaceutically acceptable salt thereof, wherein the compound is selected from:
- (1r,4R)-4-(2-ethoxyquinoline-6-sulfonamido)-N—((R)-1-(4-fluorophenyl)ethyl) cyclohexanecarboxamide;
- (1r,4S)-4-(2-ethoxyquinoline-6-sulfonamido)-N-((1S,2R)-2-hydroxy-1-phenylpropyl)cyclohexanecarboxamide;
- (1r,4R)—N—((R)-1-(4-fluorophenyl)ethyl)-4-(2-(4-methylpiperazin-1-yl)quinoline-6-sulfonamido)cyclohexanecarboxamide;
- (1r,4R)—N—((R)-1-(4-fluorophenyl)ethyl)-4-(2-(pyridin-4-yl)quinoline-6-sulfonamido)cyclohexanecarboxamide;
- (1r,4R)-4-(2-chloroquinoline-6-sulfonamido)-N—((R)-1-(4-fluorophenyl)ethyl)cyclohexanecarboxamide;
- N-((1r,4r)-4-(2-phenylpyrrolidine-1-carbonyl)cyclohexyl)quinoline-3-sulfonamide;
- (1r,4r)-N-(1-(3-fluorophenyl)ethyl)-4-(quinoline-3-sulfonamido)cyclohexanecarboxamide;
- (1r,4r)-4-(quinoline-3-sulfonamido)-N-(1-(4-(trifluoromethyl)phenyl)ethyl) cyclohexanecarboxamide;
- (1r,4R)-4-(quinoline-3-sulfonamido)-N—((R)-1-(2-(trifluoromethyl)phenyl)ethyl) cyclohexanecarboxamide;
- N-((1r,4r)-4-(4-methyl-2-phenylpiperazine-1-carbonyl)cyclohexyl)quinoline-3-sulfonamide;
- N-((1r,4r)-4-(2-(trifluoromethyl)pyrrolidine-1-carbonyl)cyclohexyl)quinoline-3-sulfonamide;
- (1r,4R)—N—((R)-1-(4-fluorophenyl)ethyl)-4-(2-methoxyquinoline-6-sulfonamido)cyclohexanecarboxamide;
- (1r,4R)—N—((R)-1-(4-fluorophenyl)ethyl)-4-(2-(2,2,2-trifluoroethoxy)quinoline-6-sulfonamido)cyclohexanecarboxamide;
- (1r,4R)-4-(2-cyclobutoxyquinoline-6-sulfonamido)-N—((R)-1-(4-fluorophenyl)ethyl) cyclohexanecarboxamide;
- (1r,4R)-4-(2-(dimethylamino)quinoline-6-sulfonamido)-N—((R)-1-(4-fluorophenyl)ethyl) cyclohexanecarboxamide;
- (1r,4R)—N—((R)-1-(4-fluorophenyl)ethyl)-4-(2-hydroxyquinoline-6-sulfonamido) cyclohexanecarboxamide;
- (1r,4R)—N—((R)-1-phenylethyl)-4-(quinoline-3-sulfonamido)cyclohexanecarboxamide;
- (1r,4R)—N—((R)-1-phenylpropyl)-4-(quinoline-3-sulfonamido)cyclohexanecarboxamide;
- (1r,4R)—N—((R)-1-(4-chlorophenyl)ethyl)-4-(quinoline-3-sulfonamido)cyclohexanecarboxamide;
- (1r,4R)—N—((R)-1-(2-fluorophenyl)ethyl)-4-(quinoline-3-sulfonamido)cyclohexanecarboxamide;
- N-((1r,4r)-4-(2-phenylpiperidine-1-carbonyl)cyclohexyl) quinoline-3-sulfonamide;
- tert-butyl 3-phenyl-4-((1r,4r)-4-(quinoline-3-sulfonamido)cyclohexanecarbonyl)piperazine-1-carboxylate;
- N-((1r,4r)-4-(2-phenylpiperazine-1-carbonyl)cyclohexyl) quinoline-3-sulfonamide;
- (1r,4r)-N-(1-(1-methyl-1H-pyrazol-4-yl)ethyl)-4-(quinoline-3-sulfonamido) cyclohexanecarboxamide;

(1r,4R)—N—((R)-1-(4-fluorophenyl)ethyl)-4-(2-(oxetan-3-yloxy)quinoline-6-sulfonamido)cyclohexanecarboxamide;
(1r,4r)-N-(1-(3,4-difluorophenyl)ethyl)-4-(quinoline-3-sulfonamido)cyclohexanecarboxamide;
(1r,4r)-N-(1-(2,4-difluorophenyl)ethyl)-4-(quinoline-3-sulfonamido)cyclohexanecarboxamide;
(1r,4R)—N—((R)-1-(4-fluorophenyl)ethyl)-4-(2-(2-methoxyethoxy)quinoline-6-sulfonamido) cyclohexanecarboxamide;
(1r,4R)-4-(2-(2-(dimethylamino)ethoxy)quinoline-6-sulfonamido)-N—((R)-1-(4-fluorophenyl)ethyl) cyclohexanecarboxamide;
(1r,4R)—N—((R)-1-(4-fluorophenyl)ethyl)-4-(2-vinylquinoline-6-sulfonamido) cyclohexanecarboxamide;
(1r,4R)—N—((R)-1-(4-fluorophenyl)ethyl)-4-(2-methylquinoline-6-sulfonamido) cyclohexanecarboxamide;
ethyl 2-(6-(N-((1R,4r)-4-((R)-1-(4-fluorophenyl)ethylcarbamoyl)cyclohexyl)sulfamoyl)quinolin-2-yloxy)acetate;
(1r,4R)-4-(2-ethylquinoline-6-sulfonamido)-N—((R)-1-(4-fluorophenyl)ethyl) cyclohexanecarboxamide;
(1r,4R)-4-(2-ethyl-1,2,3,4-tetrahydroquinoline-6-sulfonamido)-N—((R)-1-(4-fluorophenyl)ethyl)cyclohexanecarboxamide;
2-(6-(N-((1R,4r)-4-((R)-1-(4-fluorophenyl)ethylcarbamoyl)cyclohexyl)sulfamoyl)quinolin-2-yloxy)acetic acid;
(1r,4R)—N—((R)-1-(4-fluorophenyl)ethyl)-4-(2-(1-hydroxy-2-methylpropan-2-yloxy)quinoline-6-sulfonamido)cyclohexanecarboxamide;
(1r,4R)—N—((R)-1-(4-fluorophenyl)ethyl)-4-(2-(2-hydroxy-2-methylpropoxy)quinoline-6-sulfonamido)cyclohexanecarboxamide;
(1r,4R)-4-(2-ethoxyquinoline-6-sulfonamido)-N—((R)-1-(pyridin-2-yl)ethyl) cyclohexanecarboxamide;
(1r,4R)-4-(2-(oxetan-3-yloxy)quinoline-6-sulfonamido)-N—((R)-1-(pyridin-2-yl)ethyl)cyclohexanecarboxamide;
(S)-tert-butyl 3-phenyl-4-((1r,4S)-4-(quinoline-3-sulfonamido)cyclohexanecarbonyl)piperazine-1-carboxylate;
N-((1S,4r)-4-((S)-2-phenylpiperazine-1-carbonyl)cyclohexyl)quinoline-3-sulfonamide;
(1r,4R)—N—((R)-1-(4-fluorophenyl)ethyl)-4-(quinoline-3-sulfonamido)cyclohexanecarboxamide;
(1r,4R)—N—((R)-1-(4-fluorophenyl)ethyl)-4-(2-oxo-1,2,3,4-tetrahydroquinoline-6-sulfonamido)cyclohexanecarboxamide;
(1r,4R)—N—((R)-1-(4-fluorophenyl)ethyl)-4-(quinoline-6-sulfonamido)cyclohexanecarboxamide;
(1r,4R)-4-(1,4-dimethyl-1,2,3,4-tetrahydroquinoxaline-6-sulfonamido)-N—((R)-1-(4-fluorophenyl)ethyl)cyclohexanecarboxamide;
(1r,4R)-4-(5,10-dimethyl-5,5a,6,7,8,9,9a, 10-octahydropyrido[3,2-b]quinoxaline-3-sulfonamido)-N—((R)-1-(4-fluorophenyl)ethyl)cyclohexanecarboxamide;
(1R,4R)-4-((5aR,9aR)-5,10-dimethyl-5,5a,6,7,8,9,9a, 10-octahydropyrido[3,2-b]quinoxaline-3-sulfonamido)-N—((R)-1-(4-fluorophenyl)ethyl)cyclohexanecarboxamide;
(1r,4R)—N—((R)-1-(4-fluorophenyl)ethyl)-4-(1-methyl-1,2,3,4-tetrahydroquinoline-7-sulfonamido)cyclohexanecarboxamide;
(1r,4R)—N—((R)-1-(4-fluorophenyl)ethyl)-4-(1,2,3,4-tetrahydroquinoxaline-6-sulfonamido)cyclohexanecarboxamide;
(1r,4R)—N—((R)-1-(4-fluorophenyl)ethyl)-4-(1,2,3,4-tetrahydroquinoline-7-sulfonamido)cyclohexanecarboxamide;
(1r,4R)—N—((R)-1-(4-fluorophenyl)ethyl)-4-(1,2,3,4-tetrahydroquinoline-6-sulfonamido)cyclohexanecarboxamide;
(1r,4r)-4-(1-methyl-1,2,3,4-tetrahydroquinoline-7-sulfonamido)-N-(1-(pyridin-2-yl)ethyl)cyclohexanecarboxamide;
(1r,4r)-4-(1-methyl-1,2,3,4-tetrahydroquinoline-7-sulfonamido)-N-(1-(pyridin-3-yl)ethyl)cyclohexanecarboxamide;
(1r,4r)-4-(1-methyl-1,2,3,4-tetrahydroquinoline-7-sulfonamido)-N-(1-(pyridin-4-yl)ethyl)cyclohexanecarboxamide;
(1S,4R)—N—((R)-1-(4-fluorophenyl)ethyl)-4-((5aS, 9aS)-5,5a,6,7,8,9,9a, 10-octahydropyrido[3,2-b]quinoxaline-3-sulfonamido)cyclohexanecarboxamide;
methyl 2-(7-(N-((1R,4r)-4-((R)-1-(4-fluorophenyl)ethylcarbamoyl)cyclohexyl)sulfamoyl)-3,4-dihydroquinolin-1(2H)-yl)acetate;
(1r,4R)—N—((R)-1-(4-fluorophenyl)ethyl)-4-(3-methylquinoline-8-sulfonamido) cyclohexanecarboxamide;
2-(7-(N-((1R,4r)-4-((R)-1-(4-fluorophenyl)ethylcarbamoyl)cyclohexyl)sulfamoyl)-3,4-dihydroquinolin-1(2H)-yl)acetic acid;
(1r,4R)—N—((R)-1-(4-fluorophenyl)ethyl)-4-(2-isobutyl-1,2,3,4-tetrahydroquinoline-6-sulfonamido)cyclohexanecarboxamide;
(1r,4R)—N—((R)-1-(4-fluorophenyl)ethyl)-4-(2-methyl-1,2,3,4-tetrahydroquinoline-7-sulfonamido)cyclohexanecarboxamide;
(1r,4R)—N—((R)-1-(4-fluorophenyl)ethyl)-4-(2-methyl-1,2,3,4-tetrahydroquinoline-6-sulfonamido)cyclohexanecarboxamide;
(1r,4R)-4-((S)-2-ethyl-1,2,3,4-tetrahydroquinoline-6-sulfonamido)-N—((R)-1-(4-fluorophenyl)ethyl)cyclohexanecarboxamide;
(1r,4R)-4-((R)-2-ethyl-1,2,3,4-tetrahydroquinoline-6-sulfonamido)-N—((R)-1-(4-fluorophenyl)ethyl)cyclohexanecarboxamide;
tert-butyl 3-phenyl-4-((1r,4r)-4-(1,2,3,4-tetrahydroquinoline-6-sulfonamido)cyclohexanecarbonyl) piperazine-1-carboxylate;
tert-butyl 3-phenyl-4-((1r,4r)-4-(1,2,3,4-tetrahydroquinoline-7-sulfonamido)cyclohexanecarbonyl) piperazine-1-carboxylate;
N-((1r,4r)-4-(2-phenylpiperazine-1-carbonyl)cyclohexyl)-1,2,3,4-tetrahydroquinoline-6-sulfonamide;
N-((1r,4r)-4-(2-phenylpiperazine-1-carbonyl)cyclohexyl)-1,2,3,4-tetrahydroquinoline-7-sulfonamide;
N-((1r,4r)-4-(3-phenylmorpholine-4-carbonyl)cyclohexyl)-1,2,3,4-tetrahydroquinoline-6-sulfonamide;
N-((1r,4r)-4-(3-phenylmorpholine-4-carbonyl)cyclohexyl)-1,2,3,4-tetrahydroquinoline-7-sulfonamide;
tert-butyl 3-phenyl-4-((1r,4r)-4-(2-(trifluoromethyl)-1,2,3,4-tetrahydroquinoline-6-sulfonamido)cyclohexanecarbonyl)piperazine-1-carboxylate;
N-((1r,4r)-4-(2-phenylpiperazine-1-carbonyl)cyclohexyl)-2-(trifluoromethyl)-1,2,3,4-tetrahydroquinoline-6-sulfonamide;

(1r,4R)—N—((R)-1-(4-fluorophenyl)ethyl)-4-(4-(2,2,2-trifluoroacetamido)-1-(2,2,2-trifluoroacetyl)-1,2,3,4-tetrahydroquinoline-6-sulfonamido)cyclohexanecarboxamide;

(1r,4R)—N—((R)-1-(4-fluorophenyl)ethyl)-4-(4-(2,2,2-trifluoroacetamido)-1,2,3,4-tetrahydroquinoline-6-sulfonamido)cyclohexanecarboxamide;

N-((1r,4r)-4-(2-phenylpiperazine-1-carbonyl)cyclohexyl)-2-(trifluoromethyl)-1,2,3,4-tetrahydroquinoline-7-sulfonamide;

(1r,4R)—N—((R)-1-(4-fluorophenyl)ethyl)-4-(6-methyl-1,2,3,4-tetrahydroquinoline-7-sulfonamido)cyclohexanecarboxamide;

(1r,4R)-4-(4,4-dimethyl-2-oxo-1,2,3,4-tetrahydroquinoline-7-sulfonamido)-N—((R)-1-(4-fluorophenyl)ethyl) cyclohexanecarboxamide;

(1r,4R)-4-(4,4-dimethyl-1,2,3,4-tetrahydroquinoline-7-sulfonamido)-N—((R)-1-(4-fluorophenyl)ethyl)cyclohexanecarboxamide;

(1r,4R)—N—((R)-1-(4-fluorophenyl)ethyl)-4-(2-(2-methoxyethylamino)quinoline-6-sulfonamido)cyclohexanecarboxamide;

(1r,4R)—N—((R)-1-(4-fluorophenyl)ethyl)-4-(2-phenylquinoline-6-sulfonamido) cyclohexanecarboxamide;

3-(6-(N-((1R,4r)-4-((R)-1-(4-fluorophenyl)ethylcarbamoyl)cyclohexyl)sulfamoyl)quinolin-2-ylamino)propanoic acid;

2-ethoxy-N-((1r,4r)-4-(2-phenylpiperazine-1-carbonyl)cyclohexyl)quinoline-6-sulfonamide (1r,4S)-4-(2-ethoxyquinoline-6-sulfonamido)-N—((S)-2-hydroxy-1-phenylethyl) cyclohexanecarboxamide;

(1r,4S)-4-(2-ethoxyquinoline-6-sulfonamido)-N—((S)-2-hydroxy-2-methyl-1-phenylpropyl) cyclohexanecarboxamide;

6-(N-((1R,4r)-4-((R)-1-(4-fluorophenyl)ethylcarbamoyl)cyclohexyl)sulfamoyl)-N-(2-methoxyethyl) quinoline-2-carboxamide;

(R)-tert-butyl 3-((1r,4R)-4-(2-ethoxyquinoline-6-sulfonamido)cyclohexanecarboxamido)-3-phenylpropanoate;

isobutyl 7-(N-((1R,4r)-4-((R)-1-(4-fluorophenyl)ethylcarbamoyl)cyclohexyl)sulfamoyl)-4,4-dimethyl-3,4-dihydroquinoline-1(2H)-carboxylate;

(1r,4R)—N—((R)-1-(4-fluorophenyl)ethyl)-4-(2-morpholinoquinoline-6-sulfonamido) cyclohexanecarboxamide;

diisobutyl 6-(N-((1R,4r)-4-((R)-1-(4-fluorophenyl)ethylcarbamoyl)cyclohexyl)sulfamoyl)-2,3-dihydroquinoxaline-1,4-dicarboxylate;

(1r,4R)-4-(2-(2-(dimethylamino)ethylamino)quinoline-6-sulfonamido)-N—((R)-1-(4-fluorophenyl)ethyl)cyclohexanecarboxamide;

(1r,4R)—N—((R)-1-(4-fluorophenyl)ethyl)-4-(2-(piperidin-1-yl)quinoline-6-sulfonamido)cyclohexanecarboxamide;

isobutyl 7-(N-((1R,4r)-4-((R)-1-(4-fluorophenyl)ethylcarbamoyl)cyclohexyl)sulfamoyl)-3,4-dihydroquinoxaline-1(2H)-carboxylate;

(1r,4R)—N—((R)-1-(4-fluorophenyl)ethyl)-4-(2-(pyridin-3-yl)quinoline-6-sulfonamido)cyclohexanecarboxamide;

3-(6-(N-((1R,4r)-4-((R)-1-(4-fluorophenyl)ethylcarbamoyl)cyclohexyl)sulfamoyl)quinolin-2-yl)propanoic acid;

methyl 7-(N-((1R,4r)-4-((R)-1-(4-fluorophenyl)ethylcarbamoyl)cyclohexyl)sulfamoyl)-3,4-dihydroquinoxaline-1(2H)-carboxylate;

(1r,4R)—N—((R)-1-(4-fluorophenyl)ethyl)-4-(1-oxo-1,2,3,4-tetrahydroisoquinoline-7-sulfonamido)cyclohexanecarboxamide;

methyl 7-(N-((1R,4r)-4-((R)-1-(4-fluorophenyl)ethylcarbamoyl)cyclohexyl)sulfamoyl)-1-methyl-1,2,3,4-tetrahydroquinoline-2-carboxylate;

7-(N-((1R,4r)-4-((R)-1-(4-fluorophenyl)ethylcarbamoyl)cyclohexyl)sulfamoyl)-1-methyl-1,2,3,4-tetrahydroquinoline-2-carboxylic acid;

(1r,4R)-4-(2-(2,6-dimethylpyridin-4-yl)quinoline-6-sulfonamido)-N—((R)-1-(4-fluorophenyl)ethyl)cyclohexanecarboxamide;

(R)-3-((1r,4R)-4-(2-ethoxyquinoline-6-sulfonamido)cyclohexanecarboxamido)-3-phenylpropanoic acid;

(1r,4R)—N—((R)-1-(4-fluorophenyl)ethyl)-4-(2-(2-methylpyridin-4-yl)quinoline-6-sulfonamido)cyclohexanecarboxamide;

(1r,4R)—N—((R)-1-(4-fluorophenyl)ethyl)-4-(2-(pyridin-2-yl)quinoline-6-sulfonamido)cyclohexanecarboxamide;

(1r,4R)-4-(2-ethoxyquinoline-6-sulfonamido)-N—((R)-1-(4-fluorophenyl)ethyl)-1-methylcyclohexanecarboxamide;

tert-butyl 4-(6-(N-((1R,4r)-4-((R)-1-(4-fluorophenyl)ethylcarbamoyl)cyclohexyl)sulfamoyl) quinolin-2-yl)piperazine-1-carboxylate;

2-ethoxy-N-((1S,4r)-4-((S)-2-phenylpiperazine-1-carbonyl)cyclohexyl)quinoline-6-sulfonamide;

(R)-1-tert-butyl 3-methyl 4-((1r,4R)-4-(2-ethoxyquinoline-6-sulfonamido) cyclohexanecarbonyl)piperazine-1,3-dicarboxylate;

(R)-methyl 1-((1r,4R)-4-(2-ethoxyquinoline-6-sulfonamido)cyclohexanecarbonyl)piperazine-2-carboxylate;

(1r,4R)-4-(2-(4,7-diazaspiro[2.5]octan-7-yl)quinoline-6-sulfonamido)-N—((R)-1-(4-fluorophenyl)ethyl)cyclohexanecarboxamide;

(1r,4R)—N—((R)-1-(4-fluorophenyl)ethyl)-4-(2-(piperazin-1-yl)quinoline-6-sulfonamido)cyclohexanecarboxamide;

N-ethyl-7-(N-((1R,4r)-4-((R)-1-(4-fluorophenyl)ethylcarbamoyl)cyclohexyl)sulfamoyl)-3,4-dihydroquinoxaline-1(2H)-carboxamide;

methyl 4-(6-(N-((1R,4r)-4-((R)-1-(4-fluorophenyl)ethylcarbamoyl)cyclohexyl)sulfamoyl)quinolin-2-yl)piperazine-2-carboxylate;

(R)-1-((1r,4R)-4-(2-ethoxyquinoline-6-sulfonamido)cyclohexanecarbonyl)piperazine-2-carboxylic acid;

(1r,4R)—N—((R)-1-(4-fluorophenyl)ethyl)-4-(2-(3-(piperazin-1-yl)prop-1-ynyl)quinoline-6-sulfonamido)cyclohexanecarboxamide;

(1r,4R)—N—((R)-1-(4-fluorophenyl)ethyl)-4-(2-(3-(trifluoromethyl)piperazin-1-yl)quinoline-6-sulfonamido) cyclohexanecarboxamide;

3-(6-(N-((1R,4r)-4-((R)-1-(4-fluorophenyl)ethylcarbamoyl)cyclohexyl)sulfamoyl)quinolin-2-yl)benzoic acid;

(S)-7-(N-((1R,4S)-4-((R)-1-(4-fluorophenyl)ethylcarbamoyl)cyclohexyl)sulfamoyl)-1-methyl-1,2,3,4-tetrahydroquinoline-2-carboxylic acid;

(R)-7-(N-((1R,4R)-4-((R)-1-(4-fluorophenyl)ethylcarbamoyl)cyclohexyl)sulfamoyl)-1-methyl-1,2,3,4-tetrahydroquinoline-2-carboxylic acid;

(1r,4r)-methyl 4-(2-(2,6-dimethylpyridin-4-yl)quinoline-6-sulfonamido)cyclohexanecarboxylate;

(1r,4r)-4-(2-(2,6-dimethylpyridin-4-yl)quinoline-6-sulfonamido)-N-(2-hydroxy-2-methyl-1-phenylpropyl)cyclohexanecarboxamide;

2-(2,6-dimethylpyridin-4-yl)-N-((1r,4r)-4-(2-phenylpiperazine-1-carbonyl)cyclohexyl)quinoline-6-sulfonamide;

2-(2,6-dimethylpyridin-4-yl)-N-((1R,4r)-4-((R)-2-phenylpiperazine-1-carbonyl)cyclohexyl) quinoline-6-sulfonamide;

(1r,4R)—N—((R)-2-hydroxy-2-methyl-1-phenylpropyl)-4-(2-(4-methylpiperazin-1-yl)quinoline-6-sulfonamido)cyclohexanecarboxamide;

2-(4-methylpiperazin-1-yl)-N-((1r,4r)-4-(2-phenylpiperazine-1-carbonyl)cyclohexyl)quinoline-6-sulfonamide;

N-((1S,4r)-4-((S)-3-isopropylmorpholine-4-carbonyl)cyclohexyl)-2-(4-methylpiperazin-1-yl)quinoline-6-sulfonamide;

2-(2,6-dimethylpyridin-4-yl)-N-((1S,4r)-4-((S)-3-isopropylmorpholine-4-carbonyl)cyclohexyl)quinoline-6-sulfonamide;

(S)—((S)-2-((1r,4S)-4-(2-ethoxyquinoline-6-sulfonamido)cyclohexanecarboxamido)-2-phenylethyl) 2-amino-3-methylbutanoate;

di-tert-butyl (S)-2-((1r,4S)-4-(2-ethoxyquinoline-6-sulfonamido)cyclohexanecarboxamido)-2-phenylethyl phosphate;

(S)-2-((1r,4S)-4-(2-ethoxyquinoline-6-sulfonamido)cyclohexanecarboxamido)-2-phenylethyl dihydrogen phosphate;

(S)-((1S,2S)-1-((1r,4S)-4-(2-ethoxyquinoline-6-sulfonamido)cyclohexanecarboxamido)-1-phenylpropan-2-yl) 2-amino-3-methylbutanoate;

(S)—((S)-2-((1r,4S)-4-(2-ethoxyquinoline-6-sulfonamido)cyclohexanecarboxamido)-2-phenylethyl) 3-methyl-2-(methylamino)butanoate;

(S)—((S)-2-((1r,4S)-4-(2-ethoxyquinoline-6-sulfonamido)cyclohexanecarboxamido)-2-phenylethyl) 2-amino-3-phenylpropanoate;

2-phenyl-N-((1r,4r)-4-(1,2,3,4-tetrahydroisoquinoline-2-carbonyl)cyclohexyl)-1H-benzo[d]imidazole-5-sulfonamide;

N-((1r,4r)-4-(decahydroisoquinoline-2-carbonyl)cyclohexyl)-2-phenyl-1H-benzo[d]imidazole-5-sulfonamide;

(1r,4r)-4-(2-phenyl-1H-benzo[d]imidazole-5-sulfonamido)-N-(quinolin-6-yl)cyclohexanecarboxamide; and N-((1r,4r)-4-(5-cyclohexyl-1,3,4-oxadiazol-2-yl)cyclohexyl)-1,2,3,4-tetrahydroisoquinoline-7-sulfonamide.

17. A pharmaceutical composition, comprising:
a compound according to claim 1, or a pharmaceutically acceptable salt thereof; and
a pharmaceutically acceptable excipient or carrier.

18. The method of treating metabolic syndrome, Syndrome X, insulin resistance, decreased glucose tolerance, non-insulin-dependent diabetes mellitus, Type II diabetes, Type I diabetes, diabetic complications, comprising administering to the mammal a therapeutically effective amount of a compound according to claim 1, or a pharmaceutically acceptable salt thereof.

19. The method according to claim 18, wherein the disease or condition is insulin resistance, decreased glucose tolerance, non-insulin-dependent diabetes mellitus, Type II diabetes, or Type I diabetes.

20. A pharmaceutical composition, comprising a therapeutically effective amount of a compound according to claim 1, or a pharmaceutically acceptable salt thereof, in combination with a therapeutically effective amount of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid; or aspirin.

* * * * *